United States Patent
Li et al.

(10) Patent No.: US 9,624,228 B2
(45) Date of Patent: Apr. 18, 2017

(54) INHIBITORS OF ERK AND METHODS OF USE

(71) Applicant: KURA ONCOLOGY, INC., La Jolla, CA (US)

(72) Inventors: Liansheng Li, San Diego, CA (US); Tao Wu, Carlsbad, CA (US); Jun Feng, San Diego, CA (US); Pingda Ren, San Diego, CA (US); Yi Liu, San Diego, CA (US)

(73) Assignee: Kura Oncology, Inc., La Jolla, CA (US)

( * ) Notice: Subject to any disclaimer, the term of this patent is extended or adjusted under 35 U.S.C. 154(b) by 0 days.

(21) Appl. No.: 15/026,581

(22) PCT Filed: Oct. 3, 2014

(86) PCT No.: PCT/US2014/059197
§ 371 (c)(1),
(2) Date: Mar. 31, 2016

(87) PCT Pub. No.: WO2015/051341
PCT Pub. Date: Apr. 9, 2015

(65) Prior Publication Data
US 2016/0237091 A1 Aug. 18, 2016

Related U.S. Application Data

(60) Provisional application No. 61/886,552, filed on Oct. 3, 2013, provisional application No. 62/032,446, filed on Aug. 1, 2014.

(51) Int. Cl.
C07D 487/04 (2006.01)
A61K 31/4439 (2006.01)
(Continued)

(52) U.S. Cl.
CPC .......... *C07D 487/04* (2013.01); *A61K 9/0053* (2013.01); *A61K 31/4439* (2013.01);
(Continued)

(58) Field of Classification Search
CPC ............ A61K 31/4439; A61K 31/4745; A61K 31/513; A61K 31/5377; A61K 31/5517;
(Continued)

(56) References Cited

U.S. PATENT DOCUMENTS 3,984,556 A 10/1976 Hardtmann
4,042,704 A 8/1977 Coombs
(Continued)

FOREIGN PATENT DOCUMENTS

EP 2455381 A1 5/2012
WO WO-9964004 A1 12/1999
(Continued)

OTHER PUBLICATIONS

Foster, et al. Synthesis of proxl-benzoisoallopurinol. J. Org. Chem., 1980, 45 (15), pp. 3072-3077. DOI: 10.1021/jo01303a027.
(Continued)

*Primary Examiner* — Savitha Rao
(74) *Attorney, Agent, or Firm* — Wilson Sonsini Goodrich & Rosati

(57) ABSTRACT

The present invention provides chemical entities or compounds and pharmaceutical compositions thereof that are capable of modulating certain protein kinases such as ERK (MAPK). Also provided are methods of using such compounds or compositions, and methods of using these compositions to modulate the activities of one or more of these kinases, especially for therapeutic applications such as the treatment disorders such as cancer.

17 Claims, 1 Drawing Sheet

(51) Int. Cl.
*A61K 31/513* (2006.01)
*C07D 471/04* (2006.01)
*A61K 9/00* (2006.01)
*A61K 31/4745* (2006.01)
*A61K 31/5377* (2006.01)
*A61K 31/5517* (2006.01)
*A61K 45/06* (2006.01)
*C07D 519/00* (2006.01)

(52) U.S. Cl.
CPC ........ *A61K 31/4745* (2013.01); *A61K 31/513* (2013.01); *A61K 31/5377* (2013.01); *A61K 31/5517* (2013.01); *A61K 45/06* (2013.01); *C07D 471/04* (2013.01); *C07D 519/00* (2013.01)

(58) Field of Classification Search
CPC .... A61K 45/06; C07D 471/04; C07D 487/04; C07D 519/00
See application file for complete search history.

(56) References Cited

U.S. PATENT DOCUMENTS

| | | | |
|---|---|---|---|
| 4,352,931 | A | 10/1982 | Cuny et al. |
| 5,116,843 | A | 5/1992 | Mertens et al. |
| 6,596,726 | B1 | 7/2003 | Bridges et al. |
| 2005/0203063 | A1 | 9/2005 | Deshaies et al. |
| 2005/0222239 | A1 | 10/2005 | Chen et al. |
| 2008/0227767 | A1 | 9/2008 | Szarek et al. |
| 2010/0056800 | A1 | 3/2010 | Stambuli |
| 2014/0296203 | A1 | 10/2014 | Lim et al. |
| 2015/0258074 | A1 | 9/2015 | Wilson et al. |
| 2015/0266895 | A1 | 9/2015 | Wilson et al. |
| 2016/0068532 | A1 | 3/2016 | Lim et al. |
| 2016/0176896 | A1 | 6/2016 | Cortez et al. |

FOREIGN PATENT DOCUMENTS

| | | | |
|---|---|---|---|
| WO | WO-0222604 | A1 | 3/2002 |
| WO | WO-03101985 | A1 | 12/2003 |
| WO | WO-2005028475 | A2 | 3/2005 |
| WO | WO-2006052378 | A1 | 5/2006 |
| WO | WO-2007097937 | A1 | 8/2007 |
| WO | WO-2008153858 | A1 | 12/2008 |
| WO | WO-2008156739 | A1 | 12/2008 |
| WO | WO-2009046025 | A1 | 4/2009 |
| WO | WO-2009105500 | A1 | 8/2009 |
| WO | WO-2010107742 | A2 | 9/2010 |
| WO | WO-2011041152 | A1 | 4/2011 |
| WO | WO-2012030685 | A2 | 3/2012 |
| WO | WO-2012036997 | A1 | 3/2012 |
| WO | WO-2012058127 | A2 | 5/2012 |
| WO | WO-2012087772 | A1 | 6/2012 |
| WO | WO-2012170845 | A2 | 12/2012 |
| WO | WO-2014137719 | A1 | 9/2014 |
| WO | WO-2014179154 | A2 | 11/2014 |
| WO | WO-2016095088 | A1 | 6/2016 |
| WO | WO-2016095089 | A1 | 6/2016 |
| WO | WO-2016100050 | A1 | 6/2016 |
| WO | WO-2016100051 | A1 | 6/2016 |
| WO | WO-2016100147 | A1 | 6/2016 |
| WO | WO-2016100152 | A1 | 6/2016 |

OTHER PUBLICATIONS

PubChem. Compound Summary for CID 336305. URL:<https://pubchem.ncbi.nlm.nih.gov/compound/336305#section=Top>. Accessed on Jan. 18, 2017. 14 pages.

Sequeria, et al. Synthesis of fused indazole derivatives. Indian Journal of Chemistry, Section B: Organic Chemistry Including Medicinal Chemistry (1987), 26B, (5), 436-439.

International search report and written opinion dated Jan. 22, 2015 for PCT/US2014/059197.

PubChem. Compound Summary for CID 13481918. http://pubchem.ncbi.nlm.nih.gov/compound/13481918. Accessed on Feb. 2, 2015. 1-8 pages.

PubChem. Compound Summary for CID 18347999. http://pubchem.ncbi.nlm.nih.gov/compound/18347999. Accessed on Feb. 2, 2015. 1-9 pages.

PubChem. Compound Summary for CID 70205837. http://pubchem.ncbi.nlm.nih.gov/compound/70205837#section=Top. Accessed on Feb. 2, 2015. 1-9 pages.

Tsuruo, et al. Platelet aggregation in the formation of tumor metastasis. Proc Jpn Acad Ser B Phys Biol Sci. 2008;84(6):189-98.

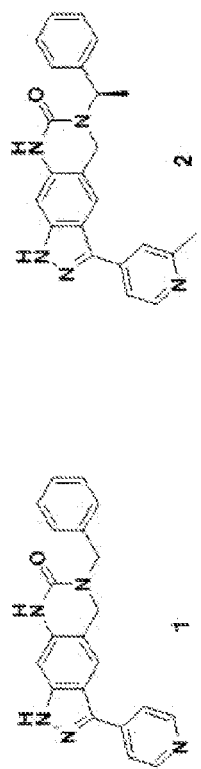

INHIBITORS OF ERK AND METHODS OF USE

CROSS-REFERENCE

This application claims the benefit of U.S. Provisional Application Ser. No. 61/886,552, filed on Oct. 3, 2013, and U.S. Provisional Application Ser. No. 62/032,446 filed on Aug. 1, 2014, each of which is incorporated herein by reference in its entirety.

BACKGROUND OF THE INVENTION

ERK kinases are serine/threonine kinases that mediate intracellular signal transduction pathways involved in tumor growth, progression and metastasis. ERK is involved in the Ras/Raf/MEK/ERK pathway, which plays a central role in regulating cellular processes by relaying extracellular signals from ligand-bound cell surface receptor tyrosine kinases (RTKs) such as ErbB (e.g. EGFR, Her-2, etc), VEGF, PDGF, and FGF receptor tyrosine kinases. Activation of an RTK triggers a series of phosphorylation events, beginning with the activation of Ras, followed by recruitment and activation of Raf. Activated Raf then phosphorylates MAP kinase kinase (MEK) 1/2, which then phosphorylates ERK 1/2. ERK phosphorylation by MEK occurs on Y204 and T202 for ERK1 and Y185 and T183 for ERK2 (Ahn et al., *Methods in Enzymology* 2001, 332, 417-431). Phosphorylated ERK dimerizes and translocates to and accumulates in the nucleus (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell* 2000, 6, 1343-1354). ERK2 phosphorylates a multitude of regulatory proteins, including the protein kinases Rsk90 and MAPKAP2 ((Bjorbaek et al., 1995, *J. Biol. Chem.* 270, 18848; Rouse et al., 1994, *Cell* 78, 1027), and transcription factors such as ATF2, Elk-1, c-Fos, and c-Myc (Raingeaud et al., 1996, *Mol. Cell Biol.* 16, 1247; Chen et al., 1993, *Proc. Natl. Acad. Sci. U.S.A.* 90, 10952; Oliver et al., 1995, *Proc. Soc. Exp. Biol. Med.* 210, 162). Overall, treatment of cells with growth factors leads to the activation of ERK1 and ERK2 which results in proliferation and, in some cases, differentiation (Lewis et al., *Adv. Cancer Res.* 1998, 74, 49-139).

A wealth of studies have shown that genetic mutations and/or overexpression of protein kinases in the Ras/Raf/MEK/ERK pathway lead to uncontrolled cell proliferation and tumor formation in proliferative diseases such as cancer. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., Science 1993, 260, 1834-1837). Recently, bRaf mutations have been identified in more than malignant melanomas (60%), thyroid cancers (greater than 40%) and colorectal cancers. These mutations in bRaf result in a constitutively active Ras/Raf/MEK/ERK kinase cascade. Studies of primary tumor samples and cell lines have also shown constitutive or overactivation of the Ras/Raf/MEK/ERK kinase pathway in cancers of pancreas, colon, lung, ovary and kidney (Hoshino, R. et al., Oncogene 1999, 18, 813-822). Further, ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol.* 16, 589).

In view of the multitude of upstream (e.g. Ras, Raf) and downstream (e.g. ATF2, c-Fos, c-Myc) signaling proteins in the Raf/Ras/MEK/ERK pathway that have been implicated in a wide range of disorders, including but not limited to cancer, ERK has emerged as a prime target for drug development.

SUMMARY OF THE INVENTION

Thus, there exists a considerable need for ERK inhibitors, pharmaceutical compositions comprising such ERK inhibitor, and the uses of such ERK inhibitors for treatment and/or diagnosis of a variety of diseases. The present invention addresses this need and provides related advantages as well.

In one aspect, the invention provides a compound of Formula I:

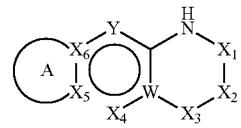

or a pharmaceutically acceptable salt or prodrug thereof; wherein:

is

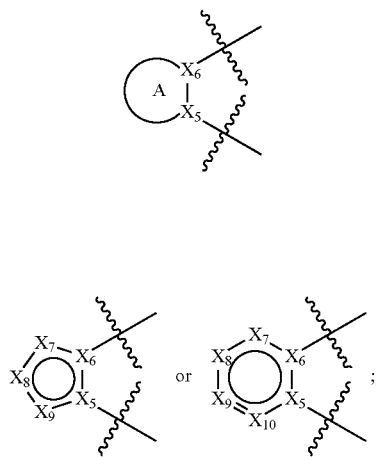

$X_1$ is C=O, C=S, SO, $SO_2$, or $PO_2^-$;
Y is $CR_5$;
$X_2$ is $NR_1$ or $CR_1R_1'$ and $X_3$ is a bond, $CR_3R_3'$ or C=O; or
$X_2$-$X_3$ is $R_1C$=$CR_3$ or $R_1C$=N or N=$CR_3$ or $NR_{12}$—$CR_{11}$=$CR_3$;
$X_4$ is N, $CR_4$, C=O; $X_5$ is N or C;
$X_6$ is N or C;
$X_7$ is O, N, $NR_{72}$ or $CR_{71}$;
$X_8$ is O, N, $NR_{82}$ or $CR_{81}$;
$X_9$ is O, N, $NR_{22}$ or $CR_{21}$;
$X_{10}$ is O, N, $NR_{92}$ or $CR_{91}$;

$R_1$ is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{1-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{1-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{1-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R_{32}$, —$NR^{31}(C)(=O)R^{32}$, —$NR^{31}C(O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —P(O)$OR^{31}OR^{32}$, —$SC(=O)NR^{31}R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —$C(=O)NR^{31}$, —$S(O)_{0-2}R^{31}$, —$C(=S)OR^{31}$, —$C(=O)SR^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —NR$^{31}$C(=O)—, —NR$^{31}$C(=O)NR$^{32}$—, —NR$^{31}$S(O)$_{0-2}$—, —S(O)$_{0-2}$N($R^{31}$)—, —C(=S)O—, —C(=O)S—, —NR$^{31}$C(=NR$^{32}$)NR$^{32}$—, —NR$^{31}$C(=NR$^{32}$)O—, —NR$^{31}$C(=NR$^{32}$)S—, —OC(=O)O—, —OC(=O)NR$^{31}$—, —OC(=O)S—, —SC(=O)S—, —P(O)OR$^{31}$O—, —SC(=O)NR$^{31}$—;

each of $R_3$, $R_3'$ and $R_4$ is independently hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl-C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{13}$ substituents; or $R_3'$ is —OR$^6$, —NR$^6$R$^{34}$, —S(O)$_{0-2}$R$^6$, —C(=O)R$^6$, —C(=O)OR$^6$, —OC(=O)R$^6$, —C(=O)N(R$^{34}$)R$^6$, or —N(R$^{34}$)C(=O)R$^6$, wherein R$^6$ together with R$^{34}$ can optionally form a heterocyclic ring;

each of $R_5$, $R_{71}$, $R_{81}$ and $R_{91}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$;

$R_6$ is hydrogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{14}$ or $R_{15}$ substituents;

each of $R_{72}$, $R_{82}$ and $R_{92}$ is independently hydrogen, —C$_{1-10}$alkyl, —C$_{2-10}$alkenyl, —C$_{2-10}$alkynyl, —C$_{1-10}$heteroalkyl, —C$_{3-10}$aryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, —S(O)$_{0-2}$R$^{31}$, —C(=S)OR$^{31}$, —C(=O)SR$^{31}$;

each of $R_{10}$ and $R_{14}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent $R_{11}$ substituents;

each of $R_{11}$, $R_{12}$, $R_{13}$ and $R_{15}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$;

each of $R^{31}$, $R^{32}$, $R^{33}$ and $R^{34}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, or wherein R$^{31}$ together with R$^{32}$ form a heterocyclic ring;

wherein ring A comprises one or more heteroatoms selected from N, O, or S;

wherein if $X_7$ is O or $X_2$-$X_3$ is $R_1C=CR_3$, ring A comprises at least two heteroatoms selected from N, O, or S; and wherein if $X_3$ is O or N, or $X_2$-$X_3$ is $R_1C=N$, at least one of $X_7$ or $X_9$ is not N.

In some embodiments, the invention provides a compound of Formula I-A:

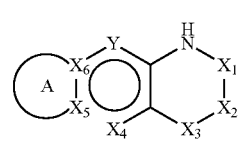

or a pharmaceutically acceptable salt or prodrug thereof.

In some embodiments, the invention provides a compound of Formula I-B:

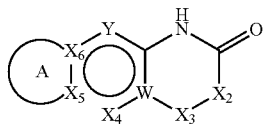

or a pharmaceutically acceptable salt or prodrug thereof.

In some cases, the invention provides a compound of Formula II:

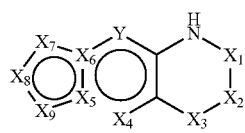

or a pharmaceutically acceptable salt or prodrug thereof.

In some embodiments, $X_1$ is C=O. In some embodiments, $X_2$ is $NR_1$. In some embodiments, $X_5$ is N and $X_6$ is C. In other embodiments, $X_5$ is C and $X_6$ is C. In some embodiments, $X_9$ is $CR_{21}$.

In some embodiments, the invention provides a compound of Formula II-A:

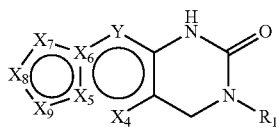

or a pharmaceutically acceptable salt or prodrug thereof.

In other embodiments, the invention provides a compound of Formula II-B:

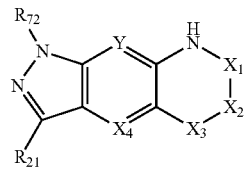

or a pharmaceutically acceptable salt or prodrug thereof.

In further embodiments, the invention provides a compound of Formula II-C:

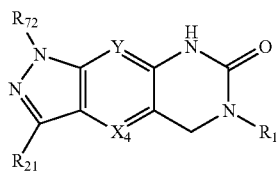

or a pharmaceutically acceptable salt or prodrug thereof.

In yet other embodiments, the invention provides a compound of Formula II-D:

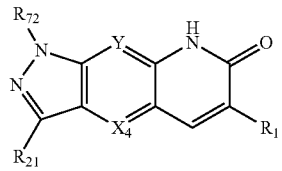

or a pharmaceutically acceptable salt or prodrug thereof.

In some embodiments, the invention provides a compound of Formula II-E:

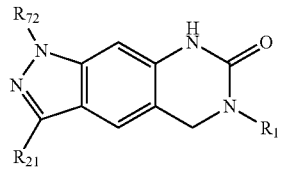

or a pharmaceutically acceptable salt or prodrug thereof.

In some embodiments, the invention provides a compound of Formula II-F:

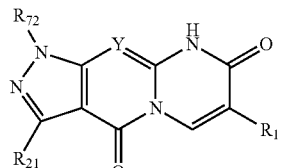

or a pharmaceutically acceptable salt or prodrug thereof.

In some embodiments, the invention provides a compound of Formula II-G:

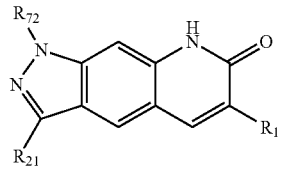

or a pharmaceutically acceptable salt or prodrug thereof.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $R_{21}$ is selected from the group consisting of -L-$C_{1-10}$heteroalkyl, -L-$C_{3-10}$aryl, -L-$C_{1-10}$hetaryl, -L-$C_{3-10}$cycloalkyl, and -L-$C_{1-10}$heterocyclyl, each of which is unsubstituted or substituted by one or more independent $R_{12}$ substituents; and L is bond. In some embodiments, $R_{21}$ is -L-$C_{1-10}$hetaryl unsubstituted or substituted by one or more independent $R_{12}$ substituents; and L is bond. In some embodiments, the $C_{1-10}$hetaryl of $R_{21}$ comprises one or more nitrogen atoms. In some embodiments, the $C_{1-10}$hetaryl of $R_{21}$ is selected from the group consisting of pyrazolyl, pyridinyl, pyrazinyl, pyrimidinyl, and pyridazinyl. In some embodiments, the $C_{1-10}$hetaryl of $R_{21}$ is unsubstituted. In other embodiments, the $C_{1-10}$hetaryl or $R_{21}$ is substituted with one, two, or three independent $R_{12}$ substituents. In some embodiments, each $R_{12}$ substituent is independently selected from the group consisting of —$C_{1-10}$alkyl, —$C_{2-10}$alkenyl, —$C_{2-10}$ alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl. In further embodiments, each $R_{12}$ substituent is independently selected from the group consisting -Me, -Et, -i-Pr, -n-Pr, OH, —OMe, —OEt, —OPr.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $R_1$ is —$C_{1-10}$alkyl, —$C_{1-10}$heterocyclyl, —$C_{1-10}$alkyl-$C_{3-10}$heterocyclyl, —$C_{1-10}$alkyl-$C_{3-10}$aryl, —$C_{1-10}$alkyl $C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents. In other embodiments, $R_1$ is —$C_{1-10}$alkyl, —$C_{1-10}$heterocyclyl, —$C_{1-10}$alkyl-$C_{3-10}$heterocyclyl, —$C_{1-10}$alkyl-$C_{3-10}$aryl, —$C_{1-10}$alkyl $C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents. In yet other embodiments, $R_1$ is —$C_{1-10}$alkyl-$C_{3-10}$aryl, —$C_{1-10}$alkyl-$C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents. In yet other embodiments, $R_1$ is —$C_{1-10}$alkyl-$C_{3-10}$aryl or —$C_{1-10}$heterocyclyl-$C_{3-10}$aryl, unsubstituted or substituted by one or more independent $R_{10}$ or $R_{11}$ substituents. In further embodiments, wherein $R_1$ is

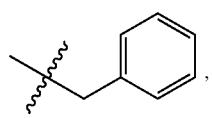 [SMILES: *Cc1ccccc1]

unsubstituted or substituted by one or more independent $R_{10}$ or $R_{11}$ substituents. In some embodiments, R1 is $R_1$ is —$C_{1-10}$heterocyclyl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents. In some embodiments, $R_1$ is

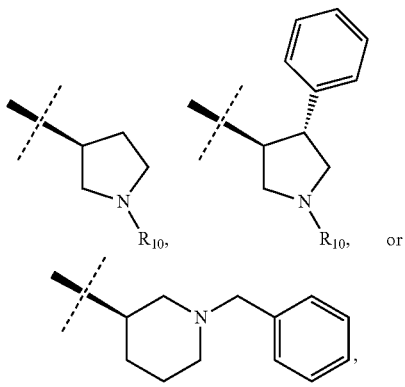

unsubstituted or substituted by one or more independent $R_{10}$ or $R_{11}$ substituents.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $R_{72}$ is H.

In other cases, the invention provides a compound of Formula III:

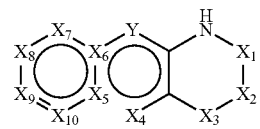

or a pharmaceutically acceptable salt or prodrug thereof.

In some embodiments, $X_1$ is C=O. In some embodiments, $X_2$ is $NR_1$. In some embodiments, $X_5$ is N and $X_6$ is C. In other embodiments, $X_5$ is C and $X_6$ is C. In some embodiments, $X_8$ is N and $X_{10}$ is N. In some embodiments, $X_9$ is $CR_{21}$.

In further embodiments, the invention provides a compound of Formula III-A:

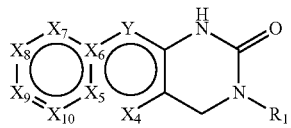

or a pharmaceutically acceptable salt or prodrug thereof.

In some embodiments, the invention provides a compound of Formula III-B:

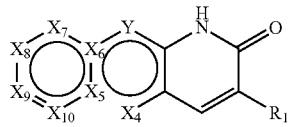

or a pharmaceutically acceptable salt or prodrug thereof.

In yet other cases, the invention provides a compound of Formula IV-A:

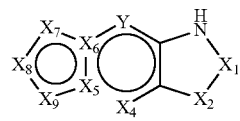

or a pharmaceutically acceptable salt or prodrug thereof.

In some embodiments, $X_1$ is C=O. In some embodiments, $X_2$ is $NR_1$. In some embodiments, $X_5$ is N and $X_6$ is C. In other embodiments, $X_5$ is C and $X_6$ is C. In some embodiments, $X_8$ is N. In some embodiments, $X_9$ is $CR_{21}$.

In some embodiments, the invention provides a compound of Formula IV-B:

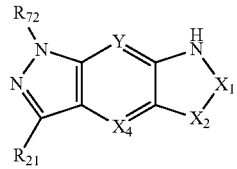

or a pharmaceutically acceptable salt or prodrug thereof.

In other embodiments, the invention provides a compound of Formula IV-C:

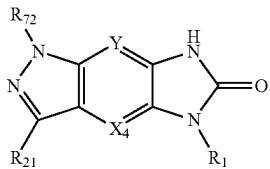

or a pharmaceutically acceptable salt or prodrug thereof.

In yet other embodiments, the invention provides a compound of Formula IV-D:

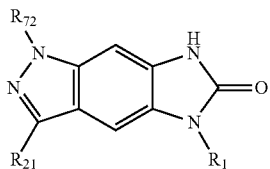

or a pharmaceutically acceptable salt or prodrug thereof.

In yet other cases, the invention provides a compound of Formula V-A:

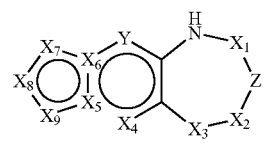

or a pharmaceutically acceptable salt or prodrug thereof.

In some embodiments, $X_1$ is C=O. In some embodiments, $X_2$ is $CR_1R_1'$. In some embodiments, $X_5$ is N and $X_6$ is C. In other embodiments, $X_5$ is C and $X_6$ is C. In some embodiments, $X_8$ is N. In some embodiments, $X_9$ is $CR_{21}$.

In some embodiments, the invention provides a compound of Formula IV-B:

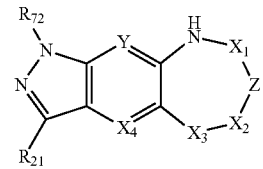

or a pharmaceutically acceptable salt or prodrug thereof.

In other embodiments, the invention provides a compound of Formula IV-C:

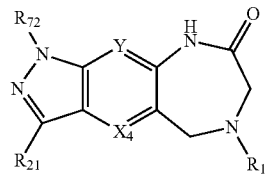

or a pharmaceutically acceptable salt or prodrug thereof.

In yet other embodiments, the invention provides a compound of Formula IV-D:

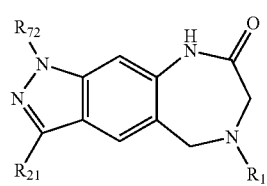

or a pharmaceutically acceptable salt or prodrug thereof.

In some embodiments of Formula I (including I-A and I-B), Formula II (including Formula II', II-A, II-B, II-C, II-D, II-E and II-F), Formula III (including Formula III-A and III-B), Formula IV (including IV-A, IV-B, IV-C and IV-D) and Formula V (including V-A, V-B, V-C and V-D), $R_5$ is hydrogen.

In some embodiments of Formula I (including I-A and I-B), Formula II (including Formula II', II-A, II-B, II-C, II-D, II-E and II-F), Formula III (including Formula III-A and III-B), Formula IV (including IV-A, IV-B, IV-C and IV-D) and Formula V (including V-A, V-B, V-C and V-D), $X_4$ is $CR_4$. In further embodiments, $X_4$ is $CR_4$ and $R_4$ is H. In other embodiments, $X_4$ is N.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $X_9$ is $CR_{21}$ or $NR_{22}$ and $R_{21}$ or $R_{22}$ is halogen, —CN, -L-$C_{3-10}$aryl, -L-$C_{1-10}$hetaryl, -L-$C_{3-10}$cycloalkyl, or -L-$C_{1-10}$heterocyclyl, unsubstituted or substituted by one or more independent $R_{12}$ substituents.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $X_9$ is $CR_{21}$ and $R_{21}$ is halogen or CN. In other embodiments, $X_9$ is $CR_{21}$ and $R_{21}$ is -L-$C_{3-10}$aryl, -L-$C_{10}$hetaryl, -L-$C_{3-10}$cycloalkyl, or -L-$C_{3-10}$heterocyclyl, unsubstituted or substituted by one or more independent $R_{12}$ substituents. In further embodiments, $X_9$ is $CR_{21}$ and $R_2$ is -L-$C_{1-10}$hetaryl or -L-$C_{3-10}$heterocyclyl, unsubstituted or substituted by one or more independent $R_{12}$ substituents.

In another aspect, the invention provides a method of inhibiting activity of a protein kinase present in a cell, comprising contacting said cell with an effective amount of a compound, pharmaceutically acceptable salt, or prodrug disclosed herein. In some embodiments, the protein kinase is ERK.

In some embodiments, the compound inhibits ERK at an IC50 value of less than about 1000 nM. In other embodiments, the compound inhibits ERK at an IC50 value of less than about 100 nM. In further embodiments, the compound inhibits ERK at an IC50 value of less than about 10 nM.

In some embodiments, the contacting step takes place in vitro. In other embodiments, the contacting step takes place in vivo.

The still yet another aspect, the invention provides a method of ameliorating a disorder comprising administering to a subject in need thereof an effective amount of a compound, pharmaceutically acceptable salt, or prodrug of a compound of any of the preceding claims, wherein the disorder is selected from the group consisting of cancer, bone disorder, inflammatory disease, immune disease, nervous system disease, metabolic disease, respiratory disease, and cardiac disease.

In some embodiments, the disorder is cancer selected from the group consisting of breast cancer, pancreatic cancer, non-small cell lung cancer (NSCLC), thyroid cancer, seminomas, melanoma, bladder cancer, liver cancer, kidney cancer, myelodysplastic syndrome (MDS), acute myelogenous leukemia (AML), and colorectal cancer. In further embodiments, the cancer is melanoma or colorectal cancer.

In some embodiments, the disorder is mediated by ERK 1 and/or ERK2.

In some embodiments, the method further comprises administering another anti-cancer agent.

The present invention also provides a pharmaceutical composition comprising the compound disclosed herein and a pharmaceutically acceptable excipient. In some embodiments, the compound is present in a therapeutically effective amount. In some embodiments, the composition is formulated in an oral dosage. In some embodiments, the composition is formulated as a tablet or a capsule.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows the biological data from the ERK kinase inhibition, p90RSK ELISA, and cellular proliferation assays for compounds provided by the invention wherein, the following symbols are used: + (greater than 1000 nM), ++ (250 nM to 1000 nM), +++ (50 nM to 250 nM), and ++++ (less than 50 nM).

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like, when the molecule contains an acidic functionality; and when the molecule contains a basic functionality, salts of organic or inorganic acids, such as hydrochloride, hydrobromide, tartrate, mesylate (methane sulfonate), ethane sulfonate, acetate, maleate, oxalate, phosphate, and the like. In a compound with more than one basic moiety, more than one of the basic moieties may be converted to the salt form, including but not limited to a bis- or tris-salt. Alternatively, a compound having more than one basic moiety may form a salt at only one of the basic moieties.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

The term "isolated compound" or "isolated agent" refers to a biological, pharmaceutical, or chemical compound or other moiety that is isolated to a purity of greater than 90%.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"ERK1 and/or ERK2 activity" as applied to a biologically active agent refers to the agent's ability to modulate signal transduction mediated by ERK1 and/or ERK2. For example, modulation of ERK1 and/or ERK2 activity is evidenced by alteration in signaling output from the Ras/Raf/MEK/ERK pathway.

"Subject" refers to an animal, such as a mammal, for example a human. The methods described herein can be useful in both human therapeutics and veterinary applications. In some embodiments, the subject is a mammal. In some embodiments, the subject is human.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, the connections of compound name moieties are at the leftmost recited moiety. That is, the substituent name starts with a linking moiety, continues with any linking moieties, and ends with a terminal moiety. For example, "-L-$C_{1-10}$alkyl-$C_{3-10}$cycloalkyl" has a terminal group —$C_{3-10}$cycloalkyl group attached to a linking —$C_{1-10}$alkyl moiety which is attached to an element L, which is itself connected to the chemical species bearing the substituent.

Unless otherwise stated, structures depicted herein are also meant to include compounds which differ only in the presence of one or more isotopically enriched atoms. For example, compounds having the present structures except for the replacement of hydrogen by deuterium or tritium, or the replacement of carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

As used herein, the term "heteroatom" or "ring heteroatom" is meant to include oxygen (O), nitrogen (N), sulfur (S), phosphorus (P), and silicon (Si).

As used herein, the term "alkyl" is used to mean an alkyl having 1-10 carbons that is 1, 2, 3, 4, 5, 6, 7, 8, 9, or 10 carbons in a straight or branched configuration. In all embodiments of this invention, the term "alkyl" includes both branched and straight chain alkyl groups, or a combination thereof. Alkyl groups are fully saturated, unsubstituted or substituted, and can include di- and multivalent radicals, having the number of carbon atoms designated (i.e. $C_{1-10}$ means one to ten carbons and $C_{2-10}$ means two to ten carbons). Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, and the like. An alkyl is unsubstituted or substituted.

The term "alkenyl" refers to a straight or branched hydrocarbon chain radical group consisting solely of carbon and hydrogen atoms, containing at least one double bond, and having from two to ten carbon atoms (i.e. $C_{2-10}$alkenyl). Whenever it appears herein, a numerical range such as "$C_{2-10}$" refers to each integer in the given range; e.g., "$C_{2-10}$alkenyl" means that the alkenyl group may consist of 2 carbon atoms, 3 carbon atoms, etc., up to and including 10 carbon atoms. In certain embodiments, an alkenyl comprises two to eight carbon atoms (e.g., —$C_{2-8}$alkenyl). In other embodiments, an alkenyl comprises two to five carbon atoms (e.g., —$C_{2-5}$alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. An alkenyl is unsubstituted or substituted.

The term "alkynyl" refers to a straight or branched hydrocarbon chain radical group consisting solely of carbon and hydrogen atoms, containing at least one triple bond, and having from two to ten carbon atoms (i.e. —$C_{2-10}$alkynyl). Whenever it appears herein, a numerical range such as "$C_{2-10}$" refers to each integer in the given range; e.g., "$C_{2-10}$alkynyl" means that the alkynyl group may consist of 2 carbon atoms, 3 carbon atoms, etc., up to and including 10 carbon atoms. In certain embodiments, an alkynyl comprises two to eight carbon atoms (e.g., —$C_{2-8}$alkynyl). In other embodiments, an alkynyl has two to five carbon atoms (e.g., —$C_{2-5}$alkynyl). The alkynyl is attached to the rest of the molecule by a single bond, for example, ethynyl, propynyl, butynyl, pentynyl, hexynyl, and the like. An alkynyl is unsubstituted or substituted.

The term "heteroalkyl" refers to a straight or branched chain radical group, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. The alkyl portion of the moiety is unsubstituted or substituted. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, CH=CH—N($CH_3$)—$CH_3$, O—$CH_3$, —O—$CH_2$—$CH_3$, and CN. Up to two or three heteroatoms may be consecutive, such as, for example, —$CH_2$—NH—O$CH_3$ and $CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and $CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity.

Thus, the term "heteroalkyl" should not be interpreted herein as excluding specific heteroalkyl groups, such as —NR'R" or the like.

The term "aromatic" or "aryl" refers to an aromatic radical with three to sixteen carbon atoms (e.g., —$C_{3-16}$aromatic or —$C_{3-16}$aryl) which has at least one ring having a conjugated pi electron system which is carbocyclic (e.g., phenyl, fluorenyl, and naphthyl). Whenever it appears herein, a numerical range such as "$C_{3-10}$" refers to each integer in the given range; e.g., "—$C_{3-10}$aryl" means that the aryl group may consist of 3 ring atoms, 4 ring atoms, etc., up to and including 10 ring atoms. The term includes monocyclic or fused-ring polycyclic (i.e., rings which share adjacent pairs of ring atoms) groups. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxynaphthyl, 4-(trifluoromethyl)naphthyl, 2-iodo-4-methylnaphthyl, and the like. An aryl moiety is unsubstituted or substituted.

The term "heteroaryl" or, alternatively, "heteroaromatic", "hetaryl", 'heteroar" or "hetar" refers to an aromatic radical with one to sixteen carbon atoms (e.g., —$C_{1-16}$heteroaryl) that further includes one or more ring heteroatoms selected from nitrogen, oxygen and sulfur, and which may be a monocyclic, bicyclic, tricyclic or tetracyclic ring system. Whenever it appears herein, a numerical range such as "$C_{1-10}$" refers to each integer in the given range; e.g., "—$C_{1-10}$hetaryl" means that the heteroaryl group may consist of 1 carbon atoms, 2 carbon atoms, etc., up to and including 10 carbon atoms. An "N-containing heteroaromatic" or "N-containing heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[f]pyridinyl, isothiazolyl, imidazolyl, indazolyl, indolyl, indazolyl, isoindolyl, indolinyl, isoindolinyl, isoquinolyl, indolizinyl, isoxazolyl, 5, 8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). A heteroaryl moiety is unsubstituted or substituted.

The term "cycloalkyl" refers to a saturated or partially unsaturated ring structure with three to ten carbon atoms (i.e. —$C_{3-10}$cycloalkyl). Whenever it appears herein, a numerical range such as "$C_{3-10}$" refers to each integer in the given range; e.g., "—$C_{3-10}$cycloalkyl" means that the cycloalkyl group may consist of 3 carbon atoms, 4 carbon atoms, etc., up to and including 10 carbon atoms. The term includes monocyclic or fused-ring polycyclic (i.e., rings which share adjacent pairs of ring atoms) groups. A cycloalkyl moiety is unsubstituted or substituted.

The term "heterocyclyl", "hetcyclyl", or "heterocycloalkyl" refers to a 3-, 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Whenever it appears herein, a numerical range such as "$C_{1-10}$" refers to each integer in the given range; e.g., "—$C_{1-10}$heterocyclyl" means that the heterocycloalkyl group may consist of 1 carbon atoms, 2 carbon atoms, etc., up to and including 10 carbon atoms. Examples of heterocyclyl include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and chromanyl. A hetereocycloalkyl moiety is unsubstituted or substituted.

The term "—$C_{1-10}$alkyl-$C_{3-10}$aryl" refers to an aryl group, which contains 3 to 10 carbons, attached to a linking alkyl group, branched or straight chain and containing 1 to 10 carbon atoms, such as for example, 1-phenylethyl, and the like. Either portion of the moiety is unsubstituted or substituted.

The term "—$C_{1-10}$alkyl-$C_{1-10}$hetaryl" refers to a hetaryl group, which contains 1 to 10 carbons and at least one heteroatom, attached to a linking alkyl group, branched or straight chain and containing 1 to 10 carbon atoms, such as for example, 2-pyrimidinylethyl, and the like. Either portion of the moiety is unsubstituted or substituted.

The term "—$C_{1-10}$alkyl-$C_{3-10}$cycloalkyl" refers to a cycloalkyl group, which contains 3 to 10 carbons, attached to a linking alkyl group, branched or straight chain and containing 1 to 10 carbon atoms such as for example, 2-cyclopropylethyl, and the like. Either portion of the moiety is unsubstituted or substituted.

The term "—$C_{1-10}$alkyl-$C_{1-10}$heterocyclyl" refers to a heterocyclyl group, which contains 1 to 10 carbons, attached to a linking alkyl group, branched or straight chain and containing 1 to 10 carbon atoms such as for example, 4-piperidinyleth-1-yl, and the like. Either portion of the moiety is unsubstituted or substituted.

The term "—$C_{2-10}$alkenyl-$C_{3-10}$aryl" refers to an aryl group, which contains 3 to 10 carbons, attached to a linking alkenyl group, branched or straight chain and containing 2 to 10 carbon atoms, such as for example, 1-phenylvinyl, and the like. Either portion of the moiety is unsubstituted or substituted.

The term "—$C_{2-10}$alkenyl-$C_{1-10}$hetaryl" refers to a hetaryl group, which contains 1 to 10 carbons and at least one heteroatom, attached to a linking alkenyl group, branched or straight chain and containing 2 to 10 carbon atoms, such as for example, 2-pyrimidinylvinyl, and the like. Either portion of the moiety is unsubstituted or substituted.

The term "—$C_{2-10}$alkenyl-$C_{3-10}$cycloalkyl" refers to a cycloalkyl group, which contains 3 to 10 carbons, attached to a linking alkenyl group, branched or straight chain and containing 2 to 10 carbon atoms such as for example, 2-cyclopropylvinyl, and the like. Either portion of the moiety is unsubstituted or substituted.

The term "—$C_{2-10}$alkenyl-$C_{1-10}$heterocyclyl" refers to a heterocyclyl group, which contains 1 to 10 carbons, attached to a linking alkenyl group, branched or straight chain and containing 2 to 10 carbon atoms such as for example, 4-piperidinylethen-1-yl, and the like. Either portion of the moiety is unsubstituted or substituted.

The term "—$C_{2-10}$alkynyl-$C_{3-10}$aryl" refers to an aryl group, which contains 3 to 10 carbons, attached to a linking alkynyl group, branched or straight chain and containing 2 to 10 carbon atoms, such as for example, 1-phenylethynyl, and the like. Either portion of the moiety is unsubstituted or substituted.

The term "—$C_{2-10}$alkynyl-$C_{1-10}$hetaryl" refers to a hetaryl group, which contains 1 to 10 carbons and at least one heteroatom, attached to a linking alkynyl group, branched or straight chain and containing 2 to 10 carbon atoms, such as for example, 2-pyrimidinylethynyl, and the like. Either portion of the moiety is unsubstituted or substituted.

The term "—$C_{2-10}$alkynyl-$C_{3-10}$cycloalkyl" refers to a cycloalkyl group, which contains 3 to 10 carbons, attached to a linking alkynyl group, branched or straight chain and containing 2 to 10 carbon atoms such as for example, 2-cyclopropylethynyl, and the like. Either portion of the moiety is unsubstituted or substituted.

The term "—$C_{2-10}$alkynyl-$C_{1-10}$heterocyclyl" refers to a heterocyclyl group, which contains 1 to 10 carbons, attached to a linking alkynyl group, branched or straight chain and containing 2 to 10 carbon atoms such as for example, 4-piperidethyn-1-yl, and the like. Either portion of the moiety is unsubstituted or substituted.

The term "—$C_{1-10}$heteroalkyl-$C_{3-10}$aryl" refers to an aryl group, which contains 3 to 10 carbons, attached to a linking heteroalkyl group, branched or straight chain and containing 1 to 10 carbon atoms and at least one heteroatom, such as for example, 1-phenylethoxyethyl, and the like. Either portion of the moiety is unsubstituted or substituted.

The term "—$C_{1-10}$heteroalkyl-$C_{1-10}$hetaryl" refers to a hetaryl group, which contains 1 to 10 carbons and at least one heteroatom, attached to a linking heteroalkyl group, branched or straight chain and containing 1 to 10 carbon atoms and at least 1 heteroatom, such as for example, 2-pyrimidinylethoxyethyl, and the like. Either portion of the moiety is unsubstituted or substituted.

The term "—$C_{1-10}$heteroalkyl-$C_{3-10}$cycloalkyl" refers to a cycloalkyl group, which contains 3 to 10 carbons, attached to a linking heteroalkyl group, branched or straight chain and containing 1 to 10 carbon atoms and at least one heteroatom, such as for example, 2-cyclopropylethoxyethyl, and the like. Either portion of the moiety is unsubstituted or substituted.

The term "—$C_{1-10}$heteroalkyl-$C_{1-10}$heterocyclyl" refers to a heterocyclyl group, which contains 1 to 10 carbons, attached to a linking heteroalkyl group, branched or straight chain and containing 1 to 10 carbon atoms and at least one heteroatom, such as for example, 4-piperidinylethoxyeth-1-yl, and the like. Either portion of the moiety is unsubstituted or substituted.

The term "—$C_{1-10}$alkoxy-$C_{3-10}$aryl" refers to an aryl group, which contains 3 to 10 carbons, attached to a linking oxygen atom that is further connected to an alkyl group, branched or straight chain and containing 1 to 10 carbon atoms, such as for example, 1-phenoxyethyl, and the like. Either portion of the moiety is unsubstituted or substituted.

The term "—$C_{1-10}$alkoxy-$C_{1-10}$hetaryl" refers to a hetaryl group, which contains 1 to 10 carbons and at least one heteroatom, attached to a linking oxygen atom that is further connected to an alkyl group, branched or straight chain and containing 1 to 10 carbon atoms, such as for example, 2-pyrimidoxyethyl, and the like. Either portion of the moiety is unsubstituted or substituted.

The term "—$C_{1-10}$alkoxy-$C_{3-10}$cycloalkyl" refers to a cycloalkyl group, which contains 3 to 10 carbons, attached to a linking oxygen atom that is further connected to an alkyl group, branched or straight chain and containing 1 to 10 carbon atoms such as for example, 2-cyclopropoxyethyl, and the like. Either portion of the moiety is unsubstituted or substituted.

The term "—$C_{1-10}$alkoxy-$C_{1-10}$heterocyclyl" refers to a heterocyclyl group, which contains 1 to 10 carbons, attached to a linking oxygen atom that is further connected to an alkyl group, branched or straight chain and containing 1 to 10 carbon atoms such as for example, 4-piperidoxyeth-1-yl, and the like. Either portion of the moiety is unsubstituted or substituted.

The term "—$C_{3-10}$aryl-$C_{1-10}$alkyl" refers to an alkyl group, branched or straight chain and containing 1 to 10 carbon atoms, attached to a linking aryl group, which contains 3 to 10 carbons, such as for example, 4-ethylphenyl, and the like. Either portion of the moiety is unsubstituted or substituted.

The term "—$C_{3-10}$aryl-$C_{2-10}$alkenyl" refers to an alkenyl group, branched or straight chain and containing 2 to 10 carbon atoms, attached to a linking aryl group, which contains 3 to 10 carbons, such as for example, 4-ethenylphenyl, and the like. Either portion of the moiety is unsubstituted or substituted.

The term "—$C_{3-10}$aryl-$C_{2-10}$alkynyl" refers to an alkynyl group, branched or straight chain and containing 2 to 10 carbon atoms, attached to a linking aryl group, which contains 3 to 10 carbons, such as for example, 4-ethynylphenyl, and the like. Either portion of the moiety is unsubstituted or substituted.

The term "—$C_{3-10}$aryl-$C_{1-10}$hetaryl" refers to a hetaryl group, which contains 1 to 10 carbons and at least one heteroatom, attached to a linking aryl group, which contains 3 to 10 carbons, such as for example, 4-pyrimidinylphen-4-yl, and the like. Either portion of the moiety is unsubstituted or substituted.

The term "—$C_{3-10}$aryl-$C_{3-10}$cycloalkyl" refers to a cycloalkyl group, which contains 3 to 10 carbons, attached to a linking aryl group, which contains 3 to 10 carbons, such as for example, 4-cyclopropylphenyl, and the like. Either portion of the moiety is unsubstituted or substituted.

The term "—$C_{3-10}$aryl-$C_{1-10}$heterocyclyl" refers to a heterocyclyl group, which contains 1 to 10 carbons and at least one heteroatom, attached to a linking aryl group, which contains 3 to 10 carbons, such as for example, 4-piperidinylphen-4-yl, and the like. Either portion of the moiety is unsubstituted or substituted.

The term "—C$_{1-10}$hetaryl-C$_{1-10}$alkyl" refers to an alkyl group, branched or straight chain and containing 1 to 10 carbon atoms, attached to a linking hetaryl group, which contains 1 to 10 carbons and at least one heteroatom, such as for example, 4-ethylpyrimidin-2-yl, and the like. Either portion of the moiety is unsubstituted or substituted.

The term "—C$_{1-10}$hetaryl-C$_{2-10}$alkenyl" refers to an alkenyl group, branched or straight chain and containing 2 to 10 carbon atoms, attached to a linking hetaryl group, which contains 1 to 10 and at least one heteroatom carbons, such as for example, 4-ethenylpyrimidin-2-yl, and the like. Either portion of the moiety is unsubstituted or substituted.

The term "—C$_{1-10}$hetaryl-C$_{2-10}$alkynyl" refers to an alkynyl group, branched or straight chain and containing 2 to 10 carbon atoms, attached to a linking hetaryl group, which contains 1 to 10 and at least one heteroatom carbons, such as for example, 4-ethynylpyrimidin-2-yl, and the like. Either portion of the moiety is unsubstituted or substituted.

The term "—C$_{1-10}$hetaryl-C$_{3-10}$aryl" refers to an aryl group, which contains 1 to 10 carbons, attached to a linking hetaryl group, which contains 1 to 10 carbons and at least one heteroatom, such as for example, 4-phenylpyrimidin-2-yl, and the like. Either portion of the moiety is unsubstituted or substituted.

The term "—C$_{1-10}$hetaryl-C$_{3-10}$cycloalkyl" refers to a cycloalkyl group, which contains 3 to 10 carbons, attached to a linking hetaryl group, which contains 1 to 10 carbons and at least one heteroatom, such as for example, 4-cyclopropylpyrimidin-2-yl, and the like. Either portion of the moiety is unsubstituted or substituted.

The term "—C$_{1-10}$hetaryl-C$_{1-10}$heterocyclyl" refers to a heterocyclyl group, which contains 1 to 10 carbons and at least one heteroatom, attached to a linking hetaryl group, which contains 1 to 10 carbons and at least one heteroatom, such as for example, 4-piperidinylpyrimidin-2-yl, and the like. Either portion of the moiety is unsubstituted or substituted.

The term "—C$_{3-10}$cycloalkyl-C$_{1-10}$alkyl" refers to an alkyl group, branched or straight chain and containing 1 to 10 carbon atoms, attached to a linking cycloalkyl group, which contains 3 to 10 carbons, such as for example, 2-ethylcyclopentyl, and the like. Either portion of the moiety is unsubstituted or substituted.

The term "—C$_{3-10}$cycloalkyl-C$_{2-10}$alkenyl" refers to an alkenyl group, branched or straight chain and containing 2 to 10 carbon atoms, attached to a linking cycloalkyl group, which contains 3 to 10 carbons, such as for example, 2-ethenylcyclopentyl, and the like. Either portion of the moiety is unsubstituted or substituted.

The term "—C$_{3-10}$cycloalkyl-C$_{2-10}$alkynyl" refers to an alkynyl group, branched or straight chain and containing 2 to 10 carbon atoms, attached to a linking cycloalkyl group, which contains 3 to 10 carbons, such as for example, 2-ethynylcyclopentyl, and the like. Either portion of the moiety is unsubstituted or substituted.

The term "—C$_{3-10}$cycloalkyl-C$_{3-10}$aryl" refers to an aryl group, which contains 3 to 10 carbons, attached to a linking cycloalkyl group, which contains 3 to 10 carbons, such as for example, 2-phenylcyclopentyl, and the like. Either portion of the moiety is unsubstituted or substituted.

The term "—C$_{3-10}$cycloalkyl-C$_{1-10}$hetaryl" refers to a hetaryl group, which contains 1 to 10 carbons and at least one heteroatom, attached to a linking cycloalkyl group, which contains 3 to 10 carbons, such as for example, 4-pyrimidinylcyclopent-2-yl, and the like. Either portion of the moiety is unsubstituted or substituted.

The term "—C$_{3-10}$cycloalkyl-C$_{1-10}$heterocyclyl" refers to a heterocyclyl group, which contains 1 to 10 carbons and at least one heteroatom, attached to a linking cycloalkyl group, which contains 3 to 10 carbons, such as for example, 4-piperidinylcyclopent-2-yl, and the like. Either portion of the moiety is unsubstituted or substituted.

The term "—C$_{1-10}$heterocyclyl-C$_{1-10}$alkyl" refers to an alkyl group, branched or straight chain and containing 1 to 10 carbon atoms, attached to a linking heterocyclyl group, which contains 1 to 10 carbons and at least one heteroatom, such as for example, 4-ethylpiperidin-2-yl, and the like. Either portion of the moiety is unsubstituted or substituted.

The term "—C$_{1-10}$heterocyclyl-C$_{2-10}$alkenyl" refers to an alkenyl group, branched or straight chain and containing 2 to 10 carbon atoms, attached to a linking heterocyclyl group, which contains 1 to 10 and at least one heteroatom carbons, such as for example, 4-ethenylpiperidin-2-yl, and the like. Either portion of the moiety is unsubstituted or substituted.

The term "—C$_{1-10}$heterocyclyl-C$_{2-10}$alkynyl" refers to an alkynyl group, branched or straight chain and containing 2 to 10 carbon atoms, attached to a linking heterocyclyl group, which contains 1 to 10 and at least one heteroatom carbons, such as for example, 4-ethynylpiperidin-2-yl, and the like. Either portion of the moiety is unsubstituted or substituted.

The term "—C$_{1-10}$heterocyclyl-C$_{3-10}$aryl" refers to an aryl group, which contains 1 to 10 carbons, attached to a linking heterocyclyl group, which contains 1 to 10 carbons and at least one heteroatom, such as for example, 4-phenylpiperidin-2-yl, and the like. Either portion of the moiety is unsubstituted or substituted.

The term "—C$_{1-10}$heterocyclyl-C$_{1-10}$hetaryl" refers to a hetaryl group, which contains 1 to 10 carbons and at least one heteroatom, attached to a linking heterocyclyl group, which contains 1 to 10 carbons and at least one heteroatom, such as for example, 4-pyrimidinylpiperidin-2-yl, and the like. Either portion of the moiety is unsubstituted or substituted.

The term "—C$_{1-10}$heterocyclyl-C$_{3-10}$cycloalkyl" refers to a cycloalkyl group, which contains 3 to 10 carbons, attached to a linking heterocyclyl group, which contains 1 to 10 carbons and at least one heteroatom, such as for example, 4-cyclopropylpiperidin-2-yl, and the like. Either portion of the moiety is unsubstituted or substituted.

The term "halo" or "halogen" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like. A haloalkyl moiety can be further substituted or not further substituted.

The term "amine" or "amino" refers to a —NR'R" moiety, where each R is independently hydrogen, —C$_1$-C$_{10}$alkyl, —C$_{1-10}$heteroalkyl, —C$_{1-10}$haloalkyl, —C$_{3-10}$aryl, —C$_{1-10}$alkyl-C$_{3-10}$aryl, —C$_{1-10}$heteroaryl, —C$_{1-10}$alkyl-C$_{1-10}$hetaryl, —C$_{3-10}$cycloalkyl, —C$_{1-10}$alkyl-C$_{3-10}$cycloalkyl, —C$_{1-10}$heterocyclyl, or —C$_{1-10}$alkyl-C$_{1-10}$heterocyclyl, unless stated otherwise specifically in the specification. When both R' and R" of a —NR'R" moiety are not hydrogen, R' and R" can be combined with the nitrogen atom to form a 4-, 5-, 6-, or 7-membered ring. For example, —NR'R" is meant to include, but not be limited to, 1-pyrrolidinyl and 4-morpholinyl. Unless stated otherwise specifically in the specification, an amino group is optionally substituted by one or more substituent which independently is:
—C$_{1-10}$alkyl, —C$_{1-10}$heteroalkyl, —C$_{2-10}$alkenyl, —C$_{2-10}$alkynyl, —C$_{1-10}$heteroalkyl, —C$_{3-10}$cycloalkyl, —$C_{1-10}$heterocyclyl, —$C_{3-10}$aryl, —$C_{1-10}$alkyl-$C_{3-10}$aryl, —$C_{1-10}$hetaryl, —$C_{1-10}$alkyl-$C_{1-10}$hetaryl, halo, —OH, —CN, —$CF_3$, —$OCF_3$, —$NO_2$, —$SiMe_3$, —OR', —SR', —OC(O)—R', —N(R')$_2$, —C(O)R', —C(O)OR', —OC(O)N(R')$_2$, —C(O)N(R')$_2$, —N(R')C(O)OR', —N(R')C(O)R', —N(R')C(O)N(R')$_2$, —N(R')C(NR') N(R')$_2$, —N(R')S(O)$_t$R' (where t is 1 or 2), —S(O)$_t$OR' (where t is 1 or 2), —S(O)$_t$N(R')$_2$ (where t is 1 or 2), or $PO_3$(R')$_2$, where each R' is independently hydrogen, —$C_{1-10}$alkyl, —$C_{1-10}$heteroalkyl, haloalkyl, —$C_{1-10}$aryl, —$C_{1-10}$alkyl-$C_{3-10}$aryl, —$C_{1-10}$heteroaryl, —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl, or —$C_{1-10}$alkyl-$C_{1-10}$heterocyclyl.

The term "amide" or "amido" refers to a chemical moiety with formula —C(O)N(R')$_2$ or —NHC(O)R', where R' is selected from the group consisting of hydrogen, —$C_{1-10}$alkyl, —$C_{1-10}$heteroalkyl, haloalkyl, —$C_{3-10}$aryl, —$C_{1-10}$alkyl-$C_{3-10}$aryl, —$C_{1-10}$hetaryl (bonded through a ring carbon), —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl (bonded through a ring carbon), or —$C_{1-10}$alkyl-$C_{1-10}$heterocyclyl. In some embodiments, an amide is a $C_1$-$C_4$ radical, which includes the amide carbonyl in the total number of carbons in the radical. The R'$_2$ of —N(R')$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocyclyl. An amide may be an amino acid or a peptide molecule attached to a compound of Formula II or III, thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

The term "acyl" or "carbonyl" refers to the structure —C(=O)—R, in which R is hydrogen, —$C_{1-10}$alkyl, —$C_{1-10}$heteroalkyl, haloalkyl, —$C_{3-10}$aryl, —$C_{1-10}$alkyl-$C_{3-10}$aryl, —$C_{1-10}$hetaryl (bonded through a ring carbon), —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl (bonded through a ring carbon), or —$C_{1-10}$alkyl-$C_{1-10}$heterocyclyl. Unless stated otherwise specifically in the specification, the R group of an acyl moiety is optionally substituted by one or more substituent which independently is: —$C_{1-10}$alkyl, —$C_{1-10}$heteroalkyl, —$C_{2-10}$alkenyl, —$C_{2-10}$alkynyl, —$C_{3-10}$cycloalkyl, —$C_{1-10}$heterocyclyl, —$C_{3-10}$aryl, —$C_{1-10}$alkyl-$C_{3-10}$aryl, —$C_{1-10}$hetaryl, —$C_{1-10}$alkyl-$C_{1-10}$hetaryl, halo, —OH, —CN, —$CF_3$, —$OCF_3$, —$NO_2$, —$SiMe_3$, —OR', —SR', —OC(O)—R', —N(R')$_2$, —C(O)R', —C(O)OR', —OC(O)N(R')$_2$, —C(O)N(R')$_2$, —N(R')C(O)OR', —N(R')C(O)R, —N(R')C(O)N(R')$_2$, —N(R')C(NR') N(R')$_2$, —N(R')S(O)$_t$R' (where t is 1 or 2), —S(O)$_t$OR' (where t is 1 or 2), —S(O)$_t$N(R')$_2$ (where t is 1 or 2), or $PO_3$(R')$_2$, where each R' is independently hydrogen, —$C_{1-10}$alkyl, —$C_{1-10}$heteroalkyl, haloalkyl, —$C_{3-10}$aryl, —$C_{1-10}$alkyl-$C_{3-10}$aryl, —$C_{1-10}$heteroaryl, —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl, or —$C_{1-10}$alkyl-$C_{1-10}$heterocyclyl.

The term "carboxyl" or "carboxy" refers to the structure —C(=O)—OR, in which R is hydrogen, —$C_{1-10}$alkyl, —$C_{1-10}$heteroalkyl, haloalkyl, —$C_{3-10}$aryl, —$C_{1-10}$alkyl-$C_{3-10}$aryl, —$C_{1-10}$hetaryl (bonded through a ring carbon), —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl (bonded through a ring carbon), or —$C_{1-10}$alkyl-$C_{1-10}$heterocyclyl. Unless stated otherwise specifically in the specification, the R group of a carboxyl moiety is optionally substituted by one or more substituent which independently is: —$C_{1-10}$alkyl, —$C_{1-10}$heteroalkyl, —$C_{2-10}$alkenyl, —$C_{2-10}$alkynyl, —$C_{3-10}$cycloalkyl, —$C_{1-10}$heterocyclyl, —$C_{3-10}$aryl, —$C_{1-10}$alkyl-$C_{3-10}$aryl, —$C_{1-10}$hetaryl, —$C_{1-10}$alkyl-$C_{1-10}$hetaryl, halo, —OH, —CN, —$CF_3$, —$OCF_3$, —$NO_2$, —$SiMe_3$, —OR', —SR', —OC(O)—R', —N(R')$_2$, —C(O)R', —C(O)OR', —OC(O)N(R')$_2$, —C(O)N(R)$_2$, —N(R')C(O)OR', —N(R')C(O)R', —N(R')C(O)N(R')$_2$, —N(R')C(NR') N(R')$_2$, —N(R')S(O)$_t$R' (where t is 1 or 2), —S(O)$_t$OR' (where t is 1 or 2), —S(O)$_t$N(R')$_2$ (where t is 1 or 2), or $PO_3$(R')$_2$, where each R' is independently hydrogen, —$C_{1-10}$alkyl, —$C_{1-10}$heteroalkyl, haloalkyl, —$C_{3-10}$aryl, —$C_{1-10}$alkyl-$C_{3-10}$aryl, —$C_{1-10}$heteroaryl, —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl, or —$C_{1-10}$alkyl-$C_{1-10}$heterocyclyl.

The term "oxo" refers to an oxygen atom that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

As used herein, 0-2 in the context of —$S(O)_{(0-2)}$— are integers of 0, 1, and 2.

The term "sulfonamidyl" or "sulfonamido" refers to the structure —S(=O)$_2$—NR'R', where each R' is selected independently from the group consisting of hydrogen, —$C_{1-10}$alkyl, —$C_{3-10}$cycloalkyl, —$C_{3-10}$aryl, —$C_{1-10}$heteroaryl (bonded through a ring carbon) and —$C_{1-10}$-$C_{1-10}$heterocyclyl (bonded through a ring carbon). The R' groups in —NR'R' of the —S(=O)$_2$—NR'R' radical may be taken together with the nitrogen to which it is attached to form a 4-, 5-, 6-, or 7-membered ring. Unless stated otherwise specifically in the specification, the R' group of a sulfonamido moiety is optionally substituted by one or more substituent which independently is: —$C_{1-10}$alkyl, —$C_{1-10}$heteroalkyl, —$C_{2-10}$alkenyl, —$C_{2-10}$alkynyl, —$C_{3-10}$cycloalkyl, —$C_{1-10}$heterocyclyl, —$C_{3-10}$aryl, —$C_{1-10}$alkyl-$C_{3-10}$aryl, —$C_{1-10}$hetaryl, —$C_{1-10}$alkyl-$C_{1-10}$hetaryl, halo, —OH, —CN, —$CF_3$, —$OCF_3$, —$NO_2$, —$SiMe_3$, —OR', —SR', —OC(O)—R', —N(R')$_2$, —C(O)R', —C(O)OR', —C(O)OR', OC(O)N(R')$_2$, —C(O)N(R')$_2$, —N(R')C(O)OR', —N(R')C(O)R', —N(R')C(O)N(R)$_2$, —N(R')C(NR')N(R')$_2$, —N(R')S(O)$_t$R (where t is 1 or 2), —S(O)$_t$OR (where t is 1 or 2), —S(O)$_t$N(R')$_2$ (where t is 1 or 2), or $PO_3$(R')$_2$, where each R is independently hydrogen, —$C_{1-10}$alkyl, —$C_{1-10}$heteroalkyl, haloalkyl, —$C_{3-10}$aryl, —$C_{1-10}$alkyl-$C_{3-10}$aryl, —$C_{1-10}$heteroaryl, —$C_{1-10}$alkyl-$C_{1-10}$hetaryl, —$C_{3-10}$cycloalkyl, —$C_{1-10}$alkyl-$C_{3-10}$cycloalkyl, —$C_{1-10}$heterocyclyl, or —$C_{1-10}$alkyl-$C_{1-10}$heterocyclyl.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The present invention includes all manner of rotamers and conformationally restricted states of a compound of the invention.

A. Generic Formulas and Detailed Description

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

A compound or a pharmaceutically acceptable or prodrug salt thereof is provided, wherein the compound has Formula I:

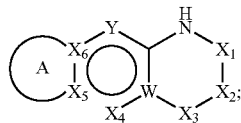

wherein:

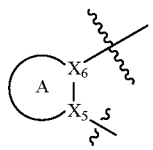

is

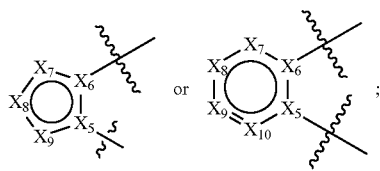

$X_1$ is C=O, C=S, SO, SO$_2$, or PO$_2^-$; Y is CR$_5$; W is N or C;

$X_2$ is NR$_1$ or CR$_1$R$_1$' and $X_3$ is null, CR$_3$R$_3$' or C=O; or $X_2$-$X_3$ is R$_1$C=CR$_3$ or R$_1$C=N or N=CR$_3$ or NR$_{12}$—CR$_{11}$=CR$_3$;

$X_4$ is N or CR$_4$; $X_5$ is N or C; $X_6$ is N or C; $X_7$ is O, N, NR$_{72}$ or CR$_{71}$; $X_8$ is O, N, NR$_{82}$ or CR$_{81}$; $X_9$ is O, N, NR$_{22}$ or CR$_{21}$; $X_{10}$ is O, N, NR$_{92}$ or CR$_{91}$;

R$_1$ is —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$aryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_1$' is hydrogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_{21}$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$, —C(=O)R$^{32}$, —NR$^{31}$C(O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, -L-C$_{1-10}$heterocyclyl, -L-C$_{1-10}$alkyl-C$_{3-10}$aryl, -L-C$_{1-10}$alkyl-C$_{1-10}$hetaryl, -L-C$_{1-10}$alkyl-C$_{3-10}$cycloalkyl, -L-C$_{1-10}$alkyl-C$_{1-10}$heterocyclyl, -L-C$_{2-10}$alkenyl-C$_{3-10}$aryl, -L-C$_{2-10}$alkenyl-C$_{1-10}$hetaryl, -L-C$_{2-10}$alkenyl-C$_{3-10}$cycloalkyl, -L-C$_{2-10}$alkenyl-C$_{1-10}$heterocyclyl, -L-C$_{2-10}$alkynyl-C$_{3-10}$aryl, -L-C$_{2-10}$alkynyl-C$_{1-10}$hetaryl, -L-C$_{2-10}$alkynyl-C$_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents;

$R_{22}$ is hydrogen, —OH, —$CF_3$, —C(O)$R^{31}$, —$CO_2R^{31}$, —C(=O)$NR^{31}$, —S(O)$_{0-2}R^{31}$, —C(=S)$OR^{31}$, —C(=O)$SR^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl $C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, —S(O)$_{0-2}$N($R^{31}$)—, —C(=S)O—, —C(=O)S—, —$NR^{31}$C(=$NR^{32}$)$NR^{32}$—, —$NR^{31}$C(=$NR^{32}$)O—, —$NR^{31}$C(=$NR^{32}$)S—, —OC(=O)O—, —OC(=O)$NR^{31}$—, —OC(=O)S—, —SC(=O)S—, —P(O)$OR^{31}$O—, —SC(=O)$NR^{31}$—;

each of $R_3$, $R_3'$ and $R_4$ is independently hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{32}R^{33}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$SR^{31}$, —P(O)$OR^{31}OR^{32}$, —SC(=O)$NR^{31}R^{32}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{1-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{13}$ substituents; or $R_3'$ is —$OR^6$, —$NR^6R^{34}$, —S(O)$_{0-2}R^6$, —C(=O)$R^6$, —C(=O)$OR^6$, —OC(=O)$R^6$, —C(=O)N($R^{34}$)$R^6$, or —N($R^{34}$)C(=O)$R^6$, wherein $R^6$ together with $R^{34}$ can optionally form a heterocyclic ring; or $R_3'$ is —$OR^6$, —$NR^6R^{34}$, —S(O)$_{0-2}R^6$, —C(=O)$R^6$, —C(=O)$OR^6$, —OC(=O)$R^6$, —C(=O)N($R^{34}$)$R^6$, or —N($R^{34}$)C(=O)$R^6$, wherein $R^6$ together with $R^{34}$ can optionally form a heterocyclic ring;

each of $R_5$, $R_{71}$, $R_{81}$ and $R_{91}$ is independently hydrogen, halogen, —$C_{1-10}$alkyl, —$C_{2-10}$alkenyl, —$C_{2-10}$ alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{32}R^{33}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$SR^{31}$, —P(O)$OR^{31}OR^{32}$, or —SC(=O)$NR^{31}NR^{32}$;

$R_6$ is hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

each of $R_{72}$, $R_{82}$ and $R_{92}$ is independently hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, —$S(O)_{0-2}R^{31}$, —$C(=S)OR^{31}$, —$C(=O)SR^{31}$;

each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, or —$SC(=O)NR^{31}NR^{32}$;

each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring;

wherein ring A comprises one or more heteroatoms selected from N, O, or S; and wherein if $X_7$ is O or $X_2$-$X_3$ is $R_1C=CR_3$, ring A comprises at least two heteroatoms selected from N, O, or S; and wherein if $X_2$-$X_3$ is $R_1C=N$, at least one of $X_7$ or $X_9$ is not N.

In some embodiments of Formula I, $X_1$ is C=O, $X_2$ is $NR_1$ or $CR_1R_1'$, and $X_3$ is $CR_3R_3'$. In some embodiments, $X_1$ is C=O, $X_2$ is $NR_1$, and $X_3$ is C=O. In some embodiments, $X_1$ is C=S, $X_2$ is $CR_1R_1'$, and $X_3$ is $CR_3R_3'$. In some embodiments, $X_1$ is $SO_2$, $X_2$ is $NR_1$, and $X_3$ is $CR_3R_3'$. In some embodiments, $X_1$ is $SO_2$, and $X_2$ and $X_3$ is $R_{11}C=CR_3$.

In some embodiments of Formula I, W is C, Y is $CR_5$, $X_4$ is N or $CR_4$, $X_5$ is C and $X_6$ is C. In some embodiments, W is C, Y is $CR_5$, $X_4$ is $CR_4$, $X_5$ is N or C and $X_6$ is C. In some embodiments, W is C, Y is $CR_5$, $X_4$ is $CR_4$, $X_5$ is C and $X_6$ is C. In some embodiments, W is C, Y is $CR_5$, $X_4$ is $CR_4$, $X_5$ is N and $X_6$ is C. In some embodiments, W is C, Y is $CR_5$, $X_4$ is $CR_4$, $X_5$ is C and $X_6$ is N. In some embodiments, W is N, Y is $CR_5$, $X_4$ is C=O, $X_5$ is C and $X_6$ is C. In some embodiments, W is N, Y is $CR_5$, $X_4$ is C=O, $X_5$ is C and $X_6$ is N.

In some embodiments of Formula I, $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_{71}$, $X_8$ is N and $X_9$ is $NR_{22}$. In some embodiments, $X_7$ is $CR_{71}$, $X_8$ is N and $X_9$ is $CR_{21}$. In some embodiments, $X_7$ is O, $X_8$ is N and $X_9$ is $CR_{21}$. In some embodiments, $X_7$ is O, $X_8$ is $CR_8$ and $X_9$ is $NR_{22}$.

In some embodiments of Formula I, $X_1$ is C=O, $X_2$ is $NR_1$ or $CR_1R_1'$, $X_3$ is $CR_3R_3'$ or C=O, W is N or C, Y is N or $CR_5$, $X_4$ is N, C=O or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_1$ is C=O, $X_2$ is $NR_1$ or $CR_1R_1'$, $X_3$ is $CR_3R_3'$, W is C, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_1$ is C=O, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula I, $R_1$ is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{1-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula I, $R_1'$ is hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$cycloalkyl, —$C_{1-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula I, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, —$SC(=O)NR^{31}R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula I, $R_{22}$ is hydrogen, —OH, —$CF_3$, —$C(O)R^{31}$, —$CO_2R^{31}$, —$C(=O)NR^{31}$, —$S(O)_{0-2}R^{31}$, —$C(=O)SR^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl- $C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents. In some embodiments, $R_{22}$ is —OH, —$CF_3$, —C(O)$R^{31}$, —$CO_2R^{31}$, —C(=O)$NR^{31}$, —S(O)$_{0-2}$$R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —C(O)$R^{31}$, —$CO_2R^{31}$, —C(=O)$NR^{31}$, —S(O)$_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is —OH, —$CF_3$, —C(O)$R^{31}$, —$CO_2R^{31}$, —C(=O)$NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula I, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, —S(O)$_{0-2}$N($R^{31}$)—, —C(=S)O—, —C(=O)S—, —$NR^{31}$C(=$NR^{32}$)$NR^{32}$—, —$NR^{31}$C(=$NR^{32}$)O—, —$NR^{31}$C(=$NR^{32}$)S—, —OC(=O)O—, —OC(=O)$NR^{31}$—, —OC(=O)S—, —SC(=O)S—, —P(O)O$R^{31}$O—, —SC(=O)$NR^{31}$—. In some embodiments, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula I, $R_3$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{32}R^{33}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$SR^{31}$, —P(O)$OR^{31}OR^{32}$, —SC(=O)$NR^{31}R^{32}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —$NO_2$, —CN, —S(O)$_{0-2}R^{31}$, —$C_{1-10}$alkyl, —$C_{2-10}$alkenyl, or —$C_{2-10}$alkynyl. In some embodiments, $R_3$ is hydrogen, halogen, —OH, —$CF_3$, or —$C_{1-10}$alkyl.

In some embodiments of Formula I, $R_3$' is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$SO_2NR^{31}R^{32}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{32}R^{33}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$SR^{31}$, —P(O)$OR^{31}OR^{32}$, —SC(=O)$NR^{31}R^{32}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_3'$ is hydrogen, halogen, —OH, —$CF_3$, or —$C_{1-10}$alkyl.

In some embodiments of Formula I, $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring. In some embodiments, $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring. In some embodiments, $R_3'$ is —$OR^6$ or —$NR^6R^{34}$, wherein $R^6$ together with $R^{34}$ can optionally form a heterocyclic ring.

In some embodiments of Formula I, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, —$SC(=O)NR^{31}R^{32}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula I, $R_5$ is hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, or —$SC(=O)NR^{31}NR^{32}$. In some embodiments, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula I, $R_6$ is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents. In some embodiments, $R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents.

In some embodiments of Formula I, each of $R_{71}$, $R_{81}$ and $R_{91}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, or —$SC(=O)NR^{31}NR^{32}$. In some embodiments, each of $R_{71}$, $R_{81}$ and $R_{91}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, or —$C_{1-10}$alkyl. In some embodiments, each of $R_{71}$, $R_{81}$ and $R_{91}$ is independently hydrogen.

In some embodiments of Formula I, each of $R_{72}$, $R_{82}$ and $R_{92}$ is independently hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, —$S(O)_{0-2}R^{31}$, —$C(=S)OR^{31}$, —$C(=O)SR^{31}$. In some embodiments, each of $R_{72}$, $R_{82}$ and $R_{92}$ is independently hydrogen, —$C_{1-10}$alkyl, —$C_{3-10}$alkyl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen or —$C_{1-10}$alkyl. In some embodiments, each of $R_{72}$, $R_{82}$ and $R_{92}$ is independently hydrogen.

In some embodiments of Formula I, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$alkyl, —$C_{1-10}$hetaryl, or —$C_{1-10}$heterocyclyl, optionally substituted by one or more independent $R_{11}$ substituents.

In some embodiments of Formula I, each of $R_{11}$, $R_{12}$, $R_{13}$ and $R_{15}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^3)SR^{33}$, —$OC(=O)OR^{33}$, —$OC(=O)NR^{31}R^{32}$, —$OC(=O) SR^{31}$, —$SC(=O)SR^{31}$, —$P(O)OR^{31}OR^{32}$, or —$SC(=O)NR^{31}NR^{32}$. In some embodiments, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula I, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl.

In some embodiments of Formula I, $X_1$ is C=O, $X_2$ is $NR_1$ or $CR_1R_1'$, $X_3$ is $CR_3R_3'$ or C=O, W is C, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{22}$ or $CR_{21}$, and $X_{10}$ is N or $CR_{91}$; $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, —$N(R^{31})$C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring;

each of $R_5$, $R_{71}$, and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$, $R^{32}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring; and wherein ring A comprises one or more heteroatoms selected from N, O, or S.

In some embodiments of Formula I, $X_1$ is C=O, $X_2$ is $NR_1$ or $CR_1R_1'$, $X_3$ is $CR_3R_3'$, W is C, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{21}$ or $CR_{21}$, and $X_{10}$ is N or $CR_{91}$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_1'$ is hydrogen —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})$C(=O)—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents; or $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring;

each of $R_5$ and $R_{71}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{3-10}$cycloalkyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein ring A comprises one or more heteroatoms selected from N, O, or S.

In some embodiments of Formula I, $X_1$ is C=O, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, —$C(=O)N(R^{31})$—, or —$N(R^{31})C(=O)$—;

each of $R_3$, $R_3'$ and $R_4$ is independently hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl; or $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring;

$R_5$ is hydrogen, halogen, or —$C_{1-10}$alkyl;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein ring A comprises one or more heteroatoms selected from N, O, or S.

In some embodiments of Formula I, $X_1$ is C=O, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—; or $R_3'$ is —$OR^6$ or —$NR^6R^{34}$, wherein $R^6$ together with $R^{34}$ can optionally form a heterocyclic ring;

each of $R_3$, $R_3'$ and $R_4$ is independently hydrogen, halogen, —OH, —$CF_3$, or —$C_{1-10}$alkyl; or $R_3'$ is —$OR^6$ or —$NR^6R^{34}$, wherein $R^6$ together with $R^{34}$ can optionally form a heterocyclic ring;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$;

each of $R^{31}$ and $R^{34}$ is independently hydrogen or —$C_{1-10}$alkyl; and wherein ring A comprises one or more heteroatoms selected from N, O, or S.

The invention also provides a compound as defined above, wherein the compound is of Formula I-A:

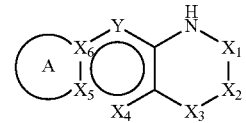

or a pharmaceutically acceptable salt or prodrug thereof, and wherein the substituents are as defined above.

In some embodiments of Formula I-A, $X_1$ is C=O, $X_2$ is $NR_1$ or $CR_1R_1'$, and $X_3$ is $CR_3R_3'$. In some embodiments, $X_1$ is C=O, $X_2$ is $NR_1$, and $X_3$ is C=O. In some embodiments, $X_1$ is C=S, $X_2$ is $CR_1R_1'$, and $X_3$ is $CR_3R_3'$. In some embodiments, $X_1$ is $SO_2$, $X_2$ is $NR_1$, and $X_3$ is $CR_3R_3'$. In some embodiments, $X_1$ is $SO_2$, and $X_2$ and $X_3$ is $R_{11}C=CR_3$.

In some embodiments of Formula I-A, $X_4$ is N or $CR_4$, $X_5$ is C and $X_6$ is C. In some embodiments, $X_4$ is $CR_4$, $X_5$ is N or C and $X_6$ is C. In some embodiments, Y is $CR_5$, $X_4$ is $CR_4$, $X_5$ is C and $X_6$ is C. In some embodiments, $X_4$ is $CR_4$, $X_5$ is N and $X_6$ is C. In some embodiments, $X_4$ is $CR_4$, $X_5$ is C and $X_6$ is N.

In some embodiments of Formula I-A, $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_{71}$, $X_8$ is N and $X_9$ is $NR_{22}$. In some embodiments, $X_7$ is $CR_{71}$, $X_8$ is N and $X_9$ is $CR_{21}$. In some embodiments, $X_7$ is O, $X_8$ is N and $X_9$ is $CR_{21}$. In some embodiments, $X_7$ is O, $X_8$ is $CR_8$ and $X_9$ is $NR_{22}$.

In some embodiments of Formula I-A, $X_1$ is C=O, $X_2$ is $NR_1$ or $CR_1R_1'$, $X_3$ is $CR_3R_3'$ or C=O, $X_4$ is N or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_1$ is C=O, $X_2$ is $NR_1$ or $CR_1R_1'$, $X_3$ is $CR_3R_3'$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_1$ is C=O, $X_2$ is $NR_1$, $X_3$ is $CR_3R_3'$, $X_4$ is $CR_4$, $X_5$ is C, $X_6$ is C, $X_7$ is $NR_{72}$, $X_8$ is N, and $X_9$ is $CR_{21}$.

In some embodiments of Formula I-A, $R_1$ is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-n}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula I-A, $R_1'$ is hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$cycloalkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$ MY', —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula I-A, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, —$SC(=O)NR^{31}R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$NR^{31}$C(=O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$NR^{31}$C(=O)$R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, -L-$C_{1-10}$alkyl, -L-$C_{3-10}$aryl, -L-$C_{1-10}$hetaryl, -L-$C_{\_\_10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula I-A, $R_{22}$ is hydrogen, —OH, —$CF_3$, —C(O)$R^{31}$, —$CO_2R^{31}$, —C(=O)$NR^{31}$, —S(O)$_{0-2}R^{31}$, —C(=S)O$R^{31}$, —C(=O)S$R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents. In some embodiments, $R_{22}$ is —OH, —$CF_3$, —C(O)$R^{31}$, —$CO_2R^{31}$, —C(=O)$NR^{31}$, —S(O)$_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —C(O)$R^{31}$, —$CO_2R^{31}$, —C(=O)$NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula I-A, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, —S(O)$_{0-2}$N($R^{31}$)—, —C(=S)O—, —C(=O)S—, —$NR^{31}$C(=$NR^{32}$)$NR^{32}$—, —$NR^{31}$C(=$NR^{32}$)O—, —$NR^{31}$C(=$NR^{32}$)S—, —OC(=O)O—, —OC(=O)$NR^{31}$—, —OC(=O)S—, —SC(=O)S—, —P(O)O$R^{31}$O—, —SC(=O)$NR^{31}$—. In some embodiments, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula I-A, $R_3$ is hydrogen, halogen, —OH, —$CF_3$, —$OCF_3$, —$OR^{31}$, —$NR^{31}$, $R^{32}$, —C(O)$R^{31}$, —$CO_2R^{31}$, —C(=O)$NR^{31}$, —$NO_2$, —CN, —S(O)$_{0-2}R^{31}$, —$SO_2NR^{31}R^{32}$, —$NR^{31}$C(=O)$R^{32}$, —$NR^{31}$C(=O)O$R^{32}$, —$NR^{31}$C(=O)$NR^{32}R^{33}$, —$NR^{31}$S(O)$_{0-2}R^{32}$, —C(=S)O$R^{31}$, —C(=O)S$R^{31}$, —$NR^{31}$C(=$NR^{32}$)$NR^{32}R^{33}$, —$NR^{31}$C(=$NR^{32}$)O$R^{33}$, —$NR^{31}$C(=$NR^{32}$)S$R^{33}$, —OC(=O)O$R^{33}$, —OC(=O)$NR^{31}R^{32}$, —OC(=O)S$R^{31}$, —SC(=O)S$R^{31}$, —P(O)O$R^{31}$O$R^{32}$, —SC(=O)$NR^{31}R^{32}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{13}$ substituents. In some embodiments, $R_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{2-10}$alkenyl, or —C$_{2-10}$alkynyl, each of which is unsubstituted or substituted by one or more independent $R_{13}$ substituents. In some embodiments, $R_3$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, $R_3$ is hydrogen, halogen, —OH, —CF$_3$, or —C$_{1-10}$alkyl.

In some embodiments of Formula I-A, $R_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{13}$ substituents. In some embodiments, $R_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, $R_3$' is hydrogen, halogen, —OH, —CF$_3$, or —C$_{1-10}$alkyl.

In some embodiments of Formula I-A, $R_3$' is —OR$^6$, —NR$^6$R$^{34}$, —S(O)$_{0-2}$R$^6$, —C(=O)R$^6$, —C(=O)OR$^6$, —OC(=O)R$^6$, —C(=O)N(R$^{34}$)R$^6$, or —N(R$^{34}$)C(=O)R$^6$, wherein R$^6$ together with R$^{34}$ can optionally form a heterocyclic ring. In some embodiments, $R_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring. In some embodiments, $R_3$' is —OR$^6$ or —NR$^6$R$^{34}$, wherein R$^6$ together with R$^{34}$ can optionally form a heterocyclic ring.

In some embodiments of Formula I-A, $R_4$ is hydrogen, halogen, —OH, —CF$_3$, —OCF$_3$, —OR$^{31}$, —NR$^{31}$, R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{13}$ substituents. In some embodiments, $R_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_4$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, R$_4$ is hydrogen, halogen, —OH, —CF$_3$, or —C$_{1-10}$alkyl.

In some embodiments of Formula I-A, R$_5$ is hydrogen, halogen, —C$_{1-10}$alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$. In some embodiments, R$_5$ is hydrogen, halogen, —C$_{1-10}$alkyl, —C$_{3-10}$aryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, or —C$_{1-10}$alkyl. In some embodiments, R$_5$ is hydrogen.

In some embodiments of Formula I-A, R$_6$ is —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents. In some embodiments, R$_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents. In some embodiments, R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents.

In some embodiments of Formula I-A, each of R$_{71}$, R$_{81}$ and R$_{91}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^3$)OR$^{33}$, —NR$^{31}$C(=NR$^3$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$. In some embodiments, each of R$_{71}$, R$_{81}$ and R$_{91}$ is independently hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of R$_{71}$, R$_{81}$ and R$_{91}$ is independently hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of R$_{71}$, R$_{81}$ and R$_{91}$ is independently hydrogen, halogen, or —C$_{1-10}$alkyl. In some embodiments, each of R$_{71}$, R$_{81}$ and R$_{91}$ is independently hydrogen.

In some embodiments of Formula I-A, each of R$_{72}$, R$_{82}$ and R$_{92}$ is independently hydrogen, —C$_{1-10}$ alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, —S(O)$_{0-2}$R$^{31}$, —C(=S)OR$^{31}$, —C(=O)SR$^{31}$. In some embodiments, each of R$_{72}$, R$_{82}$ and R$_{92}$ is independently hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$. In some embodiments, each of R$_{72}$, R$_{82}$ and R$_{92}$ is independently hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$. In some embodiments, each of R$_{72}$, R$_{82}$ and R$_{92}$ is independently hydrogen or —C$_{1-10}$alkyl. In some embodiments, each of R$_{72}$, R$_{82}$ and R$_{92}$ is independently hydrogen.

In some embodiments of Formula I-A, each of R$_{10}$ and R$_{14}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent R$_{11}$ substituents. In some embodiments, each of R$_{10}$ and R$_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents. In some embodiments, each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents.

In some embodiments of Formula I-A, each of R$_{11}$, R$_{12}$, R$_{13}$ and R$_{15}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, or —$SC(=O)NR^{31}NR^{32}$. In some embodiments, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently halogen, —$C_{1-10}$ alkyl, —OH or —$CF_3$.

In some embodiments of Formula I-A, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl.

In some embodiments of Formula I-A, $X_1$ is C=O, $X_2$ is $NR_1$ or $CR_1R_1'$, $X_3$ is $CR_3R_3'$ or C=O, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{22}$ or $CR_{21}$, and $X_{10}$ is N or $CR_{91}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring;

each of $R_5$, $R_{71}$, and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$, $R^{32}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring; and wherein ring A comprises one or more heteroatoms selected from N, O, or S.

In some embodiments of Formula I-A, $X_1$ is C=O, $X_2$ is $NR_1$ or $CR_1R_1'$, $X_3$ is $CR_3R_3'$, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{21}$ or $CR_{21}$, and $X_{10}$ is N or $CR_{91}$;

$R_1$ is —$C_{1-10}$alkyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_1'$ is hydrogen —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents; or $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring;

each of $R_5$ and $R_{71}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{3-10}$cycloalkyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein ring A comprises one or more heteroatoms selected from N, O, or S.

In some embodiments of Formula I-A, $X_1$ is C=O, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, —$C(=O)N(R^{31})$—, or —$N(R^{31})C(=O)$—;

each of $R_3$, $R_3'$ and $R_4$ is independently hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl; or $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring;

$R_5$ is hydrogen, halogen, or —$C_{1-10}$alkyl;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —$C(O)R^{31}$, —$CO_2R^{31}$, —$C(=O)NR^{31}$, or —$S(O)_{0-2}R^{31}$; each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein ring A comprises one or more heteroatoms selected from N, O, or S.

In some embodiments of Formula I-A, $X_1$ is C=O, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—; or $R_3'$ is —$OR^6$ or —$NR^6R^{34}$, wherein $R^6$ together with $R^{34}$ can optionally form a heterocyclic ring;

each of $R_3$, $R_3'$ and $R_4$ is independently hydrogen, halogen, —OH, —$CF_3$, or —$C_{1-10}$alkyl; or $R_3'$ is —$OR^6$ or —$NR^6R^{34}$, wherein $R^6$ together with $R^{34}$ can optionally form a heterocyclic ring;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$;

each of $R^{31}$ and $R^{34}$ is independently hydrogen or —$C_{1-10}$alkyl; and wherein ring A comprises one or more heteroatoms selected from N, O, or S.

The invention also provides a compound as defined above, wherein the compound is of Formula I-B:

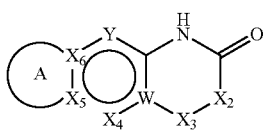

or a pharmaceutically acceptable salt or prodrug thereof, and wherein the substituents are as defined above.

In some embodiments of Formula I-B, $X_2$ is $NR_1$ or $CR_1R_1'$, and $X_3$ is $CR_3R_3'$. In some embodiments, $X_2$ is $NR_1$, and $X_3$ is C=O. In some embodiments, $X_2$ is $CR_1R_1'$, and $X_3$ is $CR_3R_3'$. In some embodiments, $X_2$ is $NR_1$, and $X_3$ is $CR_3R_3'$. In some embodiments, $X_2$ and $X_3$ are $R_{11}C=CR_3$.

In some embodiments of Formula I-B, W is C, Y is $CR_5$, $X_4$ is N or $CR_4$, $X_5$ is C and $X_6$ is C. In some embodiments, W is C, Y is $CR_5$, $X_4$ is $CR_4$, $X_5$ is N or C and $X_6$ is C. In some embodiments, W is C, Y is $CR_5$, $X_4$ is $CR_4$, $X_5$ is C and $X_6$ is C. In some embodiments, W is C, Y is $CR_5$, $X_4$ is $CR_4$, $X_5$ is N and $X_6$ is C. In some embodiments, W is C, Y is $CR_5$, $X_4$ is $CR_4$, $X_5$ is C and $X_6$ is N. In some embodiments, W is N, Y is $CR_5$, $X_4$ is C=O, $X_5$ is C and $X_6$ is C. In some embodiments, W is N, Y is $CR_5$, $X_4$ is C=O, $X_5$ is C and $X_6$ is N.

In some embodiments of Formula I-B, $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_{71}$, $X_8$ is N and $X_9$ is $NR_{22}$. In some embodiments, $X_7$ is $CR_{71}$, $X_8$ is N and $X_9$ is $CR_{21}$. In some embodiments, $X_7$ is O, $X_8$ is N and $X_9$ is $CR_{21}$. In some embodiments, $X_7$ is O, $X_8$ is $CR_8$ and $X_9$ is $NR_{22}$.

In some embodiments of Formula I-B, $X_2$ is $NR_1$ or $CR_1R_1'$, $X_3$ is $CR_3R_3'$ or C=O, W is N or C, Y is N or $CR_5$, $X_4$ is N, C=O or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_2$ is $NR_1$ or $CR_1R_1'$, $X_3$ is $CR_3R_3'$, W is C, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula I-B, $R_1$ is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{1-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$cycloalkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula I-B, $R_1'$ is hydrogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$heteroalkyl-$C_{3-10}$aryl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —$C_{3-10}$aryl-$C_{1-10}$heterocyclyl, —$C_{1-10}$hetaryl-$C_{1-10}$alkyl, —$C_{1-10}$hetaryl-$C_{2-10}$alkenyl, —$C_{1-10}$hetaryl-$C_{2-10}$alkynyl, —$C_{3-10}$hetaryl-$C_{3-10}$aryl, —$C_{1-10}$hetaryl-$C_{3-10}$cycloalkyl, —$C_{1-10}$hetaryl-$C_{1-10}$heterocyclyl, —$C_{3-10}$cycloalkyl-$C_{1-10}$alkyl, —$C_{3-10}$cycloalkyl-$C_{2-10}$alkenyl, —$C_{3-10}$cycloalkyl-$C_{2-10}$alkynyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{2-10}$alkenyl, —$C_{1-10}$heterocyclyl-$C_{2-10}$alkynyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula I-B, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, —$SC(=O)NR^{31}R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula I-B, $R_{22}$ is hydrogen, —OH, —$CF_3$, —$C(O)R^{31}$, —$CO_2R^{31}$, —$C(=O)NR^{31}$, —$S(O)_{0-2}R^{31}$, —$C(=S)OR^{31}$, —$C(=O)SR^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, -L-$C_{1-10}$heterocyclyl, -L-$C_{1-10}$alkyl-$C_{3-10}$aryl, -L-$C_{1-10}$alkyl-$C_{1-10}$hetaryl, -L-$C_{1-10}$alkyl-$C_{3-10}$cycloalkyl, -L-$C_{1-10}$alkyl-$C_{1-10}$heterocyclyl, -L-$C_{2-10}$alkenyl-$C_{3-10}$aryl, -L-$C_{2-10}$alkenyl-$C_{1-10}$hetaryl, -L-$C_{2-10}$alkenyl-$C_{3-10}$cycloalkyl, -L-$C_{2-10}$alkenyl-$C_{1-10}$heterocyclyl, -L-$C_{2-10}$alkynyl-$C_{3-10}$aryl, -L-$C_{2-10}$alkynyl-$C_{1-10}$hetaryl, -L-$C_{2-10}$alkynyl-$C_{3-10}$cycloalkyl, -L-$C_{2-10}$alkynyl-$C_{1-10}$heterocyclyl, -L-$C_{1-10}$heteroalkyl-$C_{3-10}$aryl, -L-$C_{1-10}$heteroalkyl-$C_{1-10}$hetaryl, -L-$C_{1-10}$heteroalkyl-$C_{3-10}$cycloalkyl, -L-$C_{1-10}$heteroalkyl-$C_{1-10}$heterocyclyl, -L-$C_{1-10}$alkoxy-$C_{3-10}$aryl, -L-$C_{1-10}$alkoxy-$C_{1-10}$hetaryl, -L-$C_{1-10}$alkoxy-$C_{3-10}$cycloalkyl, -L-$C_{1-10}$alkoxy-$C_{1-10}$heterocyclyl, -L-$C_{3-10}$aryl-$C_{1-10}$alkyl, -L-$C_{3-10}$aryl-$C_{2-10}$alkenyl, -L-$C_{3-10}$aryl-$C_{2-10}$alkynyl, -L-$C_{3-10}$aryl-$C_{1-10}$hetaryl, -L-$C_{3-10}$aryl-$C_{3-10}$cycloalkyl, -L-$C_{3-10}$aryl-$C_{1-10}$heterocyclyl, -L-$C_{1-10}$hetaryl-$C_{1-10}$alkyl, -L-$C_{1-10}$hetaryl-$C_{2-10}$alkenyl, -L-$C_{1-10}$hetaryl-$C_{2-10}$alkynyl, -L-$C_{1-10}$hetaryl-$C_{3-10}$aryl, -L-$C_{1-10}$hetaryl-$C_{3-10}$cycloalkyl, -L-$C_{1-10}$hetaryl-$C_{1-10}$heterocyclyl, -L-$C_{3-10}$cycloalkyl-$C_{1-10}$alkyl, -L-$C_{3-10}$cycloalkyl-$C_{2-10}$alkenyl, -L-$C_{3-10}$cycloalkyl-$C_{2-10}$alkynyl, -L-$C_{3-10}$cycloalkyl-$C_{3-10}$aryl, -L-$C_{3-10}$cycloalkyl-$C_{1-10}$hetaryl, -L-$C_{3-10}$cycloalkyl-$C_{1-10}$heterocyclyl, -L-$C_{1-10}$heterocyclyl-$C_{1-10}$alkyl, -L-$C_{1-10}$heterocyclyl-$C_{2-10}$alkenyl, -L-$C_{1-10}$heterocyclyl-$C_{2-10}$alkynyl, -L-$C_{1-10}$heterocyclyl-$C_{3-10}$aryl, -L-$C_{1-10}$heterocyclyl-$C_{1-10}$hetaryl, or -L-$C_{1-10}$heterocyclyl-$C_{3-10}$cycloalkyl, each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula I-B, L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, —$S(O)_{0-2}N(R^{31})$—, —$C(=S)O$—, —$C(=O)S$—, —$NR^{31}C(=O)NR^{32}$—, —NR—, —$NR^{31}C(=NR^{32})S$—, —$OC(=O)O$—, —$OC(=O)NR^{31}$—, —$OC(=O)S$—, —$SC(=S)S$—, —$P(O)OR^{31}O$—, —$SC(=O)NR^{31}$—. In some embodiments, L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—. In some embodiments, L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—. In some embodiments, L is a bond, —N(R$^{31}$)—, —C(=O)N(R$^{31}$)—, or —N(R$^{31}$)C(=O)—. In some embodiments, L is a bond, —N(R$^{31}$)—, or —C(=O)N(R$^{31}$)—.

In some embodiments of Formula I-B, R$_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{13}$ substituents. In some embodiments, R$_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_3$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, R$_3$ is hydrogen, halogen, —OH, —CF$_3$, or —C$_{1-10}$alkyl.

In some embodiments of Formula I-B, R$_3$' is hydrogen, halogen, —OH, —CF$_3$, —OCF$_3$, —OR$^{31}$, —NR$^{31}$, R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{2-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{13}$ substituents. In some embodiments, R$_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_3$' is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, R$_3$' is hydrogen, halogen, —OH, —CF$_3$, or —C$_{1-10}$alkyl.

In some embodiments of Formula I-B, R$_3$' is —OR$^6$, —NR$^6$R$^{34}$, —S(O)$_{0-2}$R$^6$, —C(=O)R$^6$, —C(=O)OR$^6$, —OC(=O)R$^6$, —C(=O)N(R$^{34}$)R$^6$, or —N(R$^{34}$)C(=O)R$^6$, wherein R$^6$ together with R$^{34}$ can optionally form a heterocyclic ring. In some embodiments, R$_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring. In some embodiments, R$_3$' is —OR$^6$ or —NR$^6$R$^{34}$, wherein R$^6$ together with R$^{34}$ can optionally form a heterocyclic ring.

In some embodiments of Formula I-B, R$_4$ is hydrogen, halogen, —OH, —CF$_3$, —OCF$_3$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC (=O)OR$^{33}$, —OC(=O)NR$^{31}$R$^{32}$, —OC(=O)SR$^{31}$, —SC(=O)SR$^{31}$, —P(O)OR$^{31}$OR$^{32}$, —SC(=O)NR$^{31}$R$^{32}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, R$_4$ is hydrogen, halogen, —OH, —CF$_3$, or —C$_{1-10}$alkyl.

In some embodiments of Formula I-B, R$_5$ is hydrogen, halogen, —C$_{1-10}$alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$. In some embodiments, R$_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, —C$_{1-10}$alkyl, —C$_{3-10}$aryl, —C$_{1-10}$hetaryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, or —C$_{1-10}$alkyl. In some embodiments, R$_5$ is hydrogen.

In some embodiments of Formula I-B, R$_6$ is —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{2-10}$alkenyl-C$_{3-10}$aryl, —C$_{2-10}$alkenyl-C$_{1-10}$hetaryl, —C$_{2-10}$alkenyl-C$_{3-10}$cycloalkyl, —C$_{2-10}$alkenyl-C$_{1-10}$heterocyclyl, —C$_{2-10}$alkynyl-C$_{3-10}$aryl, —C$_{2-10}$alkynyl-C$_{1-10}$hetaryl, —C$_{2-10}$alkynyl-C$_{3-10}$cycloalkyl, —C$_{2-10}$alkynyl-C$_{1-10}$heterocyclyl, —C$_{1-10}$heteroalkyl-C$_{3-10}$aryl, —C$_{1-10}$heteroalkyl-C$_{1-10}$hetaryl, —C$_{1-10}$heteroalkyl-C$_{3-10}$cycloalkyl, —C$_{1-10}$heteroalkyl-C$_{1-10}$heterocyclyl, —C$_{1-10}$alkoxy-C$_{3-10}$aryl, —C$_{1-10}$alkoxy-C$_{1-10}$hetaryl, —C$_{1-10}$alkoxy-C$_{3-10}$cycloalkyl, —C$_{1-10}$alkoxy-C$_{1-10}$heterocyclyl, —C$_{3-10}$aryl-C$_{1-10}$alkyl, —C$_{3-10}$aryl-C$_{2-10}$alkenyl, —C$_{3-10}$aryl-C$_{1-10}$alkynyl, —C$_{3-10}$aryl-C$_{3-10}$hetaryl, —C$_{3-10}$aryl-C$_{3-10}$cycloalkyl, —C$_{3-10}$aryl-C$_{1-10}$heterocyclyl, —C$_{1-10}$hetaryl-C$_{1-10}$alkynyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents. In some embodiments, R$_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents. In some embodiments, R$_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents. In some embodiments, R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents.

In some embodiments of Formula I-B, each of R$_{71}$, R$_{81}$ and R$_{91}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{3}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$. In some embodiments, each of R$_{71}$, $R_{81}$ and $R_{91}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, or —$C_{1-10}$alkyl. In some embodiments, each of $R_{71}$, $R_{81}$ and $R_{91}$ is independently hydrogen.

In some embodiments of Formula I-B, each of $R_{72}$, $R_{82}$ and $R_{92}$ is independently hydrogen, —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, —$S(O)_{0-2}R^{31}$, —$C(=S)OR^{31}$, —$C(=O)SR^{31}$. In some embodiments, each of $R_{72}$, $R_{82}$ and $R_{92}$ is independently hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen, —$C_{1-10}$alkyl, —$C_{3-10}$aryl, or —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen or —$C_{1-10}$alkyl. In some embodiments, each of $R_{72}$, $R_{82}$ and $R_{92}$ is independently hydrogen.

In some embodiments of Formula I-B, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula I-B, each of $R_{11}$, $R_{12}$, $R_{13}$ and $R_{15}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$SO_2NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{32}R^{33}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)SR^{31}$, —$P(O)OR^{31}OR^{32}$, or —$SC(=O)NR^{31}NR^{32}$. In some embodiments, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula I-B, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl.

In some embodiments of Formula I-B, $X_2$ is $NR_1$ or $CR_1R_1'$, $X_3$ is $CR_3R_3'$ or $C=O$, W is C, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{22}$ or $CR_{21}$, and $X_{10}$ is N or $CR_{91}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)$ $OR^6$, $-OC(=O)R^6$, $-C(=O)N(R^{34})R^6$, or $-N(R^{34})C(=O)R^6$, wherein $R^6$ together with $R^{34}$ can optionally form a heterocyclic ring;

each of $R_5$, $R_{71}$, and $R_{81}$ is independently hydrogen, halogen, $-C_{1-10}$alkyl, $-C_{3-10}$aryl, $-C_{1-10}$hetaryl, $-C_{3-10}$cycloalkyl, $-C_{1-10}$heterocyclyl, $-OH$, $-CF_3$, $-OCF_3$, $-OR^{31}$, $-NR^{31}R^{32}C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

$R_6$ is $-C_{1-10}$alkyl, $-C_{3-10}$aryl, $-C_{1-10}$hetaryl, $-C_{3-10}$cycloalkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{3-10}$cycloalkyl-$C_{1-10}$alkyl, $-C_{3-10}$cycloalkyl-$C_{3-10}$aryl, $-C_{3-10}$cycloalkyl-$C_{1-10}$hetaryl, $-C_{3-10}$cycloalkyl-$C_{1-10}$heterocyclyl, $-C_{1-10}$heterocyclyl-$C_{1-10}$alkyl, $-C_{1-10}$heterocyclyl-$C_{3-10}$aryl, $-C_{1-10}$heterocyclyl-$C_{1-10}$hetaryl, or $-C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, $-C_{1-10}$alkyl, $-C_{3-10}$aryl, $-C_{1-10}$hetaryl, $-C_{3-10}$cycloalkyl, $-C_{1-10}$heterocyclyl, $-OH$, $-CF_3$, $-C(O)R^{31}$, $-CO_2R^{31}$, $-C(=O)NR^{31}$, or $-S(O)_{0-2}R^{31}$;

each of $R_{10}$ and $R_{14}$ is independently $-C_{1-10}$alkyl, $-C_{2-10}$alkenyl, $-C_{2-10}$alkynyl, $-C_{1-10}$heteroalkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-C_{3-10}$aryl, $-C_{3-10}$cycloalkyl, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

each of $R^{31}$, $R^{32}$ and $R^{34}$ is independently hydrogen, $-C_{1-10}$alkyl, $-C_{3-10}$aryl, or $-C_{3-10}$cycloalkyl, or wherein $R^{31}$ together with $R^{32}$ form a heterocyclic ring; and wherein ring A comprises one or more heteroatoms selected from N, O, or S.

In some embodiments of Formula I-B, $X_2$ is $NR_1$ or $CR_1R_1'$, $X_3$ is $CR_3R_3'$, W is C, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{21}$ or $CR_{21}$, and $X_{10}$ is N or $CR_{91}$;

$R_1$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_1'$ is hydrogen $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is $-OH$, $-CF_3$, $-C(O)R^{31}$, $-CO_2R^{31}$, $-C(=O)NR^{31}$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$;

each of $R_3$, $R_3'$ and $R_4$ is independently hydrogen, halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ alkyl, $-C_{2-10}$alkenyl, or $-C_{2-10}$alkynyl, each of which is unsubstituted or substituted by one or more independent $R_{13}$ substituents; or $R_3'$ is $-OR^6$, $-NR^6R^{34}$, $-C(=O)N(R^{34})R^6$, or $-N(R^{34})C(=O)R^6$, wherein $R^6$ together with $R^{34}$ can optionally form a heterocyclic ring;

each of $R_5$ and $R_{71}$ is independently hydrogen, halogen, $-C_{1-10}$alkyl, $-C_{3-10}$aryl, $-C_{3-10}$cycloalkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

$R_6$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen, $-C_{1-10}$alkyl, $-C_{3-10}$aryl, $-C_{3-10}$cycloalkyl, $-OH$, $-CF_3$, $-C(O)R^{31}$, $-CO_2R^{31}$, $-C(=O)NR^{31}$, or $-S(O)_{0-2}R^{31}$;

each of $R_{10}$ and $R_{14}$ independently $-C_{1-10}$alkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

each of $R^{31}$, $R^{32}$ and $R^{34}$ is independently hydrogen or $-C_{1-10}$alkyl, or wherein $R^{31}$ together with $R^{32}$ form a heterocyclic ring; and wherein ring A comprises one or more heteroatoms selected from N, O, or S.

In some embodiments of Formula I-B, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-N(R^{31})-$, $-C(=O)N(R^{31})-$, or $-N(R^{31})C(=O)-$;

each of $R_3$, $R_3'$ and $R_4$ is independently hydrogen, halogen, $-OH$, $-CF_3$, $-OCF_3$, $-OR^{31}$, $-NR^{31}R^{32}$, $-NO_2$, $-CN$, $-S(O)_{0-2}R^{31}$, $-C_{1-10}$alkyl, $-C_{2-10}$alkenyl, or $-C_{2-10}$alkynyl; or $R_3'$ is $-OR^6$, $-NR^6R^{34}$, $-C(=O)N(R^{34})R^6$, or $-N(R^{34})C(=O)R^6$, wherein $R^6$ together with $R^{34}$ can optionally form a heterocyclic ring;

$R_5$ is hydrogen, halogen, or $-C_{1-10}$alkyl;

$R_6$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen, $-C_{1-10}$alkyl, $-OH$, $-CF_3$, $-C(O)R^{31}$, $-CO_2R^{31}$, $-C(=O)NR^{31}$, or $-S(O)_{0-2}R^{31}$;

each of $R_{10}$ and $R_{14}$ is independently $-C_{1-10}$alkyl, $-C_{3-10}$aryl, $-C_{1-10}$hetaryl, or $-C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein ring A comprises one or more heteroatoms selected from N, O, or S.

In some embodiments of Formula I-B, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—; or $R_3'$ is —$OR^6$ or —$NR^6R^{34}$, wherein $R^6$ together with $R^{34}$ can optionally form a heterocyclic ring;

each of $R_3$, $R_3'$ and $R_4$ is independently hydrogen, halogen, —OH, —$CF_3$, or —$C_{1-10}$alkyl; or $R_3'$ is —$OR^6$ or —$NR^6R^{34}$, wherein $R^6$ together with $R^{34}$ can optionally form a heterocyclic ring;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$;

each of $R^{31}$ and $R^{34}$ is independently hydrogen or —$C_{1-10}$alkyl; and wherein ring A comprises one or more heteroatoms selected from N, O, or S.

The invention also provides a compound as defined above, wherein the compound is of Formula II:

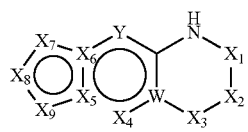

or a pharmaceutically acceptable salt or prodrug thereof, and wherein the substituents are as defined above.

In some embodiments of Formula II, $X_1$ is C=O, $X_2$ is $NR_1$ or $CR_1R_1'$, and $X_3$ is $CR_3R_3'$. In some embodiments, $X_1$ is C=O, $X_2$ is $NR_1$ or $CR_1R_1'$, and $X_3$ is C=O. In some embodiments, $X_1$ is C=S, $X_2$ is $CR_1$, and $X_3$ is $CR_3R_3'$. In some embodiments, $X_1$ is $SO_2$, $X_2$ is $NR_1$, and $X_3$ is $CR_3R_3'$. In some embodiments, $X_1$ is $SO_2$, and $X_2$ and $X_3$ is $R_{11}C=CR_3$.

In some embodiments of Formula II, W is C, Y is $CR_5$, $X_4$ is N or $CR_4$, $X_5$ is C and $X_6$ is C. In some embodiments, W is C, Y is $CR_5$, $X_4$ is $CR_4$, $X_5$ is N or C and $X_6$ is C. In some embodiments, W is C, Y is $CR_5$, $X_4$ is $CR_4$, $X_5$ is C and $X_6$ is C. In some embodiments, W is C, Y is $CR_5$, $X_4$ is $CR_4$, $X_5$ is C and $X_6$ is C. In some embodiments, W is C, Y is $CR_5$, $X_4$ is $CR_4$, $X_5$ is C and $X_6$ is N. In some embodiments, W is C, Y is $CR_5$, $X_4$ is $CR_4$, $X_5$ is C and $X_6$ is N. In some embodiments, W is N, Y is $CR_5$, $X_4$ is C=O, $X_5$ is C and $X_6$ is C. In some embodiments, W is N, Y is $CR_5$, $X_4$ is C=O, $X_5$ is C and $X_6$ is N.

In some embodiments of Formula II, $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_7$, $X_8$ is N and $X_9$ is $NR_{22}$. In some embodiments, $X_7$ is $CR_7$, $X_8$ is N and $X_9$ is $CR_{21}$. In some embodiments, $X_7$ is O, $X_8$ is N and $X_9$ is $CR_2$. In some embodiments, $X_7$ is O, $X_8$ is $CR_{81}$ and $X_9$ is $NR_{21}$.

In some embodiments of Formula II, $X_1$ is C=O, $X_2$ is $NR_1$ or $CR_1R_1'$, $X_3$ is $CR_3R_3'$ or C=O, W is N or C, Y is N or $CR_5$, $X_4$ is N, C=O or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_1$ is C=O, $X_2$ is $NR_1$ or $CR_1R_1'$, $X_3$ is $CR_3R_3'$, W is C, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_1$ is C=O, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula II, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II, $R_{21}$ is hydrogen, halogen, —OH, —$CF_3$, —$OCF_3$, —$OR^{31}$, —$NR^{31}$, $R^{32}$, —C(O)R$^{31}$, —CO$_2$R$^{31}$, —C(=O)NR$^{31}$, —NO$_2$, —CN, —S(O)$_{0-2}$R$^{31}$, —NR$^{31}$C(=O)R$^{32}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents. In some embodiments, R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —NR$^{31}$C(=O)R$^{32}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents. In some embodiments, R$_{21}$ is halogen, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents. In some embodiments, R$_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents.

In some embodiments on Formula II, R$_{22}$ is hydrogen, —OH, —CF$_3$, —C(O)R$^{31}$, —CO$_2$R$^{31}$, —C(=O)NR$^{31}$, —S(O)$_{0-2}$R$^{31}$, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents. In some embodiments, R$_{22}$ is —OH, —CF$_3$, —C(O)R$^{31}$, —CO$_2$R$^{31}$, —C(=O)NR$^{31}$, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl each of which is unsubstituted or substituted by one or more independent R$_{12}$ substituents. In some embodiments, R$_{22}$ is —OH, —CF$_3$, —C(O)R$^{31}$, —CO$_2$R$^{31}$, —C(=O)NR$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents. In some embodiments, R$_{22}$ is -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents.

In some embodiments of Formula II, L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—. In some embodiments, L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—. In some embodiments, L is a bond, —N(R$^{31}$)—, —C(=O)N(R$^{31}$)—, or —N(R$^{31}$)C(=O)—. In some embodiments, L is a bond, —N(R$^{31}$)—, or —C(=O)N(R$^{31}$)—.

In some embodiments of Formula II, R$_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_3$ is hydrogen, halogen, —OH, —CF$_3$, or —C$_{1-10}$alkyl.

In some embodiments of Formula II, R$_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_3$' is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{2-10}$alkenyl, or —C$_{2-10}$alkynyl. In some embodiments, R$_3$' is hydrogen, halogen, —OH, —CF$_3$, or —C$_{1-10}$alkyl.

In some embodiments of Formula II, R$_3$' is —OR$^6$, —NR$^6$R$^{34}$, —S(O)$_{0-2}$R$^6$, —C(=O)R$^6$, —C(=O)OR$^6$, —OC(=O) R$^6$, —C(=O)N(R$^{34}$)R$^6$, or —N(R$^{34}$)C(=O) R$^6$, wherein R$^6$ together with R$^{34}$ can optionally form a heterocyclic ring. In some embodiments, R$_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring. In some embodiments, R$_3$' is —OR$^6$ or —NR$^6$R$^{34}$, wherein R$^6$ together with R$^{34}$ can optionally form a heterocyclic ring.

In some embodiments of Formula II, R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{2-10}$alkenyl, or —C$_{2-10}$alkynyl. In some embodiments, R$_4$ is hydrogen, halogen, —OH, —CF$_3$, or —C$_{1-10}$alkyl.

In some embodiments of Formula II, R$_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, or —C$_{1-10}$alkyl. In some embodiments, R$_5$ is hydrogen.

In some embodiments of Formula II, R$_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl- $C_{3-10}$cycloalkyl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents.

In some embodiments of Formula II, each of $R_{71}$ and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, or —$C_{1-10}$ alkyl. In some embodiments, each of $R_{71}$ and $R_{81}$ is independently hydrogen.

In some embodiments of Formula II, each of $R_{72}$ and $R_{82}$ is independently hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$ and $R_{82}$ is independently hydrogen, —$C_{1-10}$ alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$ and $R_{82}$ is independently hydrogen or —$C_{1-10}$alkyl. In some embodiments, each of $R_{72}$ and $R_{82}$ is independently hydrogen.

In some embodiments of Formula II, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula II, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula II, $X_1$ is C=O, $X_2$ is $NR_1$ or $CR_1R_1'$, $X_3$ is $CR_3R_3'$ or C=O, W is N or C, Y is $CR_5$, $X_4$ is N, C=O or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl-$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ alkyl, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring;

each of $R_5$, $R_{71}$, and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents;

R$_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$;

each of R$_{10}$ and R$_{14}$ is independently —C$_{1-10}$alkyl, —C$_{2-10}$alkenyl, —C$_{2-10}$alkynyl, -L-C$_{1-10}$heteroalkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, R$_{13}$ and R$_{15}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

each of R$^{31}$, R$^{32}$ and R$^{34}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring; and wherein at least one of X$_5$, X$_6$, X$_7$, X$_8$ or X$_9$ comprises one or more heteroatoms selected from N, O, or S.

In some embodiments of Formula II, X$_1$ is C=O, X$_2$ is NR$_1$ or CR$_1$R$_1$', X$_3$ is CR$_3$R$_3$', W is N or C, Y is CR$_5$, X$_4$ is N, C=O or CR$_4$, X$_5$ is N or C, X$_6$ is C, X$_7$ is NR$_{72}$ or CR$_{71}$, X$_8$ is N, and X$_9$ is NR$_{21}$ or CR$_{21}$;

R$_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_1$' is hydrogen, —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

R$_{22}$ is —OH, —CF$_3$, —C(O)R$^{31}$, —CO$_2$R$^{31}$, —C(=O)NR$^{31}$, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—;

each of R$_3$, R$_3$' and R$_4$ is independently hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents; or R$_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring;

each of R$_5$ and R$_{71}$ is independently hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$;

each of R$_{10}$ and R$_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, R$_{13}$ and R$_{15}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

each of R$^{31}$, R$^{32}$ and R$^{34}$ is independently hydrogen or —C$_{1-10}$alkyl, or wherein R$^{31}$ together with R$^{32}$ form a heterocyclic ring; and wherein at least one of X$_5$, X$_6$, X$_7$, X$_8$ or X$_9$ comprises one or more heteroatoms selected from N, O, or S.

In some embodiments of Formula II, X$_1$ is C=O, X$_2$ is NR$_1$, X$_3$ is CR$_3$R$_3$', W is C, Y is CR$_5$, X$_4$ is CR$_4$, X$_5$ is C, X$_6$ is C, X$_7$ is NR$_{72}$, X$_8$ is N, and X$_9$ is CR$_{21}$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, —C(=O)N(R$^{31}$)—, or —N(R$^{31}$)C(=O)—;

each of R$_3$, R$_3$' and R$_4$ is independently hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl; or R$_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring;

R$_5$ is independently hydrogen, halogen, or —C$_{1-10}$alkyl;

R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen or —C$_{1-10}$alkyl;

each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$ and R$_{12}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$;

each of R$^{31}$, R$^{32}$ and R$^{34}$ is independently hydrogen or —C$_{1-10}$alkyl, or wherein R$^{31}$ together with R$^{32}$ form a heterocyclic ring; and wherein at least one of X$_5$, X$_6$, X$_7$, X$_8$ or X$_9$ comprises one or more heteroatoms selected from N, O, or S.

In some embodiments of Formula II, $X_1$ is C=O, $X_2$ is $NR_1$, $X_3$ is $CR_3R_3'$, W is C, Y is $CR_5$, $X_4$ is $CR_4$, $X_5$ is C, $X_6$ is C, $X_7$ is $NR_{72}$, $X_8$ is N, and $X_9$ is $CR_{21}$.

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —N($R^{31}$)—, or —C(=O)N($R^{31}$)—;

each of $R_3$, $R_3'$ and $R_4$ is independently hydrogen, halogen, —OH, —$CF_3$, or —$C_{1-10}$alkyl; or $R_3'$ is —$OR^6$ or —$NR^6R^{34}$, wherein $R^6$ together with $R^{34}$ can optionally form a heterocyclic ring;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —C(O)$R^{31}$, —$CO_2R^{31}$, —C(=O)N$R^{31}$, or —S(O)$_{0-2}R^{31}$;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$;

each of $R^{31}$ and $R^{34}$ is independently hydrogen or —$C_{1-10}$alkyl; and wherein at least one of $X_5$, $X_6$, $X_7$, $X_8$ or $X_9$ comprises one or more heteroatoms selected from N, O, or S.

The invention also provides a compound as defined above, wherein the compound is of Formula II':

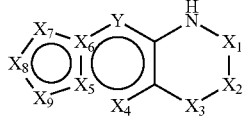

or a pharmaceutically acceptable salt or prodrug thereof, and wherein the substituents are as defined above.

In some embodiments of Formula II', $X_1$ is C=O, $X_2$ is $NR_1$ or $CR_1R_1'$, and $X_3$ is $CR_3R_3'$. In some embodiments, $X_1$ is C=O, $X_2$ is $NR_1$ or $CR_1R_1'$, and $X_3$ is C=O. In some embodiments, $X_1$ is C=S, $X_2$ is $CR_1$, and $X_3$ is $CR_3R_3'$. In some embodiments, $X_1$ is $SO_2$, $X_2$ is $NR_1$, and $X_3$ is $CR_3R_3'$. In some embodiments, $X_1$ is $SO_2$, and $X_2$ and $X_3$ is $R_{11}$C=$CR_3$.

In some embodiments of Formula II', Y is $CR_5$, $X_4$ is N or $CR_4$, $X_5$ is C and $X_6$ is C. In some embodiments, Y is $CR_5$, $X_4$ is $CR_4$, $X_5$ is N or C and $X_6$ is C. In some embodiments, Y is $CR_5$, $X_4$ is $CR_4$, $X_5$ is C and $X_6$ is C. In some embodiments, Y is $CR_5$, $X_4$ is $CR_4$, $X_5$ is N and $X_6$ is C. In some embodiments, Y is $CR_5$, $X_4$ is $CR_4$, $X_5$ is C and $X_6$ is N. In some embodiments, Y is $CR_5$, $X_4$ is C=O, $X_5$ is C and $X_6$ is C. In some embodiments, Y is $CR_5$, $X_4$ is C=O, $X_5$ is C and $X_6$ is N.

In some embodiments of Formula II', $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_7$, $X_8$ is N and $X_9$ is $NR_{22}$. In some embodiments, $X_7$ is $CR_7$, $X_8$ is N and $X_9$ is $CR_{21}$. In some embodiments, $X_7$ is O, $X_8$ is N and $X_9$ is $CR_2$. In some embodiments, $X_7$ is O, $X_8$ is $CR_{81}$ and $X_9$ is $NR_{21}$.

In some embodiments of Formula II', $X_1$ is C=O, $X_2$ is $NR_1$ or $CR_1R_1'$, $X_3$ is $CR_3R_3'$ or C=O, Y is N or $CR_5$, $X_4$ is N, C=O or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_1$ is C=O, $X_2$ is $NR_1$ or $CR_1R_1'$, $X_3$ is $CR_3R_3'$, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_1$ is C=O, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula II', $R_1$ is —$C_{1-10}$alkyl, —$C_{3-10}$aryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II', $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{3-10}$cycloalkyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II', $R_{21}$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —S(O)$_{0-2}R^{31}$, —$NR^{31}$C(=O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —S(O)$_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}$, $R^{32}$, —$C(O)R^{31}$, —$CO_2R^{31}$, —$C(=O)NR^{31}$, —$NO_2$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula II', $R_{22}$ is hydrogen, —OH, —$CF_3$, —$C(O)R^{31}$, —$CO_2R^{31}$, —$C(=O)NR^{31}$, —$S(O)_{0-2}R^{31}$ alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, —$S(O)_{0-2}R^{31}$, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II', L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—. In some embodiments, L is a bond, —$N(R^{31})$—, —$C(=O)N(R^{31})$—, or —$N(R^{31})C(=O)$—. In some embodiments, L is a bond, —$N(R^{31})$—, or —$C(=O)N(R^{31})$—.

In some embodiments of Formula II', $R_3$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{2-10}$alkenyl, or —$C_{2-10}$alkynyl. In some embodiments, $R_3$ is hydrogen, halogen, —OH, —$CF_3$, or —$C_{1-10}$alkyl.

In some embodiments of Formula II', $R_3'$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{2-10}$alkenyl, or —$C_{2-10}$alkynyl. In some embodiments, $R_3'$ is hydrogen, halogen, —OH, —$CF_3$, or —$C_{1-10}$alkyl.

In some embodiments of Formula II', $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring. In some embodiments, $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring. In some embodiments, $R_3'$ is —$OR^6$ or —$NR^6R^{34}$, wherein $R^6$ together with $R^{34}$ can optionally form a heterocyclic ring.

In some embodiments of Formula II', $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula II', $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula II', $R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents.

In some embodiments of Formula II', each of $R_{71}$ and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, or —$C_{1-10}$ alkyl. In some embodiments, each of $R_{71}$ and $R_{81}$ is independently hydrogen.

In some embodiments of Formula II', each of $R_{72}$ and $R_{82}$ is independently hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$ and $R_{82}$ is independently hydrogen, —$C_{1-10}$ alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$ and $R_{82}$ is independently hydrogen or —$C_{1-10}$alkyl. In some embodiments, each of $R_{72}$ and $R_{82}$ is independently hydrogen.

In some embodiments of Formula II', each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II', each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula II', each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula II', $X_1$ is C=O, $X_2$ is $NR_1$ or $CR_1R_1'$, $X_3$ is $CR_3R_3'$ or C=O, Y is $CR_5$, $X_4$ is N, C=O or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, —O—, —N($R^{31}$)—, —$S(O)_{0-2}$—, —C(=O)—, —C(=O)O—, —OC(=O)—, —C(=O)N($R^{31}$)—, —N($R^{31}$)C(=O)—, —$NR^{31}C(=O)O$—, —$NR^{31}C(=O)NR^{32}$—, —$NR^{31}S(O)_{0-2}$—, or —$S(O)_{0-2}N(R^{31})$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring;

each of $R_5$, $R_{71}$, and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$, $R^{32}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring; and wherein at least one of $X_5$, $X_6$, $X_7$, $X_8$ or $X_9$ comprises one or more heteroatoms selected from N, O, or S.

In some embodiments of Formula II', $X_1$ is C=O, $X_2$ is $NR_1$ or $CR_1R_1'$, $X_3$ is $CR_3R_3'$, Y is $CR_5$, $X_4$ is N, C=O or $CR_4$, $X_5$ is N or C, $X_6$ is C, $X_7$ is $NR_{72}$ or $CR_{71}$, $X_8$ is N, and $X_9$ is $NR_{21}$ or $CR_{21}$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})C(=O)$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, or —$C_{2-10}$alkynyl, each of which is unsubstituted or substituted by one or more independent $R_{13}$ substituents; or $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring;

each of $R_5$ and $R_{71}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein at least one of $X_5$, $X_6$, $X_7$, $X_8$ or $X_9$ comprises one or more heteroatoms selected from N, O, or S.

In some embodiments of Formula II', $X_1$ is C=O, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, and $X_9$ is $CR_{21}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, —C(=O)N($R^{31}$)—, or —$N(R^{31})C(=O)$—;

each of $R_3$, $R_3'$ and $R_4$ is independently hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl; or $R_3'$ is —$OR^6$, —$NR^6R^{34}$, —$C(=O)N(R^{34})R^6$, —$N(R^{34})C(=O)R^6$, wherein $R^6$ together with $R^{34}$ can optionally form a heterocyclic ring;

$R_5$ is independently hydrogen, halogen, or —$C_{1-10}$alkyl;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen or —$C_{1-10}$alkyl;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$;

each of $R^{31}$, $R^{32}$ and $R^{34}$ is independently hydrogen or —$C_{1-10}$alkyl, or wherein $R^{31}$ together with $R^{32}$ form a heterocyclic ring; and wherein at least one of $X_5$, $X_6$, $X_7$, $X_8$ or $X_9$ comprises one or more heteroatoms selected from N, O, or S.

In some embodiments of Formula II', $X_1$ is C=O, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, and $X_9$ is $CR_{21}$;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-N(R^{31})-$, or $-C(=O)N(R^{31})-$;

each of $R_3$, $R_3'$ and $R_4$ is independently hydrogen, halogen, $-OH$, $-CF_3$, or $-C_{1-10}$alkyl; or $R_3'$ is $-OR^6$ or $-NR^6R^{34}$, wherein $R^6$ together with $R^{34}$ can optionally form a heterocyclic ring;

$R_5$ is hydrogen;

$R_6$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen, $-C_{1-10}$alkyl, $-OH$, $-CF_3$, $-C(O)R^{31}$, $-CO_2R^{31}$, $-C(=O)NR^{31}$, or $-S(O)_{0-2}R^{31}$;

each of $R_{10}$ and $R_{14}$ is independently $-C_{1-10}$alkyl, $-C_{3-10}$aryl, $-C_{1-10}$hetaryl, or $-C_{1-10}$heterocyclyl, optionally substituted by one or more independent $R_{11}$ substituents;

each of $R_{11}$, $R_{12}$ and $R_{15}$ is independently hydrogen, halogen, $-C_{1-10}$alkyl, $-OH$ or $-CF_3$;

each of $R^{31}$ and $R^{34}$ is independently hydrogen or $-C_{1-10}$alkyl; and wherein at least one of $X_5, X_6, X_7, X_8$ or $X_9$ comprises one or more heteroatoms selected from N, O, or S.

The invention also provides a compound as defined above, wherein the compound is of Formula II-A:

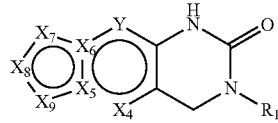

or a pharmaceutically acceptable salt or prodrug thereof, and wherein the substituents are as defined above.

In some embodiments of Formula II-A, Y is $CR_5$, $X_4$ is N or $CR_4$, $X_5$ is C and $X_6$ is C. In some embodiments, Y is $CR_5$, $X_4$ is N or $CR_4$, $X_5$ is N or C and $X_6$ is C. In some embodiments, Y is $CR_5$, $X_4$ is $CR_4$, $X_5$ is C and $X_6$ is C. In some embodiments, Y is $CR_5$, $X_4$ is $CR_4$, $X_5$ is N and $X_6$ is C. In some embodiments, $X_4$ is $CR_4$, $X_5$ is C and $X_6$ is N.

In some embodiments of Formula II-A, $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_{71}$, $X_8$ is N and $X_9$ is $NR_{22}$. In some embodiments, $X_7$ is $CR_{71}$, $X_8$ is N and $X_9$ is $CR_{21}$. In some embodiments, $X_7$ is O, $X_8$ is N and $X_9$ is $CR_{21}$. In some embodiments, $X_7$ is O, $X_8$ is $CR_8$ and $X_9$ is $NR_{21}$.

In some embodiments of Formula II-A, Y is $CR_5$, $X_4$ is N or $CR_4$, $X_5$ is N or C, $X_6$ is C, $X_7$ is N or $NR_{71}$ or $CR_7$, $X_8$ is N or $CR_{81}$, and $X_9$ is $NR_2$ or $CR_{21}$. In some embodiments, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula II-A, $R_1$ is $-C_{1-10}$alkyl, $-C_{3-10}$aryl, $-C_{1-10}$hetaryl, $-C_{3-10}$cycloalkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{3-10}$cycloalkyl-$C_{1-10}$alkyl, $-C_{3-10}$cycloalkyl-$C_{3-10}$aryl, $-C_{3-10}$cycloalkyl-$C_{1-10}$hetaryl, $-C_{3-10}$cycloalkyl-$C_{1-10}$heterocyclyl, $-C_{1-10}$heterocyclyl-$C_{1-10}$alkyl, $-C_{1-10}$heterocyclyl-$C_{3-10}$aryl, $-C_{1-10}$heterocyclyl-$C_{1-10}$hetaryl, or $-C_{1-10}$heterocyclyl-$C_{3-10}$cycloalkyl, each of which is unsubstituted or substituted by one or more independent $R_{10}$ or $R_{11}$ substituents. In some embodiments, $R_1$ is $-C_{1-10}$alkyl, $-C_{1-10}$heterocyclyl, $-C_{1-10}$alkyl-$C_{3-10}$aryl, $-C_{1-10}$alkyl-$C_{3-10}$cycloalkyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents. In some embodiments, $R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents.

In some embodiments of Formula II-A, $R_{21}$ is hydrogen, halogen, $-OH$, $-CF_3$, $-OCF_3$, $-OR^{31}$, $-NR^{31}$, $R^{32}$, $-C(O)R^{31}$, $-CO_2R^{31}$, $-C(=O)NR^{31}$, $-NO_2$, $-CN$, $-S(O)_{0-2}R^{31}$, $-NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, $-CN$, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents.

In some embodiments on Formula II-A, $R_{22}$ is hydrogen, $-OH$, $-CF_3$, $-C(O)R^{31}$, $-CO_2R^{31}$, $-C(=O)NR^{31}$, $-S(O)_{0-2}R^{31}$, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is $-OH$, $-CF_3$, $-C(O)R^{31}$, $-CO_2R^{31}$, $-C(=O)NR^{31}$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is $-OH$, $-CF_3$, $-C(O)R^{31}$, $-CO_2R^{31}$, $-C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-A, L is a bond, $-O-$, $-N(R^{31})-$, $-S(O)_{0-2}-$, $-C(=O)-$, $-C(=O)O-$, $-OC(=O)-$, $-C(=O)N(R^{31})-$, $-N(R^{31})C(=O)-$, $-NR^{31}C(=O)O-$, $-NR^{31}C(=O)NR^{32}-$, $-NR^{31}S(O)_{0-2}-$, or $-S(O)_{0-2}N(R^{31})-$. In some embodiments, L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula II-A, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —S(O)$_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula II-A, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$ or —$NR^{31}$C(=O)$R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$ or —$NR^{31}$C(=O)$R^{32}$. In some embodiments, $R_5$ is hydrogen, halogen, or —$C_{1-10}$alkyl. In some embodiments, $R_5$ is hydrogen.

In some embodiments of Formula II-A, each of $R_{71}$ and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$ or —$NR^{31}$C(=O)$R^{32}$. In some embodiments, each of $R_{71}$ and $R_{81}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$ or —$NR^{31}$C(=O)$R^{32}$. In some embodiments, each of $R_{71}$ and $R_{81}$ is independently hydrogen, halogen, or —$C_{1-10}$ alkyl. In some embodiments, each of $R_{71}$ and $R_{81}$ is independently hydrogen.

In some embodiments of Formula II-A, each of $R_{72}$ and $R_{82}$ is independently hydrogen, —$C_{1-10}$ alkyl, —$C_{3-10}$aryl, —$C_{3-10}$cycloalkyl, —$C_{1-10}$heterocyclyl, —OH, —$CF_3$, —C(O)$R^{31}$, —$CO_2R^{31}$, —C(=O)$NR^{31}$, or —S(O)$_{0-2}R^{31}$. In some embodiments, each of $R_{72}$ and $R_{82}$ is independently hydrogen, —$C_{1-10}$ alkyl, —$C_{3-10}$aryl, —$C_{3-10}$cycloalkyl, —C(O)$R^{31}$, —$CO_2R^{31}$, —C(=O)$NR^{31}$, or —S(O)$_{0-2}R^{31}$. In some embodiments, each of $R_{72}$ and $R_{82}$ is independently hydrogen or —$C_{1-10}$alkyl. In some embodiments, each of $R_{72}$ and $R_{82}$ is independently hydrogen.

In some embodiments of Formula II-A, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II-A, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$ or —$NR^{31}$C(=O)$R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$ or —$NR^{31}$C(=O)$R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —S(O)$_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula II-A, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl.

In some embodiments of Formula II-A, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$;

$R_1$ is —$C_{1-10}$alkyl, —$C_{3-10}$aryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —C(O)$R^{31}$, —$CO_2R^{31}$, —C(=O)$NR^{31}$, —S(O)$_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—;

$R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents;

each of $R_5$, $R_{71}$ and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring; and wherein at least one of $X_5$, $X_6$, $X_7$, $X_8$ and $X_9$ is a heteroatom selected from N, O, or S.

In some embodiments of Formula II-A, Y is $CR_5$, $X_4$ is N or $CR_4$, $X_5$ is N or C, $X_6$ is C, $X_7$ is $NR_{72}$ or $CR_{71}$, $X_8$ is N or $CR_{81}$, and $X_9$ is $NR_{22}$ or $CR_{21}$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{3-10}$aryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —$C(=O)N(R^{31})$—, or —$N(R^{31})C(=O)$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, $C_{1-10}$alkyl, $C_{2-10}$alkenyl, or $C_{2-10}$alkynyl, each of which is unsubstituted or substituted by one or more independent $R_{13}$ substituents;

each of $R_5$, $R_{71}$ and $R_{81}$ is independently hydrogen, halogen, $C_{1-10}$alkyl, $C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, $C_{1-10}$alkyl, $C_{3-10}$aryl, $C_{3-10}$cycloalkyl, —$C(O)R^{31}$, —$CO_2R^{31}$, —$C(=O)NR^{31}$, or —$S(O)_{0-2}R^{31}$;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$ and $R^{32}$ is independently hydrogen or —$C_{1-10}$alkyl, or wherein $R^{31}$ together with $R^{32}$ form a heterocyclic ring; and wherein at least one of $X_5$, $X_6$, $X_7$, $X_8$ and $X_9$ is a heteroatom selected from N, O, or S.

In some embodiments of Formula II-A, Y is $CR_5$, $X_4$ is $CR_4$, $X_5$ is C, $X_6$ is C, $X_7$ is $NR_{72}$ or $CR_{71}$, $X_8$ is N or $CR_{81}$, and $X_9$ is $CR_{21}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, -L-$C_{3-10}$aryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, —$C(=O)N(R^{31})$—, or —$N(R^{31})C(=O)$—;

$R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl;

each of $R_5$, $R_{71}$ and $R_{81}$ is independently hydrogen, halogen, or —$C_{1-10}$alkyl;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$, each of $R^{31}$ and $R^{32}$ is independently hydrogen or —$C_{1-10}$alkyl; and wherein at least one of $X_5$, $X_6$, $X_7$, $X_8$ and $X_9$ is a heteroatom selected from N, O, or S.

In some embodiments of Formula II-A, Y is $CR_5$, $X_4$ is $CR_4$, $X_5$ is C, $X_6$ is C, $X_7$ is $NR_{72}$ or $CR_{71}$, $X_8$ is N or $CR_{81}$, and $X_9$ is $CR_{21}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—;

$R_4$ is hydrogen, halogen, —OH, —$CF_3$, or —$C_{1-10}$alkyl;

each of $R_5$, $R_{71}$ and $R_{81}$ is independently hydrogen, halogen, or —$C_{1-10}$alkyl;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$;

each of $R^{31}$ is independently hydrogen or —$C_{1-10}$alkyl; and wherein at least one of $X_5$, $X_6$, $X_7$, $X_8$ and $X_9$ is a heteroatom selected from N, O, or S.

In some embodiments of Formula II-A, Y is $CR_5$, $X_4$ is $CR_4$, $X_5$ is C, $X_6$ is C, $X_7$ is $NR_{72}$ or $CR_{71}$, $X_8$ is N or $CR_{81}$, and $X_9$ is $CR_{21}$;

$R_1$ is —$C_{1-10}$alkyl, —$C_{1-10}$alkyl-$C_{3-10}$aryl, or —$C_{1-10}$heterocyclyl-$C_{1-10}$alkyl, each of which is unsubstituted or substituted by one or more independent $R_{10}$ or $R_{11}$ substituents;

$R_{21}$ is -L-$C_{3-10}$aryl or -L-$C_{1-10}$hetaryl, each of which is unsubstituted or substituted by one or more independent $R_{12}$ substituents;

L is a bond or —$N(R^{31})$—;

$R_4$ is hydrogen;

each of $R_5$, $R_{71}$ and $R_{81}$ is independently hydrogen or —$C_{1-10}$alkyl;

$R_{72}$ is hydrogen;

each of $R_{10}$ is independently —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently halogen, —$C_{1-10}$alkyl, —OH, —$CF_3$ or —$OR^{31}$;

each of $R^{31}$ is independently hydrogen or —$C_{1-10}$alkyl; and wherein at least one of $X_5$, $X_6$, $X_7$, $X_8$ and $X_9$ is a heteroatom selected from N, O, or S.

In some embodiments of Formula II-A, Y is $CR_5$, $X_4$ is $CR_4$, $X_5$ is C, $X_6$ is C, $X_7$ is $NR_{72}$ or $CR_{71}$, $X_8$ is N or $CR_{81}$, and $X_9$ is $CR_{21}$;

$R_1$ is —$C_{1-10}$alkyl or —$C_{1-10}$alkyl-$C_{3-10}$aryl, each of which is unsubstituted or substituted by one or more independent $R_{11}$ substituents;

$R_{21}$ is pyridyl selected from the group consisting of 2-pyridyl, 3-pyridyl and 4-pyridyl, which is unsubstituted or substituted by one or more independent $R_{12}$ substituents;

L is a bond;

$R_4$ is hydrogen;

each of $R_5$, $R_{71}$ and $R_{81}$ is independently hydrogen;

$R_{72}$ is hydrogen;

each of $R_{11}$ and $R_{12}$ is independently halogen, —$C_{1-10}$alkyl, —$CF_3$ or —$OR^{31}$;

each of $R^{31}$ is independently hydrogen or —$C_{1-10}$alkyl; and wherein at least one of $X_5$, $X_6$, $X_7$, $X_8$ and $X_9$ is a heteroatom selected from N, O, or S.

The invention also provides a compound as defined above, wherein the compound is of Formula II-B:

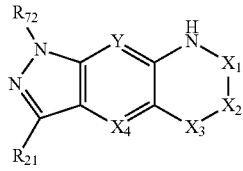

or a pharmaceutically acceptable salt or prodrug thereof, and wherein the substituents are as defined above.

In some embodiments of Formula II-B, $X_1$ is C=O, $X_2$ is $NR_1$ or $CR_1R_1'$, and $X_3$ is $CR_3R_3'$. In some embodiments, $X_1$ is C=O, $X_2$ is $NR_1$ or $CR_1R_1'$, and $X_3$ is C=O. In some embodiments, $X_1$ is C=S, $X_2$ is $CR_1$, and $X_3$ is $CR_3$. In some embodiments, $X_1$ is $SO_2$, $X_2$ is $NR_1$, and $X_3$ is $CR_3R_3'$. In some embodiments, $X_1$ is $SO_2$, and $X_2$ and $X_3$ is $R_1C=CR_3$.

In some embodiments of Formula II-B, $X_1$ is C=O or $SO_2$, $X_2$ is $NR_1$ or $CR_1R_1'$, $X_3$ is CH or C=O, Y is $CR_5$, and $X_4$ is N or $CR_4$. In some embodiments, $X_1$ is C=O or $SO_2$, $X_2$ is $NR_1$ or $CR_1R_1'$, $X_3$ is CH, Y is $CR_5$ and $X_4$ is N or $CR_4$.
In some embodiments, $X_1$ is C=O, $X_2$ is $NR_1$, $X_3$ is CH, Y is $CR_5$ and $X_4$ is $CR_4$.

In some embodiments of Formula II-B, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-B, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-B, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-B, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —N$R^{31}$C(=O)O—, —N$R^{31}$C(=O)N$R^{32}$—, —N$R^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula II-B, $R_3$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_3$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_3$ is hydrogen, halogen, —OH, —CF$_3$, —OCF$_3$, —O$R^{31}$, —N$R^{31}R^{32}$, —NO$_2$, —CN, —S(O)$_{0-2}R^{31}$, —C$_{2-10}$alkenyl, or —C$_{2-10}$alkynyl. In some embodiments, $R_3$ is hydrogen, halogen, —OH, —CF$_3$, or —C$_{1-10}$alkyl.

In some embodiments of Formula II-B, $R_3'$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_3'$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_3'$ is hydrogen, halogen, —OH, —CF$_3$, —OCF$_3$, —O$R^{31}$, —N$R^{31}R^{32}$, —NO$_2$, —CN, —S(O)$_{0-2}R^{31}$, —C$_{2-10}$alkenyl, or —C$_{2-10}$alkynyl. In some embodiments, $R_3'$ is hydrogen, halogen, —OH, —CF$_3$, or —C$_{1-10}$alkyl.

In some embodiments of Formula II-B, $R_3'$ is —O$R^6$, —N$R^6R^{34}$, —S(O)$_{0-2}R^6$, —C(=O)$R^6$, —C(=O)O$R^6$, —OC(=O)$R^6$, —C(=O)N($R^{34}$)$R^6$, or —N($R^{34}$)C(=O)$R^6$, wherein $R^6$ together with $R^{34}$ can optionally form a heterocyclic ring. In some embodiments, $R_3'$ is —O$R^6$, —N$R^6R^{34}$, —C(=O)N($R^{34}$)$R^6$, or —N($R^{34}$)C(=O)$R^6$, wherein $R^6$ together with $R^{34}$ can optionally form a heterocyclic ring. In some embodiments, $R_3'$ is —O$R^6$ or —N$R^6R^{34}$, wherein $R^6$ together with $R^{34}$ can optionally form a heterocyclic ring.

In some embodiments of Formula II-B, $R_4$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_4$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_4$ is hydrogen, halogen, —OH, —CF$_3$, —OCF$_3$, —O$R^{31}$, —N$R^{31}R^{32}$, —NO$_2$, —CN, —S(O)$_{0-2}R^{31}$, —C$_{2-10}$alkenyl, or —C$_{2-10}$alkynyl. In some embodiments, $R_4$ is hydrogen, halogen, —OH, —CF$_3$, or —C$_{1-10}$alkyl.

In some embodiments of Formula II-B, $R_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$. In some embodiments, $R_5$ is hydrogen, halogen, —C$_{1-10}$alkyl, —C$_{3-10}$aryl, —C$_{3-10}$cycloalkyl, —OH, —CF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$. In some embodiments, $R_5$ is hydrogen, halogen, or —C$_{1-10}$alkyl. In some embodiments, $R_5$ is hydrogen.

In some embodiments of Formula II-B, $R_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{14}$ or $R_{15}$ substituents. In some embodiments, $R_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{14}$ or $R_{15}$ substituents. In some embodiments, $R_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{14}$ or $R_{15}$ substituents.

In some embodiments of Formula II-B, $R_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)$R^{31}$, —CO$_2R^{31}$, —C(=O)N$R^{31}$, or —S(O)$_{0-2}R^{31}$. In some embodiments, $R_{72}$ is hydrogen, —C$_{1-10}$alkyl, —C$_{3-10}$aryl, —C$_{3-10}$cycloalkyl, —C(O)$R^{31}$, —CO$_2R^{31}$, —C(=O)N$R^{31}$, or —S(O)$_{0-2}R^{31}$. In some embodiments, $R_{72}$ is hydrogen or —C$_{1-10}$alkyl. In some embodiments, $R_{72}$ is hydrogen.

In some embodiments of Formula II-B, each of $R_{10}$ and $R_{14}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent $R_{11}$ substituents. In some embodiments, each of $R_{10}$ and $R_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent $R_{11}$ substituents. In some embodiments, each of $R_{10}$ and $R_{14}$ is independently —C$_{1-10}$alkyl, —C$_{3-10}$aryl, —C$_{1-10}$hetaryl, or —C$_{1-10}$heterocyclyl, optionally substituted by one or more independent $R_{11}$ substituents.

In some embodiments of Formula II-B, each of $R_{11}$, $R_{12}$, $R_{13}$ and $R_{15}$ is independently hydrogen, halogen, —C$_{1-10}$alkyl, —C$_{3-10}$aryl, —C$_{3-10}$cycloalkyl, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula II-B, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl.

In some embodiments of Formula II-B, $X_1$ is C=O or $SO_2$, $X_2$ is $NR_1$ or $CR_1R'_1$, $X_3$ is $CR_3R_3'$ or C=O, Y is $CR_5$ and $X_4$ is N or $CR_4$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)OR^6$, —$OC(=O)R^6$, —$C(=O)N(R^{34})R^6$, or —$N(R^{34})C(=O)R^6$, wherein $R^6$ together with $R^{34}$ can optionally form a heterocyclic ring;

$R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is independently hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$, $R^{32}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula II-B, $X_1$ is C=O or $SO_2$, $X_2$ is $NR_1$ or $CR_1R_1'$, $X_3$ is $CR_3R_3'$, Y is $CR_5$ and $X_4$ is N or $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —$C(=O)N(R^{31})$—, or —$N(R^{31})C(=O)$—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents; or $R_3'$ is —$OR^6$, —$NR^6R^{34}$, —$C(=O)N(R^{34})R^6$, or —$N(R^{34})C(=O)R^6$, wherein $R^6$ together with $R^{34}$ can optionally form a heterocyclic ring;

$R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$;

each of R$_{10}$ and R$_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, R$_{13}$ and R$_{15}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$; and each of R$^{31}$, R$^{32}$ and R$^{34}$ is independently hydrogen or —C$_{1-10}$alkyl, or wherein R$^{31}$ together with R$^{32}$ form a heterocyclic ring.

In some embodiments of Formula II-B, X$_1$ is C=O, X$_2$ is NR$_1$, X$_3$ is CR$_3$R$_3$', Y is CR$_5$ and X$_4$ is CR$_4$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OR$^{31}$, —NR$^{31}$R$^{32}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, —C(=O)N(R$^{31}$)—, or —N(R$^{31}$)C(=O)—;

each of R$_3$, R$_3$' and R$_4$ is independently hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl; or R$_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring;

R$_5$ is hydrogen, halogen, or —C$_{1-10}$alkyl;

R$_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen or —C$_{1-10}$alkyl;

each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$, R$_{12}$, R$_{13}$ and R$_{15}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$; and each of R$^{31}$, R$^{32}$ and R$^{34}$ is independently hydrogen or —C$_{1-10}$alkyl.

In some embodiments of Formula II-B, X$_1$ is C=O, X$_2$ is NR$_1$, X$_3$ is CR$_3$R$_3$', Y is CR$_5$, X$_4$ is CR$_4$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, or —C(=O)N(R$^{31}$)—;

each of R$_3$, R$_3$' and R$_4$ is independently hydrogen, halogen, —OH, —CF$_3$, or —C$_{1-10}$alkyl; or R$_3$' is —OR$^6$ or —NR$^6$R$^{34}$, wherein R$^6$ together with R$^{34}$ can optionally form a heterocyclic ring;

R$_5$ is hydrogen;

R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen;

each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$, R$_{12}$ and R$_{15}$ is independently hydrogen, halogen, —C$_{1-10}$alkyl, —OH or —CF$_3$; and each of R$^{31}$ and R$^{34}$ is independently hydrogen or —C$_{1-10}$alkyl.

In some embodiments of Formula II-B, X$_1$ is C=O, X$_2$ is NR$_1$, X$_3$ is CR$_3$R$_3$', Y is CR$_5$, X$_4$ is CR$_4$;

R$_1$ is —C$_{1-10}$alkyl, —C$_{1-10}$alkyl-C$_{3-10}$aryl, or —C$_{1-10}$heterocyclyl-C$_{1-10}$alkyl, each of which is unsubstituted or substituted by one or more independent R$_{10}$ or R$_{11}$ substituents;

R$_{21}$ is -L-C$_{3-10}$aryl or -L-C$_{1-10}$hetaryl, each of which is unsubstituted or substituted by one or more independent R$_{12}$ substituents;

L is a bond or —N(R$^{31}$)—;

each of R$_3$, R$_3$' and R$_4$ is independently hydrogen, halogen, or —C$_{1-10}$alkyl;

R$_5$ is hydrogen;

R$_{72}$ is hydrogen;

each of R$_{10}$ is independently -C$_{3-10}$aryl, —C$_{1-10}$hetaryl, or —C$_{1-10}$heterocyclyl, optionally substituted by one or more independent R$_{11}$ substituents;

each of R$_{11}$ and R$_{12}$ is independently halogen, —C$_{1-10}$alkyl, —OH, —CF$_3$ or —OR$^{31}$; and each of R$^{31}$ is independently hydrogen or —C$_{1-10}$alkyl.

In some embodiments of Formula II-B, X$_1$ is C=O, X$_2$ is NR$_1$, X$_3$ is CR$_3$R$_3$', Y is CR$_5$, X$_4$ is CR$_4$;

R$_1$ is —C$_{1-10}$alkyl or —C$_{1-10}$alkyl-C$_{3-10}$aryl, each of which is unsubstituted or substituted by one or more independent R$_{11}$ substituents;

R$_{21}$ is pyridyl selected from the group consisting of 2-pyridyl, 3-pyridyl and 4-pyridyl, which is unsubstituted or substituted by one or more independent R$_{12}$ substituents;

L is a bond;

each of R$_3$, R$_3$' and R$_4$ is independently hydrogen or —C$_{1-10}$alkyl;

R$_5$ is hydrogen;

R$_{72}$ is hydrogen;

each of R$_{11}$ and R$_{12}$ is independently halogen, —C$_{1-10}$alkyl, —CF$_3$ or —OR$^{31}$; and each of R$^{31}$ is independently hydrogen or —C$_{1-10}$alkyl.

The invention also provides a compound as defined above, wherein the compound is of Formula II-C:

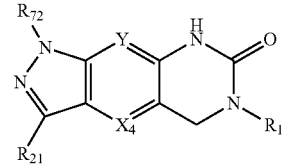

or a pharmaceutically acceptable salt or prodrug thereof, and wherein the substituents are as defined above.

In some embodiments of Formula II-C, Y is $CR_5$, $X_4$ is N or $CR_4$. In some embodiments of Formula II-C, Y is $CR_5$, $X_4$ is N or $CR_4$. In some embodiments of Formula II-C, Y is $CR_5$, $X_4$ is $CR_4$.

In some embodiments of Formula II-C, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-C, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-C, L is a bond, —O—, —N($R^{31}$)—, —$S(O)_{0-2}$—, —C(=O)—, —C(=O)O—, —OC(=O)—, —C(=O)N($R^{31}$)—, —N($R^{31}$)C(=O)—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —N($R^{31}$)—, —$S(O)_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula II-C, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula II-C, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula II-C, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, $R_{72}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, $R_{72}$ is independently hydrogen or —$C_{1-10}$alkyl. In some embodiments, $R_{72}$ is independently hydrogen.

In some embodiments of Formula II-C, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II-C, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, and $R_{13}$ is independently hydrogen, halogen, —$C_{1-10}$ alkyl, —OH or —$CF_3$.

In some embodiments of Formula II-C, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula II-C, Y is $CR_5$, $X_4$ is N or $CR_4$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$-alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OR^{31}$, —$NR^{31}R^{32}$, —$C(O)R^{31}$, —$CO_2R^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N(R^{31})—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents;

$R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula II-C, Y is $CR_5$, $X_4$ is N or $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

clyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N(R^{31})—, or —$N(R^{31})C(=O)$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents;

$R_5$ is hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, —$S(O)_{0-2}R^{31}$;

$R_{10}$ is —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula II-C, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N(R^{31})—, or —$N(R^{31})C(=O)$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl;

$R_5$ is hydrogen, halogen, or —$C_{1-10}$alkyl;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl.

In some embodiments of Formula II-C, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents;

L is a bond, —N($R^{31}$)—, or —C(=O)N($R^{31}$)—;

$R_4$ is hydrogen, halogen, —OH, —$CF_3$, or —$C_{1-10}$alkyl;

$R_5$ is hydrogen;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$; and each of $R^{31}$ is independently hydrogen or —$C_{1-10}$alkyl.

In some embodiments of Formula II-C, Y is $CR_5$, $X_4$ is $CR_4$;

$R_1$ is —$C_{1-10}$alkyl, —$C_{1-10}$alkyl-$C_{3-10}$aryl, or —$C_{1-10}$heterocyclyl-$C_{1-10}$alkyl, each of which is unsubstituted or substituted by one or more independent $R_{10}$ or $R_{11}$ substituents;

$R_{21}$ is -L-$C_{3-10}$aryl or -L-$C_{1-10}$hetaryl, each of which is unsubstituted or substituted by one or more independent $R_{12}$ substituents;

L is a bond or N($R^{31}$);

$R_4$ is hydrogen;

$R_5$ is hydrogen; $R_{72}$ is hydrogen;

each of $R_{10}$ is independently —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently halogen, —$C_{1-10}$alkyl, —OH, —$CF_3$ or —$OR^{31}$; and each of $R^{31}$ is independently hydrogen or —$C_{1-10}$alkyl.

In some embodiments of Formula II-C, Y is $CR_5$, $X_4$ is $CR_4$;

$R_1$ is —$C_{1-10}$alkyl or —$C_{1-10}$alkyl-$C_{3-10}$aryl, each of which is unsubstituted or substituted by one or more independent $R_{11}$ substituents;

$R_{21}$ is pyridyl selected from the group consisting of 2-pyridyl, 3-pyridyl and 4-pyridyl, which is unsubstituted or substituted by one or more independent $R_{12}$ substituents;

L is a bond;

$R_4$ is hydrogen;

$R_5$ is hydrogen; $R_{72}$ is hydrogen;

each of $R_{11}$ and $R_{12}$ is independently halogen, —$C_{1-10}$alkyl, —$CF_3$ or —$OR^{31}$; and each of $R^{31}$ is independently hydrogen or —$C_{1-10}$alkyl.

The invention further provides a compound as defined above, wherein the compound is of Formula II-D:

or a pharmaceutically acceptable salt or prodrug thereof, and wherein the substituents are as defined above.

In some embodiments of Formula II-D, Y is $CR_5$, $X_4$ is N or $CR_4$. In some embodiments of Formula II-D, Y is $CR_5$, $X_4$ is N or $CR_4$. In some embodiments of Formula II-D, Y is $CR_5$, $X_4$ is $CR_4$.

In some embodiments of Formula II-D, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-D, $R_{21}$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$NR^{31}$C(=O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$NR^{31}$C(=O)$R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-D, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula II-D, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —NR$^{31}$R$^{32}$, —NO$_2$, —CN, —S(O)$_{0-2}$R$^{31}$, —C$_{2-10}$alkenyl, or —C$_{2-10}$alkynyl. In some embodiments, R$_4$ is hydrogen, halogen, —OH, —CF$_3$, or —C$_{1-10}$alkyl.

In some embodiments of Formula II-D, R$_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, R$_5$ is hydrogen, halogen, or —C$_{1-10}$alkyl. In some embodiments, R$_5$ is hydrogen.

In some embodiments of Formula II-D, R$_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$. In some embodiments, R$_{72}$ is independently hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$. In some embodiments, R$_{72}$ is independently hydrogen or —C$_{1-10}$alkyl. In some embodiments, R$_{72}$ is independently hydrogen.

In some embodiments of Formula II-D, each of R$_{10}$ independently is —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent R$_{11}$ substituents. In some embodiments, each of R$_{10}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents. In some embodiments, each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents.

In some embodiments of Formula II-D, each of R$_{11}$, R$_{12}$, and R$_{13}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of R$_{11}$, R$_{12}$, and R$_{13}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of R$_{11}$, R$_{12}$, and R$_{13}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$. In some embodiments, each of R$_{11}$, R$_{12}$, and R$_{13}$ is independently hydrogen, halogen, —C$_{1-10}$ alkyl, —OH or —CF$_3$.

In some embodiments of Formula II-D, each of R$^{31}$, R$^{32}$, and R$^{33}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, or wherein R$^{31}$ together with R$^{32}$ form a heterocyclic ring. In some embodiments, each of R$^{31}$, R$^{32}$, and R$^{33}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring. In some embodiments, each of R$^{31}$, R$^{32}$, and R$^{33}$ is independently hydrogen or —C$_{1-10}$alkyl, or wherein R$^{31}$ together with R$^{32}$ form a heterocyclic ring. In some embodiments, each of R$^{31}$, R$^{32}$, and R$^{33}$ is independently hydrogen or —C$_{1-10}$alkyl.

In some embodiments of Formula II-D, Y is CR$_5$, X$_4$ is N or CR$_4$;

R$_1$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_{21}$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—;

R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, j—C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents;

R$_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$;

each of R$_{10}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$; and each of R$^{31}$ and R$^{32}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring.

In some embodiments of Formula II-D, Y is CR$_5$; X$_4$ is N or CR$_4$;

R$_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—;

R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)

$NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents;

$R_5$ is hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, —$S(O)_{0-2}R^{31}$;

$R_{10}$ is —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula II-D, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})C(=O)$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl;

$R_5$ is hydrogen, halogen, or —$C_{1-10}$alkyl;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl.

In some embodiments of Formula II-D, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—;

$R_4$ is hydrogen, halogen, —OH, —$CF_3$, or —$C_{1-10}$alkyl;

$R_5$ is hydrogen;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$; and each of $R^{31}$ is independently hydrogen or —$C_{1-10}$alkyl.

In some embodiments of Formula II-D, Y is $CR_5$, $X_4$ is $CR_4$;

$R_1$ is —$C_{1-10}$alkyl, —$C_{1-10}$alkyl-$C_{3-10}$aryl, or —$C_{1-10}$heterocyclyl-$C_{1-10}$alkyl, each of which is unsubstituted or substituted by one or more independent $R_{10}$ or $R_{11}$ substituents;

$R_{21}$ is -L-$C_{3-10}$aryl or -L-$C_{1-10}$hetaryl, each of which is unsubstituted or substituted by one or more independent $R_{12}$ substituents;

L is a bond or $N(R^{31})$;

$R_4$ is hydrogen;

$R_5$ is hydrogen; $R_{72}$ is hydrogen;

each of $R_{10}$ is independently —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently halogen, —$C_{1-10}$alkyl, —OH, —$CF_3$ or —$OR^{31}$; and each of $R^{31}$ is independently hydrogen or —$C_{1-10}$alkyl.

In some embodiments of Formula II-D, Y is $CR_5$, $X_4$ is $CR_4$;

$R_1$ is —$C_{1-10}$alkyl or —$C_{1-10}$alkyl-$C_{3-10}$aryl, each of which is unsubstituted or substituted by one or more independent $R_{11}$ substituents;

$R_{21}$ is pyridyl selected from the group consisting of 2-pyridyl, 3-pyridyl and 4-pyridyl, which is unsubstituted or substituted by one or more independent $R_{12}$ substituents;

L is a bond;

$R_4$ is hydrogen;

$R_5$ is hydrogen; $R_{72}$ is hydrogen;

each of $R_{11}$ and $R_{12}$ is independently halogen, —$C_{1-10}$alkyl, —$CF_3$ or —$OR^{31}$; and each of $R^{31}$ is independently hydrogen or —$C_{1-10}$alkyl.

The invention also provides a compound as defined above, wherein the compound is of Formula II-E:

or a pharmaceutically acceptable salt or prodrug thereof, and wherein the substituents are as defined above.

In some embodiments of Formula II-E, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-E, $R_{21}$ is hydrogen, halogen, —OH, —$CF_3$, —$OCF_3$, —$OR^{31}$, —$NR^{31}$, $R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-E, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl; L is a bond; and $R_1$ is —$C_{1-10}$alkyl-$C_{3-10}$aryl, —$C_{1-10}$alkyl-$C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl; L is a bond; and $R_1$ is

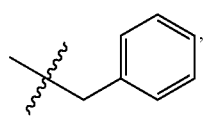

unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl; L is a bond; and $R_1$ is

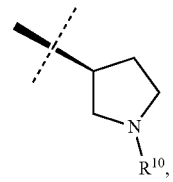

unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl; L is a bond; and $R_1$ is

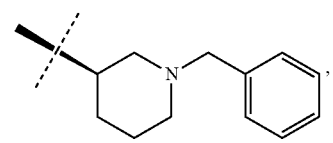

unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is —$C_{1-10}$alkyl-$C_{3-10}$aryl, —$C_{1-10}$alkyl-$C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is

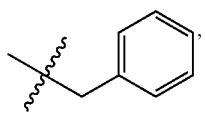

unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is

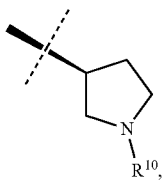

unsubstituted or substituted by one or more independent $R_{10}$ or $R_{11}$ substituents.

In some embodiments of Formula II-E, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is

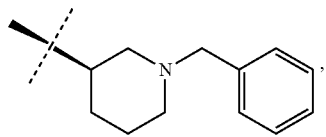

unsubstituted or substituted by one or more independent $R_{10}$ or $R_{11}$ substituents.

In some embodiments of Formula II-E, L is a bond, —O—, —N($R^{31}$)—, —S(O)$_{0-2}$—, —C(=O), —C(=O)O—, —OC(=O)—, —C(=O)N($R^{31}$)—, —N($R^{31}$)C(=O)—, —N$R^{31}$C(=O)O—, —N$R^{31}$C(=O)N$R^{32}$—, —N$R^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula II-E, $R_{72}$ is hydrogen, —$C_{1-10}$alkyl, —$C_{3-10}$aryl, —$C_{1-10}$hetaryl, $C_{3-10}$cycloalkyl, —$C_{1-10}$heterocyclyl, —OH, —$CF_3$, —C(O)$R^{31}$, —$CO_2R^{31}$, —C(=O)N$R^{31}$, or —S(O)$_{0-2}R^{31}$. In some embodiments, $R_{72}$ is independently hydrogen, —$C_{1-10}$alkyl, —$C_{3-10}$aryl, —$C_{3-10}$cycloalkyl, —C(O)$R^{31}$, —$CO_2R^{31}$, —C(=O)N$R^{31}$, or —S(O)$_{0-2}R^{31}$. In some embodiments, $R_{72}$ is independently hydrogen or —$C_{1-10}$alkyl. In some embodiments, $R_{72}$ is independently hydrogen.

In some embodiments of Formula II-E, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II-E, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$ or —N$R^{31}$C(=O)$R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$ or —N$R^{31}$C(=O)$R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —S(O)$_{0-2}R^{31}$. In some embodiments, each of $R_{11}$, $R_{12}$, and $R_{13}$ is independently hydrogen, halogen, —$C_{1-10}$ alkyl, —OH or —$CF_3$.

In some embodiments of Formula II-E, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula II-E, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$, -L-$C_{1-10}$alkyl, -L-$C_{2-10}$alkenyl, -L-$C_{2-10}$alkynyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —N$R^{31}$C(=O)O—, —N$R^{31}$C(=O)N$R^{32}$—, —N$R^{31}$S(O)$_{0-2}$—, or —S(O)$_{0-2}$N($R^{31}$)—;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —C(O)$R^{31}$, —$CO_2R^{31}$, —C(=O)N$R^{31}$, or —S(O)$_{0-2}R^{31}$;

each of $R_{10}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$ or —N$R^{31}$C(=O)$R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula II-E, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})C(=O)$—;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, —$S(O)_{0-2}R^{31}$;

$R_{10}$ is —$C_{1-10}$alkyl, —$C_{3-10}$aryl, —$C_{1-10}$hetaryl, $C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula II-E, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})C(=O)$—;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl.

In some embodiments of Formula II-E, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_2$, is halogen, —CN, -L-$C_{3-10}$aryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$ or —CN; and each of $R^{31}$ is independently hydrogen or —$C_{1-10}$alkyl.

In some embodiments of Formula II-E, $R_1$ is —$C_{1-10}$alkyl, —$C_{1-10}$alkyl-$C_{3-10}$aryl, or —$C_{1-10}$heterocyclyl-$C_{1-10}$alkyl, each of which is unsubstituted or substituted by one or more independent $R_{10}$ or $R_{11}$ substituents;

$R_2$, is -L-$C_{3-10}$aryl or -L-$C_{1-10}$hetaryl, each of which is unsubstituted or substituted by one or more independent $R_{12}$ substituents;

L is a bond or $N(R^{31})$;

$R_{72}$ is hydrogen;

each of $R_{10}$ is independently —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently halogen, —$C_{1-10}$alkyl, —OH, —$CF_3$ or —$OR^{31}$; and each of $R^{31}$ is independently hydrogen or —$C_{1-10}$alkyl.

In some embodiments of Formula II-E, $R_1$ is —$C_{1-10}$alkyl or —$C_{1-10}$alkyl-$C_{3-10}$aryl, each of which is unsubstituted or substituted by one or more independent $R_{11}$ substituents;

$R_{21}$ is pyridyl selected from the group consisting of 2-pyridyl, 3-pyridyl and 4-pyridyl, which is unsubstituted or substituted by one or more independent $R_{12}$ substituents;

L is a bond;

$R_{72}$ is hydrogen;

each of $R_{11}$ and $R_{12}$ is independently halogen, —$C_{1-10}$alkyl, —$CF_3$ or —$OR^{31}$; and each of $R^{31}$ is independently hydrogen or —$C_{1-10}$alkyl.

The invention further provides a compound as defined above, wherein the compound is of Formula II-F:

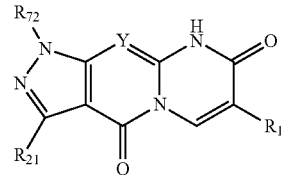

or a pharmaceutically acceptable salt or prodrug thereof, and wherein the substituents are as defined above.

In some embodiments of Formula II-F, Y is $CR_5$, $X_4$ is N or $CR_4$. In some embodiments of Formula II-F, Y is $CR_5$, $X_4$ is N or $CR_4$. In some embodiments of Formula II-F, Y is $CR_5$, $X_4$ is $CR_4$.

In some embodiments of Formula II-F, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{3-10}$cycloalkyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-F, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-F, L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—. In some embodiments, L is a bond, —$N(R^{31})$—, —$C(=O)N(R^{31})$—, or —$N(R^{31})C(=O)$—. In some embodiments, L is a bond, —$N(R^{31})$—, or —$C(=O)N(R^{31})$—.

In some embodiments of Formula II-F, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula II-F, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula II-F, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, $R_{72}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, $R_{72}$ is independently hydrogen or —$C_{1-10}$alkyl. In some embodiments, $R_{72}$ is independently hydrogen.

In some embodiments of Formula II-F, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II-F, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, and $R_{13}$ is independently hydrogen, halogen, —$C_{1-10}$ alkyl, —OH or —$CF_3$.

In some embodiments of Formula II-F, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula II-F, Y is $CR_5$, $X_4$ is N or $CR_4$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-

$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —N$R^{31}$C(=O)O—, —N$R^{31}$C(=O)N$R^{32}$—, —N$R^{31}$S(O)$_{0-2}$—, or —S(O)$_{0-2}$N($R^{31}$)—;

$R_4$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents;

$R_5$ is hydrogen, halogen, —C$_{1-10}$alkyl, —C$_{3-10}$aryl, —C$_{3-10}$cycloalkyl, —C$_{1-10}$heterocyclyl, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$;

$R_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)$R^{31}$, —CO$_2R^{31}$, —C(=O)N$R^{31}$, or —S(O)$_{0-2}R^{31}$;

each of $R_{10}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, optionally substituted by one or more independent $R_{11}$ substituents;

each of $R_{11}$, $R_{12}$, and $R_{13}$ is independently hydrogen, halogen, —C$_{1-10}$alkyl, —C$_{3-10}$aryl, —C$_{3-10}$cycloalkyl, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$; and each of $R^{31}$ and $R^{32}$ is independently hydrogen, —C$_{1-10}$alkyl, —C$_{3-10}$aryl, or —C$_{3-10}$cycloalkyl, or wherein $R^{31}$ together with $R^{32}$ form a heterocyclic ring.

In some embodiments of Formula II-F, Y is CR$_5$, X$_4$ is N or CR$_4$;

$R_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{10}$ or $R_{11}$ substituents;

$R_{21}$ is halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—;

$R_4$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{1-10}$alkyl, —C$_{2-10}$alkenyl, or —C$_{2-10}$alkynyl, each of which is unsubstituted or substituted by one or more independent $R_{13}$ substituents;

$R_5$ is hydrogen, halogen, —OH, —CF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$;

$R_{72}$ is hydrogen, —C$_{1-10}$alkyl, —C$_{3-10}$aryl, —C$_{3-10}$cycloalkyl, —C(O)$R^{31}$, —CO$_2R^{31}$, —C(=O)N$R^{31}$, —S(O)$_{0-2}R^{31}$;

$R_{10}$ is —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent $R_{11}$ substituents;

each of $R_{11}$, $R_{12}$, and $R_{13}$ is independently hydrogen, halogen, —C$_{1-10}$alkyl, —OH, —CF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$; and each of $R^{31}$ and $R^{32}$ is independently hydrogen or —C$_{1-10}$alkyl, or wherein $R^{31}$ together with $R^{32}$ form a heterocyclic ring.

In some embodiments of Formula II-F, Y is CR$_5$, X$_4$ is CR$_4$, $R_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{10}$ or $R_{11}$ substituents;

$R_{21}$ is halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—;

$R_4$ is hydrogen, halogen, —OH, —CF$_3$, —OCF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$, —C$_{1-10}$alkyl, —C$_{2-10}$alkenyl, or —C$_{2-10}$alkynyl;

$R_5$ is hydrogen, halogen, or —C$_{1-10}$alkyl;

$R_{72}$ is hydrogen or —C$_{1-10}$alkyl;

each of $R_{10}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent $R_{11}$ substituents;

each of $R_{11}$ and $R_{12}$ is independently hydrogen, halogen, —C$_{1-10}$alkyl, —OH, —CF$_3$, —O$R^{31}$, —N$R^{31}R^{32}$, —C(O)$R^{31}$, —CO$_2R^{31}$, —C(=O)N$R^{31}$, —NO$_2$, —CN, —S(O)$_{0-2}R^{31}$ or —N$R^{31}$C(=O)$R^{32}$; and each of $R^{31}$ and $R^{32}$ is independently hydrogen or —C$_{1-10}$alkyl.

In some embodiments of Formula II-F, Y is CR$_5$, X$_4$ is CR$_4$;

$R_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{10}$ or $R_{11}$ substituents;

$R_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents;

L is a bond, —N($R^{31}$)—, or —C(=O)N($R^{31}$)—;

$R_4$ is hydrogen, halogen, —OH, —CF$_3$, or —C$_{1-10}$alkyl;

$R_5$ is hydrogen;

$R_{72}$ is hydrogen;

each of $R_{10}$ is independently —C$_{1-10}$alkyl, —C$_{3-10}$aryl, —C$_{1-10}$hetaryl, or —C$_{1-10}$heterocyclyl, optionally substituted by one or more independent $R_{11}$ substituents;

each of $R_{11}$ and $R_{12}$ is independently hydrogen, halogen, —C$_{1-10}$alkyl, —OH or —CF$_3$; and each of $R^{31}$ is independently hydrogen or —C$_{1-10}$alkyl.

In some embodiments of Formula II-F, Y is CR$_5$, X$_4$ is CR$_4$;

$R_1$ is —C$_{1-10}$alkyl, —C$_{1-10}$alkyl-C$_{3-10}$aryl, or —C$_{1-10}$heterocyclyl-C$_{1-10}$alkyl, each of which is unsubstituted or substituted by one or more independent $R_{10}$ or $R_{11}$ substituents;

$R_{21}$ is -L-$C_{3-10}$aryl or -L-$C_{1-10}$hetaryl, each of which is unsubstituted or substituted by one or more independent $R_{12}$ substituents;

L is a bond or —N($R^{31}$)—;

$R_4$ is hydrogen;

$R_5$ is hydrogen; $R_{72}$ is hydrogen;

each of $R_{10}$ is independently —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently halogen, —$C_{1-10}$alkyl, —OH, —$CF_3$ or —$OR^{31}$; and each of $R^{31}$ is independently hydrogen or —$C_{1-10}$alkyl.

In some embodiments of Formula II-F, Y is $CR_5$, $X_4$ is $CR_4$;

$R_1$ is —$C_{1-10}$alkyl or —$C_{1-10}$alkyl-$C_{3-10}$aryl, each of which is unsubstituted or substituted by one or more independent $R_{11}$ substituents;

$R_{21}$ is pyridyl selected from the group consisting of 2-pyridyl, 3-pyridyl and 4-pyridyl, which is unsubstituted or substituted by one or more independent $R_{12}$ substituents;

L is a bond;

$R_4$ is hydrogen;

$R_5$ is hydrogen; $R_{72}$ is hydrogen;

each of $R_{11}$ and $R_{12}$ is independently halogen, —$C_{1-10}$alkyl, —$CF_3$ or —$OR^{31}$; and each of $R^{31}$ is independently hydrogen or —$C_{1-10}$alkyl.

The invention further provides a compound as defined above, wherein the compound is of Formula II-G:

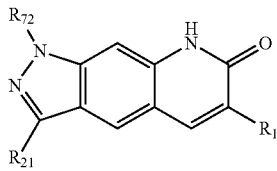

or a pharmaceutically acceptable salt or prodrug thereof, and wherein the substituents are as defined above.

In some embodiments of Formula II-G, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula II-G, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula II-G, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R^{31}$ is independently hydrogen or —$C_{1-10}$alkyl; L is a bond; and $R_1$ is —$C_{1-10}$alkyl-$C_{3-10}$aryl, —$C_{1-10}$alkyl-$C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R^{31}$ is independently hydrogen or —$C_{1-10}$alkyl; L is a bond; and $R_1$ is

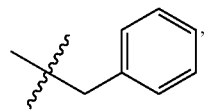 [SMILES: *Cc1ccccc1]

unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$ alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl; L is a bond; and $R_1$ is

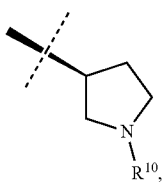

unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; wherein the $C_{1-10}$hetaryl of $R_{21}$ comprises one or more nitrogen atoms; each $R_{12}$ substituent, when present, is independently selected from the group consisting of —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl; L is a bond; and $R_1$ is

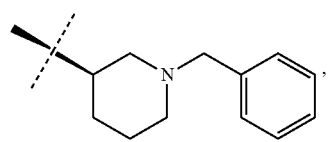

unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is —$C_{1-10}$alkyl-$C_{3-10}$aryl, —$C_{1-10}$alkyl-$C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is

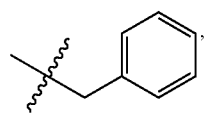

unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is

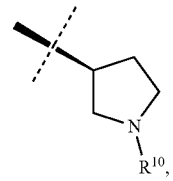

unsubstituted or substituted by one or more independent $R_{10}$ or $R_{11}$ substituents.

In some embodiments of Formula II-G, $R_{21}$ is -L-$C_{1-10}$hetaryl unsubstituted or substituted by one or more independent $R_{12}$ substituents; the $C_{1-10}$hetaryl of $R_{21}$ is selected from the group consisting of pyrazolyl, pyridinyl, pyrazinyl, pyrimidinyl, and pyridazinyl; each $R_{12}$ substituent, when present, is independently selected from the group consisting -Me, -Et, -i-Pr, -n-Pr, OH, —OMe, —OEt, —OPr; L is a bond; and $R_1$ is

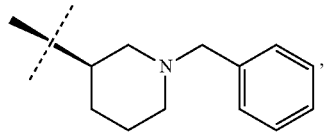

unsubstituted or substituted by one or more independent $R_{10}$ or $R_{11}$ substituents.

In some embodiments of Formula II-G, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula II-G, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —C(O)$R^{31}$, —$CO_2R^{31}$, —C(=O)$NR^{31}$, or —S(O)$_{0-2}R^{31}$. In some embodiments, $R_{72}$ is independently hydrogen, —$C_{1-10}$alkyl, —$C_{3-10}$aryl, —$C_{3-10}$cycloalkyl, —C(O)$R^{31}$, —$CO_2R^{31}$, —C(=O)$NR^{31}$, or —S(O)$_{0-2}R^{31}$. In some embodiments, $R_{72}$ is independently hydrogen or —$C_{1-10}$alkyl. In some embodiments, $R_{72}$ is independently hydrogen.

In some embodiments of Formula II-G, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula II-G, each of $R_{11}$, $R_{12}$, and $R_{13}$ is independently hydrogen, halogen, $-C_{1-10}$alkyl, $-C_{3-10}$aryl, $-C_{3-10}$cycloalkyl, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$. In some embodiments, each of $R_{11}$, $R_{12}$, and $R_{13}$ is independently hydrogen, halogen, $-C_{1-10}$alkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$. In some embodiments, each of $R_{11}$, $R_{12}$, and $R_{13}$ is independently hydrogen, halogen, $-C_{1-10}$alkyl, $-OH$, $-CF_3$, $-OR^3$, $-NR^{31}R^{32}$, $-NO_2$, $-CN$, or $-S(O)_{0-2}R^{31}$. In some embodiments, each of $R_{11}$, $R_{12}$, and $R_{13}$ is independently hydrogen, halogen, $-C_{1-10}$ alkyl, $-OH$ or $-CF_3$.

In some embodiments of Formula II-G, each of $R^{31}$, $R^{32}$, and $R^{33}$ is independently hydrogen, halogen, $-C_{1-10}$alkyl, $-C_{2-10}$alkenyl, $-C_{2-10}$alkynyl, $-C_{1-10}$heteroalkyl, $-C_{3-10}$aryl, $-C_{1-10}$hetaryl, $-C_{3-10}$cycloalkyl, $-C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, $-C_{1-10}$alkyl, $-C_{3-10}$aryl, or $-C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or $-C_{1-10}$alkyl, or wherein $R^{31}$ together with $R^{32}$ form a heterocyclic ring. In some embodiments, each of $R^{31}$, $R^{32}$, and $R^{33}$ is independently hydrogen or $-C_{1-10}$alkyl.

In some embodiments of Formula II-G;

$R_1$ is $-C_{1-10}$alkyl, $-C_{3-10}$aryl, $-C_{1-10}$hetaryl, $-C_{3-10}$cycloalkyl, $-C_{1-10}$heterocyclyl, $-C_{1-10}$alkyl-$C_{3-10}$aryl, $-C_{1-10}$hetaryl, $-C_{1-10}$alkyl-$C_{3-10}$cycloalkyl, $-C_{1-10}$alkyl-$C_{1-10}$heterocyclyl, $-C_{3-10}$cycloalkyl-$C_{1-10}$alkyl, $-C_{3-10}$cycloalkyl-$C_{3-10}$aryl, $-C_{3-10}$cycloalkyl-$C_{1-10}$hetaryl, $-C_{3-10}$cycloalkyl-$C_{1-10}$heterocyclyl, $-C_{1-10}$heterocyclyl-$C_{1-10}$alkyl, $-C_{1-10}$heterocyclyl-$C_{3-10}$aryl, $-C_{1-10}$heterocyclyl-$C_{1-10}$hetaryl, or $-C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-O-$, $-N(R^{31})-$, $-S(O)_{0-2}-$, $-C(=O)-$, $-C(=O)O-$, $-OC(=O)-$, $-C(=O)N(R^{31})-$, $-N(R^{31})C(=O)-$, $-NR^{31}C(=O)O-$, $-NR^{31}C(=O)NR^{32}-$, $-NR^{31}S(O)_{0-2}-$, or $-S(O)_{0-2}N(R^{31})-$;

$R_{72}$ is hydrogen, $-C_{1-10}$alkyl, $-C_{3-10}$aryl, $-C_{1-10}$hetaryl, $-C_{3-10}$cycloalkyl, $-C_{1-10}$heterocyclyl, $-OH$, $-CF_3$, $-C(O)R^{31}$, $-CO_2R^{31}$, $-C(=O)NR^{31}$, or $-S(O)_{0-2}R^{31}$;

each of $R_{10}$ is independently $-C_{1-10}$alkyl, $-C_{2-10}$alkenyl, $-C_{2-10}$alkynyl, $-C_{1-10}$heteroalkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, and $R_{13}$ is independently hydrogen, halogen, $-C_{1-10}$alkyl, $-C_{3-10}$aryl, $-C_{3-10}$cycloalkyl, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$; and each of $R^{31}$ and $R^{32}$ is independently hydrogen, $-C_{1-10}$alkyl, $-C_{3-10}$aryl, or $-C_{3-10}$cycloalkyl, or wherein $R^{31}$ together with $R^{32}$ form a heterocyclic ring.

In some embodiments of Formula II-G;

$R_1$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$;

$R_{72}$ is hydrogen, $-C_{1-10}$alkyl, $-C_{3-10}$aryl, $-C_{3-10}$cycloalkyl, $-C(O)R^{31}$, $-CO_2R^{31}$, $-C(=O)NR^{31}$, $-S(O)_{0-2}R^{31}$;

$R_{10}$ is $-C_{1-10}$alkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, and $R_{13}$ is independently hydrogen, halogen, $-C_{1-10}$alkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$; and each of $R^{31}$ and $R^{32}$ is independently hydrogen or $-C_{1-10}$alkyl, or wherein $R^{31}$ together with $R^{32}$ form a heterocyclic ring.

In some embodiments of Formula II-G;

$R_1$ is $C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$;

$R_{72}$ is hydrogen or $-C_{1-10}$alkyl;

each of $R_{10}$ is independently $-C_{1-10}$alkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$ and $R_{12}$ is independently hydrogen, halogen, $-C_{1-10}$alkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$; and each of $R^{31}$ and $R^{32}$ is independently hydrogen or $-C_{1-10}$alkyl.

In some embodiments of Formula II-G;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-CN$, -L-$C_{1-10}$alkyl, -L-$C_{3-10}$cycloalkyl, or -L-$C_{1-10}$heterocyclyl, each of which is unsubstituted or substituted by one or more independent $R_{12}$ substituents;

L is a bond, $-N(R^{31})-$, or $-C(=O)N(R^{31})-$;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$; and each of $R^{31}$ is independently hydrogen or —$C_{1-10}$alkyl.

In some embodiments of Formula II-G;

$R_1$ is —$C_{1-10}$alkyl, —$C_{1-10}$alkyl-$C_{3-10}$aryl, or —$C_{1-10}$heterocyclyl-$C_{1-10}$alkyl, each of which is unsubstituted or substituted by one or more independent $R_{10}$ or $R_{11}$ substituents;

$R_{21}$ is -L-$C_{3-10}$aryl or -L-$C_{1-10}$hetaryl, each of which is unsubstituted or substituted by one or more independent $R_{12}$ substituents;

L is a bond or N($R^{31}$);

$R_{72}$ is hydrogen;

each of $R_{10}$ is independently —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently halogen, —$C_{1-10}$alkyl, —OH, —$CF_3$ or —$OR^{31}$; and each of $R^{31}$ is independently hydrogen or —$C_{1-10}$alkyl.

In some embodiments of Formula II-G;

$R_1$ is —$C_{1-10}$alkyl or —$C_{1-10}$alkyl-$C_{3-10}$aryl, each of which is unsubstituted or substituted by one or more independent $R_{11}$ substituents;

$R_{21}$ is pyridyl selected from the group consisting of 2-pyridyl, 3-pyridyl and 4-pyridyl, which is unsubstituted or substituted by one or more independent $R_{12}$ substituents;

L is a bond;

each of $R_{11}$ and $R_{12}$ is independently halogen, —$C_{1-10}$alkyl, —$CF_3$ or —$OR^{31}$; and each of $R^{31}$ is independently hydrogen or —$C_{1-10}$alkyl.

The invention also provides a compound as defined above, wherein the compound is of Formula III:

or a pharmaceutically acceptable salt or prodrug thereof, and wherein the substituents are as defined above.

In some embodiments of Formula III, $X_1$ is C═O, $X_2$ is $NR_1$ or $CR_1R_1'$, and $X_3$ is $CR_3R_3'$. In some embodiments, $X_1$ is C═O, $X_2$ is $NR_1$ or $CR_1R_1'$, and $X_3$ is C═O. In some embodiments, $X_1$ is C═S, $X_2$ is $CR_1R_1'$, and $X_3$ is $CR_3R_3'$. In some embodiments, $X_1$ is $SO_2$, $X_2$ is $NR_{12}$, and $X_3$ is $CR_3R_3'$. In some embodiments, $X_1$ is $SO_2$, and $X_2$ and $X_3$ is $R_1C$═$CR_3$.

In some embodiments of Formula III, Y is $CR_5$, $X_4$ is N or $CR_4$, $X_5$ is C and $X_6$ is C. In some embodiments, Y is $CR_5$, $X_4$ is N or $CR_4$, $X_5$ is N or C and $X_6$ is C. In some embodiments, Y is $CR_5$, $X_4$ is $CR_4$, $X_5$ is C and $X_6$ is C. In some embodiments, Y is $CR_5$, $X_4$ is $CR_4$, $X_5$ is N and $X_6$ is C. In some embodiments, Y is $CR_5$, $X_4$ is $CR_4$, $X_5$ is C and $X_6$ is N.

In some embodiments of Formula III, $X_7$ is $CR_{71}$, $X_8$ is N, $X_9$ is $CR_{21}$, and $X_{10}$ is N. In some embodiments, $X_7$ is $CR_{71}$, $X_8$ is N, $X_9$ is $CR_{21}$, and $X_{10}$ is $CR_{91}$. In some embodiments, $X_7$ is $NR_{72}$, $X_8$ is $CR_{81}$, $X_9$ is $CR_{21}$, and $X_{10}$ is N. In some embodiments, $X_7$ is $NR_{72}$, $X_8$ is $CR_{81}$, $X_9$ is $CR_{21}$, and $X_{10}$ is $CR_{91}$. In some embodiments, $X_7$ is $CR_{71}$, $X_8$ is $CR_{81}$, $X_9$ is $NR_{22}$, and $X_{10}$ is N. In some embodiments, $X_7$ is $CR_{71}$, $X_8$ is $CR_{81}$, $X_9$ is $NR_{22}$, and $X_{10}$ is $CR_{91}$.

In some embodiments of Formula III, $X_1$ is C═O or $SO_2$, $X_2$ is $NR_1$ or $CR_1R_1'$, $X_3$ is $CR_3R_3'$ or C═O, Y is $CR_5$, $X_4$ is N or $CR_4$, $X_5$ is N or C, $X_6$ is C, $X_7$ is N or $NR_7$ or $CR_{71}$, $X_8$ is N or $CR_{81}$, $X_9$ is $NR_{22}$ or $CR_{21}$, and $X_{10}$ is N or $CR_{91}$. In some embodiments, $X_1$ is C═O, $X_2$ is $NR_1$ or $CR_1R_1'$, $X_3$ is $CR_3R_3'$, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{22}$ or $CR_{21}$, and $X_{10}$ is N or $CR_{91}$. In some embodiments, $X_1$ is C═O, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$.

In some embodiments of Formula III, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents In some embodiments of Formula III, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula III, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —C(═O)$NR^{31}$, —$NO_2$, —CN, —S(O)$_{0-2}R^{31}$, —$NR^{31}$C(═O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —C(═O)$NR^{31}$, —$NO_2$, —CN, —S(O)$_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents. In some embodiments, $R_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents.

In some embodiments on Formula III, $R_{22}$ is hydrogen, —OH, —CF$_3$, —C(O)R$^{31}$, —CO$_2$R$^{31}$, —C(=O)NR$^{31}$, —S(O)$_{0-2}$R$^{31}$, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents. In some embodiments, $R_{22}$ is —OH, —CF$_3$, —C(O)R$^{31}$, —CO$_2$R$^{31}$, —C(=O)NR$^{31}$, —S(O)$_{0-2}$R$^{31}$, -L-C$_{3-10}$aryl, -L-C$_{1-10}$hetaryl, -L-C$_{3-10}$cycloalkyl, or -L-C$_{1-10}$heterocyclyl each of which is unsubstituted or substituted by one or more independent $R_{12}$ substituents. In some embodiments, $R_{22}$ is —OH, —CF$_3$, —C(O)R$^{31}$, —CO$_2$R$^{31}$, —C(=O)NR$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents. In some embodiments, $R_{22}$ is -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent $R_{12}$ substituents.

In some embodiments of Formula III, L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—. In some embodiments, L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—. In some embodiments, L is a bond, —N(R$^{31}$)—, —C(=O)N(R$^{31}$)—, or —N(R$^{31}$)C(=O)—. In some embodiments, L is a bond, —N(R$^{31}$)—, or —C(=O)N(R$^{31}$)—.

In some embodiments of Formula III, $R_3$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, —OR$^{31}$, —NR$^{31}$R$^{32}$, —C(O)R$^{31}$, —CO$_2$R$^{31}$, —R$_3$ is hydrogen, halogen, —OH, —CF$_3$, —OCF$_3$, —OR$^{31}$, —NR$^{31}$R$^{32}$, —C(O)R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_3$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{2-10}$alkenyl, or —C$_{2-10}$alkynyl. In some embodiments, $R_3$ is hydrogen, halogen, —OH, —CF$_3$, or —C$_{1-10}$alkyl.

In some embodiments of Formula III, $R_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_3$' is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_3$' is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, $R_3$' is hydrogen, halogen, —OH, —CF$_3$, or —C$_{1-10}$alkyl.

In some embodiments of Formula III, $R_3$' is —OR$^6$, —NR$^6$R$^{34}$, —S(O)$_{0-2}$R$^6$, —C(=O)R$^6$, —C(=O)OR$^6$, —OC(=O)R$^6$, —C(=O)N(R$^{34}$)R$^6$, or —N(R$^{34}$)C(=O)R$^6$, wherein R$^6$ together with R$^{34}$ can optionally form a heterocyclic ring. In some embodiments, $R_3$' is —OR$^6$, —NR$^6$R$^{34}$, —C(=O)N(R$^{34}$)R$^6$, or —N(R$^{34}$)C(=O)R$^6$, wherein R$^6$ together with R$^{34}$ can optionally form a heterocyclic ring. In some embodiments, $R_3$' is —OR$^6$ or —NR$^6$R$^{34}$, wherein R$^6$ together with R$^{34}$ can optionally form a heterocyclic ring.

In some embodiments of Formula III, $R_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent $R_{13}$ substituents. In some embodiments, $R_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent $R_{13}$ substituents. In some embodiments, $R_4$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, $R_4$ is hydrogen, halogen, —OH, —CF$_3$, or —C$_{1-10}$alkyl.

In some embodiments of Formula III, $R_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, $R_5$ is hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, $R_5$ is hydrogen, halogen, or —C$_{1-10}$alkyl. In some embodiments, $R_5$ is hydrogen.

In some embodiments of Formula III, $R_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{14}$ or $R_{15}$ substituents. In some embodiments, $R_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{14}$ or $R_{15}$ substituents. In some embodiments, $R_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent $R_{14}$ or $R_{15}$ substituents.

In some embodiments of Formula III, each of $R_{71}$, $R_{81}$ and $R_{91}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, or —$C_{1-10}$alkyl. In some embodiments, each of $R_{71}$, $R_{81}$ and $R_{91}$ is independently hydrogen.

In some embodiments of Formula III, each of $R_{72}$, $R_{82}$ and $R_{92}$ is independently hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen or —$C_{1-10}$alkyl. In some embodiments, each of $R_{72}$, $R_{82}$ and $R_{92}$ is independently hydrogen.

In some embodiments of Formula III, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula III, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula III, each of $R^{31}$, $R^{32}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$ and $R^{34}$ is independently hydrogen or —$C_{1-10}$alkyl.

In some embodiments of Formula III, $X_1$ is C=O or $SO_2$, $X_2$ is $NR_1$ or $CR_1R_1'$, $X_3$ is $CR_3R_3'$ or C=O, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{22}$ or $CR_{21}$, and $X_{10}$ is N or $CR_{91}$;

$R_1$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —$S(O)_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —$S(O)_{0-2}$N($R^{31}$)—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —$C(=O)R^6$, —$C(=O)OR^6$, —$OC(=O)$ $R^6$, —$C(=O)N(R^{34})R^6$, or —$N(R^{34})C(=O)R^6$, wherein $R^6$ together with $R^{34}$ can optionally form a heterocyclic ring;

each of $R_5$, $R_{71}$, $R_{81}$ and $R_{91}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, —$S(O)_{0-2}R^{31}$ or —$C(=O)SR^{31}$;

each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-C_{3-10}$aryl, $-C_{3-10}$cycloalkyl, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

each of $R^{31}$, $R^{32}$ and $R^{34}$ is independently hydrogen, $-C_{1-10}$alkyl, $-C_{3-10}$aryl, or $-C_{3-10}$cycloalkyl, or wherein $R^{31}$ together with $R^{32}$ form a heterocyclic ring; and wherein ring A comprises one or more heteroatoms selected from N, O, or S.

In some embodiments of Formula III, $X_1$ is $C=O$, $X_2$ is $NR_1$ or $CR_1R_1'$, $X_3$ is $CR_3R_3'$, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{22}$ or $CR_{21}$, and $X_{10}$ is N or $CR_{91}$;

$R_1$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is $-OH$, $-CF_3$, $-C(O)R^{31}$, $-CO_2R^{31}$, $-C(=O)NR^{31}$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$;

each of $R_3$, $R_3'$ and $R_4$ is independently hydrogen, halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, $-C_{1-10}$alkyl, $-C_{2-10}$alkenyl, or $-C_{2-10}$alkynyl, each of which is unsubstituted or substituted by one or more independent $R_{13}$ substituents; or $R_3'$ is $-OR^6$, $-NR^6R^{34}$, $-C(=O)N(R^{34})R^6$, or $-N(R^{34})C(=O)R^6$, wherein $R^6$ together with $R^{34}$ can optionally form a heterocyclic ring;

each of $R_5$, $R_{71}$ and $R_{91}$ is independently hydrogen, halogen, $-C_{1-10}$alkyl, $-C_{3-10}$aryl, $-C_{3-10}$cycloalkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

$R_6$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen, $-C_{1-10}$alkyl, $-C_{3-10}$aryl, $-C_{3-10}$cycloalkyl, $-C(O)R^{31}$, $-CO_2R^{31}$, $-C(=O)NR^{31}$, $-S(O)_{0-2}R^{31}$, $-C(=S)OR^{31}$, or $-C(=O)SR^{31}$;

each of $R_{10}$ and $R_{14}$ is independently $-C_{1-10}$alkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

each of $R^{31}$, $R^{32}$ and $R^{34}$ is independently hydrogen or $-C_{1-10}$alkyl, or wherein $R^{31}$ together with $R^{32}$ form a heterocyclic ring; and wherein ring A comprises one or more heteroatoms selected from N, O, or S.

In some embodiments of Formula III, $X_1$ is $C=O$, $X_2$ is $NR_{12}$, $X_3$ is $CR_3R_3'$, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is $-OH$, $-CF_3$, $-C(O)R^{31}$, $-CO_2R^{31}$, $-C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-N(R^{31})-$, $-C(=O)N(R^{31})-$, or $-N(R^{31})C(=O)-$;

each of $R_3$, $R_3'$ and $R_4$ is independently hydrogen, halogen, $-OH$, $-CF_3$, $-OCF_3$, $-OR^{31}$, $-NR^{31}R^{32}$, $-NO_2$, $-CN$, $-S(O)_{0-2}R^{31}$, $-C_{2-10}$alkenyl, or $-C_{2-10}$alkynyl; or $R_3'$ is $-OR^6$, $-NR^6R^{34}$, $-S(O)_{0-2}R^6$, $-C(=O)R^6$, $-C(=O)OR^6$, $-OC(=O)R^6$, $-C(=O)N(R^{34})R^6$, or $-N(R^{34})C(=O)R^6$, wherein $R^6$ together with $R^{34}$ can optionally form a heterocyclic ring;

each of $R_5$ and $R_{91}$ is independently hydrogen, halogen, $-C_{1-10}$alkyl, or $-OH$;

$R_6$ is $-C_{1-10}$alkyl, $-C_{3-10}$aryl, $-C_{1-10}$hetaryl, $-C_{3-10}$cycloalkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{3-10}$cycloalkyl-$C_{1-10}$alkyl, $-C_{3-10}$cycloalkyl-$C_{3-10}$aryl, $-C_{3-10}$cycloalkyl-$C_{1-10}$hetaryl, $-C_{3-10}$cycloalkyl-$C_{1-10}$heterocyclyl, $-C_{1-10}$heterocyclyl-$C_{1-10}$alkyl, $-C_{1-10}$heterocyclyl-$C_{3-10}$aryl, $-C_{1-10}$heterocyclyl-$C_{1-10}$hetaryl, or $-C_{1-10}$heterocyclyl-$C_{3-10}$cycloalkyl, each of which is unsubstituted or substituted by one or more independent $R_{14}$ or $R_{15}$ substituents;

$R_{72}$ is hydrogen or $-C_{1-10}$alkyl;

each of $R_{10}$ and $R_{14}$ is independently $-C_{1-10}$alkyl, $-C_{3-10}$aryl, $-C_{1-10}$hetaryl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-OH$, $-CF_3$, $-OR^3$, $-NR^{31}R^{32}$, $-NO_2$, $-CN$, or $-S(O)_{0-2}R^{31}$, each of $R^{31}$, $R^{32}$ and $R^{34}$ is independently hydrogen or $-C_{1-10}$alkyl; and wherein ring A comprises one or more heteroatoms selected from N, O, or S.

In some embodiments of Formula III, $X_1$ is $C=O$, $X_2$ is $NR_{12}$, $X_3$ is $CR_3R_3'$, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —N($R^{31}$)—, or —C(=O)N($R^{31}$)—;

each of $R_3$, $R_3'$ and $R_4$ is independently hydrogen, halogen, —OH, —$CF_3$, or —$C_{1-10}$alkyl; or $R_3'$ is —$OR^6$ or —$NR^6R^{34}$, wherein $R^6$ together with $R^{34}$ can optionally form a heterocyclic ring;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$;

each of $R^{31}$ and $R^{34}$ is independently hydrogen or —$C_{1-10}$alkyl; and wherein ring A comprises one or more heteroatoms selected from N, O, or S.

The invention also provides a compound as defined above, wherein the compound is of Formula III-A:

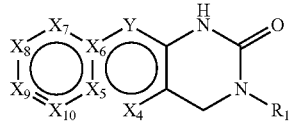

or a pharmaceutically acceptable salt or prodrug thereof, and wherein the substituents are as defined above.

In some embodiments of Formula III-A, Y is $CR_5$, $X_4$ is N or $CR_4$, $X_5$ is C and $X_6$ is C. In some embodiments, Y is $CR_5$, $X_4$ is $CR_4$, $X_5$ is N or C and $X_6$ is C. In some embodiments, Y is $CR_5$, $X_4$ is $CR_4$, $X_5$ is C and $X_6$ is C. In some embodiments, Y is $CR_5$, $X_4$ is $CR_4$, $X_5$ is N and $X_6$ is C. In some embodiments, Y is $CR_5$, $X_4$ is $CR_4$, $X_5$ is C and $X_6$ is N.

In some embodiments of Formula III-A, $X_7$ is $CR_{71}$, $X_8$ is N, $X_9$ is $CR_{21}$, and $X_{10}$ is N. In some embodiments, $X_7$ is $CR_{71}$, $X_8$ is N, $X_9$ is $CR_{21}$, and $X_{10}$ is $CR_{91}$. In some embodiments, $X_7$ is $NR_{72}$, $X_8$ is $CR_{81}$, $X_9$ is $CR_{21}$, and $X_{10}$ is N. In some embodiments, $X_7$ is $NR_{72}$, $X_8$ is $CR_{81}$, $X_9$ is $CR_{21}$, and $X_{10}$ is $CR_{91}$. In some embodiments, $X_7$ is $CR_{71}$, $X_8$ is $CR_{81}$, $X_9$ is $NR_{22}$, and $X_{10}$ is N. In some embodiments, $X_7$ is $CR_{71}$, $X_8$ is $CR_{81}$, $X_9$ is $NR_{22}$, and $X_{10}$ is $CR_{91}$.

In some embodiments of Formula III-A, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{21}$ or $CR_{21}$, and $X_{10}$ is N or $CR_{91}$. In some embodiments, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{22}$ or $CR_{21}$, and $X_{10}$ is N or $CR_{91}$. In some embodiments, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$.

In some embodiments of Formula III-A, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$heteroaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula III-A, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, hydrogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}$, $R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula III-A, $R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, —$S(O)_{0-2}R^{31}$, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula III-A, L is a bond, —O—, —N($R^{31}$)—, —$S(O)_{0-2}$—, —C(=O)—, —C(=O)O—, —OC(=O)—, —C(=O)N($R^{31}$)—, —$N(R^{31})$C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—. In some embodiments, L is a bond, —O—, —N($R^{31}$)—, —$S(O)_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula III-A, $R_4$ is hydrogen, halogen, —OH, —$CF_3$, —$OCF_3$, —$OR^{31}$, —$NR^{31}R^{32}$, —C(O)R$^{31}$, —CO$_2$R$^{31}$, —C(═O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(═O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, R$_4$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl. In some embodiments, R$_4$ is hydrogen, halogen, —OH, —CF$_3$, or —C$_{1-10}$alkyl.

In some embodiments of Formula III-A, R$_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(═O)NR$^{31}$, —NO$_2$, —CN, —S(O)$_{0-2}$R$^{31}$ or —NR$^{31}$C(═O)R$^{32}$. In some embodiments, R$_5$ is hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(═O)NR$^{31}$, —NO$_2$, —CN, —S(O)$_{0-2}$R$^{31}$ or —NR$^{31}$C(═O)R$^{32}$. In some embodiments, R$_5$ is hydrogen, halogen, or —C$_{1-10}$alkyl. In some embodiments, R$_5$ is hydrogen.

In some embodiments of Formula III-A, each of R$_{71}$, R$_{81}$ and R$_{91}$ is independently hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(═O)NR$^{31}$, —NO$_2$, —CN, —S(O)$_{0-2}$R$^{31}$ or —NR$^{31}$C(═O)R$^{32}$. In some embodiments, each of R$_{71}$, R$_{81}$ and R$_{91}$ is independently hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(═O)NR$^{31}$, —NO$_2$, —CN, —S(O)$_{0-2}$R$^{31}$ or —NR$^{31}$C(═O)R$^{32}$. In some embodiments, each of R$_{71}$, R$_{81}$ and R$_{91}$ is independently hydrogen, halogen, or —C$_{1-10}$alkyl. In some embodiments, each of R$_{71}$, R$_{81}$ and R$_{91}$ is independently hydrogen.

In some embodiments of Formula III-A, each of R$_{72}$, R$_{82}$ and R$_{92}$ is independently hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(═O)NR$^{31}$, or —S(O)$_{0-2}$R$^{31}$. In some embodiments, each of R$_{72}$, R$_{82}$ and R$_{92}$ is independently hydrogen, —C$_{1-10}$alkyl, —C$_{3-10}$aryl, —C$_{3-10}$cycloalkyl, —C(O)R$^{31}$, —CO$_2$R$^{31}$, —C(═O)NR$^{31}$, or —S(O)$_{0-2}$R$^{31}$. In some embodiments, each of R$_{72}$, R$_{82}$ and R$_{92}$ is independently hydrogen or —C$_{1-10}$alkyl. In some embodiments, each of R$_{72}$, R$_{82}$ and R$_{92}$ is independently hydrogen.

In some embodiments of Formula III-A, each of R$_{10}$ independently is —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent R$_{11}$ substituents. In some embodiments, each of R$_{10}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents. In some embodiments, each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents.

In some embodiments of Formula III-A, each of R$_{11}$, R$_{12}$, and R$_{13}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(═O) NR$^{31}$, —NO$_2$, —CN, —S(O)$_{0-2}$R$^{31}$ or —NR$^{31}$C(═O)R$^{32}$. In some embodiments, each of R$_{11}$, R$_{12}$, and R$_{13}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(═O) NR$^{31}$, —NO$_2$, —CN, —S(O)$_{0-2}$R$^{31}$ or —NR$^{31}$C(═O)R$^{32}$. In some embodiments, each of R$_{11}$, R$_{12}$, and R$_{13}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$. In some embodiments, each of R$_{11}$, R$_{12}$, and R$_{13}$ is independently hydrogen, halogen, —C$_{1-10}$ alkyl, —OH or —CF$_3$.

In some embodiments of Formula III-A, each of R$^{31}$, R$^{32}$, and R$^{33}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, or wherein R$^{31}$ together with R$^{32}$ form a heterocyclic ring. In some embodiments, each of R$^{31}$, R$^{32}$, and R$^{33}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring. In some embodiments, each of R$^{31}$, R$^{32}$, and R$^{33}$ is independently hydrogen or —C$_{1-10}$alkyl, or wherein R$^{31}$ together with R$^{32}$ form a heterocyclic ring. In some embodiments, each of R$^{31}$, R$^{32}$, and R$^{33}$ is independently hydrogen or —C$_{1-10}$alkyl.

In some embodiments of Formula III-A, Y is CR$_5$, X$_4$ is N or CR$_4$, X$_5$ is N or C, X$_6$ is C, X$_7$ is N or NR$_{72}$ or CR$_{71}$, X$_8$ is N or CR$_{81}$, X$_9$ is NR$_{22}$ or CR$_{21}$, and X$_{10}$ is N or CR$_{91}$;

R$_1$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_{21}$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(═O) NR$^{31}$, —NO$_2$, —CN, —S(O)$_{0-2}$R$^{31}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

R$_{22}$ is hydrogen, —OH, —CF$_3$, —C(O)R$^{31}$, —CO$_2$R$^{31}$, —C(═O)NR$^{31}$, —S(O)$_{0-2}$R$^{31}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(═O)—, —C(═O)O—, —OC(═O)—, —C(═O)N (R$^{31}$)—, —N(R$^{31}$)C(═O)—, —NR$^{31}$C(═O)O—, —NR$^{31}$C(═O)NR$^{32}$—, —NR$^{31}$S(O)$_{0-2}$—, or —S(O)$_{0-2}$N(R$^{31}$)—;

each of R$_3$ and R$_4$ is independently hydrogen, halogen, —OH, —CF$_3$, —OCF$_3$, —OR$^{31}$, —NR$^{31}$R$^{32}$, —C(O)R$^{31}$, —CO$_2$R$^{31}$, —C(═O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents;

each of R$_5$, R$_{71}$, R$_{81}$ and R$_{91}$ is independently hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$;

R$_{10}$ is —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

each of R$^{31}$ and R$^{32}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring; and wherein at least one of X$_5$, X$_6$, X$_7$, X$_8$, X$_9$ and X$_{10}$ is a heteroatom selected from N, O, or S.

In some embodiments of Formula III-A, Y is CR$_5$, X$_4$ is N or CR$_4$, X$_5$ is N or C, X$_6$ is C, X$_7$ is NR$_{72}$ or CR$_{71}$, X$_8$ is N, X$_9$ is NR$_{22}$ or CR$_{21}$, and X$_{10}$ is N or CR$_{91}$;

R$_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

R$_{22}$ is —OH, —CF$_3$, —C(O)R$^{31}$, —CO$_2$R$^{31}$, —C(=O)NR$^{31}$, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—;

each of R$_3$ and R$_4$ is independently hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents;

each of R$_5$, R$_{71}$ and R$_{91}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, —S(O)$_{0-2}$R$^{31}$, —C(=S)OR$^{31}$, or —C(=O)SR$^{31}$;

each of R$_{10}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

each of R$^{31}$ and R$^{32}$ is independently hydrogen or —C$_{1-10}$alkyl, or wherein R$^{31}$ together with R$^{32}$ form a heterocyclic ring; and wherein at least one of X$_5$, X$_6$, X$_7$, X$_8$, X$_9$ and X$_{10}$ is a heteroatom selected from N, O, or S.

In some embodiments of Formula III-A, Y is CR$_5$, X$_4$ is CR$_4$, X$_5$ is C, X$_6$ is C, X$_7$ is NR$_{72}$, X$_8$ is N, X$_9$ is CR$_{21}$, and X$_{10}$ is N or CR$_{91}$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OR$^{31}$, —NR$^{31}$R$^{32}$, —C(O)R$^{31}$—CO$_1$R$^{31}$, —C(=O)NR$^{31}$, —NO$_2$, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

R$_{22}$ is —OH, —CF$_3$, —C(O)R$^{31}$, —CO$_2$R$^{31}$, —C(=O)NR$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, —C(=O)N(R$^{31}$)—, or —N(R$^{31}$)C(=O)—;

each of R$_3$ and R$_4$ is independently hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{2-10}$alkenyl, or —C$_{2-10}$alkynyl;

each of R$_5$ and R$_{91}$ is independently hydrogen, halogen, or —C$_{1-10}$alkyl, R$_{72}$ is hydrogen or —C$_{1-10}$alkyl;

each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$, each of R$^{31}$ and R$^{32}$ is independently hydrogen or —C$_{1-10}$alkyl; and wherein at least one of X$_5$, X$_6$, X$_7$, X$_8$, X$_9$ and X$_{10}$ is a heteroatom selected from N, O, or S.

In some embodiments of Formula III-A, Y is CR$_5$, X$_4$ is CR$_4$, X$_5$ is C, X$_6$ is C, X$_7$ is NR$_{72}$, X$_8$ is N, X$_9$ is CR$_{21}$, and X$_{10}$ is N;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, or —C(=O)N(R$^{31}$)—;

each of R$_3$ and R$_4$ is independently hydrogen, halogen, —OH, —CF$_3$, or —C$_{1-10}$alkyl;

R$_5$ is hydrogen;

R$_{72}$ is hydrogen;

each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$ and R$_{12}$ is independently hydrogen, halogen, —C$_{1-10}$alkyl, —OH or —CF$_3$;

each of R$^{31}$ is independently hydrogen or —C$_{1-10}$alkyl; and wherein at least one of X$_5$, X$_6$, X$_7$, X$_8$, X$_9$ and X$_{10}$ is a heteroatom selected from N, O, or S.

The invention also provides a compound as defined above, wherein the compound is of Formula III-B:

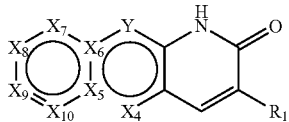

or a pharmaceutically acceptable salt or prodrug thereof, and wherein the substituents are as defined above.

In some embodiments of Formula III-B, Y is $CR_5$, $X_4$ is N or $CR_4$, $X_5$ is C and $X_6$ is C. In some embodiments, Y is $CR_5$, $X_4$ is $CR_4$, $X_5$ is N or C and $X_6$ is C. In some embodiments, Y is $CR_5$, $X_4$ is $CR_4$, $X_5$ is C and $X_6$ is C. In some embodiments, Y is $CR_5$, $X_4$ is $CR_4$, $X_5$ is N and $X_6$ is C. In some embodiments, Y is $CR_5$, $X_4$ is $CR_4$, $X_5$ is C and $X_6$ is N.

In some embodiments of Formula III-B, $X_7$ is $CR_{71}$, $X_8$ is N, $X_9$ is $CR_{21}$, and $X_{10}$ is N. In some embodiments, $X_7$ is $CR_{71}$, $X_8$ is N, $X_9$ is $CR_{21}$, and $X_{10}$ is $CR_{91}$. In some embodiments, $X_7$ is $NR_{72}$, $X_8$ is $CR_{81}$, $X_9$ is $CR_{21}$, and $X_{10}$ is N. In some embodiments, $X_7$ is $NR_{72}$, $X_8$ is $CR_{81}$, $X_9$ is $CR_{21}$, and $X_{10}$ is $CR_{91}$. In some embodiments, $X_7$ is $CR_{71}$, $X_8$ is $CR_{81}$, $X_9$ is $NR_{22}$, and $X_{10}$ is N. In some embodiments, $X_7$ is $CR_{71}$, $X_8$ is $CR_{81}$, $X_9$ is $NR_{22}$, and $X_{10}$ is $CR_{91}$.

In some embodiments of Formula III-B, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{21}$ or $CR_{21}$, and $X_{10}$ is N or $CR_{91}$. In some embodiments, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{22}$ or $CR_{21}$, and $X_{10}$ is N or $CR_{91}$. In some embodiments, Y is $CR_5$, $X_4$ is $CR_4$, $X_5$ is C, $X_6$ is C, $X_7$ is $NR_{72}$, $X_8$ is N, $X_9$ is $CR_{21}$, and $X_{10}$ is N or $CR_{91}$.

In some embodiments of Formula III-B, $R_1$ is $-C_{1-10}$alkyl, $-C_{3-10}$aryl, $-C_{1-10}$hetaryl, $-C_{3-10}$cycloalkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{3-10}$cycloalkyl-$C_{1-10}$alkyl, $-C_{3-10}$cycloalkyl-$C_{3-10}$aryl, $-C_{3-10}$cycloalkyl-$C_{1-10}$hetaryl, $-C_{3-10}$cycloalkyl-$C_{1-10}$heterocyclyl, $-C_{1-10}$heterocyclyl-$C_{1-10}$alkyl, $-C_{1-10}$heterocyclyl-$C_{3-10}$aryl, $-C_{1-10}$heterocyclyl-$C_{1-10}$hetaryl, or $-C_{1-10}$heterocyclyl-$C_{3-10}$cycloalkyl, each of which is unsubstituted or substituted by one or more independent $R_{10}$ or $R_{11}$ substituents. In some embodiments, $R_1$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents. In some embodiments, $R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents.

In some embodiments of Formula III-B, $R_{21}$ is hydrogen, halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, $-NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, hydrogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, $-NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula III-B, $R_{22}$ is hydrogen, $-OH$, $-CF_3$, $-C(O)R^{31}$, $-CO_2R^{31}$, $-C(=O)NR^{31}$, $-S(O)_{0-2}R^{31}$, -L-$C_{2-10}$alkenyl, -L-$C_{2-10}$alkynyl, -L-$C_{1-10}$heteroalkyl, -L-$C_{-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is $-OH$, $-CF_3$, $-C(O)R^{31}$, $-CO_2R^{31}$, $-C(=O)NR^{31}$, $-S(O)_{0-2}R^{31}$, -L-$C_{1-10}$alkyl, -L-$C_{3-10}$aryl, -L-$C_{1-10}$hetaryl, -L-$C_{-10}$cycloalkyl, or -L-$C_{1-10}$heterocyclyl each of which is unsubstituted or substituted by one or more independent $R_{12}$ substituents. In some embodiments, $R_{22}$ is $-OH$, $-CF_3$, $-C(O)R^{31}$, $-CO_2R^{31}$, $-C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula III-B, L is a bond, $-O-$, $-N(R^{31})-$, $-S(O)_{0-2}-$, $-C(=O)-$, $-C(=O)O-$, $-OC(=O)-$, $-C(=O)N(R^{31})-$, $-N(R^{31})C(=O)-$, $-NR^{31}C(=O)O-$, $-NR^{31}C(=O)NR^{32}-$, $-NR^{31}S(O)_{0-2}-$, or $-S(O)_{0-2}N(R^{31})-$. In some embodiments, L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$. In some embodiments, L is a bond, $-N(R^{31})-$, $-C(=O)N(R^{31})-$, or $-N(R^{31})C(=O)-$. In some embodiments, L is a bond, $-N(R^{31})-$, or $-C(=O)N(R^{31})-$.

In some embodiments of Formula III-B, $R_4$ is hydrogen, halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, $-C_{1-10}$alkyl, $-C_{2-10}$alkenyl, $-C_{2-10}$alkynyl, $-C_{1-10}$heteroalkyl, $-C_{3-10}$aryl, $-C_{1-10}$hetaryl, $-C_{3-10}$cycloalkyl, or $-C_{1-10}$heterocyclyl, each of which is unsubstituted or substituted by one or more independent $R_{13}$ substituents. In some embodiments, $R_4$ is hydrogen, halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, $-C_{1-10}$alkyl, $-C_{2-10}$alkenyl, or $-C_{2-10}$alkynyl, each of which is unsubstituted or substituted by one or more independent $R_{13}$ substituents. In some embodiments, $R_4$ is hydrogen, halogen, $-OH$, $-CF_3$, $-OCF_3$, $-OR^{31}$, $-NR^{31}R^{32}$, $-NO_2$, $-CN$, $-S(O)_{0-2}R^{31}$, $-C_{1-10}$alkyl, $-C_{2-10}$alkenyl, or $-C_{2-10}$alkynyl. In some embodiments, $R_4$ is hydrogen, halogen, $-OH$, $-CF_3$, or $-C_{1-10}$alkyl.

In some embodiments of Formula III-B, $R_5$ is hydrogen, halogen, $-C_{1-10}$alkyl, $-C_{3-10}$aryl, $-C_{1-10}$hetaryl, $-C_{3-10}$cycloalkyl, $-C_{1-10}$heterocyclyl, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$. In some embodiments, $R_5$ is hydrogen, halogen, $-C_{1-10}$alkyl, $-C_{3-10}$aryl, $-C_{3-10}$cycloalkyl, $-OH$, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula III-B, each of $R_{71}$, $R_{81}$ and $R_{91}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$, $R_{81}$ and $R_{91}$ is independently hydrogen, halogen, or —$C_{1-10}$alkyl. In some embodiments, each of $R_{71}$, $R_{81}$ and $R_{91}$ is independently hydrogen.

In some embodiments of Formula III-B, each of $R_{72}$, $R_{82}$ and $R_{92}$ is independently hydrogen, —$C_{1-10}$ alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$, $R_{82}$ and $R_{92}$ is independently hydrogen or —$C_{1-10}$alkyl. In some embodiments, each of $R_{72}$, $R_{82}$ and $R_{92}$ is independently hydrogen.

In some embodiments of Formula III-B, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula III-B, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, and $R_{13}$ is independently hydrogen, halogen, —$C_{1-10}$ alkyl, —OH or —$CF_3$.

In some embodiments of Formula III-B, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula III-B, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, $X_9$ is $NR_{22}$ or $CR_{21}$, and $X_{10}$ is N or $CR_{91}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—;

each of $R_3$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents;

each of $R_5$, $R_{71}$, $R_{81}$ and $R_{91}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

$R_{10}$ is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring; and wherein at least one of $X_5$, $X_6$, $X_7$, $X_8$, $X_9$ and $X_{10}$ is a heteroatom selected from N, O, or S.

In some embodiments of Formula III-B, Y is $CR_5$, $X_4$ is N or $CR_4$, $X_5$ is N or C, $X_6$ is C, $X_7$ is $NR_{72}$ or $CR_{71}$, $X_8$ is N, $X_9$ is $NR_{22}$ or $CR_{21}$, and $X_{10}$ is N or $CR_{91}$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

R$_{22}$ is —OH, —CF$_3$, —C(O)R$^{31}$, —CO$_2$R$^{31}$, —C(=O)NR$^{31}$, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—;

each of R$_3$ and R$_4$ is independently hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents;

each of R$_5$, R$_{71}$ and R$_{91}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, —S(O)$_{0-2}$R$^{31}$, —C(=S)OR$^{31}$, or —C(=O)SR$^{31}$;

each of R$_{10}$ is independently —C$_{1-10}$alkyl, —C$_{3-10}$alkyl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

each of R$^{31}$ and R$^{32}$ is independently hydrogen or —C$_{1-10}$alkyl, or wherein R$^{31}$ together with R$^{32}$ form a heterocyclic ring; and wherein at least one of X$_5$, X$_6$, X$_7$, X$_8$, X$_9$ and X$_{10}$ is a heteroatom selected from N, O, or S.

In some embodiments of Formula III-B, Y is CR$_5$, X$_4$ is CR$_4$, X$_5$ is C, X$_6$ is C, X$_7$ is NR$_{72}$, X$_8$ is N, X$_9$ is CR$_{21}$, and X$_{10}$ is N or CR$_{91}$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

R$_{22}$ is —OH, —CF$_3$, —C(O)R$^{31}$, —CO$_2$R$^{31}$, —C(=O)NR$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, —C(=O)N(R$^{31}$)—, or —N(R$^{31}$)C(=O)—;

each of R$_3$ and R$_4$ is independently hydrogen, halogen, —OH, —CF$_3$, —OCF$_3$, —OR$^{31}$, —NR$^{31}$R$^{32}$, —CN, —S(O)$_{0-2}$R$^{31}$, —C$_{2-10}$alkenyl, or —C$_{2-10}$alkynyl;

each of R$_5$ and R$_{91}$ is independently hydrogen, halogen, or —C$_{1-10}$alkyl, R$_{72}$ is hydrogen or —C$_{1-10}$alkyl;

each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$, each of R$^{31}$ and R$^{32}$ is independently hydrogen or —C$_{1-10}$alkyl; and wherein at least one of X$_5$, X$_6$, X$_7$, X$_8$, X$_9$ and X$_{10}$ is a heteroatom selected from N, O, or S.

In some embodiments of Formula III-B, Y is CR$_5$, X$_4$ is CR$_4$, X$_5$ is C, X$_6$ is C, X$_7$ is NR$_{72}$, X$_8$ is N, X$_9$ is CR$_{21}$, and X$_{10}$ is N;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, or —C(=O)N(R$^{31}$)—;

each of R$_3$ and R$_4$ is independently hydrogen, halogen, —OH, —CF$_3$, or —C$_{1-10}$alkyl;

R$_5$ is hydrogen;

R$_{72}$ is hydrogen;

each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$ and R$_{12}$ is independently hydrogen, halogen, —C$_{1-10}$alkyl, —OH or —CF$_3$;

each of R$^{31}$ is independently hydrogen or —C$_{1-10}$alkyl; and wherein at least one of X$_5$, X$_6$, X$_7$, X$_8$, X$_9$ and X$_{10}$ is a heteroatom selected from N, O, or S.

The invention also provides a compound of Formula IV-A:

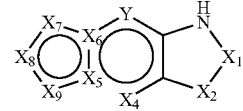

or a pharmaceutically acceptable salt or prodrug thereof, and wherein the substituents are as defined above.

In some embodiments of Formula IV-A, X$_1$ is C=O and X$_2$ is NR$_1$ or CR$_1$R$_1$'. In some embodiments, X$_1$ is C=O and X$_2$ is NR$_1$ or CR$_1$R$_1$'. In some embodiments, X$_1$ is C=S and X$_2$ is CR$_1$. In some embodiments, X$_1$ is SO$_2$ and X$_2$ is NR$_1$.

In some embodiments of Formula IV-A, Y is CR$_5$, X$_4$ is N or CR$_4$, X$_5$ is C and X$_6$ is C. In some embodiments, Y is CR$_5$, X$_4$ is CR$_4$, X$_5$ is N or C and X$_6$ is C. In some embodiments, Y is CR$_5$, X$_4$ is CR$_4$, X$_5$ is C and X$_6$ is C. In some embodiments, Y is CR$_5$, X$_4$ is CR$_4$, X$_5$ is N and X$_6$ is C. In some embodiments, Y is CR$_5$, X$_4$ is CR$_4$, X$_5$ is C and X$_6$ is N.

In some embodiments of Formula IV-A, X$_7$ is NH, X$_8$ is N and X$_9$ is CR$_{21}$. In some embodiments, X$_7$ is N and X$_8$ is CR$_{81}$ and X$_9$ is CR$_{21}$. In some embodiments, X$_7$ is CR$_7$, X$_8$ is N and X$_9$ is NR$_{22}$. In some embodiments, X$_7$ is CR$_7$, X$_8$ is N and X$_9$ is CR$_{21}$. In some embodiments, X$_7$ is O, X$_8$ is N and X$_9$ is CR$_2$. In some embodiments, X$_7$ is O, X$_8$ is CR$_{81}$ and X$_9$ is NR$_{21}$.

In some embodiments of Formula IV-A, $X_1$ is C=O, $X_2$ is $NR_1$ or $CR_1R_1'$, Y is N or $CR_5$, $X_4$ is N or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_1$ is C=O, $X_2$ is $NR_1$ or $CR_1R_1'$, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_1$ is C=O, $X_2$ is $NR_1$, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula IV-A, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{3-10}$cycloalkyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula IV-A, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula IV-A, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments on Formula IV-A, $R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is —OH, —$CF_3$, —$C(O)R^{31}$, —$CO_2R^{31}$, —$C(=O)NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula IV-A, L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—. In some embodiments, L is a bond, —$N(R^{31})$—, —$C(=O)N(R^{31})$—, or —$N(R^{31})C(=O)$—. In some embodiments, L is a bond, —$N(R^{31})$—, or —$C(=O)N(R^{31})$—.

In some embodiments of Formula IV-A, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula IV-A, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula IV-A, $R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents.

In some embodiments of Formula IV-A, each of $R_{71}$ and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, or —$C_{1-10}$ alkyl. In some embodiments, each of $R_{71}$ and $R_{81}$ is independently hydrogen.

In some embodiments of Formula IV-A, each of $R_{72}$ and $R_{82}$ is independently hydrogen, —$C_{1-10}$ alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, each of $R_{72}$ and $R_{82}$ is independently hydrogen, —$C_{1-10}$ alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, each of $R_{72}$ and $R_{82}$ is independently hydrogen or —$C_{1-10}$alkyl. In some embodiments, each of $R_{72}$ and $R_{82}$ is independently hydrogen.

In some embodiments of Formula IV-A, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula IV-A, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula IV-A, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula IV-A, $X_1$ is C=O, $X_2$ is $NR_1$ or $CR_1R_1'$, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—;

$R_4$ is hydrogen, halogen, —OH, —$CF_3$, —$OCF_3$, —$OR^{31}$, —$NR^{31}R^{32}$, —$C(O)R^{31}$, —$CO_2$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents;

each of $R_5$, $R_{71}$, and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula IV-A, $X_1$ is C=O, $X_2$ is $NR_1$ or $CR_1R_1'$, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is —$NR_{21}$ or $CR_{21}$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —$C(=O)NR^{31}$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—;

$R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents;

each of $R_5$ and $R_{71}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula IV-A, $X_1$ is C=O, $X_2$ is $NR_1$, Y is $CR_5$, $X_4$ is $CR_4$, $X_5$ is C, $X_6$ is C, $X_7$ is $NR_{72}$, $X_8$ is N, and $X_9$ is $CR_{21}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, —$C(=O)N(R^{31})$—, or —$N(R^{31})C(=O)$—;

$R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl;

$R_5$ is independently hydrogen, halogen, or —$C_{1-10}$alkyl;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen or —$C_{1-10}$alkyl;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula IV-A, $X_1$ is C=O, $X_2$ is $NR_1$, Y is $CR_5$, $X_4$ is $CR_4$, $X_5$ is C, $X_6$ is C, $X_7$ is $NR_{72}$, $X_8$ is N, and $X_9$ is $CR_{21}$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —N($R^{31}$)—, or —C(=O)N($R^{31}$)—;

$R_4$ is hydrogen, halogen, —OH, —$CF_3$, or —$C_{1-10}$alkyl;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —OH, —$CF_3$, —C(O)$R^{31}$, —$CO_2R^{31}$, —C(=O)$NR^{31}$, or —S(O)$_{0-2}R^{31}$;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$, and each of $R^{31}$ is independently hydrogen or —$C_{1-10}$alkyl.

The invention also provides a compound as defined above, wherein the compound is of Formula IV-B:

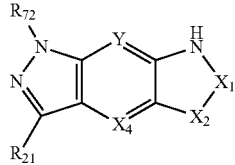

or a pharmaceutically acceptable salt or prodrug thereof, and wherein the substituents are as defined above.

In some embodiments of Formula IV-B, $X_1$ is C=O and $X_2$ is $NR_1$ or $CR_1R_1'$. In some embodiments, $X_1$ is C=O and $X_2$ is $NR_1$ or $CR_1R_1'$. In some embodiments, $X_1$ is C=S and $X_2$ is $CR_1$. In some embodiments, $X_1$ is $SO_2$ and $X_2$ is $NR_1$.

In some embodiments of Formula IV-B, $X_1$ is C=O or $SO_2$, $X_2$ is $NR_1$ or $CR_1R_1'$, Y is $CR_5$, and $X_4$ is N or $CR_4$. In some embodiments, $X_1$ is C=O or $SO_2$, $X_2$ is $NR_1$ or $CR_1R_1'$, Y is $CR_5$ and $X_4$ is N or $CR_4$. In some embodiments, $X_1$ is C=O, $X_2$ is $NR_1$, Y is $CR_5$ and $X_4$ is $CR_4$.

In some embodiments of Formula IV-B, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula IV-B, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula IV-B, $R_{21}$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$NR^{31}$C(=O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula IV-B, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula IV-B, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —S(O)$_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, or —C$_{2-10}$alkynyl, each of which is unsubstituted or substituted by one or more independent R$_{13}$ substituents. In some embodiments, $R_4$ is hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{2-10}$alkenyl, or —C$_{2-10}$alkynyl. In some embodiments, $R_4$ is hydrogen, halogen, —OH, —CF$_3$, or —C$_{1-10}$alkyl.

In some embodiments of Formula IV-B, $R_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, $R_5$ is hydrogen, halogen, —C$_{1-10}$alkyl, —C$_{3-10}$aryl, —C$_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, $R_5$ is hydrogen, halogen, or —C$_{1-10}$alkyl. In some embodiments, $R_5$ is hydrogen.

In some embodiments of Formula IV-B, $R_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$. In some embodiments, $R_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$. In some embodiments, $R_{72}$ is hydrogen or —C$_{1-10}$alkyl. In some embodiments, $R_{72}$ is hydrogen.

In some embodiments of Formula IV-B, each of $R_{10}$ and $R_{14}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent R$_{11}$ substituents. In some embodiments, each of $R_{10}$ and $R_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents. In some embodiments, each of $R_{10}$ and $R_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents.

In some embodiments of Formula IV-B, each of $R_{11}$, $R_{12}$, $R_{13}$ and $R_{15}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of $R_{11}$, $R_{12}$, $R_{13}$ and $R_{15}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of $R_{11}$, $R_{12}$, $R_{13}$ and $R_{15}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$. In some embodiments, each of $R_{11}$, $R_{12}$, $R_{13}$ and $R_{15}$ is independently hydrogen, halogen, —C$_{1-10}$ alkyl, —OH or —CF$_3$.

In some embodiments of Formula IV-B, each of R$^{31}$, R$^{32}$, R$^{33}$ and R$^{34}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, or wherein R$^{31}$ together with R$^{32}$ form a heterocyclic ring. In some embodiments, each of R$^{31}$, R$^{32}$, R$^{33}$ and R$^{34}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring. In some embodiments, each of R$^{31}$, R$^{32}$, R$^{33}$ and R$^{34}$ is independently hydrogen or —C$_{1-10}$alkyl, or wherein R$^{31}$ together with R$^{32}$ form a heterocyclic ring. In some embodiments, each of R$^{31}$, R$^{32}$, R$^{33}$ and R$^{34}$ is independently hydrogen or —C$_{1-10}$alkyl.

In some embodiments of Formula IV-B, $X_1$ is C=O or SO$_2$, $X_2$ is NR$_1$ or CR$_1$R$_1'$, Y is CR$_5$ and $X_4$ is N or CR$_4$;

$R_1$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

$R_1'$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

$R_{21}$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—;

$R_4$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents;

$R_5$ is hydrogen, halogen, —C$_{1-10}$alkyl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

$R_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents;

$R_{72}$ is independently hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$;

each of $R_{10}$ and $R_{14}$ is independently —C$_{1-10}$alkyl, —C$_{2-10}$alkenyl, —C$_{2-10}$alkynyl, —C$_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula IV-B, $X_1$ is C=O or $SO_2$, $X_2$ is $NR_1$ or $CR_1R_1'$, $X_3$ is $CR_3R_3'$, Y is $CR_5$ and $X_4$ is N or $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})C(=O)$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents;

$R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$;

each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula IV-B, $X_1$ is C=O, $X_2$ is $NR_1$, Y is $CR_5$ and $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, —C(=O)N($R^{31}$)—, or —$N(R^{31})C(=O)$—;

$R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl;

$R_5$ is hydrogen, halogen, or —$C_{1-10}$alkyl;

$R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen or —$C_{1-10}$alkyl;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$; and each of $R^{31}$ and $R^{32}$ is independently hydrogen or —$C_{1-10}$alkyl.

In some embodiments of Formula IV-B, $X_1$ is C=O, $X_2$ is $NR_1$, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —C(=O)N($R^{31}$)—;

$R_4$ is hydrogen, halogen, —OH, —$CF_3$, or —$C_{1-10}$alkyl; or $R_3'$ is —$OR^6$ or —$NR^6R^{34}$, wherein $R^6$ together with $R^{34}$ can optionally form a heterocyclic ring;

$R_5$ is hydrogen;

$R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents;

$R_{72}$ is hydrogen;

each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$, $R_{12}$ and $R_{15}$ is independently hydrogen, halogen, —$C_{1-10}$alkyl, —OH or —$CF_3$; and each of $R^{31}$ is independently hydrogen or —$C_{1-10}$alkyl.

The invention also provides a compound as defined above, wherein the compound is of Formula IV-C:

or a pharmaceutically acceptable salt or prodrug thereof, and wherein the substituents are as defined above.

In some embodiments of Formula IV-C, Y is $CR_5$, $X_4$ is N or $CR_4$. In some embodiments of Formula IV-C, Y is $CR_5$, $X_4$ is N or $CR_4$. In some embodiments of Formula IV-C, Y is $CR_5$, $X_4$ is $CR_4$.

In some embodiments of Formula IV-C, $R_1$ 1 s-$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula IV-C, $R_{21}$ is hydrogen, halogen, —OH, —$CF_3$, —$OCF_3$, —$OR^{31}$, —$NR^{31}$, $R^{32}$, —$C(O)R^{31}$, —$CO_2R^{31}$, —$C(=O)NR^{31}$, —$NO_2$, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}$, $R^{32}$, —$C(O)R^{31}$, —$CO_2R^{31}$, —$C(=O)NR^{31}$, —$NO_2$, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents In some embodiments of Formula IV-C, L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—. In some embodiments, L is a bond, —$N(R^{31})$—, —$C(=O)N(R^{31})$—, or —$N(R^{31})C(=O)$—. In some embodiments, L is a bond, —$N(R^{31})$—, or —$C(=O)N(R^{31})$—.

In some embodiments of Formula IV-C, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula IV-C, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula IV-C, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, $R_{72}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, $R_{72}$ is independently hydrogen or —$C_{1-10}$alkyl. In some embodiments, $R_{72}$ is independently hydrogen.

In some embodiments of Formula IV-C, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents In some embodiments of Formula IV-C, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, and $R_{13}$ is independently hydrogen, halogen, —$C_{1-10}$ alkyl, —OH or —$CF_3$ In some embodiments of Formula IV-C, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula IV-C, Y is $CR_5$, $X_4$ is N or $CR_4$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N$(R^{31})$—, —$N(R^{31})$C(=O)—, —$NR^{31}$C(=O)O—, —$NR^{31}$C(=O)$NR^{32}$—, —$NR^{31}$S(O)$_{0-2}$—, or —$S(O)_{0-2}N(R^{31})$—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents;

$R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula IV-C, Y is $CR_5$, $X_4$ is N or $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N$(R^{31})$—, or —$N(R^{31})$C(=O)—;

$R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents;

$R_5$ is hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, —$S(O)_{0-2}R^{31}$;

$R_{10}$ is —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula IV-C, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N$(R^{31})$—, or —$N(R^{31})$C(=O)—;

each of $R_3$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, or —$C_{2-10}$alkynyl;

$R_5$ is hydrogen, halogen, or —$C_{1-10}$alkyl;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl.

In some embodiments of Formula IV-C, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —N($R^{31}$)—, or —C(=O)N($R^{31}$)—;

each of $R_3$ and $R_4$ is independently hydrogen, halogen, —OH, —$CF_3$, or —$C_{1-10}$alkyl;

$R_5$ is hydrogen;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$; and each of $R^{31}$ is independently hydrogen or —$C_{1-10}$alkyl.

The invention also provides a compound as defined above, wherein the compound is of Formula IV-D:

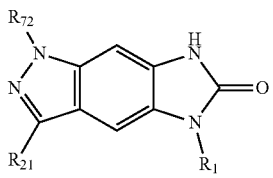

or a pharmaceutically acceptable salt or prodrug thereof, and wherein the substituents are as defined above.

In some embodiments of Formula IV-D, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula IV-D, $R_{21}$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$, —$NR^{31}$C(=O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$, —$NR^{31}$C(=O)$R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —C(O)$R^{31}$, —$CO_2R^{31}$, —C(=O)N$R^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula IV-D, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)N$R^{32}$—, —$NR^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula IV-D, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —C(O)$R^{31}$, —$CO_2R^{31}$, —C(=O)N$R^{31}$, or —S(O)$_{0-2}R^{31}$. In some embodiments, $R_{72}$ is hydrogen, —$C_{1-10}$alkyl, —$C_{3-10}$aryl, —$C_{3-10}$cycloalkyl, —C(O)$R^{31}$, —$CO_2R^{31}$, —C(=O)N$R^{31}$, or —S(O)$_{0-2}R^{31}$. In some embodiments, $R_{72}$ is hydrogen or —$C_{1-10}$alkyl. In some embodiments, $R_{72}$ is hydrogen.

In some embodiments of Formula IV-D, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents In some embodiments of Formula IV-D, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$ or —$NR^{31}$C(=O)$R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —C(O)$R^{31}$, —$CO_2R^{31}$, —C(=O)N$R^{31}$, —$NO_2$, —CN, —S(O)$_{0-2}R^{31}$ or —$NR^{31}$C(=O)$R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —S(O)$_{0-2}R^{31}$. In some embodiments, each of $R_{11}$, $R_{12}$, and $R_{13}$ is independently hydrogen, halogen, —$C_{1-10}$ alkyl, —OH or —$CF_3$.

In some embodiments of Formula IV-D, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula IV-D, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —S(O)$_{0-2}$N($R^{31}$)—;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring In some embodiments of Formula IV-D, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—;

$R_{72}$ is hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, —$S(O)_{0-2}R^{31}$;

$R_{10}$ is —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl, or wherein $R^{31}$ together with $R^{32}$ form a heterocyclic ring.

In some embodiments of Formula IV-D, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl.

In some embodiments of Formula IV-D, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —N($R^{31}$)—, or —C(=O)N($R^{31}$)—;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$; and each of $R^{31}$ is independently hydrogen or —$C_{1-10}$alkyl.

The invention also provides a compound of Formula V-A:

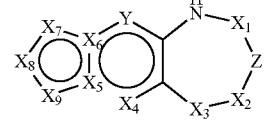

or a pharmaceutically acceptable salt or prodrug thereof, and wherein the substituents are as defined above.

In some embodiments of Formula V-A, $X_1$ is C=O, Z is $NR_1$ or $CR_1R_1'$, $X_2$ is $NR_1$ or $CR_1R_1'$, and $X_3$ is $CR_3R_3'$. In some embodiments, $X_1$ is C=O, Z is $NR_1$ or $CR_1R_1'$, $X_2$ is $NR_1$ or $CR_1R_1'$, and $X_3$ is C=O. In some embodiments, $X_1$ is C=S, Z is $NR_1$ or $CR_1R_1'$, $X_2$ is $CR_1$, and $X_3$ is $CR_3R_3'$. In some embodiments, $X_1$ is $SO_2$, Z is $NR_1$ or $CR_1R_1'$, $X_2$ is $NR_1$, and $X_3$ is $CR_3R_3'$.

In some embodiments of Formula V-A, Y is $CR_5$, $X_4$ is N or $CR_4$, $X_5$ is C and $X_6$ is C. In some embodiments, Y is $CR_5$, $X_4$ is $CR_4$, $X_5$ is N or C and $X_6$ is C. In some embodiments, Y is $CR_5$, $X_4$ is $CR_4$, $X_5$ is C and $X_6$ is C. In some embodiments, Y is $CR_5$, $X_4$ is $CR_4$, $X_5$ is N and $X_6$ is C. In some embodiments, Y is $CR_5$, $X_4$ is $CR_4$, $X_5$ is C and $X_6$ is N.

In some embodiments of Formula V-A, $X_7$ is NH, $X_8$ is N and $X_9$ is $CR_{21}$. In some embodiments, $X_7$ is N and $X_8$ is $CR_{81}$ and $X_9$ is $CR_{21}$. In some embodiments, $X_7$ is $CR_7$, $X_8$ is N and $X_9$ is $NR_{22}$. In some embodiments, $X_7$ is $CR_7$, $X_8$ is N and $X_9$ is $CR_{21}$. In some embodiments, $X_7$ is O, $X_8$ is N and $X_9$ is $CR_2$. In some embodiments, $X_7$ is O, $X_8$ is $CR_{81}$ and $X_9$ is $NR_{21}$.

In some embodiments of Formula V-A, $X_1$ is C=O, Z is $NR_1$ or $CR_1R_1'$, $X_2$ is $NR_1$ or $CR_1R_1'$, $X_3$ is $CR_3R_3'$ or C=O, Y is N or $CR_5$, $X_4$ is N or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$. In some embodiments, $X_1$ is C=O, Z is $NR_1$ or $CR_1R_1'$, $X_2$ is $NR_1$ or $CR_1R_1'$, $X_3$ is $CR_3R_3'$, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{22}$ or $CR_{21}$. In some embodiments, $X_1$ is C=O, Z is $CR_1R_1'$, $X_2$ is $NR_1$, $X_3$ is $CR_3R_3'$, Y is $CR_5$, $X_4$ is $CR_4$, $X_5$ is C, $X_6$ is C, $X_7$ is $NR_{72}$, $X_8$ is N, and $X_9$ is $CR_{21}$. In some embodiments, $X_1$ is C=O, Z is $NR_1$, $X_2$ is $X_3$ is $CR_3R_3'$, Y is $CR_5$, $X_4$ is $CR_4$, $X_5$ is C, $X_6$ is C, $X_7$ is $NR_{72}$, $X_8$ is N, and $X_9$ is $CR_{21}$.

In some embodiments of Formula V-A, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula V-A, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula V-A, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, —$NR^{31}C$(=O)$R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —C(=O)$NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents In some embodiments on Formula V-A, $R_{22}$ is hydrogen, —OH, —$CF_3$, —$C(O)R^{31}$, —$CO_2R^{31}$, —C(=O)$NR^{31}$, —$S(O)_{0-2}R^{31}$, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is —OH, —$CF_3$, —$C(O)R^{31}$, —$CO_2R^{31}$, —C(=O)$NR^{31}$, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents. In some embodiments, $R_{22}$ is —OH, —$CF_3$, —$C(O)R^{31}$, —$CO_2R^{31}$, —C(=O)$NR^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{22}$ is -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents In some embodiments of Formula V-A, L is a bond, —O—, —$N(R^{31})$—, —$S(O)_{0-2}$—, —C(=O)—, —C(=O)O—, —OC(=O)—, —C(=O)$N(R^{31})$—, —$N(R^{31})C$(=O)—, —$NR^{31}C$(=O)O—, —$NR^{31}C$(=O)$NR^{32}$—, —$NR^{31}S(O)_{0-2}$—, or —$S(O)_{0-2}N(R^{31})$—. In some embodiments, L is a bond, —O—, —$N(R^{31})$—, —$S(O)_{0-2}$—, —C(=O)—, —C(=O)O—, —OC(=O)—, —C(=O)$N(R^{31})$—, or —$N(R^{31})C$(=O)—. In some embodiments, L is a bond, —$N(R^{31})$—, —C(=O)$N(R^{31})$—, or —$N(R^{31})C$(=O)—. In some embodiments, L is a bond, —$N(R^{31})$—, or —C(=O)$N(R^{31})$—.

In some embodiments of Formula V-A, $R_3$ is hydrogen, halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —C(O)

$R^{31}$, —$CO_2R^{31}$, —C(=O)$NR^{31}$, —$NO_2$, —CN, —$S(O)_{0-2}$ $R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{2-10}$alkenyl, or —$C_{2-10}$alkynyl. In some embodiments, $R_3$ is hydrogen, halogen, —OH, —$CF_3$, or —$C_{1-10}$alkyl.

In some embodiments of Formula V-A, $R_3'$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_3'$ is hydrogen, halogen, —OH, —$CF_3$, or —$C_{1-10}$alkyl.

In some embodiments of Formula V-A, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula V-A, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula V-A, $R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents. In some embodiments, $R_6$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{14}$ or $R_{15}$ substituents.

In some embodiments of Formula V-A, each of $R_{71}$ and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$ or —$NR^{31}C(=O)R^{32}$. In some embodiments, each of $R_{71}$ and $R_{81}$ is independently hydrogen, halogen, or —$C_{1-10}$ alkyl. In some embodiments, each of $R_{71}$ and $R_{81}$ is independently hydrogen.

In some embodiments of Formula V-A, each of $R_{72}$ and $R_{82}$ is independently hydrogen, —$C_{1-10}$ alkyl, —$C_{3-10}$aryl, —$C_{1-10}$hetaryl, —$C_{3-10}$cycloalkyl, —$C_{1-10}$heterocyclyl, —OH, —$CF_3$, —C(O)$R^{31}$, —$CO_2R^{31}$, —C(=O)$NR^{31}$, or —$S(O)_{0-2}R^{31}$. In some embodiments, each of $R_{72}$ and $R_{82}$ is independently hydrogen, —$C_{1-10}$ alkyl, —$C_{3-10}$aryl, —$C_{3-10}$cycloalkyl, —C(O)$R^{31}$, —$CO_2R^{31}$, —C(=O)$NR^{31}$, or —$S(O)_{0-2}R^{31}$. In some embodiments, each of $R_{72}$ and $R_{82}$ is independently hydrogen or —$C_{1-10}$alkyl. In some embodiments, each of $R_{72}$ and $R_{82}$ is independently hydrogen In some embodiments of Formula V-A, each of $R_{10}$ and $R_{14}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ and $R_{14}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula V-A, each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^{31}$, —$NR^{31}R^{32}$, —C(O)$R^{31}$, —$CO_2R^{31}$, —C(=O)$NR^{31}$, —$NO_2$, —CN, —$S(O)_{0-2}R^{31}$ or —$NR^{31}C(=O)R^{32}$. In some embodiments, each of $R_{11}$, $R_{12}$, $R_{13}$ and $R_{15}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, $R_{13}$ and $R_{15}$ is independently hydrogen, halogen, —$C_{1-10}$ alkyl, —OH or —$CF_3$.

In some embodiments of Formula V-A, each of $R^{31}$, $R^{32}$, $R^{33}$ and $R^{34}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, $R^{33}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, $R^{33}$ and $R^{34}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula V-A, $X_1$ is C=O, Z is $NR_1$ or $CR_1R_1'$, $X_2$ is $NR_1$ or $CR_1R_1'$, $X_3$ is $CR_3R_3'$ or C=O, Y is $CR_5$, $X_4$ is N or $CR_4$, $X_5$ is N or C, $X_6$ is C, $X_7$ is N or $NR_{72}$ or $CR_{71}$, $X_8$ is N or $CR_{81}$, and $X_9$ is $NR_{22}$ or $CR_{21}$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is hydrogen, —OH, —$CF_3$, —$C(O)R^{31}$, —$CO_2R^{31}$, —C(=O)$NR^{31}$, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl each of which is unsubstituted or substituted by one or more independent $R_{12}$ substituents;

L is a bond, —O—, —N($R^{31}$)—, —$S(O)_{0-2}$—, —C(=O)—, —C(=O)O—, —OC(=O)—, —C(=O)N($R^{31}$)—, —N($R^{31}$)C(=O)—, —$NR^{31}$C(=O)O—, —$NR^{31}$C(=O)$NR^{32}$—, —$NR^{31}$S(O)$_{0-2}$—, or —$S(O)_{0-2}$N($R^{31}$)—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents; or $R_3'$ is —$OR^6$, —$NR^6R^{34}$, —$S(O)_{0-2}R^6$, —C(=O)$R^6$, —C(=O)$OR^6$, —OC(=O)$R^6$, —C(=O)N($R^{34}$)$R^6$, —N($R^{34}$)C(=O)$R^6$, wherein $R^6$ together with $R^{34}$ can optionally form a heterocyclic ring;

each of $R_5$, $R_{71}$, and $R_{81}$ is independently hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$ or —$NR^{31}$C(=O)$R^{32}$;

$R_6$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{14}$ or $R_{15}$ substituents;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —C(=O)$NR^{31}$, or —$S(O)_{0-2}R^{31}$;

each of $R_{10}$ and $R_{14}$ is independently —$C_{1-10}$alkyl, —$C_{2-10}$alkenyl, —$C_{2-10}$alkynyl, -L-$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, $R_{13}$ and $R_{15}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$ or —$NR^{31}$C(=O)$R^{32}$;

each of $R^{31}$, $R^{32}$ and $R^{34}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring; and wherein at least one of $X_5$, $X_6$, $X_7$, $X_8$ or $X_9$ comprises one or more heteroatoms selected from N, O, or S.

In some embodiments of Formula V-A, $X_1$ is C=O, Z is $NR_1$ or $CR_1R_1'$, $X_2$ is $NR_1$ or $CR_1R_1'$, $X_3$ is $CR_3R_3'$, Y is $CR_5$, $X_4$ is N or $CR_4$, $X_5$ is N or C, $X_6$ is C, $X_7$ is $NR_{72}$ or $CR_{71}$, $X_8$ is N, and $X_9$ is $NR_{21}$ or $CR_{21}$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

$R_{22}$ is —OH, —$CF_3$, —$C(O)R^{31}$, —$CO_2R^{31}$, —C(=O)$NR^{31}$, —$S(O)_{0-2}R^{31}$, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —N($R^{31}$)—, —$S(O)_{0-2}$—, —C(=O)—, —C(=O)O—, —OC(=O)—, —C(=O)N($R^{31}$)—, or —N($R^{31}$)C(=O)—;

each of $R_3$, $R_3'$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —C(=O)$NR^{31}$, —$NO_2$, —CN, —$S(O)_{0-2}R^{31}$, —$C_{2-10}$alkenyl, or —$C_{2-10}$alkynyl, each of which is unsubstituted or substituted by one or more independent $R_{13}$ substituents; or $R_3'$ is —$OR^6$, —$NR^6R^{34}$, —C(=O)N($R^{34}$)$R^6$, or —N($R^{34}$)C(=O)$R^6$, wherein $R^6$ together with $R^{34}$ can optionally form a heterocyclic ring;

each of $R_5$ and $R_{71}$ is independently hydrogen, halogen, —$C_{1-10}$alkyl, —$C_{3-10}$aryl, —$C_{3-10}$cycloalkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$;

each of R$_{10}$ and R$_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, R$_{13}$ and R$_{15}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

each of R$^{31}$, R$^{32}$ and R$^{34}$ is independently hydrogen or —C$_{1-10}$alkyl, or wherein R$^{31}$ together with R$^{32}$ form a heterocyclic ring; and wherein at least one of X$_5$, X$_6$, X$_7$, X$_8$ or X$_9$ comprises one or more heteroatoms selected from N, O, or S.

In some embodiments of Formula V-A, X$_1$ is C=O, Z is NR$_1$ or CR$_1$R$_1$, X$_2$ is NR$_1$ or CR$_1$R$_1$', X$_3$ is CR$_3$R$_3$', Y is CR$_5$, X$_4$ is CR$_4$, X$_5$ is C, X$_6$ is C, X$_7$ is NR$_{72}$, X$_8$ is N, and X$_9$ is CR$_{21}$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OR$^{31}$, —NR$^{31}$R$^{32}$, —CO$_2$R$^{31}$, —C(=O)NR$^{31}$, —NO$_2$, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, —C(=O)N(R$^{31}$)—, or —N(R$^{31}$)C(=O)—; each of R$_3$, R$_3$' and R$_4$ is independently hydrogen, halogen, —OH, —CF$_3$, —OCF$_3$, —OR$^{31}$, —NR$^{31}$R$^{32}$, —NO$_2$, —CN, —S(O)$_{0-2}$R$^{31}$, —C$_{1-10}$alkyl, —C$_{2-10}$alkenyl, or —C$_{2-10}$alkynyl; or R$_3$' is —OR$^6$, —NR$^6$R$^{34}$, —C(=O)N(R$^{34}$)R$^6$, —N(R$^{34}$)C(=O)R$^6$, wherein R$^6$ together with R$^{34}$ can optionally form a heterocyclic ring;

R$_5$ is independently hydrogen, halogen, or —C$_{1-10}$alkyl;

R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen or —C$_{1-10}$alkyl;

each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$ and R$_{12}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$;

each of R$^{31}$, R$^{32}$ and R$^{34}$ is independently hydrogen or —C$_{1-10}$alkyl, or wherein R$^{31}$ together with R$^{32}$ form a heterocyclic ring; and wherein at least one of X$_5$, X$_6$, X$_7$, X$_8$ or X$_9$ comprises one or more heteroatoms selected from N, O, or S.

In some embodiments of Formula V-A, X$_1$ is C=O, Z is NR$_1$ or CR$_1$R$_1$', X$_2$ is NR$_1$ or CR$_1$R$_1$', X$_3$ is CR$_3$R$_3$', Y is CR$_5$, X$_4$ is CR$_4$, X$_5$ is C, X$_6$ is C, X$_7$ is NR$_{72}$, X$_8$ is N, and X$_9$ is CR$_{21}$;

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, or —C(=O)N(R$^{31}$)—;

each of R$_3$, R$_3$' and R$_4$ is independently hydrogen, halogen, —OH, —CF$_3$, or —C$_{1-10}$alkyl; or R$_3$' is —OR$^6$ or —NR$^6$R$^{34}$, wherein R$^6$ together with R$^{34}$ can optionally form a heterocyclic ring;

R$_5$ is hydrogen;

R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents;

R$_{72}$ is hydrogen, —C$_{1-10}$alkyl, —OH, —CF$_3$, —C(O)R$^{31}$, —CO$_2$R$^{31}$, —C(=O)NR$^{31}$, or —S(O)$_{0-2}$R$^{31}$;

each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$, R$_{12}$ and R$_{15}$ is independently hydrogen, halogen, —C$_{1-10}$alkyl, —OH or —CF$_3$;

each of R$^{31}$ and R$^{34}$ is independently hydrogen or —C$_{1-10}$alkyl; and wherein at least one of X$_5$, X$_6$, X$_7$, X$_8$ or X$_9$ comprises one or more heteroatoms selected from N, O, or S.

The invention also provides a compound as defined above, wherein the compound is of Formula V-B:

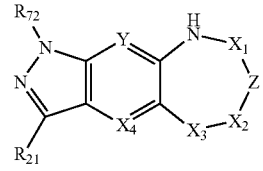

or a pharmaceutically acceptable salt or prodrug thereof, and wherein the substituents are as defined above.

In some embodiments of Formula V-B, X$_1$ is C=O, Z is NR$_1$ or CR$_1$R$_1$', X$_2$ is NR$_1$ or CR$_1$R$_1$', and X$_3$ is CR$_3$R$_3$'. In some embodiments, X$_1$ is C=O, Z is NR$_1$ or CR$_1$R$_1$', X$_2$ is NR$_1$ or CR$_1$R$_1$', and X$_3$ is C=O. In some embodiments, X$_1$ is C=S, Z is NR$_1$ or CR$_1$R$_1$', X$_2$ is NR$_1$ or CR$_1$R$_1$', and X$_3$ is CR$_3$. In some embodiments, X$_1$ is SO$_2$, is NR$_1$ or CR$_1$R$_1$', X$_2$ is NR$_1$ or CR$_1$R$_1$', and X$_3$ is CR$_3$R$_3$'.

In some embodiments of Formula V-B, X$_1$ is C=O or SO$_2$, Z is NR$_1$ or CR$_1$R$_1$', X$_2$ is NR$_1$ or CR$_1$R$_1$', X$_3$ is CH or C=O, Y is CR$_5$, and X$_4$ is N or CR$_4$. In some embodiments, X$_1$ is C=O or SO$_2$, Z is NR$_1$ or CR$_1$R$_1$', X$_2$ is NR$_1$ or CR$_1$R$_1$', X$_3$ is CH, Y is CR$_5$ and X$_4$ is N or CR$_4$. In some embodiments, X$_1$ is C=O, Z is NR$_1$ or CR$_1$R$_1$', X$_2$ is NR$_1$ or CR$_1$R$_1$', X$_3$ is CH, Y is CR$_5$ and X$_4$ is CR$_4$.

In some embodiments of Formula V-B, R$_1$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl- $C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula V-B, $R_1'$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1'$ is hydrogen, —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula V-B, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents In some embodiments of Formula V-B, L is a bond, —O—, —N($R^{31}$)—, —S(O)$_{0-2}$—, —C(=O)—, —C(=O)O—, —OC(=O)—, —C(=O)N($R^{31}$)—, —N($R^{31}$)C(=O)—, —N$R^{31}$C(=O)O—, —N$R^{31}$C(=O)N$R^{32}$—, —N$R^{31}$S(O)$_{0-2}$—, or —S(O)$_{0-2}$N($R^{31}$)—. In some embodiments, L is a bond, —O—, —N($R^{31}$)—, —S(O)$_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—

In some embodiments of Formula V-B, $R_3$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{2-10}$alkenyl, or —$C_{2-10}$alkynyl. In some embodiments, $R_3$ is hydrogen, halogen, —OH, —$CF_3$, or —$C_{1-10}$alkyl.

In some embodiments of Formula V-B, $R_3'$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_3'$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_3'$ is hydrogen, halogen, —OH, —$CF_3$, —$OCF_{39}$—$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_3'$ is hydrogen, halogen, —OH, —$CF_3$, or —$C_{1-10}$alkyl.

In some embodiments of Formula V-B, $R_4$ is hydrogen, halogen, —OH, —$CF_3$, —$OCF_{39}$—$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_{39}$—$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula V-B, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_{39}$—$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C$ —C(=O)R$^{32}$. In some embodiments, R$_5$ is hydrogen, halogen, or —C$_{1-10}$alkyl. In some embodiments, R$_5$ is hydrogen.

In some embodiments of Formula V-B, R$_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{14}$ or R$_{15}$ substituents. In some embodiments, R$_6$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents. In some embodiments, R$_6$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{14}$ or R$_{15}$ substituents.

In some embodiments of Formula V-B, R$_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$. In some embodiments, R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, or —S(O)$_{0-2}$R$^{31}$. In some embodiments, R$_{72}$ is hydrogen or —C$_{1-10}$alkyl. In some embodiments, R$_{72}$ is hydrogen.

In some embodiments of Formula V-B, each of R$_{10}$ and R$_{14}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, optionally substituted by one or more independent R$_{11}$ substituents. In some embodiments, each of R$_{10}$ and R$_{14}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents. In some embodiments, each of R$_{10}$ and R$_{14}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents.

In some embodiments of Formula V-B, each of R$_{11}$, R$_{12}$, R$_{13}$ and R$_{15}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of R$_{11}$, R$_{12}$, R$_{13}$ and R$_{15}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$. In some embodiments, each of R$_{11}$, R$_{12}$, R$_{13}$ and R$_{15}$ is independently hydrogen, halogen, —C$_{1-10}$alkyl, —OH, —CF$_3$, —OR$^3$, —NR$^{31}$R$^{32}$, —NO$_2$, —CN, or —S(O)$_{0-2}$R$^{31}$. In some embodiments, each of R$_{11}$, R$_{12}$, R$_{13}$ and R$_{15}$ is independently hydrogen, halogen, —C$_{1-10}$ alkyl, —OH or —CF$_3$.

In some embodiments of Formula V-B, each of R$^{31}$, R$^{32}$, R$^{33}$ and R$^{34}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, or wherein R$^{31}$ together with R$^{32}$ form a heterocyclic ring. In some embodiments, each of R$^{31}$, R$^{32}$, R$^{33}$ and R$^{34}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring. In some embodiments, each of R$^{31}$, R$^{32}$, R$^{33}$ and R$^{34}$ is independently hydrogen or —C$_{1-10}$alkyl, or wherein R$^{31}$ together with R$^{32}$ form a heterocyclic ring. In some embodiments, each of R$^{31}$, R$^{32}$, R$^{33}$ and R$^{34}$ is independently hydrogen or —C$_{1-10}$alkyl.

In some embodiments of Formula V-B, X$_1$ is C=O or SO$_2$, Z is NR$_1$ or CR$_1$R$_1$', X$_2$ is NR$_1$ or CR$_1$R$_1$', X$_3$ is CR$_3$R$_3$' or C=O, Y is CR$_5$ and X$_4$ is N or CR$_4$;

R$_1$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_1$' is hydrogen, —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_{21}$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{2-10}$alkenyl, -L-C$_{2-10}$alkynyl, -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—;

each of R$_3$, R$_3$' and R$_4$ is independently hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, each of which is unsubstituted or substituted by one or more independent R$_{13}$ substituents; or R$_3$' is —OR$^6$, —NR$^6$R$^{34}$, —S(O)$_{0-2}$R$^6$, —C(=O)R$^6$, —C(=O)OR$^6$, —OC(=O)R$^6$, —C(=O)N(R$^{34}$)R$^6$, or —N(R$^{34}$)C(=O)R$^6$, wherein R$^6$ together with R$^{34}$ can optionally form a heterocyclic ring;

R$_5$ is hydrogen, halogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$;

R$_6$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent $R_{14}$ or $R_{15}$ substituents;

$R_{72}$ is hydrogen, $-C_{1-10}$alkyl, $-C_{3-10}$aryl, $-C_{1-10}$hetaryl, $-C_{3-10}$cycloalkyl, $-C_{1-10}$heterocyclyl, $-OH$, $-CF_3$, $-C(O)R^{31}$, $-CO_2R^{31}$, $-C(=O)NR^{31}$, or $-S(O)_{0-2}R^{31}$;

each of $R_{10}$ and $R_{14}$ is independently $-C_{1-10}$alkyl, $-C_{2-10}$alkenyl, $-C_{2-10}$alkynyl, $-C_{1-10}$heteroalkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-C_{3-10}$aryl, $-C_{3-10}$cycloalkyl, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$; and each of $R^{31}$, $R^{32}$ and $R^{34}$ is independently hydrogen, $-C_{1-10}$alkyl, $-C_{3-10}$aryl, or $-C_{3-10}$cycloalkyl, or wherein $R^{31}$ together with $R^{32}$ form a heterocyclic ring.

In some embodiments of Formula V-B, $X_1$ is C=O or $SO_2$, Z is $NR_1$ or $CR_1R_1'$, $X_2$ is $NR_1$ or $CR_1R_1'$, $X_3$ is $CR_3R_3'$, Y is $CR_5$ and $X_4$ is N or $CR_4$;

$R_1$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OCF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-O-$, $-N(R^{31})-$, $-S(O)_{0-2}-$, $-C(=O)-$, $-C(=O)O-$, $-OC(=O)-$, $-C(=O)N(R^{31})-$, or $-N(R^{31})C(=O)-$;

each of $R_3$, $R_3'$ and $R_4$ is independently hydrogen, halogen, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$, $-C_{1-10}$alkyl, $-C_{2-10}$alkenyl, or $-C_{2-10}$alkynyl, each of which is unsubstituted or substituted by one or more independent $R_{13}$ substituents; or $R_3'$ is $-OR^6$, $-NR^6R^{34}$, $-C(=O)N(R^{34})R^6$, or $-N(R^{34})C(=O)R^6$, wherein $R^6$ together with $R^{34}$ can optionally form a heterocyclic ring;

$R_5$ is hydrogen, halogen, $-C_{1-10}$alkyl, $-C_{3-10}$aryl, $-C_{3-10}$cycloalkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$;

$R_6$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen, $-C_{1-10}$alkyl, $-C_{3-10}$aryl, $-C_{3-10}$cycloalkyl, $-C(O)R^{31}$, $-CO_2R^{31}$, $-C(=O)NR^{31}$, or $-S(O)_{0-2}R^{31}$;

each of $R_{10}$ and $R_{14}$ is independently $-C_{1-10}$alkyl, $-C_{3-10}$aryl, $-C_{1-10}$hetaryl, $-C_{3-10}$cycloalkyl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-OH$, $-CF_3$, $-OR^{31}$, $-NR^{31}R^{32}$, $-C(O)R^{31}$, $-CO_2R^{31}$, $-C(=O)NR^{31}$, $-NO_2$, $-CN$, $-S(O)_{0-2}R^{31}$ or $-NR^{31}C(=O)R^{32}$; and each of $R^{31}$, $R^{32}$ and $R^{34}$ is independently hydrogen or $-C_{1-10}$alkyl, or wherein $R^{31}$ together with $R^{32}$ form a heterocyclic ring.

In some embodiments of Formula V-B, $X_1$ is C=O, Z is $NR_1$ or $CR_1R_1'$, $X_2$ is $NR_1$ or $CR_1R_1'$, $X_3$ is $CR_3R_3'$, Y is $CR_5$ and $X_4$ is $CR_4$;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-OH$, $-CF_3$, $-OR^{31}$, $-NR^{31}R^{32}$, $-CO_{2R}^{31}$, $-C(=O)NR^{31}$, $-NO_2$, $-CN$, $-S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-N(R^{31})-$, $-C(=O)N(R^{31})-$, or $-N(R^{31})C(=O)-$;

each of $R_3$, $R_3'$ and $R_4$ is independently hydrogen, halogen, $-OH$, $-CF_3$, $-OR^{31}$, $-NR^{31}R^{32}$, $-NO_2$, $-CN$, $-S(O)_{0-2}R^{31}$, $-C_{1-10}$alkyl, $-C_{2-10}$alkenyl, or $-C_{2-10}$alkynyl; or $R_3'$ is $-OR^6$, $-NR^6R^{34}$, $-C(=O)N(R^{34})R^6$, or $-N(R^{34})C(=O)R^6$, wherein $R^6$ together with $R^{34}$ can optionally form a heterocyclic ring;

$R_5$ is hydrogen, halogen, or $-C_{1-10}$alkyl;

$R_6$ is $-C_{1-10}$alkyl, $-C_{1-10}$heterocyclyl, $-C_{1-10}$alkyl-$C_{3-10}$aryl, $-C_{1-10}$alkyl-$C_{1-10}$hetaryl, $-C_{1-10}$alkyl-$C_{3-10}$cycloalkyl, $-C_{1-10}$alkyl-$C_{1-10}$heterocyclyl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen or $-C_{1-10}$alkyl;

each of $R_{10}$ and $R_{14}$ is independently $-C_{1-10}$alkyl, $-C_{3-10}$aryl, $-C_{1-10}$hetaryl, or $-C_{1-10}$heterocyclyl, optionally substituted by one or more independent $R_{11}$ substituents;

each of $R_{11}$, $R_{12}$, $R_{13}$ and $R_{15}$ is independently hydrogen, halogen, $-C_{1-10}$alkyl, $-OH$, $-CF_3$, $-OR^3$, $-NR^{31}R^{32}$, $-NO_2$, $-CN$, or $-S(O)_{0-2}R^{31}$; and each of $R^{31}$, $R^{32}$ and $R^{34}$ is independently hydrogen or $-C_{1-10}$alkyl.

In some embodiments of Formula V-B, $X_1$ is C=O, Z is $NR_1$ or $CR_1R_1'$, $X_2$ is $NR_1$ or $CR_1R_1'$, $X_3$ is $CR_3R_3'$, Y is $CR_5$, $X_4$ is $CR_4$;

$R_1$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{10}$ or $R_{11}$ substituents;

$R_{21}$ is halogen, $-CN$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, $-N(R^{31})-$, or $-C(=O)N(R^{31})-$;

each of $R_3$, $R_3'$ and $R_4$ is independently hydrogen, halogen, $-OH$, $-CF_3$, or $-C_{1-10}$alkyl; or $R_3'$ is $-OR^6$ or $-NR^6R^{34}$, wherein $R^6$ together with $R^{34}$ can optionally form a heterocyclic ring;

$R_5$ is hydrogen;

$R_6$ is $-C_{1-10}$alkyl, $-C_{1-10}$heterocyclyl, $-C_{1-10}$alkyl-$C_{3-10}$aryl, $-C_{1-10}$heterocyclyl-$C_{1-10}$alkyl, or $-C_{1-10}$heterocyclyl-$C_{3-10}$aryl, each of which is unsubstituted or substituted by one or more independent $R_{14}$ or $R_{15}$ substituents;

$R_{72}$ is hydrogen;

each of $R_{10}$ and $R_{14}$ is independently $-C_{1-10}$alkyl, $-C_{3-10}$aryl, $-C_{1-10}$hetaryl, or $-C_{1-10}$heterocyclyl, optionally substituted by one or more independent $R_{11}$ substituents;

each of $R_{11}$, $R_{12}$ and $R_{15}$ is independently hydrogen, halogen, $-C_{1-10}$alkyl, $-OH$ or $-CF_3$; and each of $R^{31}$ and $R^{34}$ is independently hydrogen or —$C_{1-10}$alkyl.

The invention also provides a compound as defined above, wherein the compound is of Formula V-C:

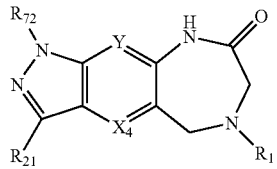

or a pharmaceutically acceptable salt or prodrug thereof, and wherein the substituents are as defined above.

In some embodiments of Formula V-C, Y is $CR_5$, and $X_4$ is N or $CR_4$. In some embodiments of Formula V-C, Y is $CR_5$, and $X_4$ is $CR_4$.

In some embodiments of Formula V-C, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula V-C, $R_{21}$ is hydrogen, halogen, —OH, —$CF_3$, —$OCF_3$, —$OR^{31}$, —$NR^{31}$, $R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}$, $R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{3-10}$cycloalkyl, or -L-$C_{1-10}$heterocyclyl, each of which is unsubstituted or substituted by one or more independent $R_{12}$ substituents.

In some embodiments of Formula V-C, L is a bond, —O—, —N($R^{31}$)—, —$S(O)_{0-2}$—, —C(=O)—, —C(=O)O—, —OC(=O)—, —C(=O)N($R^{31}$)—, —N($R^{31}$)C(=O)—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —N($R^{31}$)—, —$S(O)_{0-2}$—, —C(=O)—, —C(=O)O—, —OC(=O)—, —C(=O)N($R^{31}$)—, or —N($R^{31}$)C(=O)—. In some embodiments, L is a bond, —N($R^{31}$)—, —C(=O)N($R^{31}$)—, or —N($R^{31}$)C(=O)—. In some embodiments, L is a bond, —N($R^{31}$)—, or —C(=O)N($R^{31}$)—.

In some embodiments of Formula V-C, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{1-10}$alkyl, —$C_{2-10}$alkenyl, or —$C_{2-10}$alkynyl, each of which is unsubstituted or substituted by one or more independent $R_{13}$ substituents. In some embodiments, $R_4$ is hydrogen, halogen, —OH, —$CF_3$, —$OCF_3$, —$OR^{31}$, —$NR^{31}R^{32}$, —$NO_2$, —CN, —$S(O)_{0-2}R^{31}$, —$C_{1-10}$alkyl, —$C_{2-10}$alkenyl, or —$C_{2-10}$alkynyl. In some embodiments, $R_4$ is hydrogen, halogen, —OH, —$CF_3$, or —$C_{1-10}$alkyl.

In some embodiments of Formula V-C, $R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, —$C_{1-10}$alkyl, —$C_{3-10}$aryl, —$C_{3-10}$cycloalkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, $R_5$ is hydrogen, halogen, or —$C_{1-10}$alkyl. In some embodiments, $R_5$ is hydrogen.

In some embodiments of Formula V-C, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, $R_{72}$ is independently hydrogen, —$C_{1-10}$alkyl, —$C_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, $R_{72}$ is independently hydrogen or —$C_{1-10}$alkyl. In some embodiments, $R_{72}$ is independently hydrogen.

In some embodiments of Formula V-C, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents.

In some embodiments of Formula V-C, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^3$, —$NR^{31}R^{32}$, —$NO_2$, —CN, or —$S(O)_{0-2}R^{31}$. In some embodiments, each of $R_{11}$, $R_{12}$, and $R_{13}$ is independently hydrogen, halogen, —$C_{1-10}$ alkyl, —OH or —$CF_3$.

In some embodiments of Formula V-C, each of $R^{31}$, $R^{32}$, and $R^{33}$ is independently hydrogen, halogen, —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, or wherein $R^{31}$ together with $R^{32}$ form a heterocyclic ring. In some embodiments, each of $R^{31}$, $R^{32}$, and $R^{33}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl, or wherein $R^{31}$ together with $R^{32}$ form a heterocyclic ring. In some embodiments, each of $R^{31}$, $R^{32}$, and $R^{33}$ is independently hydrogen or —$C_{1-10}$alkyl.

In some embodiments of Formula V-C, Y is $CR_5$, $X_4$ is N or $CR_4$;

$R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents;

$R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{2-10}$alkenyl, -L-$C_{2-10}$alkynyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—;

each of $R_3$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, each of which is unsubstituted or substituted by one or more independent $R_{13}$ substituents;

$R_5$ is hydrogen, halogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$;

$R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$;

each of $R_{10}$ is independently —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen, —$C_{1-10}$alkyl, —$C_{3-10}$aryl, or —$C_{3-10}$cycloalkyl, or wherein $R^{31}$ together with $R^{32}$ form a heterocyclic ring.

In some embodiments of Formula V-C, Y is $CR_5$, $X_4$ is N or $CR_4$;

$R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents;

L is a bond, —O—, —$N(R^{31})$—, —$S(O)_{0-2}$—, —C(=O)—, —C(=O)O—, —OC(=O)—, —C(=O)N($R^{31}$)—, or —$N(R^{31})C(=O)$—;

each of $R_3$ and $R_4$ is independently hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$C_{2-10}$alkenyl, or —$C_{2-10}$alkynyl;

$R_5$ is hydrogen, halogen, or —$C_{1-10}$alkyl;

$R_{72}$ is hydrogen or —$C_{1-10}$alkyl;

each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$; and each of $R^{31}$ and $R^{32}$ is independently hydrogen or —$C_{1-10}$alkyl.

In some embodiments of Formula V-C, Y is $CR_5$, $X_4$ is $CR_4$;

$R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents;

$R_{21}$ is halogen, —CN, -L-$C_{1-10}$alkyl, -L-$C_{3-10}$cycloalkyl, or -L-$C_{1-10}$heterocyclyl, each of which is unsubstituted or substituted by one or more independent $R_{12}$ substituents;

L is a bond, —$N(R^{31})$—, or —$C(=O)N(R^{31})$—;

each of $R_3$ and $R_4$ is independently hydrogen, halogen, —OH, —$CF_3$, or —$C_{1-10}$alkyl;

$R_5$ is hydrogen;

$R_{72}$ is hydrogen;

each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents;

each of $R_{11}$ and $R_{12}$ is independently hydrogen, halogen, —$C_{1-10}$alkyl, —OH or —$CF_3$; and each of $R^{31}$ is independently hydrogen or —$C_{1-10}$alkyl.

The invention also provides a compound as defined above, wherein the compound is of Formula V-D:

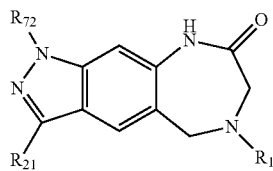

or a pharmaceutically acceptable salt or prodrug thereof, and wherein the substituents are as defined above.

In some embodiments of Formula V-D, $R_1$ is —$C_{1-10}$alkyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{3-10}$cycloalkyl-$C_{1-10}$alkyl, —$C_{3-10}$cycloalkyl-$C_{3-10}$aryl, —$C_{3-10}$cycloalkyl-$C_{1-10}$hetaryl, —$C_{3-10}$cycloalkyl-$C_{1-10}$heterocyclyl, —$C_{1-10}$heterocyclyl-$C_{1-10}$alkyl, —$C_{1-10}$heterocyclyl-$C_{3-10}$aryl, —$C_{1-10}$heterocyclyl-$C_{1-10}$hetaryl, or —$C_{1-10}$heterocyclyl-$C_{3-10}$cycloalkyl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$alkyl-$C_{1-10}$hetaryl, —$C_{1-10}$alkyl-$C_{3-10}$cycloalkyl, —$C_{1-10}$alkyl-$C_{1-10}$heterocyclyl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents. In some embodiments, $R_1$ is —$C_{1-10}$alkyl, —$C_{1-10}$heterocyclyl, —$C_{1-10}$alkyl-$C_{3-10}$aryl, —$C_{1-10}$heterocyclyl-$C_{1-10}$alkyl, or —$C_{1-10}$heterocyclyl-$C_{3-10}$aryl, each of which is unsubstituted or substituted by one or more independent $R_{10}$ or $R_{11}$ substituents.

In some embodiments of Formula V-D, $R_{21}$ is hydrogen, halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{2-10}$alkenyl, -L-$C_{2-10}$alkynyl, -L-$C_{1-10}$heteroalkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$, —$NR^{31}C(=O)R^{32}$, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents. In some embodiments, $R_{21}$ is halogen, —CN, -L-$C_{1-10}$alkyl, -L-$C_{3-10}$aryl, -L-$C_{1-10}$hetaryl, -L-$C_{3-10}$cycloalkyl, or -L-$C_{1-10}$heterocyclyl, each of which is unsubstituted or substituted by one or more independent $R_{12}$ substituents.

In some embodiments of Formula V-D, L is a bond, —O—, —$N(R^{31})$—, —$S(O)_{0-2}$—, —$C(=O)$—, —$C(=O)O$—, —$OC(=O)$—, —$C(=O)N(R^{31})$—, —$N(R^{31})C(=O)$—, —$NR^{31}C(=O)O$—, —$NR^{31}C(=O)NR^{32}$—, —$NR^{31}S(O)_{0-2}$—, or —$S(O)_{0-2}N(R^{31})$—. In some embodiments, L is a bond, —O—, —$N(R^{31})$—, —$S(O)_{0-2}$—, —$C(=O)$—, —$C(=O)O$—, —$OC(=O)$—, —$C(=O)N(R^{31})$—, or —$N(R^{31})C(=O)$—. In some embodiments, L is a bond, —$N(R^{31})$—, —$C(=O)N(R^{31})$—, or —$N(R^{31})C(=O)$—. In some embodiments, L is a bond, —$N(R^{31})$—, or —$C(=O)N(R^{31})$—.

In some embodiments of Formula V-D, $R_{72}$ is hydrogen, —$C_{1-10}$alkyl, —$C_{3-10}$aryl, —$C_{1-10}$hetaryl, —$C_{3-10}$cycloalkyl, —$C_{1-10}$heterocyclyl, —OH, —$CF_3$, —$C(O)R^{31}$, —$CO_2R^{31}$, —$C(=O)NR^{31}$, or —$S(O)_{0-2}R^{31}$. In some embodiments, $R_{72}$ is independently hydrogen, —$C_{1-10}$alkyl, —$c_{3-10}$aryl, —$C_{3-10}$cycloalkyl, —$C(O)R^{31}$, —$CO_2R^{31}$, —$C(=O)NR^{31}$, or —$S(O)_{0-2}R^{31}$. In some embodiments, $R_{72}$ is independently hydrogen or —$C_{1-10}$alkyl. In some embodiments, $R_{72}$ is independently hydrogen.

In some embodiments of Formula V-D, each of $R_{10}$ independently is —$C_{1-10}$alkyl, —$C_{2-10}$alkenyl, —$C_{2-10}$alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, —$C_{3-10}$cycloalkyl, or —$C_{1-10}$heterocyclyl, optionally substituted by one or more independent $R_{11}$ substituents. In some embodiments, each of $R_{10}$ is independently —$C_{1-10}$alkyl, —$C_{3-10}$aryl, —$C_{1-10}$hetaryl, or —$C_{1-10}$heterocyclyl, optionally substituted by one or more independent $R_{11}$ substituents In some embodiments of Formula V-D, each of $R_{11}$, $R_{12}$, and $R_{13}$ is independently hydrogen, halogen, —$C_{1-10}$alkyl, —$C_{3-10}$aryl, —$C_{3-10}$cycloalkyl, —OH, —$CF_3$, —$OCF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —$OR^{31}$, —$NR^{31}R^{32}$, —$C(O)R^{31}$, —$CO_2R^{31}$, —$C(=O)NR^{31}$, —$NO_2$, —CN, —$S(O)_{0-2}R^{31}$ or —$NR^{31}C(=O)R^{32}$. In some embodiments, each of $R_{11}$, $R_{12}$, and $R_{13}$ is independently hydrogen, halogen, —$C_{1-10}$alkyl, —OH, —$CF_3$, —OR$^3$, —NR$^{31}$R$^{32}$, —NO$_2$, —CN, or —S(O)$_{0-2}$R$^{31}$. In some embodiments, each of R$_{11}$, R$_{12}$, and R$_{13}$ is independently hydrogen, halogen, —C$_{1-10}$ alkyl, —OH or —CF$_3$.

In some embodiments of Formula V-D, each of R$^{31}$, R$^{32}$, and R$^{33}$ is independently hydrogen, halogen, —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, or wherein R$^{31}$ together with R$^{32}$ form a heterocyclic ring. In some embodiments, each of R$^{31}$, R$^{32}$, and R$^{33}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring. In some embodiments, each of R$^{31}$, R$^{32}$, and R$^{33}$ is independently hydrogen or —C$_{1-10}$alkyl, or wherein R$^{31}$ together with R$^{32}$ form a heterocyclic ring. In some embodiments, each of R$^{31}$, R$^{32}$, and R$^{33}$ is independently hydrogen or —C$_{1-10}$alkyl.

In some embodiments of Formula V-D,

R$_1$ is —C$_{1-10}$alkyl, —C$_{3-10}$aryl, —C$_{1-10}$hetaryl, —C$_{3-10}$cycloalkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{3-10}$cycloalkyl-C$_{1-10}$alkyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{3-10}$aryl, —C$_{1-10}$heterocyclyl-$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_{21}$ is hydrogen, halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{2-10}$alkenyl, -L-C$_{2-10}$alkynyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, —N(R$^{31}$)C(=O)—, —NR$^{31}$C(=O)O—, —NR$^{31}$C(=O)NR$^{32}$—, —NR$^{31}$S(O)$_{0-2}$—, or —S(O)$_{0-2}$N(R$^{31}$)—;

R$_{72}$ is hydrogen, —C$_{1-10}$alkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, or —S(O)$_{0-2}$R$^{31}$;

each of R$_{10}$ is independently —C$_{1-10}$alkyl, —C$_{2-10}$alkenyl, —C$_{2-10}$alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —C$_{3-10}$aryl, —C$_{3-10}$cycloalkyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$; and each of R$^{31}$ and R$^{32}$ is independently hydrogen, —C$_{1-10}$alkyl, —C$_{3-10}$aryl, or —C$_{3-10}$cycloalkyl, or wherein R$^{31}$ together with R$^{32}$ form a heterocyclic ring.

In some embodiments of Formula V-D,

R$_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—;

R$_{72}$ is hydrogen, —C$_{1-10}$alkyl, —C$_{3-10}$aryl, —C$_{3-10}$cycloalkyl, —C(O)R$^{31}$, —CO$_2$R$^{31}$, —C(=O)NR$^{31}$, —S(O)$_{0-2}$R$^{31}$;

R$_{10}$ is —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$, R$_{12}$, and R$_{13}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$; and each of R$^{31}$ and R$^{32}$ is independently hydrogen or —C$_{1-10}$alkyl, or wherein R$^{31}$ together with R$^{32}$ form a heterocyclic ring In some embodiments of Formula V-D, R$_1$ is —C$_{1-10}$alkyl, —C$_{1-10}$heterocyclyl, —C$_{1-10}$alkyl-C$_{3-10}$aryl, —C$_{1-10}$alkyl-C$_{1-10}$hetaryl, —C$_{1-10}$alkyl-C$_{3-10}$cycloalkyl, —C$_{1-10}$alkyl-C$_{1-10}$heterocyclyl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —O—, —N(R$^{31}$)—, —S(O)$_{0-2}$—, —C(=O)—, —C(=O)O—, —OC(=O)—, —C(=O)N(R$^{31}$)—, or —N(R$^{31}$)C(=O)—;

R$_{72}$ is hydrogen or —C$_{1-10}$alkyl;

each of R$_{10}$ is independently —C$_{1-10}$alkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

each of R$_{11}$ and R$_{12}$ is independently hydrogen, halogen, —C$_{1-10}$alkyl, —OH, —CF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$ or —NR$^{31}$C(=O)R$^{32}$; and each of R$^{31}$ and R$^{32}$ is independently hydrogen or —C$_{1-10}$alkyl.

In some embodiments of Formula V-D,

R$_1$ is —C$_{1-10}$alkyl, —C$_{1-10}$heterocyclyl, —C$_{1-10}$alkyl-C$_{3-10}$aryl, —C$_{1-10}$heterocyclyl-C$_{1-10}$alkyl, or —C$_{1-10}$heterocyclyl-C$_{3-10}$aryl, each of which is unsubstituted or substituted by one or more independent R$_{10}$ or R$_{11}$ substituents;

R$_{21}$ is halogen, —CN, -L-C$_{1-10}$alkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond, —N(R$^{31}$)—, or —C(=O)N(R$^{31}$)—;

R$_{72}$ is hydrogen;

each of R$_{10}$ is independently —C$_{1-10}$alkyl, —C$_{3-10}$aryl, —C$_{1-10}$hetaryl, or —C$_{1-10}$heterocyclyl, optionally substituted by one or more independent R$_{11}$ substituents;

each of R$_{11}$ and R$_{12}$ is independently hydrogen, halogen, —C$_{1-10}$alkyl, —OH or —CF$_3$; and each of R$^{31}$ is independently hydrogen or —C$_{1-10}$alkyl.

Additional embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D) are described below.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkyl, which is unsubstituted. In some embodiments, $R_1$ is —$C_{1-10}$alkyl, substituted by one or more independent $R_{10}$ substituents. In some embodiments, $R_1$ is —$C_{1-10}$alkyl, substituted by one or more independent $R_{11}$ substituents. In some embodiments, $R_1$ is —$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkenyl, which is unsubstituted. In some embodiments, $R_1$ is —$C_{1-10}$alkenyl, substituted by one or more independent $R_{10}$ substituents. In some embodiments, $R_1$ is —$C_{1-10}$alkenyl, substituted by one or more independent $R_{11}$ substituents. In some embodiments, $R_1$ is —$C_{1-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkynyl, which is unsubstituted. In some embodiments, $R_1$ is —$C_{2-10}$alkynyl, substituted by one or more independent $R_{10}$ substituents. In some embodiments, $R_1$ is —$C_{2-10}$alkynyl, substituted by one or more independent $R_{11}$ substituents. In some embodiments, $R_1$ is —$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heteroalkyl, which is unsubstituted. In some embodiments, $R_1$ is —$C_{1-10}$heteroalkyl, substituted by one or more independent $R_{10}$ substituents. In some embodiments, $R_1$ is —$C_{1-10}$heteroalkyl, substituted by one or more independent $R_{11}$ substituents. In some embodiments, $R_1$ is —$C_{1-10}$heteroalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$aryl, which is unsubstituted. In some embodiments, $R_1$ is —$C_{3-10}$aryl, substituted by one or more independent $R_{10}$ substituents. In some embodiments, $R_1$ is —$C_{3-10}$aryl, substituted by one or more independent $R_{11}$ substituents. In some embodiments, $R_1$ is —$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$hetaryl, which is unsubstituted. In some embodiments, $R_1$ is —$C_{1-10}$hetaryl, substituted by one or more independent $R_{10}$ substituents. In some embodiments, $R_1$ is —$C_{1-10}$hetaryl, substituted by one or more independent $R_{11}$ substituents. In some embodiments, $R_1$ is —$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$cycloalkyl, which is unsubstituted. In some embodiments, $R_1$ is —$C_{3-10}$cycloalkyl, substituted by one or more independent $R_{10}$ substituents. In some embodiments, $R_1$ is —$C_{3-10}$cycloalkyl, substituted by one or more independent $R_{11}$ substituents. In some embodiments, $R_1$ is —$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl, which is unsubstituted. In some embodiments, $R_1$ is —$C_{1-10}$heterocyclyl, substituted by one or more independent $R_{10}$ substituents. In some embodiments, $R_1$ is —$C_{1-10}$heterocyclyl, substituted by one or more independent $R_{11}$ substituents. In some embodiments, $R_1$ is —$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkyl-$C_{3-10}$aryl, which is unsubstituted. In some embodiments, $R_1$ is —$C_{1-10}$alkyl-$C_{3-10}$aryl, substituted by one or more independent $R_{10}$ substituents. In some embodiments, $R_1$ is —$C_{1-10}$alkyl-$C_{3-10}$aryl, substituted by one or more independent $R_{11}$ substituents. In some embodiments, $R_1$ is —$C_{1-10}$alkyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkyl-$C_{1-10}$hetaryl, which is unsubstituted. In some embodiments, $R_1$ is —$C_{1-10}$alkyl-$C_{1-10}$hetaryl, substituted by one or more independent $R_{10}$ substituents. In some embodiments, $R_1$ is —$C_{1-10}$alkyl-$C_{1-10}$hetaryl, substituted by one or more independent $R_{11}$ substituents. In some embodiments, $R_1$ is —$C_{1-10}$alkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkyl-$C_{3-10}$cycloalkyl, which is unsubstituted. In some embodiments, $R_1$ is —$C_{1-10}$alkyl-$C_{3-10}$cycloalkyl, substituted by one or more independent $R_{10}$ substituents. In some embodiments, $R_1$ is —$C_{1-10}$alkyl-$C_{3-10}$cycloalkyl, substituted by one or more independent $R_{11}$ substituents. In some embodiments, $R_1$ is —$C_{1-10}$alkyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkyl-$C_{1-10}$heterocyclyl, which is unsubstituted. In some embodiments, $R_1$ is —$C_{1-10}$alkyl-$C_{1-10}$heterocyclyl, substituted by one or more independent $R_{10}$ substituents. In some embodiments, $R_1$ is —$C_{1-10}$alkyl-$C_{1-10}$heterocyclyl, substituted by one or more independent $R_{11}$ substituents. In some embodiments, $R_1$ is —$C_{1-10}$alkyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkenyl-$C_{3-10}$aryl, which is unsubstituted. In some embodiments, $R_1$ is —$C_{2-10}$alkenyl-$C_{3-10}$aryl, substituted by one or more independent $R_{10}$ substituents. In some embodiments, $R_1$ is —$C_{2-10}$alkenyl-$C_{3-10}$aryl, substituted by one or more independent $R_{11}$ substituents. In some embodiments, $R_1$ is —$C_{2-10}$alkenyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkenyl-$C_{1-10}$hetaryl, which is unsubstituted. In some embodiments, $R_1$ is —$C_{2-10}$alkenyl-$C_{1-10}$hetaryl, substituted by one or more independent $R_{10}$ substituents. In some embodiments, $R_1$ is —$C_{2-10}$alkenyl-$C_{1-10}$hetaryl, substituted by one or more independent $R_{11}$ substituents. In some embodiments, $R_1$ is —$C_{2-10}$alkenyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkenyl-$C_{3-10}$cycloalkyl, which is unsubstituted. In some embodiments, $R_1$ is —$C_{2-10}$alkenyl-$C_{3-10}$cycloalkyl, substituted by one or more independent $R_{10}$ substituents. In some embodiments, $R_1$ is —$C_{2-10}$alkenyl-$C_{3-10}$cycloalkyl, substituted by one or more independent $R_{11}$ substituents. In some embodiments, $R_1$ is —$C_{2-10}$alkenyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkenyl-$C_{1-10}$heterocyclyl, which is unsubstituted. In some embodiments, $R_1$ is —$C_{2-10}$alkenyl-$C_{1-10}$heterocyclyl, substituted by one or more independent $R_{10}$ substituents. In some embodiments, $R_1$ is —$C_{2-10}$alkenyl-$C_{1-10}$heterocyclyl, substituted by one or more independent $R_{11}$ substituents. In some embodiments, $R_1$ is —$C_{2-10}$alkenyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkynyl-$C_{3-10}$aryl, which is unsubstituted. In some embodiments, $R_1$ is —$C_{2-10}$alkynyl-$C_{3-10}$aryl, substituted by one or more independent $R_{10}$ substituents. In some embodiments, $R_1$ is —$C_{2-10}$alkynyl-$C_{3-10}$aryl, substituted by one or more independent $R_{11}$ substituents. In some embodiments, $R_1$ is —$C_{2-10}$alkynyl-$C_{3-10}$aryl, substituted by one or more independent $R_{10}$ or $R_{11}$ substituents.

In various embodiments of compounds of Formula I (including I-A and I-B), Formula II (including II-A, II-B, II-C and II-D) and IIII (including III-A and III-B), $R_1$ is —$C_{2-10}$alkynyl-$C_{1-10}$hetaryl, which is unsubstituted. In some embodiments, $R_1$ is —$C_{2-10}$alkynyl-$C_{1-10}$hetaryl, substituted by one or more independent $R_{10}$ substituents. In some embodiments, $R_1$ is —$C_{2-10}$alkynyl-$C_{1-10}$hetaryl, substituted by one or more independent $R_{11}$ substituents. In some embodiments, $R_1$ is —$C_{2-10}$alkynyl-$C_{1-10}$hetaryl, substituted by one or more independent $R_{10}$ or $R_{11}$ substituents.

In various embodiments of compounds of Formula I (including I-A and I-B), Formula II (including II-A, II-B, II-C and II-D) and IIII (including III-A and III-B), $R_1$ is —$C_{2-10}$alkynyl-$C_{3-10}$cycloalkyl, which is unsubstituted. In some embodiments, $R_1$ is —$C_{2-10}$alkynyl-$C_{3-10}$cycloalkyl, substituted by one or more independent $R_{10}$ substituents. In some embodiments, $R_1$ is —$C_{2-10}$alkynyl-$C_{3-10}$cycloalkyl, substituted by one or more independent $R_{11}$ substituents. In some embodiments, $R_1$ is —$C_{2-10}$alkynyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{2-10}$alkynyl-$C_{1-10}$heterocyclyl, which is unsubstituted. In some embodiments, $R_1$ is —$C_{2-10}$alkynyl-$C_{1-10}$heterocyclyl, substituted by one or more independent $R_{10}$ substituents. In some embodiments, $R_1$ is —$C_{2-10}$alkynyl-$C_{1-10}$heterocyclyl, substituted by one or more independent $R_{11}$ substituents. In some embodiments, $R_1$ is —$C_{2-10}$alkynyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkoxy-$C_{3-10}$aryl, which is unsubstituted. In some embodiments, $R_1$ is —$C_{1-10}$alkoxy-$C_{3-10}$aryl, substituted by one or more independent $R_{10}$ substituents. In some embodiments, $R_1$ is —$C_{1-10}$alkoxy-$C_{3-10}$aryl, substituted by one or more independent $R_{11}$ substituents. In some embodiments, $R_1$ is —$C_{1-10}$alkoxy-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkoxy-$C_{1-10}$hetaryl, which is unsubstituted. In some embodiments, $R_1$ is —$C_{1-10}$alkoxy-$C_{1-10}$hetaryl, substituted by one or more independent $R_{10}$ substituents. In some embodiments, $R_1$ is —$C_{1-10}$alkoxy-$C_{1-10}$hetaryl, substituted by one or more independent $R_{11}$ substituents. In some embodiments, $R_1$ is —$C_{1-10}$alkoxy-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkoxy-$C_{3-10}$cycloalkyl, which is unsubstituted. In some embodiments, $R_1$ is —$C_{1-10}$alkoxy-$C_{3-10}$cycloalkyl, substituted by one or more independent $R_{10}$ substituents. In some embodiments, $R_1$ is —$C_{1-10}$alkoxy-$C_{3-10}$cycloalkyl, substituted by one or more independent $R_{11}$ substituents. In some embodiments, $R_1$ is —$C_{1-10}$alkoxy-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$alkoxy-$C_{1-10}$heterocyclyl, which is unsubstituted. In some embodiments, $R_1$ is —$C_{1-10}$alkoxy-$C_{1-10}$heterocyclyl, substituted by one or more independent $R_{10}$ substituents. In some embodiments, $R_1$ is —$C_{1-10}$alkoxy-$C_{1-10}$heterocyclyl, substituted by one or more independent $R_{11}$ substituents. In some embodiments, $R_1$ is —$C_{1-10}$alkoxy-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heteroalkyl-$C_{1-10}$hetaryl, which is unsubstituted. In some embodiments, $R_1$ is —$C_{1-10}$ heteroalkyl-$C_{1-10}$hetaryl, substituted by one or more independent $R_{10}$ substituents. In some embodiments, $R_1$ is —$C_{1-10}$ heteroalkyl-$C_{1-10}$heteraryl, substituted by one or more independent $R_{11}$ substituents. In some embodiments, $R_1$ is —$C_{1-10}$ heteroalkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$ heteroalkyl-$C_{1-10}$hetaryl, which is unsubstituted. In some embodiments, $R_1$ is —$C_{1-10}$ heteroalkyl-$C_{1-10}$hetaryl, substituted by one or more independent $R_{10}$ substituents. In some embodiments, $R_1$ is —$C_{1-10}$heteroalkyl-$C_{1-10}$hetaryl, substituted by one or more independent $R_{11}$ substituents. In some embodiments, $R_1$ is —$C_{1-10}$heteroalkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heteroalkyl-$C_{3-10}$cycloalkyl, which is unsubstituted. In some embodiments, $R_1$ is —$C_{1-10}$heteroalkyl-$C_{3-10}$cycloalkyl, substituted by one or more independent $R_{10}$ substituents. In some embodiments, $R_1$ is —$C_{1-10}$heteroalkyl-$C_{3-10}$cycloalkyl, substituted by one or more independent $R_{11}$ substituents. In some embodiments, $R_1$ is —$C_{1-10}$heteroalkyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heteroalkyl-$C_{1-10}$heterocyclyl, which is unsubstituted. In some embodiments, $R_1$ is —$C_{1-10}$heteroalkyl-$C_{1-10}$heterocyclyl, substituted by one or more independent $R_{10}$ substituents. In some embodiments, $R_1$ is $C_{1-10}$heteroalkyl-$C_{1-10}$heterocyclyl, substituted by one or more independent $R_{11}$ substituents. In some embodiments, $R_1$ is —$C_{1-10}$heteroalkyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$aryl-$C_{1-10}$alkyl, which is unsubstituted. In some embodiments, $R_1$ is —$C_{3-10}$aryl-$C_{1-10}$alkyl, substituted by one or more independent $R_{10}$ substituents. In some embodiments, $R_1$ is —$C_{3-10}$aryl-$C_{1-10}$alkyl, substituted by one or more independent $R_{11}$ substituents. In some embodiments, $R_1$ is —$C_{3-10}$aryl-$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$aryl-$C_{2-10}$alkenyl, which is unsubstituted. In some embodiments, $R_1$ is —$C_{3-10}$aryl-$C_{2-10}$alkenyl, substituted by one or more independent $R_{10}$ substituents. In some embodiments, $R_1$ is —$C_{3-10}$aryl-$C_{2-10}$alkenyl, substituted by one or more independent $R_{11}$ substituents. In some embodiments, $R_1$ is —$C_{3-10}$aryl-$C_{2-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$aryl-$C_{2-10}$alkynyl, which is unsubstituted. In some embodiments, $R_1$ is —$C_{3-10}$aryl-$C_{2-10}$alkynyl, substituted by one or more independent $R_{10}$ substituents. In some embodiments, $R_1$ is —$C_{3-10}$aryl-$C_{2-10}$alkynyl, substituted by one or more independent $R_{11}$ substituents. In some embodiments, $R_1$ is —$C_{3-10}$aryl-$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$aryl-$C_{3-10}$hetaryl, which is unsubstituted. In some embodiments, $R_1$ is —$C_{3-10}$aryl-$C_{3-10}$hetaryl, substituted by one or more independent $R_{10}$ substituents. In some embodiments, $R_1$ is —$C_{3-10}$aryl-$C_{3-10}$hetaryl, substituted by one or more independent $R_{11}$ substituents. In some embodiments, $R_1$ is —$C_{3-10}$aryl-$C_{3-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3\text{-}10}$aryl-$C_{3\text{-}10}$cycloalkyl, which is unsubstituted. In some embodiments, $R_1$ is —$C_{3\text{-}10}$aryl-$C_{3\text{-}10}$cycloalkyl, substituted by one or more independent $R_{10}$ substituents. In some embodiments, $R_1$ is —$C_{3\text{-}10}$aryl-$C_{3\text{-}10}$cycloalkyl, substituted by one or more independent $R_{11}$ substituents. In some embodiments, $R_1$ is —$C_{3\text{-}10}$aryl-$C_{3\text{-}10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3\text{-}10}$aryl-$C_{1\text{-}10}$heterocyclyl, which is unsubstituted. In some embodiments, $R_1$ is —$C_{3\text{-}10}$aryl-$C_{1\text{-}10}$heterocyclyl, substituted by one or more independent $R_{10}$ substituents. In some embodiments, $R_1$ is —$C_{3\text{-}10}$aryl-$C_{1\text{-}10}$ heterocyclyl, substituted by one or more independent $R_{11}$ substituents. In some embodiments, $R_1$ is —$C_{3\text{-}10}$aryl-$C_{1\text{-}10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1\text{-}10}$hetaryl-$C_{1\text{-}10}$alkyl, which is unsubstituted. In some embodiments, $R_1$ is —$C_{1\text{-}10}$hetaryl-$C_{1\text{-}10}$alkyl, substituted by one or more independent $R_{10}$ substituents. In some embodiments, $R_1$ is —$C_{1\text{-}10}$hetaryl-$C_{1\text{-}10}$alkyl, substituted by one or more independent $R_{11}$ substituents. In some embodiments, $R_1$ is —$C_{1\text{-}10}$hetaryl-$C_{1\text{-}10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1\text{-}10}$hetaryl-$C_{2\text{-}10}$alkenyl, which is unsubstituted. In some embodiments, $R_1$ is —$C_{1\text{-}10}$hetaryl-$C_{2\text{-}10}$alkenyl, substituted by one or more independent $R_{10}$ substituents. In some embodiments, $R_1$ is —$C_{1\text{-}10}$hetaryl-$C_{2\text{-}10}$alkenyl, substituted by one or more independent $R_{11}$ substituents. In some embodiments, $R_1$ is —$C_{1\text{-}10}$hetaryl-$C_{2\text{-}10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1\text{-}10}$hetaryl-$C_{2\text{-}10}$alkynyl, which is unsubstituted. In some embodiments, $R_1$ is —$C_{1\text{-}10}$hetaryl-$C_{2\text{-}10}$alkynyl, substituted by one or more independent $R_{10}$ substituents. In some embodiments, $R_1$ is —$C_{1\text{-}10}$hetaryl-$C_{2\text{-}10}$alkynyl, substituted by one or more independent $R_{11}$ substituents. In some embodiments, $R_1$ is —$C_{1\text{-}10}$hetaryl-$C_{2\text{-}10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3\text{-}10}$hetaryl-$C_{3\text{-}10}$aryl, which is unsubstituted. In some embodiments, $R_1$ is —$C_{3\text{-}10}$hetaryl-$C_{3\text{-}10}$aryl, substituted by one or more independent $R_{10}$ substituents. In some embodiments, $R_1$ is —$C_{3\text{-}10}$hetaryl-$C_{3\text{-}10}$aryl, substituted by one or more independent $R_{11}$ substituents. In some embodiments, $R_1$ is —$C_{3\text{-}10}$hetaryl-$C_{3\text{-}10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1\text{-}10}$hetaryl-$C_{3\text{-}10}$cycloalkyl, which is unsubstituted. In some embodiments, $R_1$ is —$C_{1\text{-}10}$hetaryl-$C_{3\text{-}10}$cycloalkyl, substituted by one or more independent $R_{10}$ substituents. In some embodiments, $R_1$ is —$C_{1\text{-}10}$hetaryl-$C_{3\text{-}10}$cycloalkyl, substituted by one or more independent $R_{11}$ substituents. In some embodiments, $R_1$ is —$C_{1\text{-}10}$hetaryl-$C_{3\text{-}10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1\text{-}10}$hetaryl-$C_{1\text{-}10}$heterocyclyl, which is unsubstituted. In some embodiments, $R_1$ is —$C_{1\text{-}10}$hetaryl-$C_{1\text{-}10}$heterocyclyl, substituted by one or more independent $R_{10}$ substituents. In some embodiments, $R_1$ is —$C_{1\text{-}10}$hetaryl-$C_{1\text{-}10}$heterocyclyl, substituted by one or more independent $R_{11}$ substituents. In some embodiments, $R_1$ is —$C_{1\text{-}10}$hetaryl-$C_{1\text{-}10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3\text{-}10}$cycloalkyl-$C_{1\text{-}10}$alkyl, which is unsubstituted. In some embodiments, $R_1$ is —$C_{3\text{-}10}$cycloalkyl-$C_{1\text{-}10}$alkyl, substituted by one or more independent $R_{10}$ substituents. In some embodiments, $R_1$ is —$C_{3\text{-}10}$cycloalkyl-$C_{1\text{-}10}$alkyl, substituted by one or more independent $R_{11}$ substituents. In some embodiments, $R_1$ is —$C_{3\text{-}10}$cycloalkyl-$C_{1\text{-}10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3\text{-}10}$cycloalkyl-$C_{2\text{-}10}$alkenyl, which is unsubstituted. In some embodiments, $R_1$ is —$C_{3\text{-}10}$cycloalkyl-$C_{2\text{-}10}$alkenyl, substituted by one or more independent $R_{10}$ substituents. In some embodiments, $R_1$ is —$C_{3\text{-}10}$cycloalkyl-$C_{2\text{-}10}$alkenyl, substituted by one or more independent $R_{11}$ substituents. In some embodiments, $R_1$ is —$C_{3\text{-}10}$cycloalkyl-$C_{2\text{-}10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3\text{-}10}$cycloalkyl-$C_{2\text{-}10}$alkynyl, which is unsubstituted. In some embodiments, $R_1$ is —$C_{3\text{-}10}$cycloalkyl-$C_{2\text{-}10}$alkynyl, substituted by one or more independent $R_{10}$ substituents. In some embodiments, $R_1$ is —$C_{3\text{-}10}$cycloalkyl-$C_{2\text{-}10}$alkynyl, substituted by one or more independent $R_{11}$ substituents. In some embodiments, $R_1$ is —$C_{3\text{-}10}$cycloalkyl-$C_{2\text{-}10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$cycloalkyl-$C_{3-10}$aryl, which is unsubstituted. In some embodiments, $R_1$ is —$C_{3-10}$cycloalkyl-$C_{3-10}$aryl, substituted by one or more independent $R_{10}$ substituents. In some embodiments, $R_1$ is —$C_{3-10}$cycloalkyl-$C_{3-10}$aryl, substituted by one or more independent $R_{11}$ substituents. In some embodiments, $R_1$ is —$C_{3-10}$cycloalkyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$cycloalkyl-$C_{1-10}$hetaryl, which is unsubstituted. In some embodiments, $R_1$ is —$C_{3-10}$cycloalkyl-$C_{1-10}$hetaryl, substituted by one or more independent $R_{10}$ substituents. In some embodiments, $R_1$ is —$C_{3-10}$cycloalkyl-$C_{1-10}$hetaryl, substituted by one or more independent $R_{11}$ substituents. In some embodiments, $R_1$ is —$C_{3-10}$cycloalkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{3-10}$cycloalkyl-$C_{1-10}$heterocyclyl, which is unsubstituted. In some embodiments, $R_1$ is —$C_{3-10}$cycloalkyl-$C_{1-10}$heterocyclyl, substituted by one or more independent $R_{10}$ substituents. In some embodiments, $R_1$ is —$C_{3-10}$cycloalkyl-$C_{1-10}$heterocyclyl, substituted by one or more independent $R_{11}$ substituents. In some embodiments, $R_1$ is —$C_{3-10}$cycloalkyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl-$C_{1-10}$alkyl, which is unsubstituted. In some embodiments, $R_1$ is —$C_{1-10}$heterocyclyl-$C_{1-10}$alkyl, substituted by one or more independent $R_{10}$ substituents. In some embodiments, $R_1$ is —$C_{1-10}$heterocyclyl-$C_{1-10}$alkyl, substituted by one or more independent $R_{11}$ substituents. In some embodiments, $R_1$ is —$C_{1-10}$heterocyclyl-$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl-$C_{2-10}$alkenyl, which is unsubstituted. In some embodiments, $R_1$ is —$C_{1-10}$heterocyclyl-$C_{2-10}$alkenyl, substituted by one or more independent $R_{10}$ substituents. In some embodiments, $R_1$ is —$C_{1-10}$heterocyclyl-$C_{2-10}$alkenyl, substituted by one or more independent $R_{11}$ substituents. In some embodiments, $R_1$ is —$C_{1-10}$heterocyclyl-$C_{2-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl-$C_{2-10}$alkynyl, which is unsubstituted. In some embodiments, $R_1$ is —$C_{1-10}$heterocyclyl-$C_{2-10}$alkynyl, substituted by one or more independent $R_{10}$ substituents. In some embodiments, $R_1$ is —$C_{1-10}$heterocyclyl-$C_{2-10}$alkynyl, substituted by one or more independent $R_{11}$ substituents. In some embodiments, $R_1$ is —$C_{1-10}$heterocyclyl-$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl-$C_{3-10}$aryl, which is unsubstituted. In some embodiments, $R_1$ is —$C_{1-10}$heterocyclyl-$C_{3-10}$aryl, substituted by one or more independent $R_{10}$ substituents. In some embodiments, $R_1$ is —$C_{1-10}$heterocyclyl-$C_{3-10}$aryl, substituted by one or more independent $R_{11}$ substituents. In some embodiments, $R_1$ is —$C_{1-10}$heterocyclyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl-$C_{1-10}$hetaryl, which is unsubstituted. In some embodiments, $R_1$ is —$C_{1-10}$heterocyclyl-$C_{1-10}$hetaryl, substituted by one or more independent $R_{10}$ substituents. In some embodiments, $R_1$ is —$C_{1-10}$heterocyclyl-$C_{1-10}$hetaryl, substituted by one or more independent $R_{11}$ substituents. In some embodiments, $R_1$ is —$C_{1-10}$heterocyclyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1$ is —$C_{1-10}$heterocyclyl-$C_{3-10}$cycloalkyl, which is unsubstituted. In some embodiments, $R_1$ is —$C_{1-10}$heterocyclyl-$C_{3-10}$cycloalkyl, substituted by one or more independent $R_{10}$ substituents. In some embodiments, $R_1$ is —$C_{1-10}$heterocyclyl-$C_{3-10}$cycloalkyl, substituted by one or more independent $R_{11}$ substituents. In some embodiments, $R_1$ is —$C_{1-10}$heterocyclyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is hydrogen.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkyl, which is unsubstituted. In some embodiments, $R_1'$ is —$C_{1-10}$alkyl, substituted by one or more independent $R_{10}$ substituents. In some embodiments, $R_1'$ is —$C_{1-10}$alkyl, substituted by one or more independent $R_{11}$ substituents. In some embodiments, $R_1'$ is —$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkenyl, which is unsubstituted. In some embodiments, $R_1'$ is —$C_{1-10}$alkenyl, substituted by one or more independent $R_{10}$ substituents. In some embodiments, $R_1'$ is —$C_{1-10}$alkenyl, substituted by one or more independent $R_{11}$ substituents. In some embodiments, $R_1'$ is —$C_{1-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkynyl, which is unsubstituted. In some embodiments, $R_1'$ is —$C_{2-10}$alkynyl, substituted by one or more independent $R_{10}$ substituents. In some embodiments, $R_1'$ is —$C_{2-10}$alkynyl, substituted by one or more independent $R_{11}$ substituents. In some embodiments, $R_1'$ is —$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heteroalkyl, which is unsubstituted. In some embodiments, $R_1'$ is —$C_{1-10}$heteroalkyl, substituted by one or more independent $R_{10}$ substituents. In some embodiments, $R_1'$ is —$C_{1-10}$heteroalkyl, substituted by one or more independent $R_{11}$ substituents. In some embodiments, $R_1'$ is —$C_{1-10}$heteroalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$aryl, which is unsubstituted. In some embodiments, $R_1'$ is —$C_{3-10}$aryl, substituted by one or more independent $R_{10}$ substituents. In some embodiments, $R_1'$ is —$C_{3-10}$aryl, substituted by one or more independent $R_{11}$ substituents. In some embodiments, $R_1'$ is —$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$hetaryl, which is unsubstituted. In some embodiments, $R_1'$ is —$C_{1-10}$hetaryl, substituted by one or more independent $R_{10}$ substituents. In some embodiments, $R_1'$ is —$C_{1-10}$hetaryl, substituted by one or more independent $R_{11}$ substituents. In some embodiments, $R_1'$ is —$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl, which is unsubstituted. In some embodiments, $R_1'$ is —$C_{3-10}$cycloalkyl, substituted by one or more independent $R_{10}$ substituents. In some embodiments, $R_1'$ is —$C_{3-10}$cycloalkyl, substituted by one or more independent $R_{11}$ substituents. In some embodiments, $R_1'$ is —$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl, which is unsubstituted. In some embodiments, $R_1'$ is —$C_{1-10}$heterocyclyl, substituted by one or more independent $R_{10}$ substituents. In some embodiments, $R_1'$ is —$C_{1-10}$heterocyclyl, substituted by one or more independent $R_{11}$ substituents. In some embodiments, $R_1'$ is —$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkyl-$C_{3-10}$aryl, which is unsubstituted. In some embodiments, $R_1'$ is —$C_{1-10}$alkyl-$C_{3-10}$aryl, substituted by one or more independent $R_{10}$ substituents. In some embodiments, $R_1'$ is —$C_{1-10}$alkyl-$C_{3-10}$aryl, substituted by one or more independent $R_{11}$ substituents. In some embodiments, $R_1'$ is —$C_{1-10}$alkyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkyl-$C_{1-10}$hetaryl, which is unsubstituted. In some embodiments, $R_1'$ is —$C_{1-10}$alkyl-$C_{1-10}$hetaryl, substituted by one or more independent $R_{10}$ substituents. In some embodiments, $R_1'$ is —$C_{1-10}$alkyl-$C_{1-10}$hetaryl, substituted by one or more independent $R_{11}$ substituents. In some embodiments, $R_1'$ is —$C_{1-10}$alkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkyl-$C_{3-10}$cycloalkyl, which is unsubstituted. In some embodiments, $R_1'$ is —$C_{1-10}$alkyl-$C_{3-10}$cycloalkyl, substituted by one or more independent $R_{10}$ substituents. In some embodiments, $R_1'$ is —$C_{1-10}$alkyl-$C_{3-10}$cycloalkyl, substituted by one or more independent $R_{11}$ substituents. In some embodiments, $R_1'$ is —$C_{1-10}$alkyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkyl-$C_{1-10}$heterocyclyl, which is unsubstituted. In some embodiments, $R_1'$ is —$C_{1-10}$alkyl-$C_{1-10}$heterocyclyl, substituted by one or more independent $R_{10}$ substituents. In some embodiments, $R_1'$ is —$C_{1-10}$alkyl-$C_{1-10}$heterocyclyl, substituted by one or more independent $R_{11}$ substituents. In some embodiments, $R_1'$ is —$C_{1-10}$alkyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkenyl-$C_{3-10}$aryl, which is unsubstituted. In some embodiments, $R_1'$ is —$C_{2-10}$alkenyl-$C_{3-10}$aryl, substituted by one or more independent $R_{10}$ substituents. In some embodiments, $R_1'$ is —$C_{2-10}$alkenyl-$C_{3-10}$aryl, substituted by one or more independent $R_{11}$ substituents. In some embodiments, $R_1'$ is —$C_{2-10}$alkenyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkenyl-$C_{1-10}$hetaryl, which is unsubstituted. In some embodiments, $R_1'$ is —$C_{2-10}$alkenyl-$C_{1-10}$hetaryl, substituted by one or more independent $R_{10}$ substituents. In some embodiments, $R_1'$ is —$C_{2-10}$alkenyl-$C_{1-10}$hetaryl, substituted by one or more independent $R_{11}$ substituents. In some embodiments, $R_1'$ is —$C_{2-10}$alkenyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkenyl-$C_{3-10}$cycloalkyl, which is unsubstituted. In some embodiments, $R_1'$ is —$C_{2-10}$alkenyl-$C_{3-10}$cycloalkyl, substituted by one or more independent $R_{10}$ substituents. In some embodiments, $R_1'$ is —$C_{2-10}$alkenyl-$C_{3-10}$cycloalkyl, substituted by one or more independent $R_{11}$ substituents. In some embodiments, $R_1'$ is —$C_{2-10}$alkenyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkenyl-$C_{1-10}$heterocyclyl, which is unsubstituted. In some embodiments, $R_1'$ is —$C_{2-10}$alkenyl-$C_{1-10}$heterocyclyl, substituted by one or more independent $R_{10}$ substituents. In some embodiments, $R_1'$ is —$C_{2-10}$alkenyl-$C_{1-10}$heterocyclyl, substituted by one or more independent $R_{11}$ substituents. In some embodiments, $R_1'$ is —$C_{2-10}$alkenyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkynyl-$C_{3-10}$aryl, which is unsubstituted. In some embodiments, $R_1'$ is —$C_{2-10}$alkynyl-$C_{3-10}$aryl, substituted by one or more independent $R_{10}$ substituents. In some embodiments, $R_1'$ is —$C_{2-10}$alkynyl-$C_{3-10}$aryl, substituted by one or more independent $R_{11}$ substituents. In some embodiments, $R_1'$ is —$C_{2-10}$alkynyl-$C_{3-10}$aryl, substituted by one or more independent $R_{10}$ or $R_{11}$ substituents.

In various embodiments of compounds of Formula I (including I-A and I-B), Formula II (including II-A, II-B, II-C and II-D) and IIII (including III-A and III-B), $R_1'$ is —$C_{2-10}$alkynyl-$C_{1-10}$hetaryl, which is unsubstituted. In some embodiments, $R_1'$ is —$C_{2-10}$alkynyl-$C_{1-10}$hetaryl, substituted by one or more independent $R_{10}$ substituents. In some embodiments, $R_1'$ is —$C_{2-10}$alkynyl-$C_{1-10}$hetaryl, substituted by one or more independent $R_{11}$ substituents. In some embodiments, $R_1'$ is —$C_{2-10}$alkynyl-$C_{1-10}$hetaryl, substituted by one or more independent $R_{10}$ or $R_{11}$ substituents.

In various embodiments of compounds of Formula I (including I-A and I-B), Formula II (including II-A, II-B, II-C and II-D) and IIII (including III-A and III-B), $R_1'$ is —$C_{2-10}$alkynyl-$C_{3-10}$cycloalkyl, which is unsubstituted. In some embodiments, $R_1'$ is —$C_{2-10}$alkynyl-$C_{3-10}$cycloalkyl, substituted by one or more independent $R_{10}$ substituents. In some embodiments, $R_1'$ is —$C_{2-10}$alkynyl-$C_{3-10}$cycloalkyl, substituted by one or more independent $R_{11}$ substituents. In some embodiments, $R_1'$ is —$C_{2-10}$alkynyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{2-10}$alkynyl-$C_{1-*10}$heterocyclyl, which is unsubstituted. In some embodiments, $R_1'$ is —$C_{2-10}$alkynyl-$C_{1-10}$heterocyclyl, substituted by one or more independent $R_{10}$ substituents. In some embodiments, $R_1'$ is —$C_{2-10}$alkynyl-$C_{1-10}$heterocyclyl, substituted by one or more independent $R_{11}$ substituents. In some embodiments, $R_1'$ is —$C_{2-10}$alkynyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkoxy-$C_{3-10}$aryl, which is unsubstituted. In some embodiments, $R_1'$ is —$C_{1-10}$alkoxy-$C_{3-10}$aryl, substituted by one or more independent $R_{10}$ substituents. In some embodiments, $R_1'$ is —$C_{1-10}$alkoxy-$C_{3-10}$aryl, substituted by one or more independent $R_{11}$ substituents. In some embodiments, $R_1'$ is —$C_{1-10}$alkoxy-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkoxy-$C_{1-10}$hetaryl, which is unsubstituted. In some embodiments, $R_1'$ is —$C_{1-10}$alkoxy-$C_{1-10}$hetaryl, substituted by one or more independent $R_{10}$ substituents. In some embodiments, $R_1'$ is —$C_{1-10}$alkoxy-$C_{1-10}$hetaryl, substituted by one or more independent $R_{11}$ substituents. In some embodiments, $R_1'$ is —$C_{1-10}$alkoxy-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$alkoxy-$C_{3-10}$cycloalkyl, which is unsubstituted. In some embodiments, $R_1'$ is —$C_{1-10}$alkoxy-$C_{3-10}$cycloalkyl, substituted by one or more independent $R_{10}$ substituents. In some embodiments, $R_1'$ is —$C_{1-10}$alkoxy-$C_{3-10}$cycloalkyl, substituted by one or more independent $R_{11}$ substituents. In some embodiments, $R_1'$ is —$C_{1-10}$alkoxy-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{1-10}$alkoxy-$C_{1-10}$heterocyclyl, which is unsubstituted. In some embodiments, $R_1'$ is $—C_{1-10}$alkoxy-$C_{1-10}$heterocyclyl, substituted by one or more independent $R_{10}$ substituents. In some embodiments, $R_1'$ is $—C_{1-10}$alkoxy-$C_{1-10}$heterocyclyl, substituted by one or more independent $R_{11}$ substituents. In some embodiments, $R_1'$ is $—C_{1-10}$alkoxy-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{1-10}$heteroalkyl-$C_{3-10}$aryl, which is unsubstituted. In some embodiments, $R_1'$ is $—C_{1-10}$heteroalkyl-$C_{3-10}$aryl, substituted by one or more independent $R_{10}$ substituents. In some embodiments, $R_1'$ is $—C_{1-10}$heteroalkyl-$C_{3-10}$aryl, substituted by one or more independent $R_{11}$ substituents. In some embodiments, $R_1'$ is $—C_{1-10}$heteroalkyl-$C_{3-10}$aryl, substituted by one or more independent $R_{10}$ or $R_{11}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{1-10}$heteroalkyl-$C_{1-10}$hetaryl, which is unsubstituted. In some embodiments, $R_1'$ is $—C_{1-10}$heteroalkyl-$C_{1-10}$hetaryl, substituted by one or more independent $R_{10}$ substituents. In some embodiments, $R_1'$ is $—C_{1-10}$heteroalkyl-$C_{1-10}$hetaryl, substituted by one or more independent $R_{11}$ substituents. In some embodiments, $R_1'$ is $—C_{1-10}$heteroalkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{1-10}$heteroalkyl-$C_{3-10}$cycloalkyl, which is unsubstituted. In some embodiments, $R_1'$ is $—C_{1-10}$heteroalkyl-$C_{3-10}$cycloalkyl, substituted by one or more independent $R_{10}$ substituents. In some embodiments, $R_1'$ is $—C_{1-10}$heteroalkyl-$C_{3-10}$cycloalkyl, substituted by one or more independent $R_{11}$ substituents. In some embodiments, $R_1'$ is $—C_{1-10}$heteroalkyl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{1-10}$heteroalkyl-$C_{1-10}$heterocyclyl, which is unsubstituted. In some embodiments, $R_1'$ is $—C_{1-10}$heteroalkyl-$C_{1-10}$heterocyclyl, substituted by one or more independent $R_{10}$ substituents. In some embodiments, $R_1'$ is $—C_{1-10}$heteroalkyl-$C_{1-10}$heterocyclyl, substituted by one or more independent $R_{11}$ substituents. In some embodiments, $R_1'$ is $—C_{1-10}$heteroalkyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{3-10}$aryl-$C_{1-10}$alkyl, which is unsubstituted. In some embodiments, $R_1'$ is $—C_{3-10}$aryl-$C_{1-10}$alkyl, substituted by one or more independent $R_{10}$ substituents. In some embodiments, $R_1'$ is $—C_{3-10}$aryl-$C_{1-10}$alkyl, substituted by one or more independent $R_{11}$ substituents. In some embodiments, $R_1'$ is $—C_{3-10}$aryl-$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{3-10}$aryl-$C_{2-10}$alkenyl, which is unsubstituted. In some embodiments, $R_1'$ is $—C_{3-10}$aryl-$C_{2-10}$alkenyl, substituted by one or more independent $R_{10}$ substituents. In some embodiments, $R_1'$ is $—C_{3-10}$aryl-$C_{2-10}$alkenyl, substituted by one or more independent $R_{11}$ substituents. In some embodiments, $R_1'$ is $—C_{3-10}$aryl-$C_{2-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{3-10}$aryl-$C_{2-10}$alkynyl, which is unsubstituted. In some embodiments, $R_1'$ is $—C_{3-10}$aryl-$C_{2-10}$alkynyl, substituted by one or more independent $R_{10}$ substituents. In some embodiments, $R_1'$ is $—C_{3-10}$aryl-$C_{2-10}$alkynyl, substituted by one or more independent $R_{11}$ substituents. In some embodiments, $R_1'$ is $—C_{3-10}$aryl-$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{3-10}$aryl-$C_{3-10}$hetaryl, which is unsubstituted. In some embodiments, $R_1'$ is $—C_{3-10}$aryl-$C_{3-10}$hetaryl, substituted by one or more independent $R_{10}$ substituents. In some embodiments, $R_1'$ is $—C_{3-10}$aryl-$C_{3-10}$hetaryl, substituted by one or more independent $R_{11}$ substituents. In some embodiments, $R_1'$ is $—C_{3-10}$aryl-$C_{3-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{3-10}$aryl-$C_{3-10}$cycloalkyl, which is unsubstituted. In some embodiments, $R_1'$ is $—C_{3-10}$aryl-$C_{3-10}$cycloalkyl, substituted by one or more independent $R_{10}$ substituents. In some embodiments, $R_1'$ is $—C_{3-10}$aryl-$C_{3-10}$cycloalkyl, substituted by one or more independent $R_{11}$ substituents. In some embodiments, $R_1'$ is $—C_{3-10}$aryl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is $—C_{3-10}$aryl-$C_{1-10}$heterocyclyl, which is unsubstituted. In some embodiments, $R_1'$ is $—C_{3-10}$aryl-$C_{1-10}$heterocyclyl, substituted by one or more independent $R_{10}$ substituents. In some embodiments, $R_1'$ is $—C_{3-10}$aryl-$C_{1-10}$heterocyclyl, substituted by one or more independent $R_{11}$ substituents. In some embodiments, $R_1'$ is —$C_{3-10}$aryl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$hetaryl-$C_{1-10}$alkyl, which is unsubstituted. In some embodiments, $R_1'$ is —$C_{1-10}$hetaryl-$C_{1-10}$alkyl, substituted by one or more independent $R_{10}$ substituents. In some embodiments, $R_1'$ is —$C_{1-10}$hetaryl-$C_{1-10}$alkyl, substituted by one or more independent $R_{11}$ substituents. In some embodiments, $R_1'$ is —$C_{1-10}$hetaryl-$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$hetaryl-$C_{2-10}$alkenyl, which is unsubstituted. In some embodiments, $R_1'$ is —$C_{1-10}$hetaryl-$C_{2-10}$alkenyl, substituted by one or more independent $R_{10}$ substituents. In some embodiments, $R_1'$ is —$C_{1-10}$hetaryl-$C_{1-10}$alkenyl, substituted by one or more independent $R_{11}$ substituents. In some embodiments, $R_1'$ is —$C_{1-10}$hetaryl-$C_{2-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$hetaryl-$C_{2-10}$alkynyl, which is unsubstituted. In some embodiments, $R_1'$ is —$C_{1-10}$hetaryl-$C_{2-10}$alkynyl, substituted by one or more independent $R_{10}$ substituents. In some embodiments, $R_1'$ is —$C_{1-10}$hetaryl-$C_{2-10}$alkynyl, substituted by one or more independent $R_{11}$ substituents. In some embodiments, $R_1'$ is —$C_{1-10}$hetaryl-$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$hetaryl-$C_{3-10}$aryl, which is unsubstituted. In some embodiments, $R_1'$ is —$C_{3-10}$hetaryl-$C_{3-10}$aryl, substituted by one or more independent $R_{10}$ substituents. In some embodiments, $R_1'$ is —$C_{3-10}$hetaryl-$C_{3-10}$aryl, substituted by one or more independent $R_{11}$ substituents. In some embodiments, $R_1'$ is —$C_{3-10}$hetaryl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$hetaryl-$C_{3-10}$cycloalkyl, which is unsubstituted. In some embodiments, $R_1'$ is —$C_{1-10}$hetaryl-$C_{3-10}$cycloalkyl, substituted by one or more independent $R_{10}$ substituents. In some embodiments, $R_1'$ is —$C_{1-10}$hetaryl-$C_{3-10}$cycloalkyl, substituted by one or more independent $R_{11}$ substituents. In some embodiments, $R_1'$ is —$C_{1-10}$hetaryl-$C_{3-10}$cycloalkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$hetaryl-$C_{1-10}$heterocyclyl, which is unsubstituted. In some embodiments, $R_1'$ is —$C_{1-10}$hetaryl-$C_{1-10}$heterocyclyl, substituted by one or more independent $R_{10}$ substituents. In some embodiments, $R_1'$ is —$C_{1-10}$hetaryl-$C_{1-10}$heterocyclyl, substituted by one or more independent $R_{11}$ substituents. In some embodiments, $R_1'$ is —$C_{1-10}$hetaryl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl-$C_{1-10}$alkyl, which is unsubstituted. In some embodiments, $R_1'$ is —$C_{3-10}$cycloalkyl-$C_{1-10}$alkyl, substituted by one or more independent $R_{10}$ substituents. In some embodiments, $R_1'$ is —$C_{3-10}$cycloalkyl-$C_{1-10}$alkyl, substituted by one or more independent $R_{11}$ substituents. In some embodiments, $R_1'$ is —$C_{3-10}$cycloalkyl-$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl-$C_{2-10}$alkenyl, which is unsubstituted. In some embodiments, $R_1'$ is —$C_{3-10}$cycloalkyl-$C_{2-10}$alkenyl, substituted by one or more independent $R_{10}$ substituents. In some embodiments, $R_1'$ is —$C_{3-10}$cycloalkyl-$C_{2-10}$alkenyl, substituted by one or more independent $R_{11}$ substituents. In some embodiments, $R_1'$ is —$C_{3-10}$cycloalkyl-$C_{2-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl-$C_{2-10}$alkynyl, which is unsubstituted. In some embodiments, $R_1'$ is —$C_{3-10}$cycloalkyl-$C_{2-10}$alkynyl, substituted by one or more independent $R_{10}$ substituents. In some embodiments, $R_1'$ is —$C_{3-10}$cycloalkyl-$C_{2-10}$alkynyl, substituted by one or more independent $R_{11}$ substituents. In some embodiments, $R_1'$ is —$C_{3-10}$cycloalkyl-$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl-$C_{3-10}$aryl, which is unsubstituted. In some embodiments, $R_1'$ is —$C_{3-10}$cycloalkyl-$C_{3-10}$aryl, substituted by one or more independent $R_{10}$ substituents. In some embodiments, $R_1'$ is —$C_{3-10}$cycloalkyl-$C_{3-10}$aryl, substituted by one or more independent $R_{11}$ substituents. In some embodiments, $R_1'$ is —$C_{3-10}$cycloalkyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl-$C_{1-10}$hetaryl, which is unsubstituted. In some embodiments, $R_1'$ is —$C_{3-10}$cycloalkyl-$C_{1-10}$hetaryl, substituted by one or more independent $R_{10}$ substituents. In some embodiments, $R_1'$ is —$C_{3-10}$cycloalkyl-$C_{1-10}$hetaryl, substituted by one or more independent $R_{11}$ substituents. In some embodiments, $R_1'$ is —$C_{3-10}$cycloalkyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{3-10}$cycloalkyl-$C_{1-10}$heterocyclyl, which is unsubstituted. In some embodiments, $R_1'$ is —$C_{3-10}$cycloalkyl-$C_{1-10}$heterocyclyl, substituted by one or more independent $R_{10}$ substituents. In some embodiments, $R_1'$ is —$C_{3-10}$cycloalkyl-$C_{1-10}$heterocyclyl, substituted by one or more independent $R_{11}$ substituents. In some embodiments, $R_1'$ is —$C_{3-10}$cycloalkyl-$C_{1-10}$heterocyclyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl-$C_{1-10}$alkyl, which is unsubstituted. In some embodiments, $R_1'$ is —$C_{1-10}$heterocyclyl-$C_{1-10}$alkyl, substituted by one or more independent $R_{10}$ substituents. In some embodiments, $R_1'$ is —$C_{1-10}$heterocyclyl-$C_{1-10}$alkyl, substituted by one or more independent $R_{11}$ substituents. In some embodiments, $R_1'$ is —$C_{1-10}$heterocyclyl-$C_{1-10}$alkyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl-$C_{2-10}$alkenyl, which is unsubstituted. In some embodiments, $R_1'$ is —$C_{1-10}$heterocyclyl-$C_{2-10}$alkenyl, substituted by one or more independent $R_{10}$ substituents. In some embodiments, $R_1'$ is —$C_{1-10}$heterocyclyl-$C_{2-10}$alkenyl, substituted by one or more independent $R_{11}$ substituents. In some embodiments, $R_1'$ is —$C_{1-10}$heterocyclyl-$C_{2-10}$alkenyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl-$C_{2-10}$alkynyl, which is unsubstituted. In some embodiments, $R_1'$ is —$C_{1-10}$heterocyclyl-$C_{2-10}$alkynyl, substituted by one or more independent $R_{10}$ substituents. In some embodiments, $R_1'$ is —$C_{1-10}$heterocyclyl-$C_{2-10}$alkynyl, substituted by one or more independent $R_{11}$ substituents. In some embodiments, $R_1'$ is —$C_{1-10}$heterocyclyl-$C_{2-10}$alkynyl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl-$C_{3-10}$aryl, which is unsubstituted. In some embodiments, $R_1'$ is —$C_{1-10}$heterocyclyl-$C_{3-10}$aryl, substituted by one or more independent $R_{10}$ substituents. In some embodiments, $R_1'$ is —$C_{1-10}$heterocyclyl-$C_{3-10}$aryl, substituted by one or more independent $R_{11}$ substituents. In some embodiments, $R_1'$ is —$C_{1-10}$heterocyclyl-$C_{3-10}$aryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl-$C_{1-10}$hetaryl, which is unsubstituted. In some embodiments, $R_1'$ is —$C_{1-10}$heterocyclyl-$C_{1-10}$hetaryl, substituted by one or more independent $R_{10}$ substituents. In some embodiments, $R_1'$ is —$C_{1-10}$heterocyclyl-$C_{1-10}$hetaryl, substituted by one or more independent $R_{11}$ substituents. In some embodiments, $R_1'$ is —$C_{1-10}$heterocyclyl-$C_{1-10}$hetaryl, substituted by one or more independent $R_{10}$ or $R_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_1'$ is —$C_{1-10}$heterocyclyl-$C_{3-10}$cycloalkyl, which is unsubstituted. In some embodiments, $R_1'$ is —$C_{1-10}$heterocyclyl-$C_{3-10}$cycloalkyl, substituted by one or more independent $R_{10}$ substituents. In some embodiments, $R_1'$ is —$C_{1-10}$heterocyclyl-$C_{3-10}$cycloalkyl, substituted by one or more independent $R_{11}$ substituents. In some embodiments, $R_1'$ is —$C_{1-10}$heterocyclyl-$C_{3-10}$cycloalkyl, substituted by one or more independent $R_{10}$ or $R_{11}$ substituents.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $R_1$ is —$C_{1-10}$alkyl, —$C_{1-10}$heterocyclyl, —$C_{1-10}$alkyl-$C_{3-10}$heterocyclyl, —$C_{1-10}$alkyl-$C_{3-10}$aryl, —$C_{1-10}$alkyl $C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents. In other embodiments, $R_1$ is —$C_{1-10}$alkyl, —$C_{1-10}$heterocyclyl, —$C_{1-10}$alkyl-$C_{3-10}$heterocyclyl, —$C_{1-10}$alkyl-$C_{3-10}$aryl, —$C_{1-10}$alkyl $C_{1-10}$hetaryl, —$C_{1-10}$heterocyclyl-$C_{1-10}$alkyl, or $C_{1-10}$heterocyclyl-$C_{3-10}$aryl, unsubstituted or substituted by one or more independent $R_{10}$ or $R_{11}$ substituents. In yet other embodiments, $R_1$ is —$C_{1-10}$alkyl-$C_{3-10}$aryl, —$C_{1-10}$alkyl-$C_{1-10}$hetaryl, —$C_{1-10}$heterocyclyl-$C_{1-10}$alkyl, or —$C_{1-10}$heterocyclyl-$C_{3-10}$aryl, unsubstituted or substituted by one or more independent $R_{10}$ or $R_{11}$ substituents. In yet other embodiments, $R_1$ is —$C_{1-10}$alkyl-$C_{3-10}$aryl or —$C_{1-10}$heterocyclyl-$C_{3-10}$aryl, unsubstituted or substituted by one or more independent $R_{10}$ or $R_{11}$ substituents. In further embodiments, wherein $R_1$ is unsubstituted or substituted by one or more independent $R_{10}$ or $R_{11}$ substituents. In some embodiments, R1 is $R_1$ is —$C_{1-10}$heterocyclyl, —$C_{1-10}$heterocyclyl-$C_{1-10}$alkyl, or —C$_{1-10}$heterocyclyl-C$_{3-10}$aryl, unsubstituted or substituted by one or more independent R$_{10}$ or R$_{11}$ substituents. In some embodiments, R$_1$ is —

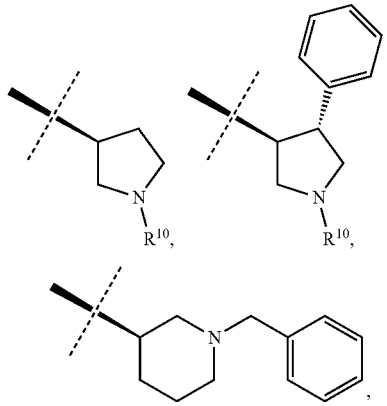

unsubstituted or substituted by one or more independent R$_{10}$ or R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), each of R$_1$ or R$_1$' is independently a substituent as shown below:

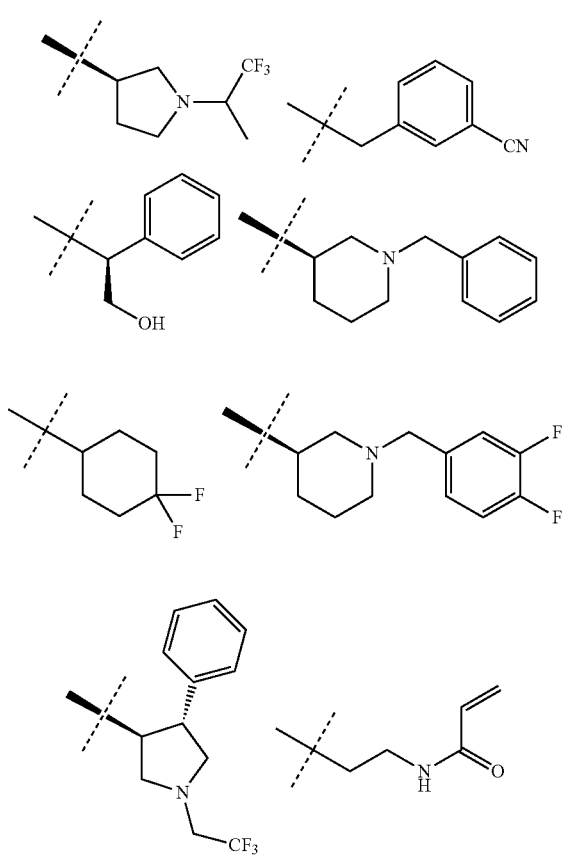

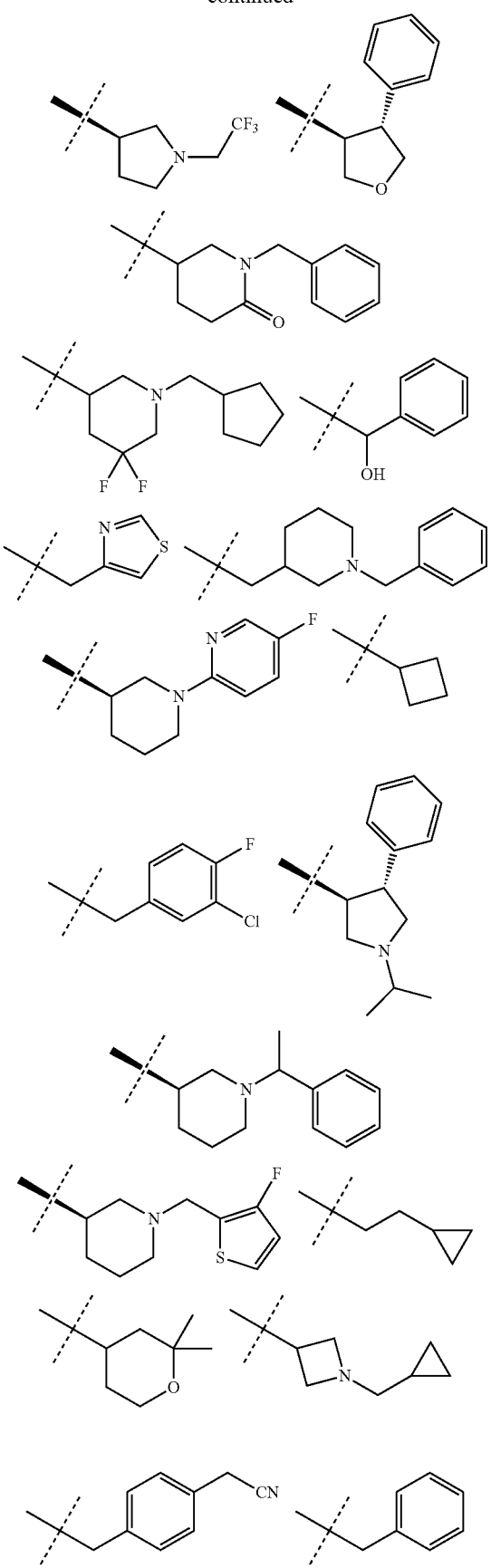

-continued

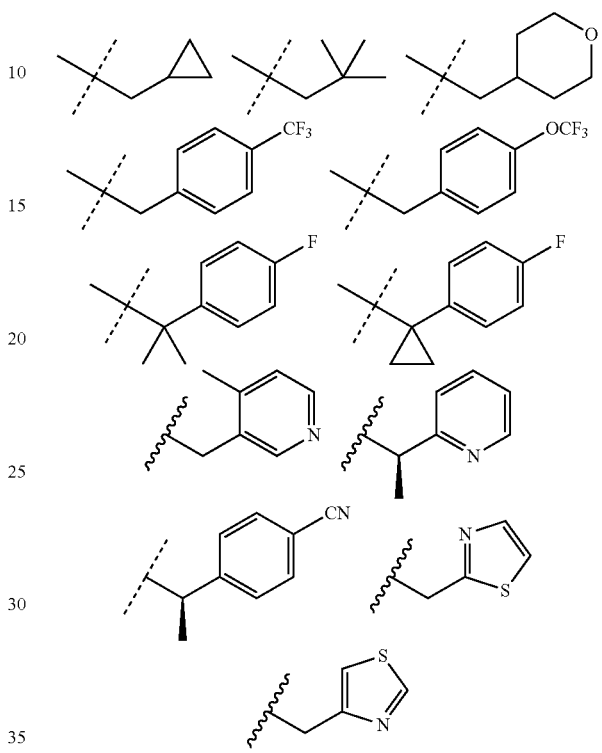

In further embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), each of $R_1$ or $R_1'$ is independently a substituent as shown below:

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is halogen, which is F, Cl, Br or I. In some embodiments, $R_{21}$ is —OH. In some embodiments, $R_{21}$ is —$CF_3$. In some embodiments, $R_{21}$ is —$OCF_3$. In some embodiments, $R_{21}$ is —$OR^{31}$. In some embodiments, $R_{21}$ is —$NR^{31}R^{32}$. In some embodiments, $R_{21}$ is —$C(O)R^{31}$. In some embodiments, $R_{21}$ is —$CO_2R^{31}$. In some embodiments, $R_{21}$ is —$C(\!\!=\!\!O)NR^{31}$. In some embodiments, $R_{21}$ is —$NO_2$. In some embodiments, $R_2$ is —CN. In some embodiments, $R_{21}$ is —$S(O)_{0\text{-}2}R^{31}$. In some embodiments, $R_{21}$ is —$SO_2NR^{31}R^{32}$. In some embodiments, $R_{21}$ is —$NR^{31}C(\!\!=\!\!O)R^{32}$. In some embodiments, $R_{21}$ is —$NR^{31}C(\!\!=\!\!O)OR^{32}$. In some embodiments, $R_{21}$ is —$NR^{31}C(\!\!=\!\!O)NR^{32}R^{33}$. In some embodiments, $R_{21}$ is —$NR^{31}S(O)_{0\text{-}2}R^{32}$. In some embodiments, $R_{21}$ is —$C(\!\!=\!\!S)OR^{31}$. In some embodiments, $R_{21}$ is —$C(\!\!=\!\!O)SR^{31}$. In some embodiments, $R_{21}$ is —$NR^{31}C(\!\!=\!\!NR^{32})NR^{32}R^{33}$. In some embodiments, $R_{21}$ is —$NR^{31}C(\!\!=\!\!NR^{32})OR^{33}$. In some embodiments, $R_{21}$ is —$NR^{31}C(\!\!=\!\!NR^{32})SR^{33}$. In some embodiments, $R_{21}$ is —$OC(\!\!=\!\!O)OR^{33}$. In some embodiments, $R_{21}$ is —$OC(\!\!=\!\!O)NR^{31}R^{32}$. In some embodiments, $R_{21}$ is —$OC(\!\!=\!\!O)SR^{31}$. In some embodiments, $R_{21}$ is —$SC(\!\!=\!\!O)SR^{31}$. In some embodiments, $R_{21}$ is —$P(O)OR^{31}OR^{32}$. In some embodiments, $R_{21}$ is —$SC(\!\!=\!\!O)NR^{31}R^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkyl, which is unsubstituted. In some embodiments, $R_{21}$ is -L-$C_{1-10}$alkyl, which is substituted by one or more independent $R_{12}$ substituents. In some embodiments, $R_{21}$ is -L-$C_{1-10}$alkyl, which is unsubstituted and L is a bond. In some embodiments, $R_{21}$ is -L-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkenyl, which is unsubstituted. In some embodiments, $R_{21}$ is -L-$C_{2-10}$alkenyl, which is substituted by one or more independent $R_{12}$ substituents. In some embodiments, $R_{21}$ is -L-$C_{2-10}$alkenyl, which is unsubstituted and L is a bond. In some embodiments, $R_{21}$ is -L-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkynyl, which is unsubstituted. In some embodiments, $R_{21}$ is -L-$C_{2-10}$alkynyl, which is substituted by one or more independent $R_{12}$ substituents. In some embodiments, $R_{21}$ is -L-$C_{2-10}$alkynyl, which is unsubstituted and L is a bond. In some embodiments, $R_{21}$ is -L-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heteroalkyl, which is unsubstituted. In some embodiments, $R_{21}$ is -L-$C_{1-10}$heteroalkyl, which is substituted by one or more independent $R_{12}$ substituents. In some embodiments, $R_{21}$ is -L-$C_{1-10}$heteroalkyl, which is unsubstituted and L is a bond. In some embodiments, $R_{21}$ is -L-$C_{1-10}$heteroalkyl, which is substituted by one or more independent $R_{12}$ substituents, where L is a bond In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl, which is unsubstituted. In some embodiments, $R_{21}$ is -L-$C_{3-10}$aryl, which is substituted by one or more independent $R_{12}$ substituents. In some embodiments, $R_{21}$ is -L-$C_{3-10}$aryl, which is unsubstituted and L is a bond. In some embodiments, $R_{21}$ is -L-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl, which is unsubstituted. In some embodiments, $R_{21}$ is -L-$C_{1-10}$hetaryl, which is substituted by one or more independent $R_{12}$ substituents. In some embodiments, $R_{21}$ is -L-$C_{1-10}$hetaryl, which is unsubstituted and L is a bond. In some embodiments, $R_{21}$ is -L-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl, which is unsubstituted. In some embodiments, $R_{21}$ is -L-$C_{3-10}$cycloalkyl, which is substituted by one or more independent $R_{12}$ substituents. In some embodiments, $R_{21}$ is -L-$C_{3-10}$cycloalkyl, which is unsubstituted and L is a bond. In some embodiments, $R_{21}$ is -L-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl, which is unsubstituted. In some embodiments, $R_{21}$ is -L-$C_{1-10}$heterocyclyl, which is substituted by one or more independent $R_{12}$ substituents. In some embodiments, $R_{21}$ is -L-$C_{1-10}$heterocyclyl, which is unsubstituted and L is a bond. In some embodiments, $R_{21}$ is -L-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkyl-$C_{3-10}$aryl, which is unsubstituted. In some embodiments, $R_{21}$ is -L-$C_{1-10}$alkyl-$C_{3-10}$aryl, which is substituted by one or more independent $R_{12}$ substituents. In some embodiments, $R_{21}$ is -L-$C_{1-10}$alkyl-$C_{3-10}$aryl, which is unsubstituted and L is a bond. In some embodiments, $R_{21}$ is -L-$C_{1-10}$alkyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkyl-$C_{1-10}$hetaryl, which is unsubstituted. In some embodiments, $R_{21}$ is -L-$C_{1-10}$alkyl-$C_{1-10}$hetaryl, which is substituted by one or more independent $R_{12}$ substituents. In some embodiments, $R_{21}$ is -L-$C_{1-10}$alkyl-$C_{1-10}$hetaryl, which is unsubstituted and L is a bond. In some embodiments, $R_{21}$ is -L-$C_{1-10}$alkyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkyl-$C_{3-10}$cycloalkyl, which is unsubstituted. In some embodiments, $R_{21}$ is -L-$C_{1-10}$alkyl-$C_{3-10}$cycloalkyl, which is substituted by one or more independent $R_{12}$ substituents. In some embodiments, $R_{21}$ is -L-$C_{1-10}$alkyl-$C_{3-10}$cycloalkyl, which is unsubstituted and L is a bond. In some embodiments, $R_{21}$ is -L-$C_{1-10}$alkyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkyl-$C_{1-10}$heterocyclyl, which is unsubstituted. In some embodiments, $R_{21}$ is -L-$C_{1-10}$alkyl-$C_{1-10}$heterocyclyl, which is substituted by one or more independent $R_{12}$ substituents. In some embodiments, $R_{21}$ is -L-$C_{1-10}$alkyl-$C_{1-10}$heterocyclyl, which is unsubstituted and L is a bond. In some embodiments, $R_{21}$ is -L-$C_{1-10}$alkyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkenyl-$C_{3-10}$aryl, which is unsubstituted. In some embodiments, $R_{21}$ is -L-$C_{2-10}$alkenyl-$C_{3-10}$aryl, which is substituted by one or more independent $R_{12}$ substituents. In some embodiments, $R_{21}$ is -L-$C_{2-10}$alkenyl-$C_{3-10}$aryl, which is unsubstituted and L is a bond. In some embodiments, $R_{21}$ is -L-$C_{2-10}$alkenyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkenyl-$C_{1-10}$hetaryl, which is unsubstituted. In some embodiments, $R_{21}$ is -L-$C_{2-10}$alkenyl-$C_{1-10}$hetaryl, which is substituted by one or more independent $R_{12}$ substituents. In some embodiments, $R_{21}$ is -L-$C_{2-10}$alkenyl-$C_{1-10}$hetaryl, which is unsubstituted and L is a bond. In some embodiments, $R_{21}$ is -L-$C_{2-10}$alkenyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkenyl-$C_{3-10}$cycloalkyl, which is unsubstituted. In some embodiments, $R_{21}$ is -L-$C_{2-10}$alkenyl-$C_{3-10}$cycloalkyl, which is substituted by one or more independent $R_{12}$ substituents. In some embodiments, $R_{21}$ is -L-$C_{2-10}$alkenyl-$C_{3-10}$cycloalkyl, which is unsubstituted and L is a bond. In some embodiments, $R_{21}$ is -L-$C_{2-10}$alkenyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkenyl-$C_{1-10}$heterocyclyl, which is unsubstituted. In some embodiments, $R_{21}$ is -L-$C_{2-10}$alkenyl-$C_{1-10}$heterocyclyl, which is substituted by one or more independent $R_{12}$ substituents. In some embodiments, $R_{21}$ is -L-$C_{2-10}$alkenyl-$C_{1-10}$heterocyclyl, which is unsubstituted and L is a bond. In some embodiments, $R_{21}$ is -L-$C_{2-10}$alkenyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkynyl-$C_{3-10}$aryl, which is unsubstituted. In some embodiments, $R_{21}$ is -L-$C_{2-10}$alkynyl-$C_{3-10}$aryl, which is substituted by one or more independent $R_{12}$ substituents. In some embodiments, $R_{21}$ is -L-$C_{2-10}$alkynyl-$C_{3-10}$aryl, which is unsubstituted and L is a bond. In some embodiments, $R_{21}$ is -L-$C_{2-10}$alkynyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkynyl-$C_{1-10}$hetaryl, which is unsubstituted. In some embodiments, $R_{21}$ is -L-$C_{2-10}$alkynyl-$C_{1-10}$hetaryl, which is substituted by one or more independent $R_{12}$ substituents. In some embodiments, $R_{21}$ is -L-$C_{2-10}$alkynyl-$C_{1-10}$hetaryl, which is unsubstituted and L is a bond. In some embodiments, $R_{21}$ is -L-$C_{2-10}$alkynyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkynyl-$C_{3-10}$cycloalkyl, which is unsubstituted. In some embodiments, $R_{21}$ is -L-$C_{2-10}$alkynyl-$C_{3-10}$cycloalkyl, which is substituted by one or more independent $R_{12}$ substituents. In some embodiments, $R_{21}$ is -L-$C_{2-10}$alkynyl-$C_{3-10}$cycloalkyl, which is unsubstituted and L is a bond. In some embodiments, $R_{21}$ is -L-$C_{2-10}$alkynyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{2-10}$alkynyl-$C_{1-10}$heterocyclyl, which is unsubstituted. In some embodiments, $R_{21}$ is -L-$C_{2-10}$alkynyl-$C_{1-10}$heterocyclyl, which is substituted by one or more independent $R_{12}$ substituents. In some embodiments, $R_{21}$ is -L-$C_{2-10}$alkynyl-$C_{1-10}$heterocyclyl, which is unsubstituted and L is a bond. In some embodiments, $R_{21}$ is -L-$C_{2-10}$alkynyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkoxy-$C_{3-10}$aryl, which is unsubstituted. In some embodiments, $R_{21}$ is -L-$C_{1-10}$alkoxy-$C_{3-10}$aryl, which is substituted by one or more independent $R_{12}$ substituents. In some embodiments, $R_{21}$ is -L-$C_{1-10}$alkoxy-$C_{3-10}$aryl, which is unsubstituted and L is a bond. In some embodiments, $R_{21}$ is -L-$C_{1-10}$alkoxy-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkoxy-$C_{1-10}$hetaryl, which is unsubstituted.

In some embodiments, $R_{21}$ is -L-$C_{1-10}$alkoxy-$C_{1-10}$hetaryl, which is substituted by one or more independent $R_{12}$ substituents. In some embodiments, $R_{21}$ is -L-$C_{1-10}$alkoxy-$C_{1-10}$hetaryl, which is unsubstituted and L is a bond. In some embodiments, $R_{21}$ is -L-$C_{1-10}$alkoxy-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkoxy-$C_{3-10}$cycloalkyl, which is unsubstituted. In some embodiments, $R_{21}$ is -L-$C_{1-10}$alkoxy-$C_{3-10}$cycloalkyl, which is substituted by one or more independent $R_{12}$ substituents. In some embodiments, $R_{21}$ is -L-$C_{1-10}$alkoxy-$C_{3-10}$cycloalkyl, which is unsubstituted and L is a bond. In some embodiments, $R_{21}$ is -L-$C_{1-10}$alkoxy-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$alkoxy-$C_{1-10}$heterocyclyl, which is unsubstituted. In some embodiments, $R_{21}$ is -L-$C_{1-10}$alkoxy-$C_{1-10}$heterocyclyl, which is substituted by one or more independent $R_{12}$ substituents. In some embodiments, $R_{21}$ is -L-$C_{1-10}$alkoxy-$C_{1-10}$heterocyclyl, which is unsubstituted and L is a bond. In some embodiments, $R_{21}$ is -L-$C_{1-10}$alkoxy-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heteroalkyl-$C_{3-10}$aryl, which is unsubstituted. In some embodiments, $R_{21}$ is -L-$C_{1-10}$heteroalkyl-$C_{3-10}$aryl, which is substituted by one or more independent $R_{12}$ substituents. In some embodiments, $R_{21}$ is -L-$C_{1-10}$heteroalkyl-$C_{3-10}$aryl, which is unsubstituted and L is a bond. In some embodiments, $R_{21}$ is -L-$C_{1-10}$heteroalkyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heteroalkyl-$C_{1-10}$hetaryl, which is unsubstituted. In some embodiments, $R_{21}$ is -L-$C_{1-10}$heteroalkyl-$C_{1-10}$hetaryl, which is substituted by one or more independent $R_{12}$ substituents. In some embodiments, $R_{21}$ is -L-$C_{1-10}$heteroalkyl-$C_{1-10}$hetaryl, which is unsubstituted and L is a bond. In some embodiments, $R_{21}$ is -L-$C_{1-10}$heteroalkyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heteroalkyl-$C_{3-10}$cycloalkyl, which is unsubstituted. In some embodiments, $R_{21}$ is -L-$C_{1-10}$heteroalkyl-$C_{3-10}$cycloalkyl, which is substituted by one or more independent $R_{12}$ substituents. In some embodiments, $R_{21}$ is -L-$C_{1-10}$heteroalkyl-$C_{3-10}$cycloalkyl, which is unsubstituted and L is a bond. In some embodiments, $R_{21}$ is -L-$C_{1-10}$heteroalkyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heteroalkyl-$C_{1-10}$heterocyclyl, which is unsubstituted. In some embodiments, $R_{21}$ is -L-$C_{1-10}$heteroalkyl-$C_{1-10}$heterocyclyl, which is substituted by one or more independent $R_{12}$ substituents. In some embodiments, $R_{21}$ is -L-$C_{1-10}$heteroalkyl-$C_{1-10}$heterocyclyl, which is unsubstituted and L is a bond. In some embodiments, $R_{21}$ is -L-$C_{1-10}$heteroalkyl-$C_{1-10}$heterocyclyl, which is substituted by one or more independent $R_{12}$ substituents, where L is a bond In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl-$C_{1-10}$alkyl, which is unsubstituted. In some embodiments, $R_{21}$ is -L-$C_{3-10}$aryl-$C_{1-10}$alkyl, which is substituted by one or more independent $R_{12}$ substituents. In some embodiments, $R_{21}$ is -L-$C_{3-10}$aryl-$C_{1-10}$alkyl, which is unsubstituted and L is a bond. In some embodiments, $R_{21}$ is -L-$C_{3-10}$aryl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl-$C_{2-10}$alkenyl, which is unsubstituted. In some embodiments, $R_{21}$ is -L-$C_{3-10}$aryl-$C_{2-10}$alkenyl, which is substituted by one or more independent $R_{12}$ substituents. In some embodiments, $R_{21}$ is -L-$C_{3-10}$aryl-$C_{2-10}$alkenyl, which is unsubstituted and L is a bond. In some embodiments, $R_{21}$ is -L-$C_{3-10}$aryl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl-$C_{2-10}$alkynyl, which is unsubstituted. In some embodiments, $R_{21}$ is -L-$C_{3-10}$aryl-$C_{2-10}$alkynyl, which is substituted by one or more independent $R_{12}$ substituents. In some embodiments, $R_{21}$ is -L-$C_{3-10}$aryl-$C_{2-10}$alkynyl, which is unsubstituted and L is a bond. In some embodiments, $R_{21}$ is -L-$C_{3-10}$aryl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl-$C_{1-10}$hetaryl, which is unsubstituted. In some embodiments, $R_{21}$ is -L-$C_{3-10}$aryl-$C_{1-10}$hetaryl, which is substituted by one or more independent $R_{12}$ substituents. In some embodiments, $R_{21}$ is -L-$C_{3-10}$aryl-$C_{1-10}$hetaryl, which is unsubstituted and L is a bond. In some embodiments, $R_{21}$ is -L-$C_{3-10}$aryl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl-$C_{3-10}$cycloalkyl, which is unsubstituted. In some embodiments, $R_{21}$ is -L-$C_{3-10}$aryl-$C_{3-10}$cycloalkyl, which is substituted by one or more independent $R_{12}$ substituents. In some embodiments, $R_{21}$ is -L-$C_{3-10}$aryl-$C_{3-10}$cycloalkyl, which is unsubstituted and L is a bond. In some embodiments, $R_{21}$ is -L-$C_{3-10}$aryl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$aryl-$C_{1-10}$heterocyclyl, which is unsubstituted. In some embodiments, $R_{21}$ is -L-$C_{3-10}$aryl-$C_{1-10}$heterocyclyl, which is substituted by one or more independent $R_{12}$ substituents. In some embodiments, $R_{21}$ is -L-$C_{3-10}$aryl-$C_{1-10}$heterocyclyl, which is unsubstituted and L is a bond. In some embodiments, $R_{21}$ is -L-$C_{3-10}$aryl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl-$C_{1-10}$alkyl, which is unsubstituted. In some embodiments, $R_{21}$ is -L-$C_{1-10}$hetaryl-$C_{1-10}$alkyl, which is substituted by one or more independent $R_{12}$ substituents. In some embodiments, $R_{21}$ is -L-$C_{1-10}$hetaryl-$C_{1-10}$alkyl, which is unsubstituted and L is a bond. In some embodiments, $R_{21}$ is -L-$C_{1-10}$hetaryl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl-$C_{2-10}$alkenyl, which is unsubstituted. In some embodiments, $R_{21}$ is -L-$C_{1-10}$hetaryl-$C_{2-10}$alkenyl, which is substituted by one or more independent $R_{12}$ substituents. In some embodiments, $R_{21}$ is -L-$C_{1-10}$hetaryl-$C_{2-10}$alkenyl, which is unsubstituted and L is a bond. In some embodiments, $R_{21}$ is -L-$C_{1-10}$hetaryl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl-$C_{2-10}$alkynyl, which is unsubstituted. In some embodiments, $R_{21}$ is -L-$C_{1-10}$hetaryl-$C_{2-10}$alkynyl, which is substituted by one or more independent $R_{12}$ substituents. In some embodiments, $R_{21}$ is -L-$C_{1-10}$hetaryl-$C_{2-10}$alkynyl, which is unsubstituted and L is a bond. In some embodiments, $R_{21}$ is -L-$C_{1-10}$hetaryl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl-$C_{3-10}$aryl, which is unsubstituted. In some embodiments, $R_{21}$ is -L-$C_{1-10}$hetaryl-$C_{3-10}$aryl, which is substituted by one or more independent $R_{12}$ substituents. In some embodiments, $R_{21}$ is -L-$C_{1-10}$hetaryl-$C_{3-10}$aryl, which is unsubstituted and L is a bond. In some embodiments, $R_{21}$ is -L-$C_{1-10}$hetaryl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl-$C_{3-10}$cycloalkyl, which is unsubstituted. In some embodiments, $R_{21}$ is -L-$C_{1-10}$hetaryl-$C_{3-10}$cycloalkyl, which is substituted by one or more independent $R_{12}$ substituents. In some embodiments, $R_{21}$ is -L-$C_{1-10}$hetaryl-$C_{3-10}$cycloalkyl, which is unsubstituted and L is a bond. In some embodiments, $R_{21}$ is -L-$C_{1-10}$hetaryl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$hetaryl-$C_{1-10}$heterocyclyl, which is unsubstituted. In some embodiments, $R_{21}$ is -L-$C_{1-10}$hetaryl-$C_{1-10}$heterocyclyl, which is substituted by one or more independent $R_{12}$ substituents. In some embodiments, $R_{21}$ is -L-$C_{1-10}$hetaryl-$C_{1-10}$heterocyclyl, which is unsubstituted and L is a bond. In some embodiments, $R_{21}$ is -L-$C_{1-10}$hetaryl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl-$C_{1-10}$alkyl, which is unsubstituted. In some embodiments, $R_{21}$ is -L-$C_{3-10}$cycloalkyl-$C_{1-10}$alkyl, which is substituted by one or more independent $R_{12}$ substituents. In some embodiments, $R_{21}$ is -L-$C_{3-10}$cycloalkyl-$C_{1-10}$alkyl, which is unsubstituted and L is a bond. In some embodiments, $R_{21}$ is -L-$C_{3-10}$cycloalkyl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl-$C_{2-10}$alkenyl, which is unsubstituted. In some embodiments, $R_{21}$ is -L-$C_{3-10}$cycloalkyl-$C_{2-10}$alkenyl, which is substituted by one or more independent $R_{12}$ substituents. In some embodiments, $R_{21}$ is -L-$C_{3-10}$cycloalkyl-$C_{2-10}$alkenyl, which is unsubstituted and L is a bond. In some embodiments, $R_{21}$ is -L-$C_{3-10}$cycloalkyl- $C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl-$C_{2-10}$alkynyl, which is unsubstituted. In some embodiments, $R_{21}$ is -L-$C_{3-10}$cycloalkyl-$C_{2-10}$alkynyl, which is substituted by one or more independent $R_{12}$ substituents. In some embodiments, $R_{21}$ is -L-$C_{3-10}$cycloalkyl-$C_{2-10}$alkynyl, which is unsubstituted and L is a bond. In some embodiments, $R_{21}$ is -L-$C_{3-10}$cycloalkyl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl-$C_{3-10}$aryl, which is unsubstituted. In some embodiments, $R_{21}$ is -L-$C_{3-10}$cycloalkyl-$C_{3-10}$aryl, which is substituted by one or more independent $R_{12}$ substituents. In some embodiments, $R_{21}$ is -L-$C_{3-10}$cycloalkyl-$C_{3-10}$aryl, which is unsubstituted and L is a bond. In some embodiments, $R_{21}$ is -L-$C_{3-10}$cycloalkyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl-$C_{1-10}$hetaryl, which is unsubstituted. In some embodiments, $R_{21}$ is -L-$C_{3-10}$cycloalkyl-$C_{1-10}$hetaryl, which is substituted by one or more independent $R_{12}$ substituents. In some embodiments, $R_{21}$ is -L-$C_{3-10}$cycloalkyl-$C_{1-10}$hetaryl, which is unsubstituted and L is a bond. In some embodiments, $R_{21}$ is -L-$C_{3-10}$cycloalkyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{3-10}$cycloalkyl-$C_{1-10}$heterocyclyl, which is unsubstituted. In some embodiments, $R_{21}$ is -L-$C_{3-10}$cycloalkyl-$C_{1-10}$heterocyclyl, which is substituted by one or more independent $R_{12}$ substituents. In some embodiments, $R_{21}$ is -L-$C_{3-10}$cycloalkyl-$C_{1-10}$heterocyclyl, which is unsubstituted and L is a bond. In some embodiments, $R_{21}$ is -L-$C_{3-10}$cycloalkyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl-$C_{1-10}$alkyl, which is unsubstituted. In some embodiments, $R_{21}$ is -L-$C_{1-10}$heterocyclyl-$C_{1-10}$alkyl, which is substituted by one or more independent $R_{12}$ substituents. In some embodiments, $R_{21}$ is -L-$C_{1-10}$heterocyclyl-$C_{1-10}$alkyl, which is unsubstituted and L is a bond. In some embodiments, $R_{21}$ is -L-$C_{1-10}$heterocyclyl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl-$C_{2-10}$alkenyl, which is unsubstituted. In some embodiments, $R_{21}$ is -L-$C_{1-10}$heterocyclyl-$C_{2-10}$alkenyl, which is substituted by one or more independent $R_{12}$ substituents. In some embodiments, $R_{21}$ is -L-$C_{1-10}$heterocyclyl-$C_{2-10}$alkenyl, which is unsubstituted and L is a bond. In some embodiments, $R_{21}$ is -L-$C_{1-10}$heterocyclyl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl-$C_{2-10}$alkynyl, which is unsubstituted. In some embodiments, $R_{21}$ is -L-$C_{1-10}$heterocyclyl-$C_{2-10}$alkynyl, which is substituted by one or more independent $R_{12}$ substituents. In some embodiments, $R_{21}$ is -L-$C_{1-10}$heterocyclyl-$C_{2-10}$alkynyl, which is unsubstituted and L is a bond. In some embodiments, $R_{21}$ is -L-$C_{1-10}$heterocyclyl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl-$C_{3-10}$aryl, which is unsubstituted. In some embodiments, $R_{21}$ is -L-$C_{1-10}$heterocyclyl-$C_{3-10}$aryl, which is substituted by one or more independent $R_{12}$ substituents. In some embodiments, $R_{21}$ is L-$C_{1-10}$heterocyclyl-$C_{3-10}$aryl, which is unsubstituted and L is a bond. In some embodiments, $R_{21}$ is -L-$C_{1-10}$heterocyclyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl-$C_{1-10}$hetaryl, which is unsubstituted. In some embodiments, $R_{21}$ is -L-$C_{1-10}$heterocyclyl-$C_{1-10}$hetaryl, which is substituted by one or more independent $R_{12}$ substituents. In some embodiments, $R_{21}$ is -L-$C_{1-10}$heterocyclyl-$C_{1-10}$hetaryl, which is unsubstituted and L is a bond. In some embodiments, $R_{21}$ is -L-$C_{1-10}$heterocyclyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is -L-$C_{1-10}$heterocyclyl-$C_{3-10}$cycloalkyl, which is unsubstituted. In some embodiments, $R_{21}$ is -L-$C_{1-10}$heterocyclyl-$C_{3-10}$cycloalkyl, which is substituted by one or more independent $R_{12}$ substituents. In some embodiments, $R_{21}$ is -L-$C_{1-10}$heterocyclyl-$C_{3-10}$cycloalkyl, which is unsubstituted and L is a bond. In some embodiments, $R_{21}$ is -L-$C_{1-10}$heterocyclyl-$C_{3-10}$cycloalkyl, which is substituted by one or more independent $R_{12}$ substituents, where L is a bond.

In some embodiments of Formula I (including I-A and I-B), Formula II (including Formula II', II-A, II-B, II-C, II-D, II-E, II-F and II-G), Formula III (including Formula III-A and III-B), Formula IV (including IV-A, IV-B, IV-C and IV-D) and Formula V (including V-A, V-B, V-C and V-D), $R_{21}$ is selected from the group consisting of -L-$C_{1-10}$heteroalkyl, -L-$C_{3-10}$aryl, -L-$C_{1-10}$hetaryl, -L-$C_{3-10}$cycloalkyl, and -L-$C_{1-10}$heterocyclyl, each of which is unsubstituted or substituted by one or more independent $R_{12}$ substituents; and L is bond. In some embodiments, $R_{21}$ is -L-$C_{1-10}$hetaryl unsubstituted or substituted by one or more independent $R_{12}$ substituents; and L is bond. In some embodiments, the $C_{1-10}$hetaryl of $R_{21}$ comprises one or more nitrogen atoms. In some embodiments, the $C_{1-10}$hetaryl of $R_{21}$ is selected from the group consisting of pyrazolyl, pyridinyl, pyrazinyl, pyrimidinyl, and pyridazinyl. In some embodiments, the $C_{1-10}$hetaryl of $R_{21}$ is unsubstituted. In other embodiments, the $C_{1-10}$hetaryl or $R_{21}$ is substituted with one, two, or three independent $R_{12}$ substituents. In some embodiments, each $R_{12}$ substituent is independently selected from the group consisting of —$C_{1-10}$alkyl, —$C_{2-10}$alkenyl, —$C_{2-10}$ alkynyl, —$C_{1-10}$heteroalkyl, —$C_{3-10}$aryl, —$C_{1-10}$hetaryl, —$C_{3-10}$cycloalkyl, —$C_{1-10}$heterocyclyl, —OH, —$CF_3$, —$OCF_3$, —$OR^{31}$; wherein each $R_{31}$ is independently hydrogen or —$C_{1-10}$alkyl. In further embodiments, each $R_{12}$ substituent is independently selected from the group consisting -Me, -Et, -i-Pr, -n-Pr, OH, —OMe, —OEt, —OPr.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{21}$ is a substituent as shown below:

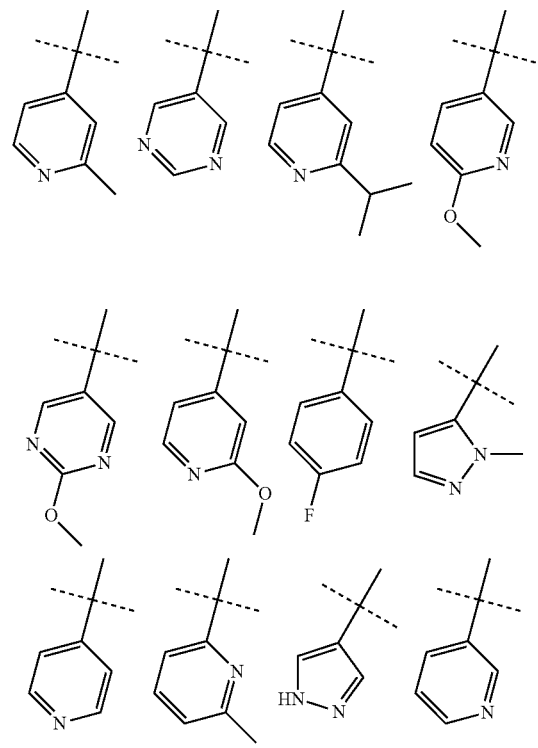

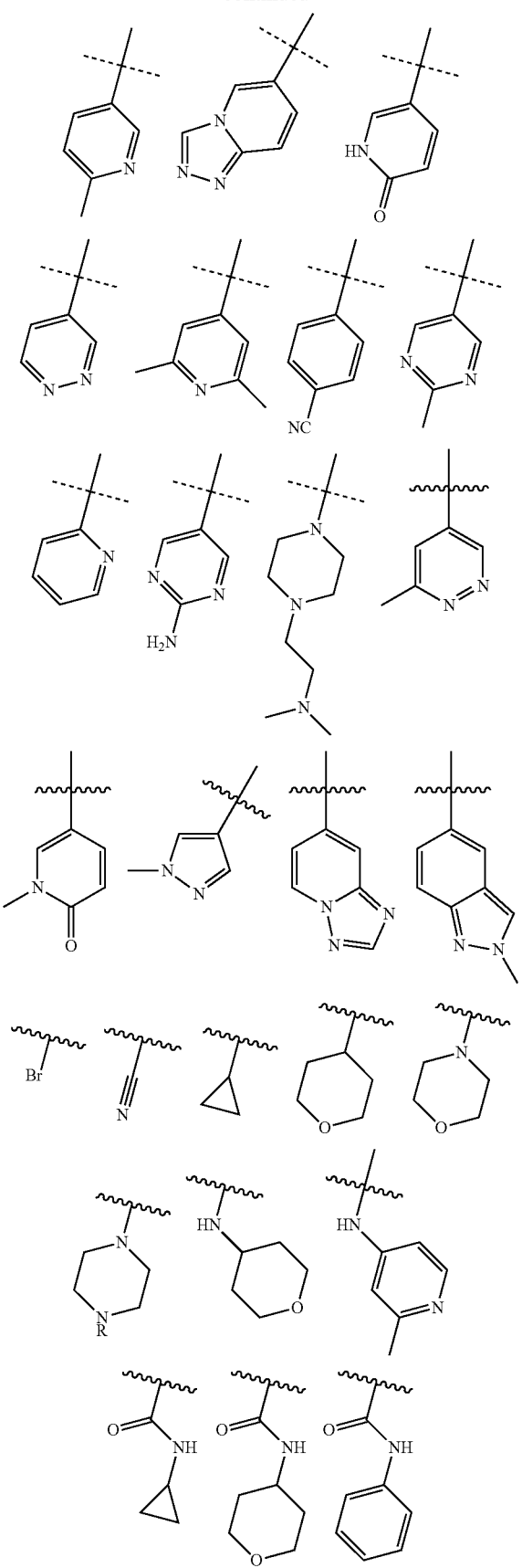

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is —OH. In some embodiments, $R_{22}$ is —$CF_3$. In some embodiments, $R_{22}$ is —$C(O)R^{31}$. In some embodiments, $R_{22}$ is —$CO_2R^{31}$. In some embodiments, $R_{22}$ is —$C(=O)NR^{31}$. In some embodiments, $R_{22}$ is —$S(O)_{0-2}R^{31}$. In some embodiments, $R_{22}$ is —$C(=S)OR^{31}$. In some embodiments, $R_{22}$ is —$C(=O)SR^{31}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkyl, which is unsubstituted. In some embodiments, $R_{22}$ is -L-$C_{1-10}$alkyl, which is substituted by one or more independent $R_{12}$ substituents. In some embodiments, $R_{22}$ is -L-$C_{1-10}$alkyl, which is unsubstituted and L is a bond. In some embodiments, $R_{22}$ is -L-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkenyl, which is unsubstituted. In some embodiments, $R_{22}$ is -L-$C_{2-10}$alkenyl, which is substituted by one or more independent $R_{12}$ substituents. In some embodiments, $R_{22}$ is -L-$C_{2-10}$alkenyl, which is unsubstituted and L is a bond. In some embodiments, $R_{22}$ is -L-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkynyl, which is unsubstituted. In some embodiments, $R_{22}$ is -L-$C_{2-10}$alkynyl, which is substituted by one or more independent $R_{12}$ substituents. In some embodiments, $R_{22}$ is -L-$C_{2-10}$alkynyl, which is unsubstituted and L is a bond. In some embodiments, $R_{22}$ is -L-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$heteroalkyl, which is unsubstituted. In some embodiments, $R_{22}$ is -L-$C_{1-10}$heteroalkyl, which is substituted by one or more independent $R_{12}$ substituents. In some embodiments, $R_{22}$ is -L-$C_{1-10}$heteroalkyl, which is unsubstituted and L is a bond. In some embodiments, $R_{22}$ is -L-$C_{1-10}$heteroalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl, which is unsubstituted. In some embodiments, $R_{22}$ is -L-$C_{3-10}$aryl, which is substituted by one or more independent $R_{12}$ substituents. In some embodiments, $R_{22}$ is -L-$C_{3-10}$aryl, which is unsubstituted and L is a bond. In some embodiments, $R_{22}$ is -L-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl, which is unsubstituted. In some embodiments, $R_{22}$ is -L-$C_{1-10}$hetaryl, which is substituted by one or more independent $R_{12}$ substituents. In some embodiments, $R_{22}$ is -L-$C_{1-10}$hetaryl, which is unsubstituted and L is a bond. In some embodiments, $R_{22}$ is -L-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$cycloalkyl, which is unsubstituted. In some embodiments, $R_{22}$ is -L-$C_{3-10}$cycloalkyl, which is substituted by one or more independent $R_{12}$ substituents. In some embodiments, $R_{22}$ is -L-$C_{3-10}$cycloalkyl, which is unsubstituted and L is a bond. In some embodiments, $R_{22}$ is -L-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$heterocyclyl, which is unsubstituted. In some embodiments, $R_{22}$ is -L-$C_{1-10}$heterocyclyl, which is substituted by one or more independent $R_{12}$ substituents. In some embodiments, $R_{22}$ is -L-$C_{1-10}$heterocyclyl, which is unsubstituted and L is a bond. In some embodiments, $R_{22}$ is -L-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkyl-$C_{3-10}$aryl, which is unsubstituted. In some embodiments, $R_{22}$ is -L-$C_{1-10}$alkyl-$C_{3-10}$aryl, which is substituted by one or more independent $R_{12}$ substituents. In some embodiments, $R_{22}$ is -L-$C_{1-10}$alkyl-$C_{3-10}$aryl, which is unsubstituted and L is a bond. In some embodiments, $R_{22}$ is -L-$C_{1-10}$alkyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkyl-$C_{1-10}$hetaryl, which is unsubstituted. In some embodiments, $R_{22}$ is -L-$C_{1-10}$alkyl-$C_{1-10}$hetaryl, which is substituted by one or more independent $R_{12}$ substituents. In some embodiments, $R_{22}$ is -L-$C_{1-10}$alkyl-$C_{1-10}$hetaryl, which is unsubstituted and L is a bond. In some embodiments, $R_{22}$ is -L-$C_{1-10}$alkyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkyl-$C_{3-10}$cycloalkyl, which is unsubstituted. In some embodiments, $R_{22}$ is -L-$C_{1-10}$alkyl-$C_{3-10}$cycloalkyl, which is substituted by one or more independent $R_{12}$ substituents. In some embodiments, $R_{22}$ is -L-$C_{1-10}$alkyl-$C_{3-10}$cycloalkyl, which is unsubstituted and L is a bond. In some embodiments, $R_{22}$ is -L-$C_{1-10}$alkyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkyl-$C_{1-10}$heterocyclyl, which is unsubstituted. In some embodiments, $R_{22}$ is -L-$C_{1-10}$alkyl-$C_{1-10}$heterocyclyl, which is substituted by one or more independent $R_{12}$ substituents. In some embodiments, $R_{22}$ is -L-$C_{1-10}$alkyl-$C_{1-10}$heterocyclyl, which is unsubstituted and L is a bond. In some embodiments, $R_{22}$ is -L-$C_{1-10}$alkyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkenyl-$C_{3-10}$aryl, which is unsubstituted. In some embodiments, $R_{22}$ is -L-$C_{2-10}$alkenyl-$C_{3-10}$aryl, which is substituted by one or more independent $R_{12}$ substituents. In some embodiments, $R_{22}$ is -L-$C_{2-10}$alkenyl-$C_{3-10}$aryl, which is unsubstituted and L is a bond. In some embodiments, $R_{22}$ is -L-$C_{2-10}$alkenyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkenyl-$C_{1-10}$hetaryl, which is unsubstituted. In some embodiments, $R_{22}$ is -L-$C_{2-10}$alkenyl-$C_{1-10}$hetaryl, which is substituted by one or more independent $R_{12}$ substituents. In some embodiments, $R_{22}$ is -L-$C_{2-10}$alkenyl-$C_{1-10}$hetaryl, which is unsubstituted and L is a bond. In some embodiments, $R_{22}$ is -L-$C_{2-10}$alkenyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkenyl-$C_{3-10}$cycloalkyl, which is unsubstituted. In some embodiments, $R_{22}$ is -L-$C_{2-10}$alkenyl-$C_{3-10}$cycloalkyl, which is substituted by one or more independent $R_{12}$ substituents. In some embodiments, $R_{22}$ is -L-$C_{2-10}$alkenyl-$C_{3-10}$cycloalkyl, which is unsubstituted and L is a bond. In some embodiments, $R_{22}$ is -L-$C_{2-10}$alkenyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkenyl-$C_{1-10}$heterocyclyl, which is unsubstituted. In some embodiments, $R_{22}$ is -L-$C_{2-10}$alkenyl-$C_{1-10}$heterocyclyl, which is substituted by one or more independent $R_{12}$ substituents. In some embodiments, $R_{22}$ is -L-$C_{2-10}$alkenyl-$C_{1-10}$heterocyclyl, which is unsubstituted and L is a bond. In some embodiments, $R_{22}$ is -L-$C_{2-10}$alkenyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkynyl-$C_{3-10}$aryl, which is unsubstituted. In some embodiments, $R_{22}$ is -L-$C_{2-10}$alkynyl-$C_{3-10}$aryl, which is substituted by one or more independent $R_{12}$ substituents. In some embodiments, $R_{22}$ is -L-$C_{2-10}$alkynyl-$C_{3-10}$aryl, which is unsubstituted and L is a bond. In some embodiments, $R_{22}$ is -L-$C_{2-10}$alkynyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkynyl-$C_{1-10}$hetaryl, which is unsubstituted. In some embodiments, $R_{22}$ is -L-$C_{2-10}$alkynyl-$C_{1-10}$hetaryl, which is substituted by one or more independent $R_{12}$ substituents. In some embodiments, $R_{22}$ is -L-$C_{2-10}$alkynyl-$C_{1-10}$hetaryl, which is unsubstituted and L is a bond. In some embodiments, $R_{22}$ is -L-$C_{2-10}$alkynyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkynyl-$C_{3-10}$cycloalkyl, which is unsubstituted. In some embodiments, $R_{22}$ is -L-$C_{2-10}$alkynyl-$C_{3-10}$cycloalkyl, which is substituted by one or more independent $R_{12}$ substituents. In some embodiments, $R_{22}$ is -L-$C_{2-10}$alkynyl-$C_{3-10}$cycloalkyl, which is unsubstituted and L is a bond. In some embodiments, $R_{22}$ is -L-$C_{2-10}$alkynyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{2-10}$alkynyl-$C_{1-10}$heterocyclyl, which is unsubstituted. In some embodiments, $R_{22}$ is -L-$C_{2-10}$alkynyl-$C_{1-10}$heterocyclyl, which is substituted by one or more independent $R_{12}$ substituents. In some embodiments, $R_{22}$ is -L-$C_{2-10}$alkynyl-$C_{1-10}$heterocyclyl, which is unsubstituted and L is a bond. In some embodiments, $R_{22}$ is -L-$C_{2-10}$alkynyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkoxy-$C_{3-10}$aryl, which is unsubstituted. In some embodiments, $R_{22}$ is -L-$C_{1-10}$alkoxy-$C_{3-10}$aryl, which is substituted by one or more independent $R_{12}$ substituents. In some embodiments, $R_{22}$ is -L-$C_{1-10}$alkoxy-$C_{3-10}$aryl, which is unsubstituted and L is a bond. In some embodiments, $R_{22}$ is -L-$C_{1-10}$alkoxy-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkoxy-$C_{1-10}$hetaryl, which is unsubstituted. In some embodiments, $R_{22}$ is -L-$C_{1-10}$alkoxy-$C_{1-10}$hetaryl, which is substituted by one or more independent $R_{12}$ substituents. In some embodiments, $R_{22}$ is -L-$C_{1-10}$alkoxy-$C_{1-10}$hetaryl, which is unsubstituted and L is a bond. In some embodiments, $R_{22}$ is -L-$C_{1-10}$alkoxy-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkoxy-$C_{3-10}$cycloalkyl, which is unsubstituted. In some embodiments, $R_{22}$ is -L-$C_{1-10}$alkoxy-$C_{3-10}$cycloalkyl, which is substituted by one or more independent $R_{12}$ substituents. In some embodiments, $R_{22}$ is -L-$C_{1-10}$alkoxy-$C_{3-10}$cycloalkyl, which is unsubstituted and L is a bond. In some embodiments, $R_{22}$ is -L-$C_{1-10}$alkoxy-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$alkoxy-$C_{1-10}$heterocyclyl, which is unsubstituted. In some embodiments, $R_{22}$ is -L-$C_{1-10}$alkoxy-$C_{1-10}$heterocyclyl, which is substituted by one or more independent $R_{12}$ substituents. In some embodiments, $R_{22}$ is -L-$C_{1-10}$alkoxy-$C_{1-10}$heterocyclyl, which is unsubstituted and L is a bond. In some embodiments, $R_{22}$ is -L-$C_{1-10}$alkoxy-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$heteroalkyl-$C_{3-10}$aryl, which is unsubstituted. In some embodiments, $R_{22}$ is -L-$C_{1-10}$heteroalkyl-$C_{3-10}$aryl, which is substituted by one or more independent $R_{12}$ substituents. In some embodiments, $R_{22}$ is -L-$C_{1-10}$heteroalkyl-$C_{3-10}$aryl, which is unsubstituted and L is a bond. In some embodiments, $R_{22}$ is -L-$C_{1-10}$heteroalkyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$heteroalkyl-$C_{1-10}$hetaryl, which is unsubstituted. In some embodiments, $R_{22}$ is -L-$C_{1-10}$heteroalkyl-$C_{1-10}$hetaryl, which is substituted by one or more independent $R_{12}$ substituents. In some embodiments, $R_{22}$ is -L-$C_{1-10}$heteroalkyl-$C_{1-10}$hetaryl, which is unsubstituted and L is a bond. In some embodiments, $R_{22}$ is -L-$C_{1-10}$heteroalkyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$heteroalkyl-$C_{3-10}$cycloalkyl, which is unsubstituted. In some embodiments, $R_{22}$ is -L-$C_{1-10}$heteroalkyl-$C_{3-10}$cycloalkyl, which is substituted by one or more independent $R_{12}$ substituents. In some embodiments, $R_{22}$ is -L-$C_{1-10}$heteroalkyl-$C_{3-10}$cycloalkyl, which is unsubstituted and L is a bond. In some embodiments, $R_{22}$ is -L-$C_{1-10}$heteroalkyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$heteroalkyl-$C_{1-10}$heterocyclyl, which is unsubstituted. In some embodiments, $R_{22}$ is -L-$C_{1-10}$heteroalkyl-$C_{1-10}$heterocyclyl, which is substituted by one or more independent $R_{12}$ substituents. In some embodiments, $R_{22}$ is -L-$C_{1-10}$heteroalkyl-$C_{1-10}$heterocyclyl, which is unsubstituted and L is a bond. In some embodiments, $R_{22}$ is -L-$C_{1-10}$heteroalkyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl-$C_{1-10}$alkyl, which is unsubstituted. In some embodiments, $R_{22}$ is -L-$C_{3-10}$aryl-$C_{1-10}$alkyl, which is substituted by one or more independent $R_{12}$ substituents. In some embodiments, $R_{22}$ is -L-$C_{3-10}$aryl-$C_{1-10}$alkyl, which is unsubstituted and L is a bond. In some embodiments, $R_{22}$ is -L-$C_{3-10}$aryl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl-$C_{2-10}$alkenyl, which is unsubstituted. In some embodiments, $R_{22}$ is -L-$C_{3-10}$aryl-$C_{2-10}$alkenyl, which is substituted by one or more independent $R_{12}$ substituents. In some embodiments, $R_{22}$ is -L-$C_{3-10}$aryl-$C_{2-10}$alkenyl, which is unsubstituted and L is a bond. In some embodiments, $R_{22}$ is -L-$C_{3-10}$aryl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl-$C_{2-10}$alkynyl, which is unsubstituted. In some embodiments, $R_{22}$ is -L-$C_{3-10}$aryl-$C_{2-10}$alkynyl, which is substituted by one or more independent $R_{12}$ substituents. In some embodiments, $R_{22}$ is -L-$C_{3-10}$aryl-$C_{2-10}$alkynyl, which is unsubstituted and L is a bond. In some embodiments, $R_{22}$ is -L-$C_{3-10}$aryl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl-$C_{1-10}$hetaryl, which is unsubstituted. In some embodiments, $R_{22}$ is -L-$C_{3-10}$aryl-$C_{1-10}$hetaryl, which is substituted by one or more independent $R_{12}$ substituents. In some embodiments, $R_{22}$ is -L-$C_{3-10}$aryl-$C_{1-10}$hetaryl, which is unsubstituted and L is a bond. In some embodiments, $R_{22}$ is -L-$C_{3-10}$aryl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl-$C_{3-10}$cycloalkyl, which is unsubstituted. In some embodiments, $R_{22}$ is -L-$C_{3-10}$aryl-$C_{3-10}$cycloalkyl, which is substituted by one or more independent $R_{12}$ substituents. In some embodiments, $R_{22}$ is -L-$C_{3-10}$aryl-$C_{3-10}$cycloalkyl, which is unsubstituted and L is a bond. In some embodiments, $R_{22}$ is -L-$C_{3-10}$aryl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$aryl-$C_{1-10}$heterocyclyl, which is unsubstituted. In some embodiments, $R_{22}$ is -L-$C_{3-10}$aryl-$C_{1-10}$heterocyclyl, which is substituted by one or more independent $R_{12}$ substituents. In some embodiments, $R_{22}$ is -L-$C_{3-10}$aryl-$C_{1-10}$heterocyclyl, which is unsubstituted and L is a bond. In some embodiments, $R_{22}$ is -L-$C_{3-10}$aryl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl-$C_{1-10}$alkyl, which is unsubstituted. In some embodiments, $R_{22}$ is -L-$C_{1-10}$hetaryl-$C_{1-10}$alkyl, which is substituted by one or more independent $R_{12}$ substituents. In some embodiments, $R_{22}$ is -L-$C_{1-10}$hetaryl-$C_{1-10}$alkyl, which is unsubstituted and L is a bond. In some embodiments, $R_{22}$ is -L-$C_{1-10}$hetaryl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl-$C_{2-10}$alkenyl, which is unsubstituted. In some embodiments, $R_{22}$ is -L-$C_{1-10}$hetaryl-$C_{2-10}$alkenyl, which is substituted by one or more independent $R_{12}$ substituents. In some embodiments, $R_{22}$ is -L-$C_{1-10}$hetaryl-$C_{2-10}$alkenyl, which is unsubstituted and L is a bond. In some embodiments, $R_{22}$ is -L-$C_{1-10}$hetaryl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl-$C_{2-10}$alkynyl, which is unsubstituted. In some embodiments, $R_{22}$ is -L-$C_{1-10}$hetaryl-$C_{2-10}$alkynyl, which is substituted by one or more independent $R_{12}$ substituents. In some embodiments, $R_{22}$ is -L-$C_{1-10}$hetaryl-$C_{2-10}$alkynyl, which is unsubstituted and L is a bond. In some embodiments, $R_{22}$ is -L-$C_{1-10}$hetaryl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl-$C_{3-10}$aryl, which is unsubstituted. In some embodiments, $R_{22}$ is -L-$C_{1-10}$hetaryl-$C_{3-10}$aryl, which is substituted by one or more independent $R_{12}$ substituents. In some embodiments, $R_{22}$ is -L-$C_{1-10}$hetaryl-$C_{3-10}$aryl, which is unsubstituted and L is a bond. In some embodiments, $R_{22}$ is -L-$C_{1-10}$hetaryl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl-$C_{3-10}$cycloalkyl, which is unsubstituted. In some embodiments, $R_{22}$ is -L-$C_{1-10}$hetaryl-$C_{3-10}$cycloalkyl, which is substituted by one or more independent $R_{12}$ substituents. In some embodiments, $R_{22}$ is -L-$C_{1-10}$hetaryl-$C_{3-10}$cycloalkyl, which is unsubstituted and L is a bond. In some embodiments, $R_{22}$ is -L-$C_{1-10}$hetaryl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{1-10}$hetaryl-$C_{1-10}$heterocyclyl, which is unsubstituted. In some embodiments, $R_{22}$ is -L-$C_{1-10}$hetaryl-$C_{1-10}$heterocyclyl, which is substituted by one or more independent $R_{12}$ substituents. In some embodiments, $R_{22}$ is -L-$C_{1-10}$hetaryl-$C_{1-10}$heterocyclyl, which is unsubstituted and L is a bond. In some embodiments, $R_{22}$ is -L-

$C_{1-10}$hetaryl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$cycloalkyl-$C_{1-10}$alkyl, which is unsubstituted. In some embodiments, $R_{22}$ is -L-$C_{3-10}$cycloalkyl-$C_{1-10}$alkyl, which is substituted by one or more independent $R_{12}$ substituents. In some embodiments, $R_{22}$ is -L-$C_{3-10}$cycloalkyl-$C_{1-10}$alkyl, which is unsubstituted and L is a bond. In some embodiments, $R_{22}$ is -L-$C_{3-10}$cycloalkyl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$cycloalkyl-$C_{2-10}$alkenyl, which is unsubstituted. In some embodiments, $R_{22}$ is -L-$C_{3-10}$cycloalkyl-$C_{2-10}$alkenyl, which is substituted by one or more independent $R_{12}$ substituents. In some embodiments, $R_{22}$ is -L-$C_{3-10}$cycloalkyl-$C_{2-10}$alkenyl, which is unsubstituted and L is a bond. In some embodiments, $R_{22}$ is -L-$C_{3-10}$cycloalkyl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$cycloalkyl-$C_{2-10}$alkynyl, which is unsubstituted. In some embodiments, $R_{22}$ is -L-$C_{3-10}$cycloalkyl-$C_{2-10}$alkynyl, which is substituted by one or more independent $R_{12}$ substituents. In some embodiments, $R_{22}$ is -L-$C_{3-10}$cycloalkyl-$C_{2-10}$alkynyl, which is unsubstituted and L is a bond. In some embodiments, $R_{22}$ is -L-$C_{3-10}$cycloalkyl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$cycloalkyl-$C_{3-10}$aryl, which is unsubstituted. In some embodiments, $R_{22}$ is -L-$C_{3-10}$cycloalkyl-$C_{3-10}$aryl, which is substituted by one or more independent $R_{12}$ substituents. In some embodiments, $R_{22}$ is -L-$C_{3-10}$cycloalkyl-$C_{3-10}$aryl, which is unsubstituted and L is a bond. In some embodiments, $R_{22}$ is -L-$C_{3-10}$cycloalkyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is -L-$C_{3-10}$cycloalkyl-$C_{1-10}$hetaryl, which is unsubstituted. In some embodiments, $R_{22}$ is -L-$C_{3-10}$cycloalkyl-$C_{1-10}$hetaryl, which is substituted by one or more independent $R_{12}$ substituents. In some embodiments, $R_{22}$ is -L-$C_{3-10}$cycloalkyl-$C_{1-10}$hetaryl, which is unsubstituted and L is a bond. In some embodiments, $R_{22}$ is -L-$C_{3-10}$cycloalkyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{3-10}$cycloalkyl-$C_{1-10}$heterocyclyl, which is unsubstituted. In some embodiments, $R_{22}$ is -L-$C_{3-10}$cycloalkyl-$C_{1-10}$heterocyclyl, which is substituted by one or more independent $R_{12}$ substituents. In some embodiments, $R_{22}$ is -L-$C_{3-10}$cycloalkyl-$C_{1-10}$heterocyclyl, which is unsubstituted and L is a bond. In some embodiments, $R_{22}$ is -L-$C_{3-10}$cycloalkyl-$C_{1-10}$heterocyclyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{1-10}$heterocyclyl-$C_{1-10}$alkyl, which is unsubstituted. In some embodiments, $R_{22}$ is -L-$C_{1-10}$heterocyclyl-$C_{1-10}$alkyl, which is substituted by one or more independent $R_{12}$ substituents. In some embodiments, $R_{22}$ is L-$C_{1-10}$heterocyclyl-$C_{1-10}$alkyl, which is unsubstituted and L is a bond. In some embodiments, $R_{22}$ is -L-$C_{1-10}$heterocyclyl-$C_{1-10}$alkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{1-10}$heterocyclyl-$C_{2-10}$alkenyl, which is unsubstituted. In some embodiments, $R_{22}$ is -L-$C_{1-10}$heterocyclyl-$C_{2-10}$alkenyl, which is substituted by one or more independent $R_{12}$ substituents. In some embodiments, $R_{22}$ is -L-$C_{1-10}$heterocyclyl-$C_{2-10}$alkenyl, which is unsubstituted and L is a bond. In some embodiments, $R_{22}$ is -L-$C_{1-10}$heterocyclyl-$C_{2-10}$alkenyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{1-10}$heterocyclyl-$C_{2-10}$alkynyl, which is unsubstituted. In some embodiments, $R_{22}$ is -L-$C_{1-10}$heterocyclyl-$C_{2-10}$alkynyl, which is substituted by one or more independent $R_{12}$ substituents. In some embodiments, $R_{22}$ is -L-$C_{1-10}$heterocyclyl-$C_{2-10}$alkynyl, which is unsubstituted and L is a bond. In some embodiments, $R_{22}$ is -L-$C_{1-10}$heterocyclyl-$C_{2-10}$alkynyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{1-10}$heterocyclyl-$C_{3-10}$aryl, which is unsubstituted. In some embodiments, $R_{22}$ is -L-$C_{1-10}$heterocyclyl-$C_{3-10}$aryl, which is substituted by one or more independent $R_{12}$ substituents. In some embodiments, $R_{22}$ is L-$C_{1-10}$heterocyclyl-$C_{3-10}$aryl, which is unsubstituted and L is a bond. In some embodiments, $R_{22}$ is -L-$C_{1-10}$heterocyclyl-$C_{3-10}$aryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{1-10}$heterocyclyl-$C_{1-10}$hetaryl, which is unsubstituted. In some embodiments, $R_{22}$ is -L-$C_{1-10}$heterocyclyl-$C_{1-10}$hetaryl, which is substituted by one or more independent $R_{12}$ substituents. In some embodiments, $R_{22}$ is -L-$C_{1-10}$heterocyclyl-$C_{1-10}$hetaryl, which is unsubstituted and L is a bond. In some embodiments, $R_{22}$ is -L-$C_{1-10}$heterocyclyl-$C_{1-10}$hetaryl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is L-$C_{1-10}$heterocyclyl-$C_{3-10}$cycloalkyl, which is unsubstituted. In some embodiments, $R_{22}$ is -L-$C_{1-10}$heterocyclyl-$C_{3-10}$cycloalkyl, which is substituted by one or more independent $R_{12}$ substituents. In some embodiments, $R_{22}$ is -L-$C_{1-10}$heterocyclyl-$C_{3-10}$cycloalkyl, which is unsubstituted and L is a bond. In some embodiments, $R_{22}$ is -L-$C_{1-10}$heterocyclyl-$C_{3-10}$cycloalkyl, which is substituted by one or more independent $R_{12}$ substituents, where L is a bond.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{22}$ is a substituent as shown below:

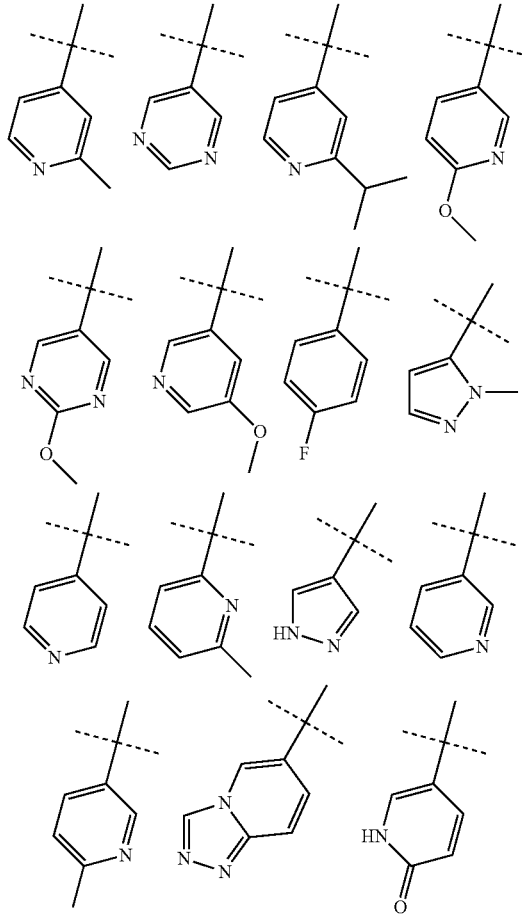

-continued

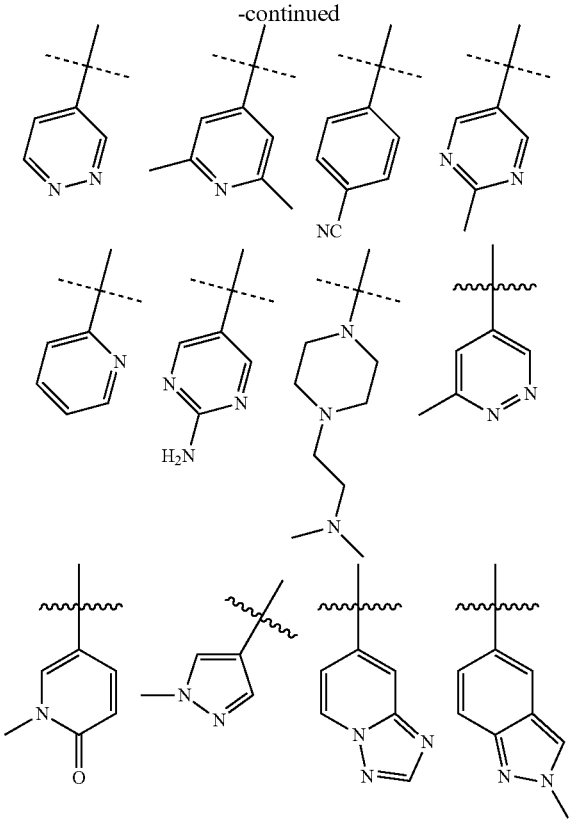

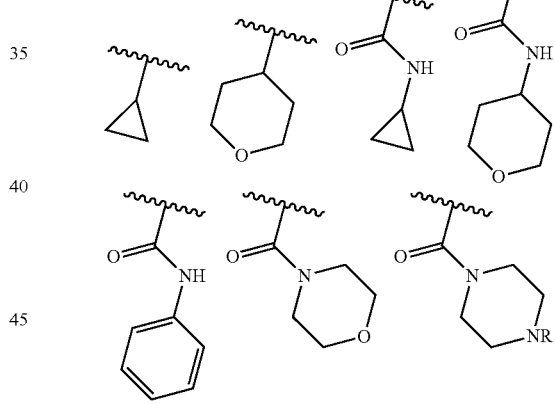

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), L is a bond. In some embodiments, L is —O—. In some embodiments, N($R^{31}$). In some embodiments, L is S(O)$_{0-2}$. In some embodiments, L is C(=O). In some embodiments, L is C(=O)O. In some embodiments, L is OC(=O). In some embodiments, L is C(=O)N($R^{31}$). In some embodiments, L is N($R^{31}$)C(=O). In some embodiments, L is N$R^{31}$C(=O)O. In some embodiments, L is N$R^{31}$C(=O)N$R^{32}$. In some embodiments, L is N$R^{31}$S(O)$_{0-2}$. In some embodiments, L is S(O)$_{0-2}$N($R^{31}$). In some embodiments, L is C(=S)O. In some embodiments, L is C(=O)S. In some embodiments, L is N$R^{31}$C(=N$R^{32}$)N$R^{32}$. In some embodiments, L is N$R^{31}$C(=N$R^{32}$)O. In some embodiments, L is NR$^{31}$C(=NR$^{32}$)S. In some embodiments, L is OC(=O)O. In some embodiments, L is OC(=O)NR$^{31}$. In some embodiments, L is OC(=O)S. In some embodiments, L is SC(=O) S. In some embodiments, L is P(O)OR$^{31}$O. In some embodiments, L is SC(=O)NR$^{31}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is hydrogen. In some embodiments, R$_3$ is halogen, which is F, Cl, Br, or I. In some embodiments, R$_3$ is —OH. In some embodiments, R$_3$ is —CF$_3$. In some embodiments, R$_3$ is —OCF$_3$. In some embodiments, R$_3$ is —OR$^{31}$. In some embodiments, R$_3$ is —NR$^{31}$R$^{32}$. In some embodiments, R$_3$ is —C(O)R$^{31}$. In some embodiments, R$_3$ is CO$_2$R$^{31}$. In some embodiments, R$_3$ is —C(=O)NR$^{31}$. In some embodiments, R$_3$ is —NO$_2$. In some embodiments, R$_3$ is —CN. In some embodiments, R$_3$ is —S(O)$_{0-2}$R$^{31}$. In some embodiments, R$_3$ is —SO$_2$NR$^{31}$R$^{32}$. In some embodiments, R$_3$ is —NR$^{31}$C(=O)R$^{32}$. In some embodiments, R$_3$ is —NR$^{31}$C(=O)OR$^{32}$. In some embodiments, R$_3$ is —NR$^{31}$C(=O)NR$^{32}$R$^{33}$. In some embodiments, R$_3$ is —NR$^{31}$S(O)$_{0-2}$R$^{32}$. In some embodiments, R$_3$ is —C(=S)OR$^{31}$. In some embodiments, R$_3$ is —C(=O)SR$^{31}$. In some embodiments, R$_3$ is —NR$^{31}$C(=NR$^{32}$)NR$^{32}$R$^{33}$. In some embodiments, R$_3$ is —NR$^{31}$C(=NR$^{32}$)OR$^{33}$. In some embodiments, R$_3$ is —NR$^{31}$C(=NR$^{32}$)SR$^{33}$. In some embodiments, R$_3$ is —OC(=O)OR$^{33}$. In some embodiments, R$_3$ is —OC(=O)NR$^{31}$R$^{32}$. In some embodiments, R$_3$ is —OC(=O)SR$^{31}$. In some embodiments, R$_3$ is —SC(=O)SR$^{31}$. In some embodiments, R$_3$ is —P(O)OR$^{31}$OR$^{32}$. In some embodiments, R$_3$ is —SC(=O)NR$^{31}$R$^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$alkyl, which is unsubstituted. In some embodiments, R$_3$ is —C$_{1-10}$alkyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{2-10}$alkenyl, which is unsubstituted. In some embodiments, R$_3$ is —C$_{2-10}$alkenyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{2-10}$alkynyl, which is unsubstituted. In some embodiments, R$_3$ is —C$_{2-10}$alkynyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$heteroalkyl, which is unsubstituted. In some embodiments, R$_3$ is —C$_{1-10}$heteroalkyl, which is substituted by one or more independent R$_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{3-10}$aryl, which is unsubstituted. In some embodiments, R$_3$ is —C$_{3-10}$aryl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$hetaryl, which is unsubstituted. In some embodiments, R$_3$ is —C$_{1-10}$hetaryl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{3-10}$cycloalkyl, which is unsubstituted. In some embodiments, R$_3$ is —C$_{3-10}$cycloalkyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$heterocyclyl, which is unsubstituted. In some embodiments, R$_3$ is —C$_{1-10}$heterocyclyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$alkyl-C$_{3-10}$aryl, which is unsubstituted. In some embodiments, R$_3$ is —C$_{1-10}$alkyl-C$_{3-10}$aryl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$alkyl-C$_{1-10}$hetaryl, which is unsubstituted. In some embodiments, R$_3$ is —C$_{1-10}$alkyl-C$_{1-10}$hetaryl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is —C$_{1-10}$alkyl-C$_{3-10}$cycloalkyl, which is unsubstituted. In some embodiments, R$_3$ is —C$_{1-10}$alkyl-C$_{3-10}$cycloalkyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_3$ is C$_{1-10}$alkyl-C$_{1-10}$heterocyclyl, which is unsubstituted. In some embodiments, R$_3$ is —C$_{1-10}$alkyl-C$_{1-10}$heterocyclyl, which is substituted by one or more independent R$_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkenyl-$C_{3-10}$aryl, which is unsubstituted. In some embodiments, $R_3$ is —$C_{1-10}$alkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkenyl-$C_{1-10}$hetaryl, which is unsubstituted. In some embodiments, $R_3$ is —$C_{2-10}$alkenyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkenyl-$C_{3-10}$cycloalkyl, which is unsubstituted. In some embodiments, $R_3$ is —$C_{2-10}$alkenyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkenyl-$C_{1-10}$heterocyclyl, which is unsubstituted. In some embodiments, $R_3$ is —$C_{2-10}$alkenyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkynyl-$C_{3-10}$aryl, which is unsubstituted. In some embodiments, $R_3$ is —$C_{2-10}$alkynyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkynyl-$C_{1-10}$hetaryl, which is unsubstituted. In some embodiments, $R_3$ is —$C_{2-10}$alkynyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkynyl-$C_{3-10}$cycloalkyl, which is unsubstituted. In some embodiments, $R_3$ is —$C_{2-10}$alkynyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{2-10}$alkynyl-$C_{1-10}$heterocyclyl, which is unsubstituted. In some embodiments, $R_3$ is —$C_{2-10}$alkynyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$alkoxy-$C_{3-10}$aryl, which is unsubstituted. In some embodiments, $R_3$ is —$C_{1-10}$alkoxy-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$alkoxy-$C_{1-10}$hetaryl, which is unsubstituted. In some embodiments, $R_3$ is —$C_{1-10}$alkoxy-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$alkoxy-$C_{3-10}$cycloalkyl, which is unsubstituted. In some embodiments, $R_3$ is —$C_{1-10}$alkoxy-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$alkoxy-$C_{1-10}$heterocyclyl, which is unsubstituted. In some embodiments, $R_3$ is —$C_{1-10}$alkoxy-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heteroalkyl-$C_{3-10}$aryl, which is unsubstituted. In some embodiments, $R_3$ is —$C_{1-10}$heteroalkyl-$C_{3-10}$aryl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heteroalkyl-$C_{1-10}$hetaryl, which is unsubstituted. In some embodiments, $R_3$ is —$C_{1-10}$heteroalkyl-$C_{1-10}$hetaryl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heteroalkyl-$C_{3-10}$cycloalkyl, which is unsubstituted. In some embodiments, $R_3$ is —$C_{1-10}$heteroalkyl-$C_{3-10}$cycloalkyl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heteroalkyl-$C_{1-10}$heterocyclyl, which is unsubstituted. In some embodiments, $R_3$ is —$C_{1-10}$heteroalkyl-$C_{1-10}$heterocyclyl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$aryl-$C_{1-10}$alkyl, which is unsubstituted. In some embodiments, $R_3$ is —$C_{3-10}$aryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$aryl-$C_{2-10}$alkenyl, which is unsubstituted. In some embodiments, $R_3$ is —$C_{3-10}$aryl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$aryl-$C_{2-10}$alkynyl, which is unsubstituted. In some embodiments, $R_3$ is —$C_{3-10}$aryl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$aryl-$C_{3-10}$hetaryl, which is unsubstituted. In some embodiments, $R_3$ is —$C_{3-10}$aryl-$C_{3-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is —$C_{3-10}$aryl-$C_{3-10}$cycloalkyl, which is unsubstituted. In some embodiments, $R_3$ is —$C_{3-10}$aryl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$aryl-$C_{1-10}$heterocyclyl, which is unsubstituted. In some embodiments, $R_3$ is —$C_{3-10}$aryl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$hetaryl-$C_{1-10}$alkyl, which is unsubstituted. In some embodiments, $R_3$ is —$C_{1-10}$hetaryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$hetaryl-$C_{2-10}$alkenyl, which is unsubstituted. In some embodiments, $R_3$ is —$C_{1-10}$hetaryl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$hetaryl-$C_{2-10}$alkynyl, which is unsubstituted. In some embodiments, $R_3$ is —$C_{1-10}$hetaryl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$hetaryl-$C_{3-10}$aryl, which is unsubstituted. In some embodiments, $R_3$ is —$C_{3-10}$hetaryl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$hetaryl-$C_{3-10}$cycloalkyl, which is unsubstituted. In some embodiments, $R_3$ is —$C_{1-10}$hetaryl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$hetaryl-$C_{1-10}$heterocyclyl, which is unsubstituted. In some embodiments, $R_3$ is —$C_{1-10}$hetaryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$cycloalkyl-$C_{1-10}$alkyl, which is unsubstituted. In some embodiments, $R_3$ is —$C_{3-10}$cycloalkyl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$cycloalkyl-$C_{2-10}$alkenyl, which is unsubstituted. In some embodiments, $R_3$ is —$C_{3-10}$cycloalkyl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$cycloalkyl-$C_{2-10}$alkynyl, which is unsubstituted. In some embodiments, $R_3$ is —$C_{3-10}$cycloalkyl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$cycloalkyl-$C_{3-10}$aryl, which is unsubstituted. In some embodiments, $R_3$ is —$C_{3-10}$cycloalkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$cycloalkyl-$C_{1-10}$hetaryl, which is unsubstituted. In some embodiments, $R_3$ is —$C_{3-10}$cycloalkyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{3-10}$cycloalkyl-$C_{1-10}$heterocyclyl, which is unsubstituted. In some embodiments, $R_3$ is —$C_{3-10}$cycloalkyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heterocyclyl-$C_{1-10}$alkyl, which is unsubstituted. In some embodiments, $R_3$ is —$C_{3-10}$cycloalkyl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heterocyclyl-$C_{2-10}$alkenyl, which is unsubstituted. In some embodiments, $R_3$ is —$C_{1-10}$heterocyclyl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heterocyclyl-$C_{2-10}$alkynyl, which is unsubstituted. In some embodiments, $R_3$ is —$C_{1-10}$heterocyclyl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heterocyclyl-$C_{3-10}$aryl, which is unsubstituted. In some embodiments, $R_3$ is —$C_{1-10}$heterocyclyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heterocyclyl-$C_{1-10}$hetaryl, which is unsubstituted. In some embodiments, $R_3$ is —$C_{1-10}$heterocyclyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3$ is $C_{1-10}$heterocyclyl-$C_{3-10}$cycloalkyl, which is unsubstituted. In some embodiments, $R_3$ is —$C_{1-10}$heterocyclyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is hydrogen. In some embodiments, $R_3'$ is halogen, which is F, Cl, Br, or I. In some embodiments, $R_3'$ is —OH. In some embodiments, $R_3'$ is —$CF_3$. In some embodiments, $R_3'$ is —$OCF_3$. In some embodiments, $R_3'$ is —$OR^{31}$. In some embodiments, $R_3'$ is —$NR^{31}R^{32}$. In some embodiments, $R_3'$ is —$C(O)R^{31}$. In some embodiments, $R_3'$ is —$CO_2R^{31}$. In some embodiments, $R_3'$ is —$C(=O)NR^{31}$. In some embodiments, $R_3'$ is —$NO_2$. In some embodiments, $R_3'$ is —CN. In some embodiments, $R_3'$ is —$S(O)_{0-2}R^{31}$. In some embodiments, $R_3'$ is —$SO_2NR^{31}R^{32}$. In some embodiments, $R_3'$ is —$NR^{31}C(=O)R^{32}$. In some embodiments, $R_3'$ is —$NR^{31}C(=O)OR^{32}$. In some embodiments, $R_3'$ is —$NR^{31}C(=O)NR^{32}R^{33}$. In some embodiments, $R_3'$ is —$NR^{31}S(O)_{0-2}R^{32}$. In some embodiments, $R_3'$ is —$C(=S)OR^{31}$. In some embodiments, $R_3'$ is —$C(=O)SR^{31}$. In some embodiments, $R_3'$ is —$NR^{31}C(=NR^{32})NR^{32}R^{33}$. In some embodiments, $R_3'$ is —$NR^{31}C(=NR^{32})OR^{33}$. In some embodiments, $R_3'$ is —$NR^{31}C(=NR^{32})SR^{33}$. In some embodiments, $R_3'$ is —$OC(=O)OR^{33}$. In some embodiments, $R_3'$ is —$OC(=O)NR^{31}R^{32}$. In some embodiments, $R_3'$ is —$OC(=O)SR^{31}$. In some embodiments, $R_3'$ is —$SC(=O)SR^{31}$. In some embodiments, $R_3'$ is —$P(O)OR^{31}OR^{32}$. In some embodiments, $R_3'$ is —$SC(=O)NR^{31}R^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkyl, which is unsubstituted. In some embodiments, $R_3'$ is —$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkenyl, which is unsubstituted. In some embodiments, $R_3'$ is —$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkynyl, which is unsubstituted. In some embodiments, $R_3'$ is —$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heteroalkyl, which is unsubstituted. In some embodiments, $R_3'$ is —$C_{1-10}$heteroalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$aryl, which is unsubstituted. In some embodiments, $R_3'$ is —$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$hetaryl, which is unsubstituted. In some embodiments, $R_3'$ is —$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is —$C_{3-10}$cycloalkyl, which is unsubstituted. In some embodiments, $R_3'$ is —$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heterocyclyl, which is unsubstituted. In some embodiments, $R_3'$ is —$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkyl-$C_{3-10}$aryl, which is unsubstituted. In some embodiments, $R_3'$ is —$C_{1-10}$alkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkyl-$C_{1-10}$hetaryl, which is unsubstituted. In some embodiments, $R_3'$ is —$C_{1-10}$alkyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkyl-$C_{3-10}$cycloalkyl, which is unsubstituted. In some embodiments, $R_3'$ is —$C_{1-10}$alkyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkyl-$C_{1-10}$heterocyclyl, which is unsubstituted. In some embodiments, $R_3'$ is —$C_{1-10}$alkyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkenyl-$C_{3-10}$aryl, which is unsubstituted. In some embodiments, $R_3'$ is —$C_{1-10}$alkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkenyl-$C_{1-10}$hetaryl, which is unsubstituted. In some embodiments, $R_3'$ is —$C_{2-10}$alkenyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkenyl-$C_{3-10}$cycloalkyl, which is unsubstituted. In some embodiments, $R_3'$ is —$C_{2-10}$alkenyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkenyl-$C_{1-10}$heterocyclyl, which is unsubstituted. In some embodiments, $R_3'$ is —$C_{2-10}$alkenyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkynyl-$C_{3-10}$aryl, which is unsubstituted. In some embodiments, $R_3'$ is —$C_{2-10}$alkynyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkynyl-$C_{1-10}$hetaryl, which is unsubstituted. In some embodiments, $R_3'$ is —$C_{2-10}$alkynyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkynyl-$C_{3-10}$cycloalkyl, which is unsubstituted.

In some embodiments, $R_3'$ is $—C_{2-10}$alkynyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{2-10}$alkynyl-$C_{1-10}$heterocyclyl, which is unsubstituted. In some embodiments, $R_3'$ is $—C_{2-10}$alkynyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkoxy-$C_{3-10}$aryl, which is unsubstituted. In some embodiments, $R_3'$ is $—C_{1-10}$alkoxy-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkoxy-$C_{1-10}$hetaryl, which is unsubstituted. In some embodiments, $R_3'$ is $—C_{1-10}$alkoxy-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkoxy-$C_{3-10}$cycloalkyl, which is unsubstituted. In some embodiments, $R_3'$ is $—C_{1-10}$alkoxy-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$alkoxy-$C_{1-10}$heterocyclyl, which is unsubstituted. In some embodiments, $R_3'$ is $—C_{1-10}$alkoxy-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heteroalkyl-$C_{3-10}$aryl, which is unsubstituted. In some embodiments, $R_3'$ is $—C_{1-10}$heteroalkyl-$C_{3-10}$aryl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heteroalkyl-$C_{1-10}$hetaryl, which is unsubstituted. In some embodiments, $R_3'$ is $—C_{1-10}$heteroalkyl-$C_{1-10}$hetaryl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heteroalkyl-$C_{3-10}$cycloalkyl, which is unsubstituted. In some embodiments, $R_3'$ is $—C_{1-10}$heteroalkyl-$C_{3-10}$cycloalkyl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heteroalkyl-$C_{1-10}$heterocyclyl, which is unsubstituted. In some embodiments, $R_3'$ is $—C_{1-10}$heteroalkyl-$C_{1-10}$heterocyclyl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $—C_{3-10}$aryl-$C_{1-10}$alkyl, which is unsubstituted. In some embodiments, $R_3'$ is $—C_{3-10}$aryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$aryl-$C_{2-10}$alkenyl, which is unsubstituted. In some embodiments, $R_3'$ is $—C_{3-10}$aryl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$aryl-$C_{2-10}$alkynyl, which is unsubstituted. In some embodiments, $R_3'$ is $—C_{3-10}$aryl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$aryl-$C_{3-10}$hetaryl, which is unsubstituted. In some embodiments, $R_3'$ is $—C_{3-10}$aryl-$C_{3-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$aryl-$C_{3-10}$cycloalkyl, which is unsubstituted. In some embodiments, $R_3'$ is $—C_{3-10}$aryl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$aryl-$C_{1-10}$heterocyclyl, which is unsubstituted. In some embodiments, $R_3'$ is $—C_{3-10}$aryl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$hetaryl-$C_{1-10}$alkyl, which is unsubstituted. In some embodiments, $R_3'$ is —$C_{1-10}$hetaryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$hetaryl-$C_{2-10}$alkenyl, which is unsubstituted. In some embodiments, $R_3'$ is —$C_{1-10}$hetaryl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$hetaryl-$C_{2-10}$alkynyl, which is unsubstituted. In some embodiments, $R_3'$ is —$C_{1-10}$hetaryl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$hetaryl-$C_{3-10}$aryl, which is unsubstituted. In some embodiments, $R_3'$ is —$C_{3-10}$hetaryl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$hetaryl-$C_{3-10}$cycloalkyl, which is unsubstituted. In some embodiments, $R_3'$ is —$C_{1-10}$hetaryl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$hetaryl-$C_{1-10}$heterocyclyl, which is unsubstituted. In some embodiments, $R_3'$ is —$C_{1-10}$hetaryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$cycloalkyl-$C_{1-10}$alkyl, which is unsubstituted. In some embodiments, $R_3'$ is —$C_{3-10}$cycloalkyl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$cycloalkyl-$C_{2-10}$alkenyl, which is unsubstituted. In some embodiments, $R_3'$ is —$C_{3-10}$cycloalkyl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$cycloalkyl-$C_{2-10}$alkynyl, which is unsubstituted. In some embodiments, $R_3'$ is —$C_{3-10}$cycloalkyl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$cycloalkyl-$C_{3-10}$aryl, which is unsubstituted. In some embodiments, $R_3'$ is —$C_{3-10}$cycloalkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$cycloalkyl-$C_{1-10}$hetaryl, which is unsubstituted. In some embodiments, $R_3'$ is —$C_{3-10}$cycloalkyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{3-10}$cycloalkyl-$C_{1-10}$heterocyclyl, which is unsubstituted. In some embodiments, $R_3'$ is —$C_{3-10}$cycloalkyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heterocyclyl-$C_{1-10}$alkyl, which is unsubstituted. In some embodiments, $R_3'$ is —$C_{3-10}$cycloalkyl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heterocyclyl-$C_{2-10}$alkenyl, which is unsubstituted. In some embodiments, $R_3'$ is —$C_{1-10}$heterocyclyl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heterocyclyl-$C_{2-10}$alkynyl, which is unsubstituted. In some embodiments, $R_3'$ is —$C_{1-10}$heterocyclyl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heterocyclyl-$C_{3-10}$aryl, which is unsubstituted. In some embodiments, $R_3'$ is —$C_{1-10}$heterocyclyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is —$C_{1-10}$heterocyclyl-$C_{1-10}$hetaryl, which is unsubstituted. In some embodiments, $R_3'$ is —$C_{1-10}$heterocyclyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is $C_{1-10}$heterocyclyl-$C_{3-10}$cycloalkyl, which is unsubstituted. In some embodiments, $R_3'$ is —$C_{1-10}$heterocyclyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_3'$ is —$OR^6$. In some embodiments, $R_3'$ is $NR^6R^{34}$, wherein $R^6$ together with $R^{34}$ can optionally form a heterocyclic ring. In some embodiments, $R_3'$ is $S(O)_{0-2}R^6$. In some embodiments, $R_3'$ is $C(=O)R^6$. In some embodiments, $R_3'$ is $C(=O)OR^6$. In some embodiments, $R_3'$ is $OC(=O)R^6$. In some embodiments, $R_3'$ is $C(=O)N(R^{34})R^6$, wherein $R^6$ together with $R^{34}$ can optionally form a heterocyclic ring. In some embodiments, $R_3'$ is or $N(R^{34})C(=O)R^6$, wherein $R^6$ together with $R^{34}$ can optionally form a heterocyclic ring;

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is hydrogen. In some embodiments, $R_4$ is halogen, which is F, Cl, Br, or I. In some embodiments, $R_4$ is —OH. In some embodiments, $R_4$ is —$CF_3$. In some embodiments, $R_4$ is —$OCF_3$. In some embodiments, $R_4$ is —$OR^{31}$. In some embodiments, $R_4$ is —$NR^{31}R^{32}$. In some embodiments, $R_4$ is —$C(O)R^{31}$. In some embodiments, $R_4$ is $CO_2R^{31}$. In some embodiments, $R_4$ is —$C(=O)NR^{31}$. In some embodiments, $R_4$ is —$NO_2$. In some embodiments, $R_4$ is —CN. In some embodiments, $R_4$ is —$S(O)_{0-2}R^{31}$. In some embodiments, $R_4$ is —$SO_2NR^{31}R^{32}$. In some embodiments, $R_4$ is —$NR^{31}C(=O)R^{32}$. In some embodiments, $R_4$ is —$NR^{31}C(=O)OR^{32}$. In some embodiments, $R_4$ is —$NR^{31}C(=O)NR^{32}R^{33}$. In some embodiments, $R_4$ is —$NR^{31}S(O)_{0-2}R^{32}$. In some embodiments, $R_4$ is —$C(=S)OR^{31}$. In some embodiments, $R_4$ is —$C(=O)SR^{31}$. In some embodiments, $R_4$ is —$NR^{31}C(=NR^{32})NR^{32}R^{33}$. In some embodiments, $R_4$ is —$NR^{31}C(=NR^{32})OR^{33}$. In some embodiments, $R_4$ is —$NR^{31}C(=NR^{32})SR^{33}$. In some embodiments, $R_4$ is —$OC(=O)OR^{33}$. In some embodiments, $R_4$ is —$OC(=O)NR^{31}R^{32}$. In some embodiments, $R_4$ is —$OC(=O)SR^{31}$. In some embodiments, $R_4$ is —$SC(=O)SR^{31}$. In some embodiments, $R_4$ is —$P(O)OR^{31}OR^{32}$. In some embodiments, $R_4$ is —$SC(=O)NR^{31}R^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkyl, which is unsubstituted. In some embodiments, $R_4$ is —$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkenyl, which is unsubstituted. In some embodiments, $R_4$ is —$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkynyl, which is unsubstituted. In some embodiments, $R_4$ is —$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heteroalkyl, which is unsubstituted. In some embodiments, $R_4$ is —$C_{1-10}$heteroalkyl, which is substituted by one or more independent $R_{13}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl, which is unsubstituted. In some embodiments, $R_4$ is —$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$hetaryl, which is unsubstituted. In some embodiments, $R_4$ is —$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl, which is unsubstituted. In some embodiments, $R_4$ is —$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl, which is unsubstituted. In some embodiments, $R_4$ is —$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkyl-$C_{3-10}$aryl, which is unsubstituted. In some embodiments, $R_4$ is —$C_{1-10}$alkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkyl-$C_{1-10}$hetaryl, which is unsubstituted. In some embodiments, $R_4$ is —$C_{1-10}$alkyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkyl-$C_{3-10}$cycloalkyl, which is unsubstituted. In some embodiments, $R_4$ is —$C_{1-10}$alkyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkyl-$C_{1-10}$heterocyclyl, which is unsubstituted. In some embodiments, $R_4$ is —$C_{1-10}$alkyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkenyl-$C_{3-10}$aryl, which is unsubstituted. In some embodiments, $R_4$ is —$C_{2-10}$alkenyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkenyl-$C_{1-10}$hetaryl, which is unsubstituted. In some embodiments, $R_4$ is —$C_{2-10}$alkenyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkenyl-$C_{3-10}$cycloalkyl, which is unsubstituted. In some embodiments, $R_4$ is —$C_{2-10}$alkenyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is —$C_{2-10}$alkenyl-$C_{1-10}$heterocyclyl, which is unsubstituted. In some embodiments, $R_4$ is —$C_{2-10}$alkenyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkynyl-$C_{3-10}$aryl, which is unsubstituted. In some embodiments, $R_4$ is —$C_{2-10}$alkynyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkynyl-$C_{1-10}$hetaryl, which is unsubstituted. In some embodiments, $R_4$ is —$C_{2-10}$alkynyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkynyl-$C_{3-10}$cycloalkyl, which is unsubstituted. In some embodiments, $R_4$ is —$C_{2-10}$alkynyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{2-10}$alkynyl-$C_{1-10}$heterocyclyl, which is unsubstituted. In some embodiments, $R_4$ is —$C_{2-10}$alkynyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkoxy-$C_{3-10}$aryl, which is unsubstituted. In some embodiments, $R_4$ is —$C_{1-10}$alkoxy-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkoxy-$C_{1-10}$hetaryl, which is unsubstituted. In some embodiments, $R_4$ is —$C_{1-10}$alkoxy-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkoxy-$C_{3-10}$cycloalkyl, which is unsubstituted. In some embodiments, $R_4$ is —$C_{1-10}$alkoxy-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$alkoxy-$C_{1-10}$heterocyclyl, which is unsubstituted. In some embodiments, $R_4$ is —$C_{1-10}$alkoxy-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heteroalkyl-$C_{3-10}$aryl, which is unsubstituted. In some embodiments, $R_4$ is —$C_{1-10}$heteroalkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heteroalkyl-$C_{1-10}$hetaryl, which is unsubstituted. In some embodiments, $R_4$ is —$C_{1-10}$heteroalkyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heteroalkyl-$C_{3-10}$cycloalkyl, which is unsubstituted. In some embodiments, $R_4$ is —$C_{1-10}$heteroalkyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heteroalkyl-$C_{1-10}$heterocyclyl, which is unsubstituted. In some embodiments, $R_4$ is —$C_{1-10}$heteroalkyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl-$C_{1-10}$alkyl, which is unsubstituted. In some embodiments, $R_4$ is —$C_{3-10}$aryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl-$C_{2-10}$alkenyl, which is unsubstituted. In some embodiments, $R_4$ is —$C_{3-10}$aryl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl-$C_{2-10}$alkynyl, which is unsubstituted. In some embodiments, $R_4$ is —$C_{3-10}$aryl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl-$C_{3-10}$hetaryl, which is unsubstituted. In some embodiments, $R_4$ is —$C_{3-10}$aryl-$C_{3-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl-$C_{3-10}$cycloalkyl, which is unsubstituted. In some embodiments, $R_4$ is —$C_{3-10}$aryl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$aryl-$C_{1-10}$heterocyclyl, which is unsubstituted. In some embodiments, $R_4$ is —$C_{3-10}$aryl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$hetaryl-$C_{1-10}$alkyl, which is unsubstituted. In some embodiments, $R_4$ is —$C_{1-10}$hetaryl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$hetaryl-$C_{2-10}$alkenyl, which is unsubstituted. In some embodiments, $R_4$ is —$C_{1-10}$hetaryl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$hetaryl-$C_{2-10}$alkynyl, which is unsubstituted. In some embodiments, $R_4$ is —$C_{1-10}$hetaryl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is —$C_{3-10}$hetaryl-$C_{3-10}$aryl, which is unsubstituted. In some embodiments, $R_4$ is —$C_{3-10}$hetaryl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$hetaryl-$C_{3-10}$cycloalkyl, which is unsubstituted.

In some embodiments, $R_4$ is $-C_{1-10}$hetaryl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$hetaryl-$C_{1-10}$heterocyclyl, which is unsubstituted. In some embodiments, $R_4$ is $-C_{1-10}$hetaryl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl-$C_{1-10}$alkyl, which is unsubstituted. In some embodiments, $R_4$ is $-C_{3-10}$cycloalkyl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl-$C_{2-10}$alkenyl, which is unsubstituted. In some embodiments, $R_4$ is $-C_{3-10}$cycloalkyl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl-$C_{2-10}$alkynyl, which is unsubstituted. In some embodiments, $R_4$ is $-C_{3-10}$cycloalkyl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl-$C_{3-10}$aryl, which is unsubstituted. In some embodiments, $R_4$ is $-C_{3-10}$cycloalkyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl-$C_{1-10}$hetaryl, which is unsubstituted. In some embodiments, $R_4$ is $-C_{3-10}$cycloalkyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{3-10}$cycloalkyl-$C_{1-10}$heterocyclyl, which is unsubstituted. In some embodiments, $R_4$ is $-C_{3-10}$cycloalkyl-$C_{1-10}$heterocyclyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl-$C_{1-10}$alkyl, which is unsubstituted. In some embodiments, $R_4$ is $-C_{1-10}$heterocyclyl-$C_{1-10}$alkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl-$C_{2-10}$alkenyl, which is unsubstituted. In some embodiments, $R_4$ is $-C_{1-10}$heterocyclyl-$C_{2-10}$alkenyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl-$C_{2-10}$alkynyl, which is unsubstituted. In some embodiments, $R_4$ is $-C_{1-10}$heterocyclyl-$C_{2-10}$alkynyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl-$C_{3-10}$aryl, which is unsubstituted. In some embodiments, $R_4$ is $-C_{1-10}$heterocyclyl-$C_{3-10}$aryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl-$C_{1-10}$hetaryl, which is unsubstituted. In some embodiments, $R_4$ is $-C_{1-10}$heterocyclyl-$C_{1-10}$hetaryl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_4$ is $C_{1-10}$heterocyclyl-$C_{3-10}$cycloalkyl, which is unsubstituted. In some embodiments, $R_4$ is $-C_{1-10}$heterocyclyl-$C_{3-10}$cycloalkyl, which is substituted by one or more independent $R_{13}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_5$ is hydrogen. In some embodiments, $R_5$ is halogen, which is F, Cl, Br, or I. In some embodiments, $R_5$ is $-C_{1-10}$alkyl. In some embodiments, $R_5$ is $-C_{2-10}$alkenyl. In some embodiments, $R_5$ is $-C_{2-10}$alkynyl. In some embodiments, $R_5$ is $-C_{1-10}$heteroalkyl. In some embodiments, $R_5$ is $-C_{3-10}$aryl. In some embodiments, $R_5$ is $C_{1-10}$hetaryl. In some embodiments, $R_5$ is $-C_{3-10}$cycloalkyl. In some embodiments, $R_5$ is $-C_{1-10}$heterocyclyl. In some embodiments, $R_5$ is —OH. In some embodiments, $R_5$ is —CF$_3$. In some embodiments, $R_5$ is —OCF$_3$. In some embodiments, $R_5$ is —OR$^{31}$. In some embodiments, $R_5$ is —NR$^{31}$R$^{32}$. In some embodiments, $R_5$ is —C(O)R$^{31}$. In some embodiments, $R_5$ is CO$_2$R$^{31}$. In some embodiments, $R_5$ is —C(=O)NR$^{31}$. In some embodiments, $R_5$ is —NO$_2$. In some embodiments, $R_5$ is —CN. In some embodiments, $R_5$ is —S(O)$_{0-2}$R$^{31}$. In some embodiments, $R_5$ is —SO$_2$NR$^{31}$R$^{32}$. In some embodiments, $R_5$ is —NR$^{31}$C(=O)R$^{32}$. In some embodiments, $R_5$ is —NR$^{31}$C(=O)OR$^{32}$. In some embodiments, $R_5$ is —NR$^{31}$C(=O)NR$^{32}$R$^{33}$. In some embodiments, $R_5$ is —NR$^{31}$S(O)$_{0-2}$R$^{32}$. In some embodiments, $R_5$ is —C(=S)OR$^{31}$. In some embodiments, $R_5$ is —C(=O)SR$^{31}$. In some embodiments, $R_5$ is —NR$^{31}$C(=NR$^{32}$)NR$^{32}$R$^{33}$. In some embodiments, $R_5$ is —NR$^{31}$C(=NR$^{32}$)OR$^{33}$. In some embodiments, $R_5$ is —NR$^{31}$C(=NR$^{32}$)SR$^{33}$. In some embodiments, $R_5$ is —OC(=O)OR$^{33}$. In some embodiments, $R_5$ is —OC(=O)NR$^{31}$R$^{32}$. In some embodiments, $R_5$ is —OC(=O)SR$^{31}$.

In some embodiments, $R_5$ is —SC(=O)SR$^{31}$. In some embodiments, $R_5$ is —P(O)OR$^{31}$OR$^{32}$. In some embodiments, $R_5$ is —SC(=O)NR$^{31}$NR$^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{1-10}$alkyl, which is unsubstituted. In some embodiments, $R_6$ is —$C_{1-10}$alkyl, substituted by one or more independent $R_{14}$ substituents. In some embodiments, $R_6$ is —$C_{1-10}$alkyl, substituted by one or more independent $R_{15}$ substituents. In some embodiments, $R_6$ is —$C_{1-10}$alkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{1-10}$alkenyl, which is unsubstituted. In some embodiments, $R_6$ is —$C_{1-10}$alkenyl, substituted by one or more independent $R_{14}$ substituents. In some embodiments, $R_6$ is —$C_{1-10}$alkenyl, substituted by one or more independent $R_{15}$ substituents. In some embodiments, $R_6$ is —$C_{1-10}$alkenyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{2-10}$alkynyl, which is unsubstituted. In some embodiments, $R_6$ is —$C_{2-10}$alkynyl, substituted by one or more independent $R_{14}$ substituents. In some embodiments, $R_6$ is —$C_{2-10}$alkynyl, substituted by one or more independent $R_{15}$ substituents. In some embodiments, $R_6$ is —$C_{2-10}$alkynyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{1-10}$heteroalkyl, which is unsubstituted. In some embodiments, $R_6$ is —$C_{1-10}$heteroalkyl, substituted by one or more independent $R_{14}$ substituents. In some embodiments, $R_6$ is —$C_{1-10}$heteroalkyl, substituted by one or more independent $R_{15}$ substituents. In some embodiments, $R_6$ is —$C_{1-10}$heteroalkyl, substituted by one or more independent $R_{14}$ or $R_{15}$ substituents In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{3-10}$aryl, which is unsubstituted. In some embodiments, $R_6$ is —$C_{3-10}$aryl, substituted by one or more independent $R_{14}$ substituents. In some embodiments, $R_6$ is —$C_{3-10}$aryl, substituted by one or more independent $R_{15}$ substituents. In some embodiments, $R_6$ is —$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{1-10}$hetaryl, which is unsubstituted. In some embodiments, $R_6$ is —$C_{1-10}$hetaryl, substituted by one or more independent $R_{14}$ substituents. In some embodiments, $R_6$ is —$C_{1-10}$hetaryl, substituted by one or more independent $R_{15}$ substituents. In some embodiments, $R_6$ is —$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{3-10}$cycloalkyl, which is unsubstituted. In some embodiments, $R_6$ is —$C_{3-10}$cycloalkyl, substituted by one or more independent $R_{14}$ substituents. In some embodiments, $R_6$ is —$C_{3-10}$cycloalkyl, substituted by one or more independent $R_{15}$ substituents. In some embodiments, $R_6$ is —$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl, which is unsubstituted. In some embodiments, $R_6$ is —$C_{1-10}$heterocyclyl, substituted by one or more independent $R_{14}$ substituents. In some embodiments, $R_6$ is —$C_{1-10}$heterocyclyl, substituted by one or more independent $R_{15}$ substituents. In some embodiments, $R_6$ is —$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkyl-$C_{3-10}$aryl, which is unsubstituted. In some embodiments, $R_6$ is —$C_{1-10}$alkyl-$C_{3-10}$aryl, substituted by one or more independent $R_{14}$ substituents. In some embodiments, $R_6$ is —$C_{1-10}$alkyl-$C_{3-10}$aryl, substituted by one or more independent $R_{15}$ substituents. In some embodiments, $R_6$ is —$C_{1-10}$alkyl-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkyl-$C_{1-10}$hetaryl, which is unsubstituted. In some embodiments, $R_6$ is —$C_{1-10}$alkyl-$C_{1-10}$hetaryl, substituted by one or more independent $R_{14}$ substituents. In some embodiments, $R_6$ is —$C_{1-10}$alkyl-$C_{1-10}$hetaryl, substituted by one or more independent $R_{15}$ substituents. In some embodiments, $R_6$ is —$C_{1-10}$alkyl-$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkyl-$C_{3-10}$cycloalkyl, which is unsubstituted. In some embodiments, $R_6$ is —$C_{1-10}$alkyl-$C_{3-10}$cycloalkyl, substituted by one or more independent $R_{14}$ substituents. In some embodiments, $R_6$ is —$C_{1-10}$alkyl-$C_{3-10}$cycloalkyl, substituted by one or more independent $R_{15}$ substituents. In some embodiments, $R_6$ is —$C_{1-10}$alkyl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkyl-$C_{1-10}$heterocyclyl, which is unsubstituted. In some embodiments, $R_6$ is —$C_{1-10}$alkyl-$C_{1-10}$heterocyclyl, substituted by one or more independent $R_{14}$ substituents. In some embodiments, $R_6$ is —$C_{1-10}$alkyl-$C_{1-10}$heterocyclyl, substituted by one or more independent $R_{15}$ substituents. In some embodiments, $R_6$ is —$C_{1-10}$alkyl-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{2-10}$alkenyl-$C_{3-10}$aryl, which is unsubstituted. In some embodiments, $R_6$ is —$C_{2-10}$alkenyl-$C_{3-10}$aryl, substituted by one or more independent $R_{14}$ substituents. In some embodiments, $R_6$ is —$C_{2-10}$alkenyl-$C_{3-10}$aryl, substituted by one or more independent $R_{15}$ substituents. In some embodiments, $R_6$ is —$C_{2-10}$alkenyl-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{2-10}$alkenyl-$C_{1-10}$hetaryl, which is unsubstituted. In some embodiments, $R_6$ is —$C_{2-10}$alkenyl-$C_{1-10}$hetaryl, substituted by one or more independent $R_{14}$ substituents. In some embodiments, $R_6$ is —$C_{2-10}$alkenyl-$C_{1-10}$hetaryl, substituted by one or more independent $R_{15}$ substituents. In some embodiments, $R_6$ is —$C_{2-10}$alkenyl-$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{2-10}$alkenyl-$C_{3-10}$cycloalkyl, which is unsubstituted. In some embodiments, $R_6$ is —$C_{2-10}$alkenyl-$C_{3-10}$cycloalkyl, substituted by one or more independent $R_{14}$ substituents. In some embodiments, $R_6$ is —$C_{2-10}$alkenyl-$C_{3-10}$cycloalkyl, substituted by one or more independent $R_{15}$ substituents. In some embodiments, $R_6$ is —$C_{2-10}$alkenyl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{2-10}$alkenyl-$C_{1-10}$heterocyclyl, which is unsubstituted. In some embodiments, $R_6$ is —$C_{2-10}$alkenyl-$C_{1-10}$heterocyclyl, substituted by one or more independent $R_{14}$ substituents. In some embodiments, $R_6$ is $C_{2-10}$alkenyl-$C_{1-10}$heterocyclyl, substituted by one or more independent $R_{15}$ substituents. In some embodiments, $R_6$ is —$C_{2-10}$alkenyl-$C_{1-10}$heterocyclyl, substituted by one or more independent $R_{14}$ or $R_{15}$ substituents.

In various embodiments of compounds of Formula I (including I-A and I-B), Formula II (including II-A, II-B, II-C and II-D) and IIII (including III-A and III-B), $R_6$ is —$C_{2-10}$alkynyl-$C_{1-10}$hetaryl, which is unsubstituted. In some embodiments, $R_6$ is —$C_{2-10}$alkynyl-$C_{1-10}$hetaryl, substituted by one or more independent $R_{14}$ substituents. In some embodiments, $R_6$ is —$C_{2-10}$alkynyl-$C_{1-10}$hetaryl, substituted by one or more independent $R_{15}$ substituents. In some embodiments, $R_6$ is —$C_{2-10}$alkynyl-$C_{1-10}$hetaryl, substituted by one or more independent $R_{14}$ or $R_{15}$ substituents.

In various embodiments of compounds of Formula I (including I-A and I-B), Formula II (including II-A, II-B, II-C and II-D) and IIII (including III-A and III-B), $R_6$ is —$C_{2-10}$alkynyl-$C_{3-10}$cycloalkyl, which is unsubstituted. In some embodiments, $R_6$ is —$C_{2-10}$alkynyl-$C_{3-10}$cycloalkyl, substituted by one or more independent $R_{14}$ substituents. In some embodiments, $R_6$ is —$C_{2-10}$alkynyl-$C_{3-10}$cycloalkyl, substituted by one or more independent $R_{15}$ substituents. In some embodiments, $R_6$ is —$C_{2-10}$alkynyl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{2-10}$alkynyl-$C_{1-10}$heterocyclyl, which is unsubstituted. In some embodiments, $R_6$ is —$C_{2-10}$alkynyl-$C_{1-10}$heterocyclyl, substituted by one or more independent $R_{14}$ substituents. In some embodiments, $R_6$ is $C_{2-10}$alkynyl-$C_{1-10}$heterocyclyl, substituted by one or more independent $R_{15}$ substituents. In some embodiments, $R_6$ is —$C_{2-10}$alkynyl-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkoxy-$C_{3-10}$aryl, which is unsubstituted. In some embodiments, $R_6$ is —$C_{1-10}$alkoxy-$C_{3-10}$aryl, substituted by one or more independent $R_{14}$ substituents. In some embodiments, $R_6$ is —$C_{1-10}$alkoxy-$C_{3-10}$aryl, substituted by one or more independent $R_{15}$ substituents. In some embodiments, $R_6$ is —$C_{1-10}$alkoxy-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkoxy-$C_{1-10}$hetaryl, which is unsubstituted. In some embodiments, $R_6$ is —$C_{1-10}$alkoxy-$C_{1-10}$hetaryl, substituted by one or more independent $R_{14}$ substituents. In some embodiments, $R_6$ is —$C_{1-10}$alkoxy-$C_{1-10}$hetaryl, substituted by one or more independent $R_{15}$ substituents. In some embodiments, $R_6$ is —$C_{1-10}$alkoxy-$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkoxy-$C_{3-10}$cycloalkyl, which is unsubstituted. In some embodiments, $R_6$ is —$C_{1-10}$alkoxy-$C_{3-10}$cycloalkyl, substituted by one or more independent $R_{14}$ substituents. In some embodiments, $R_6$ is —$C_{1-10}$alkoxy-$C_{3-10}$cycloalkyl, substituted by one or more independent $R_{15}$ substituents. In some embodiments, $R_6$ is —$C_{1-10}$alkoxy-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$alkoxy-$C_{1-10}$heterocyclyl, which is unsubstituted. In some embodiments, $R_6$ is —$C_{1-10}$alkoxy-$C_{1-10}$heterocyclyl, substituted by one or more independent $R_{14}$ substituents. In some embodiments, $R_6$ is —$C_{1-10}$alkoxy-$C_{1-10}$heterocyclyl, substituted by one or more independent $R_{15}$ substituents. In some embodiments, $R_6$ is —$C_{1-10}$alkoxy-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heteroalkyl-$C_{3-10}$aryl, which is unsubstituted. In some embodiments, $R_6$ is —$C_{1-10}$heteroalkyl-$C_{3-10}$aryl, substituted by one or more independent $R_{14}$ substituents. In some embodiments, $R_6$ is —$C_{1-10}$heteroalkyl-$C_{3-10}$aryl, substituted by one or more independent $R_{15}$ substituents. In some embodiments, $R_6$ is —$C_{1-10}$heteroalkyl-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heteroalkyl-$C_{1-10}$hetaryl, which is unsubstituted. In some embodiments, $R_6$ is —$C_{1-10}$heteroalkyl-$C_{1-10}$hetaryl, substituted by one or more independent $R_{14}$ substituents. In some embodiments, $R_6$ is —$C_{1-10}$heteroalkyl-$C_{1-10}$hetaryl, substituted by one or more independent $R_{15}$ substituents. In some embodiments, $R_6$ is —$C_{1-10}$heteroalkyl-$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heteroalkyl-$C_{3-10}$cycloalkyl, which is unsubstituted. In some embodiments, $R_6$ is —$C_{1-10}$heteroalkyl-$C_{3-10}$cycloalkyl, substituted by one or more independent $R_{14}$ substituents. In some embodiments, $R_6$ is —$C_{1-10}$heteroalkyl-$C_{3-10}$cycloalkyl, substituted by one or more independent $R_{15}$ substituents. In some embodiments, $R_6$ is —$C_{1-10}$heteroalkyl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heteroalkyl-$C_{1-10}$heterocyclyl, which is unsubstituted. In some embodiments, $R_6$ is —$C_{1-10}$heteroalkyl-$C_{1-10}$heterocyclyl, substituted by one or more independent $R_{14}$ substituents. In some embodiments, $R_6$ is —$C_{1-10}$heteroalkyl-$C_{1-10}$heterocyclyl, substituted by one or more independent $R_{15}$ substituents. In some embodiments, $R_6$ is —$C_{1-10}$heteroalkyl-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{3-10}$aryl-$C_{1-10}$alkyl, which is unsubstituted. In some embodiments, $R_6$ is —$C_{3-10}$aryl-$C_{1-10}$alkyl, substituted by one or more independent $R_{14}$ substituents. In some embodiments, $R_6$ is —$C_{3-10}$aryl-$C_{1-10}$alkyl, substituted by one or more independent $R_{15}$ substituents. In some embodiments, $R_6$ is —$C_{3-10}$aryl-$C_{1-10}$alkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$aryl-$C_{2-10}$alkenyl, which is unsubstituted. In some embodiments, $R_6$ is —$C_{3-10}$aryl-$C_{2-10}$alkenyl, substituted by one or more independent $R_{14}$ substituents. In some embodiments, $R_6$ is —$C_{3-10}$aryl-$C_{2-10}$alkenyl, substituted by one or more independent $R_{15}$ substituents. In some embodiments, $R_6$ is —$C_{3-10}$aryl-$C_{2-10}$alkenyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$aryl-$C_{2-10}$alkynyl, which is unsubstituted. In some embodiments, $R_6$ is —$C_{3-10}$aryl-$C_{2-10}$alkynyl, substituted by one or more independent $R_{14}$ substituents. In some embodiments, $R_6$ is —$C_{3-10}$aryl-$C_{2-10}$alkynyl, substituted by one or more independent $R_{15}$ substituents. In some embodiments, $R_6$ is —$C_{3-10}$aryl-$C_{2-10}$alkynyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$aryl-$C_{3-10}$hetaryl, which is unsubstituted. In some embodiments, $R_6$ is —$C_{3-10}$aryl-$C_{3-10}$hetaryl, substituted by one or more independent $R_{14}$ substituents. In some embodiments, $R_6$ is —$C_{3-10}$aryl-$C_{3-10}$hetaryl, substituted by one or more independent $R_{15}$ substituents. In some embodiments, $R_6$ is —$C_{3-10}$aryl-$C_{3-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$aryl-$C_{3-10}$cycloalkyl, which is unsubstituted. In some embodiments, $R_6$ is —$C_{3-10}$aryl-$C_{3-10}$cycloalkyl, substituted by one or more independent $R_{14}$ substituents. In some embodiments, $R_6$ is —$C_{3-10}$aryl-$C_{3-10}$cycloalkyl, substituted by one or more independent $R_{15}$ substituents. In some embodiments, $R_6$ is —$C_{3-10}$aryl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$aryl-$C_{1-10}$heterocyclyl, which is unsubstituted. In some embodiments, $R_6$ is —$C_{3-10}$-aryl-$C_{1-10}$heterocyclyl, substituted by one or more independent $R_{14}$ substituents. In some embodiments, $R_6$ is —$C_{3-10}$aryl-$C_{1-10}$heterocyclyl, substituted by one or more independent $R_{15}$ substituents. In some embodiments, $R_6$ is —$C_{3-10}$aryl-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$hetaryl-$C_{1-10}$alkyl, which is unsubstituted. In some embodiments, $R_6$ is —$C_{1-10}$hetaryl-$C_{1-10}$alkyl, substituted by one or more independent $R_{14}$ substituents. In some embodiments, $R_6$ is —$C_{1-10}$hetaryl-$C_{1-10}$alkyl, substituted by one or more independent $R_{15}$ substituents. In some embodiments, $R_6$ is —$C_{1-10}$hetaryl-$C_{1-10}$alkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$hetaryl-$C_{2-10}$alkenyl, which is unsubstituted. In some embodiments, $R_6$ is —$C_{1-10}$hetaryl-$C_{2-10}$alkenyl, substituted by one or more independent $R_{14}$ substituents. In some embodiments, $R_6$ is —$C_{1-10}$hetaryl-$C_{2-10}$alkenyl, substituted by one or more independent $R_{15}$ substituents. In some embodiments, $R_6$ is —$C_{1-10}$hetaryl-$C_{2-10}$alkenyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$hetaryl-$C_{2-10}$alkynyl, which is unsubstituted. In some embodiments, $R_6$ is —$C_{1-10}$hetaryl-$C_{2-10}$alkynyl, substituted by one or more independent $R_{14}$ substituents. In some embodiments, $R_6$ is —$C_{1-10}$hetaryl-$C_{2-10}$alkynyl, substituted by one or more independent $R_{15}$ substituents. In some embodiments, $R_6$ is —$C_{1-10}$hetaryl-$C_{2-10}$alkynyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$hetaryl-$C_{3-10}$aryl, which is unsubstituted. In some embodiments, $R_6$ is —$C_{3-10}$hetaryl-$C_{3-10}$aryl, substituted by one or more independent $R_{14}$ substituents. In some embodiments, $R_6$ is —$C_{3-10}$hetaryl-$C_{3-10}$aryl, substituted by one or more independent $R_{15}$ substituents. In some embodiments, $R_6$ is —$C_{3-10}$hetaryl-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$hetaryl-$C_{3-10}$cycloalkyl, which is unsubstituted. In some embodiments, $R_6$ is —$C_{1-10}$hetaryl-$C_{3-10}$cycloalkyl, substituted by one or more independent $R_{14}$ substituents. In some embodiments, $R_6$ is —$C_{1-10}$hetaryl-$C_{3-10}$cycloalkyl, substituted by one or more independent $R_{15}$ substituents. In some embodiments, $R_6$ is —$C_{1-10}$hetaryl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$hetaryl-$C_{1-10}$heterocyclyl, which is unsubstituted. In some embodiments, $R_6$ is —$C_{1-10}$hetaryl-$C_{1-10}$heterocyclyl, substituted by one or more independent $R_{14}$ substituents. In some embodiments, $R_6$ is —$C_{1-10}$hetaryl-$C_{1-10}$heterocyclyl, substituted by one or more independent $R_{15}$ substituents. In some embodiments, $R_6$ is —$C_{1-10}$hetaryl-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$cycloalkyl-$C_{1-10}$alkyl, which is unsubstituted. In some embodiments, $R_6$ is —$C_{3-10}$cycloalkyl-$C_{1-10}$alkyl, substituted by one or more independent $R_{14}$ substituents. In some embodiments, $R_6$ is —$C_{3-10}$cycloalkyl-$C_{1-10}$alkyl, substituted by one or more independent $R_{15}$ substituents. In some embodiments, $R_6$ is —$C_{3-10}$cycloalkyl-$C_{1-10}$alkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$cycloalkyl-$C_{2-10}$alkenyl, which is unsubstituted. In some embodiments, $R_6$ is —$C_{3-10}$cycloalkyl-$C_{2-10}$alkenyl, substituted by one or more independent $R_{14}$ substituents. In some embodiments, $R_6$ is —$C_{3-10}$cycloalkyl-$C_{2-10}$alkenyl, substituted by one or more independent $R_{15}$ substituents. In some embodiments, $R_6$ is —$C_{3-10}$cycloalkyl-$C_{2-10}$alkenyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is $C_{3-10}$cycloalkyl-$C_{2-10}$alkynyl, which is unsubstituted. In some embodiments, $R_6$ is —$C_{3-10}$cycloalkyl-$C_{2-10}$alkynyl, substituted by one or more independent $R_{14}$ substituents. In some embodiments, $R_6$ is —$C_{3-10}$cycloalkyl-$C_{2-10}$alkynyl, substituted by one or more independent $R_{15}$ substituents. In some embodiments, $R_6$ is —$C_{3-10}$cycloalkyl-$C_{2-10}$alkynyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$cycloalkyl-$C_{3-10}$aryl, which is unsubstituted. In some embodiments, $R_6$ is —$C_{3-10}$cycloalkyl-$C_{3-10}$aryl, substituted by one or more independent $R_{14}$ substituents. In some embodiments, $R_6$ is —$C_{3-10}$cycloalkyl-$C_{3-10}$aryl, substituted by one or more independent $R_{15}$ substituents. In some embodiments, $R_6$ is —$C_{3-10}$cycloalkyl-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$cycloalkyl-$C_{1-10}$hetaryl, which is unsubstituted. In some embodiments, $R_6$ is —$C_{3-10}$cycloalkyl-$C_{1-10}$hetaryl, substituted by one or more independent $R_{14}$ substituents. In some embodiments, $R_6$ is —$C_{3-10}$cycloalkyl-$C_{1-10}$hetaryl, substituted by one or more independent $R_{15}$ substituents. In some embodiments, $R_6$ is —$C_{3-10}$cycloalkyl-$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{3-10}$cycloalkyl-$C_{1-10}$heterocyclyl, which is unsubstituted. In some embodiments, $R_6$ is —$C_{3-10}$cycloalkyl-$C_{1-10}$heterocyclyl, substituted by one or more independent $R_{14}$ substituents. In some embodiments, $R_6$ is —$C_{3-10}$cycloalkyl-$C_{1-10}$heterocyclyl, substituted by one or more independent $R_{15}$ substituents. In some embodiments, $R_6$ is —$C_{3-10}$cycloalkyl-$C_{1-10}$heterocyclyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl-$C_{1-10}$alkyl, which is unsubstituted. In some embodiments, $R_6$ is —$C_{1-10}$heterocyclyl-$C_{1-10}$alkyl, substituted by one or more independent $R_{14}$ substituents. In some embodiments, $R_6$ is —$C_{1-10}$heterocyclyl-$C_{1-10}$alkyl, substituted by one or more independent $R_{15}$ substituents. In some embodiments, $R_6$ is —$C_{1-10}$heterocyclyl-$C_{1-10}$alkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl-$C_{2-10}$alkenyl, which is unsubstituted. In some embodiments, $R_6$ is —$C_{1-10}$heterocyclyl-$C_{2-10}$alkenyl, substituted by one or more independent $R_{14}$ substituents. In some embodiments, $R_6$ is —$C_{1-10}$heterocyclyl-$C_{2-10}$alkenyl, substituted by one or more independent $R_{15}$ substituents. In some embodiments, $R_6$ is —$C_{1-10}$heterocyclyl-$C_{2-10}$alkenyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl-$C_{2-10}$alkynyl, which is unsubstituted. In some embodiments, $R_6$ is —$C_{1-10}$heterocyclyl-$C_{2-10}$alkynyl, substituted by one or more independent $R_{14}$ substituents. In some embodiments, $R_6$ is —$C_{1-10}$heterocyclyl-$C_{2-10}$alkynyl, substituted by one or more independent $R_{15}$ substituents. In some embodiments, $R_6$ is —$C_{1-10}$heterocyclyl-$C_{2-10}$alkynyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl-$C_{3-10}$aryl, which is unsubstituted. In some embodiments, $R_6$ is —$C_{1-10}$heterocyclyl-$C_{3-10}$aryl, substituted by one or more independent $R_{14}$ substituents. In some embodiments, $R_6$ is —$C_{1-10}$heterocyclyl-$C_{3-10}$aryl, substituted by one or more independent $R_{15}$ substituents. In some embodiments, $R_6$ is —$C_{1-10}$heterocyclyl-$C_{3-10}$aryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl-$C_{1-10}$hetaryl, which is unsubstituted. In some embodiments, $R_6$ is —$C_{1-10}$heterocyclyl-$C_{1-10}$hetaryl, substituted by one or more independent $R_{14}$ substituents. In some embodiments, $R_6$ is —$C_{1-10}$heterocyclyl-$C_{1-10}$hetaryl, substituted by one or more independent $R_{15}$ substituents. In some embodiments, $R_6$ is —$C_{1-10}$heterocyclyl-$C_{1-10}$hetaryl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_6$ is —$C_{1-10}$heterocyclyl-$C_{3-10}$cycloalkyl, which is unsubstituted. In some embodiments, $R_6$ is —$C_{1-10}$heterocyclyl-$C_{3-10}$cycloalkyl, substituted by one or more independent $R_{14}$ substituents. In some embodiments, $R_6$ is —$C_{1-10}$heterocyclyl-$C_{3-10}$cycloalkyl, substituted by one or more independent $R_{15}$ substituents. In some embodiments, $R_6$ is —$C_{1-10}$heterocyclyl-$C_{3-10}$cycloalkyl, substituted by one or more independent $R_{14}$ or $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{71}$ is hydrogen. In some embodiments, $R_{71}$ is halogen, which is F, Cl, Br, or I. In some embodiments, $R_{71}$ is —$C_{1-10}$alkyl. In some embodiments, $R_{71}$ is —$C_{2-10}$alkenyl. In some embodiments, $R_{71}$ is —$C_{2-10}$alkynyl. In some embodiments, $R_{71}$ is —$C_{1-10}$heteroalkyl. In some embodiments, $R_{71}$ is —$C_{3-10}$aryl. In some embodiments, $R_{71}$ is —$C_{1-10}$hetaryl. In some embodiments, $R_{71}$ is —$C_{3-10}$cycloalkyl. In some embodiments, $R_{71}$ is —$C_{1-10}$heterocyclyl. In some embodiments, $R_{71}$ is —OH. In some embodiments, $R_{71}$ is —$CF_3$. In some embodiments, $R_{71}$ is —$OCF_3$. In some embodiments, $R_{71}$ is —$OR^{31}$. In some embodiments, $R_{71}$ is —$NR^{31}R^{32}$. In some embodiments, $R_{71}$ is —$C(O)R^{31}$. In some embodiments, $R_{71}$ is $CO_2R^{31}$. In some embodiments, $R_{71}$ is —$C(=O)NR^{31}$. In some embodiments, $R_{71}$ is —$NO_2$. In some embodiments, $R_{71}$ is —CN. In some embodiments, $R_{71}$ is —$S(O)_{0-2}R^{31}$. In some embodiments, $R_{71}$ is —$SO_2NR^{31}R^{32}$. In some embodiments, $R_{71}$ is —$NR^{31}C(=O)R^{32}$. In some embodiments, $R_{71}$ is —$NR^{31}C(=O)OR^{32}$. In some embodiments, $R_{71}$ is —$NR^{31}C(=O)NR^{32}R^{33}$. In some embodiments, $R_{71}$ is —$NR^{31}S(O)_{0-2}R^{32}$. In some embodiments, $R_{71}$ is —$C(=S)OR^{31}$. In some embodiments, $R_{71}$ is —$C(=O)SR^{31}$. In some embodiments, $R_{71}$ is —$NR^{31}C(=NR^{32})NR^{32}R^{33}$. In some embodiments, $R_{71}$ is —$NR^{31}C(=NR^{32})OR^{33}$. In some embodiments, $R_{71}$ is —$NR^{31}C(=NR^{32})SR^{33}$. In some embodiments, $R_{71}$ is —$OC(=O)OR^{33}$. In some embodiments, $R_{71}$ is —$OC(=O)NR^{31}R^{32}$. In some embodiments, $R_{71}$ is —$OC(=O)SR^{31}$. In some embodiments, $R_{71}$ is —$SC(=O)SR^{31}$. In some embodiments, $R_{71}$ is —$P(O)OR^{31}OR^{32}$. In some embodiments, $R_{71}$ is —$SC(=O)NR^{31}NR^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{72}$ is hydrogen. In some embodiments, $R_{72}$ is —$C_{1-10}$alkyl. In some embodiments, $R_{72}$ is —$C_{2-10}$alkenyl. In some embodiments, $R_{72}$ is —$C_{2-10}$alkynyl. In some embodiments, $R_{72}$ is —$C_{1-10}$heteroalkyl. In some embodiments, $R_{72}$ is —$C_{3-10}$aryl. In some embodiments, $R_{72}$ is —$C_{1-10}$hetaryl. In some embodiments, $R_{72}$ is —$C_{3-10}$cycloalkyl. In some embodiments, $R_{72}$ is —$C_{1-10}$heterocyclyl. In some embodiments, $R_{72}$ is —OH. In some embodiments, $R_{72}$ is —$CF_3$. In some embodiments, $R_{72}$ is —$C(O)R^{31}$. In some embodiments, $R_{72}$ is —$CO_2R^{31}$. In some embodiments, $R_{72}$ is —$C(=O)NR^{31}$. In some embodiments, $R_{72}$ is —$S(O)_{0-2}R^{31}$. In some embodiments, $R_{72}$ is —$C(=S)OR^{31}$. In some embodiments, $R_{72}$ is —$C(=O)SR^{31}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{81}$ is hydrogen. In some embodiments, $R_{81}$ is halogen, which is F, Cl, Br, or I. In some embodiments, $R_{81}$ is —$C_{1-10}$alkyl. In some embodiments, $R_{81}$ is —$C_{2-10}$alkenyl. In some embodiments, $R_{81}$ is —$C_{2-10}$alkynyl. In some embodiments, $R_{81}$ is —$C_{1-10}$heteroalkyl. In some embodiments, $R_{81}$ is —$C_{3-10}$aryl. In some embodiments, $R_{81}$ is —$C_{1-10}$hetaryl. In some embodiments, $R_{81}$ is —$C_{3-10}$cycloalkyl. In some embodiments, $R_{81}$ is —$C_{1-10}$heterocyclyl. In some embodiments, $R_{81}$ is —OH. In some embodiments, $R_{81}$ is —$CF_3$. In some embodiments, $R_{81}$ is —$OCF_3$. In some embodiments, $R_{81}$ is —$OR^{31}$. In some embodiments, $R_{81}$ is —$NR^{31}R^{32}$. In some embodiments, $R_{81}$ is —$C(O)R^{31}$. In some embodiments, $R_{81}$ is —$CO_2R^{31}$. In some embodiments, $R_{81}$ is —$C(=O)NR^{31}$. In some embodiments, $R_{81}$ is —$NO_2$. In some embodiments, $R_{81}$ is —CN. In some embodiments, $R_{81}$ is —$S(O)_{0-2}R^{31}$. In some embodiments, $R_{81}$ is —$SO_2NR^{31}R^{32}$. In some embodiments, $R_{81}$ is —$NR^{31}C(=O)R^{32}$. In some embodiments, $R_{81}$ is —$NR^{31}C(=O)OR^{32}$. In some embodiments, $R_{81}$ is —$NR^{31}C(=O)NR^{32}R^{33}$. In some embodiments, $R_{81}$ is —$NR^{31}S(O)_{0-2}R^{32}$. In some embodiments, $R_{81}$ is —$C(=S)OR^{31}$. In some embodiments, $R_{81}$ is —$C(=O)SR^{31}$. In some embodiments, $R_8$ is —$NR^{31}C(=NR^{32})NR^{32}R^{33}$. In some embodiments, $R_{81}$ is —$NR^{31}C(=NR^{32})OR^{33}$. In some embodiments, $R_{81}$ is —$NR^{31}C(=NR^{32})SR^{33}$. In some embodiments, $R_{81}$ is —$OC(=O)OR^{33}$. In some embodiments, $R_{81}$ is —$OC(=O)NR^{31}R^{32}$. In some embodiments, $R_{81}$ is —$OC(=O)SR^{31}$. In some embodiments, $R_{81}$ is —$SC(=O)SR^{31}$. In some embodiments, $R_{81}$ is —$P(O)OR^{31}OR^{32}$. In some embodiments, $R_{81}$ is —$SC(=O)NR^{31}NR^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{82}$ is hydrogen. In some embodiments, $R_{82}$ is —$C_{1-10}$alkyl. In some embodiments, $R_{82}$ is —$C_{2-10}$alkenyl. In some embodiments, $R_{82}$ is —$C_{2-10}$alkynyl. In some embodiments, $R_{82}$ is —$C_{1-10}$heteroalkyl. In some embodiments, $R_{82}$ is —$C_{3-10}$aryl. In some embodiments, $R_{82}$ is —$C_{1-10}$hetaryl. In some embodiments, $R_{82}$ is —$C_{3-10}$cycloalkyl. In some embodiments, $R_{82}$ is —$C_{1-10}$heterocyclyl. In some embodiments, $R_{82}$ is —OH. In some embodiments, $R_{82}$ is —$CF_3$. In some embodiments, $R_{82}$ is —$C(O)R^{31}$. In some embodiments, $R_{82}$ is —$CO_2R^{31}$. In some embodiments, $R_{82}$ is —$C(=O)NR^{31}$. In some embodiments, $R_{82}$ is —$S(O)_{0-2}R^{31}$. In some embodiments, $R_{82}$ is —$C(=S)OR^{31}$. In some embodiments, $R_{82}$ is —$C(=O)SR^{31}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{91}$ is hydrogen. In some embodiments, $R_{91}$ is halogen, which is F, —Cl, Br, or I. In some embodiments, $R_{91}$ is —$C_{1-10}$alkyl. In some embodiments, $R_{91}$ is —$C_{2-10}$alkenyl. In some embodiments, $R_{91}$ is —$C_{2-10}$alkynyl. In some embodiments, $R_{91}$ is —$C_{1-10}$heteroalkyl. In some embodiments, $R_{91}$ is —$C_{3-10}$aryl. In some embodiments, $R_{91}$ is —$C_{1-10}$hetaryl. In some embodiments, $R_{91}$ is —$C_{3-10}$cycloalkyl. In some embodiments, $R_{91}$ is —$C_{1-10}$heterocyclyl. In some embodiments, $R_{91}$ is —OH. In some embodiments, $R_{91}$ is —$CF_3$. In some embodiments, $R_{91}$ is —$OCF_3$. In some embodiments, $R_{91}$ is —$OR^{31}$. In some embodiments, $R_{91}$ is —$NR^{31}R^{32}$. In some embodiments, $R_{91}$ is —$C(O)R^{31}$. In some embodiments, $R_{91}$ is —$CO_2R^{31}$. In some embodiments, $R_{91}$ is —$C(=O)NR^{31}$. In some embodiments, $R_{91}$ is —$NO_2$. In some embodiments, $R_{91}$ is —CN. In some embodiments, $R_{91}$ is —$S(O)_{0-2}R^{31}$. In some embodiments, $R_{91}$ is —$SO_2NR^{31}R^{32}$. In some embodiments, $R_{91}$ is —$NR^{31}C(=O)R^{32}$. In some embodiments, $R_{91}$ is —$NR^{31}C(=O)OR^{32}$. In some embodiments, $R_{91}$ is —$NR^{31}C(=O)NR^{32}R^{33}$. In some embodiments, $R_{91}$ is —$NR^{31}S(O)_{0-2}R^{32}$. In some embodiments, $R_{91}$ is —$C(=S)OR^{31}$. In some embodiments, $R_{91}$ is —$C(=O)SR^{31}$. In some embodiments, $R_9$ is —$NR^{31}C(=NR^{32})NR^{32}R^{33}$. In some embodiments, $R_9$ is —$NR^{31}C(=NR^{32})OR^{33}$. In some embodiments, $R_{91}$ is —$NR^{31}C(=NR^{32})SR^{33}$. In some embodiments, $R_{91}$ is —OC(=O)OR$^{33}$. In some embodiments, R$_{91}$ is —OC(=O)NR$^{31}$R$^{32}$. In some embodiments, R$_{91}$ is —OC(=O)SR$^{31}$. In some embodiments, R$_{91}$ is —SC(=O)SR$^{31}$. In some embodiments, R$_{91}$ is —P(O)OR$^{31}$OR$^{32}$. In some embodiments, R$_{91}$ is —SC(=O)NR$^{31}$NR$^{32}$;

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{92}$ is hydrogen. In some embodiments, R$_{92}$ is —C$_{1-10}$alkyl. In some embodiments, R$_{92}$ is —C$_{2-10}$alkenyl. In some embodiments, R$_{92}$ is —C$_{2-10}$alkynyl. In some embodiments, R$_{92}$ is —C$_{1-10}$heteroalkyl. In some embodiments, R$_{92}$ is —C$_{3-10}$aryl. In some embodiments, R$_{92}$ is —C$_{1-10}$hetaryl. In some embodiments, R$_{92}$ is —C$_{3-10}$cycloalkyl. In some embodiments, R$_{92}$ is —C$_{1-10}$heterocyclyl. In some embodiments, R$_{92}$ is —OH. In some embodiments, R$_{92}$ is —CF$_3$. In some embodiments, R$_{92}$ is —C(O)R$^{31}$. In some embodiments, R$_{92}$ is —CO$_2$R$^{31}$. In some embodiments, R$_{92}$ is —C(=O)NR$^{31}$. In some embodiments, R$_{92}$ is —S(O)$_{0-2}$R$^{31}$. In some embodiments, R$_{92}$ is —C(=S)OR$^{31}$. In some embodiments, R$_{92}$ is —C(=O)SR$^{31}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is —C$_{1-10}$alkyl, which is unsubstituted. In some embodiments, R$_{10}$ is —C$_{1-10}$alkyl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is C$_{2-10}$alkenyl, which is unsubstituted. In some embodiments, R$_{10}$ is —C$_{2-10}$alkenyl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is C$_{2-10}$alkynyl, which is unsubstituted. In some embodiments, R$_{10}$ is —C$_{2-10}$alkynyl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is —C$_{1-10}$heteroalkyl, which is unsubstituted. In some embodiments, R$_{10}$ is —C$_{1-10}$heteroalkyl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is —C$_{3-10}$aryl, which is unsubstituted. In some embodiments, R$_{10}$ is —C$_{3-10}$aryl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is —C$_{1-10}$hetaryl, which is unsubstituted. In some embodiments, R$_{10}$ is —C$_{1-10}$hetaryl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is —C$_{3-10}$cycloalkyl, which is unsubstituted. In some embodiments, R$_{10}$ is —C$_{3-10}$cycloalkyl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{10}$ is —C$_{1-10}$heterocyclyl, which is unsubstituted. In some embodiments, R$_{10}$ is —C$_{1-10}$heterocyclyl, which is substituted by one or more independent R$_{11}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{14}$ is —C$_{1-10}$alkyl, which is unsubstituted. In some embodiments, R$_{14}$ is —C$_{1-10}$alkyl, which is substituted by one or more independent R$_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{14}$ is —C$_{2-10}$alkenyl, which is unsubstituted. In some embodiments, R$_{14}$ is —C$_{2-10}$alkenyl, which is substituted by one or more independent R$_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{14}$ is —C$_{2-10}$alkynyl, which is unsubstituted. In some embodiments, R$_{14}$ is —C$_{2-10}$alkynyl, which is substituted by one or more independent R$_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{14}$ is —C$_{1-10}$heteroalkyl, which is unsubstituted. In some embodiments, R$_{14}$ is —C$_{1-10}$heteroalkyl, which is substituted by one or more independent R$_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{14}$ is —C$_{3-10}$aryl, which is unsubstituted. In some embodiments, R$_{14}$ is —C$_{3-10}$aryl, which is substituted by one or more independent R$_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), R$_{14}$ is —C$_{1-10}$hetaryl, which is unsubstituted. In some embodiments, $R_{14}$ is —$C_{1-10}$hetaryl, which is substituted by one or more independent $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{14}$ is —$C_{3-10}$cycloalkyl, which is unsubstituted. In some embodiments, $R_{14}$ is —$C_{3-10}$cycloalkyl, which is substituted by one or more independent $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{14}$ is —$C_{1-10}$heterocyclyl, which is unsubstituted. In some embodiments, $R_{14}$ is —$C_{1-10}$heterocyclyl, which is substituted by one or more independent $R_{15}$ substituents.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{11}$ is hydrogen. In some embodiments, $R_{11}$ is halogen, which is F, Cl, Br, or I. In some embodiments, $R_{11}$ is —$C_{1-10}$alkyl. In some embodiments, $R_{11}$ is —$C_{2-10}$alkenyl. In some embodiments, $R_{11}$ is —$C_{2-10}$alkynyl. In some embodiments, $R_{11}$ is —$C_{1-10}$heteroalkyl. In some embodiments, $R_{11}$ is —$C_{1-10}$aryl. In some embodiments, $R_{11}$ is —$C_{1-10}$hetaryl. In some embodiments, $R_{11}$ is —$C_{3-10}$cycloalkyl. In some embodiments, $R_{11}$ is —$C_{1-10}$heterocyclyl. In some embodiments, $R_{11}$ is —OH. In some embodiments, $R_{11}$ is —$CF_3$. In some embodiments, $R_{11}$ is —$OCF_3$. In some embodiments, $R_{11}$ is —$OR^{31}$. In some embodiments, $R_{11}$ is —$NR^{31}R^{32}$. In some embodiments, $R_{11}$ is —$C(O)R^{31}$. In some embodiments, $R_{11}$ is —$CO_2R^{31}$. In some embodiments, $R_{11}$ is —$C(=O)NR^{31}$. In some embodiments, $R_{11}$ is —$NO_2$. In some embodiments, $R_{11}$ is —CN. In some embodiments, $R_{11}$ is —$S(O)_{0-2}R^{31}$. In some embodiments, $R_{11}$ is —$SO_2NR^{31}R^{32}$. In some embodiments, $R_{11}$ is —$NR^{31}C(=O)R^{32}$. In some embodiments, $R_{11}$ is —$NR^{31}C(=O)OR^{32}$. In some embodiments, $R_{11}$ is —$NR^{31}C(=O)NR^{32}R^{33}$. In some embodiments, $R_{11}$ is —$NR^{31}S(O)_{0-2}R^{32}$. In some embodiments, $R_{11}$ is —$C(=S)OR^{31}$. In some embodiments, $R_{11}$ is —$C(=O)SR^{31}$. In some embodiments, $R_{11}$ is —$NR^{31}C(=NR^{32})NR^{32}R^{33}$. In some embodiments, $R_{11}$ is —$NR^{31}C(=NR^{32})OR^{33}$. In some embodiments, $R_{11}$ is —$NR^{31}C(=NR^{32})SR^{33}$. In some embodiments, $R_{11}$ is —$OC(=O)OR^{33}$. In some embodiments, $R_{11}$ is —$OC(=O)NR^{31}R^{32}$. In some embodiments, $R_{11}$ is —$OC(=O)SR^{31}$. In some embodiments, $R_{11}$ is —$SC(=O)SR^{31}$. In some embodiments, $R_{11}$ is —$P(O)OR^{31}OR^{32}$. In some embodiments, $R_{11}$ is or —$SC(=O)NR^{31}NR^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{12}$ is hydrogen. In some embodiments, $R_{12}$ is halogen, which is F, Cl, Br, or I. In some embodiments, $R_{12}$ is —$C_{1-10}$alkyl. In some embodiments, $R_{12}$ is —$C_{2-10}$alkenyl. In some embodiments, $R_{12}$ is —$C_{2-10}$alkynyl. In some embodiments, $R_{12}$ is —$C_{1-10}$heteroalkyl. In some embodiments, $R_{12}$ is —$C_{3-10}$aryl. In some embodiments, $R_{12}$ is —$C_{1-10}$hetaryl. In some embodiments, $R_{12}$ is —$C_{3-10}$cycloalkyl. In some embodiments, $R_{12}$ is —$C_{1-10}$heterocyclyl. In some embodiments, $R_{12}$ is —OH. In some embodiments, $R_{12}$ is —$CF_3$. In some embodiments, $R_{12}$ is —$OCF_3$. In some embodiments, $R_{12}$ is —$OR^{31}$. In some embodiments, $R_{12}$ is —$NR^{31}R^{32}$. In some embodiments, $R_{12}$ is —$C(O)R^{31}$. In some embodiments, $R_{12}$ is —$CO_2R^{31}$. In some embodiments, $R_{12}$ is —$C(=O)NR^{31}$. In some embodiments, $R_{12}$ is —$NO_2$. In some embodiments, $R_{12}$ is —CN. In some embodiments, $R_{12}$ is —$S(O)_{0-2}R^{31}$. In some embodiments, $R_{12}$ is —$SO_2NR^{31}R^{32}$. In some embodiments, $R_{12}$ is —$NR^{31}C(=O)R^{32}$. In some embodiments, $R_{12}$ is —$NR^{31}C(=O)OR^{32}$. In some embodiments, $R_{12}$ is —$NR^{31}C(=O)NR^{32}R^{33}$. In some embodiments, $R_{12}$ is —$NR^{31}S(O)_{0-2}R^{32}$. In some embodiments, $R_{12}$ is —$C(=S)OR^{31}$. In some embodiments, $R_{12}$ is —$C(=O)SR^{31}$. In some embodiments, $R_{12}$ is —$NR^{31}C(=NR^{32})NR^{32}R^{33}$. In some embodiments, $R_{12}$ is —$NR^{31}C(=NR^{32})OR^{33}$. In some embodiments, $R_{12}$ is —$NR^{31}C(=NR^{32})SR^{33}$. In some embodiments, $R_{12}$ is —$OC(=O)OR^{33}$. In some embodiments, $R_{12}$ is —$OC(=O)NR^{31}R^{32}$. In some embodiments, $R_{12}$ is —$OC(=O)SR^{31}$. In some embodiments, $R_{12}$ is —$SC(=O)SR^{31}$. In some embodiments, $R_{12}$ is —$P(O)OR^{31}OR^{32}$. In some embodiments, $R_{12}$ is —$SC(=O)NR^{31}NR^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{13}$ is hydrogen. In some embodiments, $R_{13}$ is halogen, which is F, Cl, Br, or I. In some embodiments, $R_{13}$ is —$C_{1-10}$alkyl. In some embodiments, $R_{13}$ is —$C_{2-10}$alkenyl. In some embodiments, $R_{13}$ is —$C_{2-10}$alkynyl. In some embodiments, $R_{13}$ is —$C_{1-10}$heteroalkyl. In some embodiments, $R_{13}$ is —$C_{3-10}$aryl. In some embodiments, $R_{13}$ is —$C_{1-10}$hetaryl. In some embodiments, $R_{13}$ is —$C_{3-10}$cycloalkyl. In some embodiments, $R_{13}$ is —$C_{1-10}$heterocyclyl. In some embodiments, $R_{13}$ is —OH. In some embodiments, $R_{13}$ is —$CF_3$. In some embodiments, $R_{13}$ is —$OCF_3$. In some embodiments, $R_{13}$ is —$OR^{31}$. In some embodiments, $R_{13}$ is —$NR^{31}R^{32}$. In some embodiments, $R_{13}$ is —$C(O)R^{31}$. In some embodiments, $R_{13}$ is —$CO_2R^{31}$. In some embodiments, $R_{13}$ is —$C(=O)NR^{31}$. In some embodiments, $R_{13}$ is —$NO_2$. In some embodiments, $R_{13}$ is —CN, —$S(O)_{0-2}R^{31}$. In some embodiments, $R_{13}$ is —$SO_2NR^{31}R^{32}$. In some embodiments, $R_{13}$ is —$NR^{31}C(=O)R^{32}$. In some embodiments, $R_{13}$ is —$NR^{31}C(=O)OR^{32}$. In some embodiments, $R_{13}$ is —$NR^{31}C(=O)NR^{32}R^{33}$. In some embodiments, $R_{13}$ is —$NR^{31}S(O)_{0-2}R^{32}$. In some embodiments, $R_{13}$ is —$C(=S)OR^{31}$. In some embodiments, $R_{13}$ is —$C(=O)SR^{31}$. In some embodiments, $R_{13}$ is —$NR^{31}C(=NR^{32})NR^{32}R^{33}$. In some embodiments, $R_{13}$ is —$NR^{31}C(=NR^{32})OR^{33}$. In some embodiments, $R_{13}$ is —$NR^{31}C(=NR^{32})SR^{33}$. In some embodiments, $R_{13}$ is —$OC(=O)OR^{33}$. In some embodiments, $R_{13}$ is —$OC(=O)NR^{31}R^{32}$. In some embodiments, $R_{13}$ is —$OC(=O)SR^{31}$. In some embodiments, $R_{13}$ is —$SC(=O)SR^{31}$. In some embodiments, $R_{13}$ is —$P(O)OR^{31}OR^{32}$. In some embodiments, $R_{13}$ is —$SC(=O)NR^{31}NR^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R_{15}$ is hydrogen. In some embodiments, $R_{15}$ is halogen, which is F, Cl, Br, or I. In some embodiments, $R_{15}$ is —$C_{1-10}$alkyl. In some embodiments, $R_{15}$ is —$C_{2-10}$alkenyl. In some embodiments, $R_{15}$ is —$C_{2-10}$alkynyl. In some embodiments, $R_{15}$ is —$C_{1-10}$heteroalkyl. In some embodiments, $R_{15}$ is —$C_{3-10}$aryl. In some embodiments, $R_{15}$ is —$C_{1-10}$hetaryl. In some embodiments, $R_{15}$ is —$C_{3-10}$cycloalkyl. In some embodiments, $R_{15}$ is —$C_{1-10}$heterocyclyl. In some embodiments, $R_{15}$ is —OH. In some embodiments, $R_{15}$ is —$CF_3$. In some embodiments, $R_{15}$ is —$OCF_3$. In some embodiments, $R_{15}$ is —$OR^{31}$. In some embodiments, $R_{15}$ is —$NR^{31}R^{32}$. In some embodiments, $R_{15}$ is —$C(O)R^{31}$. In some embodiments, $R_{15}$ is —$CO_2R^{31}$. In some embodiments, $R_{15}$ is —$C(=O)NR^{31}$. In some embodiments, $R_{15}$ is —$NO_2$. In some embodiments, $R_{15}$ is —CN, —$S(O)_{0-2}R^{31}$. In some embodiments, $R_{15}$ is —$SO_2NR^{31}R^{32}$. In some embodiments, $R_{15}$ is —$NR^{31}C(=O)R^{32}$. In some embodiments, $R_{15}$ is —$NR^{31}C(=O)OR^{32}$. In some embodiments, $R_{15}$ is —$NR^{31}C(=O)NR^{32}R^{33}$. In some embodiments, $R_{15}$ is —$NR^{31}S(O)_{0-2}R^{32}$. In some embodiments, $R_{15}$ is —$C(=S)OR^{31}$. In some embodiments, $R_{15}$ is —$C(=O)SR^{31}$. In some embodiments, $R_{15}$ is —$NR^{31}C(=NR^{32})NR^{32}R^{33}$. In some embodiments, $R_{15}$ is —$NR^{31}C(=NR^{32})OR^{33}$. In some embodiments, $R_{15}$ is —$NR^{31}C(=NR^{32})SR^{33}$. In some embodiments, $R_{15}$ is —$OC(=O)OR^{33}$. In some embodiments, $R_{15}$ is —$OC(=O)NR^{31}R^{32}$. In some embodiments, $R_{15}$ is —$OC(=O)SR^{31}$. In some embodiments, $R_{15}$ is —$SC(=O)SR^{31}$. In some embodiments, $R_{15}$ is —$P(O)OR^{31}OR^{32}$. In some embodiments, $R_{15}$ is —$SC(=O)NR^{31}NR^{32}$.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R^{31}$ is hydrogen. In some embodiments, $R^{31}$ is halogen, which is F, Cl, Br, or I. In some embodiments, $R^{31}$ is —$C_{1-10}$alkyl. In some embodiments, $R^{31}$ is —$C_{2-10}$alkenyl. In some embodiments, $R^{31}$ is —$C_{2-10}$alkynyl. In some embodiments, $R^{31}$ is —$C_{1-10}$heteroalkyl. In some embodiments, $R^{31}$ is —$C_{3-10}$aryl. In some embodiments, $R^{31}$ is —$C_{1-10}$hetaryl. In some embodiments, $R^{31}$ is —$C_{3-10}$cycloalkyl. In some embodiments, $R^{31}$ is —$C_{1-10}$heterocyclyl.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R^{32}$ is hydrogen. In some embodiments, $R^{32}$ is halogen, which is F, Cl, Br, or I. In some embodiments, $R^{32}$ is —$C_{1-10}$alkyl. In some embodiments, $R^{32}$ is —$C_{2-10}$alkenyl. In some embodiments, $R^{32}$ is —$C_{2-10}$alkynyl. In some embodiments, $R^{32}$ is —$C_{1-10}$heteroalkyl. In some embodiments, $R^{32}$ is —$C_{3-10}$aryl. In some embodiments, $R^{32}$ is —$C_{1-10}$hetaryl. In some embodiments, $R^{32}$ is —$C_{3-10}$cycloalkyl. In some embodiments, $R^{32}$ is —$C_{1-10}$heterocyclyl.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R^{33}$ is hydrogen. In some embodiments, $R^{33}$ is halogen, which is F, Cl, Br, or I. In some embodiments, $R^{33}$ is —$C_{1-10}$alkyl. In some embodiments, $R^{33}$ is —$C_{2-10}$alkenyl. In some embodiments, $R^{33}$ is —$C_{2-10}$alkynyl. In some embodiments, $R^{33}$ is —$C_{1-10}$heteroalkyl. In some embodiments, $R^{33}$ is —$C_{3-10}$aryl. In some embodiments, $R^{33}$ is —$C_{1-10}$hetaryl. In some embodiments, $R^{33}$ is —$C_{3-10}$cycloalkyl. In some embodiments, $R^{33}$ is —$C_{1-10}$heterocyclyl.

In various embodiments of compounds of Formula I (including I-A and I-B), Formula II (including II', II-A, II-B, II-C, II-D, II-E, II-F and II-G), Formula III (including III-A and III-B), Formula IV (including IV-A, IV-B, IV-C and IV-D) and Formula V (including V-A, V-B, V-C and V-D), $R^{34}$ is hydrogen. In some embodiments, $R^{34}$ is halogen, which is F, Cl, Br, or I. In some embodiments, $R^{34}$ is —$C_{1-10}$alkyl. In some embodiments, $R^{34}$ is —$C_{2-10}$alkenyl. In some embodiments, $R^{34}$ is —$C_{2-10}$alkynyl. In some embodiments, $R^{34}$ is —$C_{1-10}$heteroalkyl. In some embodiments, $R^{34}$ is —$C_{3-10}$aryl. In some embodiments, $R^{34}$ is —$C_{1-10}$hetaryl. In some embodiments, $R^{34}$ is —$C_{3-10}$cycloalkyl. In some embodiments, $R^{34}$ is —$C_{1-10}$heterocyclyl.

B. Reaction Schemes

The compounds disclosed herein may be prepared by the routes described below. Materials used herein are either commercially available or prepared by synthetic methods generally known in the art. These schemes are not limited to the compounds listed or by any particular substituents employed for illustrative purposes. Numbering does not necessarily correspond to that of claims or other tables.

In some embodiments, compounds are synthesized by coupling an $R^{21}$ moiety onto an N-protected indazole A-3 via a coupling reaction (e.g. Suzuki reaction) to produce a compound of Formula A-4. The intermediate A-4 is treated with an N-bromosuccinimide (NBS) reagent to install a bromide group at the allylic position as in A-5, which is then reacted with an amino group to introduce the R1 group and produce a compound of Formula A-6. Reduction of the nitro group with a zinc catalyst under acidic conditions yields the bis-amino heteroaromatic compound A-7, which is then condensed with carbonyl diimidazole (CDI) to produce a tricyclic compound of Formula A-8. Deprotection of the protecting groups under acidic conditions affords compound A-9.

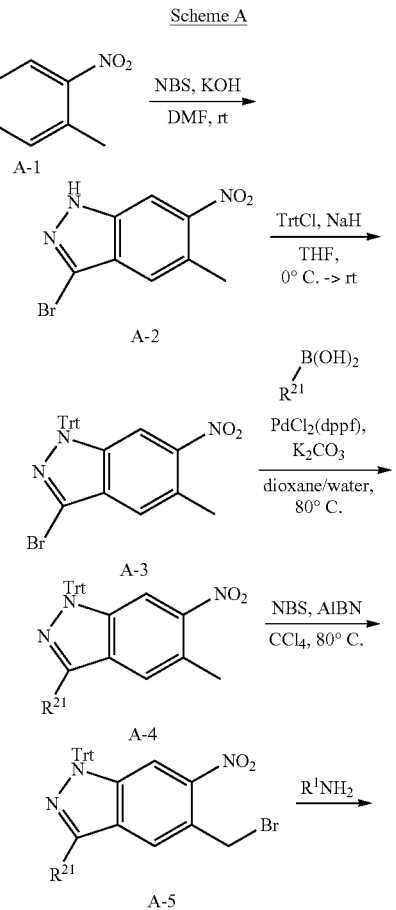

Scheme A

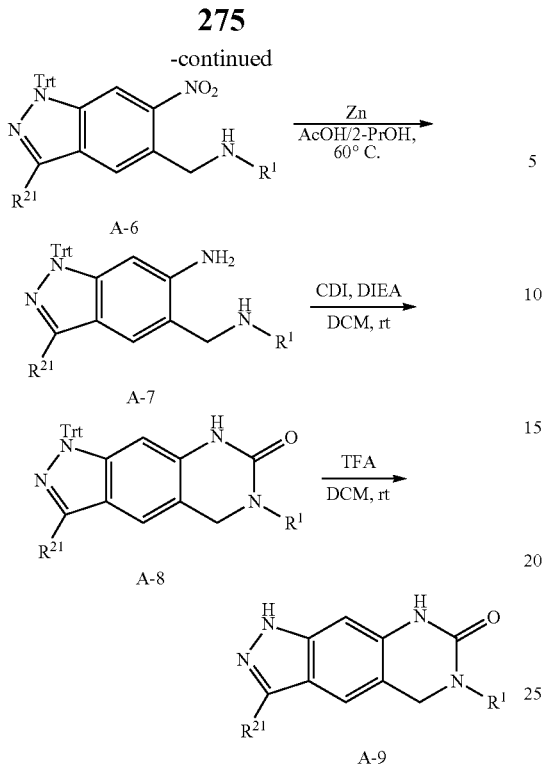

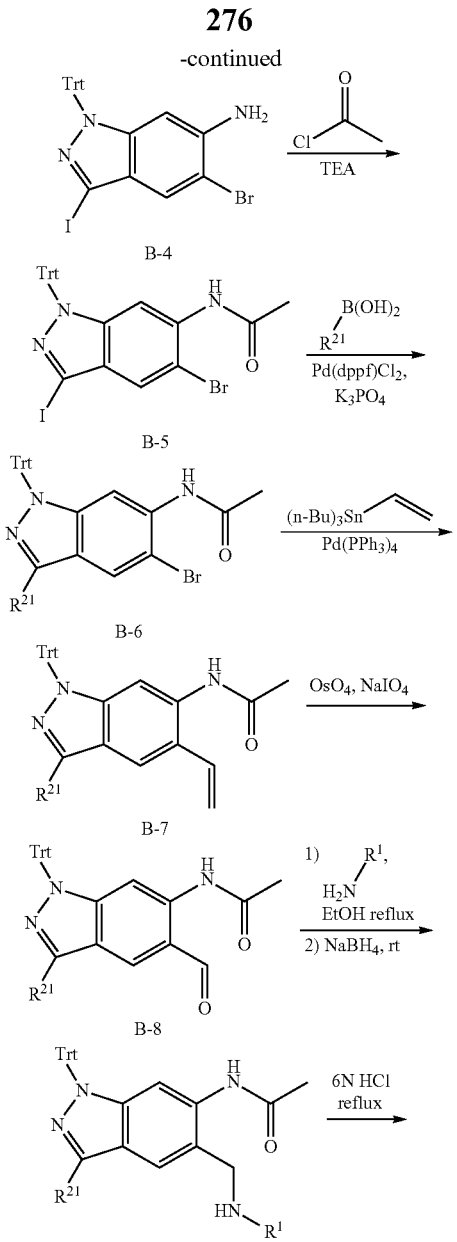

In other embodiments, the $R^{21}$ moiety is coupled onto an N-protected indazole B-5 via a first coupling reaction (e.g. Suzuki reaction) to produce a compound of Formula B-6. A vinyl group is subsequently introduced to B-6 via a second coupling reaction (e.g. Stille reaction) as in B-7, which is then treated with osmium tetroxide and sodium periodate to produce the aldehyde B-8. The intermediate B-8 is then reacted with an amino group to introduce the R1 group, followed by reduction with sodium borohydride to afford a compound of formula B-8. The protecting groups are removed under acidic conditions to afford the bis-amino indazole B-10, which is condensed with carbonyl diimidazole (CDI) to produce a tricyclic compound of Formula B-11.

Scheme B

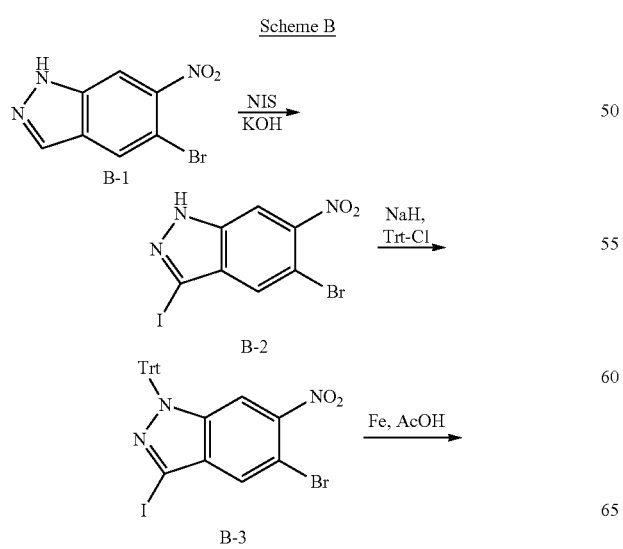

In yet other embodiments, a vinyl group can be introduced to the N-protected indazole C-1 via a first coupling reaction (e.g. Stille reaction) as in C-2, which is then treated with osmium tetroxide and sodium periodate to produce the aldehyde C-3. The intermediate C-3 is reacted with an amino group to introduce the R1 moiety as in C-4. Reduction of the nitro group with a zinc catalyst under acidic conditions yields the bis-amino heteroaromatic compound C-5, which is then condensed with carbonyl diimidazole (CDI) to produce a tricyclic compound of Formula C-6. The compound C-6 is deprotected under acidic conditions and treated with N-iodosuccinimide (NIS) to produce the iodo-indazole C-7. After installing the trityl protecting groups under basic conditions as in C-8, the $R^{21}$ group was introduced via a second coupling reaction (e.g. Stille reaction) to produce the N-protected tricyclic compound C-9. Removal of the protecting groups under acidic conditions provides compounds of Formula C-11.

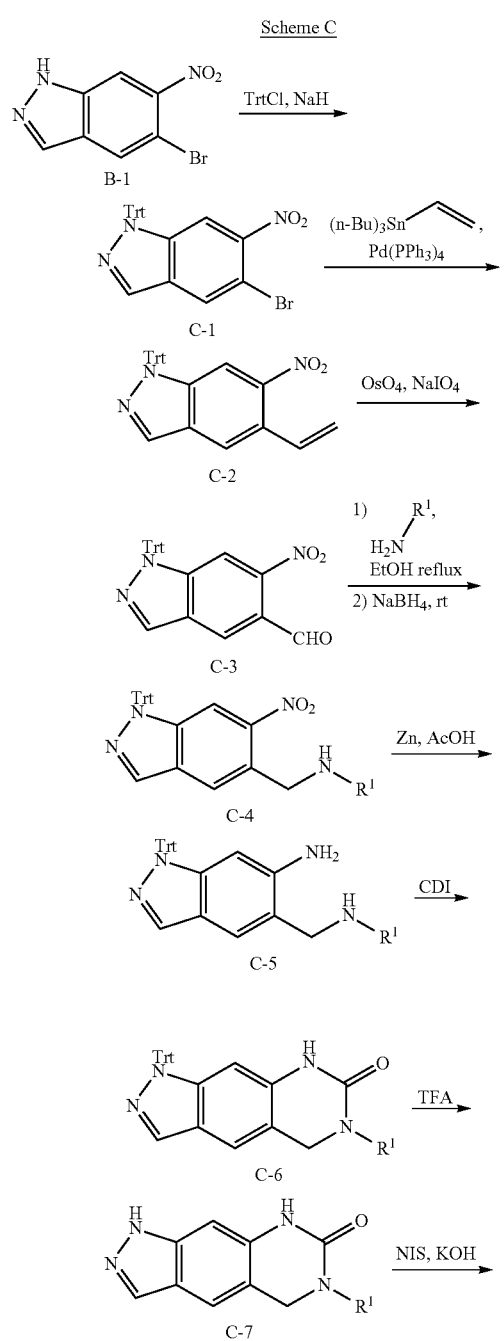

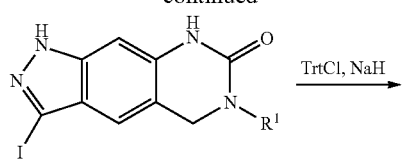

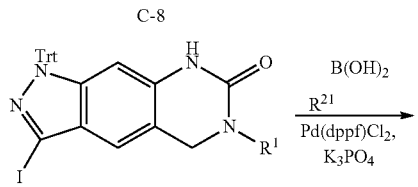

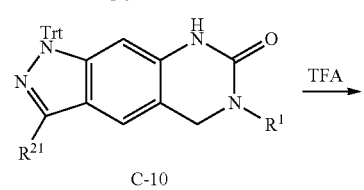

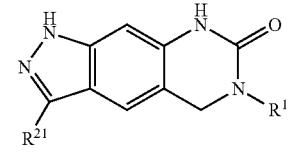

In some embodiments, N-protected indazole A-3 is brominated using NBS to provide dibromide D-1, which is then reacted with an amino group to introduce the R1 moiety to yield intermediate D-2. Reduction of the nitro group with a zinc catalyst under acidic conditions yields the bis-amino heteroaromatic compound D-3, which is then condensed with carbonyl diimidazole (CDI) to produce a tricyclic compound of Formula D-4. The $R^{21}$ group is introduced via a coupling reaction (e.g. Suzuki reaction) to produce the N-protected tricyclic compound D-5. Removal of the protecting groups under acidic conditions provides compounds of Formula D-6.

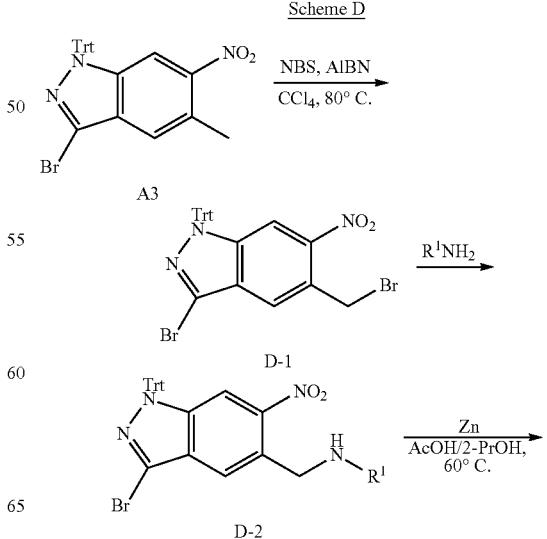

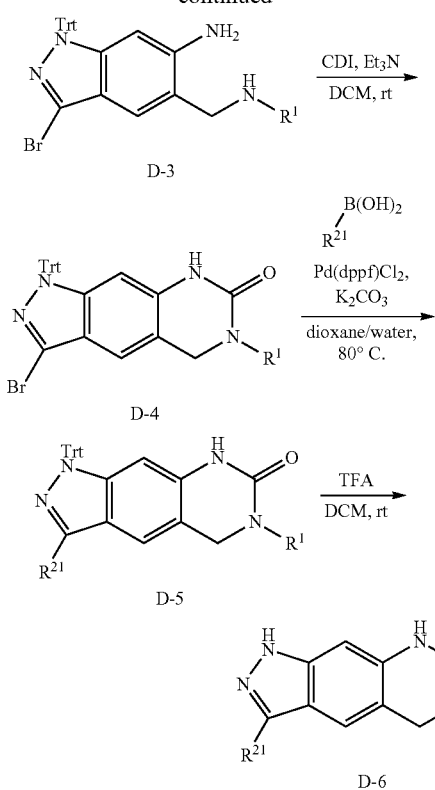

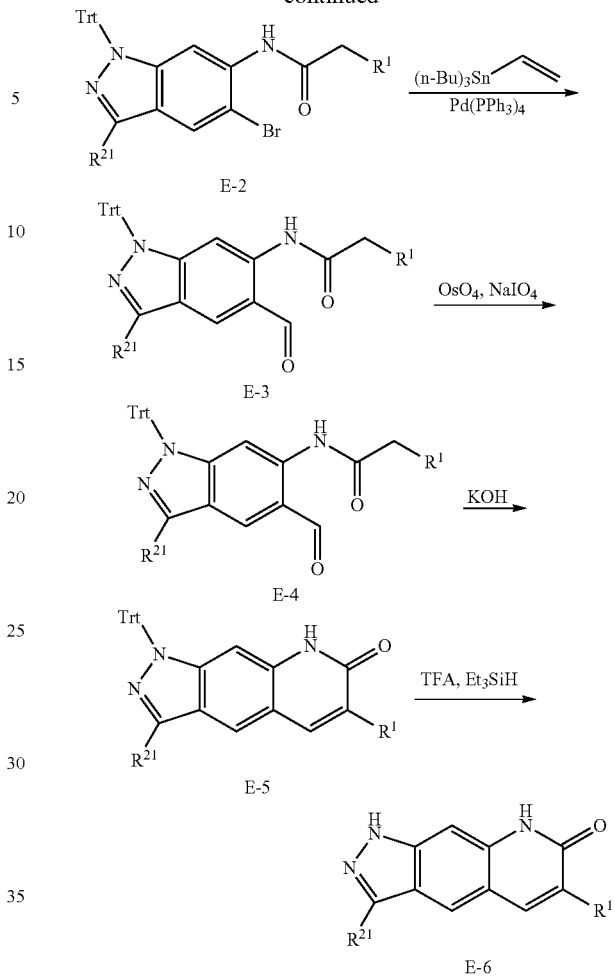

In other embodiments, intermediate B-4 is reacted with an acyl chloride to form amide E-1. The $R^{21}$ group is installed via a first coupling reaction (e.g. Suzuki reaction) to afford in intermediate E-2. A vinyl group can be introduced via a second coupling reaction (e.g. Stille reaction) as in E-3, which is then treated with osmium tetroxide and sodium periodate to produce the aldehyde E-4. The tricyclic compound E-5 is produced via an intramolecular aldol condensation under basic conditions. Removal of the protecting groups under acidic conditions yields compounds of Formula E-6.

Alternatively, intermediate B-8 can be deacetylated to form analine F-1. Treatment of F-1 with an acyl chloride in the presence of TEA furnishes the corresponding amide E-4. The tricyclic compound E-5 is produced via an intramolecular aldol condensation under basic conditions. Removal of the protecting groups under acidic conditions yields compounds of Formula E-6.

Scheme E

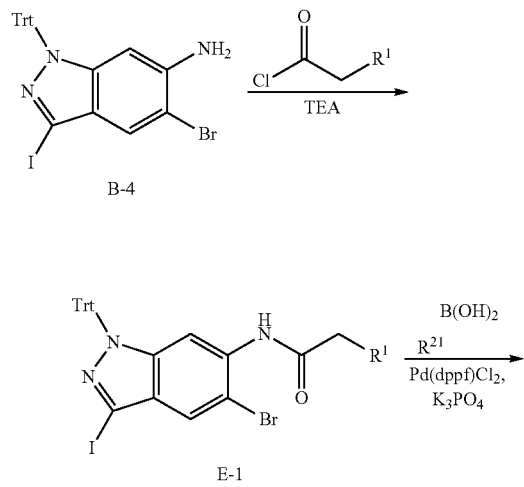

Scheme F

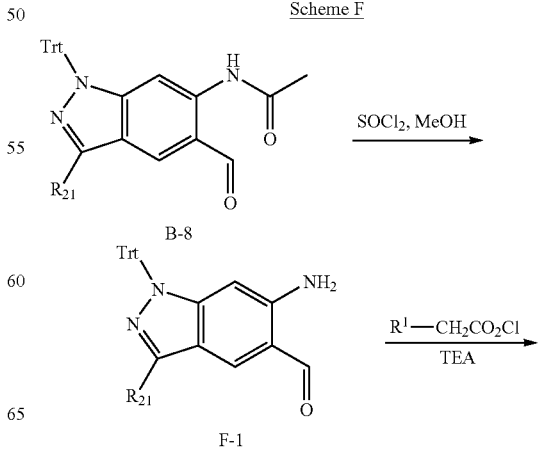

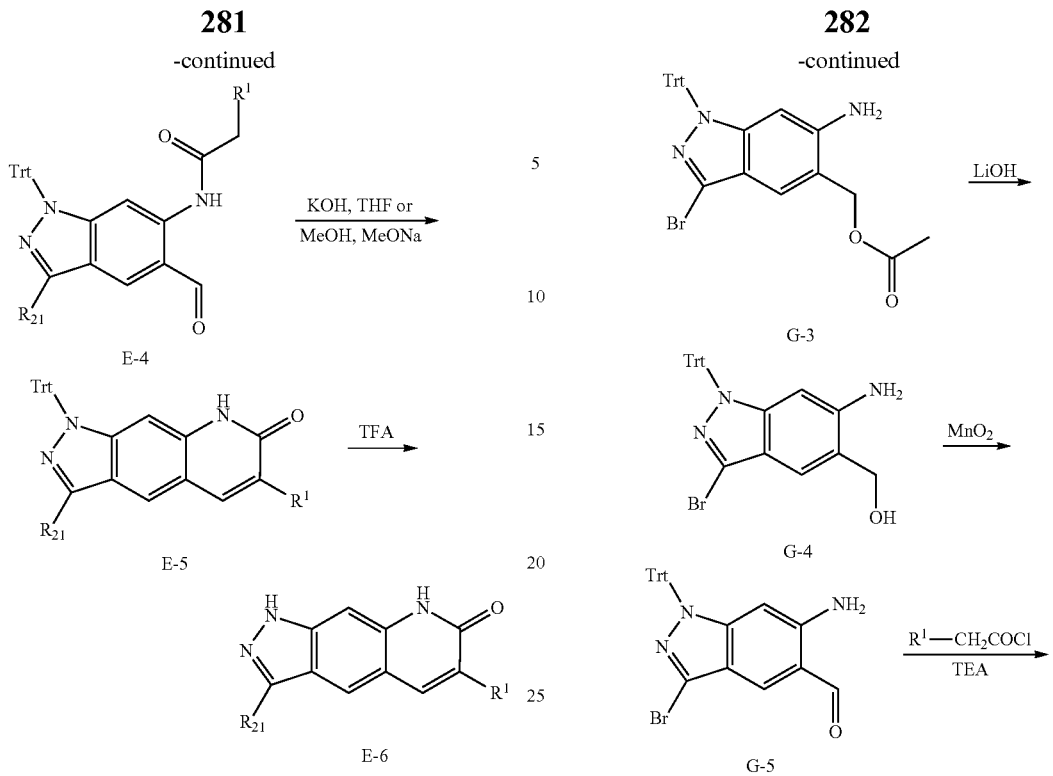

In some embodiments, dibromo compound G-1 can be treated with potassium acetate in DMF to form acetate G-2. The nitro group can be reduced in the presence of sodium thiosulfate and subsequent hydrolysis of the ester with lithium hydroxide can provide amino alcohol G-4. Oxidation of the benzylic alcohol to the aldehyde furnishes G-5. Acylation with an acyl chloride can form the corresponding amide G-6. The tricyclic compound G-7 can be formed via intramolecular aldol condensation. The R21 group can be introduced via coupling with the aryl bromide G-7 (e.g. Suzuki coupling). Removal of the protecting groups under acidic conditions yields compounds of Formula G-9.

Scheme G

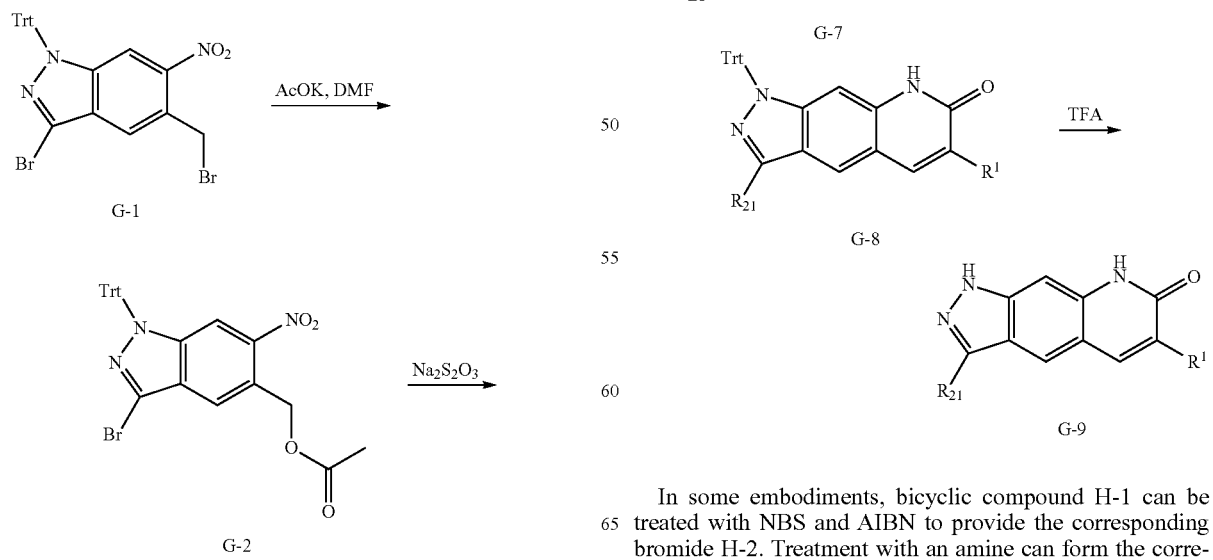

In some embodiments, bicyclic compound H-1 can be treated with NBS and AIBN to provide the corresponding bromide H-2. Treatment with an amine can form the corresponding benzylic amine H-3. Subsequent reduction of the nitro arene furnishes the aniline H-4. The tricyclic compound is formed via the addition of CDI. The $R^{21}$ group can be introduced via a coupling reaction with a boronic acid (e.g. Suzuki coupling). Removal of the protecting group via hydrogenation and treatment with Boc anhydride can furnish the Boc-protected amine H-7. Removal of the Boc group under acid conditions and reductive amination with an aldehyde can form the substituted amine H-9.

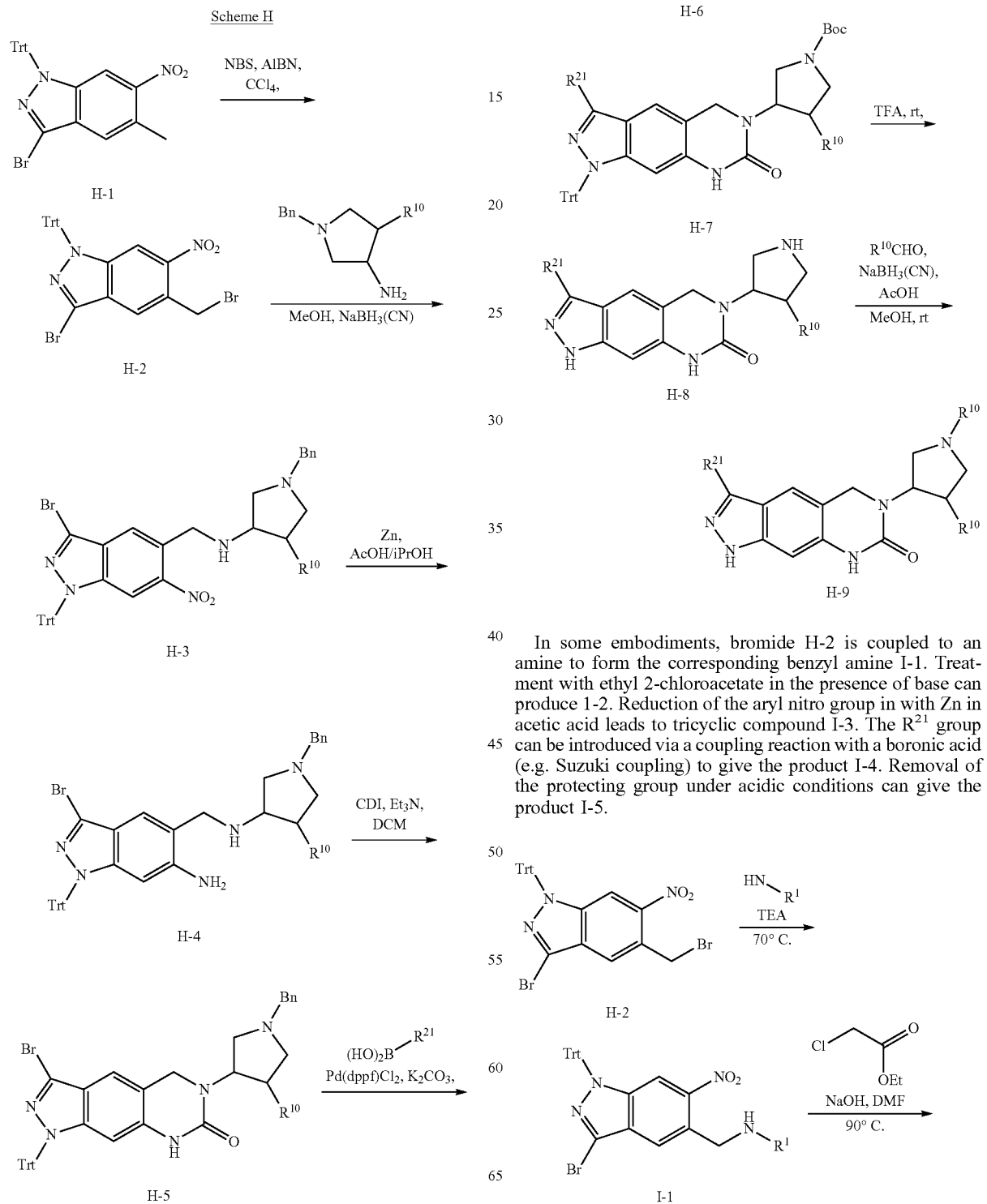

In some embodiments, bromide H-2 is coupled to an amine to form the corresponding benzyl amine I-1. Treatment with ethyl 2-chloroacetate in the presence of base can produce 1-2. Reduction of the aryl nitro group in with Zn in acetic acid leads to tricyclic compound I-3. The $R^{21}$ group can be introduced via a coupling reaction with a boronic acid (e.g. Suzuki coupling) to give the product I-4. Removal of the protecting group under acidic conditions can give the product I-5.

-continued

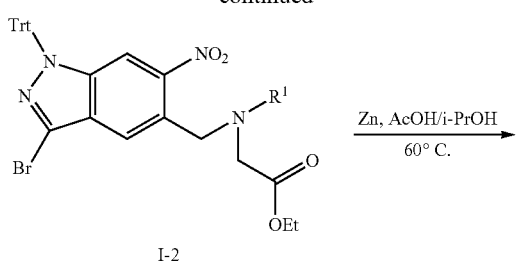
I-2

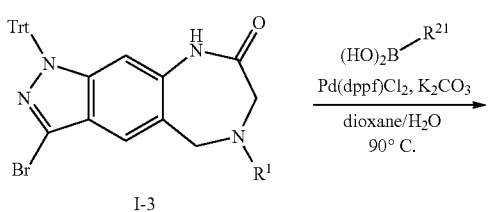
I-3

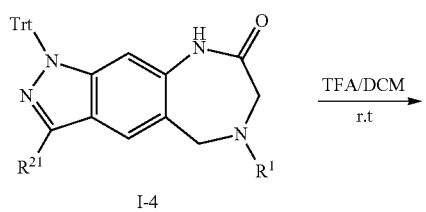
I-4

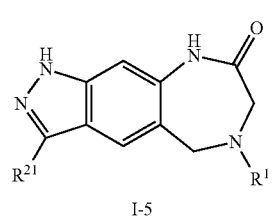
I-5

In some embodiments, aryl olefin C-2 can be hydroborated to form the linear alcohol J-1. Oxidation of the alcohol to J-2 can furnish the carboxylic acid. The acid can be coupled to an amine to form amide J-3 thereby introducing the R1 group via an amide bond-forming reaction. Reduction of the amide via borane can provide the amine J-4, and further reduction of the nitro group with zinc in acetic acid can provide analine J-5. The tricyclic compound J-6 can be formed via addition of CDI. Deprotection under acidic conditions and subsequent iodination leads to aryl iodide J-8. Protection with a Boc group give intermediate J-9 which can be coupled via a coupling reaction (i.e. Suzuki reaction) to introduce the R21 group. Removal of the Boc group gives product J-10.

Scheme J

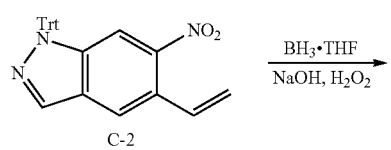
C-2

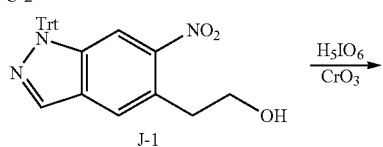
J-1

-continued

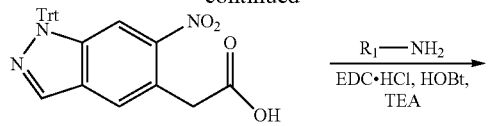
J-2

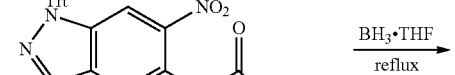
J-3

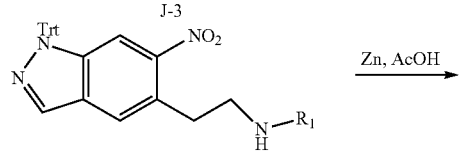
J-4

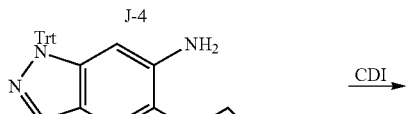
J-5

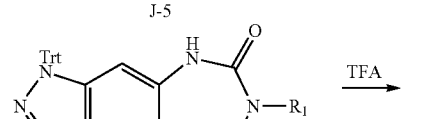
J-6

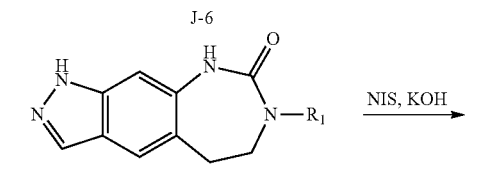
J-7

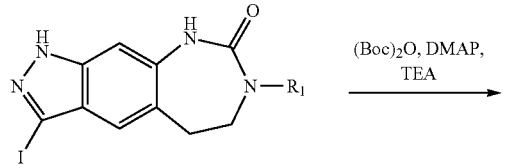
J-8

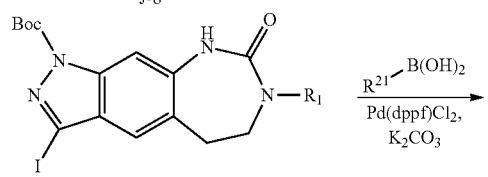
J-9

J-10

In some embodiments, aryl bromide B-1 is coupled to an amine to form K-2. Reduction of the aryl nitro group furnishes aniline K-3. Tricyclic compound K-4 is formed via addition of triphosgene. The protecting group is removed under acidic conditions to form compound K-5, which is iodinated with NIS to furnish aryl iodide K-6. Protection of the compound with a Boc group give K-7. Coupling of K-7 via a coupling reaction can introduce the R21 group (i.e. Suzuki coupling) to furnish compound K-8.

group can be introduced via a coupling reaction with a boronic acid (e.g. Suzuki coupling) to form L-3. Bromination selective furnishes L-4 which can be coupled to form L-5. Reduction of the olefin and removal of the benzyl group furnishes L-6. Deprotection under acidic conditions and subsequent reductive amination can provide L-8.

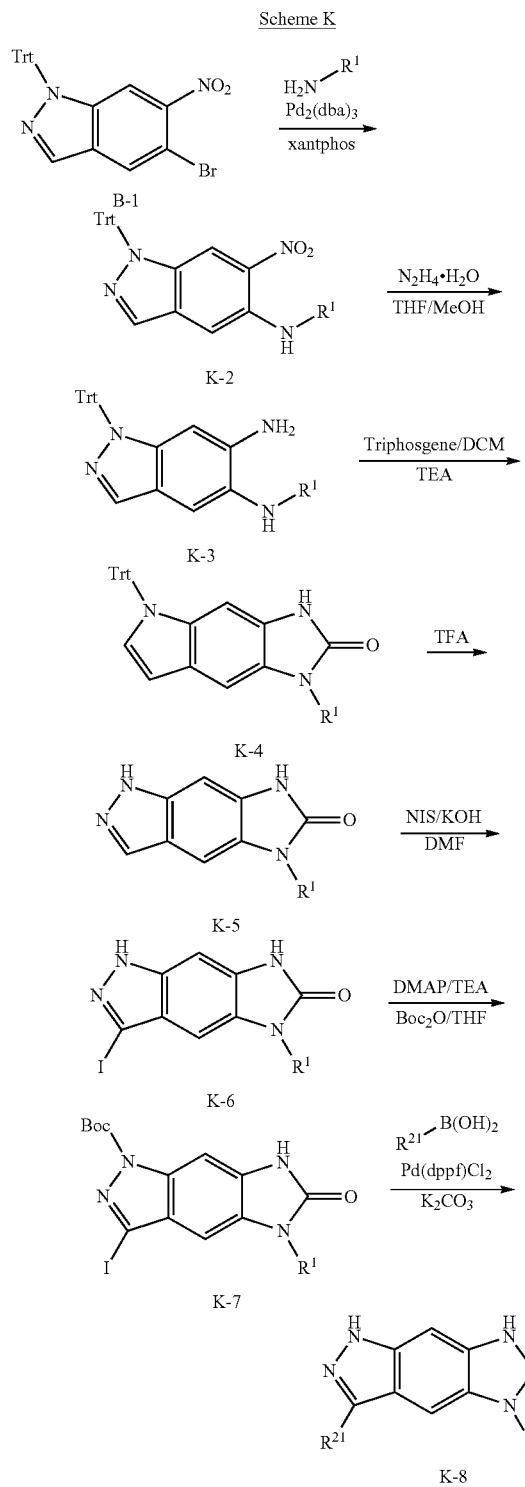

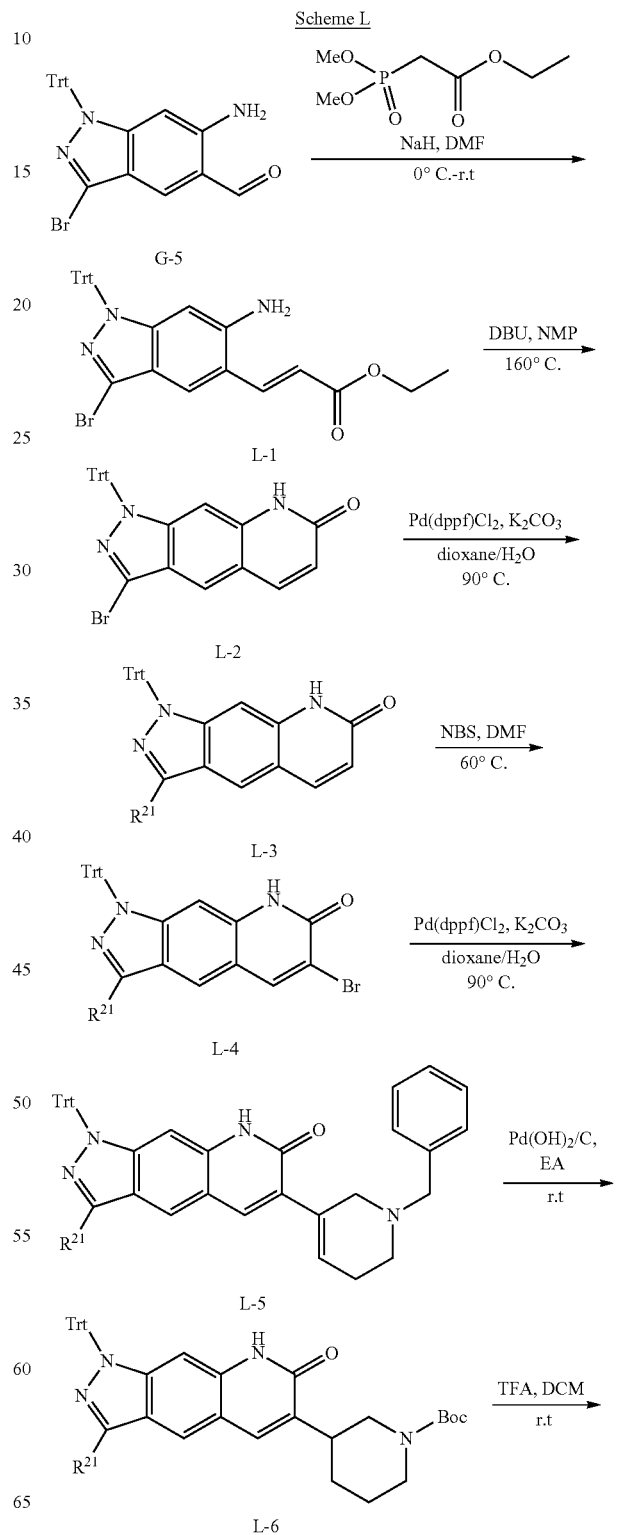

In some embodiments, aldehyde G-5 is olefinated (i.e. HWE reaction) to furnish ester L-1. Treatment with base such as DBU provides tricyclic compound L-2. The $R^{21}$

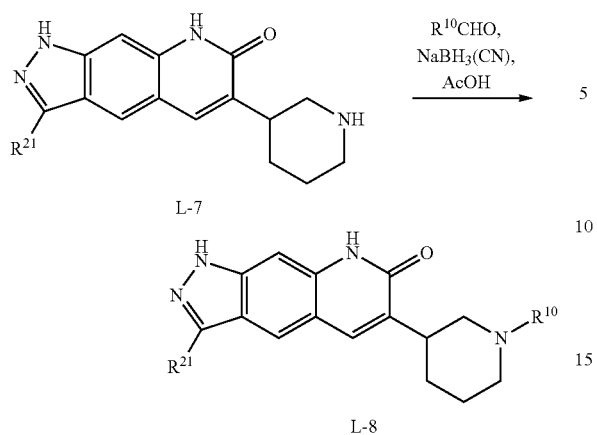

L-7

L-8

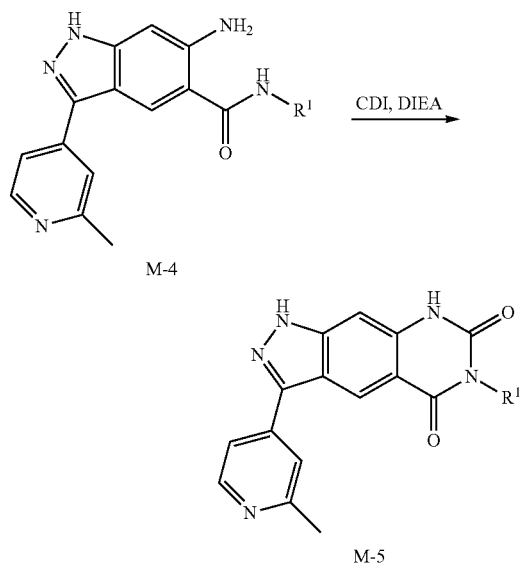

M-4

M-5

In some embodiments, aldehyde M-1 is oxidized to the acid M-2 with Jones reagent. Cleavage of the acetate group is achieved under acidic conditions to form M-3. Coupling to an amine (i.e. amide bond forming reaction) is used to introduce the R1 group thereby forming M-4. The tricyclic compound M-5 is formed by addition of CDI.

In other embodiments, compound N-1 is brominated with N-1 is selectively to form N-1. Coupling to a vinyl boronic acid or boronic ester can be used to furnish N-3 and introduce an $R^{10}$ group. Hydroboration and oxidation of the olefin can furnish alcohol N-4. Removal of the protecting group under acid conditions yields N-5.

Scheme M

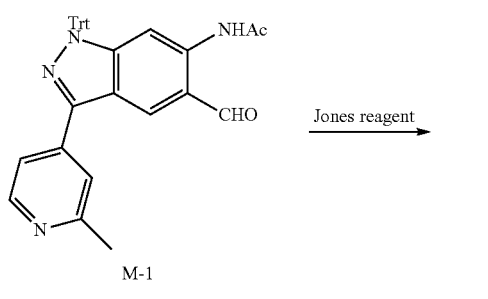

M-1

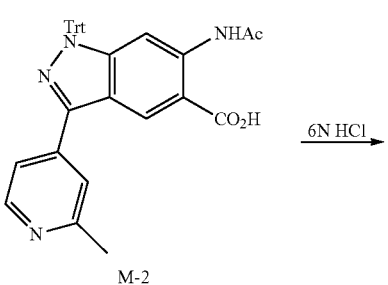

M-2

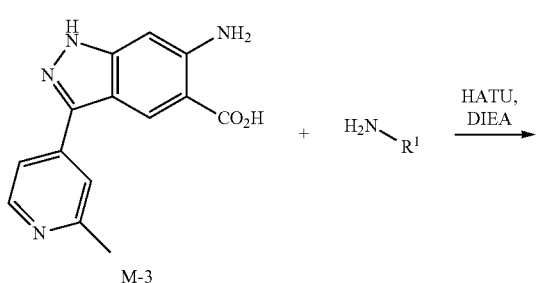

M-3

Scheme N

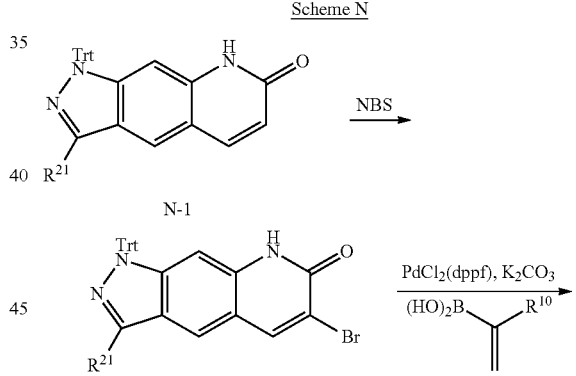

N-1

N-2

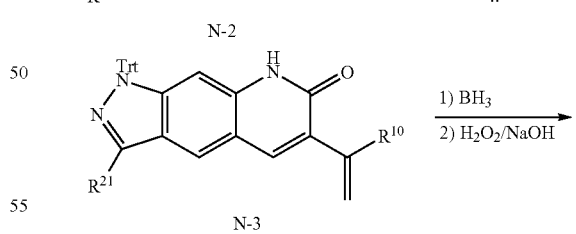

N-3

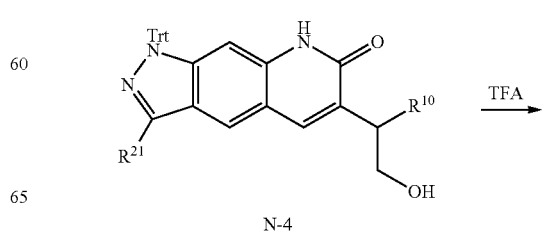

N-4

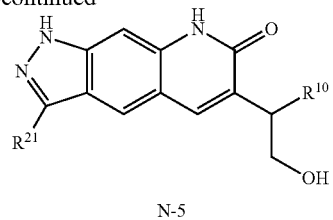

N-5

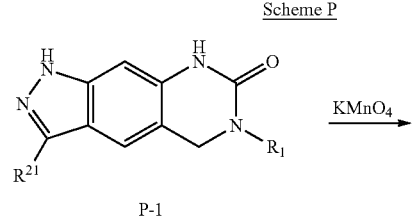

P-1

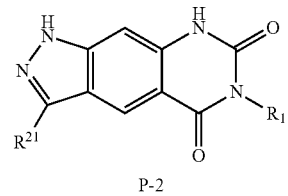

P-2

In some embodiments, compound O-1 can be selectively coupled at the pyrazole nitrogen to form O-2. Removal of the tert-butyl groups under acidic conditions can form O-3.

Scheme O

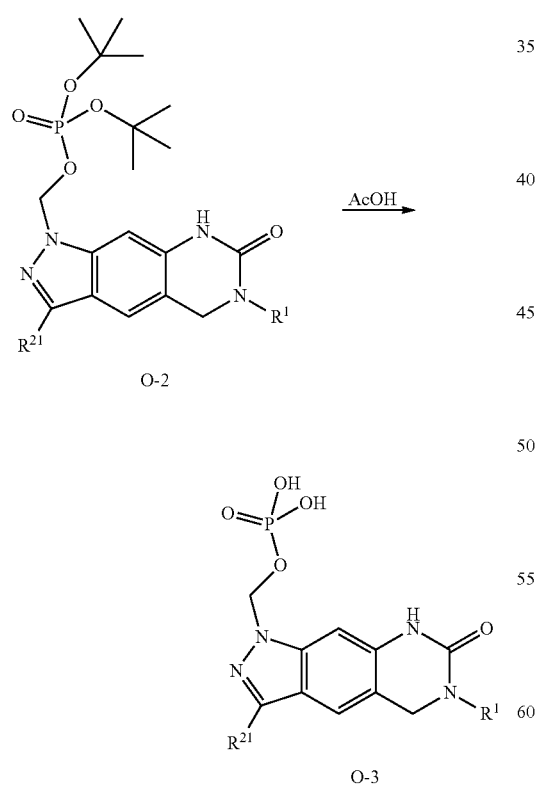

O-1

O-2

O-3

Some exemplary R¹ moieties that can be incorporated via any of Schemes A-P include but are not limited to:

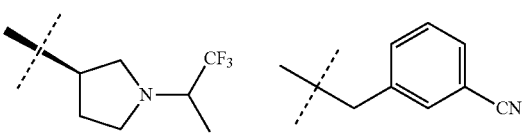

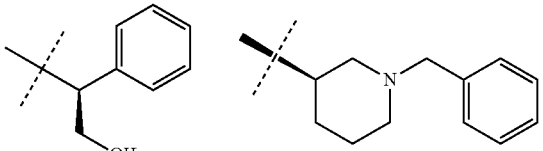

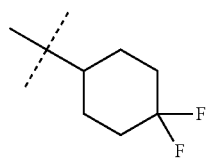

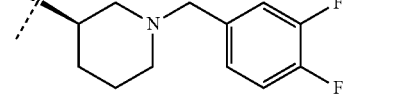

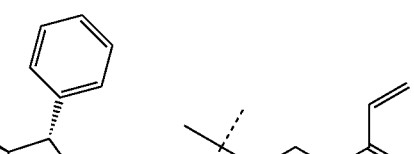

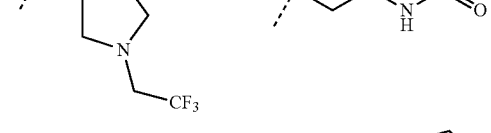

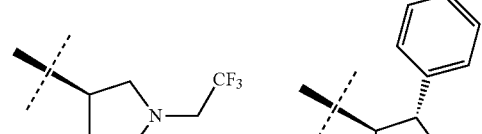

In some embodiments, a compound of the structure P-1 can be oxidized to P-2, for example, in the presence of potassium permanganate.

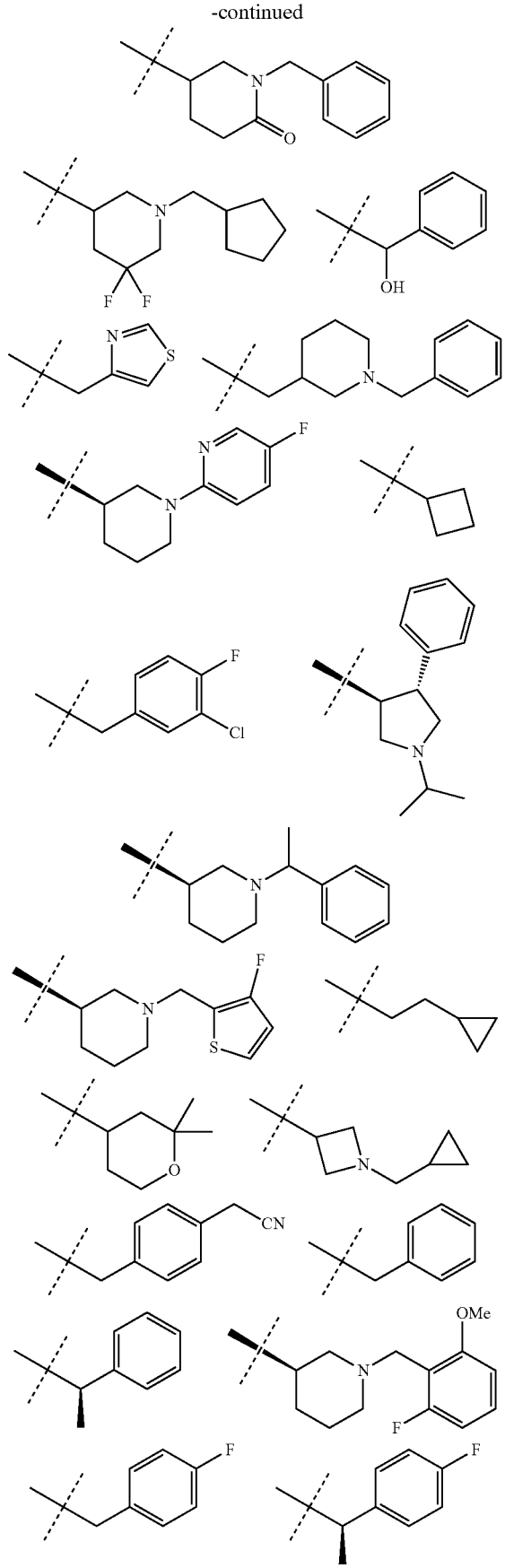
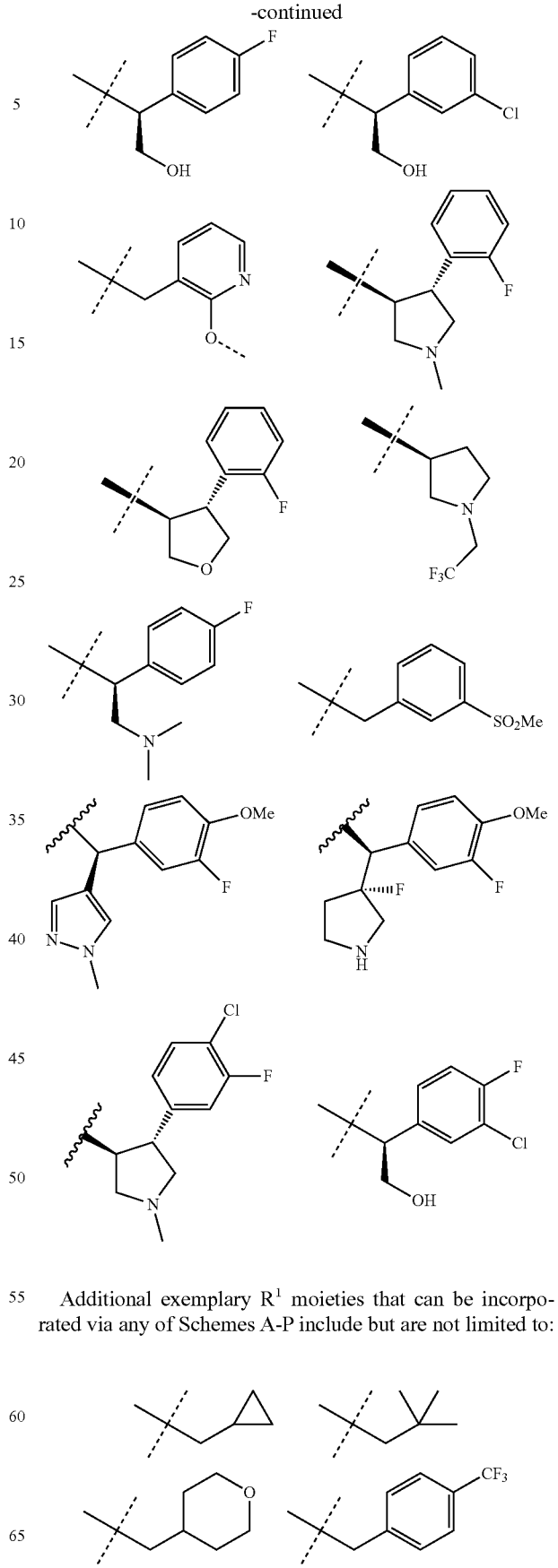
Additional exemplary R¹ moieties that can be incorporated via any of Schemes A-P include but are not limited to:
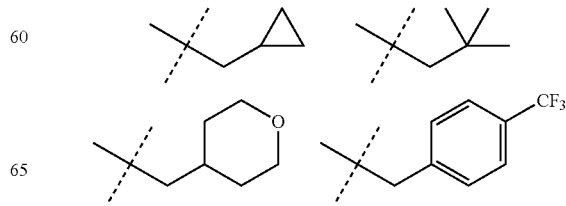

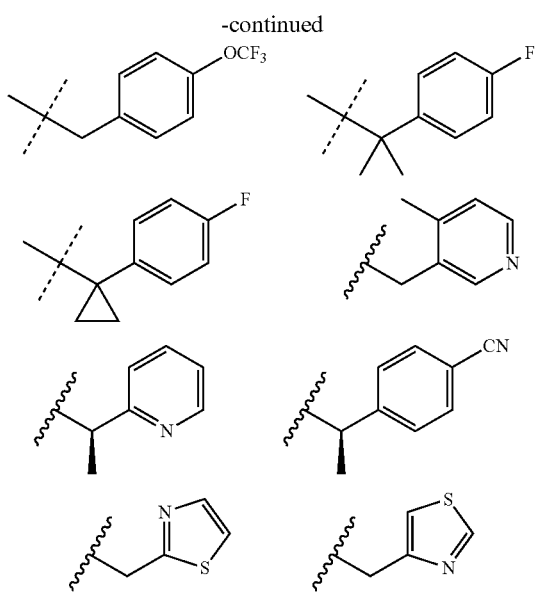

Some exemplary $R^{21}$ and/or $R^{22}$ moieties that can be incorporated via any of Schemes A-P include but are not limited to:

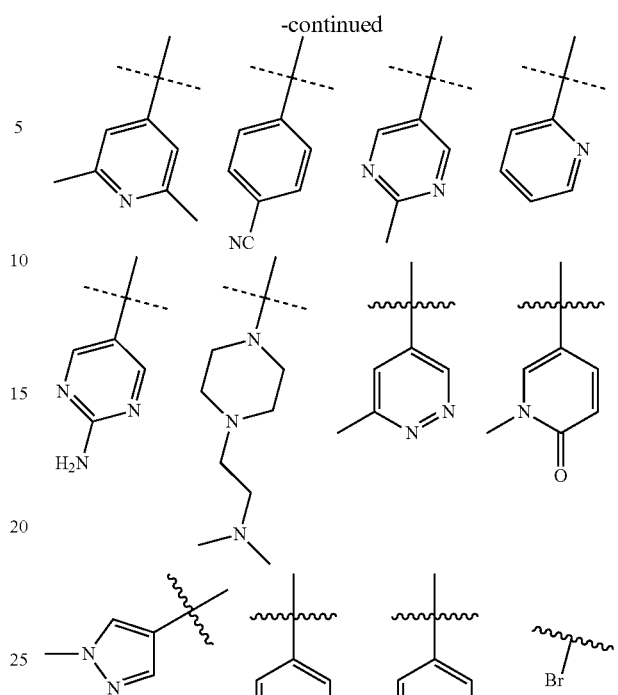

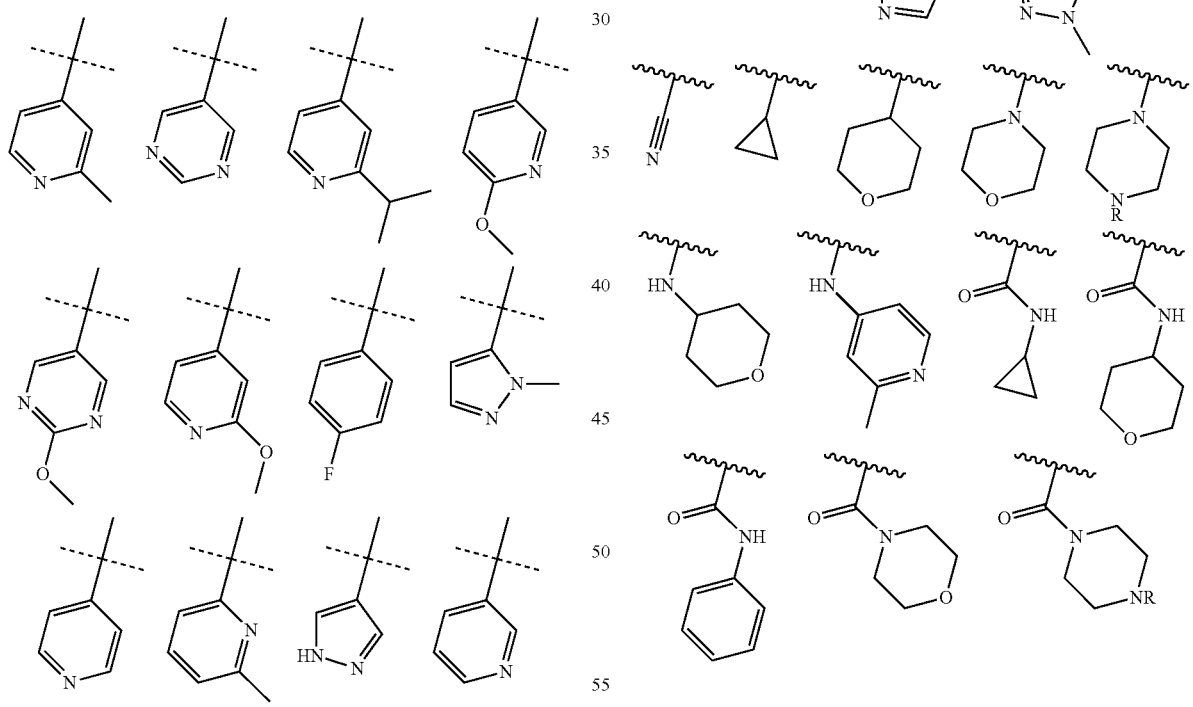

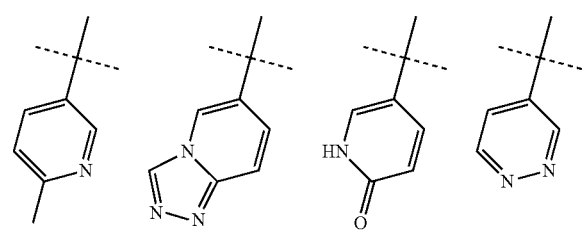

Some exemplary compounds that can be synthesized by any of Schemes A-P include but are not limited to those disclose in Table 1 (see Examples).

C. Methods of Using the Compositions Disclosed Herein

The present invention provides a method of inhibiting the activity of one or more kinases of ERK family (including ERK1 and ERK2) ERK in a cell comprising contacting the cell with an effective amount of one or more compounds disclosed herein. Inhibition of kinase activity can be assessed and demonstrated by a wide variety of ways known in the art. Non-limiting examples include (a) immunoblotting and immunoprecipitation with antibodies such as antiphosphotyrosine, anti-phosphoserine or anti-phosphothreonine antibodies that recognize phosphorylated proteins; (b) using antibodies that specifically recognize a particular phosphorylated form of a kinase substrate (e.g. anti-phospho ERK); (c) cell proliferation assays, such as but not limited to tritiated thymidine uptake assays, BrdU (5'-bromo-2'-deoxyuridine) uptake (kit marketed by Calibochem), MTS uptake (kit marketed by Promega), MTT uptake (kit marketed by Cayman Chemical), CyQUANT® dye uptake (marketed by Invitrogen).

Selective PI3Kα inhibition may also be determined by expression levels of the PI3Kα genes, its downstream signaling genes (for example by RT-PCR), or expression levels of the proteins (for example by immunocytochemistry, immunohistochemistry, Western blots) as compared to other PI3-kinases or protein kinases.

Kits and commercially available assays can be utilized for determining one or more of the above.

In some embodiments, the practice of a subject method involves a contacting step taking place in vitro. In other embodiments, the contacting step takes place in vivo.

Any of the compounds shown above may show a biological activity in an ERK inhibition assay of between about 0.5 nM and 25 μM ($IC_{50}$).

In some embodiments, one or more compounds of the invention may bind specifically to an ERK (MAPK) kinase or a protein kinase selected from the group consisting of Ras, Raf, JNK, ErbB-1 (EGFR), Her2 (ErbB-2), Her 3 (ErbB-3), Her 4 (ErbB-4), MAP2K1 (MEK1), MAP2K2 (MEK2), MAP2K3 (MEK3), MAP2K4 (MEK4), MAP2K5 (MEK5), MAP2K6 (MEK6), MAP2K7 (MEK7), CDK1, CDK2, CDK3, CDK4, CDK5, CDK6, CDK7, CDK8, CDK9, CDK11 and any other protein kinases listed in the appended tables and figures, as well as any functional mutants thereof.

In some embodiments, the IC50 of a compound of the invention for ERK1 and/or ERK2 is less than about 1 μM, less than about 100 nM, less than about 50 nM, less than about 10 nM, less than 1 nM or even less than about 0.5 nM. In some embodiments, the IC50 of a compound of the invention for ERK is less than about 1 μM, less than about 100 nM, less than about 50 nM, less than about 10 nM, less than nM or even less than about 0.5 nM. In some other embodiments, one or more compounds of the invention exhibit dual binding specificity and are capable of inhibiting an ERK kinase (e.g., ERK-1 kinase, ERK-2 kinase, etc.) as well as a protein kinase (e.g., Ras, Raf, Her-2, MEK1, etc.) with an IC50 value less than about 1 μM, less than about 100 nM, less than about 50 nM, less than about 10 nM, less than 1 nM or even less than about 0.5 nM, In some embodiments, one or more compounds of the invention may be capable of inhibiting kinases involved in the Ras-Raf-MEK-ERK pathway including, for example, Ras, Raf, JNK, ErbB-1 (EGFR), Her2 (ErB-2), Her3 (ErbB-3), Her4 (ErbB-4), MAP2K1 (MEK1), MAP2K2 (MEK2), MAP2K3 (MEK3), MAP2K4 (MEK4), MAP2K5 (MEK5), MAP2K6 (MEK6), MAP2K7 (MEK7), CDK1, CDK2, CDK3, CDK4, CDK5, CDK6, CDK7, CDK8, CDK9, CDK11, and functional mutants thereof, in some embodiments, the kinase is Ras, Raf, INK, ErbB-1 (EGFR), Her2 (ErbB-2), MAP2K1 (MEK1), CDK1, CDK2, CDK3, CDK4, CDK5, CDK6, or any other kinases listed in the Tables herein.

In still another embodiment, the compounds of the invention including but not limited to those shown in Table 1 selectively inhibit ERK 1 and/or ERK2 activity relative to one or more protein kinases including but not limited to serine/threonine kinase such as DNA-PK and mTor. Such selective inhibition can be evidenced by, e.g., the $IC_{50}$ value of the compound of the invention that can be $½$, $⅓^{rd}$, $¼^{th}$, $⅕^{th}$, $⅐^{th}$, $¹⁄₁₀^{th}$, $¹⁄₂₀^{th}$, $¹⁄₂₅^{th}$, $¹⁄₅₀^{th}$, $¹⁄₁₀₀^{th}$, $¹⁄₂₀₀^{th}$, $¹⁄₃₀₀^{th}$, $¹⁄₄₀₀^{th}$, $¹⁄₅₀₀^{th}$, $¹⁄₁₀₀₀^{th}$, $¹⁄₂₀₀₀^{th}$ or less as compared to that of a reference protein kinase. In some instances, the compounds of the invention including but not limited to those shown in Table 1 lack substantial cross-reactivity with at least about 100, 200, 300, or more protein kinases other than ERK1 or ERK2, The lack of substantial cross-reactivity with other non-ERK protein kinases can be evidenced by, e.g., at least 50%, 60%, 70%, 80%, 90% or higher kinase activity retained when the compound of the invention is applied to the protein kinase at a concentration of 1 μM, 5 μM, 10 μM or higher.

In some embodiments, one or more compounds of the invention selectively inhibits both ERK1 and ERK2 activity with an IC50 value of about 100 nM, 50 nM, 10 nM, 5 nM, 100 pM, 10 pM or even 1 pM, or less as ascertained in an in vitro kinase assay.

In some embodiments, one or more compounds of the invention competes with ATP for binding to ATP-binding site on ERK1 and/or ERK2. In some embodiments, one or more compounds of the invention binds to ERK1 and/or ERK2 at a site other than the ATP-binding site.

In some embodiments, one or more compounds of the invention are capable of inhibiting and/or otherwise modulating cellular signal transduction via one or more protein kinases or lipid kinases disclosed herein. For example, one or more compounds of the invention are capable of inhibiting or modulating the output of a signal transduction pathway. Output of signaling transduction of a given pathway can be measured by the level of phosphorylation, dephosphorylation, fragmentation, reduction, oxidation of a signaling molecule in the pathway of interest. In another specific embodiment, the output of the pathway may be a cellular or phenotypic output (e.g. modulating/inhibition of cellular proliferation, cell death, apoptosis, autophagy, phagocytocis, cell cycle progression, metastases, cell invasion, angiogenesis, vascularization, ubiquitination, translation, transcription, protein trafficking, mitochondrial function, golgi function, enodplasmic reticular function, etc). In some embodiments, one or more compounds of the invention are capable of, by way of example, causing apoptosis, causing cell cycle arrest, inhibiting cellular proliferation, inhibiting tumor growth, inhibiting angiogenesis, inhibiting vascularization, inhibiting metastases, and/or inhibiting cell invasion.

In some embodiments, one or more compounds of the invention causes apoptosis of said cell or cell cycle arrest. Cell cycle can be arrested at the G0/G1 phase, S phase, and/or G2/M phase by the subject compounds.

In some embodiments, one or more compounds of the invention including but not limited to the compounds listed above are capable of inhibiting cellular proliferation. For example, in some cases, one or more compounds of the invention listed in above may inhibit proliferation of tumor cells or tumor cell lines with a wide range of genetic makeup. In some cases, the compounds of the invention may inhibit PC3 cell proliferation in vitro or in an in vivo model such as a xenograft mouse model. In some cases, in vitro cultured PC3 cell proliferation may be inhibited with an $IC_{50}$ of less than 100 nM, 75 nM, 50 nM, 25 nM 15 nM, 10 nM, 5 nM, 3 nM 2 nM, 1 nM, 0.5 nM, 0.1 nM or less by one or more compounds of the invention listed above.

In some embodiments, proliferation of primary tumors derived from subjects (e.g. cancer patients) can be inhibited by a compound of the invention as shown by in vitro assays, or in vivo models (e.g. using the subjects' tumor cells for generating a xenograft mode). In some cases primary tumor cell line proliferation may be inhibited with an $IC_{50}$ of less than 100 nM, 75 nM, 50 nM, 25 nM, 15 nM, 10 nM, 5 nM, 3 nM, 2 nM, 1 nM, 0.5 nM, 0.1 nM or even less by one or more compounds of the invention listed in Table 1, in some cases, the average $IC_{50}$ of a compound of the invention for inhibiting a panel 10, 20, 30, 40, 50, 100 m more primary tumor cells may be about 200 nM, 100 nM, 75 nM, 50 nM, 25 nM, 15 nM, 10 nM, 5 nM, 3 nM, 2 nM, 1 nM, 0.5 nM, 0.1 nM or even less. The tumor cells that can be inhibited by the compounds of the present invention include but are not limited to pancreatic, renal (kidney), bone, nasopharyngeal, gastric, stomach, ovarian, oral, breast, blood, prostate, rectal, colon, colorectal, blial, neural, lung, and dermal cells.

In some embodiments, the compounds of the invention are effective in blocking cell proliferation signals in cells. In some cases, cell proliferation signaling may be inhibited by one or more compounds of the invention including but not limited to those shown in Table 1 as evidenced by Western blot analysis of phosphorylation of proteins such as FOXO1 (phosphorylation at T24/3a T32), GSK3β (phosphorylation at S9), PRAS40 (phosphorylation at T246), or MAPK phosphorylation. In some cases, the compounds of the invention can inhibit phosphorylation of signaling proteins and suppress proliferation of cells containing these signaling proteins but are resistant to existing chemotherapeutic agents including but not limited to rapamycin, Gleevec, dasatinib, alkylating agents, antimetabolites, anthracyclines, plant alkaloids, topoisomerase inhibitors and other antitumor agents disclosed herein.

In some embodiments, one or more compounds of the invention including but not limited to those listed above may cause cell cycle arrest. In some cases, cells treated with one or more compounds of the invention including but not limited to those listed above, may arrest or take longer to proceed through one or more cell cycle stages such as $G_0/G_1$, S, or $G_2/M$. For example, cells treated with one or more compounds of the invention may arrest or take longer to proceed through the $G_0/G_1$ cell cycle stage. In some cases, about 35%, 40%, 50%, 55%, 60%, 65%, 70% or more of cells treated with one or more compounds of the invention may be in the $G_0/G_1$ cell cycle stage. In some cases, cells exhibiting cell cycle arrest in the $G_0/G_1$ cell cycle stage in response to treatment with the compounds of the invention are tumor cells or rapidly dividing cells. In some cases, the compounds of the invention affect a comparable or a greater degree of $G_0/G_1$ arrest as compared to doxorubicin.

In some embodiments, cell signaling in tumor cells xenografted into female athymic nude mice may be inhibited by one or more compounds of the invention such as the compounds listed above. In some cases, cell signaling may be inhibited by one or more compounds of the invention as evidenced by western blot detection of phosphorylation of ERK kinase(s) extracted from homogenized tumors. In some cases, inhibition of phosphorylation may be comparable to or greater than that provided by known kinase inhibitors that also inhibit one or more isoforms of ERK under the conditions tested.

In some embodiments, the compounds of the invention including but not limited to the compounds listed above, cause a reduction in tumor volume of xenograft tumors in female nude athymic mice. For example, treatment with one or more compounds of the invention results in a reduction in the growth or tumor volume caused by engraftment of A375 (mutant B-Raf V600E), LOX (mutant B-Raf V600E) and Colo-205 (mutant B-Raf V600E), PANC-1 (mutant K-Ras G12D), MiaPaca-2 (mutant K-Ras G12C), HCT116 (mutant K-Ras G13D), H441 (mutant K-Ras G12V), H23 (mutant K-Ras G12C), MDA-MB-231 (mutant K-Ras G13D)) and LS1034 (mutant N-Ras) tumor cells in nude mice. The compounds of the invention may be administered orally, subcutaneously, or intravenously, or any other compound administration methods provided herein. In some cases, the compounds are administered once a week, every other day, once a day, twice a day, three times a day, four times a day or more. In some cases, 0.01 mg/kg of compound is administered, 0.05 mg/kg, 0.1 mg/kg, 0.2 mg/kg, 0.4 mg/kg, 0.5 mg/kg, mg/kg, 1.5 mg/kg, 2 mg/kg, 3 mg/kg, 4 mg/kg, 5 mg/kg, 7.5 mg/kg, 10 mg/kg, 100 nag/kg or more compound is administered at a time. In some cases, a significant reduction in tumor volume may be detected within 5, 10, 15, 20, 25, or 30 days of tumor engraftment.

D. Methods of Treatment

The invention also provides methods of using the compounds or pharmaceutical compositions of the present invention to treat disease conditions, including but not limited to conditions implicated by ERK1, ERK2, Ras, Raf and/or MEK kinase malfunction.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof.

In some embodiments, the method relates to the treatment of a disorder such as cancer, bone disorder, inflammatory disease, immune disease, nervous system disease, metabolic disease, respiratory disease, and cardiac disease.

In some embodiments, the method relates to the treatment of cancer such as acute myeloid leukemia, myelodysplastic syndrome (MDS), thymus, brain, lung (NSCLC and SCLC), squamous cell, seminomas, melanoma, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, endometrial, colorectal, esophageal, testicular, gynecological, thyroid, CNS, PNS, AIDS related (e.g. Lymphoma and Kaposi's Sarcoma) or Viral-Induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)). In some embodiments, the cancer is melanoma or colorectal cancer.

In some embodiments, the method relates to the treatment of a disease or a condition in a subject with a mutation in the Ras or Raf gene. In some cases, the disease is a cancer and the mutation is in the Ras gene. For example, the disease can be a melanoma in a subject with an N-Ras mutation. Alternatively, the disease can be lung cancer or colon cancer in a subject with a K-Ras mutation.

In some embodiments, the method relates to the treatment of a disease or a condition that is resistant to a Ras, Raf and/or MEK inhibitor. For example, the disease can be a melanoma that is resistant to a B-Raf and/or MEK inhibitor.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof diseases associated with malfunctioning of one or more types of ERK including but not limited to acute disseminated encephalomyelitis (ADEM), Addison's disease, antiphospholipid antibody syndrome (APS), aplastic anemia, autoimmune hepatitis, coeliac disease, Crohn's disease. Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit ERK1 and/or ERK2 as compared to all other kinases in the Ras/Raf/MEK/ERK pathway. Such selective inhibition of ERK1 and/or ERK2 may be advantageous for treating any of the diseases or conditions described herein. For example, selective inhibition of ERK2 may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of ERK2 may further provide for a reduction in the inflammatory or undesirable immune response without a concomitant reduction in the ability to reduce a bacterial, viral, and/or fungal infection. Selective inhibition of both ERK1 and ERK2 may be advantageous for inhibiting the inflammatory response in the subject to a greater degree than that would be provided for by inhibitors that selectively inhibit ERK1 or ERK2 alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold 100-fold, 250-fold, 500-fold, 750-fold or about 1000-fold or more.

In one aspect, one of more of the subject methods are effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 10%, 40%, 50%, 60%, 75%, 80%, 90% or more.

In other embodiments, the present invention provides methods of using, the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat, obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating diseases related to vasculogenesis or angiogenesis in a mammal that comprises administering to said mammal a therapeutically effective amount of a compound of the invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Subjects that can be treated with compounds of the invention, or pharmaceutically acceptable salt, ester, prodrug, solvate, hydrate or derivative of said compounds, according to the methods of this invention include, for example, subjects that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following; an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large lymphoma, B-cell immunoblastic lymphoma and small non-cleaved cell lymphoma; Kaposi's Sarcoma; viral-induced cancers including hepatitis B virus (HBV); hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer The invention also relates to a method of treating diabetes in a mammal that comprises administering to said mammal a therapeutically effective amount of a compound of the invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chrome glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (CBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universals, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more compounds of the invention or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film. It is contemplated that all local routes to the eye may be used including topical, subconjunctival, perocular, retrobulbar, subtenon, intracameral, intravitreal, intraocular, subretinal, juxtascleral and suprachoroidal administration. Systemic or parenteral administration may be feasible including but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylanmmonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnvristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammoniumr bromide, tetradecyltrimethylammonium bromide, dodecyitrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polyoxyl-40 hydrogenated castor oil, polyoxyl-60 hydrogenated castor oil or polyoxyl-100 hydrogenated castor oil.

The invention further provides methods of modulating a ERK kinase activity by contacting the kinase with an effective amount of a compound of the invention. Modulation can be inhibiting or activating kinase activity. In some embodiments, the invention provides methods of inhibiting kinase activity by contacting the kinase with an effective amount of a compound of the invention in solution. In some embodiments, the invention provides methods of inhibiting the kinase activity by contacting a cell, tissue, organ that express the kinase of interest. In some embodiments, the invention provides methods of inhibiting kinase activity in subject including but not limited to rodents and mammal (e.g., human) by administering into the subject an effective amount of a compound of the invention. In some embodiments, the percentage of inhibiting exceeds 25%, 30%, 40%, 50%, 60%, 70%, 80%, or 90%.

In some embodiments, the kinase is selected from the group consisting of ERK, including different isoforms such as ERK1 and ERK2; Ras; Raf; JNK; ErbB-1 (EGFR); Her2 (ErbB-2); Her 3 (ErbB-3); Her 4 (ErbB-4); MAP2K1 (MEK1); MAP2K2 (MEK2); MAP2K3 (MEK3); MAP2K4 (MEK4); MAP2K5 (MEK5)' MAP2K6 (MEK6); MAP2K7 (MEK7); CDK1; CDK2; CDK3; CDK4; CDK5: CDK6; CDK7; CDK8; CDK9: CDK11.

The invention further provides methods of modulating ERK activity by contacting ERK with an amount of a compound of the invention sufficient to modulate the activity of ERK. Modulate can be inhibiting or activating ERK activity. In some embodiments, the invention provides methods of inhibiting ERK by contacting ERK with an amount of a compound of the invention sufficient to inhibit the activity of ERK. In some embodiments, the invention provides methods of inhibiting ERK activity in a solution by contacting said solution with an amount of a compound of the invention sufficient to inhibit the activity of ERK in said solution. In some embodiments, the invention provides methods of inhibiting ERK activity in a cell by contacting said cell with an amount of a compound of the invention sufficient to inhibit the activity of ERK in said cell. In some embodiments, the invention provides methods of inhibiting ERK activity in a tissue by contacting said tissue with an amount of a compound of the invention sufficient to inhibit the activity of ERK in said tissue. In some embodiments, the invention provides methods of inhibiting ERK activity in an organism by contacting said organism with an amount of a compound of the invention sufficient to inhibit the activity of ERK in said organism. In some embodiments, the invention provides methods of inhibiting ERK activity in an animal by contacting said animal with an amount of a compound of the invention sufficient to inhibit the activity of ERK in said animal. In some embodiments, the invention provides methods of inhibiting ERK activity in a mammal by contacting said mammal with an amount of a compound of the invention sufficient to inhibit the activity of ERK in said mammal. In some embodiments, the invention provides methods of inhibiting ERK activity in a human by contacting said human with an amount of a compound of the invention sufficient to inhibit the activity of ERK in said human. The present invention provides methods of treating a disease mediated by ERK activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

In one aspect, the compounds or pharmaceutical compositions of the invention may present synergistic or additive efficacy when administered in combination with agents that inhibit IgE production or activity. Such combination can reduce the undesired effect of high level of IgE associated with the use of one or more ERK inhibitors, if such effect occurs. This may be useful in treatment of autoimmune and inflammatory disorders (AIID) such as rheumatoid arthritis.

For treatment of autoimmune diseases, the compounds of the invention or pharmaceutical compositions can be used in combination with commonly prescribed drugs including but not limited to Enbrel®, Remicade®, Humira®, Avonex®, and Rebif®. For treatment of respiratory diseases, the compounds of the invention or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly, They range from aspirin at very low dose which prevents platelets from sticking, to heparin/coumadin.

In another aspect, this invention also relates to methods and pharmaceutical compositions for inhibiting abnormal cell growth in a mammal which comprises an amount of a compound of the invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard: nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside: aminolevulinic acid; amsacrine; bestrabucil: bisantrene; edatraxate; defofamine; demecolcine: diaziquone: elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane: sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France): retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston): and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-1); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

This invention further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169. Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of I-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999). Great Britain Patent Application No. 9912961.1 (filed Jun. 3, 1999). U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine. LY204002, N6-mercaptopurine riboside, and vinblastine. In addition, antisense or siRNA that inhibits expression of proteins including but not limited to ATG5 (which are implicated in autophagy), may also be used.

The invention also relates to a method of and to a pharmaceutical composition for treating a cardiovascular disease in a mammal which comprises an amount of a compound of the invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents. e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, antiinflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds described herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations. e.g. diltiazem; antiallergics, e.g. cromoglycate, ketotifen or nedocronmil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone: antitussives, e.g. noscapine: bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones. e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs: inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, 1-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, f-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, mycobacterium avium complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuxinmab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a compound of the invention may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In the separate administration protocol, a compound of the invention and any of the agents described above may be administered a few minutes apart, or a few hours apart, or a few days apart.

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention is administered in a composition that comprises one or more agents, and the agent has a shorter half-life than the compound of the invention, unit dose forms of the agent and the compound of the invention may be adjusted accordingly.

The compounds described herein can be used in combination with other agents disclosed herein or other suitable agents, depending on the condition being treated. Hence, in some embodiments, the one or more compounds of the invention will be co-administered with other agents as described above. In some embodiments, the other agent is an anti-cancer agent. When used in combination therapy, the compounds described herein may be administered with the second agent simultaneously, or separately. The administration in combination can include simultaneous administration of the two agents in the same dosage form, simultaneous administration in separate dosage forms, or separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In the separate administration protocol, a compound of the invention and any of the agents described above may be administered a few minutes apart, or a few hours apart, or a few days apart.

E. Pharmaceutical Compositions and Kits

The invention provides a pharmaceutical composition comprising one or more compounds disclosed herein. In some embodiments the invention provides pharmaceutical compositions for the treatment of disorders such as hyperproliferative disorders including but not limited to cancers such as acute myeloid leukemia, lymphoma, thymus, brain, lung (NSCLC and/or SCLC), squamous cell, skin, eye, retinoblastoma, intraocular melanoma, mesothelioma, mediastinum, oral cavity and oropharyngeal, bladder, gastric, stomach, pancreatic, bladder, breast, cervical, head, neck, renal, kidney, liver, hepatobiliary system, small intestine, colon, rectum, anus, prostate, colorectal, endometrial, urethra, esophageal, testicular, gynecological, penis, testis, ovarian, endocrine system, skin, thyroid, CNS, PNS, AIDS related AIDS-Related (e.g. Lymphoma and Kaposi's Sarcoma), other viral-induced cancers, sarcomas of the soft tissue and bone, and melanomas of cutaneous and intraocular origin. Cancers includes solid tumors as well as hematological malignancies. In addition, a cancer at any stage of progression can be treated, such as primary, metastatic, and recurrent cancers.

In some embodiments, said pharmaceutical composition is for the treatment of a non-cancerous hyperproliferative disorder such as a benign tumor, for example but not limited to, for the treatment of a benign hyperplasia of the skin (e. g., psoriasis), breast, lung, kidney, pancreas, restenosis, or prostate (e. g., benign prostatic hypertrophy (BPH)).

In some embodiments, the invention provides pharmaceutical compositions for treating diseases or conditions related to an undesirable, over-active, harmful or deleterious immune response in a mammal. Such undesirable immune response can be associated with or result in e.g. asthma, emphysema, bronchitis, psoriasis, allergy, anaphylaxis, auto-immune diseases, rheumatoid arthritis, graft versus host disease, and lupus erythematosus. The pharmaceutical compositions of the present invention can be used to treat other respiratory diseases including but not limited to disease affecting the lobes of the lung, the pleural cavity, bronchial tubes, trachea, upper respiratory tract, or the nerves and muscle responsible for breathing.

The invention also provides compositions for the treatment of multiorgan failure.

The invention also provides compositions for the treatment of liver diseases (including diabetes), pancreatitis, gall bladder disease (including gallstones), or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal, which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention further provides compositions for the treatment of disorders involving platelet aggregation or platelet adhesion, including but not limited to Bernard-Soulier syndrome, Glanzmann's thrombasthenia, Scott's syndrome, von Willebrand disease. Hermansky-Pudlak Syndrome, and Gray platelet syndrome.

In some embodiments, compositions are provided for treating a disease which is skeletal muscle atrophy, skeletal or muscle hypertrophy. The invention further provides compositions for the treatment of disorders that include but are not limited to cancers as discussed herein, transplantation-related disorders (e.g., lowering rejection rates, graft-versus-host disease, etc.), muscular sclerosis (MS), allergic disorders (e.g. arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders). The disorders also include hamartoma syndromes, such as tuberous sclerosis and Cowden Disease (also termed Cowden syndrome and multiple hamartoma syndrome)

In some embodiments, the invention provides a pharmaceutical composition for treating ophthalmic disorders. The composition is formulated for ocular administration and it contains an effective amount of a compound of the present invention and a pharmaceutical excipient suitable for ocular administration. Pharmaceutical compositions of the invention suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds provided in the pharmaceutical compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds provided in the pharmaceutical compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds provided in the pharmaceutical compositions of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds provided in the pharmaceutical compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds provided in the pharmaceutical compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg per day, from 0.1 to 500 mg, from 0.5 to 100 mg, from 1 to 50 mg per day, from 2 to 40 mg per day, from 3 to 30 mg per day, from 4 to 20 mg per day, and from 5 to 10 mg per day are examples of dosages that may be used. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (e.g., a compound) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However. HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins: lysolecithins and hydrogenated lysolecithins; phospholipids and derivatives thereof; lysophospholipids and derivatives thereof; carnitine fatty acid ester salts; salts of alkylsulfates: fatty acid salts; sodium docusate; acyl lactylates; mono- and di-acetylated tartaric acid esters of mono- and di-glycerides; succinylated mono- and di-glycerides; citric acid esters of mono- and di-glycerides: and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolanmine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides: alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters: hydrophilic transesterification products of a polyol with at least one member of the group consisting of glycerides, vegetable oils, hydrogenated vegetable oils, fatty acids, and sterols; polyoxyethylene sterols, derivatives, and analogues thereof: polyoxyethylated vitamins and derivatives thereof; polyoxyethylene-polyoxypropylene block copolymers; and mixtures thereof: polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate. PEG-20 laurate. PEG-32 laurate. PEG-32 dilaurate, PEG-12 oleate, PEG-15 oleate, PEG-20 oleate. PEG-20 dioleate, PEG-32 oleate. PEG-200 oleate, PEG-400 oleate. PEG-15 stearate, PEG-32 distearate, PEG-40 stearate, PEG-100 stearate, PEG-20 dilaurate. PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate. PEG-40 glyceryl laurate, PEG-40 palm kernel oil. PEG-50 hydrogenated castor oil, PEG-40 castor oil, PEG-35 castor oil. PEG-60 castor oil, PEG-40 hydrogenated castor oil, PEG-60 (hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol. PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether. POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters: acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, 8-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobronmic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001, 139. Such patches may be constructed for continuous, pulsatile, or on demand delivery of pharmaceutical agents.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver Formulation in an appropriate manner.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also are administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect. e.g. by dividing such larger doses into several small doses for administration throughout the day.

In some embodiments, a compound of the invention is administered in a single dose. Typically, such administration can be by injection, e.g., intravenous injection, in order to introduce the agent quickly. However, other routes known in the art or disclosed herein may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744: U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

EXAMPLES

The examples and preparations provided below further illustrate and exemplify the compounds of the present invention and methods of using and preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Example 1. Synthesis of (6-benzyl-3-(pyridin-4-yl)-1,5,6,8-tetrahydro-7H-pyrazolo[4,3-g]quinazolin-7-one)

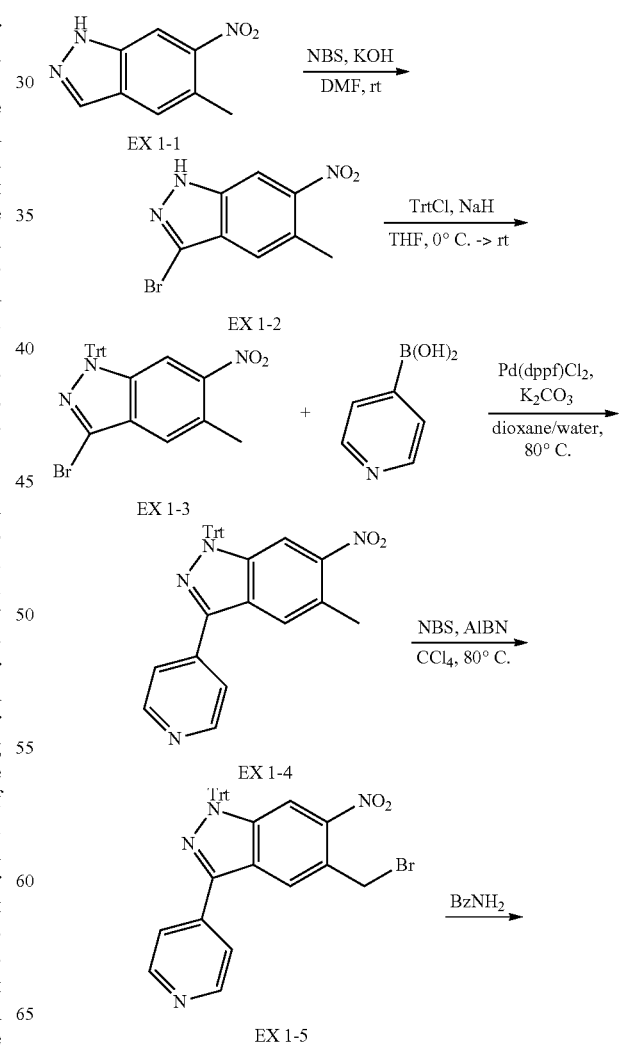

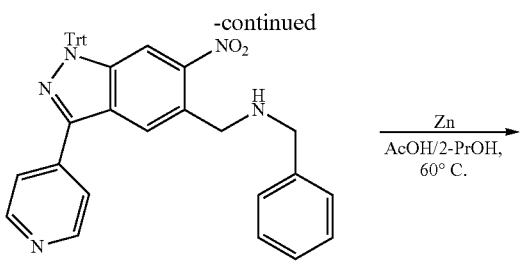

EX 1-6

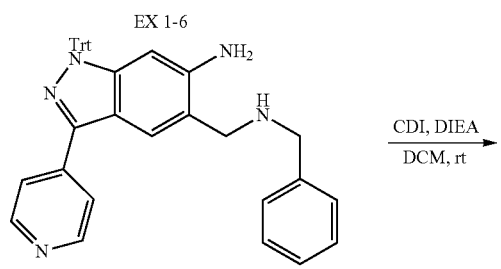

EX 1-7

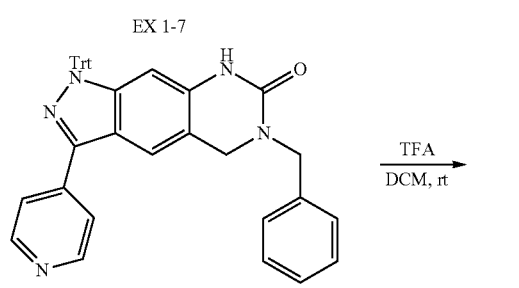

EX 1-8

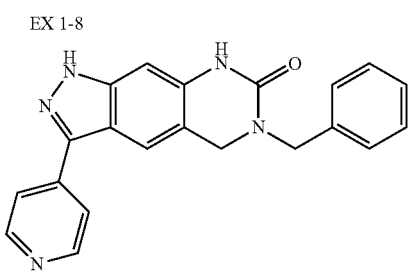

1

3-bromo-5-methyl-6-nitro-1H-indazole (EX 1-2)

To a stirred solution of 5-methyl-6-nitro-1H-indazole (1.77 g, 10 mmol) in 20 mL of dry DMF at room temperature, NBS (2.14 g, 12 mmol) was added followed by KOH (1.12 g, 20 mmol). The reaction mixture was stirred at the same temperature overnight. The reaction mixture was diluted with ethyl acetate, washed with water and saturated NH$_4$Cl aqueous solution. The organic solution was dried over anhydrous MgSO$_4$, filtered and concentrated in vacuo to give the desired product (3.1 g) as a brown solid, which was used in the next step without further purification.

3-bromo-5-methyl-6-nitro-1-trityl-1H-indazole (EX 1-3)

To a stirred solution of 3-bromo-5-methyl-6-nitro-1H-indazole (2.43 g, 9.5 mmol) in 30 mL of dry THF at 0° C., NaH (60% in mineral oil, 0.76 g, 19 mmol) was added and the reaction mixture was stirred at the same temperature for 30 min. TrtCl (3.97 g, 14.25 mmol) was added. The reaction mixture was stirred at room temperature for 6 h. Solvent was removed. The residue was dissolved in ethyl acetate and washed with brine. The organic solution was dried over anhydrous MgSO$_4$, filtered and concentrated in vacuo. The residue was purified by Biotage (25 g cartridge, 0-30% ethyl acetate in hexane) to afford the desired product (4.5 g, 95% yield) as a yellow solid.

5-methyl-6-nitro-3-(pyridin-4-yl)-1-trityl-1H-indazol (EX 1-4)

To a solution of 3-bromo-5-methyl-6-nitro-1-trityl-1H-indazole (2.0 g, 4.0 mmol) and pyridin-4-ylboronic acid (736 mg, 6.0 mmol) in 30 mL of 4:1 mixture of dioxane and water at room temperature, PdCl$_2$(dppf) (327 mg, 0.40 mmol) and K$_2$CO$_3$ (1.10 g, 8.0 mmol) were added. The reaction mixture was degassed and backfilled with nitrogen. The reaction mixture was stirred at 80° C. overnight. Solvent was removed and the residue was taken with ethyl acetate. The mixture was filtered through a pad of Celite and the filtrate was washed with brine. The organic solution was dried over anhydrous MgSO$_4$, filtered and concentrated. The residue was purified on Biotage (25 g cartridge, 10-80% ethyl acetate in hexane) to give the desired product (1.12 g, 56% yield). ESI-MS m/z: 497 [M+H]$^+$ N-benzyl-1-(6-nitro-3-(pyridin-4-yl)-1-trityl-1H-indazol-5-yl)methenamine (EX 1-6)

To a solution of 5-methyl-6-nitro-3-(pyridin-4-yl)-1-trityl-1H-indazole (222 mg, 0.45 mmol) and NBS (239 mg, 1.35 mmol) in 10 mL of CCl$_4$ at room temperature, AIBN (22 mg, 0.30 mmol) was added. The reaction mixture was stirred at 80° C. for 2 h. The mixture was cooled down to room temperature, and then benzylamine (1.64 mL, 15 mmol) was added. The resulting mixture was stirred at the same temperature for 3 h. Solvent was removed and the residue was taken with ethyl acetate, washed with saturated NH$_4$Cl aqueous solution and brine. The organic solution was dried over anhydrous MgSO$_4$, filtered and concentrated in vacuo. The residue was purified by prep-HPLC to give the desired product (58 mg, 21% yield). ESI-MS m/z: 602 [M+H]$^+$.

5-((benzylamino)methyl)-3-(pyridin-4-yl)-1-trityl-1H-indazol-6-amine (EX 1-7)

To a solution of N-benzyl-1-(6-nitro-3-(pyridin-4-yl)-1-trityl-1H-indazol-5-yl)methanamine (60 mg, 0.10 mmol) in 3 mL of 1:5 AcOH/2-PrOH mixture at room temperature, Zn dust (130 mg, 2.0 mmol) was added. The reaction mixture was stirred at 60° C. for 3 h. The reaction mixture was cooled to room temperature. Solid was removed by filtration and the filtrate was concentrated in vacuo. The residue was purified by prep-HPLC to give the desired product (36 mg, 63% yield). ESI-MS m/z: 572 [M+H]$^+$.

6-benzyl-3-(pyridin-4-yl)-1-trityl-1,5,6,8-tetrahydro-7H-pyrazolo[4,3-g]quinazolin-7-one (EX 1-8)

To a solution of 5-((benzylamino)methyl)-3-(pyridin-4-yl)-1-trityl-1H-indazol-6-amine (24 mg, 0.04 mmol) in 3 mL of DCM, Et$_3$N (42 µL, 0.24 mmol) was added followed by CDI (65 mg, 0.40 mmol). The reaction mixture was stirred at room temperature for 3 h. The mixture was concentrated in vacuo and the residue was used in the next step without further purification. ESI-MS m/z: 598 [M+H]$^+$.

6-benzyl-3-(pyridin-4-yl)-1,5,6,8-tetrahydro-7H-pyrazolo[4,3-g]quinazolin-7-one (1)

To a solution of 6-benzyl-3-(pyridin-4-yl)-1-trityl-1,5,6,8-tetrahydro-7H-pyrazolo[4,3-g]quinazolin-7-one (crude obtained from previous step) in 4 mL of DCM, 1 mL of TFA was added. The reaction mixture was stirred at room temperature for 30 min. Solvent was removed and the residue was purified by prep-HPLC to give the desired product (8 mg, 56% yield, 2 steps). $^1$H NMR (400 MHz, DMSO-d6) δ: 13.25 (br, 1H), 9.62 (s, 1H), 8.63 (dd, J=1.4, 4.6 Hz, 1H), 7.92-7.95 (m, 3H), 7.29-7.37 (m, 5H), 6.98 (s, 1H), 4.60 (s, 2H), 4.45 (s, 2H). ESI-MS m/z: 356.0 [M+H]$^+$.

Example 2. Synthesis of ((R)-3-(2-methylpyridin-4-yl)-6-(1-phenylethyl)-5,6-dihydro-1H-pyrazolo[4,3-g]quinazolin-7(8H)-one)

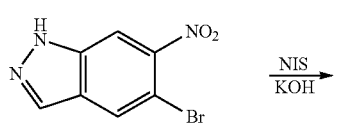

EX 2-1

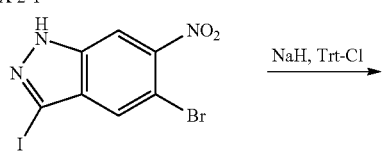

EX 2-2

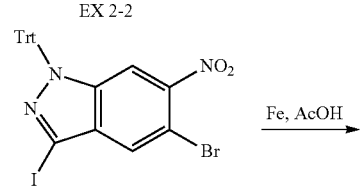

EX 2-3

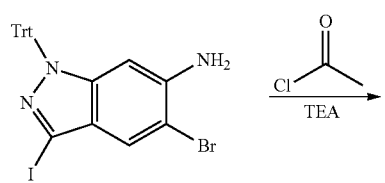

EX 2-4

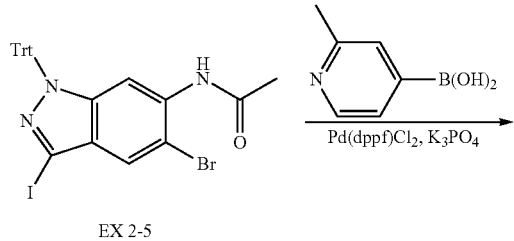

EX 2-5

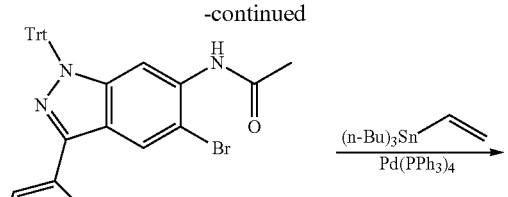

EX 2-6

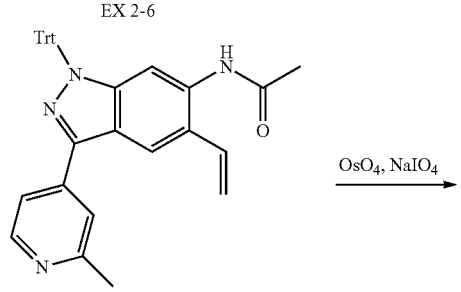

EX 2-7

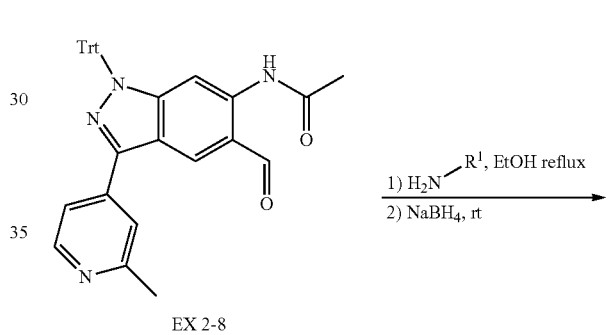

EX 2-8

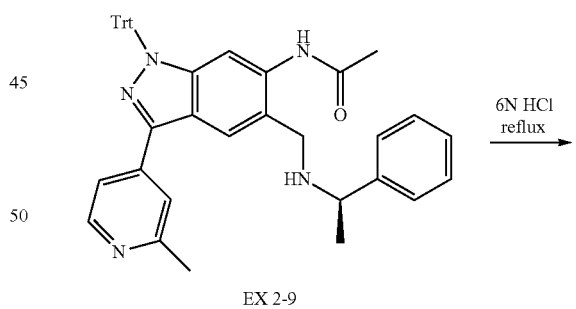

EX 2-9

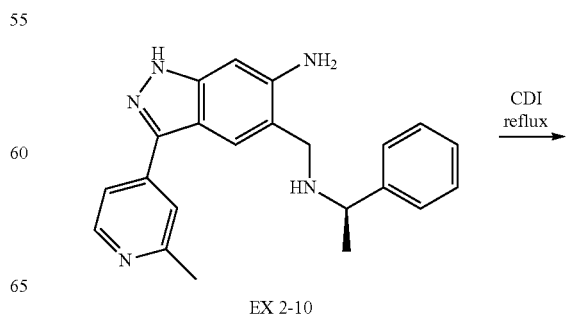

EX 2-10

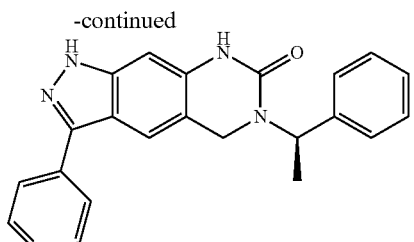

5-bromo-3-iodo-6-nitro-1H-indazole (EX 2-2)

To a stirred mixture of 5-bromo-6-nitro-1H-indazole (3.5 g, 14.5 mmol) in DMF (50 mL) at room temperature, KOH (2.84 g, 50.6 mmol, 3.5 eq) was added and the resulting mixture was stirred at room temperature for 10 min. NIS (3.58 g, 15.91 mmol, 1.1 eq) was added to the reaction mixture. The resulting mixture was stirred at room temperature for 10 h. The reaction mixture was poured into water (100 mL) and extracted with ethyl acetate (200 mL×3). The combined organic layers were washed with $H_2O$ (200 mL×3), dried over anhydrous $Na_2SO_4$, filtered and concentrated in vacuo to afford the desired product (4.2 g, 79% yield) as a yellow solid. The crude product was used directly in the next step without further purification.

5-bromo-3-iodo-6-nitro-1-trityl-1H-indazole (EX 2-3)

To a stirred mixture of 5-bromo-3-iodo-6-nitro-1H-indazole (1 g, 2.7 mmol) in THF (10 mL) at room temperature, NaH (162 mg, 4.08 mmol) was added and the resulting reaction mixture was stirred at room temperature for 30 min under a nitrogen atmosphere. To this mixture, Trt-Cl (912 mg, 3.27 mmol) was added. The resulting mixture was stirred at room temperature for 2 h. The reaction mixture was poured into water (30 mL) and extracted with ethyl acetate (80 mL×3). The combined organic layer was washed with brine, dried over anhydrous $Na_2SO_4$, filtered and concentrated in vacuo. The residue was purified by flash column chromatography on silica gel (5-20% ethyl acetate/petroleum ether) to afford the desired product (1.6 g, 96% yield) as a yellow solid.

5-bromo-3-iodo-1-trityl-1H-indazol-6-amine (EX 2-4)

To a stirred mixture of 5-bromo-3-iodo-6-nitro-1-trityl-1H-indazole (1.15 g, 1.89 mmol) in HOAc/$H_2O$ (16 mL/4 mL) at 60° C., Fe powder (530 mg, 9.46 mmol) was added. The reaction mixture was stirred at 60° C. for 6 h, and then was allowed to cool to room temperature. The reaction mixture was filtered through silica gel and rinsed with ethyl acetate (100 mL). The combined filtrate was extracted with ethyl acetate (80 mL×3). The combined organic layer was washed with $H_2O$ (80 mL×3), dried over anhydrous $Na_2SO_4$, filtrated and concentrated in vacuo to afford the desired product (750 mg, 69% yield) as a yellow solid. The crude product obtained was used directly in the next step without further purification.

N-(5-bromo-3-iodo-1-trityl-1H-indazol-6-yl)acetamide (EX 2-5)

To a stirred mixture of 5-bromo-3-iodo-1-trityl-1H-indazol-6-amine (346 mg, 0.6 mmol) in DCM (10 mL) at 0° C. $Et_3N$ (91 mg, 0.9 mmol) was added. The mixture was stirred at 0° C. for 30 min, and then a solution of acetyl chloride (61 mg, 0.78 mmol) in DCM (5 mL) was added dropwise. The resulting mixture was stirred at room temperature for 3 h. The reaction mixture was poured into water (20 mL) and extracted with DCM (50 mL×3). The combined organic layer was washed with brine (50 mL×3), dried over anhydrous $Na_2SO_4$, filtered and concentrated in vacuo to afford the desired product (350 mg, 95% yield) as a yellow solid. The product obtained was used directly in the next step without further purification.

N-(5-bromo-3-(2-methylpyridin-4-yl)-1-trityl-1H-indazol-6-yl)acetamide (EX 2-6)

To a mixture of N-(5-bromo-3-iodo-1-trityl-1H-indazol-6-yl)acetamide (173 mg, 0.278 mmol) and 2-methylpyridin-4-ylboronic acid (42 mg, 0.306 mmol) in 1,4-dioxane/$H_2O$ (8 mL/2 mL), $PdCl_2dppf$ (31 mg, 0.042 mmol) and $K_3PO_4$ $3H_2O$ (222 mg, 0.834 mmol) were added sequentially. The resulting mixture was degassed and back-filled with argon three times and then stirred at 85° C. for 4 h. The mixture was allowed to cool to room temperature. The reaction mixture was poured into water (20 mL) and extracted with ethyl acetate (60 mL×3). The combined organic layer was washed with brine (60 mL×3), dried over anhydrous $Na_2SO_4$, filtered and concentrated in vacuo. The residue was purified by flash column chromatography on silica gel (10-40% ethyl acetate/petroleum ether) to afford the desired product (46 mg, 35% yield) as a white solid.

N-(3-(2-methylpyridin-4-yl)-1-trityl-5-vinyl-1H-indazol-6-yl)acetamide (EX 2-7)

To A mixture of N-(5-bromo-3-(2-methylpyridin-4-yl)-1-trityl-1H-indazol-6-yl)acetamide (46 mg, 0.0785 mmol) and $Pd(PPh_3)_4$ (18 mg, 0.016 mmol) in toluene (6 mL), Tributyl (vinyl)tin (30 mg, 0.094 mmol) was added. The resulting mixture was degassed and back-filled with argon three times and then stirred at 115° C. for 4 h. The reaction mixture was allowed to cool to room temperature, poured into water (20 mL) and then extracted with ethyl acetate (60 mL×3). The combined organic layer was washed with brine (60 mL×3), dried over anhydrous $Na_2SO_4$, filtered and concentrated in vacuo. The residue was purified by flash column chromatography on silica gel (20-50% ethyl acetate/petroleum ether) to afford the desired product (30 mg, 90% yield) as a white solid.

N-(5-formyl-3-(2-methylpyridin-4-yl)-1-trityl-1H-indazol-6-yl)acetamide (EX 2-8)

To a stirred mixture of N-(3-(2-methylpyridin-4-yl)-1-trityl-5-vinyl-1H-indazol-6-yl)acetamide (28 mg, 0.0524 mmol) in THF (4 mL) and $H_2O$ (1 mL) at 0° C., Osmium tetroxide (5 mg) was added and the resulting mixture was stirred at 0° C. for 1 h. To this mixture, sodium periodate (56 mg, 0.262 mmol) was added. The resulting mixture was stirred at room temperature overnight. The mixture was poured into water (10 mL) and extracted with ethyl acetate (50 mL×3). The combined organic layer was washed with brine (50 mL×3), dried over anhydrous $Na_2SO_4$, filtered and concentrated in vacuo. The residue was purified by flash column chromatography on silica gel (30-60% ethyl acetate/petroleum ether) to afford the desired product (20 mg, 80% yield) as a white solid.

(R)—N-(3-(2-methylpyridin-4-yl)-5-((1-phenylethylamino)methyl)-1-trityl-1H-indazol-6-yl)acetamide (EX 2-9)

A mixture of N-(5-formyl-3-(2-methylpyridin-4-yl)-1-trityl-1H-indazol-6-yl)acetamide (84 mg, 0.157 mmol) and (R)-1-phenylethanamine (21 mg, 0.172 mmol) in EtOH was stirred at reflux for 3 h. The mixture was allowed to cool to room temperature, and then NaBH$_4$ (12 mg, 0.31 mmol) was added. The reaction mixture was stirred for 4 h, poured into water (10 mL) and extracted with ethyl acetate (40 mL×3). The combined organic layer was washed with brine (40 mL×3), dried over anhydrous Na$_2$SO$_4$, filtered and concentrated in vacuo to afford the desired product (80 mg, 65% yield) as a white solid. The product obtained was used directly in the next step without further purification.

(R)-3-(2-methylpyridin-4-yl)-5-((1-phenylethylamino)methyl)-1H-indazol-6-amine (EX 2-10)

A mixture of (R)—N-(3-(2-methylpyridin-4-yl)-5-((1-phenylethylamino)methyl)-1-trityl-1H-indazol-6-yl)acetamide (40 mg, 0.062 mmol) in 6N HCl (5 mL) was stirred at reflux for 5 h. The mixture was allowed to cool to 0° C., K$_2$CO$_3$ was added to adjust the PH to 9. The mixture was extracted with ethyl acetate (40 mL×3). The combined organic layer was washed with brine (40 mL×3), dried over anhydrous Na$_2$SO$_4$, filtered and concentrated in vacuo to afford the desired product (30 mg, 85% yield) as a white solid. The product obtained was used directly in the next step without further purification.

(R)-3-(2-methylpyridin-4-yl)-6-(1-phenylethyl)-5,6-dihydro-1H-pyrazolo[4,3-g]quinazolin-7(8H)-one (2)

To a mixture of (R)-3-(2-methylpyridin-4-yl)-5-((1-phenylethylamino)methyl)-1H-indazol-6-amine (30 mg, 0.084 mmol) in THF (5 mL), CDI (21 mg, 0.12 mmol) was added. The resulting mixture was stirred at 70° C. for 5 h. The mixture was cooled to room temperature, poured into water (10 mL) and extracted with ethyl acetate (30 mL×3). The combined organic layer was washed with brine, dried over anhydrous Na$_2$SO$_4$, filtered and concentrated in vacuo. The residue was purified by flash column chromatography on silica gel (2-10% MeOH/DCM) to afford the desired product (10 mg, 31% yield) as a white solid. $^1$H NMR (300 MHz, DMSO-d6) δ: 13.25 (s, 1H), 9.57 (s, 1H), 8.48 (d, J=5.4 Hz, 1H), 7.95 (s, 1H), 7.78 (s, 1H), 7.73 (d, J=5.1 Hz, 1H), 7.38 (m, 4H), 7.28 (m, 1H), 6.97 (s, 1H), 5.76 (m, 1H), 4.56 (d, J=4.7 Hz, 1H), 4.01 (d, J=4.9 Hz, 1H), 2.54 (s, 3H), 1.57 (d, J=7.2 Hz, 3H). ESI-MS m/z: 384.3 [M+H]$^+$.

Example 3: Synthesis of 6-(4-fluorobenzyl)-5,6-dihydro-3-(2-methylpyridin-4-yl)-1H-pyrazolo[4,3-g]quinazolin-7(8H)-one

N-((3-bromo-6-nitro-1-trityl-1H-indazol-5-yl)methyl)(4-fluorophenyl)methanamine To a solution of 3-bromo-5-methyl-6-nitro-1-trityl-1H-indazole (500 mg, 1.0 mmol) and NBS (268 mg, 1.5 mmol) in 10 mL of CCl$_4$ at room temperature, AIBN (98 mg, 0.6 mmol) was added. The reaction mixture was stirred at 80° C. overnight. The mixture was cooled down to room temperature, and the solid was removed by filtration. (4-fluorophenyl)methanamine (500 mg, 4.0 mmol) and 1 mL DMF were added. The resulting mixture as stirred at the same temperature for 1 h. The solvent was removed and the residue was taken up by ethyl acetate, washed with saturated NH$_4$Cl aqueous solution and brine. The organic solution was dried over anhydrous MgSO$_4$, filtered and concentrated in vacuo. The residue was purified by silica gel column chromatography (eluting with 15% ethyl acetate in petroleum) to give the desired product (280 mg, 45% yield). ESI-MS m/z: 621.

5-((4-fluorobenzylamino)methyl)-3-bromo-1-trityl-1H-indazol-6-amine

To a solution of N-((3-bromo-6-nitro-1-trityl-1H-indazol-5-yl)methyl)(4-fluorophenyl)methanamine (280 mg, 0.45 mmol) in 6 mL of 1:5 mixture of AcOH/2-PrOH, was added Zn dust (587 mg, 9.0 mmol). The reaction mixture was stirred at 60° C. for 1 h. The reaction mixture was cooled to room temperature. Solid was removed by filtration and the filtrate was concentrated in vacuo. The residue was dissolved in ethyl acetate, and washed with water. The organic phase was washed with brine, dried over anhydrous sodium sulfate, filtered, and concentrated in vacuo to give the desired crude product as a yellow solid (230 mg). ESI-MS m/z: 591.

6-(4-fluorobenzyl)-3-bromo-5,6-dihydro-1-trityl-1H-pyrazolo[4,3-g]quinazolin-7(8H)-one To a solution of 5-((4-fluorobenzylamino)methyl)-3-bromo-1-trityl-1H-indazol-6-amine (230 mg, 0.39 mmol) in 6 mL of DCM, Et$_3$N (433 mg, 4.3 mmol) was added followed by CDI (316 mg, 1.95 mmol). The reaction mixture was stirred at room temperature overnight. The mixture was concentrated in vacuo and the residue was purified by silica gel column (eluting with 40% ethyl acetate in petroleum) to give the desired product (180 mg, 75% yield over 2 steps). ESI-MS m/z: 617.

6-(4-fluorobenzyl)-5,6-dihydro-3-(2-methylpyridin-4-yl)-1-trityl-1H-pyrazolo[4,3-g]quinazolin-7(8H)-one To a solution of 6-(4-fluorobenzyl)-3-bromo-5,6-dihydro-1-trityl-1H-pyrazolo[4,3-g]quinazolin-7(8H)-one (135 mg, 0.22 mmol) and pyridin-4-ylboronic acid (60 mg, 0.44 mmol) in 11 mL of 10:1 mixture of dioxane and water at room temperature, PdCl$_2$(dppf) (16 mg, 0.02 mmol) and K$_2$CO$_3$ (91 mg, 0.66 mmol) were added. The reaction mixture was degassed and backfilled with nitrogen. The reaction mixture was stirred at 80° C. overnight. The solvent was removed and the residue was purified by silica gel column chromatography (eluting with 40% ethyl acetate in petroleum) to give the desired product (22 mg, 16% yield). ESI-MS m/z: 630.

6-(4-fluorobenzyl)-5,6-dihydro-3-(2-methylpyridin-4-yl)-1H-pyrazolo[4,3-g]quinazolin-7(8H)-one To a solution of 6-(4-fluorobenzyl)-5,6-dihydro-3-(2-methylpyridin-4-yl)-1-trityl-1H-pyrazolo[4,3-g]quinazolin-7(8H)-one (22 mg, 0.03 mmol) in 3 mL of DCM, was added 3 mL of TFA, and the mixture was stirred at RT for 2 h. The solvent was removed, and NH$_3$.MeOH was added to adjust the pH>8.0. The resulting mixture was concentrated in vacuo and the residue was purified by silica gel column chromatography (eluting with 7% MeOH in DCM) to give the desired product (3 mg, 22% yield). $^1$H NMR (400 MHz, DMSO-d6) δ: 13.21 (br, 1H), 9.62 (s, 1H), 8.50 (d, J=5.2 Hz, 1H), 7.96 (s, 1H), 7.80 (s, 1H), 7.74 (d, J=4.4 Hz, 1H), 7.41 (dd, J=5.6, 8.0 Hz, 2H), 7.22 (t, J=8.8 Hz, 2H), 6.97 (s, 1H), 4.58 (s, 2H), 4.45 (s, 2H), 2.55 (s, 3H). ESI-MS m/z: 388.

Example 4: Synthesis of 5,6-dihydro-3-(2-methylpyridin-4-yl)-6-((thiazol-4-yl)methyl)-1H-pyrazolo[4,3-g]quinazolin-7(8H)-one 2-((3-bromo-6-nitro-1-trityl-1H-indazol-5-yl)methyl)isoindoline-1,3-dione To a solution of 3-bromo-5-methyl-6-nitro-1-trityl-1H-indazole (4.0 g, 8.0 mmol) and NBS (2.14 mg, 12.0 mmol) in 40 mL of CCl$_4$ at room temperature, AIBN (787 mg, 4.8 mmol) was added. The reaction mixture was stirred at 80° C. overnight. The mixture was cooled down to room temperature and the solid was removed by filtration. The solvent was removed by vacuum, n-potassiophthalimide (4.44 g, 24 mmol) and 40 mL of DMF were added. The resulting mixture was stirred at the same temperature for 1 h. The solvent was removed and the residue was taken up by ethyl acetate, washed with water and brine. The organic solution was dried over anhydrous MgSO$_4$, filtered and concentrated in vacuo. The residue was purified by silica gel column chromatography (eluting with 15% ethyl acetate in petroleum) to give the desired product (2.3 g, 45% yield). ESI-MS m/z: 645

(3-bromo-6-nitro-1-trityl-1H-indazol-5-yl)methanamine

To a solution of 2-((3-bromo-6-nitro-1-trityl-1H-indazol-5-yl)methyl)isoindoline-1,3-dione (300 mg, 0.47 mmol) in methanol (6 mL), was added hydrazine hydrate (233 mg, 4.7 mmol), and the reaction was stirred at 70° C. for 2 h. The reaction mixture was cooled down to room temperature, and the solid was removed by filtration. The filtrate was concentrated in vacuo and the residue was purified by silica gel column chromatography (eluting with 50% ethyl acetate in petroleum) to give the desired product (140 mg, 58% yield). ESI-MS m/z: 515

N-((3-brom-6-nitro-1-trityl-1H-indazol-5-yl)methyl)(thiazol-4-yl)methanamine

To a mixture of (3-bromo-6-nitro-1-trityl-1H-indazol-5-yl)methanamine (380 mg, 0.74 mmol) and thiazole-4-carbaldehyde (84 mg, 0.74 mmol), was added 3 drops of acetic acid, and the resulting mixture was stirred at room temperature for 1 hour. Sodium cyanoborohydride (93 mg, 1.48 mmol) was added to the reaction. The reaction mixture was stirred at room temperature overnight. The mixture was concentrated in vacuo, and the residue was purified by silica silica gel column chromatography (eluting with 25% ethyl acetate in dichloromethane) to give the desired product (177 mg, 32% yield). ESI-MS m/z: 612.

5-(((thiazol-4-yl)methylamino)methyl)-3-bromo-1-trityl-1H-indazol-6-amine

To a solution of N-((3-bromo-6-nitro-1-trityl-1H-indazol-5-yl)methyl)(thiazol-4-yl)methanamine (177 mg, 0.29 mmol) in 12 mL of 1:5 mixture of AcOH/2-PrOH, was added Zn dust (378 mg, 5.8 mmol). The reaction mixture was stirred at 60° C. for 1 h. The reaction mixture was cooled to room temperature. Solid was removed by filtration and the filtrate was concentrated in vacuo. The residue was dissovled in ethyl acetate, and then washed with water. The organic phase was collected, washed with brine, dried over anhydrous sodium sulfate, filtered, and concentrated in vacuo to give the desired crude product as a yellow solid (158 mg). ESI-MS m/z: 582.

5-(((thiazol-4-yl)methylamino)methyl)-3-bromo-1-trityl-1H-indazol-6-amine

To a solution of 5-(((thiazol-4-yl)methylamino)methyl)-3-bromo-1-trityl-1H-indazol-6-amine (158 mg, 0.27 mmol) in 8 mL of DCM, Et$_3$N (303 mg, 43.0 mmol) was added followed by CDI (221 mg, 1.36 mmol). The reaction mixture was stirred at room temperature overnight. The mixture was concentrated in vacuo and the residue was purified by silica gel column (eluting with 4% methanol in dichloromethane) to give the desired product (65 mg, 39% yield over 2 steps). ESI-MS m/z: 606.

5,6-dihydro-3-(2-methylpyridin-4-yl)-6-((thiazol-4-yl)methyl)-1-trityl-1H-pyrazolo[4,3-g]quinazolin-7(8H)-one To a solution of 5-(((thiazol-4-yl)methylamino)methyl)-3-bromo-1-trityl-1H-indazol-6-amine (65 mg, 0.11 mmol) and pyridin-4-ylboronic acid (29 mg, 0.21 mmol) in 11 mL of 10:1 mixture of dioxane and water at room temperature, PdCl$_2$(dppf) (23 mg, 0.03 mmol) and K$_2$CO$_3$ (45 mg, 0.33 mmol) were added. The reaction mixture was degassed and backfilled with nitrogen. The reaction mixture was stirred at 80° C. overnight. The solvent was removed and the residue was purified by silica gel column chromatography (eluting with 2.5% dichloromethane in methanol) to give the desired product (38 mg, 57% yield). ESI-MS m/z: 630.

5,6-dihydro-3-(2-methylpyridin-4-yl)-6-((thiazol-4-yl)methyl)-1H-pyrazolo[4,3-g]quinazolin-7(8H)-one To a solution of 5,6-dihydro-3-(2-methylpyridin-4-yl)-6-((thiazol-4-yl)methyl)-1-trityl-1H-pyrazolo[4,3-g]quinazolin-7(8H)-one (38 mg, 0.06 mmol) in 3 mL of DCM, was added 3 mL of TFA, and the resulting mixture was stirred at RT for 2 h. The solvent was removed, NH$_3$.MeOH was added to adjust the pH>8.0. The resulting mixture was concentrated in vacuo and the residue was purified by silica gel column chromatography (eluting with 7% MeOH in DCM) to give the desired product (15 mg, 64% yield). $^1$H NMR (400 MHz, DMSO-d6) δ: 13.24 (br, 1H), 9.60 (s, 1H), 9.10 (d, J=1.6 Hz, 1H), 8.51 (d, J=5.6 Hz, 1H), 7.99 (s, 1H), 7.82 (s, 1H), 7.76 (s, 1H), 7.57 (s, 1H), 6.69 (s, 1H), 4.72 (s, 2H), 4.60 (s, 2H), 2.56 (s, 3H). ESI-MS m/z: 376.

Example 5: 5,6-dihydro-3-(2-methoxypyrimidin-5-yl)-6-((R)-1-((thiophen-2-vyl)methyl)piperidin-3-yl)-1H-pyrazolo[4,3-g]quinazolin-7(8H)-one 3-bromo-5-(bromomethyl)-6-nitro-1-trityl-1H-indazole The mixture of 3-bromo-5-methyl-6-nitro-1-trityl-1H-indazole (2 g, 4 mmol), NBS (1 g, 5.6 mmol) and AIBN (400 mg, 2.4 mmol) in 40 mL of CCl$_4$ was stirred at 80° C. overnight. The reaction mixture was concentrated in vacuo to give the desired product (2.5 g) as a brown solid, which was used in the next step without further purification.

(R)-tert-butyl 3-((3-bromo-6-nitro-1-trityl-1H-indazol-5-yl)methylamino)piperidine-1-carboxylate The mixture of 3-bromo-5-(bromomethyl)-6-nitro-1-trityl-1H-indazole (2.5 g, 4.3 mmol) and (R)-tert-butyl 3-aminopiperidine-1-carboxylate (2.5 g, 12.9 mmol) in 30 mL of THF was stirred at RT for 16 h. The mixture was concentrated in vacuo and the residue was purified by silica gel column (0-20% EA in PE) to afford the desired product (860 mg, 47.8% yield) as an orange oil.

(R)-tert-butyl 3-((6-amino-3-bromo-1-trityl-1H-indazol-5-yl)methylamino)piperidine-1-carboxylate The mixture of 3-((3-bromo-6-nitro-1-trityl-1H-indazol-5-yl)methylamino)piperidine-1-carboxylate (860 mg, 1.23 mmol) in 10 mL of 4:1 mixture of HOAc and IPA at 60° C. was stirred for 1 h. To this mixture, Zn (1.6 g, 24.7 mmol) was added. The reaction mixture was stirred at 60° C. for 1 h. Solvent was removed and the residue was taken with ethyl acetate. The mixture was filtered through a pad of Celite and the filtrate was washed with brine. The organic solution was dried over anhydrous $MgSO_4$, filtered and the residue was concentrated in vacuo to give the desired product (668 mg, 81% yield). ESI-MS m/z: 668.

(R)-tert-butyl 3-(3-bromo-7,8-dihydro-7-oxo-1-trityl-H-pyrazolo[4,3-g]quinazolin-6(5H)-yl)piperidine-1-carboxylate The mixture of (R)-tert-butyl 3-((6-amino-3-bromo-1-trityl-1H-indazol-5-yl)methylamino)piperidine-1-carboxylate (668 mg, 1 mmol), CDI (890 mg, 5.5 mmol) and $Et_3N$ (1.1 g, 11 mmol) in 10 mL of DCM was stirred at RT for 16 h. Solvent was removed and the residue was taken up by ethyl acetate, and washed with brine. The organic solution was dried over anhydrous $MgSO_4$, filtered and concentrated in vacuo. The residue was purified by silica column (0-30% EA in PE) to afford the desired product (400 mg, 58% yield) as a yellow solid. ESI-MS m/z: 692.

(R)-tert-butyl 3-(7,8-dihydro-3-(2-methoxypyrimidin-5-yl)-7-oxo-1-trityl-1H-pyrazolo[4,3-g]quinazolin-6(5H)-yl)piperidine-1-carboxylate The mixture of (R)-tert-butyl 3-(3-bromo-7,8-dihydro-7-oxo-1-trityl-1H-pyrazolo[4,3-g]quinazolin-6(5H)-yl)piperidine-1-carboxylate (400 mg, 0.56 mmol), 2-methoxypyrimidin-5-yl-5-boronic acid (250 mg, 1.65 mmol), Pd(dppf)$Cl_2$ (81 mg, 0.1 mmol) and $K_2CO_3$ (138 mg, 1 mmol) in 18 mL of 1:5 $H_2O$/dioxane was stirred at 100° C. for 16 h. Solvent was removed and the residue was taken up by ethyl acetate, and washed with brine. The organic solution was dried over anhydrous $MgSO_4$, filtered and and concentrated in vacuo. The residue was purified by silica gel column (0-50% EA in PE) to afford the desired product (270 mg, 75% yield) as a light yellow solid. ESI-MS m/z:722.

5,6-dihydro-3-(2-methoxypyrimidin-5-yl)-6-((R)-piperidin-3-yl)-1H-pyrazolo[4,3-g]quinazolin-7(8H)-one The mixture of (R)-tert-butyl 3-(7,8-dihydro-3-(2-methoxypyrimidin-5-yl)-7-oxo-1-trityl-1H-pyrazolo[4,3-g]quinazolin-6(5H)-yl)piperidine-1-carboxylate (270 mg, 0.37 mmol) and 3 mL of TFA and 7 mL of DCM. The reaction mixture was stirred at room temperature for 16 h. The mixture was concentrated in vacuo and the residue was purified by silica gel column (0-20% MeOH in DCM) to afford the desired product (130 mg, 92.8% yield) as a white solid. ESI-MS m/z: 380.

5,6-dihydro-3-(2-methoxypyrimidin-5-yl)-6-((R)-1-((thiophen-2-yl)methyl)piperidin-3-yl)-1H-pyrazolo[4,3-g]quinazolin-7(8H)-one The mixture of 5,6-dihydro-3-(2-methoxypyrimidin-5-yl)-6-((R)-piperidin-3-yl)-1H-pyrazolo[4,3-g]quinazolin-7(8H)-one (130 mg, 0.34 mmol) and thiophene-2-carbaldehyde (307 mg, 2.74 mmol) in 70 mL of 8:1 mixture of HOAc and MeOH was stirred at room temperature for 1 h. $NaBH_3CN$ (55 mg, 0.86 mmol) was added and the resulting mixture was stirred at room temperature for 16 h. The reaction mixture was concentrated in vacuo and the residue was purified by silica gel column (0-10% MeOH in DCM) to afford the desired product (110 mg, 67.5% yield) as a light yellow solid. $^1H$ NMR (400 MHz, DMSO-d6) δ: 13.05 (s, 1H), 9.45 (s, 1H), 9.14 (s, 2H), 7.94 (s, 1H), 7.42-7.41 (m, 1H), 6.96-6.91 (m, 3H), 4.5494.37 (m, 2H), 4.30-4.23 (m, 1H), 4.00 (s, 3H), 3.72-3.71 (m, 2H), 2.86-2.27 (m, 2H), 2.19-2.14 (m, 1H), 1.91-1.87 (m, 1H), 1.75-1.50 (n, 4H). ESI-MS m/z: 476.

Example 6: Synthesis of 3-(2-methylpyridin-4-yl)-6-(1-phenylethyl)-1H-pyrazolo[4,3-g]quinolin-7(8H)-one

6-amino-3-(2-methylpyridin-4-yl)-1-trityl-1H-indazole-5-carbaldehyde

To a stirred solution of N-(5-formyl-3-(2-methylpyridin-4-yl)-1-trityl-1H-indazol-6-yl)acetamide (16.0 g, 28 mmol) in 200 mL of dry MeOH at ° C., $SOCl_2$ (12 ml) was added dropwise. The reaction mixture was stirred at room temperature overnight. The solvent was removed. The residue was diluted with ethyl acetate, and washed with saturated $NaHCO_3$ aqueous solution. The organic solution was dried over anhydrous $MgSO_4$, filtered and concentrated in vacuo to give of the desired product (15 g) as a brown solid, which was used in the next step without further purification.

N-(5-formyl-3-(2-methylpyridin-4-yl)-1-trityl-1H-indazol-6-yl)-3-phenylbutanamide To a stirred solution of 6-amino-3-(2-methylpyridin-4-yl)-1-trityl-1H-indazole-5-carbaldehyde (1.5 g, 3.1 mmol) in 20 mL of dry DCM at 0° C., TEA (1.5 g, 13.7 mmol) was added followed by slow addition of 3-phenylbutanoyl chloride (1.6 g, 9.1 mmol). The reaction mixture was stirred at the same temperature for 4 h. The solvent was removed, and the residue was purified via silica gel column chromatography (eluting with DCM/MeOH=25:1) to afford the desired product (2.0 g, 95% yield) as a yellow solid.

3-(2-methylpyridin-4-yl)-6-(1-phenylethyl)-1-trityl-1H-pyrazolo[4,3-g]quinolin-7(8H)-one Condition 1:
To a solution of N-(5-formyl-3-(2-methylpyridin-4-yl)-1-trityl-1H-indazol-6-yl)-3-phenylbutanamide (2.0 g, 3.1 mmol) in 60 mL of THF at room temperature, KOH (700 mg, 12.5 mmol) and 1 mL of EtOH were added. The reaction mixture was degassed and backfilled with nitrogen. The reaction mixture was stirred at 40° C. overnight. The solvent was removed and the residue was purified via silica gel column chromatography (eluting with EA/PE=1:2) to give the desired product (50 mg, 3% yield). ESI-MS m/z: 623.

Condition 2:

To a solution of N-(5-formyl-3-(2-methylpyridin-4-yl)-1-trityl-1H-indazol-6-yl)-3-phenylbutanamide (7.0 g, 10.9 mmol) in 200 mL of MeOH, MeONa (5.5 g, 100 mmol) was added. The reaction mixture was degassed and backfilled with nitrogen. The reaction mixture was stirred at reflux overnight. The solvent was removed and the residue was purified via silica gel column chromatography (eluting with EA/PE=1:2) to give the desired product (1.3 g, 18% yield). ESI-MS m/z: 623.

3-(2-methylpyridin-4-yl)-6-(1-phenylethyl)-1H-pyrazolo[4,3-g]quinolin-7(8H)-one

To a solution of 3-(2-methylpyridin-4-yl)-6-(1-phenylethyl)-1-trityl-1H-pyrazolo[4,3-g]quinolin-7(8H)-one (1.3 g, 2.0 mmol) in 4 mL of DCM, 4 mL of TFA was added. The reaction was stirred at room temperature for 1 h. The solvent was removed and the residue was quenched by 7M $NH_3$.MeOH. The solvent was removed and the residue was purified via silica gel column chromatography (eluting with DCM/MeOH=20:1) to give the desired product (500 mg, 66% yield). $^1$H NMR (400 MHz, DMSO-d6) δ: 13.44 (br, 1H), 11.67 (s, 1H), 8.62 (s, 1H), 8.56 (d, J=5.2 Hz, 1H), 8.01 (s, 1H), 7.93 (s, 1H), 7.86 (d, J=5.2 Hz, 1H), 7.38 (s, 1H), 7.15-7.35 (m, 5H), 4.38 (q, J=7.2 Hz, 1H), 2.61 (s, 3H), 1.56 (q, J=7.2 Hz, 3H). ESI-MS m/z: 381.

Example 7: Synthesis of 3-(6-(4-methylpiperazin-1-yl)pyridin-3-yl)-6-(1-phenylethyl)-1H-pyrazolo[4,3-g]quinolin-7(8H)-one (3-bromo-6-nitro-1-trityl-1H-indazol-5-yl)methyl acetate To a stirred solution of 3-bromo-5-(bromomethyl)-6-nitro-1-trityl-1H-indazole (500 mg, 1 mmol, not pure) in 10 mL of dry DMF, AcOK (700 mg, 7 mmol) was added. The reaction mixture was stirred at room temperature for 3 h. The reaction was partitioned between EA and $H_2O$. The organic layer was concentrated in vacuo and the residue was purified via silica gel column chromatography (eluting with EA/PE=1:6) to afford the desired product (250 mg, 50% yield) as a yellow solid.

(6-amino-3-bromo-1-trityl-1H-indazol-5-yl)methyl acetate

To a stirred solution of (3-bromo-6-nitro-1-trityl-1H-indazol-5-yl)methyl acetate (500 mg, 1 mmol) in 10 mL of EtOH, $Na_2S_2O_4$ (1.7 g, 10 mmol) was added. The reaction mixture was stirred at reflux for 10 h. The solvent was removed, and the residue was partitioned between EA and $H_2O$. The organic layer was concentrated in vacuo to afford the product (350 mg, 70% yield) as a yellow solid without further purification.

(6-amino-3-bromo-1-trityl-1H-indazol-5-yl)methanol

To a solution of (6-amino-3-bromo-1-trityl-1H-indazol-5-yl)methyl acetate (350 mg, 0.65 mmol) in a mixture THF/EtOH/$H_2$ (6.0 mL, 1:1:1) at room temperature, LiOH (109 mg, 2.61 mmol) was added. The reaction mixture was stirred for 8 h. The solvent was removed and the residue was purified via silica gel column chromatography (eluting with EA/PE=1:3) to give the product (130 mg, 50% yield) as a yellow solid.

6-amino-3-bromo-1-trityl-1H-indazole-5-carbaldehyde

To a stirred solution of (6-amino-3-bromo-1-trityl-1H-indazol-5-yl)methanol (130 mg, 0.27 mmol) in 10 mL of DCM, $MnO_2$ (480 mg, 5.4 mmol) was added. The reaction mixture was stirred at room temperature for 10 h. The solid was removed by filtration and the filtrate was concentrated in vacuo to afford the product (100 mg, 70% yield) as a yellow solid without further purification.

3-bromo-6-(1-phenylethyl)-1-trityl-1H-pyrazolo[4,3-g]quinolin-7(8H)-one

To a solution of N-(3-bromo-5-formyl-1-trityl-1H-indazol-6-yl)-3-phenylbutanamide (2.0 g, 3.2 mmol) in 40 mL of MeOH, MeONa (1.73 g, 32 mmol) was added. The reaction mixture was degassed and backfilled with nitrogen. The reaction mixture was stirred at reflux overnight. The solvent was removed and the residue was purified via silica gel column chromatography (eluting with EA/PE=1:5) to give the desired product (300 mg, 15% yield). Some of the starting material (about 1.0 g) was recovered. ESI-MS m/z: 612.

3-(6-(4-methylpiperazin-1-yl)pyridin-3-yl)-6-(1-phenylethyl)-1-trityl-1H-pyrazolo[4,3-g]quinolin-7(8H)-one The mixture of 3-bromo-6-(1-phenylethyl)-1-trityl-1H-pyrazolo[4,3-g]quinolin-7(8H)-one (200 mg, 0.33 mmol), $K_2CO_3$ (100 mg, 0.72 mmol) and 1-methylpiperazine (0.5 mL) in 2 mL of DMSO was stirred at 100° C. in a sealed tube for 10 h. The residue was purified via silica gel column chromatography (eluting with EA/PE=1:2) to give the desired product (70 mg, 30% yield). ESI-MS m/z:707.

3-(6-(4-methylpiperazin-1-yl)pyridin-3-yl)-6-(1-phenylethyl)-1H-pyrazolo[4,3-g]quinolin-7(8H)-one To a solution of 3-(6-(4-methylpiperazin-1-yl)pyridin-3-yl)-6-(1-phenylethyl)-1-trityl-1H-pyrazolo[4,3-g]quinolin-7(8H)-one (70 mg, 0.1 mmol) in 2 mL of DCM, 2 mL of TFA was added. The reaction mixture was stirred at room temperature for 1 h. The solvent was removed and the residue was quenched by 7M $NH_3$.MeOH. The solvent was removed and the residue was purified via silica gel column chromatography (eluting with DCM/MeOH=20:1) to give the desired product (10 mg, 66% yield). $^1$H NMR (400 MHz, DMSO-d6) δ: 13.02 (br, 1H), 11.59 (br, 1H), 8.82 (d, J=2.0 Hz, 1H), 8.47 (s, 1H), 8.56 (dd, J=8.8, 2.0 Hz, 1H), 7.99 (s, 1H), 7.29 (m, 5H), 7.18 (m, 1H), 6.98 (d, J=8.8 Hz, 1H), 4.37 (q, J=7.2 Hz, 1H), 3.60 (m, 4H), 2.51 (m, 3H), 2.46 (m, 4H), 1.54 (d, J=7.2 Hz, 3H). ESI-MS m/z: 465.

Example 8: Synthesis of 6-(4-tert-butyl-1-(2,2,2-trifluoroethyl)pyrrolidin-3-yl)-5,6-dihydro-3-(2-methylpyridin-4-yl)-1H-pyrazolo[4,3-g]quinazolin-7(8H)-one 3,3-dimethyl-1-nitrobutan-2-ol To a mixture of pivalaldehyde (10 g, 116 mmol) and nitromethane (7.1 mg, 116 mmol) in 150 mL of methanol in an ice-bath, sodium hydroxide aqueous (4.88 g, 122 mmol, 88 ml $H_2O$) was added slowly and the temperature was allowed to rise slowly to RT. The mixture was stirred for 1 h. The solvent was removed, and the residue was dissolved in water and ethyl acetate. The mixture was washed with a solution of sodium carbonate. The organic phase was separated, dried over anhydrous sodium sulfate, filtered and concentrated in vacuo to give the desired product as a yellow oil (14 g, 82% yield). ESI-MS m/z: 148

(E)-3,3-dimethyl-1-nitrobut-1-ene

To a solution of 3,3-dimethyl-1-nitrobutan-2-ol (4.0 g, 27 mmol) in 20 mL of dichloromethane at 0° C., trifluoroacetic anhydride (3.5 g, 16.5 mmol) was slowly added followed by triethylamine and the temperature was allowed to rise slowly to room temperature. The mixture was stirred at RT for 3 h. The reaction mixture was filtered through a pad of silica gel and rinsed with dichloromethane. The filtrate was concentrated (no heating) in vacuo to give a yellow oil. The oil was taken up in 20% petroleum in ether, filtered through a pad of silica gel and rinsed with 20% petroleum in ether. The filtrate was concentrated (no heating) in vacuo to give the product as a yellow oil (3 g crude product). ESI-MS m/z: 130.

3-tert-butyl-1-benzyl-4-nitropyrrolidine

To a mixture of (E)-3,3-dimethyl-1-nitrobut-1-ene (3.5 g, 27 mmol) and TFA (307 mg, 2.7 mmol) in 300 mL of dichloromethane, N-(methoxymethyl)-N-((trimethylsilyl)methyl)(phenyl)methanamine (7.7 g, 32 mmol) was slowly added and the resulting mixture was stirred at room temperature over weekend. The solvent was removed and the residue was purified by silica gel column chromatography (eluting with 2-2.5% ethyl acetate in petroleum) to give the desired product as a yellow oil (2.3 g, 32% yield). ESI-MS m/z: 263.

4-tert-butyl-1-benzylpyrrolidin-3-amine

To a mixture of 3-tert-butyl-1-benzyl-4-nitropyrrolidine (1.2 g, 4.6 mmol) in 20 mL of methanol at 0° C., Ranney Ni (1 g) was added and the resulting mixture was stirred at room temperature for 1 h. The solid was removed by filtration and the filtrate was concentrated in vacuo to give the product as a yellow oil (2.3 g, 32% yield). ESI-MS m/z: 233.

4-tert-butyl-1-benzyl-N-((3-bromo-6-nitro-1-trityl-1H-indazol-5-yl)methyl)pyrrolidin-3-amine was synthesized by general scheme D.

5-((4-tert-butyl-1-benzylpyrrolidin-3-ylamino)methyl)-3-bromo-1-trityl-1H-indazol-6-amine was synthesized by general scheme D.

6-(4-tert-butyl-1-benzylpyrrolidin-3-yl)-3-bromo-5,6-dihydro-1-trityl-1H-pyrazolo[4,3-g]quinazolin-7(8H)-one was synthesized by general scheme D.

6-(4-tert-butyl-1-benzylpyrrolidin-3-yl)-5,6-dihydro-3-(2-methylpyridin-4-yl)-1-trityl-1H-pyrazolo[4,3-g]quinazolin-7(8H)-one was synthesized by general scheme D.

tert-butyl 3-tert-butyl-4-(7,8-dihydro-3-(2-methylpyridin-4-yl)-7-oxo-1-trityl-1H-pyrazolo[4,3-g]quinazolin-6(5H)-yl)pyrrolidine-1-carboxylate A mixture of 6-(4-tert-butyl-1-benzylpyrrolidin-3-yl)-5,6-dihydro-3-(2-methylpyridin-4-yl)-1-trityl-1H-pyrazolo[4,3-g]quinazolin-7(8H)-one (200 mg, 0.27 mmol), $(Boc)_2O$ (190 mg, 0.81 mmol) and 10% $Pd(OH)_2/C$ (50 mg) in 20 mL of ethyl acetate was stirred under $H_2$ atmosphere at room temperature overnight. The solid was removed by filtration and the filtrate was concentrated in vacuo. The residue was purified by silica gel column chromatography (eluting with 50% ethyl acetate in petroleum) to give the desired product as a yellow solid (60 mg, 30% yield). ESI-MS m/z: 747.

6-(4-tert-butylpyrrolidin-3-yl)-5,6-dihydro-3-(2-methylpyridin-4-yl)-1-trityl-1H-pyrazolo[4,3-g]quinazolin-7(8H)-one A solution of tert-butyl 3-tert-butyl-4-(7,8-dihydro-3-(2-methylpyridin-4-yl)-7-oxo-1-trityl-1H-pyrazolo[4,3-g]quinazolin-6(5H)-yl)pyrrolidine-1-carboxylate (60 mg, 0.08 mmol) in AcOH/MeOH (1:4, 6 mL) was stirred at room temperature for 1.5 h. To this mixture, $NH_3.MeOH$ was added to adjust the pH to >8.0. The mixture was concentrated in vacuo and the residue was purified by silica gel column chromatography (eluting with 8% $NH_3.MeOH$ in dichloromethane) to give the desired product as a yellow solid (30 mg, 58% yield). ESI-MS m/z: 647.

6-(4-tert-butyl-1-(2,2,2-trifluoroethyl)pyrrolidin-3-yl)-5,6-dihydro-3-(2-methylpyridin-4-yl)-1-trityl-1H-pyrazolo[4,3-g]quinazolin-7(8H)-one To a solution of 6-(4-tert-butylpyrrolidin-3-yl)-5,6-dihydro-3-(2-methylpyridin-4-yl)-1-trityl-1H-pyrazolo[4,3-g]quinazolin-7(8H)-one (30 mg, 0.05 mmol) in DMF was added 2,2,2-trifluoroethyl trifluoromethanesulfonate (22 mg, 0.09 mmol) followed by N-ethyl-N-isopropylpropan-2-amine (24 mg, 0.18 mmol). The mixture was stirred at room temperature overnight. The mixture was partitioned between water and ethyl acetate. The organic layer was washed with brine, dried over sodium sulfate, filtered and concentrated in vacuo. The residue was purified by silica gel column chromatography (eluting with 5% methanol in dichloromethane) to give the desired product as a yellow solid. (30 mg, 89% yield). ESI-MS m/z: 729.

6-(4-tert-butyl-1-(2,2,2-trifluoroethyl)pyrrolidin-3-yl)-5,6-dihydro-3-(2-methylpyridin-4-yl)-1H-pyrazolo[4,3-g]quinazolin-7(8H)-one was synthesized by general scheme D. (10 mg, 50% yield). $^1H$ NMR (400 MHz, DMSO-d6) δ: 13.22 (br, 1H), 9.47 (s, 1H), 8.54 (d, J=4.8 Hz, 1H), 8.03 (s, 1H), 7.84 (s, 1H), 7.79 (d, J=5.2 Hz, 1H), 6.96 (s, 1H), 4.91 (m, 2H), 4.65 (d, J=12.3 MHz, 1H), 4.51 (d, J=12.3 Hz, 1H), 3.34 (m, 1H), 3.20 (m, 1H), 3.02 (m, 1H), 2.91 (m, 1H), 2.73 (m, 1H), 2.58 (s, 3H), 0.85 (s, 9H). ESI-MS m/z: 487.

Example 9: Synthesis of 6-(3-chlorobenzyl)-6,7-dihydro-3-(2-methoxypyrimidin-5-yl)-[1,4]diazepino[6,5-f]indazol-8(1H,5H,9H)-one 3-bromo-5-(bromomethyl)-6-nitro-1-trityl-1H-indazole To a stirred solution of 3-bromo-5-methyl-6-nitro-1-trityl-1H-indazole (5.0 g, 10 mmol) in 150 mL of $CCl_4$, NBS (2.7 g, 15 mmol) and AIBN (1.0 g, 6.0 mmol) were added. The mixture was stirred at 80° C. overnight. The mixture was filtered and the filtrate was concentrated in vacuo. The residue was used in the next step without further purification.

N-((3-bromo-6-nitro-1-trityl-1H-indazol-5-yl)methyl)(3-chlorophenyl)methanamine

The mixture of 3-bromo-5-(bromomethyl)-6-nitro-1-trityl-1H-indazole (4.0 g, 8 mmol), (3-chlorophenyl)methanamine (7.0 g, 50 mmol) and TEA (5.0 g, 50 mmol) in 150 mL of CCl$_4$ was stirred at 70° C. for 3 h. The mixture was washed with water and concentrated in vacuo. The residue was purified by silica gel column (0-2% methanol in dichloromethane) to afford the desired product (1.6 g, 25% yield) as a yellow solid. ESI-MS m/z: 639.

Ethyl 2-(N-(3-chlorobenzyl)-N-((3-bromo-6-nitro-1-trityl-1H-indazol-5-yl)methyl)amino)acetate The mixture of N-((3-bromo-6-nitro-1-trityl-1H-indazol-5-yl)methyl)(3-chlorophenyl)methanamine (1.6 g, 2.5 mmol) and NaOH (150 mg, 3.76 mmol) in 10 mL of DMF was stirred at RT for 30 min. Ethyl 2-bromoacetate (630 mg, 3.76 mmol) was added to the mixture and the resulting mixture was stirred at 90° C. for 3 h. The mixture was cooled down, poured into water and extracted with EA (100 mL×3). The organic layer was concentrated in vacuo and the residue was purified by silica gel column (0-1% methanol in dichloromethane) to give the desired product (1.2 g, 67% yield). ESI-MS m/z: 725.

6-(3-chlorobenzyl)-3-bromo-6,7-dihydro-trityl-[1,4]diazepino[6,5-f]indazol-8(1H,5H,9H)-one To a solution of ethyl 2-(N-(3-chlorobenzyl)-N-((3-bromo-6-nitro-1-trityl-1H-indazol-5-yl)methyl)amino)acetate (1.1 g, 1.52 mmol) in AcOH/i-PrOH (20 ml/4 mL) at 60° C., Zn (2.0 g, 30.3 mmol) was added and the resulting mixture was stirred at 60° C. for 5 h. The mixture was concentrated in vacuo. The residue was diluted with EA and washed with saturated NaHCO$_3$. The organic layer was concentrated in vacuo and the residue was purified by silica gel column (0-2% methanol in dichloromethane) to give the desired product (910 mg, 93% yield). ESI-MS m/z: 649.

6-(3-chlorobenzyl)-6,7-dihydro-3-(2-methoxypyrimidin-5-yl)-1-trityl-[1,4]diazepino[6,5-f]indazol-8(1H,5H,9H)-one The mixture of 6-(3-chlorobenzyl)-3-bromo-6,7-dihydro-1-trityl-[1,4]diazepino[6,5-f]indazol-8(1H,5H,9H)-one (400 mg, 0.62 mmol), 2-methoxypyrimidin-5-yl-5-boronic acid (240 mg, 1.54 mmol), Pd(dppf)Cl$_2$ and K$_2$CO$_3$ in dioxane/H$_2$O (15 mL/1.5 mL) was stirred at 90° C. overnight. The mixture was concentrated in vacuo and the residue was purified by silica gel column (0-1% methanol in dichloromethane) to give the desired product (320 mg, 76% yield). ESI-MS m/z: 677.

6-(3-chlorobenzyl)-6,7-dihydro-3-(2-methoxypyrimidin-5-yl)-[1,4]diazepino[6,5-f]indazol-8(1H,5H,9H)-one To a solution of 6-(3-chlorobenzyl)-6,7-dihydro-3-(2-methoxypyrimidin-5-yl)-1-trityl-[1,4]diazepino[6,5-f]indazol-8(1H,5H,9H)-one (100 mg, 0.147 mmol) in 3 mL of DCM was added TFA (6 mL). The mixture was stirred at RT for 1 h. The mixture was concentrated in vacuo, and diluted with NH$_3$ in methanol. The mixture was concentrated in vacuo and the residue was purified by silica gel column (0-10% methanol in dichloromethane) to give the desired product (25 mg, 39% yield). $^1$H NMR (400 MHz, DMSO-d6) δ: 13.34 (s, 1H), 10.25 (s, 1H), 9.21 (m, 2H), 8.09 (s, 1H), 7.34-7.41 (m, 4H), 7.23 (s, 1H), 4.00 (s, 3H) 3.83 (s, 2H), 3.75 (s, 2H), 3.12 (s, 2H). ESI-MS m/z: 435.

Example 10: Synthesis of 7-(4-fluorobenzyl)-6,7-dihydro-3-(2-methoxypyrimidin-5-yl)-[1,3]diazepino[5,4-f]indazol-8(1H,5H,9H)-one 5-bromo-6-nitro-1-trityl-1H-indazole To a stirred solution of 5-bromo-6-nitro-1H-indazole (5 g, 20.7 mmol) in 60 mL of dry THF at 0° C., NaH (60% in mineral oil, 1.16 g, 29 mmol) was added and the reaction mixture was stirred at the same temperature for 30 min. TrtCl (6.92 g, 24.8 mmol) was added to the mixture. The reaction mixture was stirred at room temperature for 6 h. Solvent was removed. The residue was dissolved in ethyl acetate and washed with brine. The organic solution was dried over anhydrous MgSO$_4$, filtered and concentrated in vacuo. The residue was purified by silica gel column to afford the desired product (9 g, 90% yield) as a yellow solid.

6-nitro-1-trityl-5-vinyl-1H-indazole

To a mixture of 5-bromo-6-nitro-1-trityl-1H-indazole (9 g, 18.6 mmol) and Pd(pph$_3$)$_4$ (2.15 g, 1.86 mmol) in toluene (60 mL), Tributyl(vinyl)tin (7 g, 22.32 mmol) was added. The resulting mixture was degassed and back-filled with argon three times and then stirred at 115° C. for 4 h. The mixture was allowed to cool to room temperature. The solution was poured into water (100 mL) and extracted with EA (300 mL) three times. The organic layer was washed with brine two times, dried over Na$_2$SO$_4$, and concentrated in vacuo. The residue was purified by flash column chromatography on silica gel to afford the desired product 6-nitro-1-trityl-5-vinyl-1H-indazole (6.8 g, 85% yield) as a white solid.

2-(6-nitro-1-trityl-1H-indazol-5-yl)ethanol

To a stirred solution of 6-nitro-1-trityl-5-vinyl-1H-indazole (6.8 g, 15.77 mmol) in 60 mL of dry THF at 0° C., BH$_3$·THF (1N, 47.33 mL, 47.33 mmol) was slowly added and the reaction mixture was stirred at RT for 5 h. To this mixture, NaOH (3N, 15.77 mL, 47.33 mmol) and H$_2$O$_2$ (4.94 g, 47.33 mmol, 30%) were slowly added and the resulting mixture was stirred at RT for 5 h. The solution was poured into water (100 mL) and extracted with EA (100 mL) three times. The organic layer was washed with brine two times, dried over Na$_2$SO$_4$, and concentrated in vacuo. The residue was purified by silica gel to afford the desired product 2-(6-nitro-1-trityl-1H-indazol-5-yl)ethanol (3.9 g, 55% yield).

2-(6-nitro-1-trityl-1H-indazol-5-yl)acetic acid

The mixture of H$_5$IO$_6$ (4.94 g, 21.69 mmol) and CrO$_3$ (43 mg, 0.43 mmol) in 50 mL of CH$_3$CN:H$_2$O (99.25%:0.75%) was stirred at RT for 2 h. To this mixture, 2-(6-nitro-1-trityl-1H-indazol-5-yl)ethanol (3.9 g, 8.67 mmol) in 50 mL of CH$_3$CN:H$_2$O (99.25%:0.75%) was slowly added and the reaction mixture was stirred at RT for 3 h. The solution was poured into water (100 mL) and extracted with EA (100 mL) three times. The organic layer was washed with brine two times, dried over Na$_2$SO$_4$ and concentrated in vacuo. The residue was purified by silica gel to afford the desired product 2-(6-nitro-1-trityl-1H-indazol-5-yl)acetic acid (3.2 g, 80% yield).

N-(4-fluorobenzyl)-2-(6-nitro-1-trityl-1H-indazol-5-yl)acetamide

To a stirred solution of 2-(6-nitro-1-trityl-1H-indazol-5-yl)acetic acid (3.2 g, 6.91 mmol) in 40 mL of dry DMF, (4-fluorophenyl)methanamine (1.04 g, 8.29 mmol), EDC.HCl (2.64 g, 13.82 mmol), HOBt (1.86 g, 13.82 mmol) and TEA (2.79 g, 27.64 mmol) were added and the reaction mixture was stirred at RT overnight. The solution was poured into water (100 mL) and extracted with EA (100 mL) three times. The organic layer was washed with brine two times, dried over $Na_2SO_4$, and concentrated in vacuo. The residue was purified by silica gel column to afford the desired product N-(4-fluorobenzyl)-2-(6-nitro-1-trityl-1H-indazol-5-yl)acetamide (3.15 g, 80% yield).

N-(4-fluorobenzyl)-2-(6-nitro-1-trityl-1H-indazol-5-yl)ethanamine

To a stirred solution of N-(4-fluorobenzyl)-2-(6-nitro-1-trityl-1H-indazol-5-yl)acetamide (3.15 g, 5.53 mmol) in 30 mL of dry THF at 0° C., $BH_3$·THF (1 N, 16.6 mL, 16.6 mmol) was slowly added and the reaction mixture was stirred at reflux for 5 h. The solution was poured into water (80 mL) and extracted with EA (100 mL) three times. The organic layer was washed with brine two times, dried over $Na_2SO_4$ and concentrated in vacuo. The residue was purified by silica gel column to afford the desired product N-(4-fluorobenzyl)-2-(6-nitro-1-trityl-1H-indazol-5-yl)ethanamine (2.31 g, 75% yield).

5-(2-(4-fluorobenzylamino)ethyl)-1-trityl-1H-indazol-6-amine

To a stirred solution of N-(4-fluorobenzyl)-2-(6-nitro-1-trityl-1H-indazol-5-yl)ethanamine (2.31 g, 4.15 mmol) in 40 mL of 1:5 AcOH/2-PrOH mixture at 60° C., Zn dust (5.4 g, 83.1 mmol) was added. The reaction mixture was stirred at 60° C. for 1 h. The reaction mixture was cooled to room temperature. Solid was removed by filtration and the filtrate was concentrated in vacuo. The residue was poured into $NaHCO_3$ solution (80 mL) and extracted with EA (100 mL) three times. The organic layer was washed with brine two times, dried over $Na_2SO_4$, and concentrated in vacuo. The yellow solid 5-(2-(4-fluorobenzylamino)ethyl)-1-trityl-1H-indazol-6-amine (1.96 g, 90% yield) was collected which was used in the next step without further purification.

7-(4-fluorobenzyl)-6,7-dihydro-1-trityl-[1,3]diazepino[5,4-f]indazol-8(1H,5H,9H)-one To a solution of 5-(2-(4-fluorobenzylamino)ethyl)-1-trityl-1H-indazol-6-amine (1.96 g, 4.56 mmol) in 20 mL of DCM, $Et_3N$ (5 g, 50 mmol) and CDI (4 g, 25.1 mmol) were added. The reaction mixture was stirred at room temperature for 3 h. The solution was poured into water (40 mL) and extracted with DCM (60 mL) three times. The organic layer was washed with brine two times, dried over $Na_2SO_4$, and concentrated in vacuo. The residue was purified by silica gel to afford the desired product 7-(4-fluorobenzyl)-6,7-dihydro-1-trityl-[1,3]diazepino[5,4-f]indazol-8(1H,5H,9H)-one (1.51 g, 60% yield).

7-(4-fluorobenzyl)-6,7-dihydro-[1,3]diazepino[5,4-f]indazol-8(1H,5H,9H)-one

To a solution of 7-(4-fluorobenzyl)-6,7-dihydro-1-trityl-[1,3]diazepino[5,4-f]indazol-8(1H,5H,9H)-one (1.51 g, 2.73 mmol) in 10 mL of DCM, 5 mL of TFA was added. The reaction mixture was stirred at room temperature for 5 h. Solvent was removed and the residue was purified by prep-HPLC to give the desired product 7-(4-fluorobenzyl)-6,7-dihydro-[1,3]diazepino[5,4-f]indazol-8(1H,5H,9H)-one (677 mg, 80% yield).

7-(4-fluorobenzyl)-6,7-dihydro-3-iodo-[1,3]diazepino[5,4-f]indazol-8(1H,5H,9H)-one To a stirred mixture of 7-(4-fluorobenzyl)-6,7-dihydro-[1,3]diazepino[5,4-f]indazol-8(1H,5H,9H)-one (677 mg, 2.18 mmol) in DMF (10 mL) at room temperature, KOH (366 mg, 6.54 mmol) was added and the resulting mixture was stirred at room temperature for 10 min. NIS (540 mg, 2.4 mmol) was added to the reaction mixture. The resulting mixture was stirred at room temperature for 10 h. The reaction mixture was poured into water (20 mL) and extracted with ethyl acetate (60 mL×3). The combined organic layer was washed with $H_2O$ (200 mL×3), dried over anhydrous $Na_2SO_4$, filtered and concentrated in vacuo to afford the desired product (713 mg, 75% yield) as a yellow solid. The crude product was used directly in the next step without further purification.

tert-butyl 7-(4-fluorobenzyl)-6,7,8,9-tetrahydro-3-iodo-8-oxo-[1,3]diazepino[5,4-f]indazole-1(5H)-carboxylate To a stirred mixture of 7-(4-fluorobenzyl)-6,7-dihydro-3-iodo-[1,3]diazepino[5,4-f]indazol-8(1H,5H,9H)-one (713 mg, 1.68 mmol) in THF (10 mL) at room temperature, $(Boc)_2O$ (403 mg, 1.85 mmol), DMAP (31 mg, 0.25 mmol), TEA (339 mg, 3.36 mmol) were added. The resulting mixture was stirred at room temperature for 10 h. The reaction mixture was poured into water (20 mL) and extracted with ethyl acetate (60 mL×3). The combined organic layer was washed with $H_2O$ (200 mL×3), dried over anhydrous $Na_2SO_4$, filtered and concentrated in vacuo. The residue was purified by silica gel column to afford the desired product tert-butyl 7-(4-fluorobenzyl)-6,7,8,9-tetrahydro-3-iodo-8-oxo-[1,3]diazepino[5,4-f]indazole-1(5H)-carboxylate (720 mg, 80% yield).

7-(4-fluorobenzyl)-6,7-dihydro-3-(2-methoxypyrimidin-5-yl)-[1,3]diazepino[5,4-f]indazol-8(1H,5H,9H)-one To a mixture of tert-butyl 7-(4-fluorobenzyl)-6,7,8,9-tetrahydro-3-iodo-8-oxo-[1,3]diazepino[5,4-f]indazole-1(5H)-carboxylate (720 mg, 1.34 mmol) and 2-methoxypyrimidin-5-yl-5-boronic acid (616 mg, 4 mmol) in 1,4-dioxane/$H_2O$ (8 mL/2 mL), $PdCl_2(dppf)$ (292 mg, 0.4 mmol) and $K_2CO_3$ (553 mg, 4 mmol) were added sequentially. The resulting mixture was degassed and back-filled with argon three times and then stirred at 85° C. for 4 h. The mixture was allowed to cool to room temperature. The reaction mixture was poured into water (20 mL) and extracted with ethyl acetate (60 mL×3). The combined organic layer was washed with brine (60 mL×3), dried over anhydrous $Na_2SO_4$, filtered and concentrated in vacuo. The residue was purified by flash column chromatography on silica gel to afford the desired product 7-(4-fluorobenzyl)-6,7-dihydro-3-(2-methoxypyrimidin-5-yl)-[1,3]diazepino[5,4-f]indazol-8(1H,5H,9H)-one (392 mg, 70% yield) as a white solid. $^1H$ NMR (400 MHz, DMSO-d6) δ: 13.12 (s, 1H), 9.15 (s, 2H), 9.06 (s, 1H), 7.86 (s, 1H), 7.36 (m, 2H), 7.27 (s, 1H), 7.17 (min, 2H), 4.54 (s, 2H), 3.99 (s, 3H), 3.42 (m, 2H), 3.08 (m, 2H).

Example 11: Synthesis of 5-benzyl-3-(2-methylpyridin-4-yl)imidazo[4,5-f]indazol-6(1H,5H,7H)-one

N-benzyl-6-nitro-1-trityl-1H-indazol-5-amine

The solution of 5-bromo-6-nitro-1-trityl-1H-indazole (4 g, 8.23 mmol), phenylmethanamine (1.32 g, 12.39 mmol), $Pd_2(dba)_3$ (760 mg, 0.823 mmol), Xantphos (480 mg, 1.24 mmol), $Cs_2CO_3$ (8 g, 24.49 mmol) in dioxane (30 mL) was stirred at 110° C. under nitrogen overnight. The mixture was cooled to room temperature, and concentrated to dryness. The residue was purified by flash column chromatography on silica gel (0-5% ethyl acetate/petroleum ether to afford the desired product (2.16 g, 51% yield) as a red solid. $^1$H NMR (400 MHz, DMSO-d6) δ: 8.08 (s, 1H), 7.70 (t, J=6.0 Hz, 1H), 7.23-7.42 (m, 14H), 7.14-7.18 (m, 7H), 7.04 (s, 1H), 4.51 (d, J=6.0 Hz, 2H).

$N^5$-benzyl-1-trityl-1H-indazole-5,6-diamine

To the solution of N-benzyl-6-nitro-1-trityl-1H-indazol-5-amine and Raney Nickel (1 g) in THF (20 mL) and MeOH (10 mL) at 0° C. $N_2H_4.H_2O$ (10 mL) was added dropwise. The mixture was warmed to room temperature and stirred at this temperature for 1 h. The mixture was filtered, and the filtrate was concentrated in vacuo to give the product (2 g, 97% yield) as a gray solid which was used in the next step directly.

1-benzyl-5-tritylimidazo[4,5-f]indol-2(1H,3H,5H)-one

The solution of $N^5$-benzyl-1-trityl-1H-indazole-5,6-diamine (2 g, 4.17 mmol), TEA (1.2 mL, 4.17 mmol) in DCM (20 mL) at 0° C., triphosgene (1.19 g, 4.17 mmol) was added slowly, and the resulting mixture was stirred at room temperature under $N_2$ for 1 h. The mixture was partitioned between water and DCM. The organic layer was dried over Na2SO4, filtered and concentrated to dryness. The residue was purified by flash column chromatography on silica gel (0-30% ethyl acetate/petroleum ether to afford the desired product (720 mg, 34% yield).

5-benzylimidazo[4,5-f]indazol-6(1H,5H,7H)-one

The mixture of 5-benzyl-1-tritylimidazo[4,5-f]indazol-6(1H,5H,7H)-one (720 mg, 1.42 mmol) in TFA was stirred at room temperature for 1 h. The mixture was concentrated to dryness. NH3/MeOH (7 N) was added, and the mixture was concentrated in vacuo. The residue was purified by flash column chromatography on silica gel (0-10% MeOH/DCM) to afford the desired product (358 mg, 95% yield) as a white solid.

5-benzyl-3-iodoimidazo[4,5-f]indazol-6(1H,5H,7H)-one

To the solution of 5-benzylimidazo[4,5-f]indazol-6(1H,5H,7H)-one (620 mg, 2.35 mmol) in DMF (5 mL), KOH (657 mg, 11.74 mmol), was added and the resulting mixture was stirred at room temperature for 30 min. NIS (684 mg, 3.05 mmol) was added to the mixture and then the mixture was stirred at room temperature overnight. The mixture was partitioned between water and ethyl acetate. The organic layer was dried over $Na_2SO_4$, filtered and concentrated to dryness. The residue was purified by flash column chromatography on silica gel (0-10% MeOH/DCM) to afford the desired product (358 mg, 75% yield) as a white solid.

tert-butyl 5-benzyl-3-iodo-6-oxo-6,7-dihydroimidazo[4,5-f]indazole-1(5H)-carboxylate The mixture of 5-benzyl-3-iodoimidazo[4,5-f]indazol-6(1H,5H,7H)-one (690 mg, 1.77 mmol), DMAP (108 mg, 0.88 mmol), TEA (0.5 ml, 3.54 mmol) in THF (5 mL) was stirred at room temperature for 10 min. To this mixture, $BOC_2O$ (1.16 g, 5.3 mmol) was added, and the resulting mixture was stirred at room temperature for 1 h. The mixture was concentrated to dryness, and the residue was purified by flash column chromatography on silica gel (0-20% ethyl acetate/petroleum ether to afford the desired product (516 mg, 59% yield) as a yellow solid.

5-benzyl-3-(2-methylpyridin-4-yl)imidazo[4,5-f]indazol-6(1H,5H,7H)-one

The mixture of tert-butyl 5-benzyl-3-iodo-6-oxo-6,7-dihydroimidazo[4,5-f]indazole-1(5H)-carboxylate (250 mg, 0.51 mmol), 2-methylpyridin-4-ylboronic acid (209 mg, 1.53 mmol), $K_2CO_3$ (209 mg, 1.53 mmol), $Pd(dppf)Cl_2$ (112 mg, 0.15 mmol) in $H_2O$ (3 mL) and dioxane (12 mL) was stirred at 100° C. under nitrogen overnight. The reaction mixture was concentrated to dryness. The residue was purified by flash column chromatography on silica gel (0-10% MeOH/DCM) to afford the desired product (43 mg, 24% yield) as a brown solid, 1H NMR (400 MHz, DMSO-d6) δ: 13.24 (s, 1H), 11.08 (s, 1H), 8.52 (d, J=5.2 Hz, 1H), 7.75 (m, 2H), 7.63 (s, 1H), 7.36 (m, 4H), 7.26 (m, 1H), 7.09 (s, 1H), 5.16 (s, 2H), 2.57 (s, 3H). ESI-MS m/z: 356.1

Example 12: Synthesis of 6-(1-benzylpiperidin-3-yl)-3-(2-methylpyridin-4-yl)-1H-pyrazolo[4,3-g]quinolin-7(8H)-one

Ethyl 4-(6-amino-3-bromo-1-trityl-1H-indazol-5-yl)but-3-enoate

To a solution of Triethyl phosphonoacetate (1.06 g, 4.73 mmol) in THF (20 mL) at 0° C., NaH (145 mg, 4.73 mmol) was added and the resulting mixture was stirred for 30 min. To this mixture, 6-amino-3-bromo-1-trityl-1H-indazole-5-carbaldehyde (1.9 g, 3.94 mmol) in THF (10 mL) was added slowly and then it was stirred at RT for 1 h. The mixture was partitioned between water and EA. The organic layer was concentrated to dryness. The residue was purified by silica gel column (0-1.5% methanol in dichloromethane) to give the desired product (1.9 g, 88% yield). ESI-MS m/z: 553.

3-bromo-1-trityl-1H-pyrazolo[4,3-g]quinolin-7(8H)-one

The mixture of ethyl 4-(6-amino-3-bromo-1-trityl-1H-indazol-5-yl)but-3-enoate (1.7 g, 3.08 mmol) and DBU (9.35 g, 61.54 mmol) in NMP (170 mL) was stirred at 160° C. overnight. The mixture was concentrated in vacuo. The residue was partitioned between water and EA. The organic layer was concentrated in vacuo and the residue was purified by silica gel column (0-3% methanol in dichloromethane) to give the desired product (1.0 g, 64% yield). ESI-MS m/z: 506.

3-(2-methylpyridin-4-yl)-1-trityl-1H-pyrazolo[4,3-g]quinolin-7(8H)-one

The mixture of 3-bromo-1-trityl-1H-pyrazolo[4,3-g]quinolin-7(8H)-one (1.1 g, 2.17 mmol), 2-methylpyridin-4-yl- 4-boronic acid (743 mg, 5.43 mmol), Pd(dppf)Cl₂ (480 mg, 0.65 mmol) and K₂CO₃ (900 mg, 6.52 mmol) in dioxane/H₂O (50 mL/5 mL) was stirred at 90° C. overnight. The reaction mixture was concentrated to dryness. The residue was purified by silica gel column (0-2% methanol in dichloromethane) to give the desired product (700 mg, 64% yield). ESI-MS m/z: 519.

6-bromo-3-(2-methylpyridin-4-yl)-1-trityl-1H-pyrazolo[4,3-g]quinolin-7(8H)-one

The mixture of 3-(2-methylpyridin-4-yl)-1-trityl-1H-pyrazolo[4,3-g]quinolin-7(8H)-one (700 mg, 1.35 mmol) and NBS (1.44 g, 8.10 mmol) in DMF (15 mL) was stirred at 55° C. overnight. The mixture was poured into water and extracted with EA. The organic layer was concentrated to dryness. The residue was purified by silica gel column (DCM/MeOH=200/1-75/1) to give the desired product (450 mg, 56% yield). ESI-MS m/z: 597.

6-(1-benzyl-1,2,5,6-tetrahydropyridin-3-yl)-3-(2-methylpyridin-4-yl)-1-trityl-1H-pyrazolo[4,3-g]quinolin-7(8H)-one The mixture of 6-bromo-3-(2-methylpyridin-4-yl)-1-trityl-1H-pyrazolo[4,3-g]quinolin-7(8H)-one (170 mg, 0.28 mmol), 1-benzyl-1,2,5,6-tetrahydropyridin-3-yl-3-boronic acid (300 mg, 1.38 mmol), Pd(dppf)Cl₂ (52 mg, 0.07 mmol) and K₂CO₃ (120 mg, 0.85 mmol) in dioxane/H₂O (12 mL/3 mL) was stirred at 90° C. overnight. The reaction mixture was concentrated to dryness. The residue was purified by silica gel column (DCM/MeOH=200/1-50/1) to give the desired product (170 mg, 87% yield). ESI-MS m/z: 690.

tert-butyl 3-(7,8-dihydro-3-(2-methylpyridin-4-yl)-7-oxo-1-trityl-1H-pyrazolo[4,3-g]quinolin-6-yl)piperidine-1-carboxylate The mixture of 6-(1-benzyl-1,2,5,6-tetrahydropyridin-3-yl)-3-(2-methylpyridin-4-yl)-1-trityl-1H-pyrazolo[4,3-g]quinolin-7(8H)-one (200 mg, 0.29 mmol), Pd(OH)₂/C (300 mg) and (Boc)₂O (160 mg, 0.73 mmol) in EtOAc (15 mL) was stirred under hydrogen overnight. The mixture was filtered and the filtrate was concentrated in vacuo. The residue was purified by silica gel column (DCM/MeOH=200/1-50/1) to give the desired product (80 mg, 40% yield). ESI-MS m/z: 702.

3-(2-methylpyridin-4-yl)-6-(piperidin-3-yl)-1H-pyrazolo[4,3-]quinolin-7(8H)-one

To a solution of tert-butyl 3-(7,8-dihydro-3-(2-methylpyridin-4-yl)-7-oxo-1-trityl-H-pyrazolo[4,3-g]quinolin-6-yl)piperidine-1-carboxylate (75 mg, 0.107 mmol) in DCM (3 mL), was added TFA (3 ml) and Et₃SiH (3 drops). The mixture was stirred at RT for 2 h. The mixture was concentrated in vacuo and the residue was diluted with NH₃ (in methanol). The mixture was concentrated in vacuo and the residue (38 mg, 100% yield) was used in next step without further purification. ESI-MS m/z: 360.

6-(1-benzylpiperidin-3-yl)-3-(2-methylpyridin-4-yl)-1H-pyrazolo[4,3-g]quinolin-7(8H)-one The mixture of 3-(2-methylpyridin-4-yl)-6-(piperidin-3-yl)-1H-pyrazolo[4,3-g]quinolin-7(8H)-one (38 mg, 0.2 mmol) benzaldehyde (120 mg, 2.1 mmol) and AcOH (50 mg, 0.83 mmol) in 10 mL of MeOH was stirred at RT for 2 h. To this mixture, sodium cyanoborohydride (50 mg, 0.79 mmol) was added and the resulting mixture was stirred overnight. The reaction mixture was concentrated to dryness. The residue was purified by silica gel column (DCM/MeOH=100/1-10/1) to give the desired product (20 mg, 43% yield). ¹H NMR (400 MHz, CD₃OD) δ: 8.70 (m, 2H), 8.44 (s, 1H), 8.39 (d, J=6.4 Hz, 1H), 8.11 (s, 1H), 7.53 (s, 1H), 3.77-3.62 (m, 2H), 3.15 (m, 1H), 2.96 (s, 3H), 2.85 (s, 3H), 2.21-1.95 (m, 6H). ESI-MS m/z: 450

Example 13: Synthesis of 6-(3-chlorobenzyl)-3-(2-methylpyridin-4-yl)-1,8-dihydro-5H-pyrazolo[4,3-g]quinazoline-5,7(6H)-dione 6-acetamido-3-(2-methylpyridin-4-yl)-1-trityl-1H-indazole-5-carboxylic acid To a stirred solution of N-(5-formyl-3-(2-methylpyridin-4-yl)-1-trityl-1H-indazol-6-yl)acetamide (220 mg, 0.40 mmol) in 40 mL of acetone at room temperature, was added 20 mL of Jones reagent. The reaction mixture was stirred at room temperature for 1 h. Solvent was removed and the residue was subjected to a Flash column purification to give of the desired product (68 mg, 30%).

6-amino-3-(2-methylpyridin-4-yl)-1H-indazole-5-carboxylic acid

To a stirred solution of 6-acetamido-3-(2-methylpyridin-4-yl)-1-trityl-1H-indazole-5-carboxylic acid (268 mg, 0.50 mmol) in 10 mL of dioxane at room temperature, was added 10 mL of 6 N HCl. The reaction mixture was stirred at 100° C. for 2 h. Solvent was removed. The residue was diluted in DCM, washed with NaHCO₃ and water. The organic layer was dried and concentrated in vacuo to give 102 mg of crude product. It was used in the next step without further purifications.

6-amino-N-(3-chlorobenzyl)-3-(2-methylpyridin-4-yl)-1H-indazole-5-carboxamide

To a stirred solution of crude 6-amino-3-(2-methylpyridin-4-yl)-1H-indazole-5-carboxylic acid from previous step (14 mg, 0.05 mmol) and (3-chlorophenyl)methanamine (18 μL, 0.15 mmol) in 2 mL of dry DMF, was added HATU (29 mg, 0.075 mmol) followed by DIEA (45 μL, 0.25 mmol). The reaction mixture was stirred at room temperature for 2 h. The reaction mixture was diluted with ethyl acetate and washed with water twice. The organic layer was dried and concentrated in vacuo. The residue was purified by flash column chromatography on silica gel to give the desired product (11 mg, 54%) as a yellow powder.

6-(3-chlorobenzyl)-3-(2-methylpyridin-4-yl)-1,8-dihydro-5H-pyrazolo[4,3-g]quinazoline-5,7(6H)-dione To a solution of 6-amino-N-(3-chlorobenzyl)-3-(2-methylpyridin-4-yl)-1H-indazole-5-carboxamide (5 mg, 0.013 mmol) in 3 mL of DCM was added Et₃N (14 μL, 0.078 mmol) followed by CDI (21 mg, 0.128 mmol). The reaction mixture was stirred at room temperature overnight. Solvent was removed and the residue was subjected to prep-HPLC and prep-TLC purification to give the desired product (2.8 mg, 53% yield). ¹H NMR (500 MHz, DMSO-d6) δ: 13.62 (s, 1H), 10.56 (s, 1H), 8.75 (s, 1H), 8.594 (d, J=5.5 Hz, 1H), 7.84 (s, 1H), 7.78 (d, J=5.0 Hz, 1H), 7.41 (s, 1H), 7.28-7.36 (m, 3H), 7.13 (s, 1H), 5.12 (s, 2H), 2.59 (s, 3H). ESI-MS m/z: 417.1.

Example 14: Synthesis of 6-(2-hydroxy-1-phenylethyl)-3-(2-methylpyridin-4-yl)-1,8-dihydro-7H-pyrazolo[4,3-g]quinolin-7-one 6-bromo-3-(2-methylpyridin-4-yl)-1-trityl-1,8-dihydro-7H-pyrazolo[4,3-g]quinolin-7-one To a solution of 3-(2-methylpyridin-4-yl)-1-trityl-1,8-dihydro-7H-pyrazolo[4,3-g]quinolin-7-one (14 mg, 0.025 mmol) in 3.0 mL of DMF at room temperature was added NBS (22 mg, 0.12 mmol). The reaction mixture was stirred at 50° C. for 1 h. The reaction mixture was diluted with ethyl acetate, washed with water and dried over $Na_2SO_4$. The dried solution was concentrated and the residue was subjected to a column purification to give the desired product (12 mg, 75%).

3-(2-methylpyridin-4-yl)-6-(1-phenylvinyl)-1-trityl-1,8-dihydro-7H-pyrazolo[4,3-g]quinolin-7-one To a solution of 6-bromo-3-(2-methylpyridin-4-yl)-1-trityl-1,8-dihydro-7H-pyrazolo[4,3-g]quinolin-7-one (120 mg, 0.20 mmol) and (1-phenylvinyl)boronic acid (89 mg, 0.60 mmol) in 3.0 mL of 4:1 dioxane/water mixture at room temperature were added $PdCl_2$(dppf) (33 mg, 0.04 mmol) and $K_2CO_3$ (83 mg, 0.60 mmol). The reaction mixture was degassed and backfilled with nitrogen. The reaction mixture was stirred at 80° C. overnight. Solid was filtered off and the filtrate was concentrated in vacuo. The residue was subjected to a flash column chromatography purification to give the desired product (72 mg, 58% yield).

6-(2-hydroxy-1-phenylethyl)-3-(2-methylpyridin-4-yl)-1-trityl-1,8-dihydro-7H-pyrazolo[4,3-g]quinolin-7-one A stirred solution of 3-(2-methylpyridin-4-yl)-6-(1-phenylvinyl)-1-trityl-1,8-dihydro-7H-pyrazolo[4,3-g]quinolin-7-one (96.8 mg, 0.16 mmol) in 5 mL anhydrous THF was cooled down to 0° C. in ice-water bath, large excess of borane dimethyl sulfide complex (4 mL) was added dropwise. The reaction mixture was stirred at 0° C. for 2 h and then stirred at room temperature overnight. The reaction mixture was cooled to 0° C. and then 5 mL of deionized water was added. To the reaction mixture, was added 5 mL of 3 M NaOH, followed by 10 mL $H_2O_2$ solution dropwise, and the resulting mixture was stirred at 50° C. for 1 h. The reaction mixture was extracted 3 times with DCM. The organic layer was dried over anhydrous $Na_2SO_4$, and concentrated in vacuo to yield a brown solid as a crude product. The crude compound was used in the next step without further purification.

6-(2-hydroxy-1-phenylethyl)-3-(2-methylpyridin-4-yl)-1,8-dihydro-7H-pyrazolo[4,3-g]quinolin-7-one To a solution of the crude 6-(2-hydroxy-1-phenylethyl)-3-(2-methylpyridin-4-yl)-1-trityl-1,8-dihydro-7H-pyrazolo[4,3-g]quinolin-7-one from the previous step in 10 mL of DCM, 1 mL of TFA was added and the resulting mixture was stirred at room temperature for 2 h. The mixture was washed with saturated $NaHCO_3$ and brine, dried over anhydrous $Na_2SO_4$, and concentrated in vacuo. The residue was purified with column chromatography on silica gel (10% MeOH in DCM) to yield a yellow solid as the desired product (32 mg, 55% yield). $^1$H NMR (500 MHz, DMSO-d6) δ: 13.42 (s, 1H), 11.65 (s, 1H), 8.60 (s, 1H), 8.56 (d, J=5.0 Hz, 1H), 8.03 (s, 1H), 7.93 (s, 1H), 7.86 (d, J=5.5 Hz, 1H), 7.37 (s, 1H), 7.33 (d, J=7.0 Hz, 2H), 7.29 (t, J=7.0 Hz, 2H), 7.19 (t, J=7.5 Hz, 1H), 4.84 (t, J=5.5 Hz, 1H), 4.34 (t, J=7.5 Hz, 1H), 4.00 (m, 1H), 3.90 (m, 1H), 2.60 (s, 3H). ESI-MS m/z: 397.2.

Example 15: Synthesis of (6-benzyl-3-(2,6-dimethylpyridin-4-yl)-7-oxo-5,6,7,8-tetrahydro-1H-pyrazolo[4,3-g]quinazolin-1-yl)methyl (6-benzyl-3-(2,6-dimethylpyridin-4-yl)-7-oxo-5,6,7,8-tetrahydro-1H-pyrazolo[4,3-g]quinazolin-1-yl) methyl di-tert-butyl phosphate To a stirred solution of 6-benzyl-3-(2,6-dimethylpyridin-4-yl)-1,5,6,8-tetrahydro-7H-pyrazolo[4,3-g]quinazolin-7-one (76 mg, 0.20 mmol) in 5.0 mL of dry DMA at room temperature was added $Cs_2CO_3$ (196 mg, 0.60 mmol) followed by di-tert-butyl (chloromethyl) phosphate (78 mg, 0.30 mmol). The reaction mixture was stirred at the 40° C. for 2 h. The reaction mixture was diluted with ethyl acetate and washed with water. The organic solution was separated and dried. The solvent was removed and the residue was subjected a flash column purification to give the desired product (50 mg, 41% yield).

(6-benzyl-3-(2,6-dimethylpyridin-4-yl)-7-oxo-5,6,7,8-tetrahydro-1H-pyrazolo[4,3-g]quinazolin-1-yl) methyl dihydrogen phosphate A solution of (6-benzyl-3-(2,6-dimethylpyridin-4-yl)-7-oxo-5,6,7,8-tetrahydro-1H-pyrazolo[4,3-g]quinazolin-1-yl) methyl di-tert-butyl phosphate (80 mg, 0.132 mmol) in 4.0 mL of 1:3 $AcOH/H_2O$ was stirred at 50° C. for 12 h. The reaction mixture was concentrated in vacuo and the residue was subjected to a prep-HPLC purification to give the desired product (38 mg, 58%). $^1$H NMR (500 MHz, DMSO-d6) δ: 10.21 (s, 1H), 8.23 (br, 1H), 7.90 (s, 1H), 7.60 (s, 2H), 7.28-7.41 (m, 5H), 5.91 (s, 2H), 4.62 (s, 2H), 4.44 (s, 2H). ESI-MS m/z: 493.1.

Example 16: Synthesis of 6-(3-chloro-4-fluorobenzyl)-3-(2-methylpyridin-4-yl)-1,8-dihydro-5H-pyrazolo[4,3-g]quinazoline-5,7(6H)-dione To a stirred solution of 6-(3-chloro-4-fluorobenzyl)-3-(2-methylpyridin-4-yl)-1,5,6,8-tetrahydro-7H-pyrazolo[4,3-g] quinazolin-7-one (8 mg, 0.02 mmol) in 2 mL of DMSO at room temperature was added $KMnO_4$ (63 mg, 0.40 mmol). The reaction mixture was stirred at 60° C. for 2 h. Solid was filtered off and the resulting DMSO solution was subjected to prep-HPLC purification to give the desired product (2.5 mg 30%). $^1$H NMR (500 MHz, DMSO-d6) δ: 13.71 (br, 1H), 11.60 (br, 1H), 8.74 (s, 1H), 8.59 (d, J=5.0 Hz, 1H), 7.83 (s, 1H), 7.78 (d, J=5.5 Hz, 1H), 7.58 (dd, J=2.0, 7.0 Hz, 1H), 7.36-7.39 (m, 2H), 7.28 (s, 1H), 5.10 (s, 2H), 2.54 (s, 3H). ESI-MS m/z: 435.1.

Example 17 Inhibition Assays of ERK

The inhibition of ERK activity by the compounds disclosed herein was determined using the Z'-LYTE kinase assay kit (Life Technologies) with a Ser/Thr 3 peptide substrate (Life Technologies) according to manufacturers' instructions. The assay was run with an ERK2 enzyme (Life Technologies) concentration of 0.47 ng/μL at 100 μM ATP (approximately the ATP $K_m$ for ERK2). The IC50 values for the compounds were determined with 3-fold serial dilutions in duplicate. The compounds were first diluted in 1:3 dilutions in 100% DMSO at 100× the desired concentration, and then further diluted (1:25) in 20 mM HEPES buffer (Invitrogen) to make 4× solutions prior to adding to the enzyme solution. The final DMSO concentration in the assay was 1%. Final reaction volume was 20 μL/well in 384-well plates. Kinase reactions were conducted or 1 hour followed by the assay development reaction (1 hour) in a 20 ul/well in a 384 well plate format. One or more compounds disclosed herein exhibited an IC50 less than 10 nM when tested in this assay (see FIG. 1).

TABLE 1

In Vitro Erk2 IC50 data for selected compounds of the invention.

| No. | Chemical Structure | Erk2 IC50 (nM) | Calculated Molecular Weight | Mass Found (M + 1) |
| --- | --- | --- | --- | --- |
| 1 | 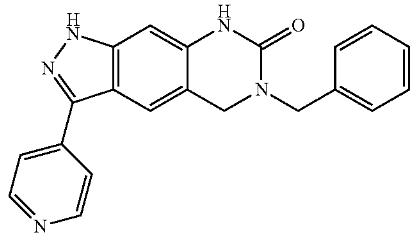 [SMILES: O=C1Nc2cc3[nH]nc(-c4ccncc4)c3cc2CN1Cc1ccccc1] | ++++ | 355.4 | 356.1 |
| 2 | 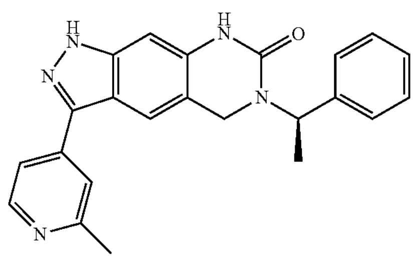 [SMILES: Cc1cc(-c2n[nH]c3cc4c(cc23)CN([C@H](C)c2ccccc2)C(=O)N4)ccn1] | ++++ | 383.5 | 384.3 |
| 3 | 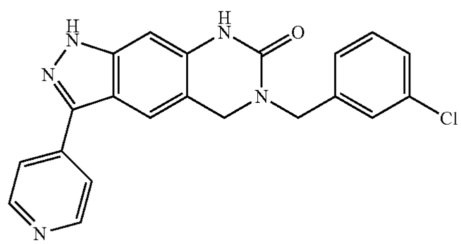 [SMILES: O=C1Nc2cc3[nH]nc(-c4ccncc4)c3cc2CN1Cc1cccc(Cl)c1] | ++++ | 389.8 | 390.1 |
| 4 | 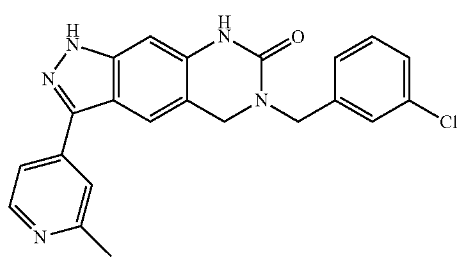 [SMILES: Cc1cc(-c2n[nH]c3cc4c(cc23)CN(Cc2cccc(Cl)c2)C(=O)N4)ccn1] | ++++ | 403.9 | 404.4 |
| 5 | 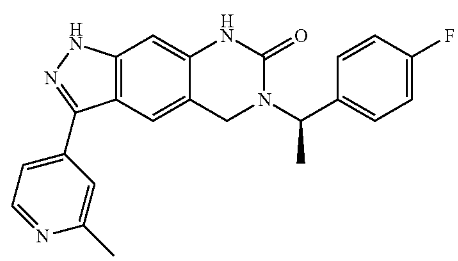 [SMILES: Cc1cc(-c2n[nH]c3cc4c(cc23)CN([C@H](C)c2ccc(F)cc2)C(=O)N4)ccn1] | +++ | 401.4 | 402.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
| --- | --- | --- | --- | --- |
| 6 | 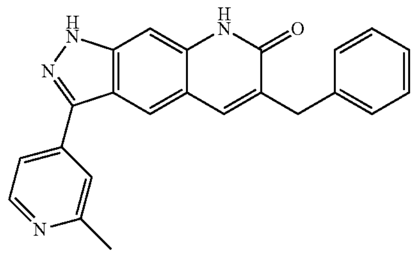 [SMILES: Cc1cc(-c2n[nH]c3cc4[nH]c(=O)c(Cc5ccccc5)cc4cc23)ccn1] | +++ | 366.4 | 367.2 |
| 7 | 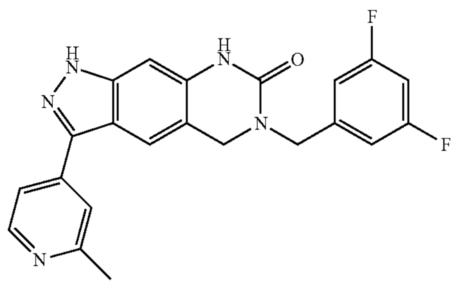 [SMILES: Cc1cc(-c2n[nH]c3cc4c(cc23)CN(Cc2cc(F)cc(F)c2)C(=O)N4)ccn1] | ++++ | 405.4 | 406.2 |
| 8 | 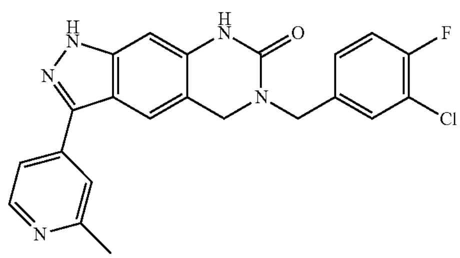 [SMILES: Cc1cc(-c2n[nH]c3cc4c(cc23)CN(Cc2ccc(F)c(Cl)c2)C(=O)N4)ccn1] | ++++ | 421.9 | 422.2 |
| 9 | 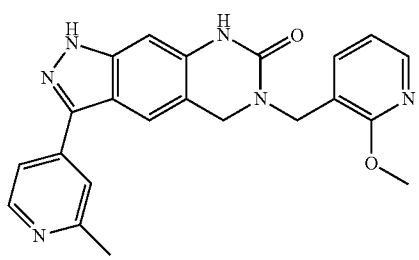 [SMILES: COc1ncccc1CN1Cc2cc3c(-c4ccnc(C)c4)n[nH]c3cc2NC1=O] | ++++ | 400.4 | 401.4 |
| 10 | 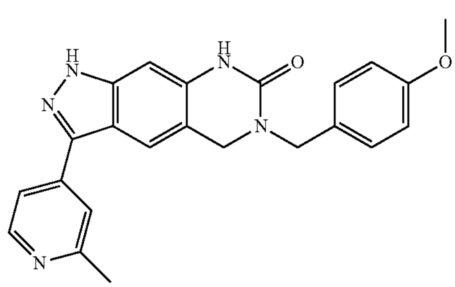 [SMILES: COc1ccc(CN2Cc3cc4c(-c5ccnc(C)c5)n[nH]c4cc3NC2=O)cc1] | ++++ | 399.4 | 400.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 11 | 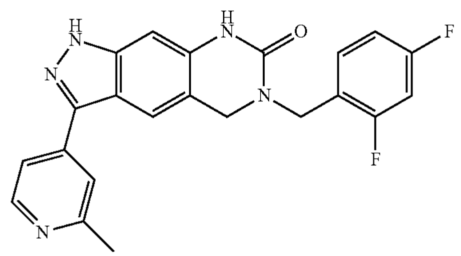 [SMILES: Cc1cc(-c2n[nH]c3cc4c(cc23)CN(Cc2ccc(F)cc2F)C(=O)N4)ccn1] | ++++ | 405.4 | 406.3 |
| 12 | 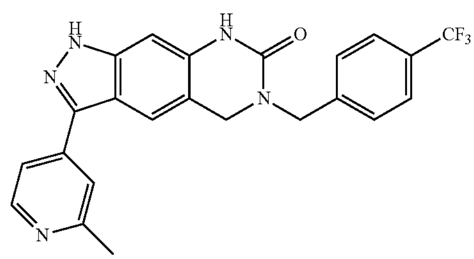 [SMILES: Cc1cc(-c2n[nH]c3cc4c(cc23)CN(Cc2ccc(C(F)(F)F)cc2)C(=O)N4)ccn1] | +++ | 437.4 | 438.2 |
| 13 | 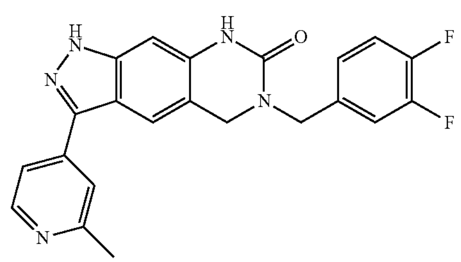 [SMILES: Cc1cc(-c2n[nH]c3cc4c(cc23)CN(Cc2ccc(F)c(F)c2)C(=O)N4)ccn1] | ++++ | 405.4 | 406.3 |
| 14 | 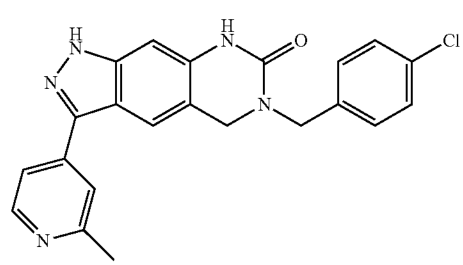 [SMILES: Cc1cc(-c2n[nH]c3cc4c(cc23)CN(Cc2ccc(Cl)cc2)C(=O)N4)ccn1] | ++++ | 403.9 | 402.5 (M − 1) |
| 15 | 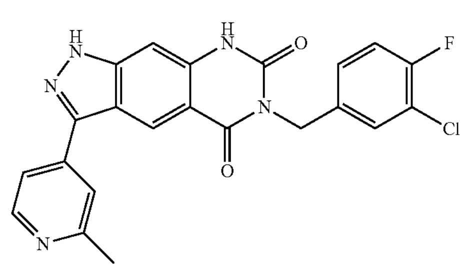 [SMILES: Cc1cc(-c2n[nH]c3cc4[nH]c(=O)n(Cc5ccc(F)c(Cl)c5)c(=O)c4cc23)ccn1] | +++ | 435.8 | 436.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 16 | 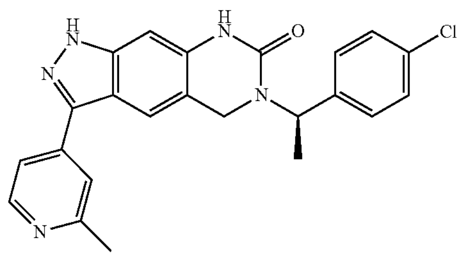 [SMILES: Cc1cc(-c2n[nH]c3cc4c(cc23)CN([C@H](C)c2ccc(Cl)cc2)C(=O)N4)ccn1] | ++++ | 417.9 | 418.2 |
| 17 | 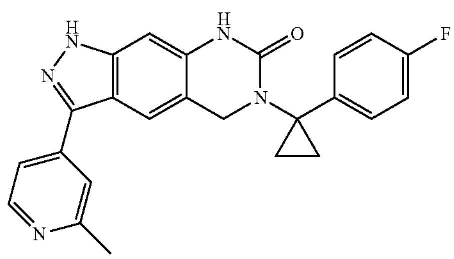 [SMILES: Cc1cc(-c2n[nH]c3cc4c(cc23)CN(C2(c3ccc(F)cc3)CC2)C(=O)N4)ccn1] | +++ | 413.4 | 414.2 |
| 18 | 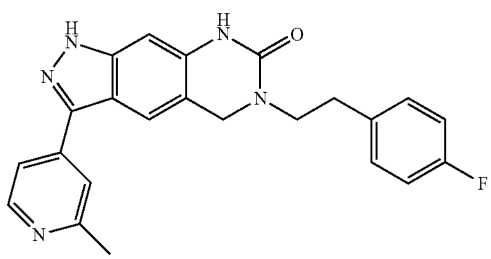 [SMILES: Cc1cc(-c2n[nH]c3cc4c(cc23)CN(CCc2ccc(F)cc2)C(=O)N4)ccn1] | ++++ | 401.4 | 402.2 |
| 19 | 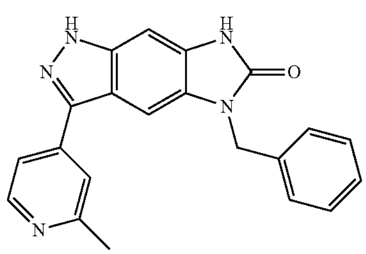 [SMILES: Cc1cc(-c2n[nH]c3cc4[nH]c(=O)n(Cc5ccccc5)c4cc23)ccn1] | ++++ | 355.4 | 356.2 |
| 20 | 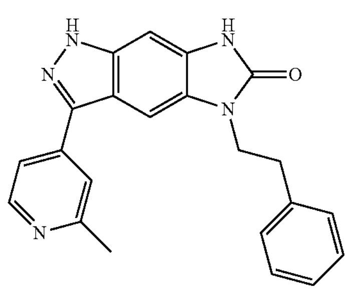 [SMILES: Cc1cc(-c2n[nH]c3cc4[nH]c(=O)n(CCc5ccccc5)c4cc23)ccn1] | +++ | 369.4 | 370.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|--------------------|----------------|-----------------------------|--------------------|
| 21  | 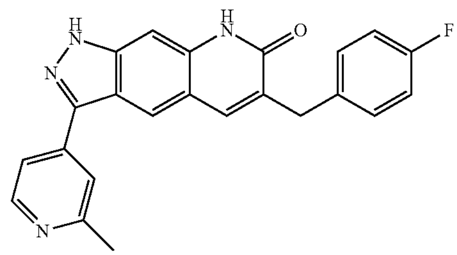 [SMILES: Cc1cc(-c2n[nH]c3cc4[nH]c(=O)c(Cc5ccc(F)cc5)cc4cc23)ccn1]                   | +++            | 384.4                       | 385.2              |
| 22  | 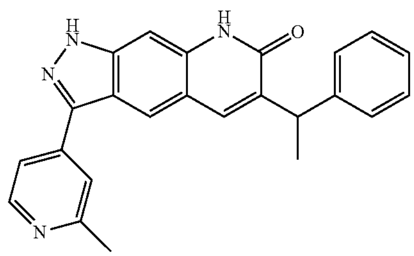 [SMILES: Cc1cc(-c2n[nH]c3cc4[nH]c(=O)c(C(C)c5ccccc5)cc4cc23)ccn1]                   | ++++           | 380.4                       | 381.2              |
| 23  | 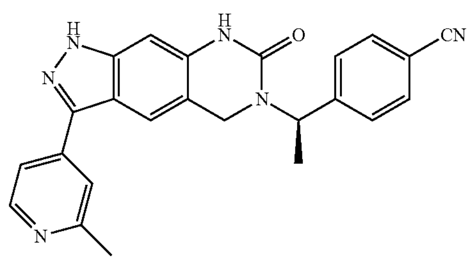 [SMILES: Cc1cc(-c2n[nH]c3cc4c(cc23)CN([C@H](C)c2ccc(C#N)cc2)C(=O)N4)ccn1]                   | ++++           | 408.5                       | 409.2              |
| 24  | 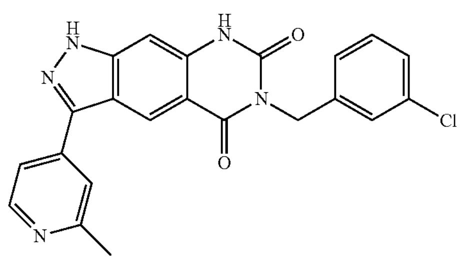 [SMILES: Cc1cc(-c2n[nH]c3cc4[nH]c(=O)n(Cc5cccc(Cl)c5)c(=O)c4cc23)ccn1]                   | +++            | 417.1                       | 418.1              |
| 25  | 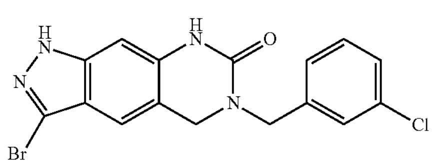 [SMILES: O=C1Nc2cc3[nH]nc(Br)c3cc2CN1Cc1cccc(Cl)c1]                   | ++             | 391.7                       | 391                |
| 26  | 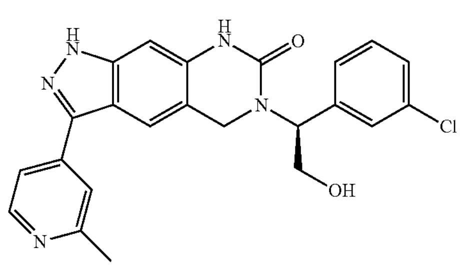 [SMILES: Cc1cc(-c2n[nH]c3cc4c(cc23)CN([C@H](CO)c2cccc(Cl)c2)C(=O)N4)ccn1]                   | ++++           | 433.9                       | 434.1              |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 27 | 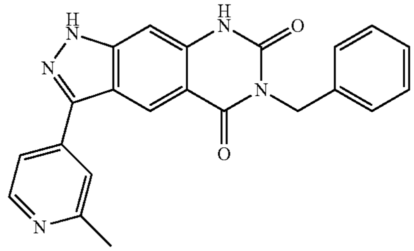 [SMILES: Cc1cc(-c2n[nH]c3cc4[nH]c(=O)n(Cc5ccccc5)c(=O)c4cc23)ccn1] | ++++ | 383.4 | 384.2 |
| 28 | 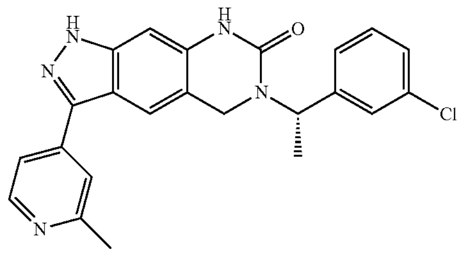 [SMILES: Cc1cc(-c2n[nH]c3cc4c(cc23)CN([C@@H](C)c2cccc(Cl)c2)C(=O)N4)ccn1] | +++ | 417.9 | 418.4 |
| 29 | 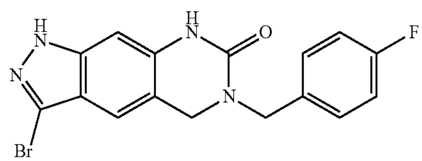 [SMILES: O=C1Nc2cc3[nH]nc(Br)c3cc2CN1Cc1ccc(F)cc1] | ++ | 374.0 | 375.2 |
| 30 | 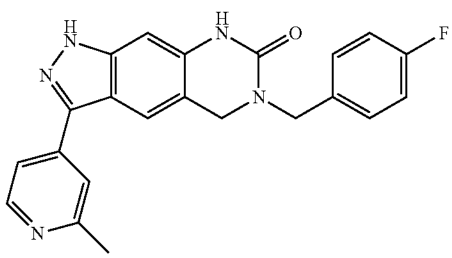 [SMILES: Cc1cc(-c2n[nH]c3cc4c(cc23)CN(Cc2ccc(F)cc2)C(=O)N4)ccn1] | ++++ | 387.4 | 388.2 |
| 31 | 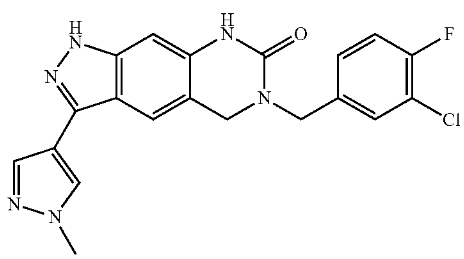 [SMILES: Cn1cc(-c2n[nH]c3cc4c(cc23)CN(Cc2ccc(F)c(Cl)c2)C(=O)N4)cn1] | ++++ | 410.8 | 411.1 |
| 32 | 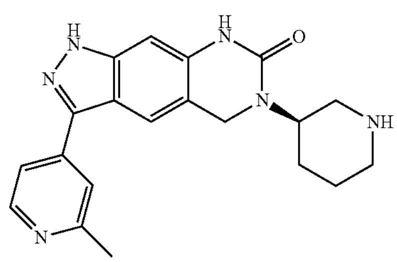 [SMILES: Cc1cc(-c2n[nH]c3cc4c(cc23)CN([C@@H]2CCCNC2)C(=O)N4)ccn1] | +++ | 362.4 | 363.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|---|---|---|---|
| 33 | 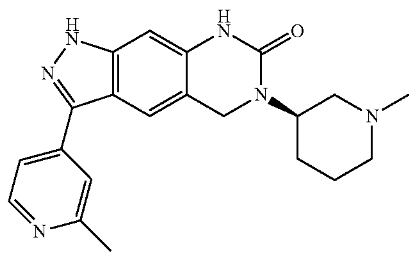 [SMILES: Cc1cc(-c2n[nH]c3cc4c(cc23)CN([C@@H]2CCCN(C)C2)C(=O)N4)ccn1] | ++++ | 376.5 | 377.3 |
| 34 | 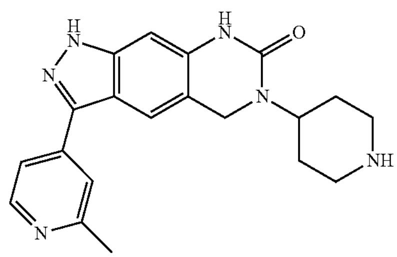 [SMILES: Cc1cc(-c2n[nH]c3cc4c(cc23)CN(C2CCNCC2)C(=O)N4)ccn1] | +++ | 362.4 | 363.2 |
| 35 | 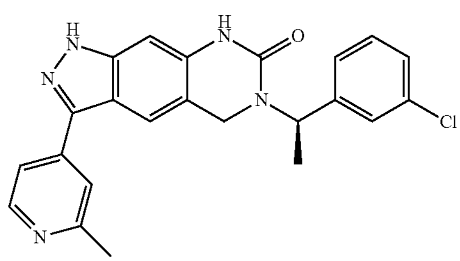 [SMILES: Cc1cc(-c2n[nH]c3cc4c(cc23)CN([C@H](C)c2cccc(Cl)c2)C(=O)N4)ccn1] | ++++ | 417.9 | 418.1 |
| 36 | 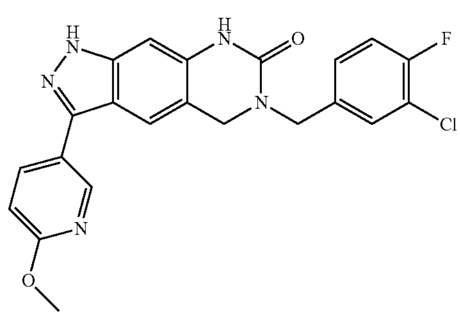 [SMILES: COc1ccc(-c2n[nH]c3cc4c(cc23)CN(Cc2ccc(F)c(Cl)c2)C(=O)N4)cn1] | ++++ | 437.9 | 438.1 |
| 37 | 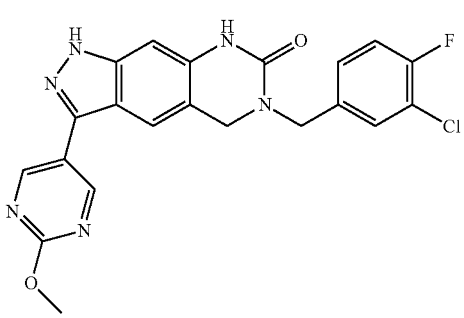 [SMILES: COc1ncc(-c2n[nH]c3cc4c(cc23)CN(Cc2ccc(F)c(Cl)c2)C(=O)N4)cn1] | ++++ | 438.8 | 439.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 38 | 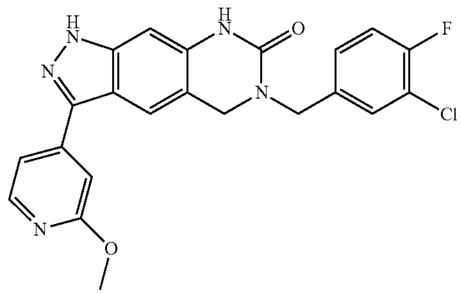 [SMILES: COc1cc(-c2n[nH]c3cc4c(cc23)CN(Cc2ccc(F)c(Cl)c2)C(=O)N4)ccn1] | ++++ | 437.9 | 438.1 |
| 39 | 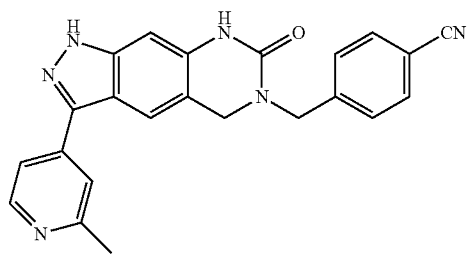 [SMILES: Cc1cc(-c2n[nH]c3cc4c(cc23)CN(Cc2ccc(C#N)cc2)C(=O)N4)ccn1] | ++++ | 394.4 | 395.2 |
| 40 | 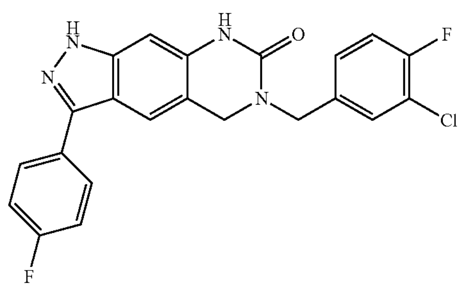 [SMILES: O=C1Nc2cc3[nH]nc(-c4ccc(F)cc4)c3cc2CN1Cc1ccc(F)c(Cl)c1] | +++ | 424.8 | 425.1 |
| 41 | 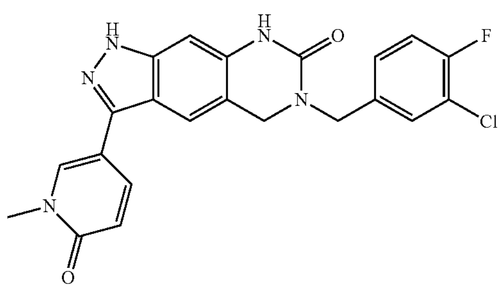 [SMILES: Cn1cc(-c2n[nH]c3cc4c(cc23)CN(Cc2ccc(F)c(Cl)c2)C(=O)N4)ccc1=O] | ++++ | 437.9 | 438.2 |
| 42 | 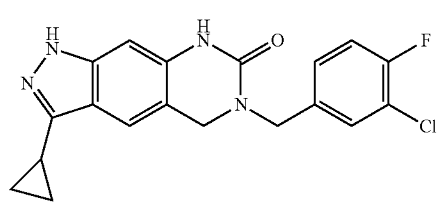 [SMILES: O=C1Nc2cc3[nH]nc(C4CC4)c3cc2CN1Cc1ccc(F)c(Cl)c1] | +++ | 370.8 | 371.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 43 | 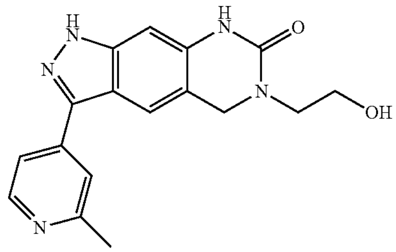 [SMILES: Cc1cc(-c2n[nH]c3cc4c(cc23)CN(CCO)C(=O)N4)ccn1] | ++++ | 323.3 | 325.2 |
| 44 | 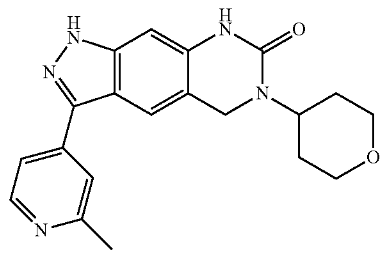 [SMILES: Cc1cc(-c2n[nH]c3cc4c(cc23)CN(C2CCOCC2)C(=O)N4)ccn1] | ++++ | 363.4 | 364.2 |
| 45 | 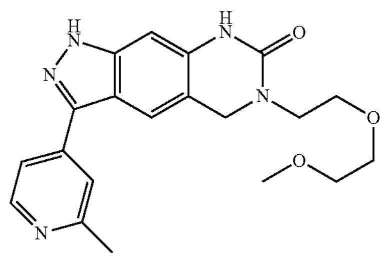 [SMILES: COCCOCCN1Cc2cc3c(-c4ccnc(C)c4)n[nH]c3cc2NC1=O] | ++++ | 381.4 | 382.2 |
| 46 | 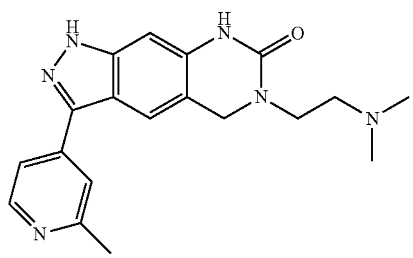 [SMILES: Cc1cc(-c2n[nH]c3cc4c(cc23)CN(CCN(C)C)C(=O)N4)ccn1] | +++ | 350.4 | 351.2 |
| 47 | 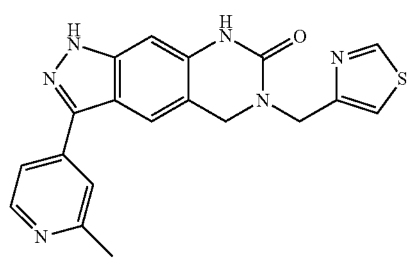 [SMILES: Cc1cc(-c2n[nH]c3cc4c(cc23)CN(Cc2cscn2)C(=O)N4)ccn1] | ++++ | 376.4 | 377.1 |
| 48 | 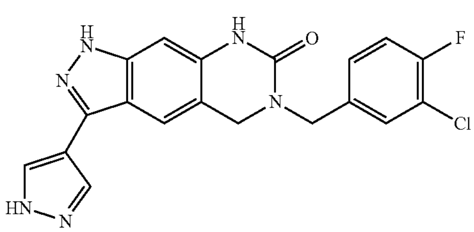 [SMILES: O=C1Nc2cc3[nH]nc(-c4cn[nH]c4)c3cc2CN1Cc1ccc(F)c(Cl)c1] | ++++ | 396.8 | 397.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 49 | 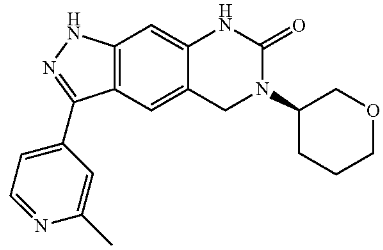 [SMILES: Cc1cc(-c2n[nH]c3cc4c(cc23)CN([C@@H]2CCCOC2)C(=O)N4)ccn1] | ++++ | 363.4 | 364.2 |
| 50 | 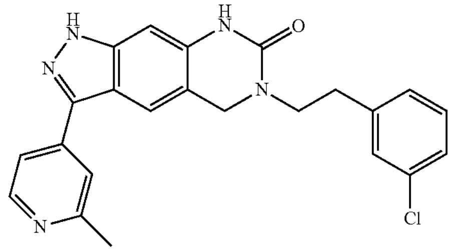 [SMILES: Cc1cc(-c2n[nH]c3cc4c(cc23)CN(CCc2cccc(Cl)c2)C(=O)N4)ccn1] | ++++ | 417.9 | 418.1 |
| 51 | 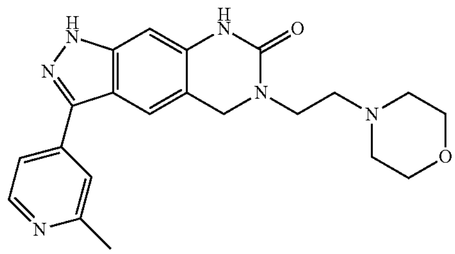 [SMILES: Cc1cc(-c2n[nH]c3cc4c(cc23)CN(CCN2CCOCC2)C(=O)N4)ccn1] | ++++ | 392.5 | 393.2 |
| 52 | 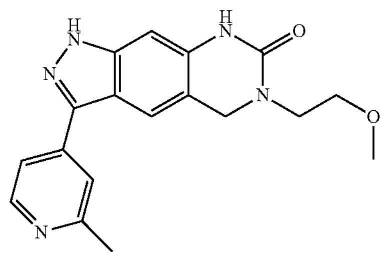 [SMILES: COCCN1Cc2cc3c(-c4ccnc(C)c4)n[nH]c3cc2NC1=O] | ++++ | 337.4 | 338.2 |
| 53 | 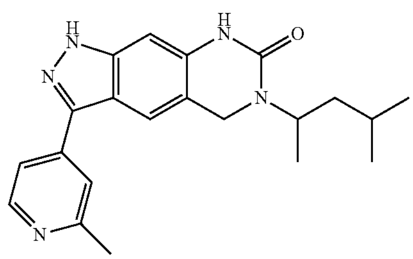 [SMILES: Cc1cc(-c2n[nH]c3cc4c(cc23)CN(C(C)CC(C)C)C(=O)N4)ccn1] | ++++ | 363.5 | 364.2 |
| 54 | 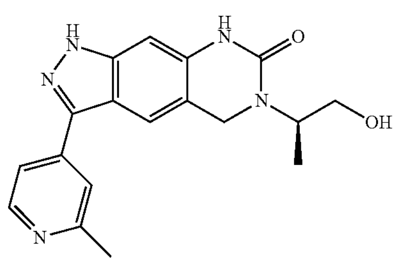 [SMILES: Cc1cc(-c2n[nH]c3cc4c(cc23)CN([C@H](C)CO)C(=O)N4)ccn1] | ++++ | 337.4 | 338.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 55 | 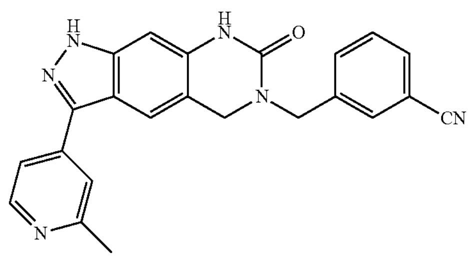 [SMILES: Cc1cc(-c2n[nH]c3cc4c(cc23)CN(Cc2cccc(C#N)c2)C(=O)N4)ccn1] | ++++ | 394.4 | 395.2 |
| 56 | 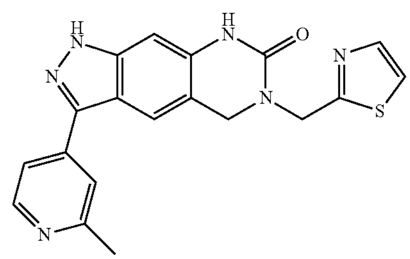 [SMILES: Cc1cc(-c2n[nH]c3cc4c(cc23)CN(Cc2nccs2)C(=O)N4)ccn1] | ++++ | 376.4 | 377.2 |
| 57 | 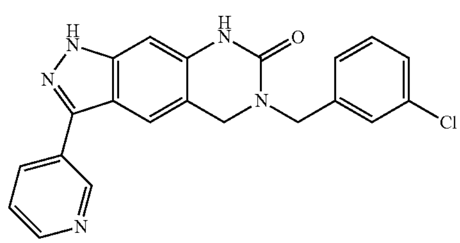 [SMILES: O=C1Nc2cc3[nH]nc(-c4cccnc4)c3cc2CN1Cc1cccc(Cl)c1] | ++++ | 389.8 | 390.1 |
| 58 | 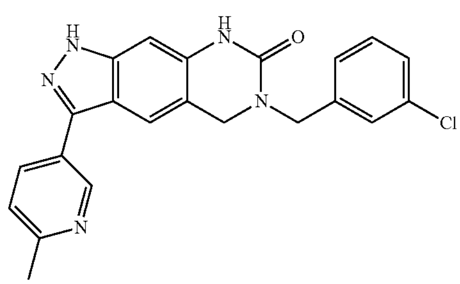 [SMILES: Cc1ccc(-c2n[nH]c3cc4c(cc23)CN(Cc2cccc(Cl)c2)C(=O)N4)cn1] | ++++ | 403.9 | 404.1 |
| 59 | 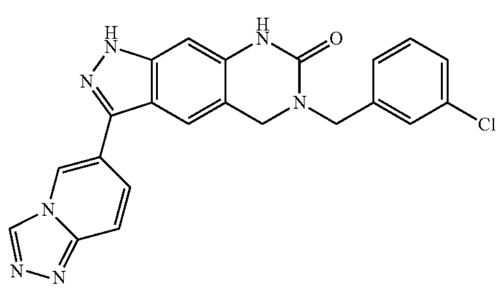 [SMILES: O=C1Nc2cc3[nH]nc(-c4ccc5nncn5c4)c3cc2CN1Cc1cccc(Cl)c1] | ++++ | 429.9 | 430.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 60 | 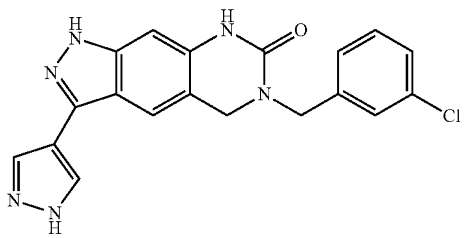 [SMILES: O=C1Nc2cc3[nH]nc(-c4cn[nH]c4)c3cc2CN1Cc1cccc(Cl)c1] | ++++ | 378.8 | 379.1 |
| 61 | 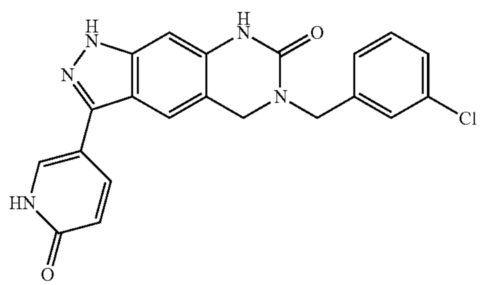 [SMILES: O=C1Nc2cc3[nH]nc(-c4ccc(=O)[nH]c4)c3cc2CN1Cc1cccc(Cl)c1] | ++++ | 405.8 | 406.1 |
| 62 | 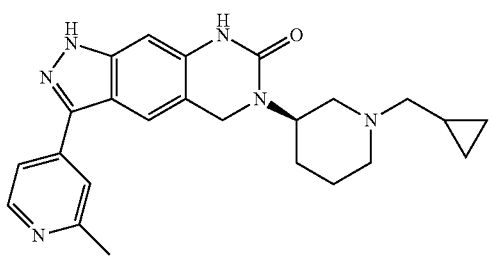 [SMILES: Cc1cc(-c2n[nH]c3cc4c(cc23)CN([C@@H]2CCCN(CC3CC3)C2)C(=O)N4)ccn1] | +++ | 416.5 | 417.3 |
| 63 | 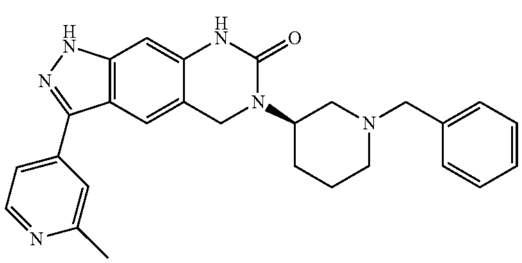 [SMILES: Cc1cc(-c2n[nH]c3cc4c(cc23)CN([C@@H]2CCCN(Cc3ccccc3)C2)C(=O)N4)ccn1] | ++++ | 452.6 | 453.3 |
| 64 | 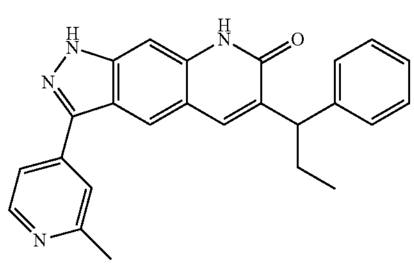 [SMILES: CCC(c1ccccc1)c1cc2cc3c(-c4ccnc(C)c4)n[nH]c3cc2[nH]c1=O] | ++++ | 394.5 | 395.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 65 | 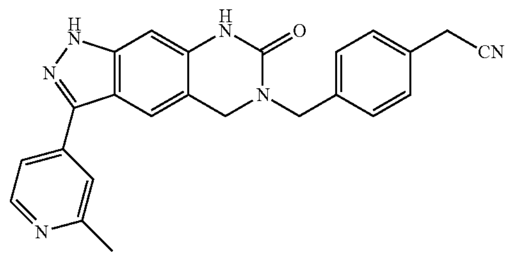 [SMILES: Cc1cc(-c2n[nH]c3cc4c(cc23)CN(Cc2ccc(CC#N)cc2)C(=O)N4)ccn1] | ++++ | 408.5 | 409.2 |
| 66 | 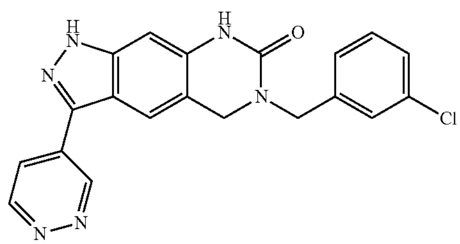 [SMILES: O=C1Nc2cc3[nH]nc(-c4ccnnc4)c3cc2CN1Cc1cccc(Cl)c1] | ++++ | 390.8 | 391.1 |
| 67 | 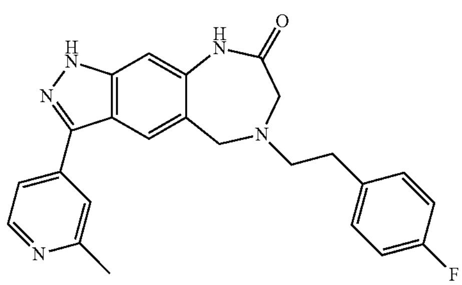 [SMILES: Cc1cc(-c2n[nH]c3cc4c(cc23)CN(CCc2ccc(F)cc2)CC(=O)N4)ccn1] | ++ | 415.5 | 416.2 |
| 68 | 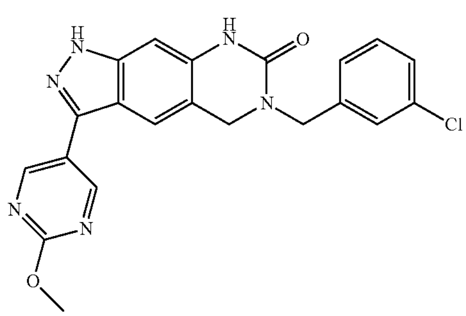 [SMILES: COc1ncc(-c2n[nH]c3cc4c(cc23)CN(Cc2cccc(Cl)c2)C(=O)N4)cn1] | ++++ | 420.9 | 421.1 |
| 69 | 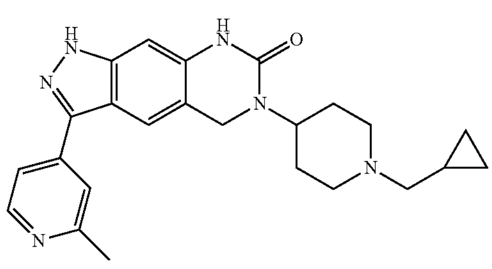 [SMILES: Cc1cc(-c2n[nH]c3cc4c(cc23)CN(C2CCN(CC3CC3)CC2)C(=O)N4)ccn1] | +++ | 416.5 | 417.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 70 | 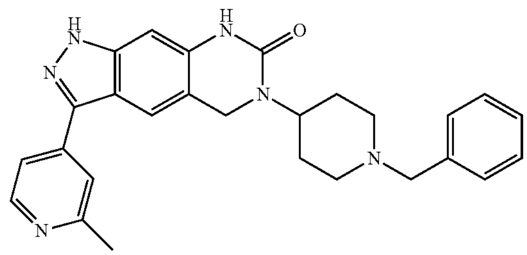 [SMILES: Cc1cc(-c2n[nH]c3cc4c(cc23)CN(C2CCN(Cc3ccccc3)CC2)C(=O)N4)ccn1] | ++++ | 452.6 | 453.3 |
| 71 | 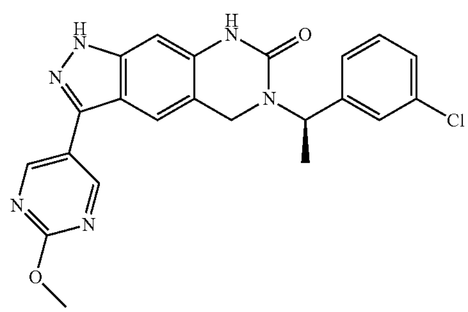 [SMILES: COc1ncc(-c2n[nH]c3cc4c(cc23)CN([C@H](C)c2cccc(Cl)c2)C(=O)N4)cn1] | ++++ | 434.9 | 435.1 |
| 72 | 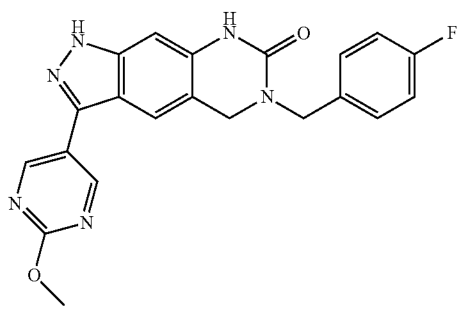 [SMILES: COc1ncc(-c2n[nH]c3cc4c(cc23)CN(Cc2ccc(F)cc2)C(=O)N4)cn1] | ++++ | 404.4 | 405.1 |
| 73 | 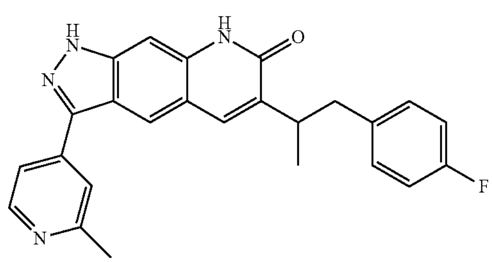 [SMILES: Cc1cc(-c2n[nH]c3cc4[nH]c(=O)c(C(C)Cc5ccc(F)cc5)cc4cc23)ccn1] | + | 412.5 | 413.2 |
| 74 | 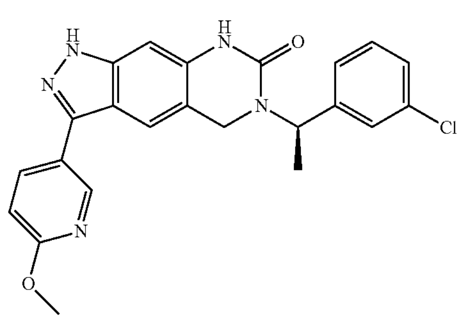 [SMILES: COc1ccc(-c2n[nH]c3cc4c(cc23)CN([C@H](C)c2cccc(Cl)c2)C(=O)N4)cn1] | +++ | 433.9 | 434.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
| --- | --- | --- | --- | --- |
| 75 | 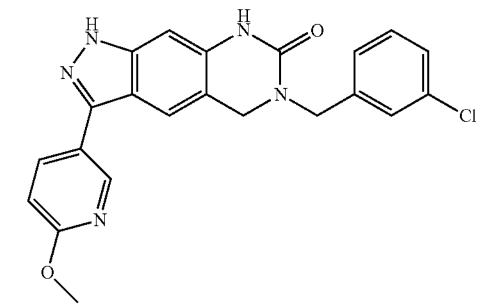 [SMILES: COc1ccc(-c2n[nH]c3cc4c(cc23)CN(Cc2cccc(Cl)c2)C(=O)N4)cn1] | ++++ | 419.9 | 420.1 |
| 76 | 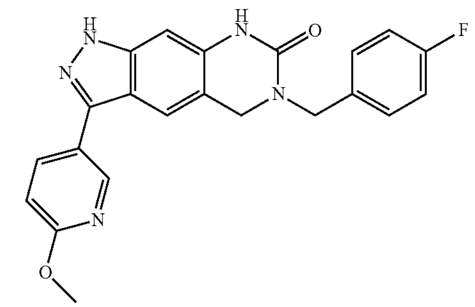 [SMILES: COc1ccc(-c2n[nH]c3cc4c(cc23)CN(Cc2ccc(F)cc2)C(=O)N4)cn1] | ++++ | 403.4 | 404.1 |
| 77 | 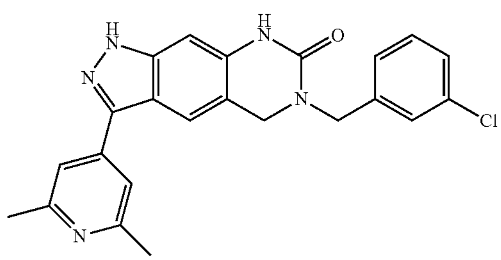 [SMILES: Cc1cc(-c2n[nH]c3cc4c(cc23)CN(Cc2cccc(Cl)c2)C(=O)N4)cc(C)n1] | ++++ | 417.9 | 418.1 |
| 78 | 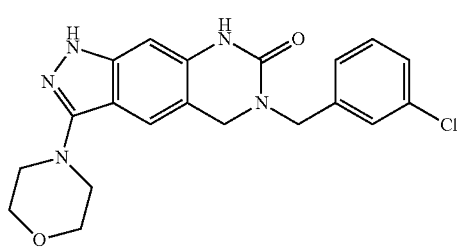 [SMILES: O=C1Nc2cc3[nH]nc(N4CCOCC4)c3cc2CN1Cc1cccc(Cl)c1] | ++++ | 397.9 | 398.1 |
| 79 | 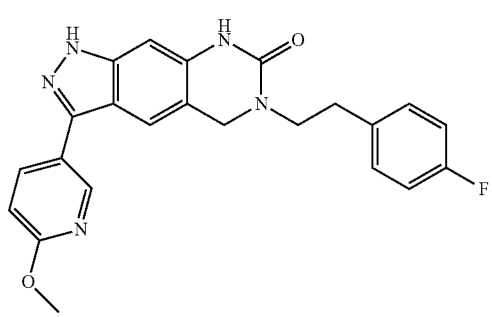 [SMILES: COc1ccc(-c2n[nH]c3cc4c(cc23)CN(CCc2ccc(F)cc2)C(=O)N4)cn1] | ++++ | 417.4 | 418.1 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 80 | 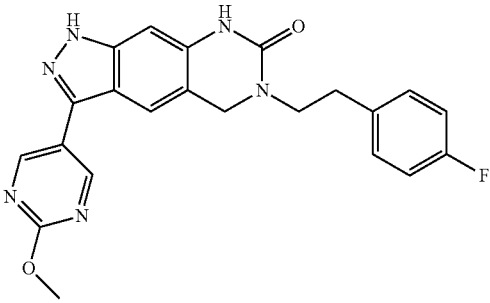 [SMILES: COc1ncc(-c2n[nH]c3cc4c(cc23)CN(CCc2ccc(F)cc2)C(=O)N4)cn1] | ++++ | 418.4 | 419.1 |
| 81 | 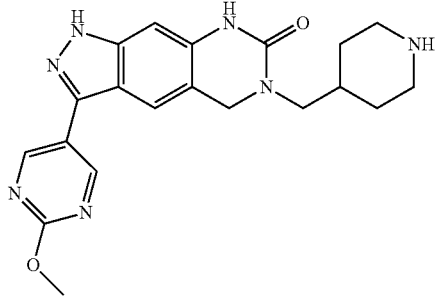 [SMILES: COc1ncc(-c2n[nH]c3cc4c(cc23)CN(CC2CCNCC2)C(=O)N4)cn1] | ++ | 393.4 | 394.2 |
| 82 | 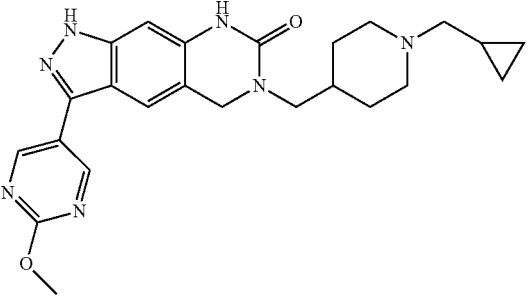 [SMILES: COc1ncc(-c2n[nH]c3cc4c(cc23)CN(CC2CCN(CC3CC3)CC2)C(=O)N4)cn1] | ++ | 447.5 | 448.3 |
| 83 | 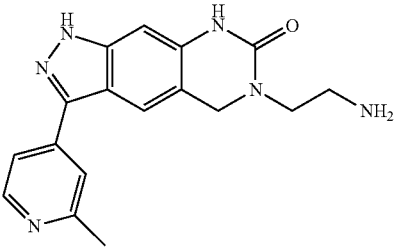 [SMILES: Cc1cc(-c2n[nH]c3cc4c(cc23)CN(CCN)C(=O)N4)ccn1] | ++++ | 322.4 | 323.2 |
| 84 | 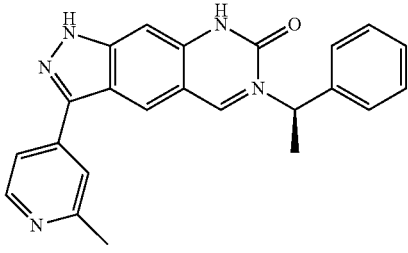 | ++++ | 380.4 | 381.2 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 85 | 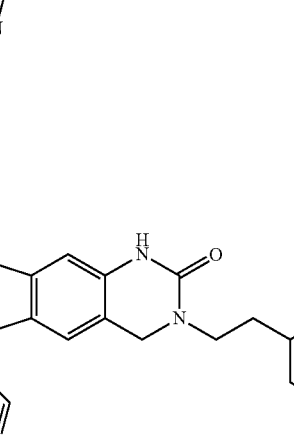 | ++++ | 433.9 | 434.1 |
| 86 | 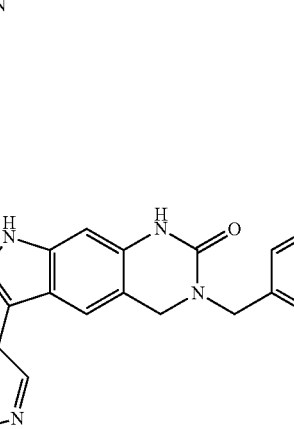 | ++++ | 434.9 | 435.1 |
| 87 | 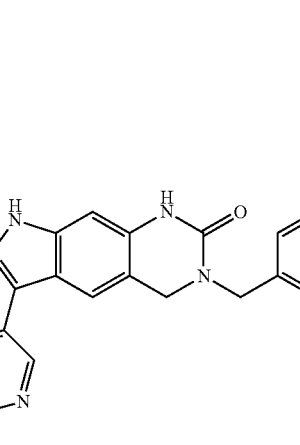 | ++++ | 421.4 | 422.1 |
| 88 | 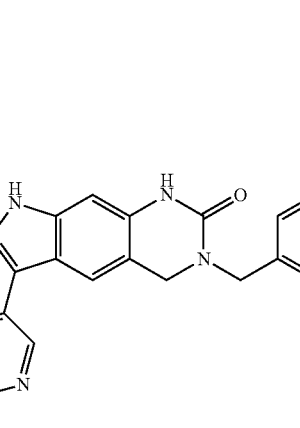 | ++++ | 422.4 | 423.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|--------------------|----------------|------------------------------|---------------------|
| 89  | 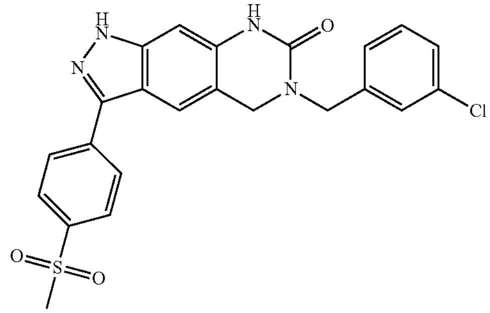 [SMILES: CS(=O)(=O)c1ccc(-c2n[nH]c3cc4c(cc23)CN(Cc2cccc(Cl)c2)C(=O)N4)cc1]                   | ++++           | 466.9                        | 467                 |
| 90  | 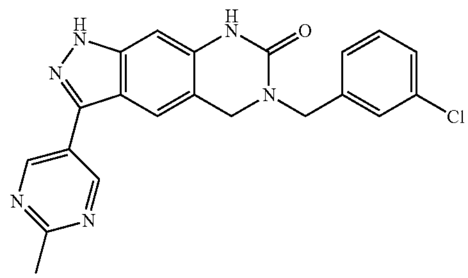 [SMILES: Cc1ncc(-c2n[nH]c3cc4c(cc23)CN(Cc2cccc(Cl)c2)C(=O)N4)cn1]                   | ++++           | 404.9                        | 405.1               |
| 91  | 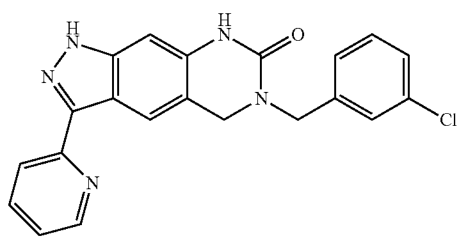 [SMILES: O=C1Nc2cc3[nH]nc(-c4ccccn4)c3cc2CN1Cc1cccc(Cl)c1]                   | +++            | 389.8                        | 390.1               |
| 92  | 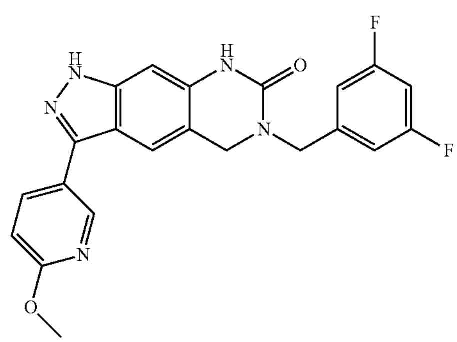 [SMILES: COc1ccc(-c2n[nH]c3cc4c(cc23)CN(Cc2cc(F)cc(F)c2)C(=O)N4)cn1]                   | ++++           | 421.4                        | 422.1               |
| 93  | 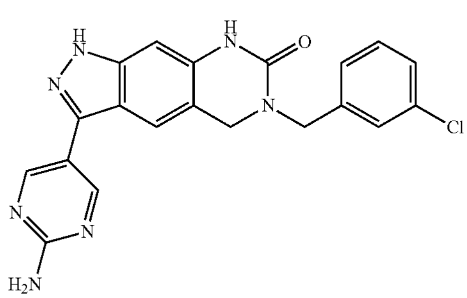 [SMILES: Nc1ncc(-c2n[nH]c3cc4c(cc23)CN(Cc2cccc(Cl)c2)C(=O)N4)cn1]                   | ++++           | 405.8                        | 406.1               |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 94 | 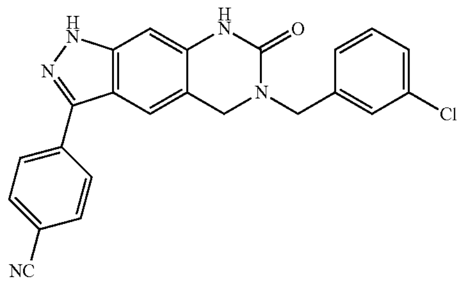 [SMILES: N#Cc1ccc(-c2n[nH]c3cc4c(cc23)CN(Cc2cccc(Cl)c2)C(=O)N4)cc1] | +++ | 413.9 | 414.1 |
| 95 | 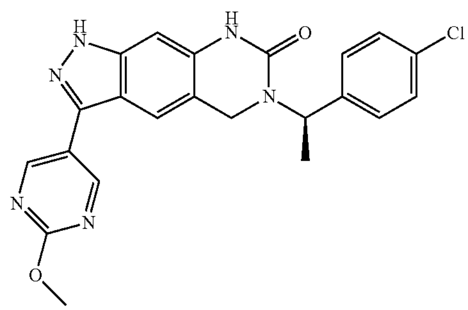 [SMILES: COc1ncc(-c2n[nH]c3cc4c(cc23)CN([C@H](C)c2ccc(Cl)cc2)C(=O)N4)cn1] | ++++ | 434.9 | 435.1 |
| 96 | 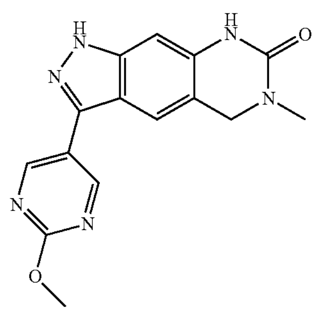 [SMILES: COc1ncc(-c2n[nH]c3cc4c(cc23)CN(C)C(=O)N4)cn1] | +++ | 310.3 | 311.1 |
| 97 | 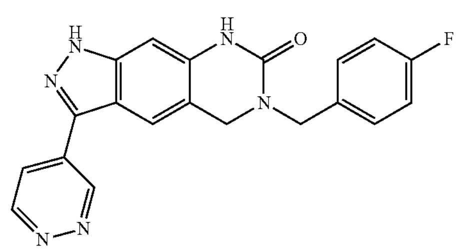 [SMILES: O=C1Nc2cc3[nH]nc(-c4ccnnc4)c3cc2CN1Cc1ccc(F)cc1] | ++++ | 374.4 | 375.1 |
| 98 | | + | 434.9 | 435.1 | ns

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 99 | 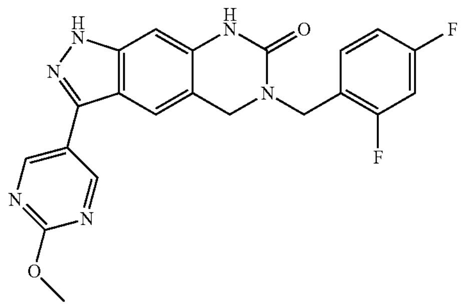 [SMILES: COc1ncc(-c2n[nH]c3cc4c(cc23)CN(Cc2ccc(F)cc2F)C(=O)N4)cn1] | ++++ | 422.4 | 423.1 |
| 100 | 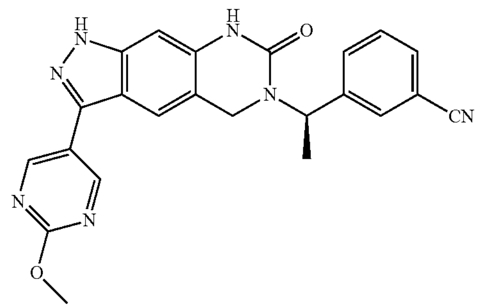 [SMILES: COc1ncc(-c2n[nH]c3cc4c(cc23)CN([C@H](C)c2cccc(C#N)c2)C(=O)N4)cn1] | ++++ | 425.4 | 426.1 |
| 101 | 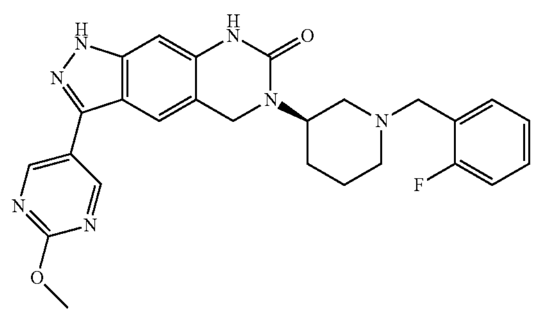 [SMILES: COc1ncc(-c2n[nH]c3cc4c(cc23)CN([C@@H]2CCCN(Cc3ccccc3F)C2)C(=O)N4)cn1] | ++++ | 487.5 | 488.2 |
| 102 | 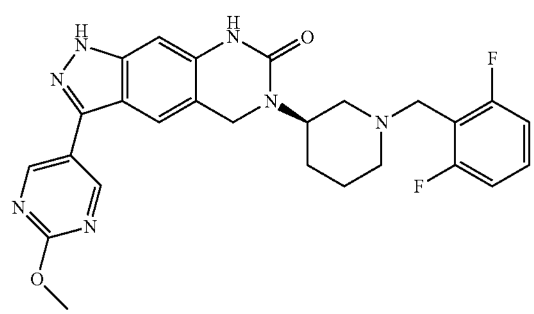 [SMILES: COc1ncc(-c2n[nH]c3cc4c(cc23)CN([C@@H]2CCCN(Cc3c(F)cccc3F)C2)C(=O)N4)cn1] | ++++ | 505.5 | 506.2 |
| 103 | 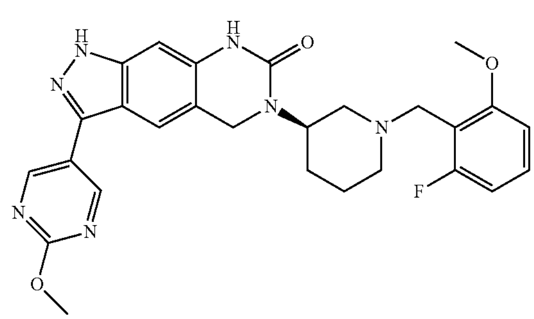 [SMILES: COc1ncc(-c2n[nH]c3cc4c(cc23)CN([C@@H]2CCCN(Cc3c(F)cccc3OC)C2)C(=O)N4)cn1] | ++++ | 517.6 | 518.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 104 | 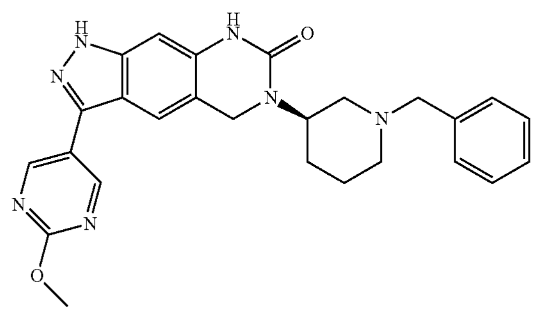 [SMILES: COc1ncc(-c2n[nH]c3cc4c(cc23)CN([C@@H]2CCCN(Cc3ccccc3)C2)C(=O)N4)cn1] | ++++ | 469.5 | 470.2 |
| 105 | 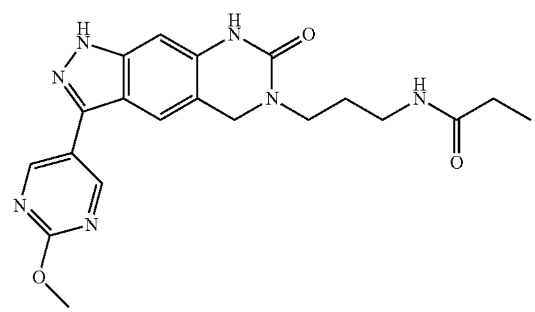 [SMILES: CCC(=O)NCCCN1Cc2cc3c(-c4cnc(OC)nc4)n[nH]c3cc2NC1=O] | ++++ | 409.4 | 410.2 |
| 106 | 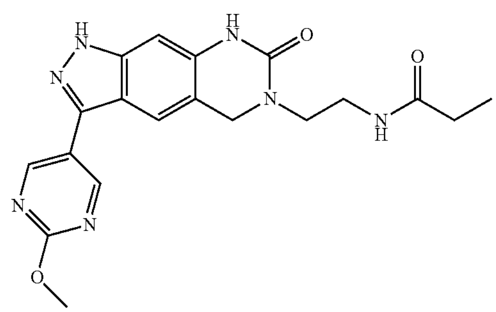 [SMILES: CCC(=O)NCCN1Cc2cc3c(-c4cnc(OC)nc4)n[nH]c3cc2NC1=O] | +++ | 395.4 | 396.2 |
| 107 | 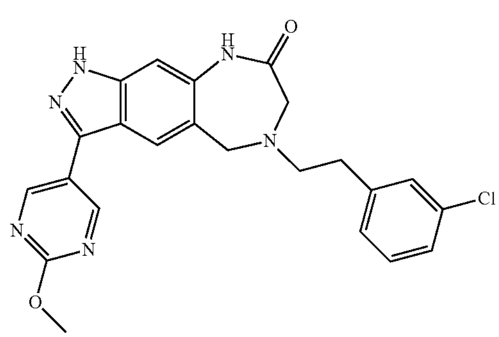 [SMILES: COc1ncc(-c2n[nH]c3cc4c(cc23)CN(CCc2cccc(Cl)c2)CC(=O)N4)cn1] | ++ | 448.9 | 449.1 |
| 108 | 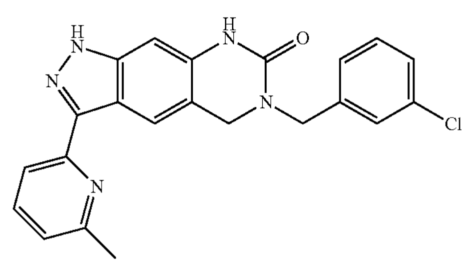 [SMILES: Cc1cccc(-c2n[nH]c3cc4c(cc23)CN(Cc2cccc(Cl)c2)C(=O)N4)n1] | +++ | 403.9 | 404.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|--------------------|----------------|-----------------------------|--------------------|
| 109 | 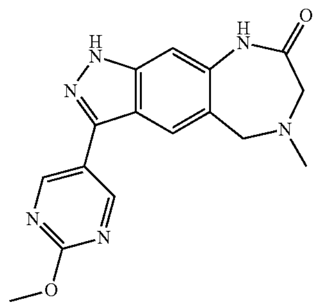 | + | 324.3 | 325.2 |
| 110 | 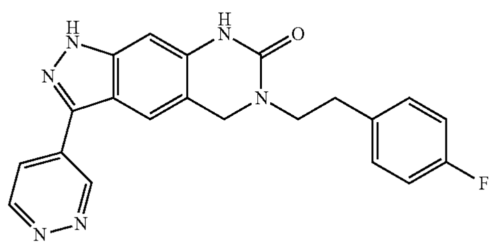 [SMILES: O=C1Nc2cc3[nH]nc(-c4ccnnc4)c3cc2CN1CCc1ccc(F)cc1] | ++++ | 388.4 | 389.2 |
| 111 | 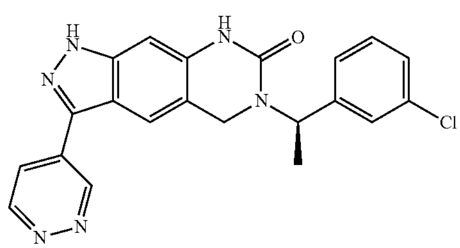 [SMILES: C[C@H](c1cccc(Cl)c1)N1Cc2cc3c(-c4ccnnc4)n[nH]c3cc2NC1=O] | ++++ | 404.9 | 405.1 |
| 112 | 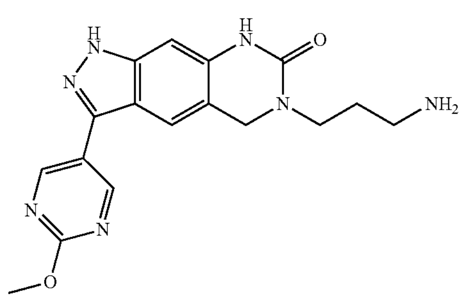 [SMILES: COc1ncc(-c2n[nH]c3cc4c(cc23)CN(CCCN)C(=O)N4)cn1] | ++++ | 353.4 | 354.2 |
| 113 | 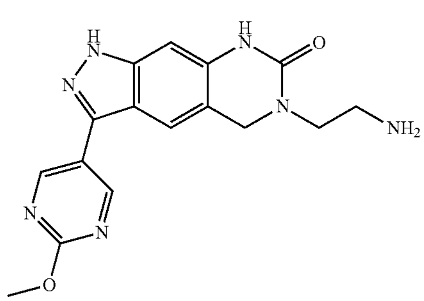 [SMILES: COc1ncc(-c2n[nH]c3cc4c(cc23)CN(CCN)C(=O)N4)cn1] | +++ | 339.4 | 340.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 114 | 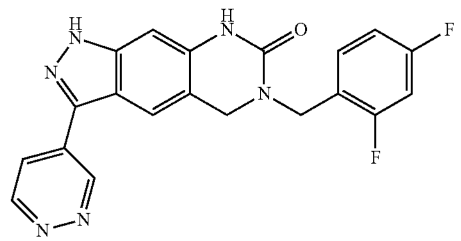 [SMILES: O=C1Nc2cc3[nH]nc(-c4ccnnc4)c3cc2CN1Cc1ccc(F)cc1F] | ++++ | 392.4 | 393.1 |
| 115 | 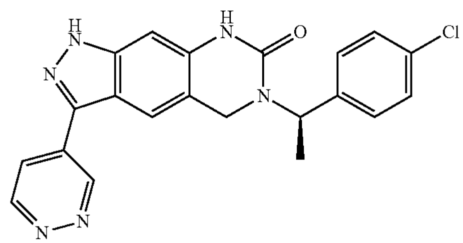 [SMILES: C[C@H](c1ccc(Cl)cc1)N1Cc2cc3c(-c4ccnnc4)n[nH]c3cc2NC1=O] | ++++ | 404.9 | 405.1 |
| 116 | 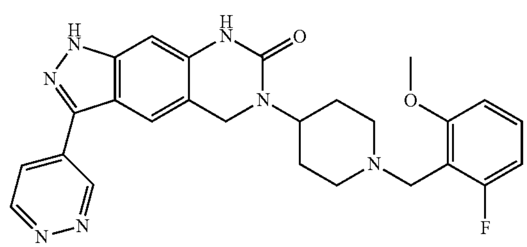 [SMILES: COc1cccc(F)c1CN1CCC(N2Cc3cc4c(-c5ccnnc5)n[nH]c4cc3NC2=O)CC1] | +++ | 487.5 | 488.2 |
| 117 | 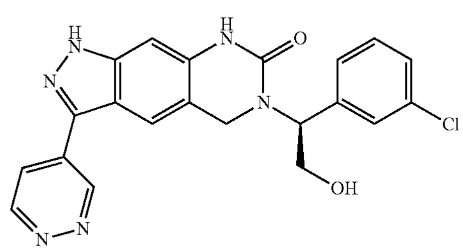 [SMILES: O=C1Nc2cc3[nH]nc(-c4ccnnc4)c3cc2CN1[C@H](CO)c1cccc(Cl)c1] | ++++ | 420.9 | 421.1 |
| 118 | 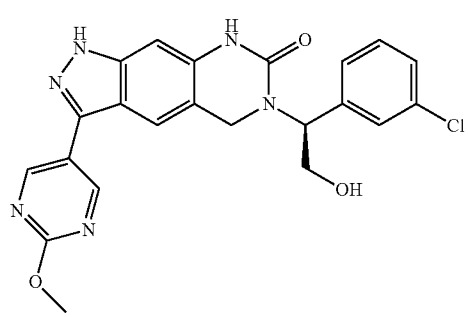 [SMILES: COc1ncc(-c2n[nH]c3cc4c(cc23)CN([C@H](CO)c2cccc(Cl)c2)C(=O)N4)cn1] | ++++ | 450.9 | 451.1 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 119 | 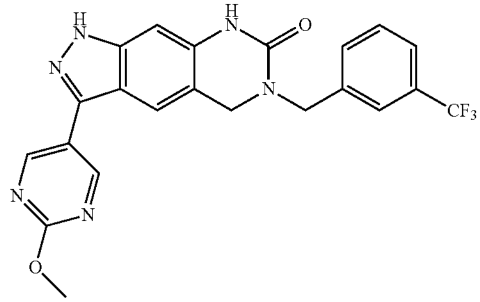 [SMILES: COc1ncc(-c2n[nH]c3cc4c(cc23)CN(Cc2cccc(C(F)(F)F)c2)C(=O)N4)cn1] | ++++ | 454.4 | 455.1 |
| 120 | 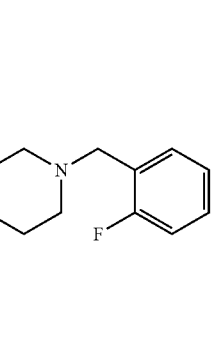 | ++++ | 439.5 | 440.1 |
| 121 | 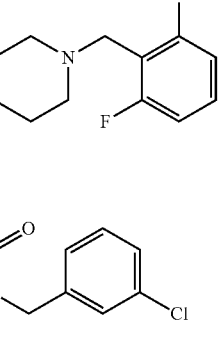 | ++++ | 457.5 | 458.2 |
| 122 | 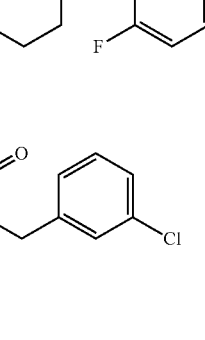 | ++++ | 475.5 | 476.2 |
| 123 | 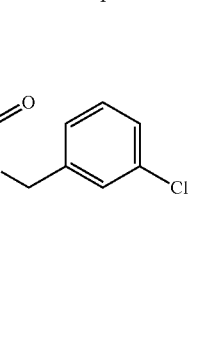 | ++++ | 390.8 | 391.1 |
| 124 | 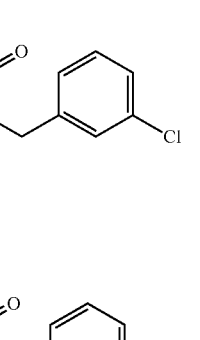 | ++++ | 424.4 | 425.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 125 | 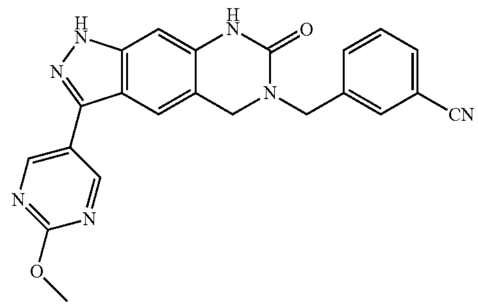 [SMILES: COc1ncc(-c2n[nH]c3cc4c(cc23)CN(Cc2cccc(C#N)c2)C(=O)N4)cn1] | ++++ | 411.4 | 412.2 |
| 126 | 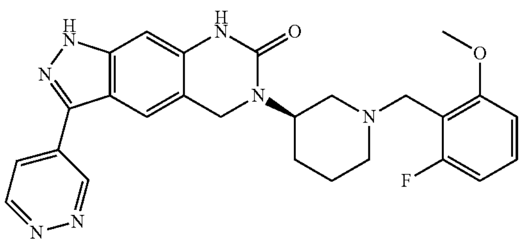 [SMILES: COc1cccc(F)c1CN1CCC[C@@H](N2Cc3cc4c(-c5ccnnc5)n[nH]c4cc3NC2=O)C1] | ++++ | 487.5 | 488.2 |
| 127 | 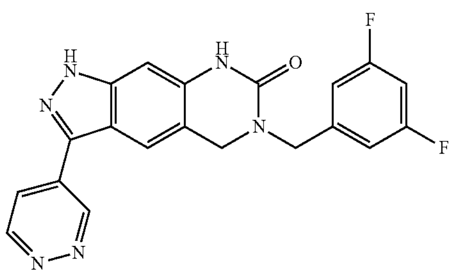 [SMILES: O=C1Nc2cc3[nH]nc(-c4ccnnc4)c3cc2CN1Cc1cc(F)cc(F)c1] | ++++ | 392.4 | 393.1 |
| 128 | 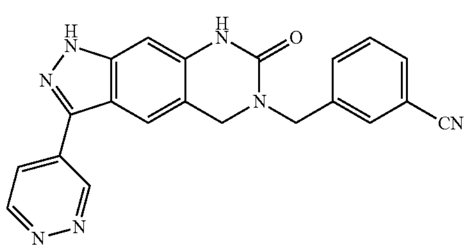 [SMILES: N#Cc1cccc(CN2Cc3cc4c(-c5ccnnc5)n[nH]c4cc3NC2=O)c1] | ++++ | 381.4 | 382.1 |
| 129 | 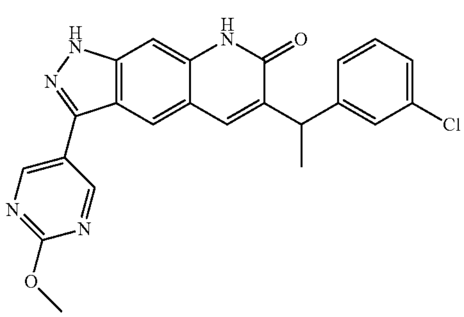 [SMILES: COc1ncc(-c2n[nH]c3cc4[nH]c(=O)c(C(C)c5cccc(Cl)c5)cc4cc23)cn1] | +++ | 431.9 | 432.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 130 | 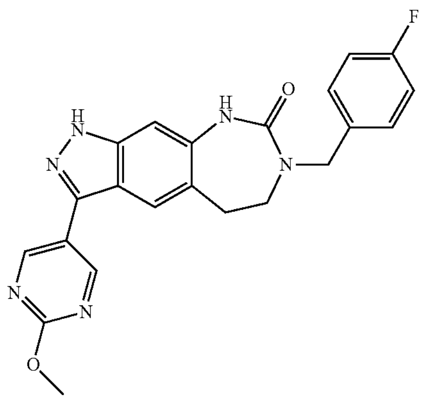 [SMILES: COc1ncc(-c2n[nH]c3cc4c(cc23)CCN(Cc2ccc(F)cc2)C(=O)N4)cn1] | +++ | 418.4 | 419.1 |
| 131 | 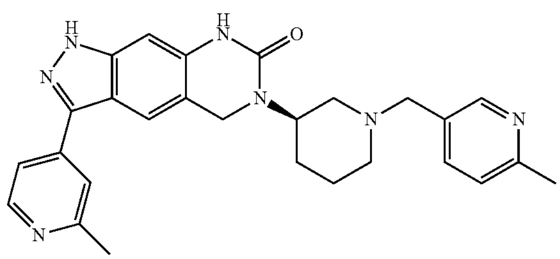 [SMILES: Cc1ccc(CN2CCC[C@@H](N3Cc4cc5c(-c6ccnc(C)c6)n[nH]c5cc4NC3=O)C2)cn1] | +++ | 467.6 | 468.2 |
| 132 | 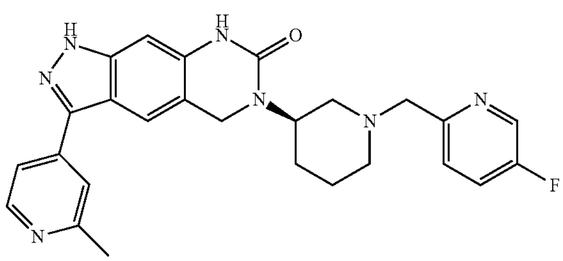 [SMILES: Cc1cc(-c2n[nH]c3cc4c(cc23)CN([C@@H]2CCCN(Cc3ccc(F)cn3)C2)C(=O)N4)ccn1] | ++++ | 471.5 | 472.2 |
| 133 | 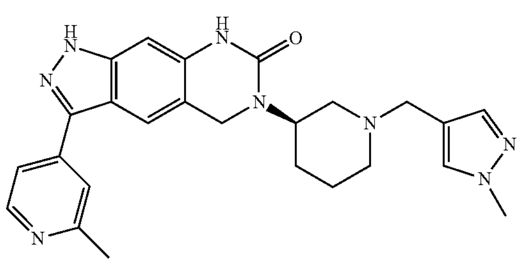 [SMILES: Cc1cc(-c2n[nH]c3cc4c(cc23)CN([C@@H]2CCCN(Cc3cnn(C)c3)C2)C(=O)N4)ccn1] | ++++ | 456.5 | 457.2 |
| 134 | 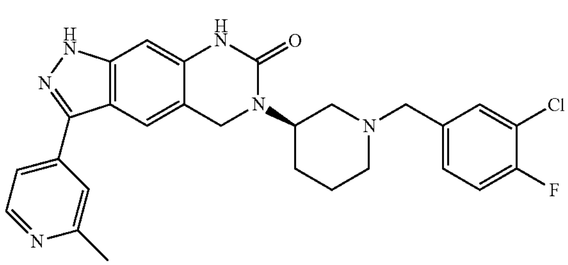 [SMILES: Cc1cc(-c2n[nH]c3cc4c(cc23)CN([C@@H]2CCCN(Cc3ccc(F)c(Cl)c3)C2)C(=O)N4)ccn1] | ++++ | 505.0 | 505.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 135 | 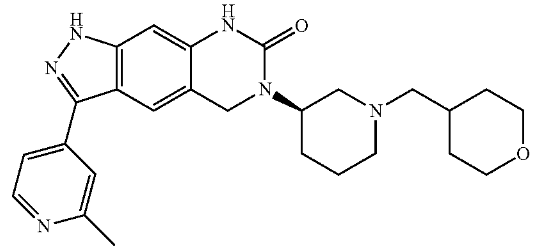 [SMILES: Cc1cc(-c2n[nH]c3cc4c(cc23)CN([C@@H]2CCCN(CC3CCOCC3)C2)C(=O)N4)ccn1] | +++ | 460.6 | 461.2 |
| 136 | 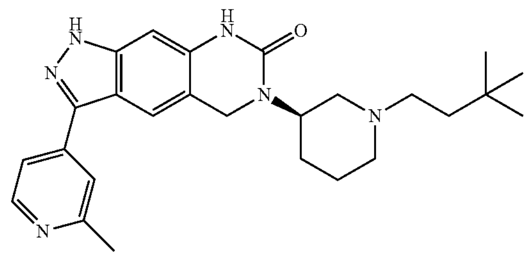 [SMILES: Cc1cc(-c2n[nH]c3cc4c(cc23)CN([C@@H]2CCCN(CCC(C)(C)C)C2)C(=O)N4)ccn1] | +++ | 446.6 | 447.3 |
| 137 | 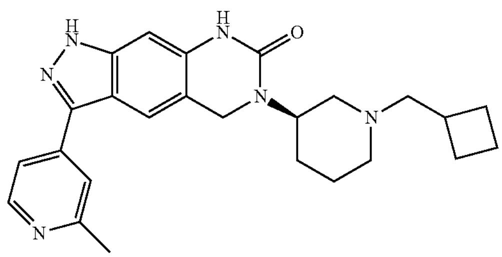 [SMILES: Cc1cc(-c2n[nH]c3cc4c(cc23)CN([C@@H]2CCCN(CC3CCC3)C2)C(=O)N4)ccn1] | +++ | 430.5 | 431.3 |
| 138 | 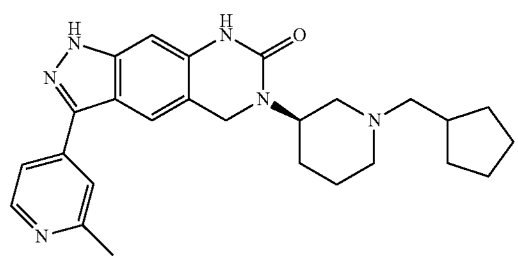 [SMILES: Cc1cc(-c2n[nH]c3cc4c(cc23)CN([C@@H]2CCCN(CC3CCCC3)C2)C(=O)N4)ccn1] | +++ | 444.6 | 445.2 |
| 139 | 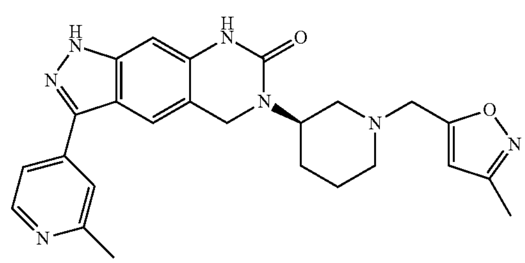 [SMILES: Cc1cc(-c2n[nH]c3cc4c(cc23)CN([C@@H]2CCCN(Cc3cc(C)no3)C2)C(=O)N4)ccn1] | ++++ | 457.5 | 458.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 140 | 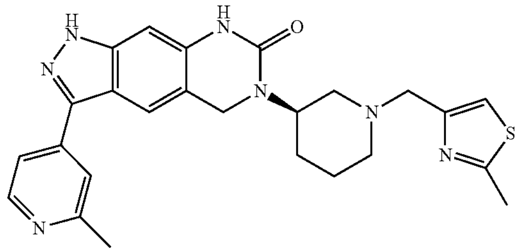 [SMILES: Cc1cc(-c2n[nH]c3cc4c(cc23)CN([C@@H]2CCCN(Cc3csc(C)n3)C2)C(=O)N4)ccn1] | ++++ | 473.6 | 474.2 |
| 141 | 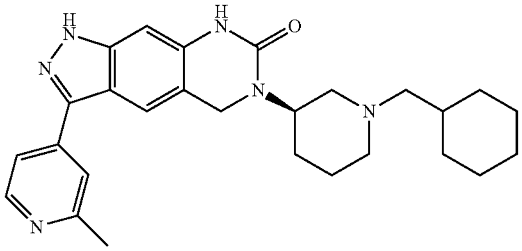 [SMILES: Cc1cc(-c2n[nH]c3cc4c(cc23)CN([C@@H]2CCCN(CC3CCCCC3)C2)C(=O)N4)ccn1] | +++ | 458.6 | 459.3 |
| 142 | 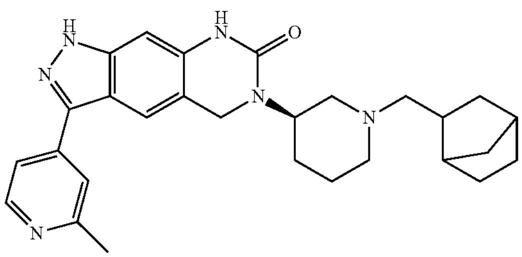 [SMILES: Cc1cc(-c2n[nH]c3cc4c(cc23)CN([C@@H]2CCCN(CC3CC5CCC3C5)C2)C(=O)N4)ccn1] | ++++ | 470.6 | 471.3 |
| 143 | 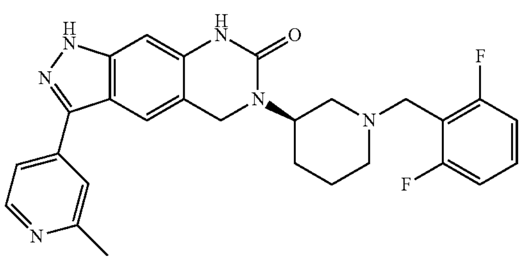 [SMILES: Cc1cc(-c2n[nH]c3cc4c(cc23)CN([C@@H]2CCCN(Cc3c(F)cccc3F)C2)C(=O)N4)ccn1] | ++++ | 488.5 | 489.2 |
| 144 | | ++++ | 500.6 | 501.2 | too

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 145 | 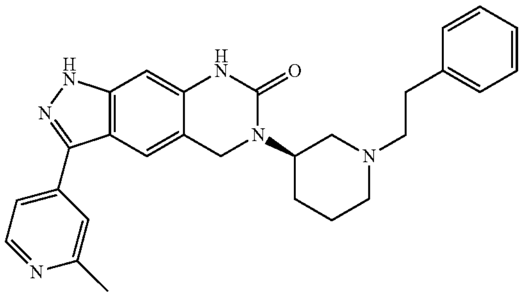 [SMILES: Cc1cc(-c2n[nH]c3cc4c(cc23)CN([C@@H]2CCCN(CCc3ccccc3)C2)C(=O)N4)ccn1] | ++++ | 466.6 | 467.2 |
| 146 | 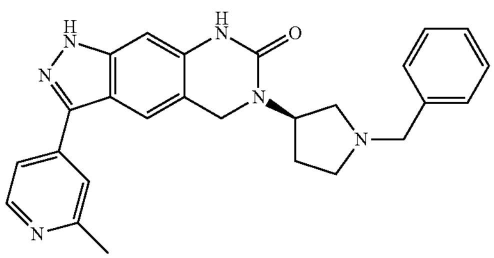 [SMILES: Cc1cc(-c2n[nH]c3cc4c(cc23)CN([C@@H]2CCN(Cc3ccccc3)C2)C(=O)N4)ccn1] | ++++ | 438.5 | 439.2 |
| 147 | 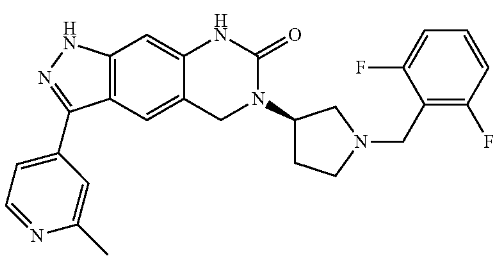 [SMILES: Cc1cc(-c2n[nH]c3cc4c(cc23)CN([C@@H]2CCN(Cc3c(F)cccc3F)C2)C(=O)N4)ccn1] | +++ | 474.5 | 475.5 |
| 148 | 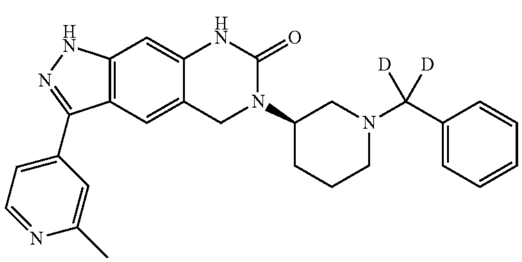 [SMILES: [2H]C([2H])(c1ccccc1)N1CCC[C@@H](N2Cc3cc4c(-c5ccnc(C)c5)n[nH]c4cc3NC2=O)C1] | ++++ | 454.6 | 455.2 |
| 149 | 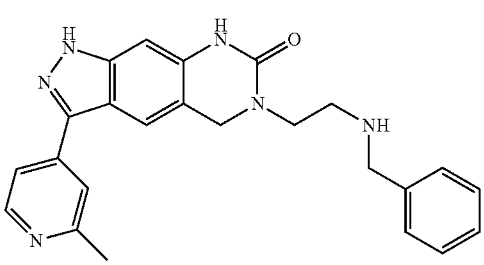 [SMILES: Cc1cc(-c2n[nH]c3cc4c(cc23)CN(CCNCc2ccccc2)C(=O)N4)ccn1] | ++++ | 412.5 | 413.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 150 | 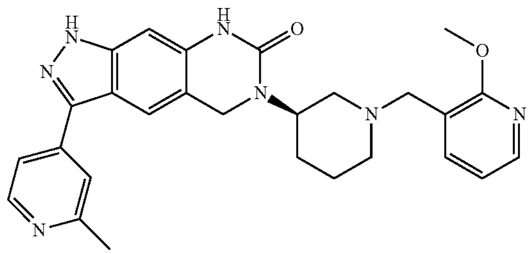 [SMILES: COc1ncccc1CN1CCC[C@@H](N2Cc3cc4c(-c5ccnc(C)c5)n[nH]c4cc3NC2=O)C1] | ++++ | 483.6 | 484.2 |
| 151 | 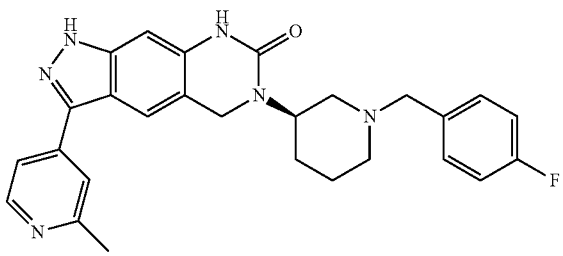 [SMILES: Cc1cc(-c2n[nH]c3cc4c(cc23)CN([C@@H]2CCCN(Cc3ccc(F)cc3)C2)C(=O)N4)ccn1] | ++++ | 470.5 | 471.2 |
| 152 | 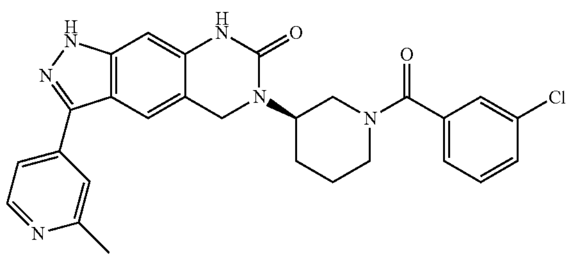 [SMILES: Cc1cc(-c2n[nH]c3cc4c(cc23)CN([C@@H]2CCCN(C(=O)c3cccc(Cl)c3)C2)C(=O)N4)ccn1] | ++++ | 501.0 | 501.2 |
| 153 | 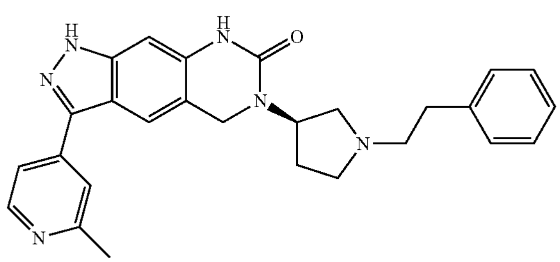 [SMILES: Cc1cc(-c2n[nH]c3cc4c(cc23)CN([C@@H]2CCN(CCc3ccccc3)C2)C(=O)N4)ccn1] | ++++ | 452.6 | 453.2 |
| 154 | 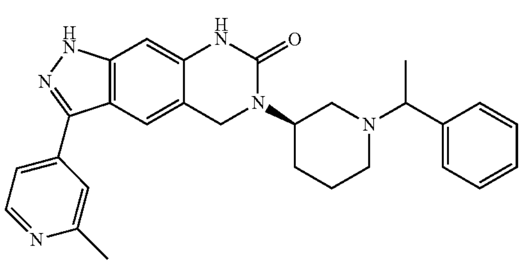 [SMILES: Cc1cc(-c2n[nH]c3cc4c(cc23)CN([C@@H]2CCCN(C(C)c3ccccc3)C2)C(=O)N4)ccn1] | ++++ | 466.6 | 467.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 155 | 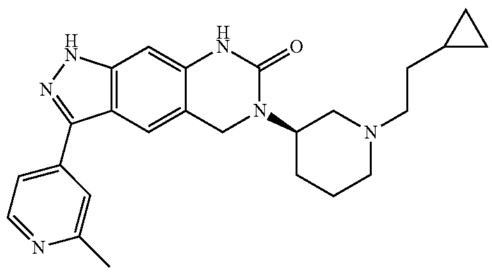 [SMILES: Cc1cc(-c2n[nH]c3cc4c(cc23)CN([C@@H]2CCCN(CCC3CC3)C2)C(=O)N4)ccn1] | ++++ | 430.5 | 431.3 |
| 156 | 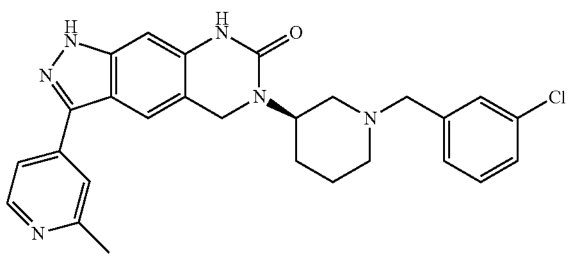 [SMILES: Cc1cc(-c2n[nH]c3cc4c(cc23)CN([C@@H]2CCCN(Cc3cccc(Cl)c3)C2)C(=O)N4)ccn1] | ++++ | 487.0 | 487.2 |
| 157 | 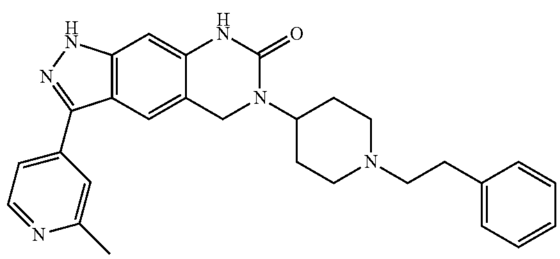 [SMILES: Cc1cc(-c2n[nH]c3cc4c(cc23)CN(C2CCN(CCc3ccccc3)CC2)C(=O)N4)ccn1] | +++ | 466.6 | 467.2 |
| 158 | 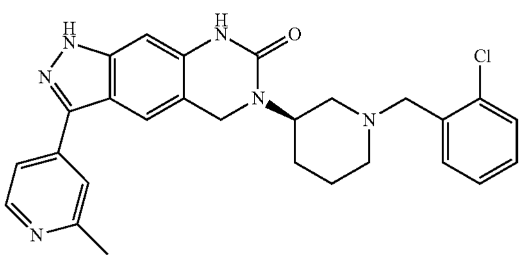 [SMILES: Cc1cc(-c2n[nH]c3cc4c(cc23)CN([C@@H]2CCCN(Cc3ccccc3Cl)C2)C(=O)N4)ccn1] | ++++ | 487.0 | 487.1 |
| 159 | 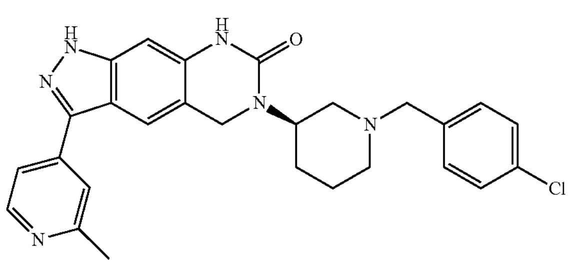 [SMILES: Cc1cc(-c2n[nH]c3cc4c(cc23)CN([C@@H]2CCCN(Cc3ccc(Cl)cc3)C2)C(=O)N4)ccn1] | ++++ | 487.0 | 487.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 160 | 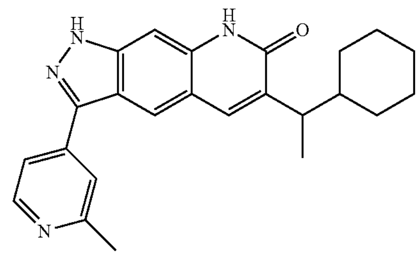 [SMILES: Cc1cc(-c2n[nH]c3cc4[nH]c(=O)c(C(C)C5CCCCC5)cc4cc23)ccn1] | +++ | 386.5 | 387.2 |
| 161 | 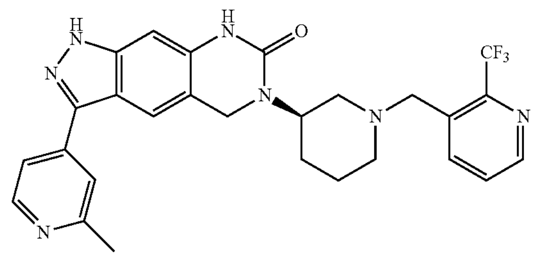 [SMILES: Cc1cc(-c2n[nH]c3cc4c(cc23)CN([C@@H]2CCCN(Cc3cccnc3C(F)(F)F)C2)C(=O)N4)ccn1] | ++++ | 521.5 | 522.2 |
| 162 | 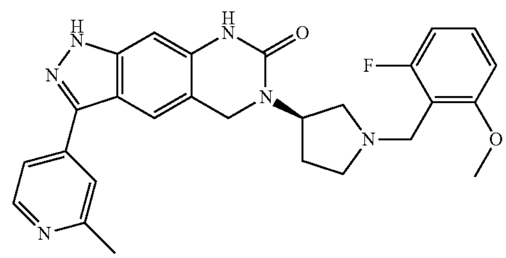 [SMILES: COc1cccc(F)c1CN1CC[C@@H](N2Cc3cc4c(-c5ccnc(C)c5)n[nH]c4cc3NC2=O)C1] | ++++ | 486.5 | 487.2 |
| 163 | 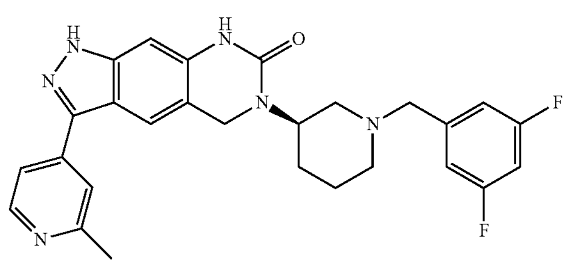 [SMILES: Cc1cc(-c2n[nH]c3cc4c(cc23)CN([C@@H]2CCCN(Cc3cc(F)cc(F)c3)C2)C(=O)N4)ccn1] | ++++ | 488.5 | 489.2 |
| 164 | 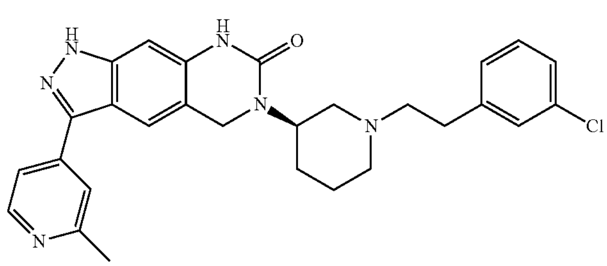 [SMILES: Cc1cc(-c2n[nH]c3cc4c(cc23)CN([C@@H]2CCCN(CCc3cccc(Cl)c3)C2)C(=O)N4)ccn1] | ++++ | 501.0 | 501.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 165 | 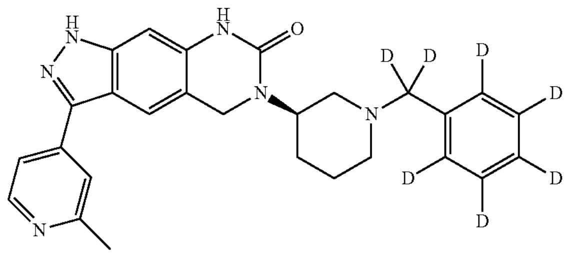 [SMILES: [2H]c1c([2H])c([2H])c(C([2H])([2H])N2CCC[C@@H](N3Cc4cc5c(-c6ccnc(C)c6)n[nH]c5cc4NC3=O)C2)c([2H])c1[2H]] | ++++ | 459.6 | 460.3 |
| 166 | 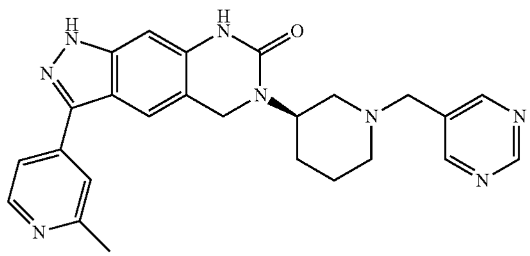 [SMILES: Cc1cc(-c2n[nH]c3cc4c(cc23)CN([C@@H]2CCCN(Cc3cncnc3)C2)C(=O)N4)ccn1] | ++++ | 454.5 | 455.5 |
| 167 | 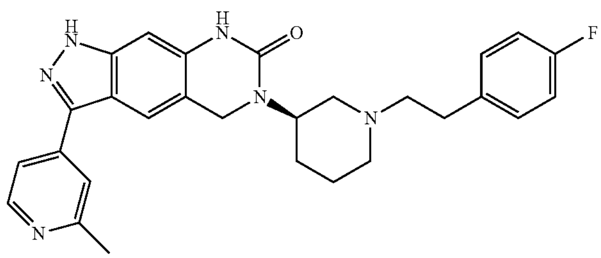 [SMILES: Cc1cc(-c2n[nH]c3cc4c(cc23)CN([C@@H]2CCCN(CCc3ccc(F)cc3)C2)C(=O)N4)ccn1] | +++ | 484.6 | 485.2 |
| 168 | 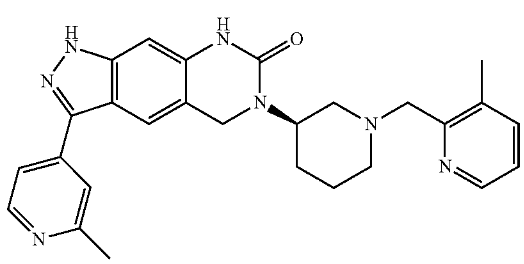 [SMILES: Cc1cc(-c2n[nH]c3cc4c(cc23)CN([C@@H]2CCCN(Cc3ncccc3C)C2)C(=O)N4)ccn1] | ++++ | 467.6 | 468.5 |
| 169 | 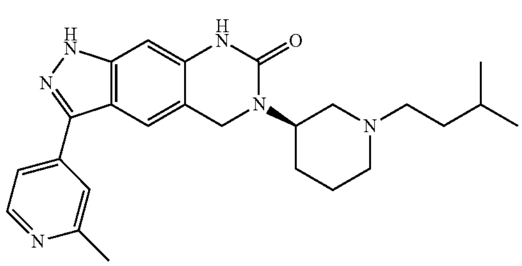 [SMILES: Cc1cc(-c2n[nH]c3cc4c(cc23)CN([C@@H]2CCCN(CCC(C)C)C2)C(=O)N4)ccn1] | ++++ | 432.6 | 433.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 170 | 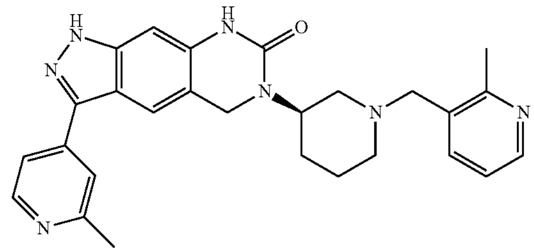 [SMILES: Cc1cc(-c2n[nH]c3cc4c(cc23)CN([C@@H]2CCCN(Cc3cccnc3C)C2)C(=O)N4)ccn1] | ++++ | 467.6 | 468.2 |
| 171 | 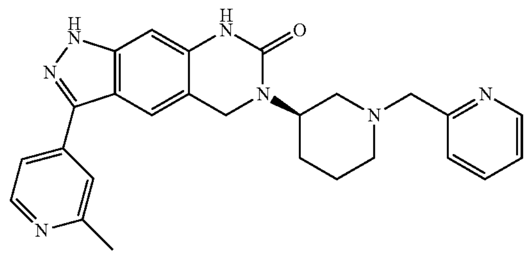 | +++ | 453.5 | 454.2 |
| 172 | 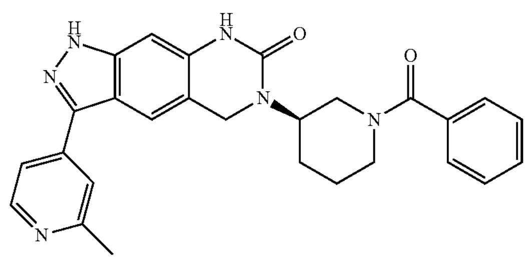 [SMILES: Cc1cc(-c2n[nH]c3cc4c(cc23)CN([C@@H]2CCCN(C(=O)c3ccccc3)C2)C(=O)N4)ccn1] | ++++ | 466.5 | 467.2 |
| 173 | 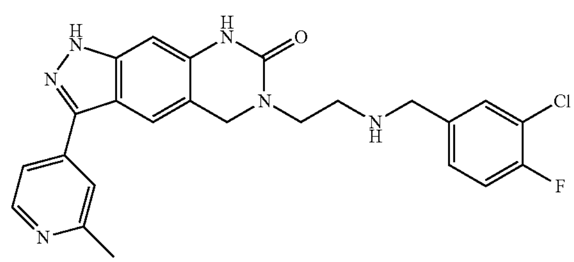 [SMILES: Cc1cc(-c2n[nH]c3cc4c(cc23)CN(CCNCc2ccc(F)c(Cl)c2)C(=O)N4)ccn1] | ++++ | 464.9 | 465.1 |
| 174 | 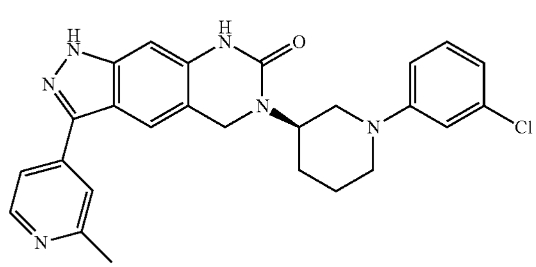 [SMILES: Cc1cc(-c2n[nH]c3cc4c(cc23)CN([C@@H]2CCCN(c3cccc(Cl)c3)C2)C(=O)N4)ccn1] | ++++ | 473.0 | 473.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 175 | 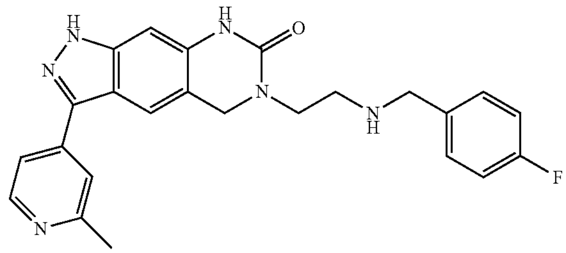 [SMILES: Cc1cc(-c2n[nH]c3cc4c(cc23)CN(CCNCc2ccc(F)cc2)C(=O)N4)ccn1] | ++++ | 430.5 | 431.2 |
| 176 | 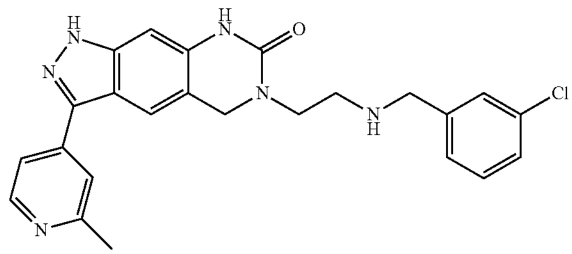 [SMILES: Cc1cc(-c2n[nH]c3cc4c(cc23)CN(CCNCc2cccc(Cl)c2)C(=O)N4)ccn1] | ++++ | 446.9 | 447.2 |
| 177 | 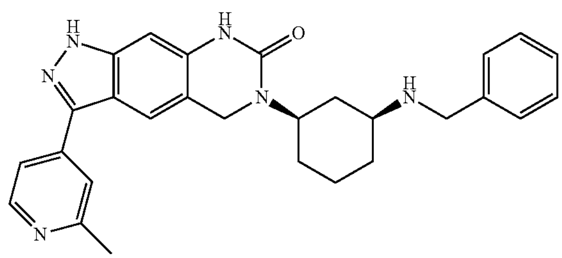 [SMILES: Cc1cc(-c2n[nH]c3cc4c(cc23)CN([C@@H]2CCC[C@H](NCc3ccccc3)C2)C(=O)N4)ccn1] | ++++ | 466.6 | 467.2 |
| 178 | 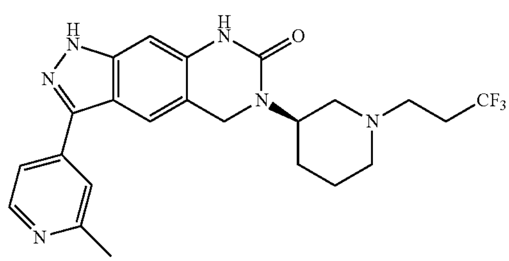 [SMILES: Cc1cc(-c2n[nH]c3cc4c(cc23)CN([C@@H]2CCCN(CCC(F)(F)F)C2)C(=O)N4)ccn1] | ++++ | 458.5 | 459.2 |
| 179 | 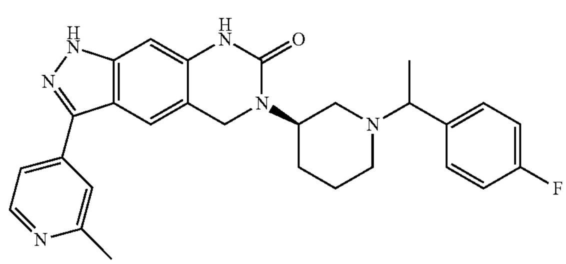 [SMILES: Cc1cc(-c2n[nH]c3cc4c(cc23)CN([C@@H]2CCCN(C(C)c3ccc(F)cc3)C2)C(=O)N4)ccn1] | +++ | 484.6 | 485.2 |
| 180 | 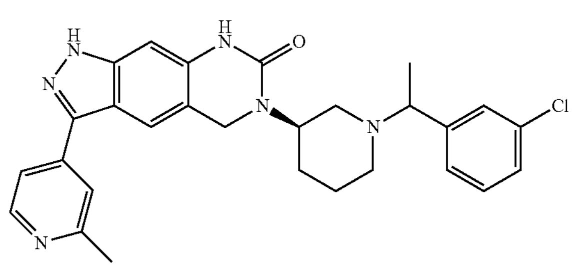 [SMILES: Cc1cc(-c2n[nH]c3cc4c(cc23)CN([C@@H]2CCCN(C(C)c3cccc(Cl)c3)C2)C(=O)N4)ccn1] | +++ | 501.0 | 501.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 181 | 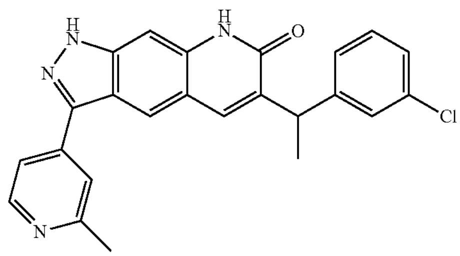 [SMILES: Cc1cc(-c2n[nH]c3cc4[nH]c(=O)c(C(C)c5cccc(Cl)c5)cc4cc23)ccn1] | +++ | 414.9 | 415.1 |
| 182 | 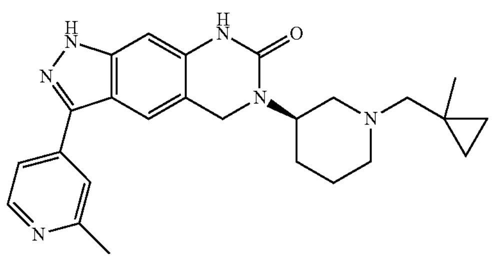 | +++ | 430.5 | 431.3 |
| 183 | 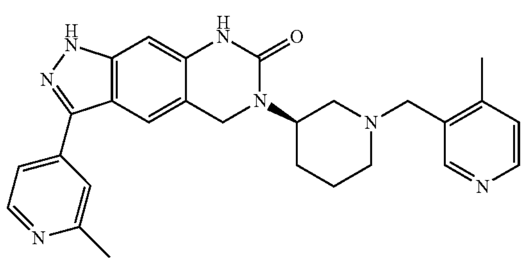 [SMILES: Cc1cc(-c2n[nH]c3cc4c(cc23)CN([C@@H]2CCCN(Cc3cnccc3C)C2)C(=O)N4)ccn1] | +++ | 467.6 | 468.2 |
| 184 | 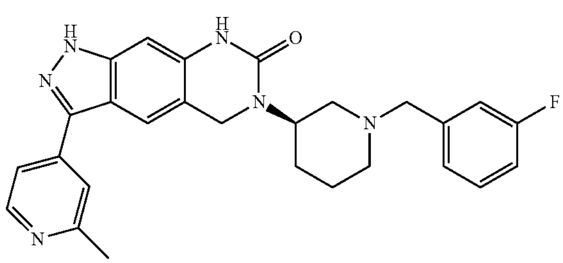 [SMILES: Cc1cc(-c2n[nH]c3cc4c(cc23)CN([C@@H]2CCCN(Cc3cccc(F)c3)C2)C(=O)N4)ccn1] | ++++ | 470.5 | 471.2 |
| 185 | 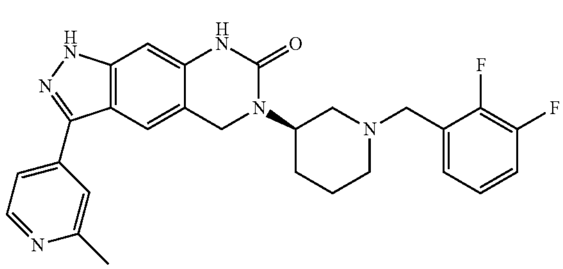 [SMILES: Cc1cc(-c2n[nH]c3cc4c(cc23)CN([C@@H]2CCCN(Cc3cccc(F)c3F)C2)C(=O)N4)ccn1] | ++++ | 488.5 | 489.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 186 | 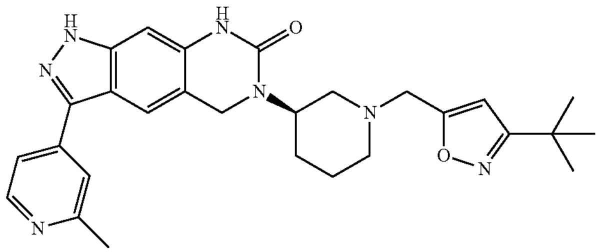 [SMILES: Cc1cc(-c2n[nH]c3cc4c(cc23)CN([C@@H]2CCCN(Cc3cc(C(C)(C)C)no3)C2)C(=O)N4)ccn1] | +++ | 499.6 | 500.3 |
| 187 | 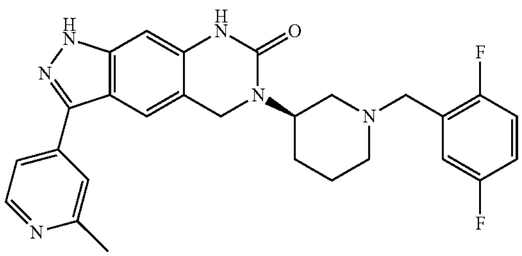 [SMILES: Cc1cc(-c2n[nH]c3cc4c(cc23)CN([C@@H]2CCCN(Cc3cc(F)ccc3F)C2)C(=O)N4)ccn1] | ++++ | 488.5 | 489.2 |
| 188 | 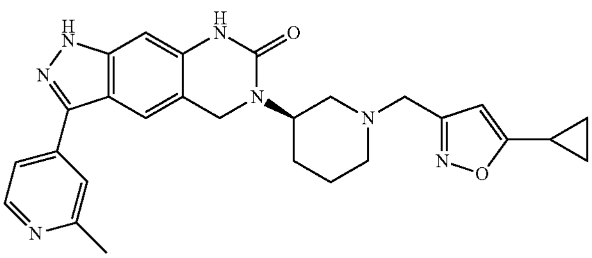 [SMILES: Cc1cc(-c2n[nH]c3cc4c(cc23)CN([C@@H]2CCCN(Cc3cc(C5CC5)on3)C2)C(=O)N4)ccn1] | ++++ | 483.6 | 484.2 |
| 189 | 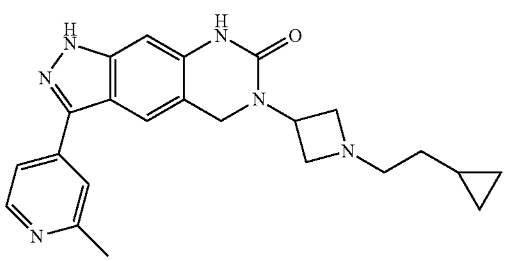 [SMILES: Cc1cc(-c2n[nH]c3cc4c(cc23)CN(C2CN(CCC3CC3)C2)C(=O)N4)ccn1] | +++ | 402.5 | 403.2 |
| 190 | 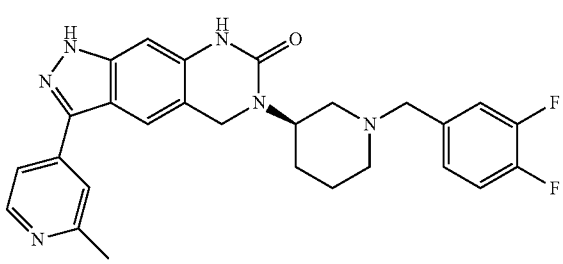 [SMILES: Cc1cc(-c2n[nH]c3cc4c(cc23)CN([C@@H]2CCCN(Cc3ccc(F)c(F)c3)C2)C(=O)N4)ccn1] | ++++ | 488.5 | 489.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 191 | 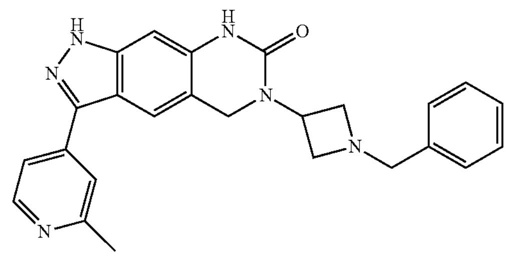 [SMILES: Cc1cc(-c2n[nH]c3cc4c(cc23)CN(C2CN(Cc3ccccc3)C2)C(=O)N4)ccn1] | ++++ | 424.5 | 425.2 |
| 192 | 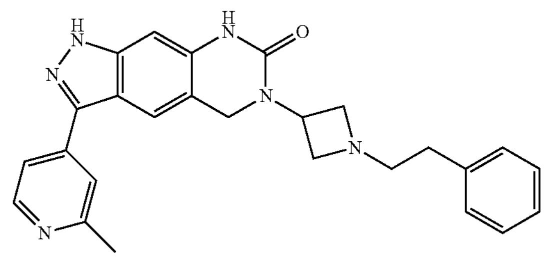 [SMILES: Cc1cc(-c2n[nH]c3cc4c(cc23)CN(C2CN(CCc3ccccc3)C2)C(=O)N4)ccn1] | +++ | 438.5 | 439.2 |
| 193 | 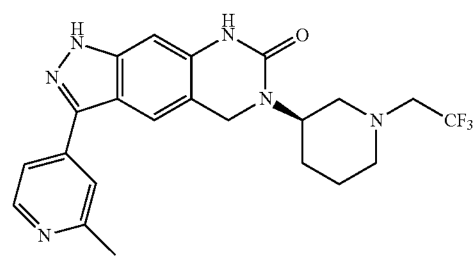 [SMILES: Cc1cc(-c2n[nH]c3cc4c(cc23)CN([C@@H]2CCCN(CC(F)(F)F)C2)C(=O)N4)ccn1] | ++++ | 444.5 | 445.2 |
| 194 | 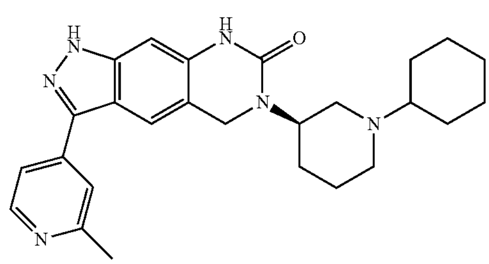 [SMILES: Cc1cc(-c2n[nH]c3cc4c(cc23)CN([C@@H]2CCCN(C3CCCCC3)C2)C(=O)N4)ccn1] | +++ | 444.6 | 445.5 |
| 195 | 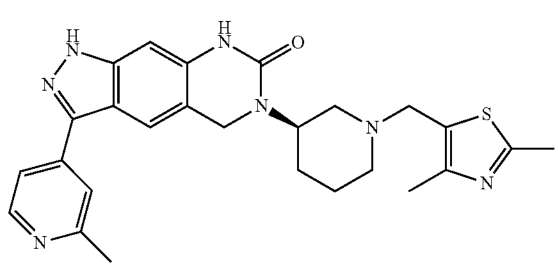 [SMILES: Cc1cc(-c2n[nH]c3cc4c(cc23)CN([C@@H]2CCCN(Cc3sc(C)nc3C)C2)C(=O)N4)ccn1] | +++ | 487.6 | 488.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 196 | 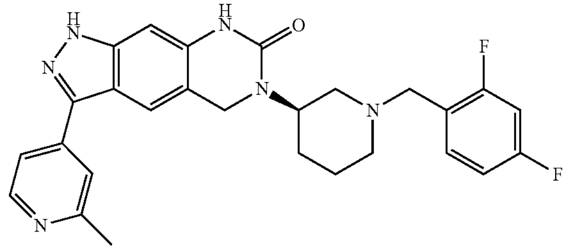 [SMILES: Cc1cc(-c2n[nH]c3cc4c(cc23)CN([C@@H]2CCCN(Cc3ccc(F)cc3F)C2)C(=O)N4)ccn1] | ++++ | 488.5 | 489.2 |
| 197 | 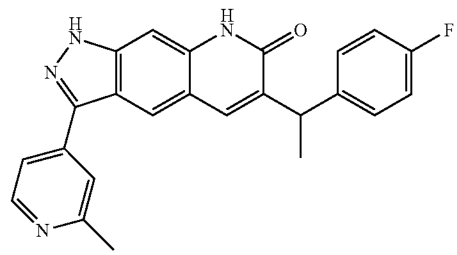 [SMILES: Cc1cc(-c2n[nH]c3cc4[nH]c(=O)c(C(C)c5ccc(F)cc5)cc4cc23)ccn1] | ++++ | 398.4 | 399.2 |
| 198 | 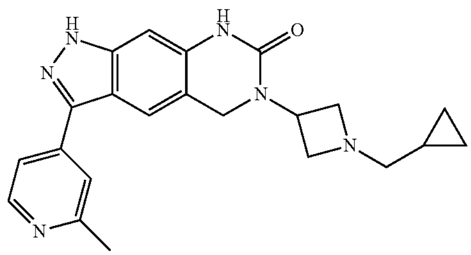 [SMILES: Cc1cc(-c2n[nH]c3cc4c(cc23)CN(C2CN(CC3CC3)C2)C(=O)N4)ccn1] | ++ | 388.5 | 389.1 |
| 199 | 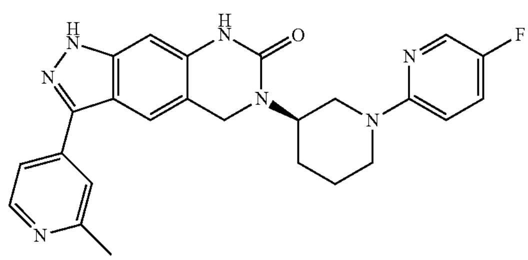 [SMILES: Cc1cc(-c2n[nH]c3cc4c(cc23)CN([C@@H]2CCCN(c3ccc(F)cn3)C2)C(=O)N4)ccn1] | ++++ | 457.5 | 458.2 |
| 200 | 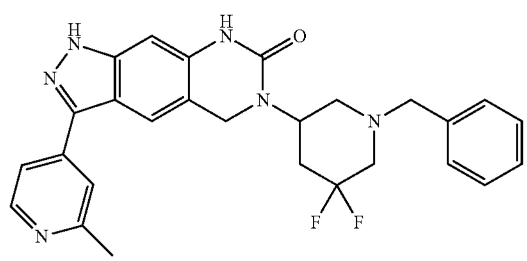 [SMILES: Cc1cc(-c2n[nH]c3cc4c(cc23)CN(C2CN(Cc3ccccc3)CC(F)(F)C2)C(=O)N4)ccn1] | ++++ | 488.5 | 489.4 |
| 201 | 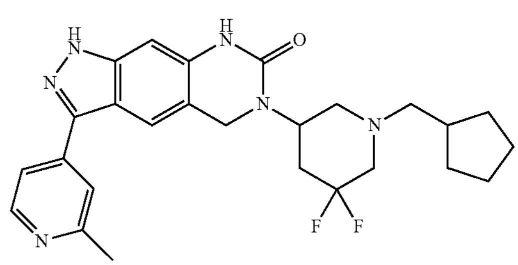 [SMILES: Cc1cc(-c2n[nH]c3cc4c(cc23)CN(C2CN(CC3CCCC3)CC(F)(F)C2)C(=O)N4)ccn1] | ++ | 480.6 | 481.5 |

… 433 434
TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 202 | 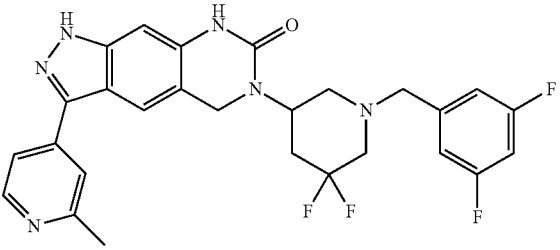 [SMILES: Cc1cc(-c2n[nH]c3cc4c(cc23)CN(C2CN(Cc3cc(F)cc(F)c3)CC(F)(F)C2)C(=O)N4)ccn1] | ++ | 524.5 | 525.5 |
| 203 | 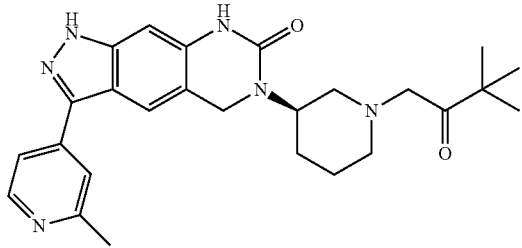 [SMILES: Cc1cc(-c2n[nH]c3cc4c(cc23)CN([C@@H]2CCCN(CC(=O)C(C)(C)C)C2)C(=O)N4)ccn1] | ++++ | 460.6 | 461.5 |
| 204 | 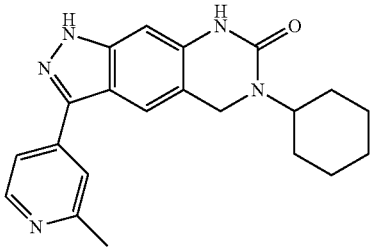 [SMILES: Cc1cc(-c2n[nH]c3cc4c(cc23)CN(C2CCCCC2)C(=O)N4)ccn1] | ++++ | 361.4 | 362.3 |
| 205 | 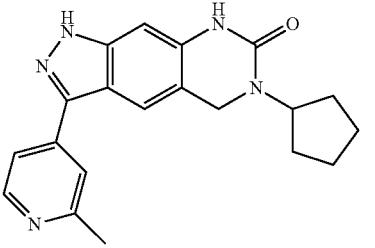 [SMILES: Cc1cc(-c2n[nH]c3cc4c(cc23)CN(C2CCCC2)C(=O)N4)ccn1] | ++++ | 347.4 | 348.3 |
| 206 | 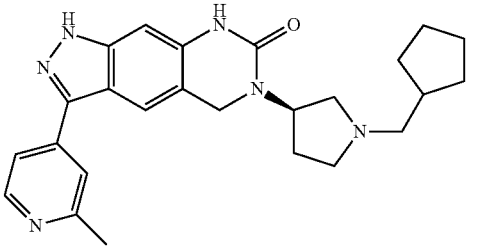 [SMILES: Cc1cc(-c2n[nH]c3cc4c(cc23)CN([C@@H]2CCN(CC3CCCC3)C2)C(=O)N4)ccn1] | ++ | 430.5 | 431.4 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|--------------------|----------------|-----------------------------|---------------------|
| 207 | 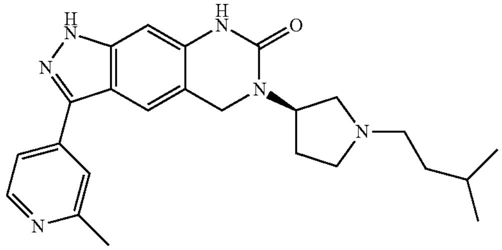 [SMILES: Cc1cc(-c2n[nH]c3cc4c(cc23)CN([C@@H]2CCN(CCC(C)C)C2)C(=O)N4)ccn1] | +++ | 418.5 | 419.4 |
| 208 | 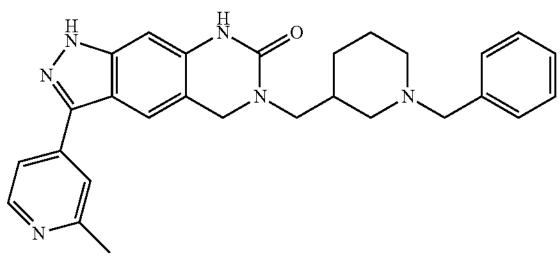 [SMILES: Cc1cc(-c2n[nH]c3cc4c(cc23)CN(CC2CCCN(Cc3ccccc3)C2)C(=O)N4)ccn1] | +++ | 466.6 | 467.5 |
| 209 | 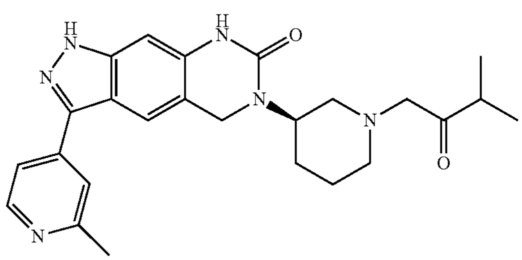 [SMILES: Cc1cc(-c2n[nH]c3cc4c(cc23)CN([C@@H]2CCCN(CC(=O)C(C)C)C2)C(=O)N4)ccn1] | ++++ | 446.5 | 447.4 |
| 210 | 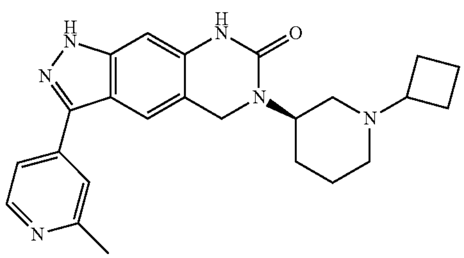 [SMILES: Cc1cc(-c2n[nH]c3cc4c(cc23)CN([C@@H]2CCCN(C3CCC3)C2)C(=O)N4)ccn1] | +++ | 416.5 | |
| 211 | 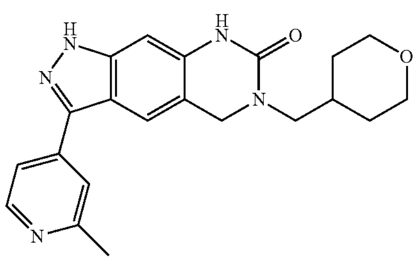 | ++++ | 377.4 | 378.2 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 212 | 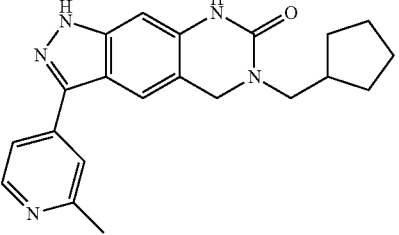 | ++++ | 361.4 | 362.2 |
| 213 | 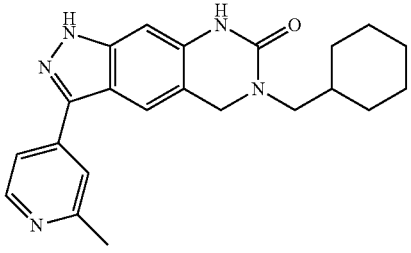 [SMILES: Cc1cc(-c2n[nH]c3cc4c(cc23)CN(CC2CCCCC2)C(=O)N4)ccn1] | ++++ | 375.2 | 376.3 |
| 214 | 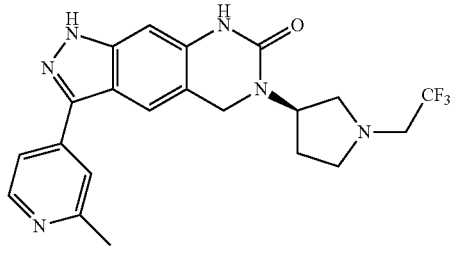 [SMILES: Cc1cc(-c2n[nH]c3cc4c(cc23)CN([C@@H]2CCN(CC(F)(F)F)C2)C(=O)N4)ccn1] | ++++ | 430.4 | 431.1 |
| 215 | 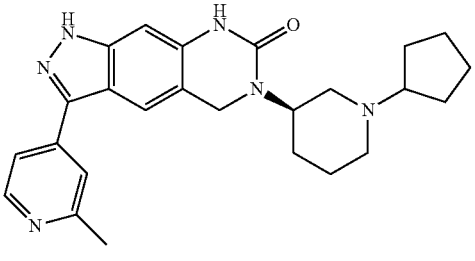 [SMILES: Cc1cc(-c2n[nH]c3cc4c(cc23)CN([C@@H]2CCCN(C3CCCC3)C2)C(=O)N4)ccn1] | +++ | 430.5 | 431.3 |
| 216 | 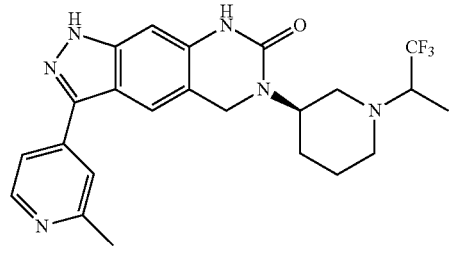 | ++++ | 458.5 | 459.3 |
| 217 | 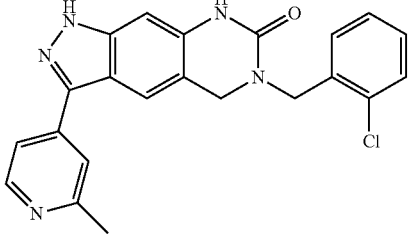 | ++++ | 403.9 | 404.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 218 | 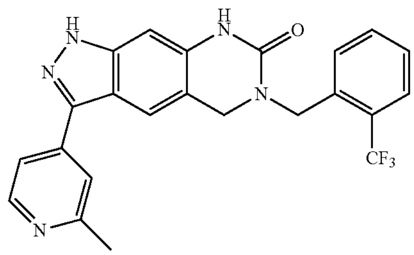 [SMILES: Cc1cc(-c2n[nH]c3cc4c(cc23)CN(Cc2ccccc2C(F)(F)F)C(=O)N4)ccn1] | ++++ | 437.4 | 438.2 |
| 219 | 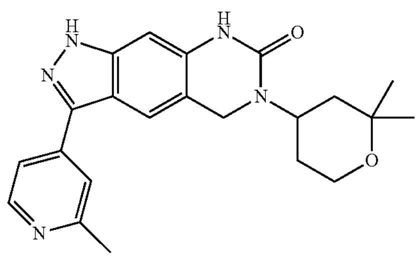 [SMILES: Cc1cc(-c2n[nH]c3cc4c(cc23)CN(C2CCOC(C)(C)C2)C(=O)N4)ccn1] | ++++ | 391.5 | 392.3 |
| 220 | 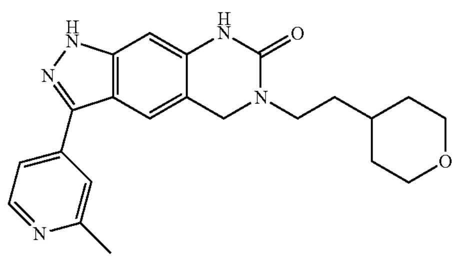 [SMILES: Cc1cc(-c2n[nH]c3cc4c(cc23)CN(CCC2CCOCC2)C(=O)N4)ccn1] | ++++ | 391.5 | 392.7 |
| 221 | 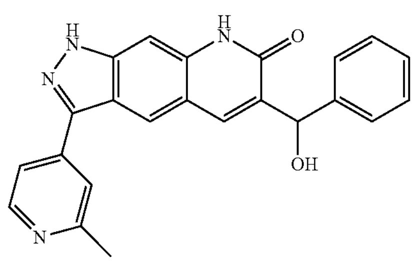 [SMILES: Cc1cc(-c2n[nH]c3cc4[nH]c(=O)c(C(O)c5ccccc5)cc4cc23)ccn1] | ++++ | 382.4 | 383.2 |
| 222 | (Racemate) | +++ | 506.5 | 507.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 223 | (Racemate) | ++++ | 424.5 | 425.3 |
| 224 | 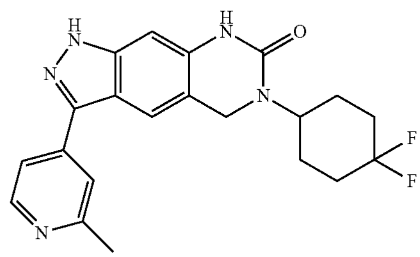 [SMILES: Cc1cc(-c2n[nH]c3cc4c(cc23)CN(C2CCC(F)(F)CC2)C(=O)N4)ccn1] | ++++ | 397.4 | 398.2 |
| 225 | 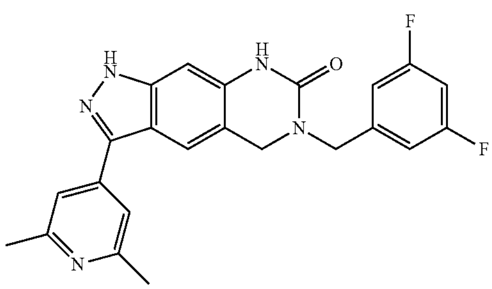 [SMILES: Cc1cc(-c2n[nH]c3cc4c(cc23)CN(Cc2cc(F)cc(F)c2)C(=O)N4)cc(C)n1] | ++++ | 419.4 | 420.1 |
| 226 | 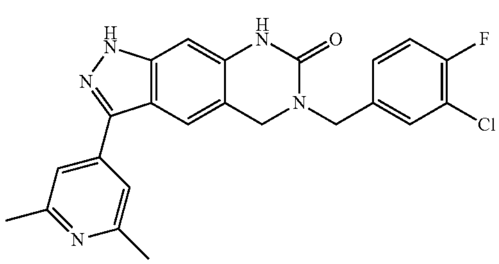 [SMILES: Cc1cc(-c2n[nH]c3cc4c(cc23)CN(Cc2ccc(F)c(Cl)c2)C(=O)N4)cc(C)n1] | ++++ | 435.9 | 436.1 |
| 227 | 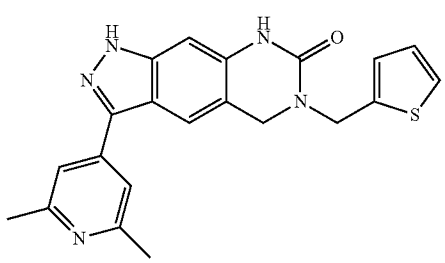 [SMILES: Cc1cc(-c2n[nH]c3cc4c(cc23)CN(Cc2cccs2)C(=O)N4)cc(C)n1] | ++++ | 389.5 | 390.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 228 | 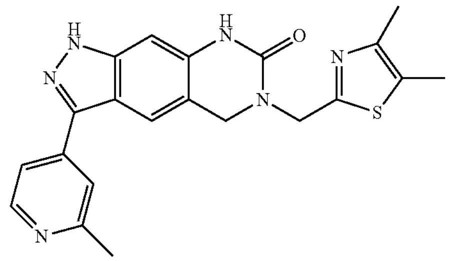 [SMILES: Cc1cc(-c2n[nH]c3cc4c(cc23)CN(Cc2nc(C)c(C)s2)C(=O)N4)ccn1] | ++++ | 404.5 | 405.1 |
| 229 | 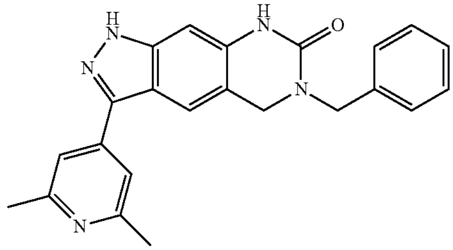 [SMILES: Cc1cc(-c2n[nH]c3cc4c(cc23)CN(Cc2ccccc2)C(=O)N4)cc(C)n1] | ++++ | 383.4 | 384.2 |
| 230 | 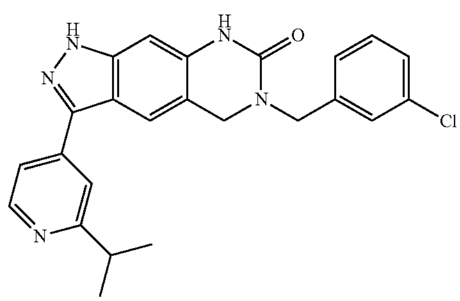 [SMILES: CC(C)c1cc(-c2n[nH]c3cc4c(cc23)CN(Cc2cccc(Cl)c2)C(=O)N4)ccn1] | | 431.9 | 432.1 |
| 231 | 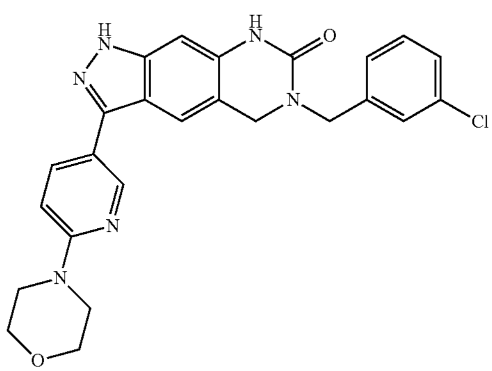 [SMILES: O=C1Nc2cc3[nH]nc(-c4ccc(N5CCOCC5)nc4)c3cc2CN1Cc1cccc(Cl)c1] | ++++ | 474.9 | 475.1 |
| 232 | 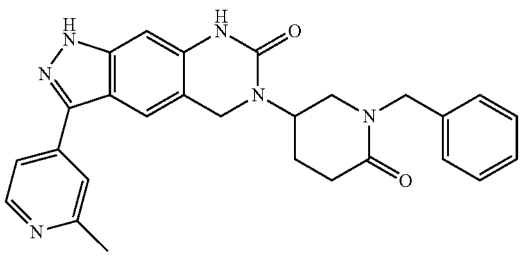 [SMILES: Cc1cc(-c2n[nH]c3cc4c(cc23)CN(C2CCC(=O)N(Cc3ccccc3)C2)C(=O)N4)ccn1] | ++++ | 466.5 | 467.2 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 233 | 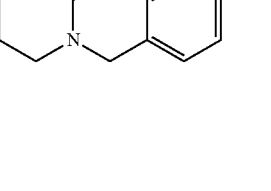 | ++++ | 451.4 | 452.2 |
| 234 | 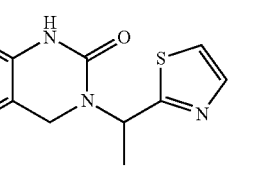 | ++++ | 390.5 | 391.1 |
| 235 | 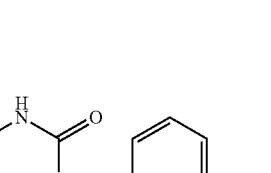 | +++ | 392.8 | 393.1 |
| 236 | 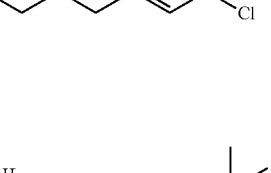 | +++ | 462.6 | 461.4 (M − 1) |
| 237 | 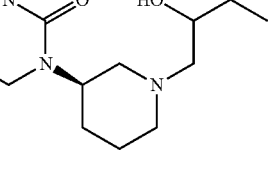 | ++++ | 444.5 | 445.2 |
| 238 | 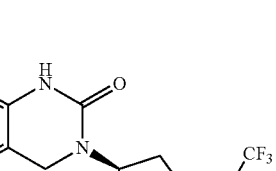 | +++ | 453.5 | 454.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|--------------------|----------------|-----------------------------|---------------------|
| 239 | 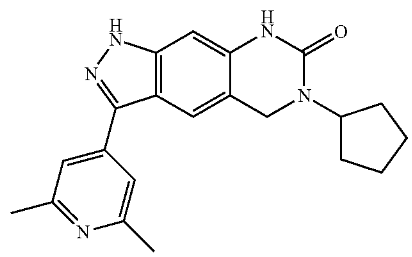 [SMILES: Cc1cc(-c2n[nH]c3cc4c(cc23)CN(C2CCCC2)C(=O)N4)cc(C)n1] | ++++ | 361.4 | 362.2 |
| 240 | 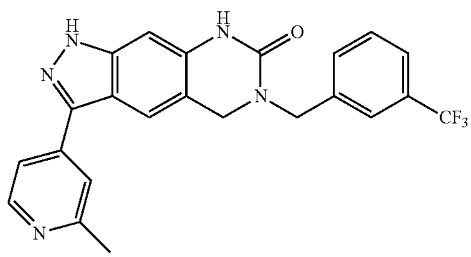 [SMILES: Cc1cc(-c2n[nH]c3cc4c(cc23)CN(Cc2cccc(C(F)(F)F)c2)C(=O)N4)ccn1] | ++++ | 437.4 | 438.2 |
| 241 | (Racemate) | ++++ | 438.5 | 439.2 |
| 242 | (Racemate) | +++ | 520.5 | 521.3 |
| 243 | 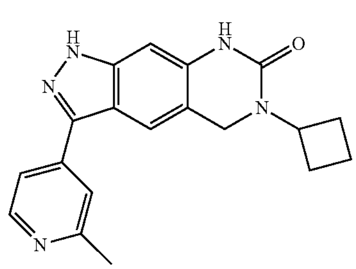 [SMILES: Cc1cc(-c2n[nH]c3cc4c(cc23)CN(C2CCC2)C(=O)N4)ccn1] | ++++ | 333.4 | 334.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 244 | 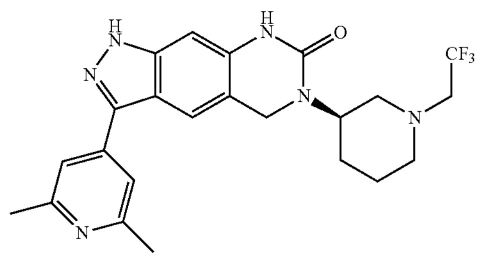 [SMILES: Cc1cc(-c2n[nH]c3cc4c(cc23)CN([C@@H]2CCCN(CC(F)(F)F)C2)C(=O)N4)cc(C)n1] | ++++ | 458.5 | 459.3 |
| 245 | 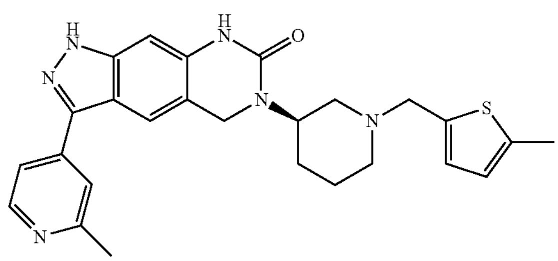 [SMILES: Cc1cc(-c2n[nH]c3cc4c(cc23)CN([C@@H]2CCCN(Cc3ccc(C)s3)C2)C(=O)N4)ccn1] | ++++ | 472.6 | 473.2 |
| 246 | 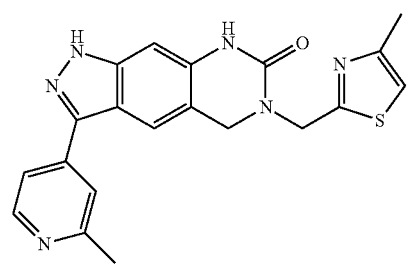 [SMILES: Cc1cc(-c2n[nH]c3cc4c(cc23)CN(Cc2nc(C)cs2)C(=O)N4)ccn1] | ++++ | 390.5 | 391.1 |
| 247 | 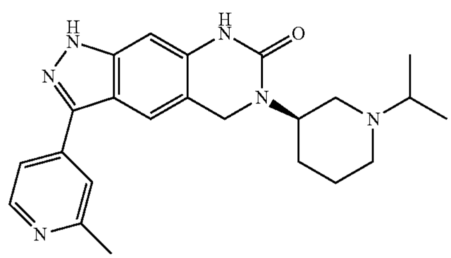 [SMILES: Cc1cc(-c2n[nH]c3cc4c(cc23)CN([C@@H]2CCCN(C(C)C)C2)C(=O)N4)ccn1] | ++++ | 404.5 | 405.3 |
| 248 (Racemate) | | ++++ | 452.6 | 453.3 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 249 | 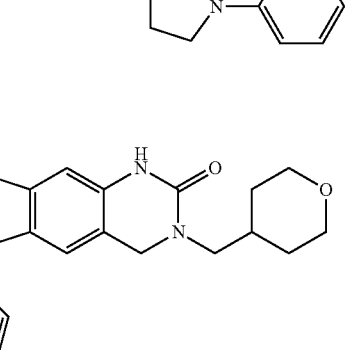 | +++ | 458.9 | 459.2 |
| 250 | 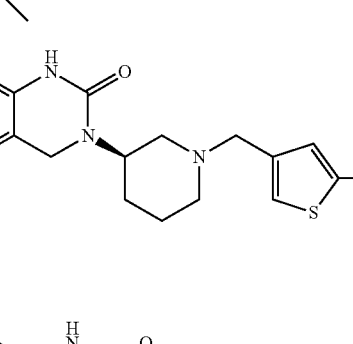 | ++++ | 391.5 | 392.2 |
| 251 | 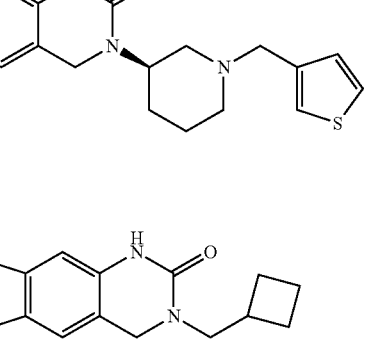 | ++++ | 472.6 | 472.3 (M − 1) |
| 252 | 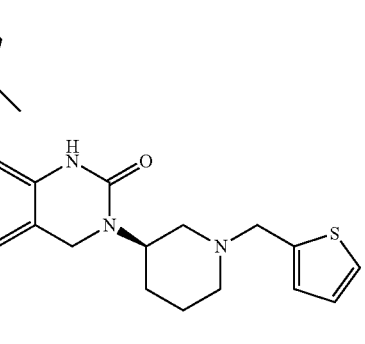 | ++++ | 458.6 | 459.2 |
| 253 | 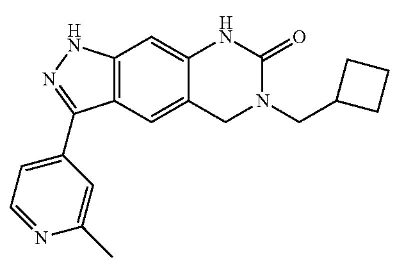 [SMILES: Cc1cc(-c2n[nH]c3cc4c(cc23)CN(CC2CCC2)C(=O)N4)ccn1] | ++++ | 347.4 | 348.2 |
| 254 | 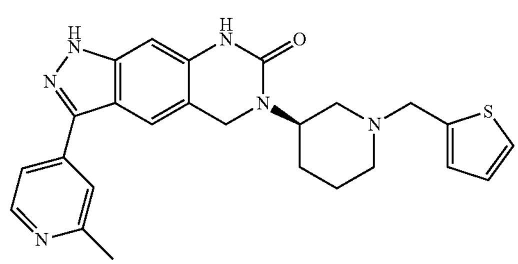 [SMILES: Cc1cc(-c2n[nH]c3cc4c(cc23)CN([C@@H]2CCCN(Cc3cccs3)C2)C(=O)N4)ccn1] | ++++ | 458.6 | 459.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 255 | 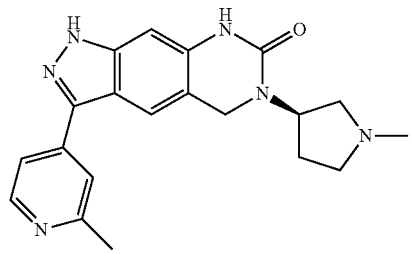 [SMILES: Cc1cc(-c2n[nH]c3cc4c(cc23)CN([C@@H]2CCN(C)C2)C(=O)N4)ccn1] | ++++ | 362.4 | 363.1 |
| 256 | 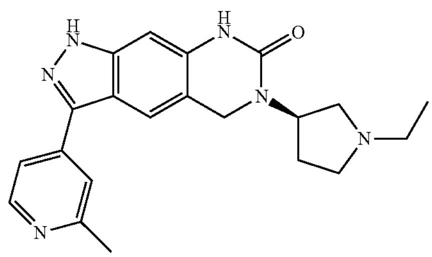 [SMILES: CCN1CC[C@@H](N2Cc3cc4c(-c5ccnc(C)c5)n[nH]c4cc3NC2=O)C1] | ++++ | 376.5 | 377.2 |
| 257 | 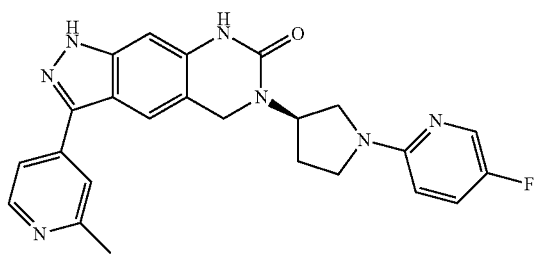 [SMILES: Cc1cc(-c2n[nH]c3cc4c(cc23)CN([C@@H]2CCN(c3ccc(F)cn3)C2)C(=O)N4)ccn1] | +++ | 443.5 | 444.2 |
| 258 | 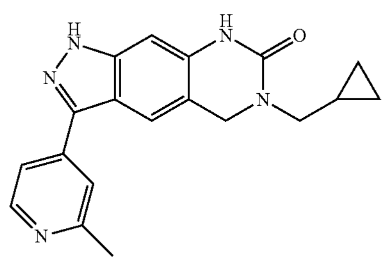 [SMILES: Cc1cc(-c2n[nH]c3cc4c(cc23)CN(CC2CC2)C(=O)N4)ccn1] | ++++ | 333.4 | 334.1 |
| 259 | 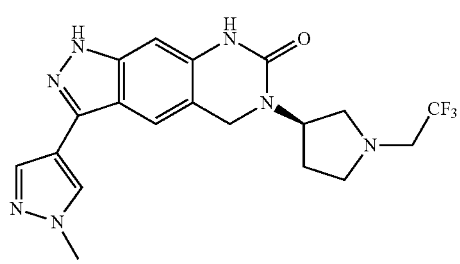 [SMILES: Cn1cc(-c2n[nH]c3cc4c(cc23)CN([C@@H]2CCN(CC(F)(F)F)C2)C(=O)N4)cn1] | ++++ | 419.4 | 420.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|-----|-------------------|----------------|----------------------------|---------------------|
| 260 | 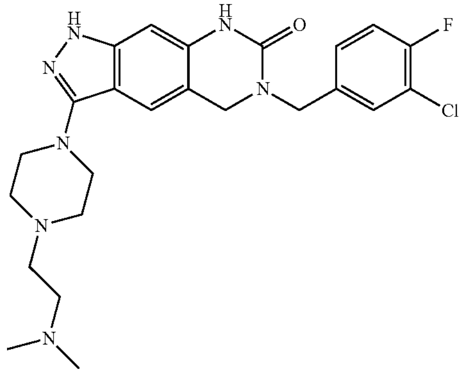 [SMILES: CN(C)CCN1CCN(c2n[nH]c3cc4c(cc23)CN(Cc2ccc(F)c(Cl)c2)C(=O)N4)CC1] | ++ | 486.0 | 486.2 |
| 261 | 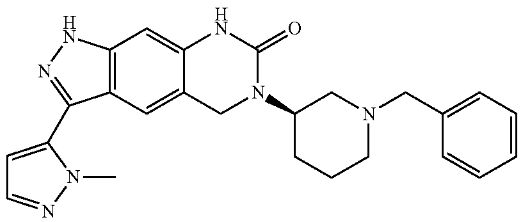 [SMILES: Cn1nccc1-c1n[nH]c2cc3c(cc12)CN([C@@H]1CCCN(Cc2ccccc2)C1)C(=O)N3] | ++++ | 441.5 | 442.2 |
| 262 | 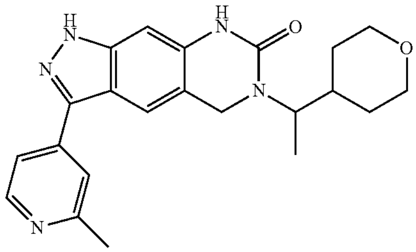 [SMILES: Cc1cc(-c2n[nH]c3cc4c(cc23)CN(C(C)C2CCOCC2)C(=O)N4)ccn1] | ++++ | 391.5 | 392.2 |
| 263 | 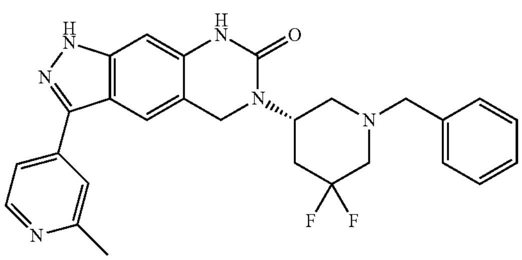 [SMILES: Cc1cc(-c2n[nH]c3cc4c(cc23)CN([C@@H]2CN(Cc3ccccc3)CC(F)(F)C2)C(=O)N4)ccn1] | ++ | 488.5 | 489.2 |
| 264 | 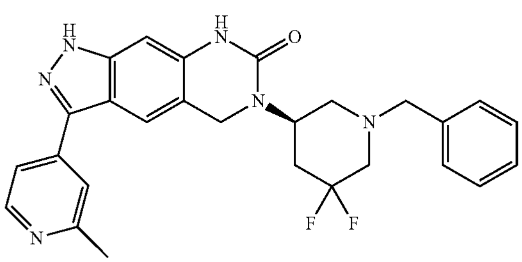 [SMILES: Cc1cc(-c2n[nH]c3cc4c(cc23)CN([C@H]2CN(Cc3ccccc3)CC(F)(F)C2)C(=O)N4)ccn1] | ++++ | 488.5 | 489.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
| --- | --- | --- | --- | --- |
| 265 | 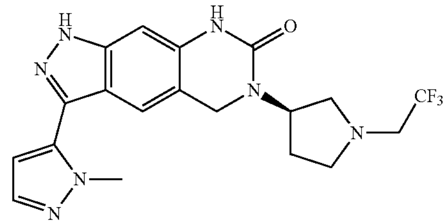 [SMILES: Cn1nccc1-c1n[nH]c2cc3c(cc12)CN([C@@H]1CCN(CC(F)(F)F)C1)C(=O)N3] | +++ | 419.4 | 420.1 |
| 266 | 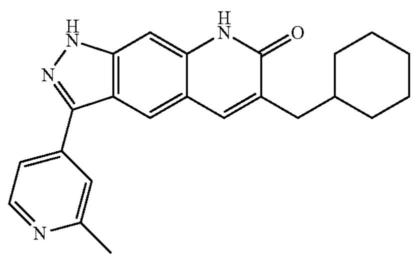 [SMILES: Cc1cc(-c2n[nH]c3cc4[nH]c(=O)c(CC5CCCCC5)cc4cc23)ccn1] | ++++ | 372.5 | 373.2 |
| 267 | 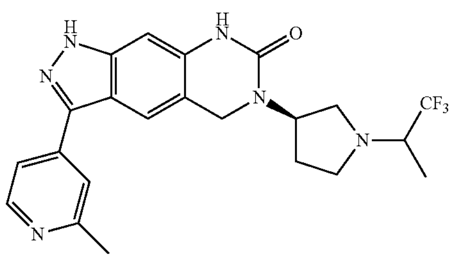 [SMILES: Cc1cc(-c2n[nH]c3cc4c(cc23)CN([C@@H]2CCN(C(C)C(F)(F)F)C2)C(=O)N4)ccn1] | ++++ | 444.5 | 445.1 |
| 268 | 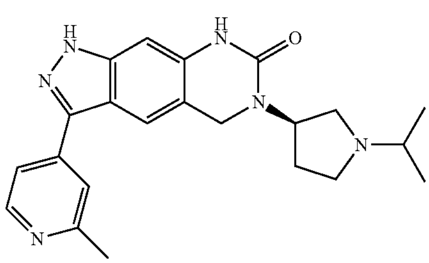 [SMILES: Cc1cc(-c2n[nH]c3cc4c(cc23)CN([C@@H]2CCN(C(C)C)C2)C(=O)N4)ccn1] | +++ | 390.5 | 391.3 |
| 269 | 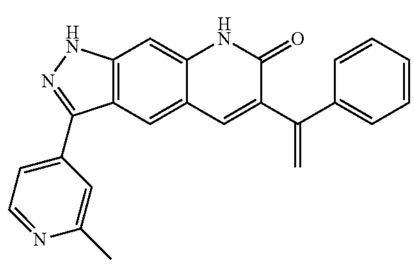 [SMILES: C=C(c1ccccc1)c1cc2cc3c(-c4ccnc(C)c4)n[nH]c3cc2[nH]c1=O] | ++++ | 378.4 | 379.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
| --- | --- | --- | --- | --- |
| 270 | 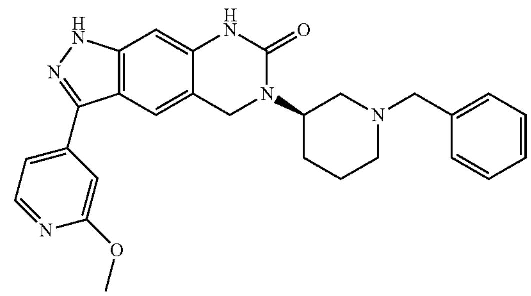 [SMILES: COc1cc(-c2n[nH]c3cc4c(cc23)CN([C@@H]2CCCN(Cc3ccccc3)C2)C(=O)N4)ccn1] | ++++ | 468.6 | 469.2 |
| 271 | 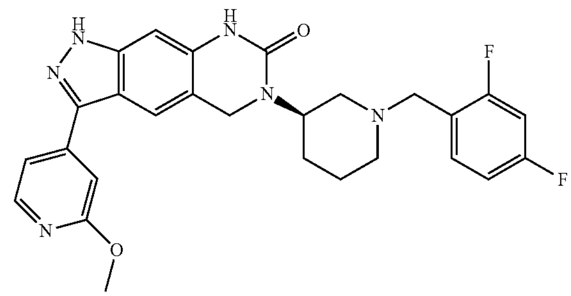 [SMILES: COc1cc(-c2n[nH]c3cc4c(cc23)CN([C@@H]2CCCN(Cc3ccc(F)cc3F)C2)C(=O)N4)ccn1] | ++++ | 504.5 | 505.2 |
| 272 | 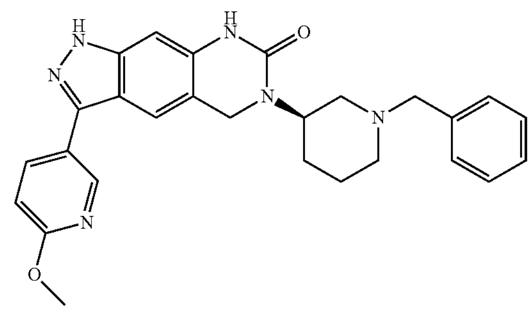 [SMILES: COc1ccc(-c2n[nH]c3cc4c(cc23)CN([C@@H]2CCCN(Cc3ccccc3)C2)C(=O)N4)cn1] | ++++ | 468.6 | 469.2 |
| 273 | 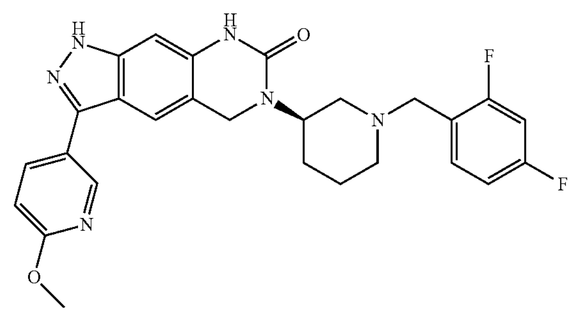 [SMILES: COc1ccc(-c2n[nH]c3cc4c(cc23)CN([C@@H]2CCCN(Cc3ccc(F)cc3F)C2)C(=O)N4)cn1] | ++++ | 504.5 | 505.2 |
| 274 | 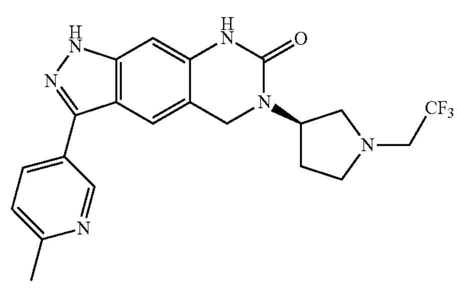 [SMILES: Cc1ccc(-c2n[nH]c3cc4c(cc23)CN([C@@H]2CCN(CC(F)(F)F)C2)C(=O)N4)cn1] | ++++ | 430.4 | 431.1 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 275 | 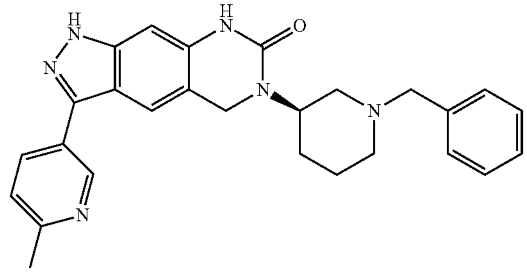 [SMILES: Cc1ccc(-c2n[nH]c3cc4c(cc23)CN([C@@H]2CCCN(Cc3ccccc3)C2)C(=O)N4)cn1] | ++++ | 452.6 | 453.2 |
| 276 | 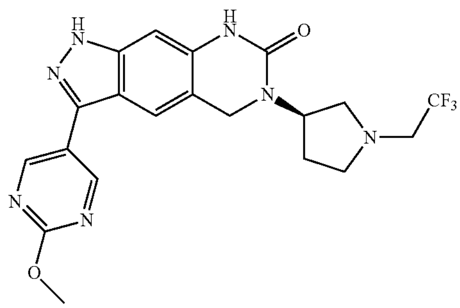 [SMILES: COc1ncc(-c2n[nH]c3cc4c(cc23)CN([C@@H]2CCN(CC(F)(F)F)C2)C(=O)N4)cn1] | ++++ | 447.4 | 448.2 |
| 277 | 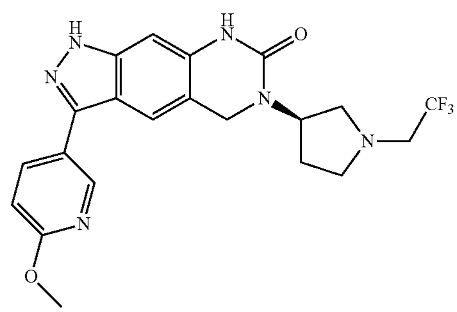 [SMILES: COc1ccc(-c2n[nH]c3cc4c(cc23)CN([C@@H]2CCN(CC(F)(F)F)C2)C(=O)N4)cn1] | ++++ | 446.4 | 447.1 |
| 278 | (Racemate) | ++++ | 452.6 | 453.2 |
| 279 | (Racemate) | ++++ | 466.6 | 467.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 280 | 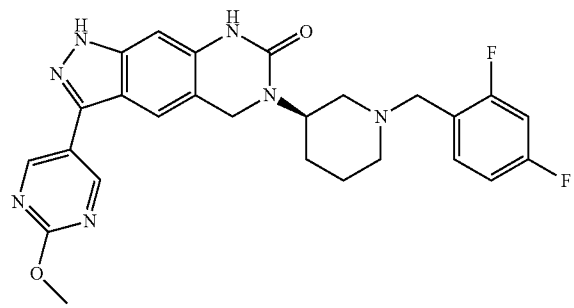 [SMILES: COc1ncc(-c2n[nH]c3cc4c(cc23)CN([C@@H]2CCCN(Cc3ccc(F)cc3F)C2)C(=O)N4)cn1] | ++++ | 505.5 | 506.2 |
| 281 | 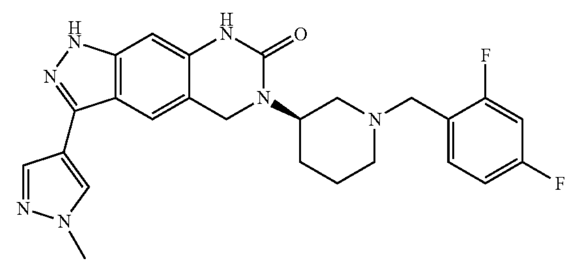 [SMILES: Cn1cc(-c2n[nH]c3cc4c(cc23)CN([C@@H]2CCCN(Cc3ccc(F)cc3F)C2)C(=O)N4)cn1] | ++++ | 477.5 | 478.2 |
| 282 | 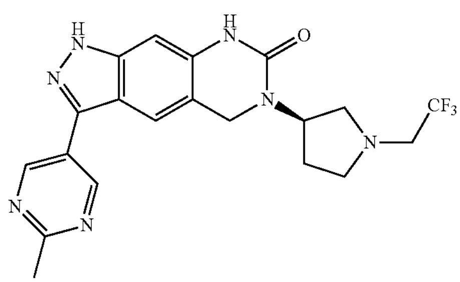 [SMILES: Cc1ncc(-c2n[nH]c3cc4c(cc23)CN([C@@H]2CCN(CC(F)(F)F)C2)C(=O)N4)cn1] | ++++ | 431.4 | 432.2 |
| 283 | 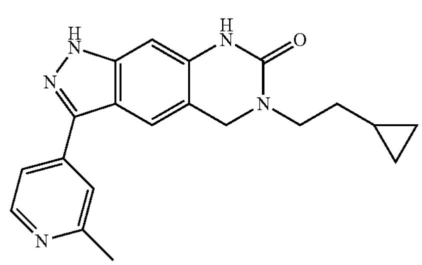 [SMILES: Cc1cc(-c2n[nH]c3cc4c(cc23)CN(CCC2CC2)C(=O)N4)ccn1] | +++ | 347.4 | 348.2 |
| 284 | 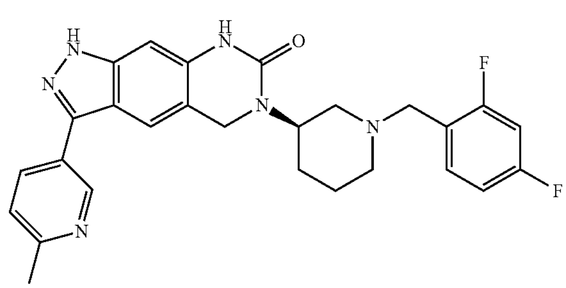 [SMILES: Cc1ccc(-c2n[nH]c3cc4c(cc23)CN([C@@H]2CCCN(Cc3ccc(F)cc3F)C2)C(=O)N4)cn1] | ++++ | 488.5 | 489.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 285 | 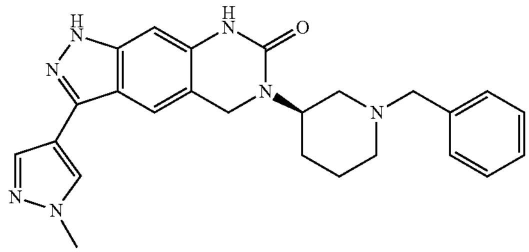 [SMILES: Cn1cc(-c2n[nH]c3cc4c(cc23)CN([C@@H]2CCCN(Cc3ccccc3)C2)C(=O)N4)cn1] | ++++ | 441.5 | 442.2 |
| 286 | 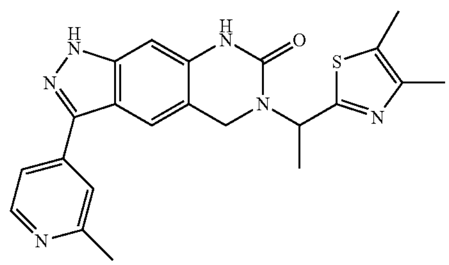 [SMILES: Cc1cc(-c2n[nH]c3cc4c(cc23)CN(C(C)c2nc(C)c(C)s2)C(=O)N4)ccn1] | ++++ | 418.5 | 419.2 |
| 287 | 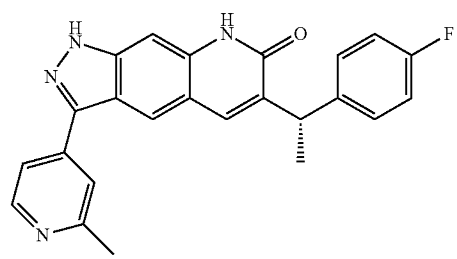 | +++ | 398.4 | 399.1 |
| 288 | 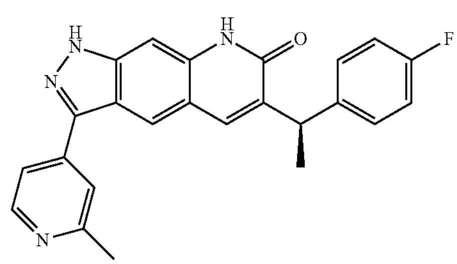 [SMILES: Cc1cc(-c2n[nH]c3cc4[nH]c(=O)c([C@H](C)c5ccc(F)cc5)cc4cc23)ccn1] | ++++ | 398.4 | 399.2 |
| 289 | 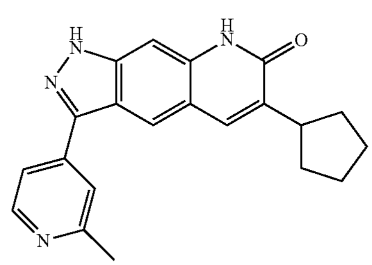 [SMILES: Cc1cc(-c2n[nH]c3cc4[nH]c(=O)c(C5CCCC5)cc4cc23)ccn1] | ++++ | 344.4 | 345.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 290 | 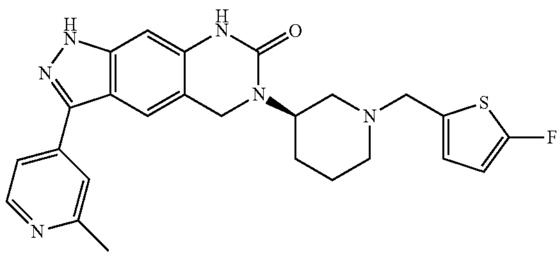 [SMILES: Cc1cc(-c2n[nH]c3cc4c(cc23)CN([C@@H]2CCCN(Cc3ccc(F)s3)C2)C(=O)N4)ccn1] | ++++ | 476.6 | 477.2 |
| 291 | 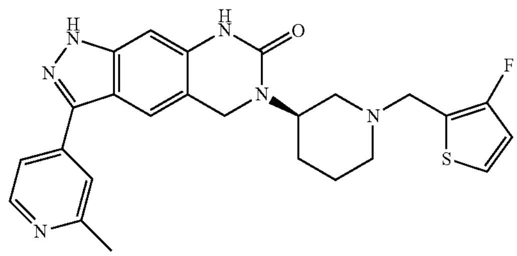 [SMILES: Cc1cc(-c2n[nH]c3cc4c(cc23)CN([C@@H]2CCCN(Cc3sccc3F)C2)C(=O)N4)ccn1] | ++++ | 476.6 | 477.3 |
| 292 | 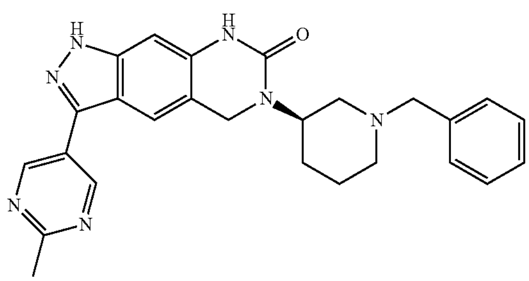 [SMILES: Cc1ncc(-c2n[nH]c3cc4c(cc23)CN([C@@H]2CCCN(Cc3ccccc3)C2)C(=O)N4)cn1] | ++++ | 453.5 | 454.3 |
| 293 | 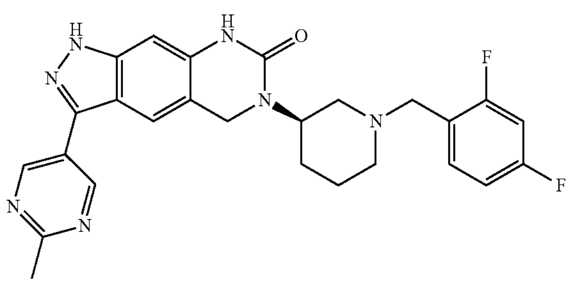 [SMILES: Cc1ncc(-c2n[nH]c3cc4c(cc23)CN([C@@H]2CCCN(Cc3ccc(F)cc3F)C2)C(=O)N4)cn1] | ++++ | 489.5 | 490.3 |
| 294 | 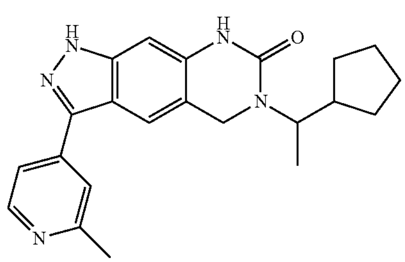 [SMILES: Cc1cc(-c2n[nH]c3cc4c(cc23)CN(C(C)C2CCCC2)C(=O)N4)ccn1] | ++++ | 375.5 | 376.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 295 | 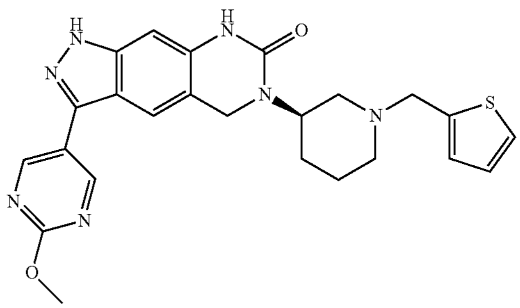 [SMILES: COc1ncc(-c2n[nH]c3cc4c(cc23)CN([C@@H]2CCCN(Cc3cccs3)C2)C(=O)N4)cn1] | ++++ | 475.6 | 476.2 |
| 296 | 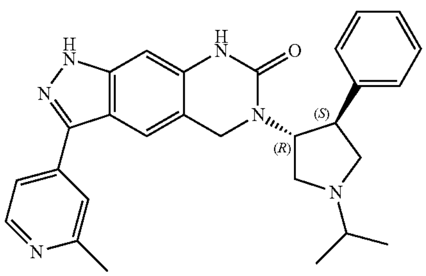 | +++ | 466.6 | 467.3 |
| 297 | 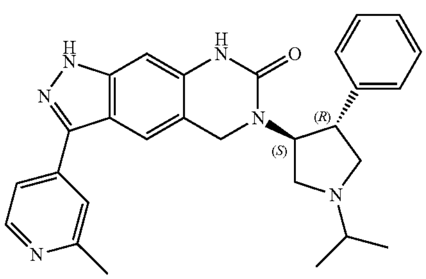 | ++++ | 466.6 | 467.2 |
| 298 | 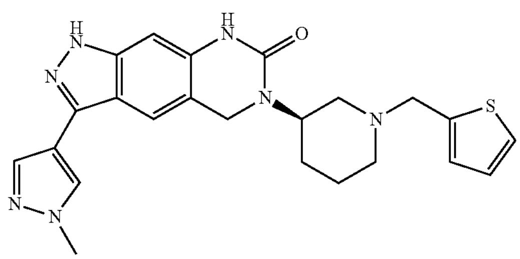 [SMILES: Cn1cc(-c2n[nH]c3cc4c(cc23)CN([C@@H]2CCCN(Cc3cccs3)C2)C(=O)N4)cn1] | ++++ | 447.6 | 448.2 |
| 299 | 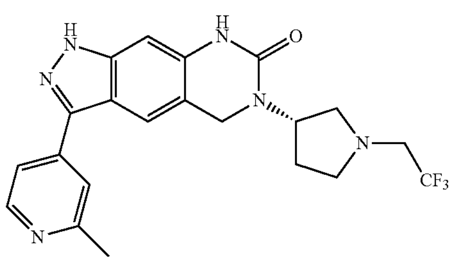 [SMILES: Cc1cc(-c2n[nH]c3cc4c(cc23)CN([C@H]2CCN(CC(F)(F)F)C2)C(=O)N4)ccn1] | ++++ | 430.4 | 431.2 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 300 | 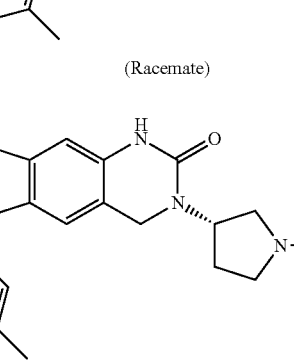 (Racemate) | ++++ | 524.5 | 525.2 |
| 301 | 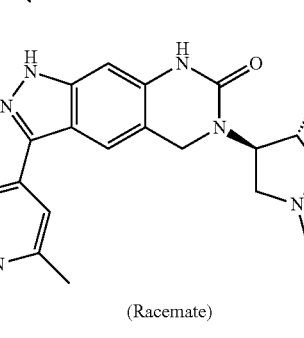 | ++++ | 438.5 | 439.2 |
| 302 | 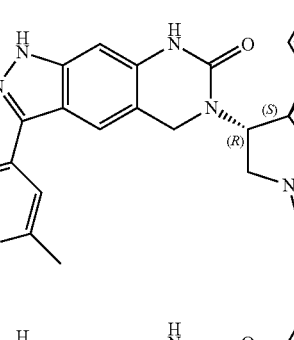 (Racemate) | ++++ | 444.5 | 445.2 |
| 303 | 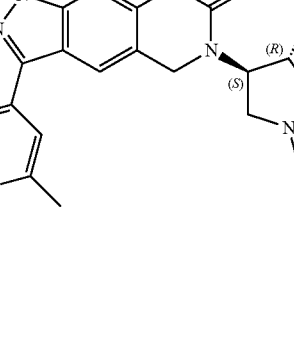 | ++ | 506.5 | 507.2 |
| 304 | 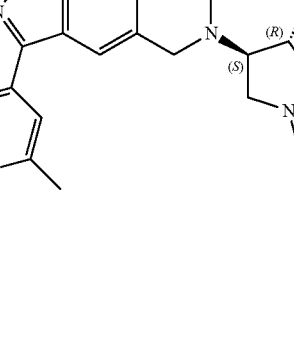 | ++++ | 506.5 | 507.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 305 | (Racemate) | +++ | 470.5 | 471.2 |
| 306 | (Racemate) | ++++ | 470.5 | 471.2 |
| 307 | 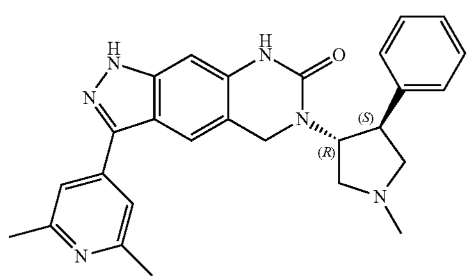 | +++ | 452.6 | 453.2 |
| 308 | 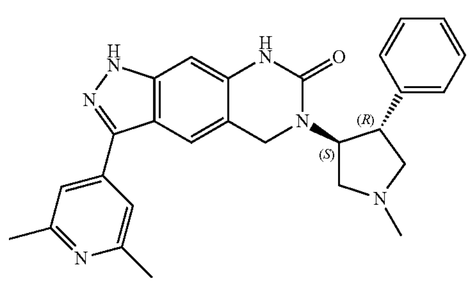 | ++++ | 452.6 | 453.2 |
| 309 | 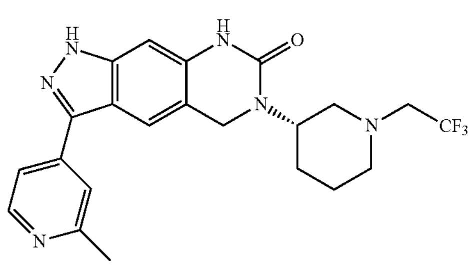 [SMILES: Cc1cc(-c2n[nH]c3cc4c(cc23)CN([C@H]2CCCN(CC(F)(F)F)C2)C(=O)N4)ccn1] | +++ | 444.5 | 445.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 310 | 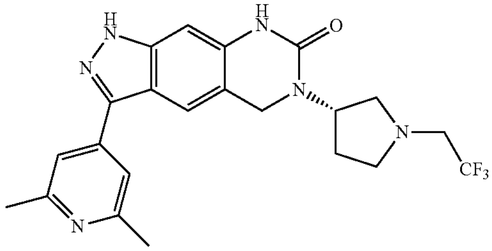 [SMILES: Cc1cc(-c2n[nH]c3cc4c(cc23)CN([C@H]2CCN(CC(F)(F)F)C2)C(=O)N4)cc(C)n1] | ++++ | 444.5 | 445.2 |
| 311 | (Racemate) | +++ | 524.5 | 525.2 |
| 312 | 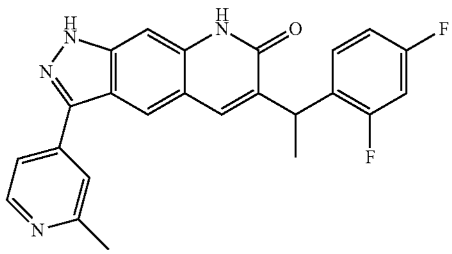 [SMILES: Cc1cc(-c2n[nH]c3cc4[nH]c(=O)c(C(C)c5ccc(F)cc5F)cc4cc23)ccn1] | +++ | 416.4 | 417.2 |
| 313 | 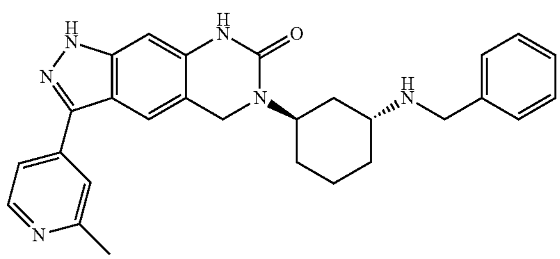 [SMILES: Cc1cc(-c2n[nH]c3cc4c(cc23)CN([C@@H]2CCC[C@@H](NCc3ccccc3)C2)C(=O)N4)ccn1] | ++++ | 466.6 | 467.3 |
| 314 | | ++++ | 373.5 | 374.2 |
| 315 | | ++++ | 447.5 | 370.1 |
| 316 | | ++++ | 464.6 | 465.3 |
| 317 | | +++ | 369.4 | 370.2 |
| 318 | 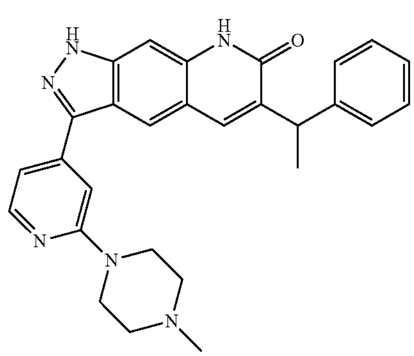 [SMILES: CC(c1ccccc1)c1cc2cc3c(-c4ccnc(N5CCN(C)CC5)c4)n[nH]c3cc2[nH]c1=O] | ++++ | 464.6 | 465.3 |

US 9,624,228 B2
477                                                              478
TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 319 | 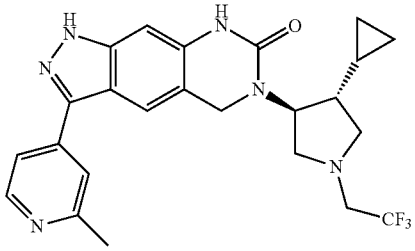<br>Racemic mixture | +++ | 470.5 | 471.2 |
| 320 | 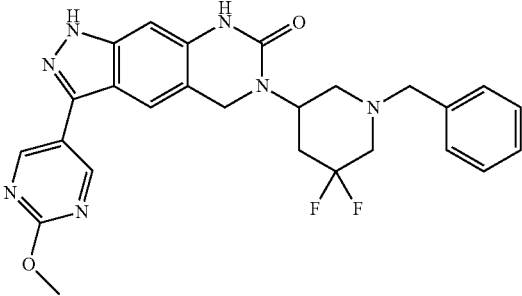 [SMILES: COc1ncc(-c2n[nH]c3cc4c(cc23)CN(C2CN(Cc3ccccc3)CC(F)(F)C2)C(=O)N4)cn1] | +++ | 505.5 | 506.3 |
| 321 | 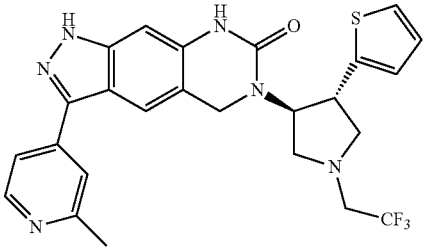<br>Racemic mixture | ++++ | 512.6 | 513.3 |
| 322 | 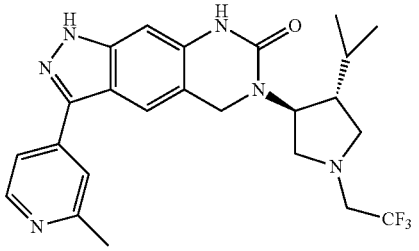<br>Racemic mixture | +++ | 472.5 | 473.3 |
| 323 | 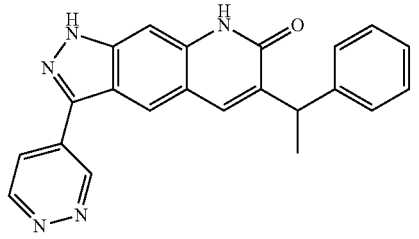 [SMILES: CC(c1ccccc1)c1cc2cc3c(-c4ccnnc4)n[nH]c3cc2[nH]c1=O] | ++++ | 367.4 | 368.2 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 324 | 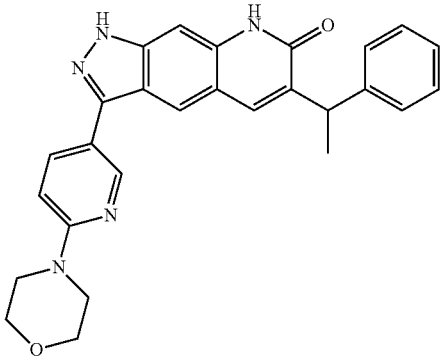 [SMILES: CC(c1ccccc1)c1cc2cc3c(-c4ccc(N5CCOCC5)nc4)n[nH]c3cc2[nH]c1=O] | +++ | 451.5 | 452.3 |
| 325 | 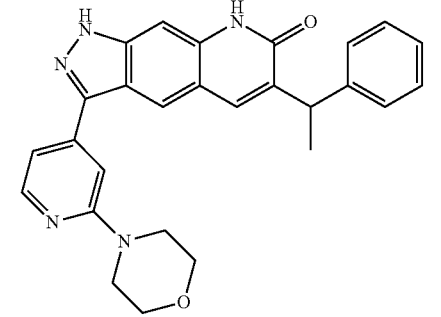 [SMILES: CC(c1ccccc1)c1cc2cc3c(-c4ccnc(N5CCOCC5)c4)n[nH]c3cc2[nH]c1=O] | ++++ | 451.5 | 452.3 |
| 326 | 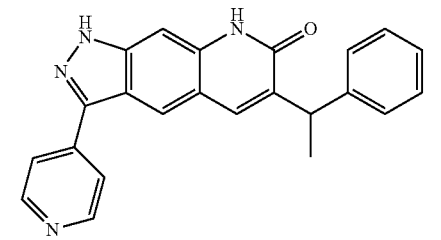 [SMILES: CC(c1ccccc1)c1cc2cc3c(-c4ccncc4)n[nH]c3cc2[nH]c1=O] | ++++ | 366.4 | 367.2 |
| 327 | 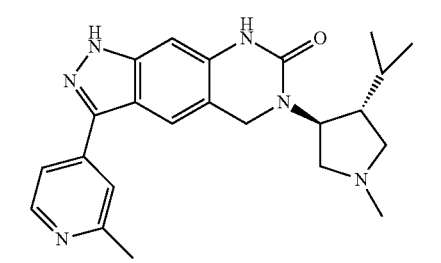<br>Racemic mixture | ++ | 404.5 | 405.3 |
| 328 | 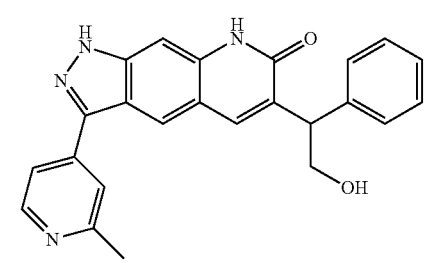 [SMILES: Cc1cc(-c2n[nH]c3cc4[nH]c(=O)c(C(CO)c5ccccc5)cc4cc23)ccn1] | ++++ | 396.4 | 397.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 329 | Racemic mixture | ++ | 486.5 | 487.4 |
| 330 | 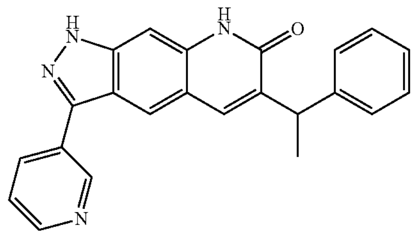 [SMILES: CC(c1ccccc1)c1cc2cc3c(-c4cccnc4)n[nH]c3cc2[nH]c1=O] | ++++ | 366.4 | 367.2 |
| 331 | Racemic mixture | ++++ | 498.4 | 499.3 |
| 332 | 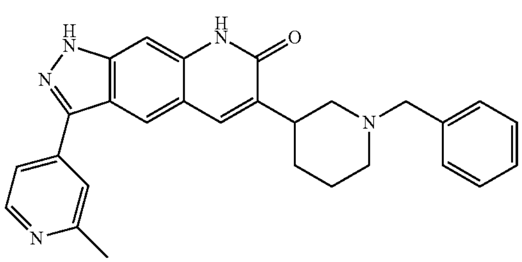 [SMILES: Cc1cc(-c2n[nH]c3cc4[nH]c(=O)c(C5CCCN(Cc6ccccc6)C5)cc4cc23)ccn1] | ++++ | 449.5 | 450.4 |
| 333 | 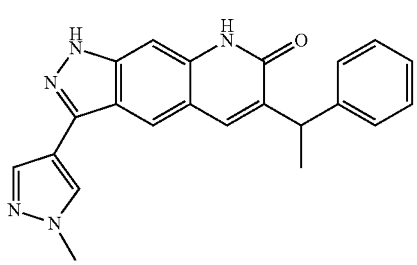 [SMILES: CC(c1ccccc1)c1cc2cc3c(-c4cnn(C)c4)n[nH]c3cc2[nH]c1=O] | ++++ | 369.4 | 370.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 334 | 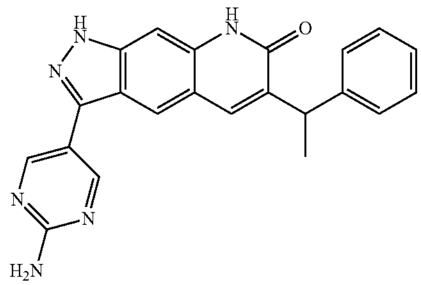 [SMILES: CC(c1ccccc1)c1cc2cc3c(-c4cnc(N)nc4)n[nH]c3cc2[nH]c1=O] | ++++ | 382.4 | 383.2 |
| 335 | 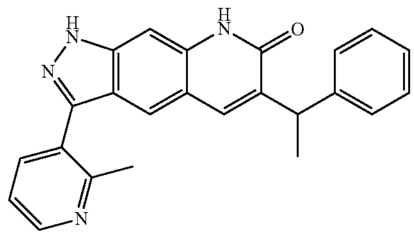 [SMILES: Cc1ncccc1-c1n[nH]c2cc3[nH]c(=O)c(C(C)c4ccccc4)cc3cc12] | ++++ | 380.4 | 381.2 |
| 336 | 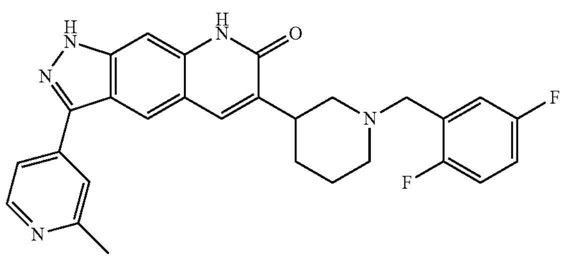 [SMILES: Cc1cc(-c2n[nH]c3cc4[nH]c(=O)c(C5CCCN(Cc6cc(F)ccc6F)C5)cc4cc23)ccn1] | ++++ | 485.5 | 486.2 |
| 338 | 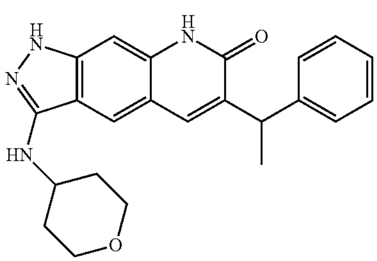 [SMILES: CC(c1ccccc1)c1cc2cc3c(NC4CCOCC4)n[nH]c3cc2[nH]c1=O] | ++++ | 388.5 | 389.2 |
| 339 | 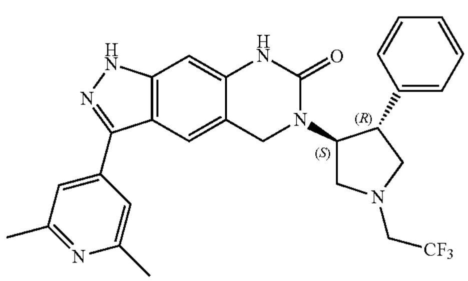 | ++++ | 520.5 | 521.4 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 340 | 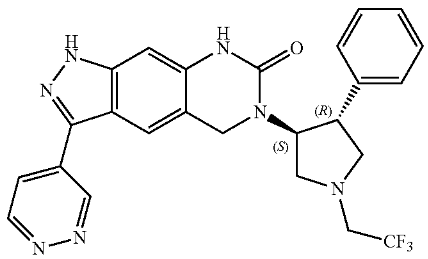 | ++++ | 493.5 | 494.4 |
| 341 | 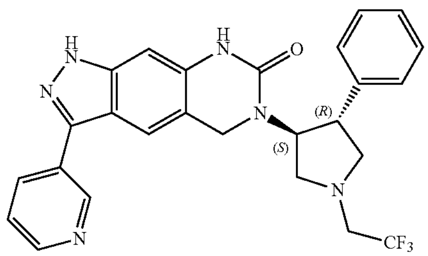 | ++++ | 492.5 | 493.3 |
| 342 | 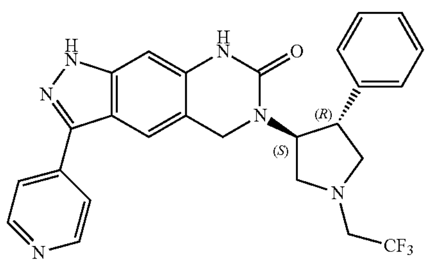 | ++++ | 492.5 | 493.3 |
| 343 | 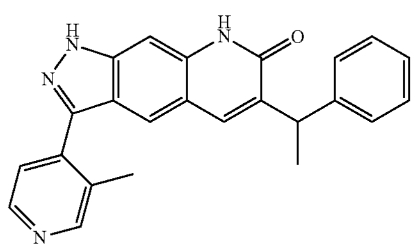 [SMILES: Cc1cnccc1-c1n[nH]c2cc3[nH]c(=O)c(C(C)c4ccccc4)cc3cc12] | +++ | 380.4 | 381.2 |
| 344 | 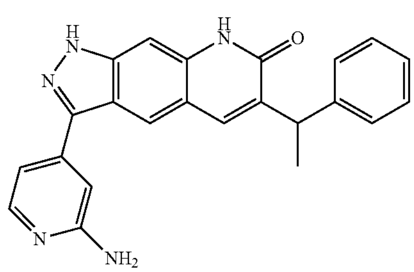 [SMILES: CC(c1ccccc1)c1cc2cc3c(-c4ccnc(N)c4)n[nH]c3cc2[nH]c1=O] | ++++ | 381.4 | 382.1 |
| 345 | 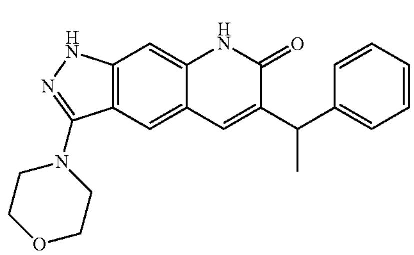 [SMILES: CC(c1ccccc1)c1cc2cc3c(N4CCOCC4)n[nH]c3cc2[nH]c1=O] | ++++ | 374.4 | 375.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 346 | 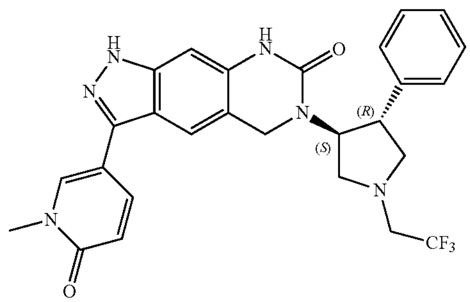 | ++++ | 522.5 | 523.3 |
| 347 | 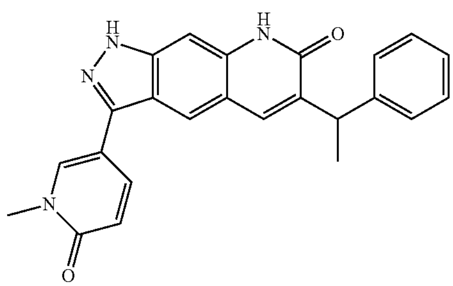 [SMILES: CC(c1ccccc1)c1cc2cc3c(-c4ccc(=O)n(C)c4)n[nH]c3cc2[nH]c1=O] | ++++ | 396.4 | 397.1 |
| 348 | 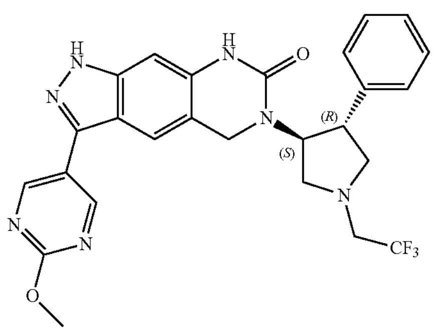 | ++++ | 523.5 | 524.4 |
| 349 | 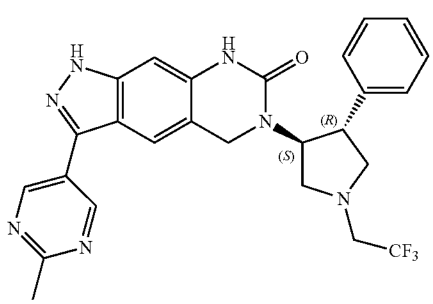 | ++++ | 507.5 | 508.3 |
| 350 | 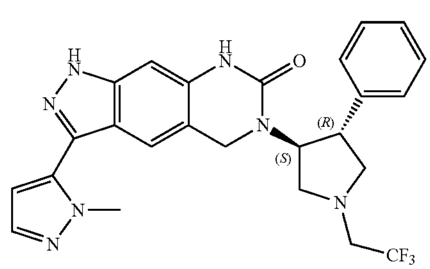 | ++ | 495.5 | 496.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 351 | 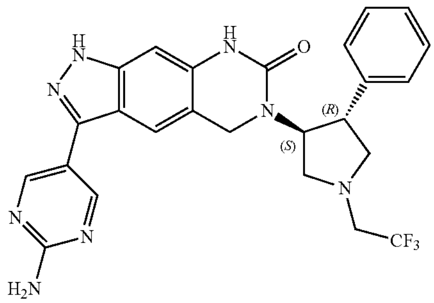 | ++++ | 508.5 | 509.2 |
| 352 | 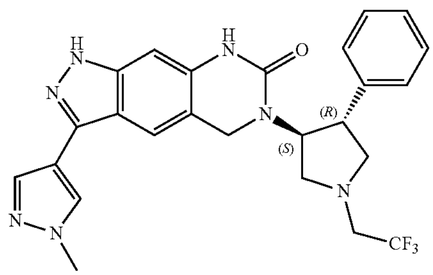 | ++++ | 495.5 | 496.2 |
| 353 | Racemic mixture | ++++ | 454.5 | 455.3 |
| 354 | Racemic mixture | ++++ | 454.5 | 455.3 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|---|---|---|---|---|
| 355 | 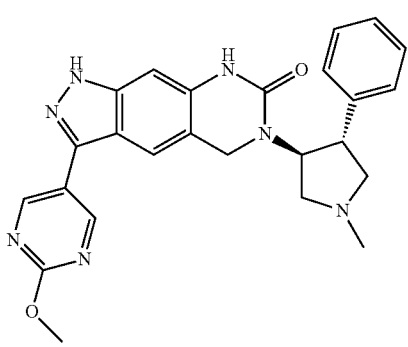<br>Racemic mixture | ++++ | 455.5 | 456.3 |
| 356 | 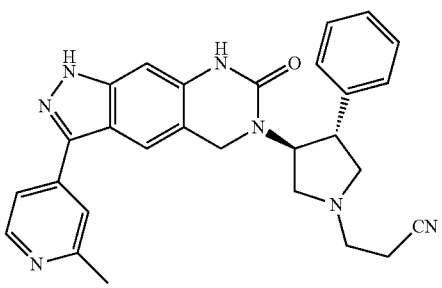<br>Racemic mixture | ++++ | 477.6 | 478.3 |
| 357 | 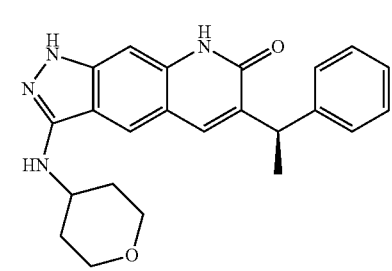 [SMILES: C[C@H](c1ccccc1)c1cc2cc3c(NC4CCOCC4)n[nH]c3cc2[nH]c1=O] | ++++ | 388.5 | 389.2 |
| 358 | 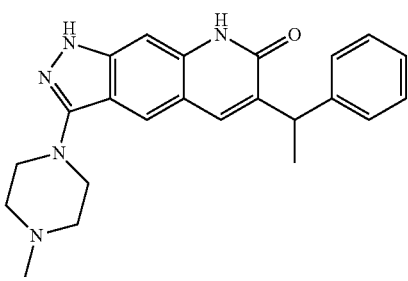 [SMILES: CC(c1ccccc1)c1cc2cc3c(N4CCN(C)CC4)n[nH]c3cc2[nH]c1=O] | +++ | 387.5 | 388.2 |

TABLE 1-continued
In Vitro Erk2 IC50 data for selected compounds of the invention.
| No. | Chemical Structure | Erk2 IC50 (nM) | Calculated Molecular Weight | Mass Found (M + 1) |
|-----|--------------------|----------------|-----------------------------|---------------------|
| 359 | 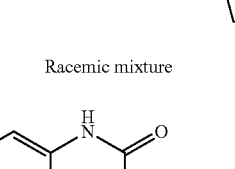 Racemic mixture | +++ | 508.6 | 509.3 |
| 360 | 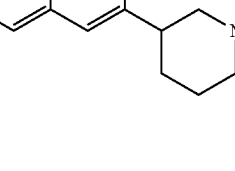 | +++ | 463.6 | 464.3 |
| 361 | 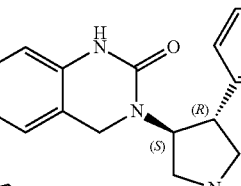 | +++ | 514.5 | 515.3 |
| 362 | 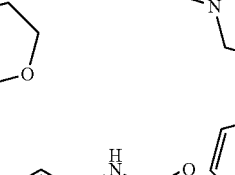 Racemic mixture | ++++ | 488.5 | 489.2 |
| 363 | 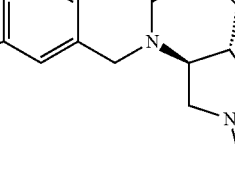 | ++++ | 466.6 | 467.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 364 | 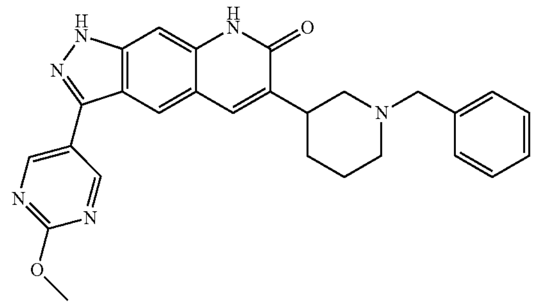 [SMILES: COc1ncc(-c2n[nH]c3cc4[nH]c(=O)c(C5CCCN(Cc6ccccc6)C5)cc4cc23)cn1] | ++++ | 466.5 | 467.3 |
| 365 | 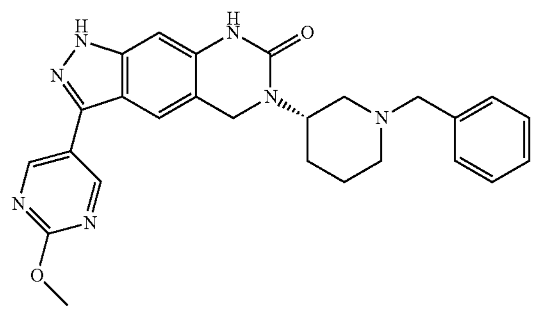 [SMILES: COc1ncc(-c2n[nH]c3cc4c(cc23)CN([C@H]2CCCN(Cc3ccccc3)C2)C(=O)N4)cn1] | +++ | 469.5 | 470.3 |
| 366 | Racemic mixture | ++++ | 463.5 | 464.2 |
| 367 | 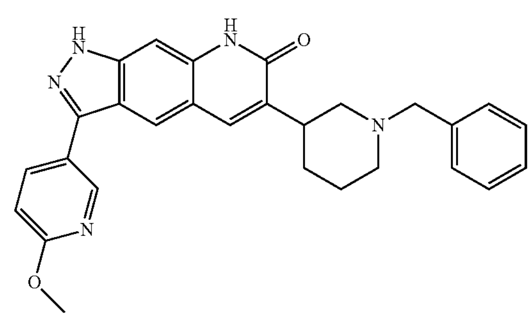 [SMILES: COc1ccc(-c2n[nH]c3cc4[nH]c(=O)c(C5CCCN(Cc6ccccc6)C5)cc4cc23)cn1] | +++ | 465.5 | 466.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 368 | 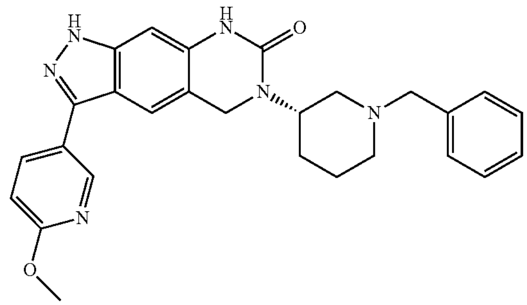 [SMILES: COc1ccc(-c2n[nH]c3cc4c(cc23)CN([C@H]2CCCN(Cc3ccccc3)C2)C(=O)N4)cn1] | +++ | 468.6 | 469.3 |
| 369 | 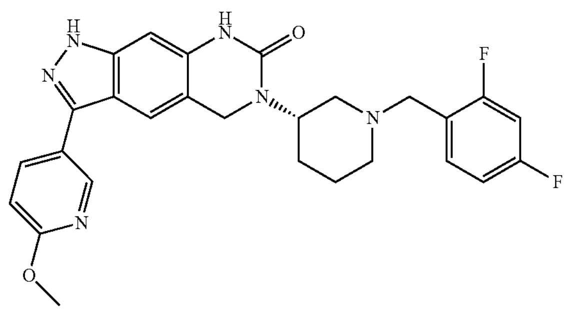 [SMILES: COc1ccc(-c2n[nH]c3cc4c(cc23)CN([C@H]2CCCN(Cc3ccc(F)cc3F)C2)C(=O)N4)cn1] | ++ | 504.5 | 505.4 |
| 370 | 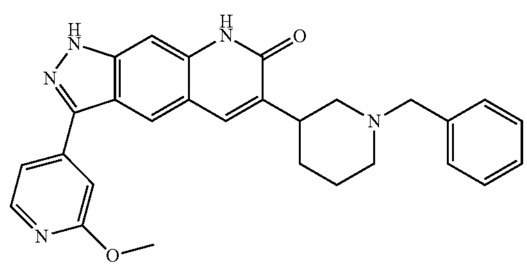 [SMILES: COc1cc(-c2n[nH]c3cc4[nH]c(=O)c(C5CCCN(Cc6ccccc6)C5)cc4cc23)ccn1] | ++++ | 465.5 | 466.4 |
| 371 | 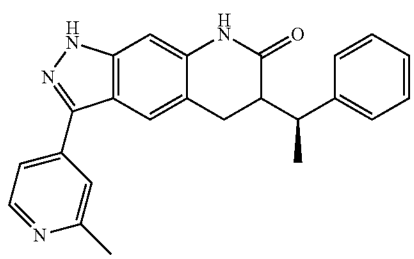 | +++ | 382.5 | 383.2 |
| 372 | 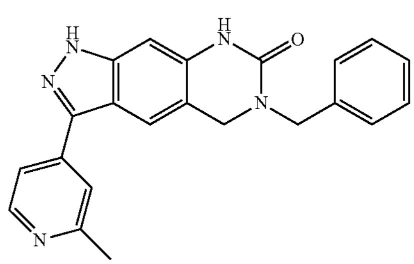 [SMILES: Cc1cc(-c2n[nH]c3cc4c(cc23)CN(Cc2ccccc2)C(=O)N4)ccn1] | ++++ | 369.4 | 370.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 373 | 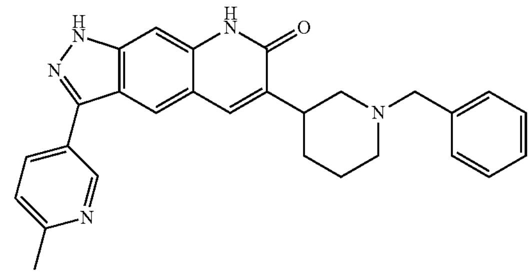 [SMILES: Cc1ccc(-c2n[nH]c3cc4[nH]c(=O)c(C5CCCN(Cc6ccccc6)C5)cc4cc23)cn1] | +++ | 449.5 | 450.3 |
| 374 | 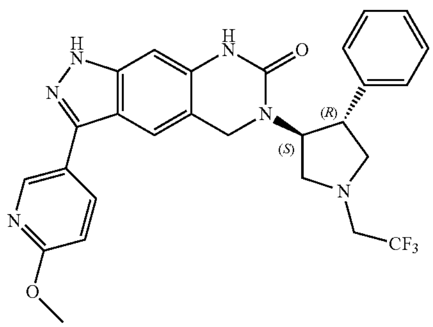 | ++++ | 522.5 | 523.3 |
| 375 | 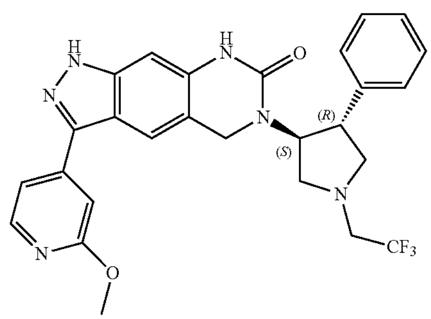 | +++ | 522.5 | 523.3 |
| 376 | Racemic mixture | ++++ | 468.6 | 469.3 |
| 377 | 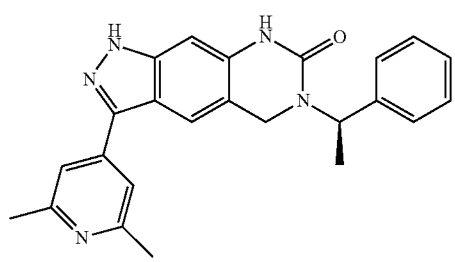 [SMILES: Cc1cc(-c2n[nH]c3cc4c(cc23)CN([C@H](C)c2ccccc2)C(=O)N4)cc(C)n1] | ++++ | 397.5 | 398.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 378 | 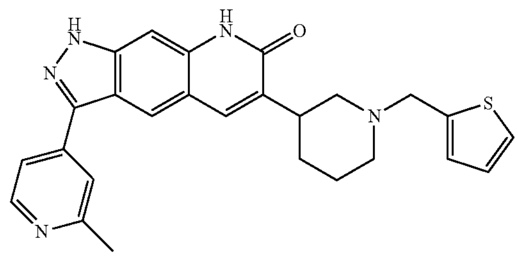 [SMILES: Cc1cc(-c2n[nH]c3cc4[nH]c(=O)c(C5CCCN(Cc6cccs6)C5)cc4cc23)ccn1] | +++ | 455.2 | 456.2 |
| 379 | Racemic mixture | ++++ | 502.2 | 503.2 |
| 380 | | | 466.3 | 467.3 |
| 381 | | | 450.2 | 451.3 |
| 382 | 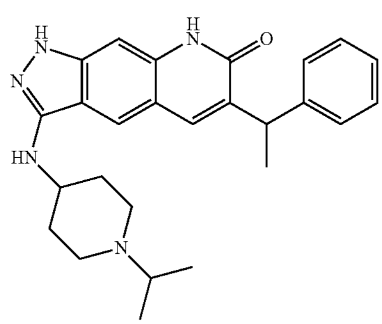 [SMILES: CC(c1ccccc1)c1cc2cc3c(NC4CCN(C(C)C)CC4)n[nH]c3cc2[nH]c1=O] | | 429.3 | 430.2 |
| 383 | 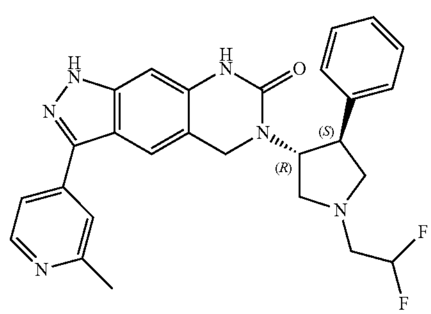 | | 488.2 | 489.3 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
| --- | --- | --- | --- | --- |
| 384 | 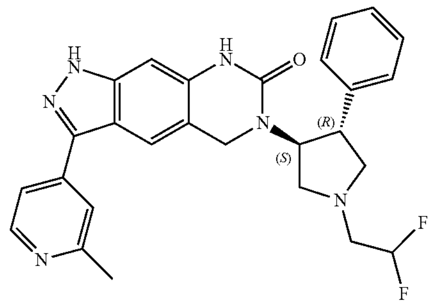 | | 488.2 | 489.3 |
| 385 | 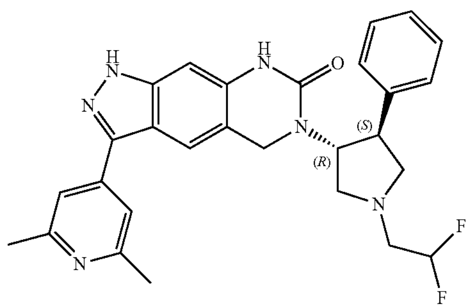 | | 502.2 | 503.3 |
| 386 | 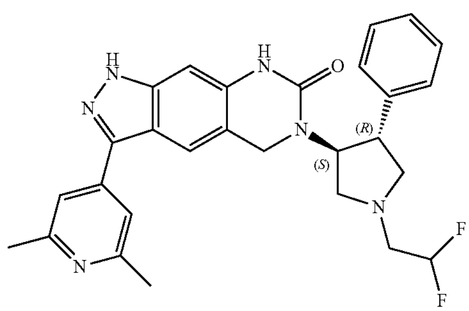 | | 502.2 | 503.3 |
| 387 (Racemic mixture) | | | 520.2 | 521.2 |

TABLE 1-continued

In Vitro Erk2 IC50 data for selected compounds of the invention.

| No. | Chemical Structure | Erk2 IC50 (nM) | Calculated Molecular Weight | Mass Found (M + 1) |
|---|---|---|---|---|
| 388 | 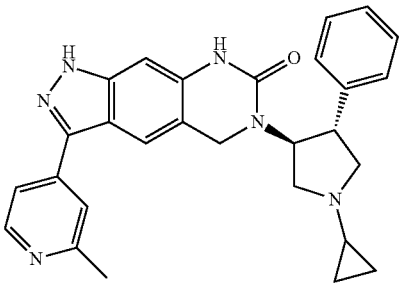 Racemic mixture | | 464.6 | 465.3 |
| 389 | 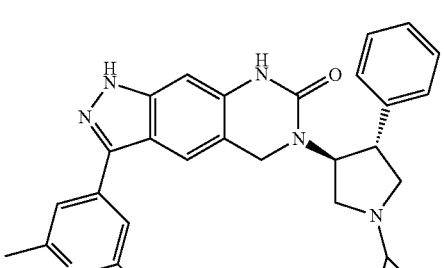 Racemic mixture | | 478.6 | 479.3 |

The following symbols are used:
+ (greater than 1000 nM),
++ (250 nM to 1000 nM),
+++ (50 nM to 250 nM), and
++++ (less than 50 nM).

Example 18. Phospho-p90 RSK ELISA Using A375 (Braf V600E) Cells

On day 1, A375 cells (melanoma cell line with a Braf V600E mutation) were grown to near 80% confluence, trypsinized, and seeded at 50,000 cells per well in a 100 µL of full growth medium (10% FBS in DMEM) in a 96-well plate. Cells were incubated at 37° C. under 5% $CO_2$ overnight prior to treatment. In preparation for the assay, an ELISA plate with the pre-coated goat anti-mouse antibody (Thermo Scientific) was treated with a mouse anti-human RSK1 antibody (monoclonal, Invitrogen) at 1:800 dilution (150 ng/well) in PBS, and the plate was placed on a plate shaker at 4° C. overnight. On day 3, the compounds were first diluted in 1:3 dilutions in 100% DMSO at 250× the desired concentration, and then further diluted (1:50) in 10% DMEM growth medium. The diluted compounds are added to the cell plate (25 µL for a 5× dilution) and the cells were treated with compounds (0.4% DMSO in 10% FBS DMEM) for 2 hours at 37° C. under 5% CO2. The cell control wells were added with vehicle only (0.4% DMSO in 10% FBS DMEM). Each concentration of the compounds was tested in duplicate. After two hours of the compound treatment, the supernatant was removed from the cell plate, and cells were lysed in 100 µl per well of cell lysis buffer (Cell Signaling Technologies) containing phosphatase and protease inhibitors (Cell Signaling Technologies) on a plate shaker at 4° C. for 20 minutes. The ELISA plate was washed four times with ELISA wash buffer (Thermo Scientific) prior to addition of 100 µL cell lysate. The lysate was incubated on the ELISA plate with gentle shaking at room temperature for 2 hours. The contents of the wells were removed, and the ELISA plate was washed four times with wash buffer, and incubated with 100 µL per well of anti-phospho-RSK1 (Thr359/Ser363) rabbit monoclonal antibody (Millipore) at dilution of 1:1000 in StartingBlock buffer (Thermo Scientific) on a plate shaker at room temperature for 1 hour. The contents of the wells were removed, the ELISA plate was washed four times with wash buffer, and was incubated with 100 µL per well of goat anti-rabbit HRP (Thermo Scientific) at dilution of 1:3000 in StartingBlock buffer (Thermo Scientific) on a plate shaker at room temperature for 1 hour. The contents of the wells were removed, the ELISA plate was washed four times with wash buffer, and then incubated with 100 µL per well of TMB substrate solution (Thermo Scientific) on a plate shaker at room temperature for 20 minutes. Finally, 100 µL of TMB stop solution (Thermo Scientific) was added to each well and the absorbance is measured at 450 nm on a Tecan plate reader. One or more compounds disclosed herein exhibit an EC50 less than 50 nM when tested in this assay (see FIG. 1).

Example 19. Tumor Cell Line Proliferation Assay

The ability of one or more compounds of the invention to inhibit tumor cell line proliferation was determined according to standard procedures known in the art. For instance, an in vitro cellular proliferation assay was performed to measure the metabolic activity of live cells. Tumor cell lines A375, WM-266-4, or HCT116 cells (ATCC) were grown to near 80% confluence, and are trypsinized and seeded at 1500 cells/well at volume of 100 per well in full growth medium (10% FBS in DMEM or 10% FBS in RPMI) in a 96 well plate. The cells were incubated at 37° C. under 5% $CO_2$ for two hours to allow for attachment to the plates. Compounds were first diluted in 1:3 dilutions in 100% DMSO at 250× the desired concentration, and then further diluted (1:50) in 10% DMEM growth medium. The diluted compounds were added to the cell plate (25 μL for a 5× dilution) and the cells are incubated with compounds (0.4% DMSO in 10% FBS DMEM) for 96 hours at 37° C. under 5% CO2. The cell control wells were added with vehicle only (0.4% DMSO in 10% FBS DMEM or in 10% FBS RPMI). Each concentration of the compounds was tested in duplicates. After 96 hours of the compound treatment, CellTiter Glo reagent (Promega) was added at a 1:5 dilution to each well of the cell plate and the cell plate was placed at room temperature for 30 minutes. The luminescence of the wells was determined using a Tecan plate reader. One or more compounds disclosed herein exhibit an IC50 less than 80 nM in A375 cells, an IC50 less than 50 nM in HCT1116 cells, and an IC50 less than 110 nM in H358 cells when tested in this assay (see FIG. 1).

TABLE 2

In Vitro IC50 data for selected compounds of the invention (the compounds numbers correspond to those provided in Table 1).

|  | 250 nM or less (+++) | 250 nM to 1000 nM (++) | Greater than 1000 nM (+) |
|---|---|---|---|
| Cellular Phospho-p90RSK IC50 (nM) | 1, 2, 3, 4, 6, 7, 8, 10, 11, 12, 13, 14, 16, 18, 22, 23, 26, 30, 31, 35, 37, 41, 50, 55, 57, 58, 63, 64, 68, 71, 72, 75, 76, 77, 78, 84, 86, 88, 90, 92, 99, 101, 102, 103, 104, 118, 120, 121, 122, 123, 126, 132, 134, 140, 141, 142, 143, 144, 146, 147, 148, 150, 153, 154, 156, 158, 161, 162, 163, 165, 174, 178, 179, 180, 181, 184, 185, 187, 188, 190, 193, 196, 197, 199, 200, 205, 211, 212, 213, 214, 216, 217, 220, 222, 224, 225, 226, 227, 228, 229, 231, 233, 234, 237, 238, 239, 240, 241, 242, 243, 244, 245, 246, 248, 249, 250, 251, 252, 253, 254, 258, 259, 261, 262, 264, 266, 267, 269, 270, 271, 272, 273, 274, 275, 276, 277, 278, 279, 280, 281, 284, 285, 286, 288, 290, 291, 292, 293, 294, 295, 297, 298, 299, 300, 301, 302, 304, 305, 306, 308, 311, 312, 316, 318, 320, 321, 323, 324, 325, 326, 328, 330, 332, 333, 334, 336, 338, 339, 340, 341, 342, 344, 345, 346, 347, 348, 349, 352, 353, 354, 356, 357, 361, 362, 364, 366, 370, 372, 380, 384, 386 | 5, 915, 17, 19, 21, 27, 36, 38, 39, 44, 45, 47, 48, 49, 53, 56, 62, 66, 70, 95, 97, 100, 110, 111, 114, 115, 124, 125, 127, 129, 136, 137, 138, 139, 145, 149, 152, 155, 159, 168, 169, 170, 172, 175, 176, 177, 182, 183, 186, 191, 192, 194, 195, 203, 204, 207, 209, 215, 218, 219, 221, 223, 230, 232,, 257, 287, 289, 307, 309, 310, 313, 315, 319, 322, 331, 351, 355, 359, 360, 367, 371, 373, 387 | 20, 32, 33, 34, 40, 42, 43, 46, 51, 54, 59, 60, 61, 67, 83, 117, 128, 131, 133, 151, 157, 160, 164, 166, 167, 171, 173, 189, 201, 202, 206, 208, 210, 235, 236, 247, 255, 256, 260, 263, 265, 268, 283, 296, 303, 314, 317, 327, 329, 335,, 343, 350, 358, 363, 365, 383, 385 |
| A375 (V599E) Cell Proliferation IC50 (nM) | 1, 3, 4, 22, 63, 64, 68, 77, 84, 101, 102, 103, 104, 134, 143, 144, 146, 148, 149, 151, 153, 154, 156, 158, 162, 165, 181, 184, 185, 187, 190, 196, 197, 212, 213, 214, 225, 237, | 2, 6, 7, 8, 10, 11, 12, 13, 14, 16, 18, 21, 23, 26, 30, 31, 35, 36, 37, 41, 92, 99, 120, 123, 132, 136, 138, 139, 140, 141, 147, 161, 163, 174, 178, 179, 180, 193, 199, 200, | 5, 9, 15, 17, 19, 20, 24, 27, 32, 33, 34, 39, 47, 49, 201, 202, 257, 317, 366 |

TABLE 2-continued

In Vitro IC50 data for selected compounds of the invention (the compounds numbers correspond to those provided in Table 1).

| | 250 nM or less (+++) | 250 nM to 1000 nM (++) | Greater than 1000 nM (+) |
|---|---|---|---|
| | 239, 240, 241, 243, 244, 245, 248, 251, 252, 254, 264, 267, 269, 270, 271, 272, 273, 275, 278, 279, 280, 281, 284, 285, 288, 291, 292, 293, 304, 305, 306, 316, 318, 324, 325, 326, 332, 333, 338, 339, 357, 362, 364 | 204, 205, 211, 216, 221, 222, 224, 226, 227, 228, 229, 231, 234, 242, 301, 308, 311, 320, 321, 323, 328, 330, 331, | |
| H358 (Kras, G12C) Cell Proliferation IC50 (nM) | 1, 35, 63, 64, 84, 101, 102, 103, 143, 144, 146, 147, 165, 174, 181, 196, 197, 214 | 30, 31, 36, 37, 39, 41, 68, 77, 99, 120, 123, 132, 134, 139, 140, 141, 161, 163, 178, 179, 180, 190, 193, 199, 200, 205, 221, 222 | 26, 27, 32, 33, 34, 47, 49, 136, 138, 201, 202, 204 |
| WM-266-4 (V599D) Cell Proliferation IC50 (nM) | 1, 3, 4, 7, 8, 10, 11, 12, 22 | 2, 5, 6, 9, 13, 14, 16, 18, 21 | 15, 17, 19, 20, 23, 24 |

Example 20. Microsome Stability Assay

The stability of one or more compounds of the invention is determined according to standard procedures known in the art. For example, stability of one or more compounds of the invention is established by an in vitro assay. In particular, an in vitro microsome stability assay is established that measures stability of one or more compounds of the invention when reacting with mouse, rat or human microsomes from liver. The microsome reaction with compounds is performed in 1.5 mL Eppendorf tube. Each tube contains 0.1 µL of 10.0 mg/ml NADPH; 75 µL of 20.0 mg/ml mouse, rat or human liver microsome; 0.4 µL, of 0.2 M phosphate buffer, and 425 µL, of ddH$_2$O. Negative control (without NADPH) tube contains 75 µL, of 20.0 mg/ml mouse, rat or human liver microsome; 0.4 µL of 0.2 M phosphate buffer, and 525 µL of ddH$_2$O. The reaction is started by adding 1.0 µL of 10.0 mM tested compound. The reaction tubes are incubated at 37° C. 100 µL sample is collected into new Eppendorf tube containing 300 µL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS). The microsome stability of one or more compounds of the present invention when assayed under this condition have T1/2 (min) well within a range required for clinical development.

Example 21. Plasma Stability Assay

The stability of one or more compounds of the invention in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A compound of the invention is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37° C. for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

Where desired, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program, Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 22. Chemical Stability Assay

The chemical stability of one or more compounds of the invention is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A compound of the invention is added from a 100 μM stock solution to an aliquot of PBS (in duplicate) to give a final assay volume of 400 μL, containing 5 test compound and 1% DMSO (for half-life determination a total sample volume of 700 μL is prepared). Reactions are incubated, with shaking, for 0 minutes and 24 hours at 37° C.; for half-life determination samples are incubated for 0, 2, 4, 6, and 24 hours. Reactions are stopped by adding immediately 100 μL of the incubation mixture to 100 μL of acetonitrile and vortexing for 5 minutes. The samples are then stored at 20° C. until analysis by HPLC-MS/MS. Where desired, a control compound or a reference compound such as chlorambucil (5 μM) is tested simultaneously with a compound of the invention of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, Cl2, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 23. Rodent Pharmacokinetic Assay

In order to study the pharmacokinetics of the compounds of the invention, the compounds are dissolved in an appropriate vehicle (e.g. 5% 1-methyl-2-pyrrolidinone, 85% polyethylene glycol 400, 10%© Solutor) and administered orally to a group of 4-10 week old mice at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

Alternatively, the compounds are dosed acutely (e.g. once) and after a time (e.g. about 0, 30 s, 1 m, 5 m, 10 m, 20 m, 30 m, 1 hr, 2 hr, 3 hr, 5 hr, 8 hr, 10 hr, 12 hr, 1 d, 2 d, etc.) blood is collected and analyzed as described below.

The results are expected to demonstrate the pharmacokinetic parameters such as absorption, distribution, metabolism, excretion, and toxicity for the compounds of the invention.

Example 24. Inhibition of Tumor Growth In Vivo

Cell lines: Human cancer cell lines with A375 (mutant B-Raf V600E), LOX (mutant B-Raf V600E) and Colo-205 (mutant B-Raf V600E), PANC-1 (mutant K-Ras G12D), MiaPaca-2 (mutant K-Ras G12C), HCT116 (mutant K-Ras G13D), H441 (mutant K-Ras G12V), H23 (mutant K-Ras G12C), MDA-MB-231 (mutant K-Ras G13D) and LS1034 (mutant N-Ras) are obtained from ATCC. The cells are maintained in cell culture in media recommended by ATCC at 37° C. in 5% $CO_2$/air. The cells are harvested during exponential growth phase Animals: 5-7 week-old female balb/c nude, CB17.SCID (severe combined immune deficiency) or SCID/beige mice are obtained from Charles River Laboratories. Animals are housed in disposable and individually ventilated cages placed in SPF rooms or barrier rooms under pathogen-free conditions. Animals are fed with sterilized standard dry granule mouse chow and have free access to sterile water. All studies are approved by the Institutional Animal Care and Use Committee of Explora Biolabs where the studies are performed, and are in accordance with Institutional Animal Care and Use Committee guidelines of Wellspring Biosciences and in accordance with the Guide for the Care and Use of Laboratory Animals (1996).

Tumor Xenograft Model: The mice are inoculated subcutaneously (2~5×10$^6$ cells in PBS or PBS:Matrigel mixture) into the right flank of 7-9 week old mice. Animal body weights are measured 3 times/week until treatment begins at which time body weights are measured daily prior to dosing. Tumor dimensions are measured 2~3 times/week using a caliper. Tumor volume is calculated using Formula I of $(L \times W^2)/2$, where L is tumor length and W is tumor width, respectively. Typically dosing will begin when an average size of 100 mm$^3$ is reached. Mice are randomized into study groups (n=9~10/group). Compounds are formulated in PBS, PEG300 (Polyethylene Glycol) or CMC/$H_2O$ (Carboxymethyl Cellulose) and administered to animals according to body weight (5 μL/mg) orally, QD or BID. Animals are sacrificed once tumors in the vehicle control group reach 2000 mm$^3$ in volume. For luciferase-transfected tumor models, tumor viability is monitored 2~3 times/week using the Xenogen IVIS® 200.

Data and Statistical Analysis: Tumor growth inhibition (TGI) is calculated as $[1-(T-T_0)/(C-C_0)]/100$, where T and $T_0$ are the mean tumor volumes for a treatment group on a specific experimental day and on the first day of treatment, respectively, for the experimental groups; C and $C_0$ are the mean tumor volumes for the control group.

The data is expressed as mean±SEM (standard error of the mean). The statistical significance in mean values is determined by ANOVA (analysis of variance) using a Dunnett's multiple-comparison post-test (GraphPad Prism®), or Tukey's test (SPSS 16.0). A P-value <0.05 is considered statistically significant.

What is claimed is:
1. A compound of Formula II-E:

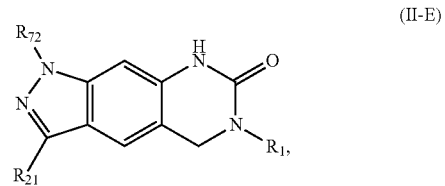

(II-E)

or a pharmaceutically acceptable salt thereof; wherein:
$R_1$ is —$C_{2-10}$alkenyl, —$C_{2-10}$alkynyl, —$C_{3-10}$aryl, —$C_{1-10}$hetaryl, —$C_{3-10}$cycloalkyl, —$C_{1-10}$heterocyclyl, —$C_{1-10}$alkyl-$C_{3-10}$cycloalkyl, —$C_{1-10}$alkyl-$C_{1-10}$heterocyclyl, —$C_{2-10}$alkenyl-$C_{3-10}$aryl, —$C_{2-10}$alkenyl-$C_{1-10}$hetaryl, —$C_{2-10}$alkenyl-$C_{3-10}$cycloalkyl, —$C_{2-10}$alkenyl-$C_{1-10}$heterocyclyl, —$C_{2-10}$alkynyl-$C_{3-10}$aryl, —$C_{2-10}$alkynyl-$C_{1-10}$hetaryl, —$C_{2-10}$alkynyl-$C_{3-10}$cycloalkyl, —$C_{2-10}$alkynyl-$C_{1-10}$heterocyclyl, —$C_{1-10}$alkoxy-$C_{3-10}$aryl, —$C_{1-10}$alkoxy-$C_{1-10}$hetaryl, —$C_{1-10}$alkoxy-$C_{3-10}$cycloalkyl, —$C_{1-10}$alkoxy-$C_{1-10}$heterocyclyl, —$C_{1-10}$heteroalkyl-$C_{1-10}$hetaryl, —$C_{1-10}$heteroalkyl-$C_{3-10}$cycloalkyl, —$C_{1-10}$heteroalkyl-$C_{1-10}$heterocyclyl, —$C_{3-10}$aryl-$C_{1-10}$alkyl, —$C_{3-10}$aryl-$C_{2-10}$alkenyl, —$C_{3-10}$aryl-$C_{2-10}$alkynyl, —$C_{3-10}$aryl-$C_{3-10}$hetaryl, —$C_{3-10}$aryl-$C_{3-10}$cycloalkyl, —C$_{3-10}$aryl-C$_{1-10}$heterocyclyl, —C$_{1-10}$hetaryl-C$_{1-10}$alkyl, —C$_{1-10}$hetaryl-C$_{2-10}$alkenyl, —C$_{1-10}$hetaryl-C$_{2-10}$alkynyl, —C$_{3-10}$hetaryl-C$_{3-10}$aryl, —C$_{1-10}$hetaryl-C$_{3-10}$cycloalkyl, —C$_{1-10}$hetaryl-C$_{1-10}$heterocyclyl, —C$_{3-10}$cycloalkyl-C$_{1-10}$alkyl, —C$_{3-10}$cycloalkyl-C$_{2-10}$alkenyl, —C$_{3-10}$cycloalkyl-C$_{2-10}$alkynyl, —C$_{3-10}$cycloalkyl-C$_{3-10}$aryl, —C$_{3-10}$cycloalkyl-C$_{1-10}$hetaryl, —C$_{3-10}$cycloalkyl-C$_{1-10}$heterocyclyl, —C$_{1-10}$heterocyclyl-C$_{1-10}$alkyl, —C$_{1-10}$heterocyclyl-C$_{2-10}$alkenyl, —C$_{1-10}$heterocyclyl-C$_{2-10}$alkynyl, —C$_{1-10}$heterocyclyl-C$_{3-10}$aryl, —C$_{1-10}$heterocyclyl-C$_{1-10}$hetaryl, or —C$_{1-10}$heterocyclyl-C$_{3-10}$cycloalkyl, each of which is unsubstituted or substituted by one or more independent R$_{10}$ or R$_{11}$ substituents;

R$_{21}$ is -L-C$_{1-10}$heteroalkyl, -L-C$_{3-10}$aryl, -L-C$_{1-10}$hetaryl, -L-C$_{3-10}$cycloalkyl, or -L-C$_{1-10}$heterocyclyl, each of which is unsubstituted or substituted by one or more independent R$_{12}$ substituents;

L is a bond;

R$_{72}$ is hydrogen, —C$_{1-10}$ alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —C(O)R$^{31}$, —CO$_2$R$^{31}$, —C(=O)NR$^{31}$, —S(O)$_{0-2}$R$^{31}$, —C(=S)OR$^{31}$, or —C(=O)SR$^{31}$;

R$_{10}$ is —C$_{1-10}$ alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, optionally substituted by one or more independent R$_{11}$ substituents;

R$_{11}$ and R$_{12}$ are independently hydrogen, halogen, —C$_{1-10}$ alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, —OR$^{31}$, —NR$^{31}$R$^{32}$, —C(O)R$^{31}$, —CO$_2$R$^{31}$, —C(=O)NR$^{31}$, —NO$_2$, —CN, —S(O)$_{0-2}$R$^{31}$, —SO$_2$NR$^{31}$R$^{32}$, —NR$^{31}$C(=O)R$^{32}$, —NR$^{31}$C(=O)OR$^{32}$, —NR$^{31}$C(=O)NR$^{32}$R$^{33}$, —NR$^{31}$S(O)$_{0-2}$R$^{32}$, —C(=S)OR$^{31}$, —C(=O)SR$^{31}$, —NR$^{31}$C(=NR$^{32}$)NR$^{32}$R$^{33}$, —NR$^{31}$C(=NR$^{32}$)OR$^{33}$, —NR$^{31}$C(=NR$^{32}$)SR$^{33}$, —OC(=O)OR$^{33}$, —OC(=O)NR$^{31}$R$^{32}$, —OC(=O)SR$^{31}$, —SC(=O)SR$^{31}$, —P(O)OR$^{31}$OR$^{32}$, or —SC(=O)NR$^{31}$NR$^{32}$;

each of R$^{31}$, R$^{32}$, and R$^{33}$ is independently hydrogen, halogen, —C$_{1-10}$ alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, or —C$_{1-10}$heterocyclyl, or —R$^{31}$ together with R$^{32}$ form a heterocyclic ring.

2. The compound of claim 1, wherein R$_{21}$ is -L-C$_{1-10}$hetaryl unsubstituted or substituted by one or more independent R$_{12}$ substituents; and wherein L is a bond.

3. The compound of claim 2, wherein the C$_{1-10}$hetaryl of R$_{21}$ comprises one or more nitrogen atoms.

4. The compound of claim 3, wherein the C$_{1-10}$hetaryl of R$_{21}$ is selected from the group consisting of pyrazolyl, pyridinyl, pyrazinyl, pyrimidinyl, and pyridazinyl.

5. The compound of claim 4, wherein the C$_{1-10}$hetaryl of R$_{21}$ is unsubstituted.

6. The compound of claim 4, wherein the C$_{1-10}$hetaryl or R$_{21}$ is substituted with one, two, or three independent R$_{12}$ substituents.

7. The compound of claim 6, wherein each R$_{12}$ substituent is independently selected from the group consisting of —C$_{1-10}$ alkyl, —C$_{2-10}$alkenyl, —C$_{2-10}$ alkynyl, —C$_{1-10}$heteroalkyl, —C$_{3-10}$aryl, —C$_{1-10}$hetaryl, —C$_{3-10}$cycloalkyl, —C$_{1-10}$heterocyclyl, —OH, —CF$_3$, —OCF$_3$, and —OR$^{31}$; wherein each R$^{31}$ is independently hydrogen or —C$_{1-10}$ alkyl.

8. The compound of claim 7, wherein each R$_{12}$ substituent is independently selected from the group consisting -Me, -Et, -i-Pr, -n-Pr, OH, —OMe, —OEt, —OPr.

9. The compound of claim 1, wherein R$_1$ is —C$_{1-10}$heterocyclyl, —C$_{1-10}$alkyl-C$_{3-10}$heterocyclyl, —C$_{1-10}$heterocyclyl-C$_{1-10}$alkyl, or —C$_{1-10}$heterocyclyl-C$_{3-10}$aryl, unsubstituted or substituted by one or more independent R$_{10}$ or R$_{11}$ substituents.

10. The compound of claim 9, wherein R$_1$ is —C$_{1-10}$heterocyclyl, —C$_{1-10}$heterocyclyl-C$_{1-10}$alkyl, or —C$_{1-10}$heterocyclyl-C$_{3-10}$aryl, unsubstituted or substituted by one or more independent R$_{10}$ or R$_{11}$ substituents.

11. The compound of claim 10, wherein R$_1$ is

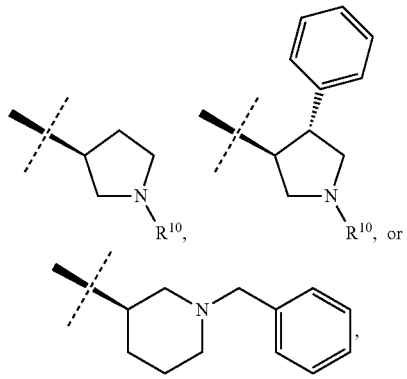

unsubstituted or substituted by one or more independent R$_{10}$ or R$_{11}$ substituents.

12. The compound of claim 1, wherein R$_{72}$ is H.

13. A method of inhibiting activity of a protein kinase present in a cell, comprising contacting said cell with an effective amount of the compound of claim 1.

14. The method of claim 13, wherein the protein kinase is ERK.

15. The method of claim 13, wherein the compound inhibits ERK at an IC50 value of less than about 100 nM.

16. A pharmaceutical composition comprising the compound of-claim 1 and a pharmaceutically acceptable excipient.

17. The pharmaceutical composition of claim 16, wherein said composition is formulated in an oral dosage.

* * * * *